(12) United States Patent
Sliz et al.

(10) Patent No.: US 12,019,083 B2
(45) Date of Patent: Jun. 25, 2024

(54) COMPOUND DISTRIBUTION IN MICROFLUIDIC DEVICES

(71) Applicant: EMULATE, Inc., Boston, MA (US)

(72) Inventors: Josiah Sliz, Boston, MA (US); Daniel Levner, Brookline, MA (US); Brian Zuckerman, Cambridge, MA (US); Norman Wen, West Roxbury, MA (US); Jonathan Rubins, Cambridge, MA (US); Tanvi Shroff, Cambridge, MA (US); Christopher David Hinojosa, Malden, MA (US); Grace Ahn, Medford, MA (US); Victor Antontsev, Somerville, MA (US); Jefferson Puerta, Malden, MA (US); David Conegliano, Boston, MA (US); S. Jordan Kerns, Reading, MA (US)

(73) Assignee: EMULATE, INC., Boston, MA (US)

(*) Notice: Subject to any disclaimer, the term of this patent is extended or adjusted under 35 U.S.C. 154(b) by 72 days.

(21) Appl. No.: 17/834,165

(22) Filed: Jun. 7, 2022

(65) Prior Publication Data

US 2022/0334139 A1    Oct. 20, 2022

Related U.S. Application Data

(63) Continuation of application No. 17/538,518, filed on Nov. 30, 2021, which is a continuation of application No. PCT/US2020/039830, filed on Jun. 26, 2020.
(Continued)

(51) Int. Cl.
*G01N 35/00* (2006.01)
*B01L 3/00* (2006.01)
(Continued)

(52) U.S. Cl.
CPC .. *G01N 35/00584* (2013.01); *B01L 3/502761* (2013.01); *C12Q 3/00* (2013.01);
(Continued)

(58) Field of Classification Search
CPC ............. G01N 35/00584; G01N 15/06; G01N 33/5008; G01N 2035/0097; B01L 3/502761; C12Q 3/00
See application file for complete search history.

(56) References Cited

U.S. PATENT DOCUMENTS 5,285,073 A    2/1994 Schelten et al. .............. 250/394
8,647,861 B2   2/2014 Ingber et al. .............. 435/289.1
(Continued)

FOREIGN PATENT DOCUMENTS

WO    WO2003/074994 A2    3/2003
WO    WO2004/059299 A1    12/2003
(Continued)

OTHER PUBLICATIONS

U.S. Appl. No. 15/105,388 US20160326477 A1, filed Nov. 10, 2016, Fernandez-Alcon, et al.
(Continued)

*Primary Examiner* — Brian J. Sines
(74) *Attorney, Agent, or Firm* — Medlen & Carroll, LLP

(57) ABSTRACT

The present invention is related to the field of microfluidics and compound distribution within microfluidic devices and their associated systems. In one embodiment, present invention aims to solve the problem of molecule and compound absorbency into the materials making up laboratory equipment, microfluidic devices and their related infrastructure, without unduly restricting gas transport within microfluidic devices.

9 Claims, 158 Drawing Sheets

Related U.S. Application Data

(60) Provisional application No. 62/867,543, filed on Jun. 27, 2019.

(51) Int. Cl.
*C12Q 3/00* (2006.01)
*G01N 15/06* (2006.01)
*G01N 33/50* (2006.01)

(52) U.S. Cl.
CPC ......... *G01N 15/06* (2013.01); *G01N 33/5008* (2013.01); *B01L 3/502707* (2013.01); *B01L 2200/0647* (2013.01); *B01L 2200/148* (2013.01); *B01L 2300/0681* (2013.01); *B01L 2300/069* (2013.01); *B01L 2300/10* (2013.01); *B01L 2400/0406* (2013.01); *G01N 2035/00544* (2013.01); *G01N 2035/0097* (2013.01)

(56) References Cited

U.S. PATENT DOCUMENTS

| | | |
|---|---|---|
| 9,121,847 B2 | 9/2015 | Kamm et al. |
| 9,261,496 B2 | 2/2016 | Kamm et al. |
| 10,532,355 B2 | 1/2020 | Trietsch et al. |
| 2012/0070878 A1 | 3/2012 | Fink et al. ............ 435/243 |
| 2013/0165900 A1 | 6/2013 | Braig et al. ............ 604/504 |
| 2014/0087362 A1 | 3/2014 | Szalay et al. ............ 435/5 |
| 2018/0326417 A1 | 11/2018 | Wikswo et al. ............ 422/502 |
| 2018/0327700 A1 | 11/2018 | Andrea et al. |
| 2022/0155328 A1* | 5/2022 | Sliz ............ B01D 19/0063 |

FOREIGN PATENT DOCUMENTS

| | | |
|---|---|---|
| WO | WO 2013/138522 | 9/2013 |
| WO | PCT/US2014/071570 | 12/2014 |
| WO | PCT/US2014/071611 | 12/2014 |
| WO | PCT/US2019/25449 | 4/2019 |

OTHER PUBLICATIONS

U.S. Appl. No. 15/248,690 US 20100058248 A1, filed Mar. 2, 2017, Hinojosa, et al.
U.S. Appl. No. 15/647,727 US 20180015464 A1, filed Jan. 18, 2018, Levner, et al.
Breslauer, D. N. et al. (2006) "Microfluidics-based systems biology," *Molecular BioSystems* 2(2), 97-112.
Naik, A. W. et al. (2016) "Active machine learning-driven experimentation to determine compound effects on protein patterns," *eLife* 5, e10047.
PCT International Search Report of International Application No. PCT/US2020/039830 dated Nov. 20, 2020.
Extended European Search Report dated Jun. 14, 2023.
SG Written Opinion 11202114127Q dated Jan. 6, 2023.
Canada Examination Report dated Nov. 21, 2022.
Kleinstreuer, et al., "Microfluidics of nano-drug delivery" *International journal of Heat and Mass Transfer*, vol. 51, Issues 23-24, pp. 5590-5597 (2008).
Al-Shyoukh, et al., "Systematic quatitative characterization of cellular responses induced by multiple signals." *BMC Syst Biol.* 5:88 pp. 1-17 (2011).
Ding, et al., "Effective drug combination for *Caenorhabditis elegans* nematodes discovered by output-driven feedback system control technique." *Sci Adv.* 3(10): pp. 1-7 (2017).
Schneider, "Automating drug discovery." *Nat Rev Drug Discov*. 17:97-113 (2018).
Tsutsui, et al., "An optimized small molecule inhibitor cocktail supports long-term maintenance of human embryonic stem cells." *Nat Commun* 2(167) pp. 1-18 (2011).

* cited by examiner

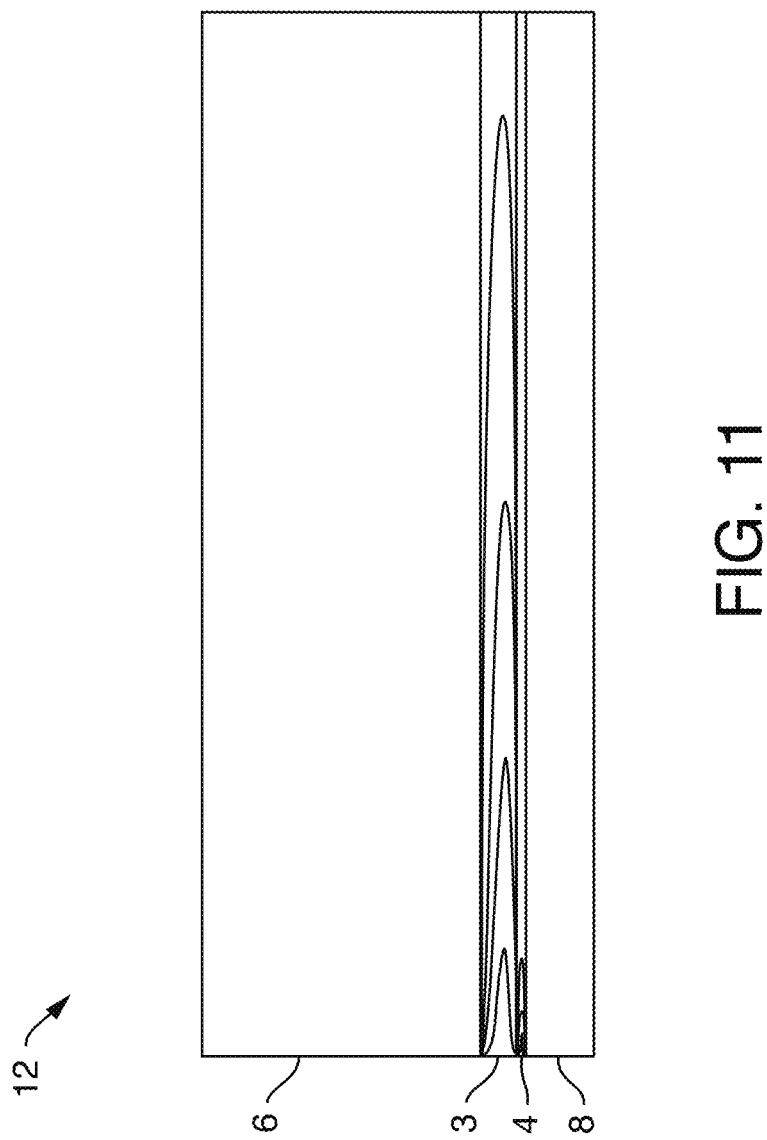

FIG. 23

| TABLE 1.1 MECHANICAL PROPERTIES OF POLYMERS | | | | | | |
|---|---|---|---|---|---|---|
| POLYMER | TENSILE STRENGTH (MPA) | FLEXURAL MODULUS/ (MODULUS OF ELASTICITY) (GPA) | ELONGATION AT BREAK (%) | STRAIN AT YIELD (%) | NOTCHED IZOD IMPACT STRENGTH | SURFACE HARDNESS |
| CARBON/HYDROGEN-CONTAINING POLYMERS | | | | | | |
| LOW-DENSITY POLYETHYLENE (LDPE) | 10 | 0.25 | 400 | 19 | 1.064 | SD 48 |
| HIGH-DENSITY POLYETHYLENE (HDPE) | 32 | 1.25 | 150 | 15 | 0.15 | SD 68 |
| CROSSLINKED POLYETHYLENE (PE) | 18 | 0.5 | 350 | N/Y | 1.064 | SD 58 |
| POLYPROPYLENE (PP) | 26 | 2 | 80 | NIY | 0.05 | RR 85 |
| ETHYLENE-PROPYLENE | 26 | 0.6 | 500 | NIY | 0.15 | RR75 |
| POLYMETHYL PENTENE | 28 | 1.5 | 15 | 6 | 0.04 | RR 70 |
| STYRENE-BUTADIENE | 28 | 1.6 | 50 | NIY | 0.08 | SD 75 |
| STYRENE-ETHYLENE BUTYLENE-STYRENE | 6 | 0.02 | 800 | NIY | 1.064 | SA 45 |
| HIGH-IMPACT POLYSTYRENE (PS) | 42 | 2.1 | 2.5 | 1.8 | 0.1 | RM 30 |
| PS, GENERAL PURPOSE | 34 | 3 | 1.6 | | | RM 80 |

FIG. 23.1 cont.

| | OXYGEN - CONTAINING POLYMERS | | | | |
|---|---|---|---|---|---|
| EPOXIES, GENERAL | 600 | 80 | 1.3 | N/A | 0.5 | RM 113 |
| ACETAL (POLYOXYMETHYLENE) | 50 | 27 | 20 | 8 | 0.10 | RM 109 |
| POLYESTERS (BISPHENOL), POLYESTER LAMINATE | 280 | 16 | 1.5 | N/A | 1.064 | RM 125 |
| POLYESTER (ELECTRICAL GRADE) | 40 | 9 | 2 | N/A | 0.4 | RM 125 |
| POLYBUTYLENE PHTHALATE | 52 | 2.1 | 250 | 4 | 0.06 | RM 70 |
| POLYETHYLENE TEREPHTHALATE (PET) | 55 | 2.3 | 300 | 3.5 | 0.02 | RM 30 |
| POLYETHER ETHER KETONE (PEEK) | 92 | 3.7 | 50 | 4.3 | 0.083 | RM 99 |
| DIALLYLIOSPHTHALATE | 82 | 11.3 | 0.9 | N/A | 0.37 | RM 112 |
| DIALLYL PHTHALATE | 70 | 10.6 | 0.9 | N/A | 0.41 | RM 112 |
| ALKYD RESIN GLASS FIBER, REINFORCED | 72 | 8.6 | 0.8 | N/A | 0.24 | RM 125 |
| POLYARYLATES | 68 | 2.2 | 50 | 8.8 | 0.29 | RR 125 |
| POLYCARBONATE (PC) | 50 | 2.1 | 200 | 3.5 | 0.05 | RM 70 |
| POLYPHENYLENE OXIDE | 65 | 2.5 | 60 | 4.5 | 0.16 | RR 119 |
| PHENOL - FORMALDEHYDE | 45 | 6.5 | 1.2 | N/A | 0.024 | RM 114 |

FIG. 23.2 cont.

| | | | | | |
|---|---|---|---|---|---|
| STYRENE - MALEI C | 52 | 3 | 1.8 | 2 | 0.03 | RL 105 |
| CELLULOSE ACETATE | 30 | 1.7 | 60 | 4 | 0.26 | RR 71 |
| CELLULOSE PROPIONATE | 35 | 1.76 | 60 | 4 | 0.13 | RR 94 |
| CELLULOSE ACETATE BUTYRATE | 70 | 2.9 | 2.5 | N/A | 0.02 | RM 92 |
| ETHYLENE VINYL ACETATE | 17 | 0.02 | 750 | N/A | 1.064 | SA 85 |
| NITROGEN-CONTAINING POLYMERS | | | | | | |
| POLYAMIDE (PA) 6 | 40 | 1 | 60 | 4.5 | 0.25 | SD 7S |
| PA 4,6 | 100 | 1 | 30 | 11 | 0.1 | SD 85 |
| PA 11 | 52 | 0.9 | 320 | 20 | 0.05 | RR 105 |
| PA 6,9 | 50 | 1.4 | 15 | 10 | 0.06 | SD 78 |
| PA 12 | 50 | 1.4 | 200 | 6 | 0.06 | RR 105 |
| PA 6,6 | 59 | 1.2 | 60 | 4.5 | 0.11 | RR 90 |
| PA 6, 12 | 51 | 1.4 | 300 | 7 | 0.04 | RR 105 |
| NYLON/ACRYLONITRILE - BUTADIENE - STYRENE (ABS) ALLOY | 47 | 2.14 | 270 | 6 | 0.85 | RR 99 |
| PA - IMIDE | 185 | 4.58 | 12 | 8 | 0.13 | RM 109 |
| POLYIMIDE | 72 | 2.45 | 8 | 4 | 0.08 | RM 100 |
| POLYETHERIMIDE | 105 | 3.3 | 60 | 8 | 0.1 | RM 109 |

| | | | | |
|---|---|---|---|---|
| POLYURETHANE (PU) THERMOPLASTIC ELASTOMER | 24 | 0.003 | 700 | N/Y | 1.064 | SA 70 |
| ETHER ESTER AMIDE ELASTOMER | | | | | | |
| UREA FORMALDEHYDE | 57 | 10 | 0.6 | N/A | 0.02 | RM 115 |
| STYRENE ACRYLONITRILE | 72 | 3.6 | 2.4 | 3.5 | 0.02 | RM 80 |
| ABS | 34 | 2.1 | 6 | 2 | 0.18 | RR 96 |
| ACRYLATE - STYRENE ACRYLONITRILE | 35 | 2.5 | 10 | 3.3 | 0.1 | RR 106 |
| FLUORINE-CONTAINING POLYMERS | | | | | | |
| POLYTETRAFLUOROETHYLENE | 25 | 0.70 | 400 | 70 | 0.16 | RM 69 |
| POLYVINYLFLOURIDE | 40 | 1.4 | 150 | 30 | 0.18 | SD 80 |
| POLYVINYLIDENE FLUORIDE | 100 | 5.5 | 6 | N/A | 0.12 | SD 90 |
| PERFLUOROALKOXYETHYLENE | 29 | 0.7 | 300 | 85 | 1.064 | SD 60 |
| ETHYLENE TETRAFLUORO ETHYLENE | 28 | 1.4 | 150 | 15 | 1.064 | RR SO |
| ETHYLENE CHLOROTRIFLUORO ETHYLENE | 30 | 1.7 | 200 | 5 | 1.064 | RR 93 |
| FLUORINATED ETHYLENE PROPYLENE | 14 | 0.6 | 150 | 6 | 1.064 | RR 45 |
| CHLORINE-CONTAINING POLYMERS | | | | | | |

FIG. 23.3 cont.

| | | | | |
|---|---|---|---|---|
| CHLORINATED (POLYVINYL CHLORIDE) PVC | 58 | 3.1 | 30 | 5 | 0.06 | SA 70 |
| UNPLASTICIZED PVC (UPVC) | 51 | 3 | 60 | 3.5 | 0.08 | RR 110 |
| PLASTICIZED PVC | 14 - 20 | 0.007  0.03 | 280 - 9S | NY | 1.05+ | SA 85 |
| SULFUR - CONTAINING POLYMERS | | | | | | |
| POLYPHENYLENE SULFIDE | 91 | 13.8 | 0.6 | N/A | 0.6 | RR 121 |
| POLYSULFONE | 70 | 2.6S | 80 | 5.5 | 0.07 | RM 69 |
| POLYETHERSULFONE | 84 | 2.6 | 60 | 6.6 | 0.084 | RM 85 |
| SILICON - CONTAINING POLYMERS | | | | | | |
| SILICONES | 28 | 3.5 | 2 | N/A | 0.02 | RM 80 |
| POLYDIMETHYLSILOXANE | | 0.001 - 0.002 | | | | |

*THESE ARE TYPICAL ROOM - TEMPERATURE VALUES OF NOTCHED IZOD IMPACT STRENGTH. A MATERIAL THAT DOES NOT BREAK IN THE IZOD TEST IS GIVEN A VALUE OF 1.06 + KJ/M; THE + INDICATES THAT IT HAS A HIGHER IMPACT ENERGY THAN THE TEST CAN GENERATE.

N/A = IF MATERIAL IS BRITTLE AND DOES NOT EXHIBIT YIELD POINT
NY = IF MATERIAL IS DUCTILE AND DOES NOT EXHIBIT YIELD POINT
RM = ROCKWELL M 123 HARDNESS (HARD)
RR = ROCKWELL R 112 HARDNESS
SA 65 = SHORE A 65 HARDNESS (SOFT)
SD 75 = SHORE D75 HARDNESS

FIG. 23.4 cont.

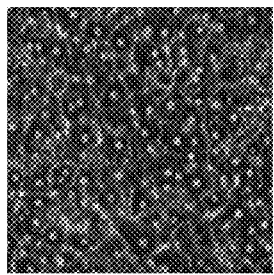 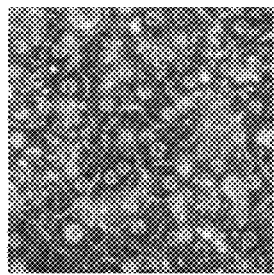 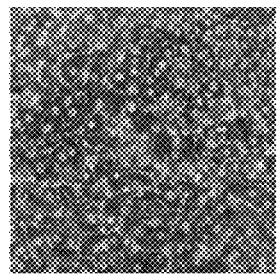 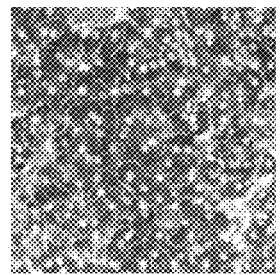
FIG. 46A　　FIG. 46B　　FIG. 46C　　FIG. 46D
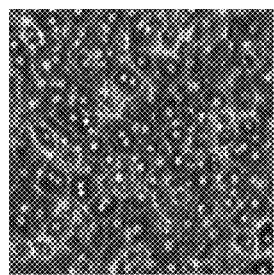 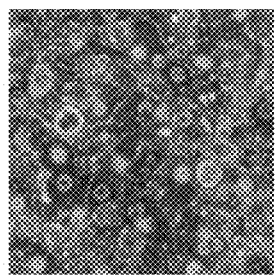 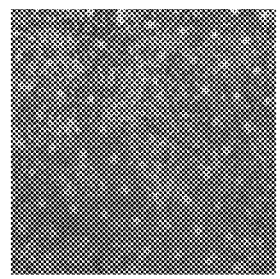 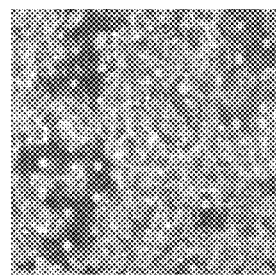
FIG. 47A　　FIG. 47B　　FIG. 47C　　FIG. 47D
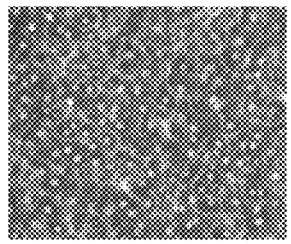 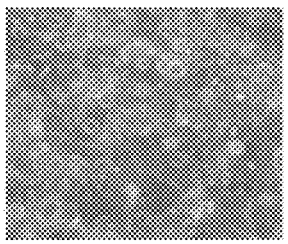 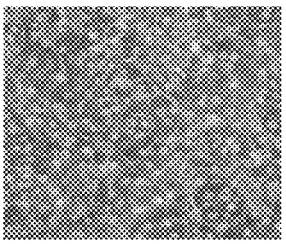 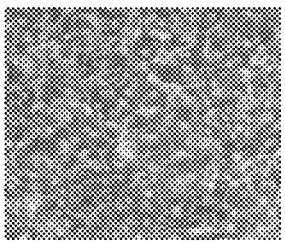
FIG. 48A　　FIG. 48B　　FIG. 48C　　FIG. 48D
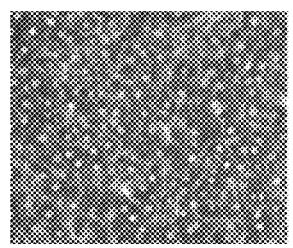 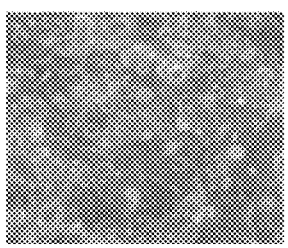 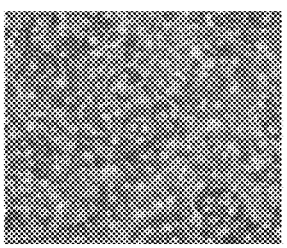 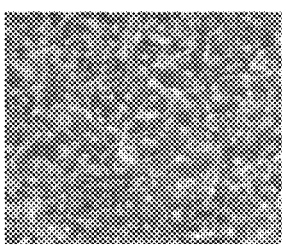
FIG. 49A　　FIG. 49B　　FIG. 49C　　FIG. 49D

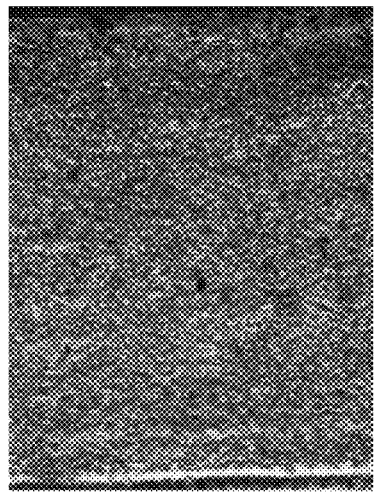
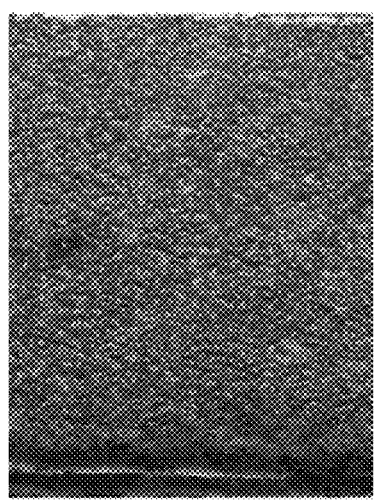
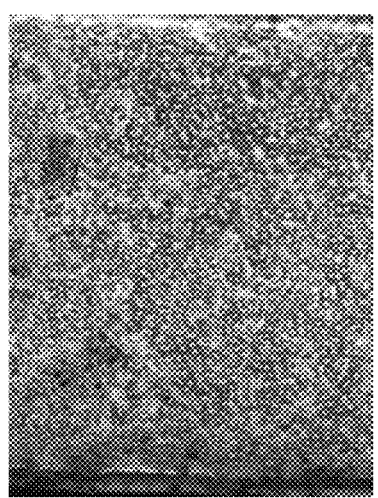
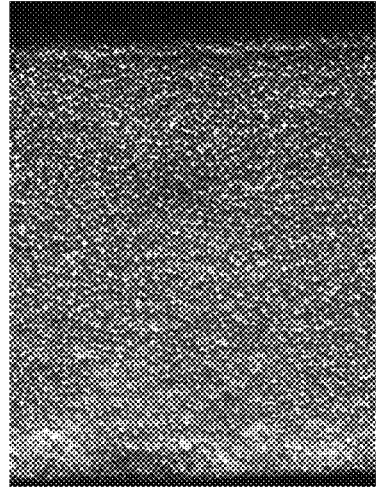
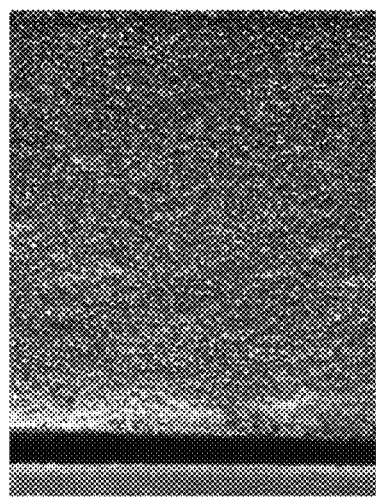
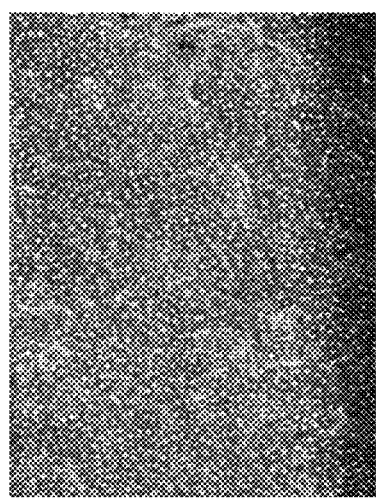

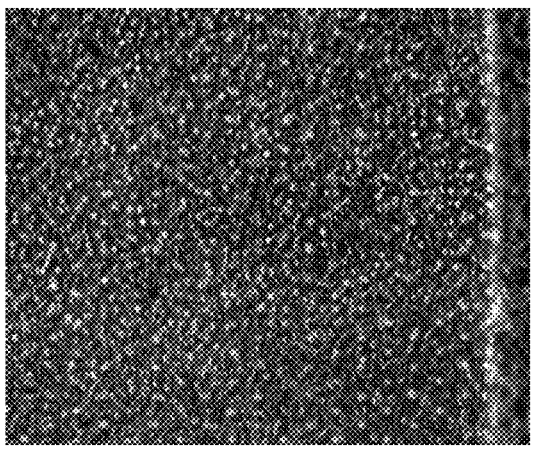
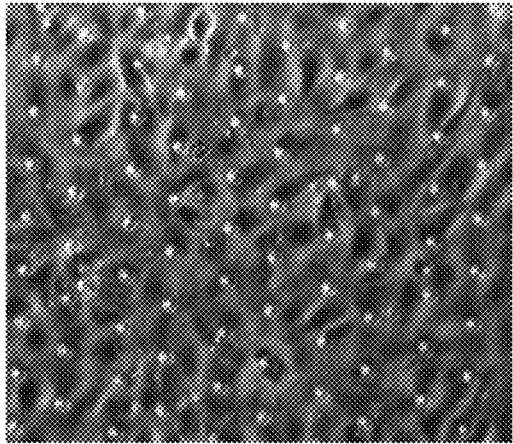
FIG. 57A  FIG. 57B
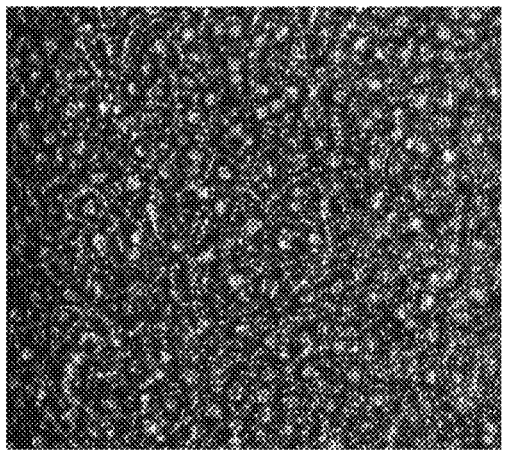
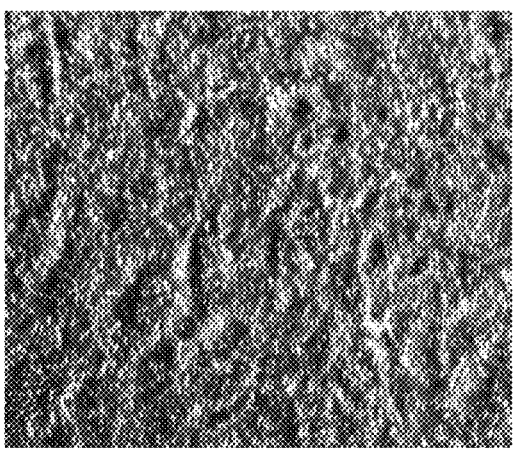
FIG. 58A  FIG. 58B
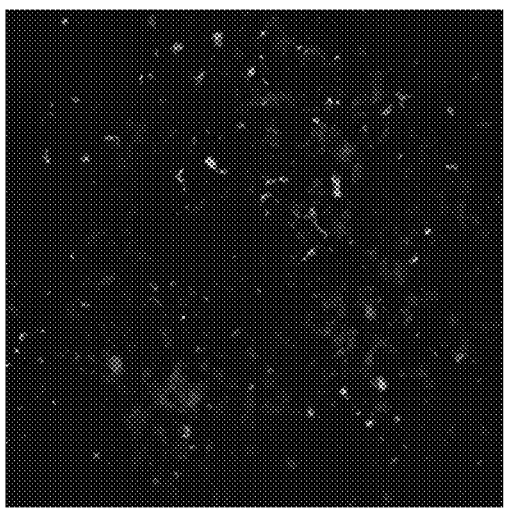
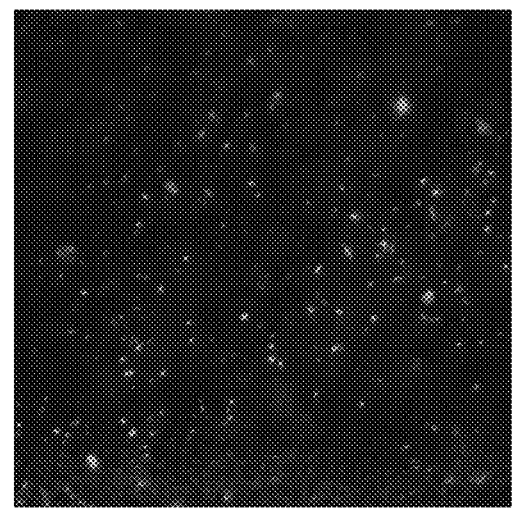
FIG. 59A  FIG. 59B

| n | CHIP | CONDITIONS | FLOWRATE [µL/hr] | CELL TYPE | INSTRUMENT |
|---|------|------------|------------------|-----------|------------|
| 3 | COP | 100% O2 HIGH FR | T: 150 B: 150 | T: HEPATOCYTES B: LSEC | CULTURE MODULE |
| 3 | COP | 5% CO2 HIGH FR | T: 150 B: 150 | T: HEPATOCYTES B: LSEC | CULTURE MODULE |
| 3 | COP | 5% CO2 15mM HEPES HIGH FR | T: 150 B: 150 | T: HEPATOCYTES B: LSEC | CULTURE MODULE |
| 3 | COP | 5% CO2 HIGHER FR | T: 300 B: 300 | T: HEPATOCYTES B: LSEC | SYRINGE PUMP |
| 2 | PDMS | 5% CO2 HIGHER FR | T: 300 B: 300 | T: HEPATOCYTES B: LSEC | SYRINGE PUMP |
| 3 | PDMS | 5% CO2 CONTROL | T: 30 B: 30 | T: HEPATOCYTES B: LSEC | CULTURE MODULE |

FIG. 64

| COMPOUND | MW | logP | PDMS - CHIP MATERIAL (PARTITION COEFFICIENT) | POD MATERIAL (PARTITION COEFFICIENT) |
|---|---|---|---|---|
| METHOTREXATE | 454 | -1.85 | MINIMAL | NOT TESTED |
| FIALURIDINE | 372 | -0.9 | MINIMAL | NOT TESTED |
| CAFFEINE | 194 | -0.1 | MINIMAL | MINIMAL |
| CYCLOPHOSPHAMIDE | 261 | 0.8 | MINIMAL | MINIMAL |
| ANTIPYRINE | 188 | 0.38 | MINIMAL | MINIMAL* |
| DIGOXIN | 781 | 1.26 | MINIMAL | MINIMAL |
| TOPOTECAN | 421 | 1.52 | MINIMAL | MINIMAL |
| PHENACETIN | 179 | 1.58 | MINIMAL | MINIMAL |
| S-MEPHENYTOIN | 218 | 1.69 | MINIMAL | MINIMAL |
| TOLBUTAMIDE | 270 | 2.34 | MINIMAL | NOT TESTED |
| ESTRONE-3-SULFATE | 350 | 3.83 | MINIMAL | MINIMAL |
| DICLOFENAC | 296 | 4.51 | MINIMAL | MINIMAL |
| VALSARTAN | 436 | 5.8 | MINIMAL | MINIMAL |
| NAVITOCLAX | 975 | 9.6 | MINIMAL | MINIMAL |
| BARDOXOLONE | 492 | 5.92 | QUALITATIVE-ABSORBED | NOT TESTED |
| BOSENTAN | 552 | 2.8 | 1 | NOT TESTED |
| PERFENIDONE | 185 | 1.9 | 1.75 | 1.3 |
| FEXOFENADINE | 502 | 2.8 | 2.5 | NOT TESTED |

FIG. 76

| COMPOUND | MW | logP | PDMS - CHIP MATERIAL (PARTITION COEFFICIENT) | POD MATERIAL (PARTITION COEFFICIENT) |
|---|---|---|---|---|
| COUMARIN | 146 | 1.4 | 2.5 | 3 |
| TACRINE | 198 | 2.7 | 2.5 | 0.3 |
| LORAZEPAM | 321 | 2.39 | 3.5 | 1.2 |
| RHODAMINE B | 479 | 2.4 | 3.5 | MINIMAL |
| QUINIDINE | 324 | 2.9 | 9.8 | MINIMAL |
| DIAZEPAM | 285 | 2.82 | 25 | 11 |
| KETOCONAZOLE | 5331 | 4.35 | 25 | NOT TESTED |
| NICOTINE | 162 | 1.2 | 60 | 1.5 |
| DEXTROMETHORPHAN | 271 | 3.97 | 75 | NOT TESTED |
| STAUROSPORINE | 467 | 3.2 | 123 | 6 |
| MIDAZOLAM | 326 | 3.89 | 201 | 4.05 |
| BUPROPION | 240 | 3.6 | >160 | 9.46 |
| BUFURALOL | 261 | 3.5 | >216 | 4.77 |
| AMITRIPTYLINE | 277 | 4.92 | >1000 | 175 |
| CISAPRIDE | 466 | 3.4 | >1000 | 1000 |
| TERFENADINE | 472 | 7 | >2000 | NOT TESTED |

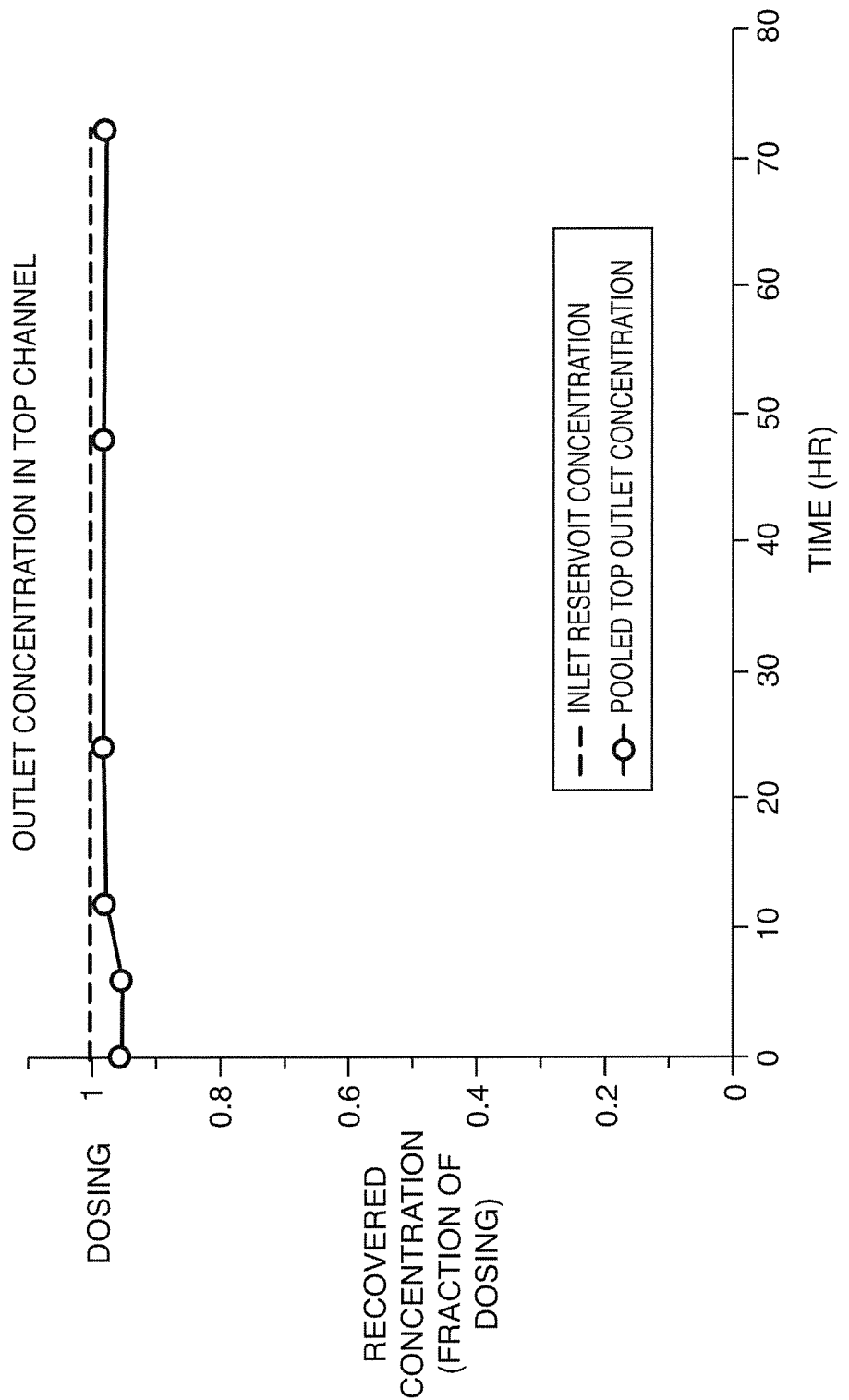

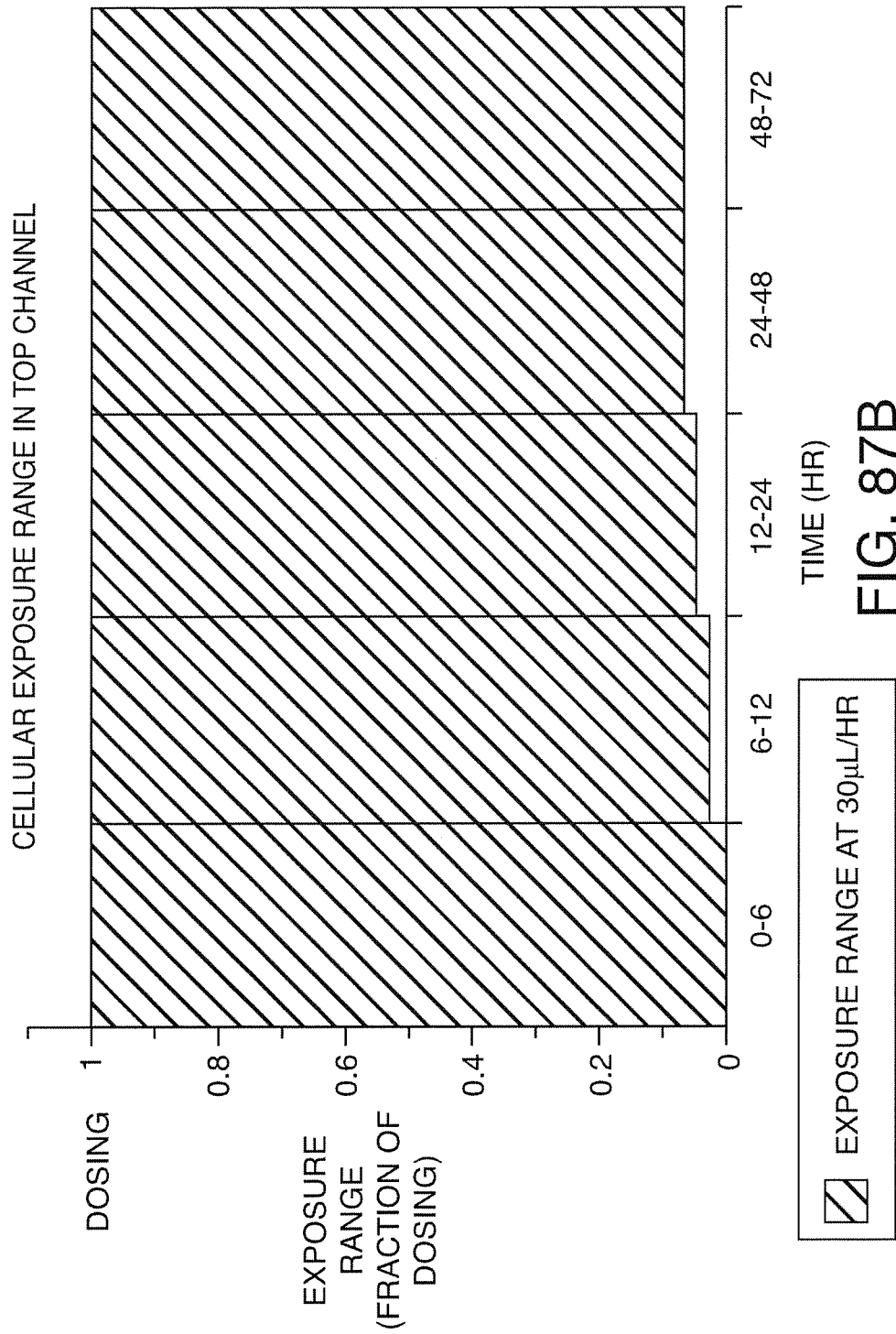

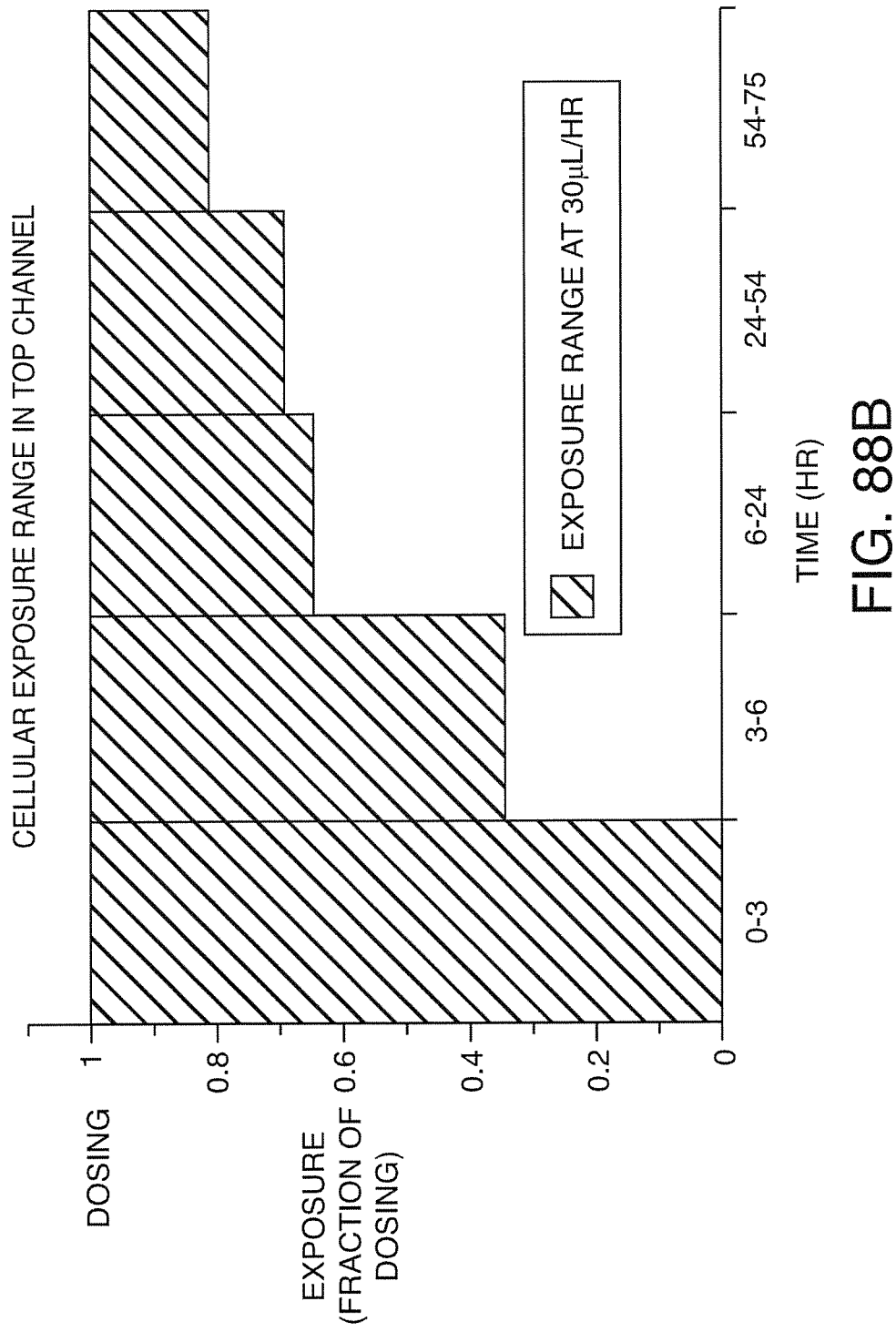

| EXPOSURE PERIOD (HR) | POTENTIAL EXPOSURE CONCENTRATION RANGE (μM) | | | |
|---|---|---|---|---|
| | TOP CHANNEL | | BOTTOM CHANNEL | |
| | MINIMUM | MAXIMUM | MINIMUM | MAXIMUM |
| 3 - 6 | 0.171 | 102.000 | 0.150 | 93.900 |
| 6 - 24 | 34.733 | 102.000 | 52.247 | 93.900 |
| 24 - 54 | 65.100 | 102.000 | 67.733 | 93.900 |
| 54 - 75 | 70.033 | 102.000 | 75.067 | 93.900 |
| 75+ | 83.467 | 102.000 | 86.700 | 93.900 |

FIG. 89

| DURATION OF DOSING (HR) | RECOMMENDED TIME POINTS (HR) |
|---|---|
| < 3 | 0.5, 1, 1.5, 2, 3 |
| 6 | 0.5, 1, 2, 4, 6 |
| 12 | 1, 3, 6, 9, 12 |
| 24 | 2, 3, 6, 12, 24 |
| 48 | 1, 3, 6, 24, 48 |
| 72+ | 1, 6, 24, 48, 72 |

FIG. 91

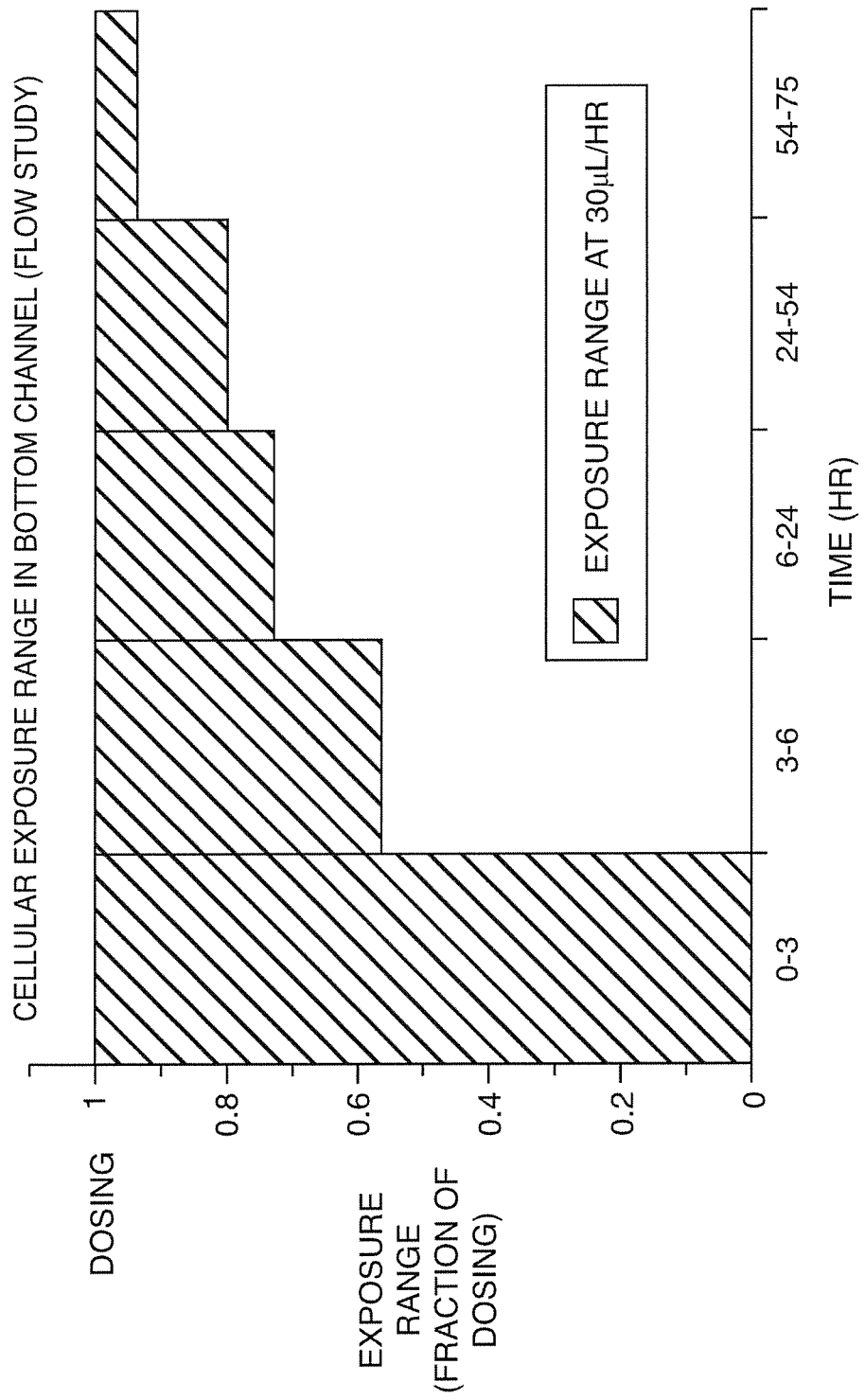

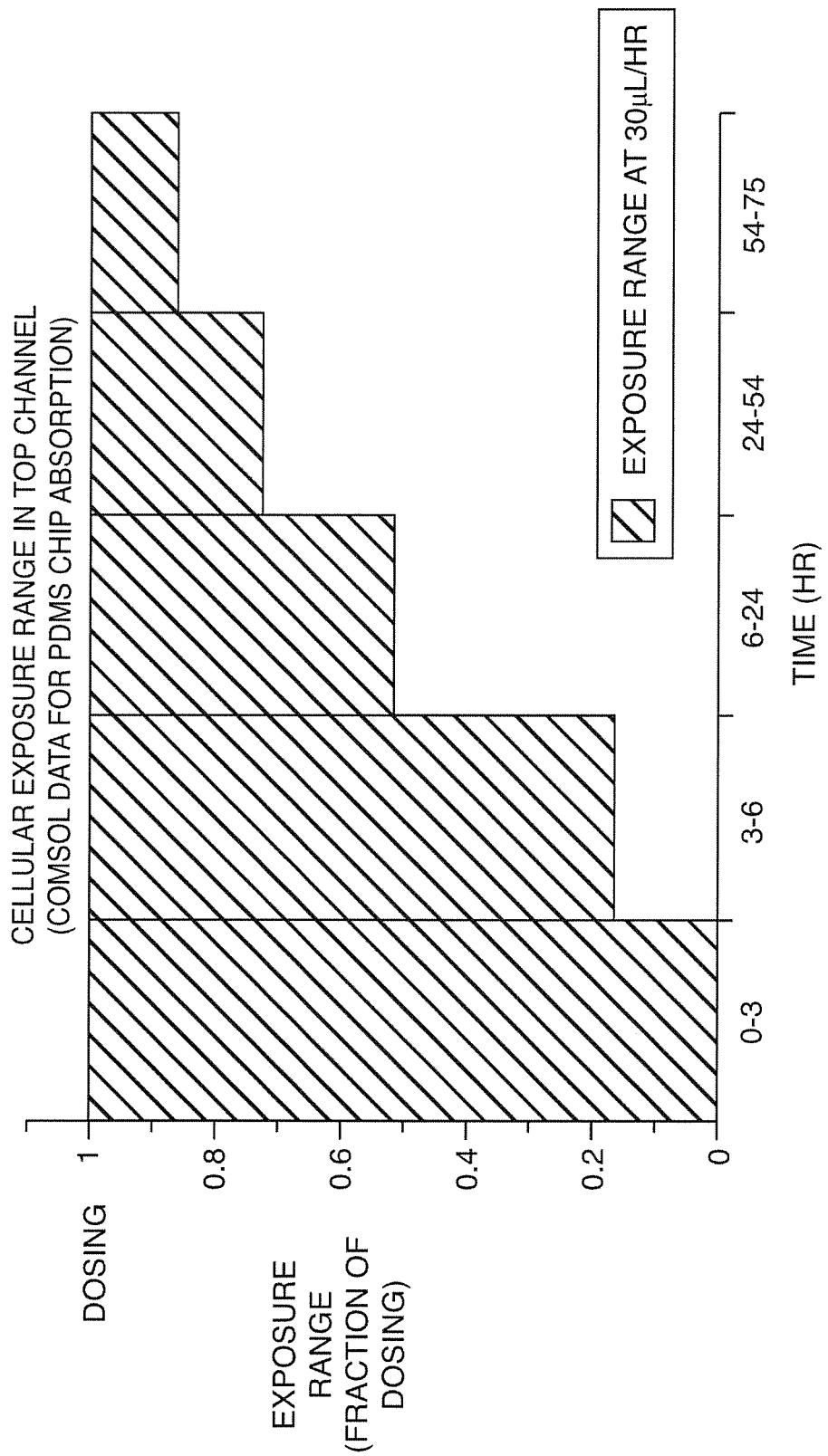

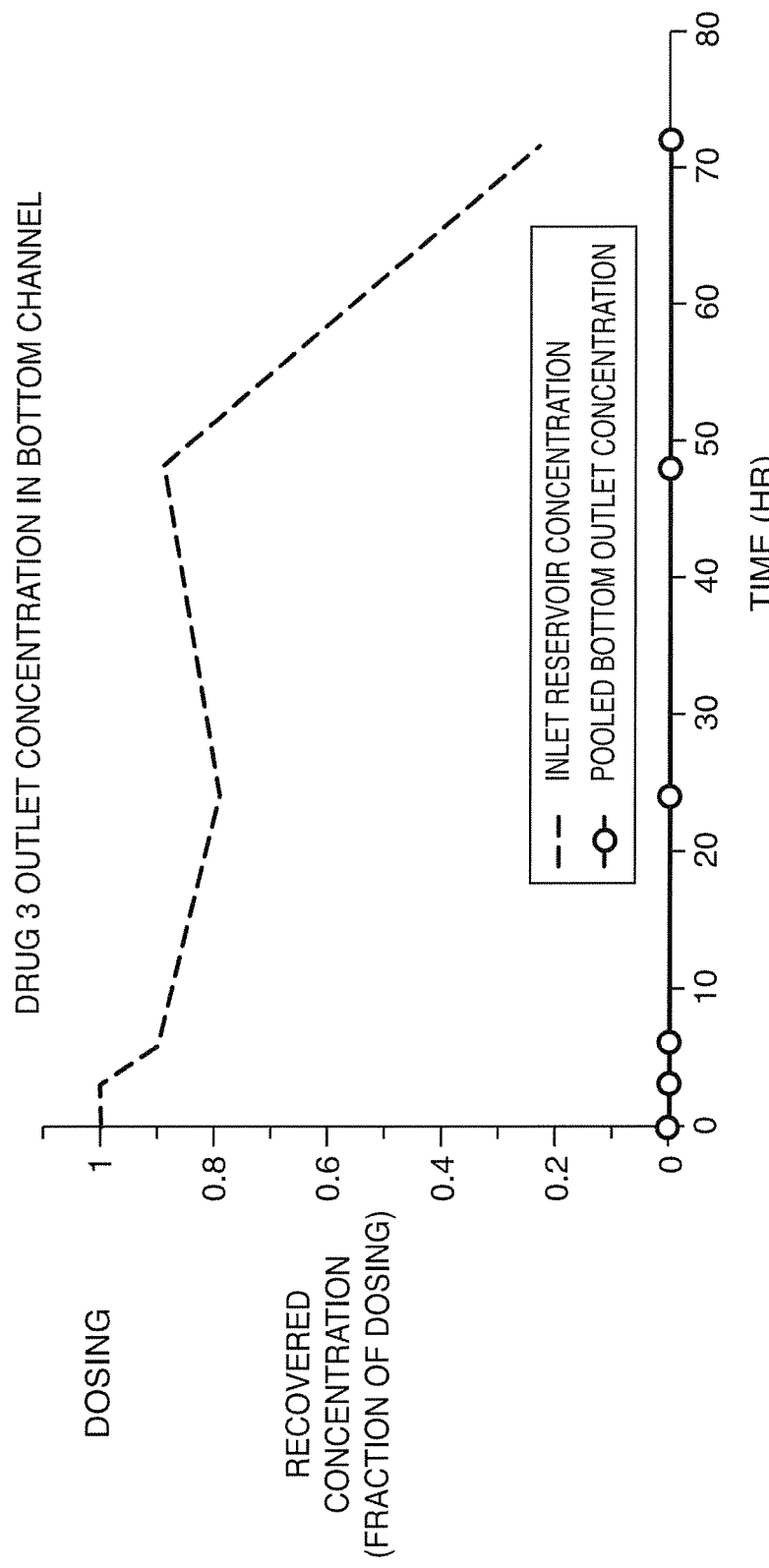

COMPOUND DISTRIBUTION IN MICROFLUIDIC DEVICES

CROSS-REFERENCE TO RELATED APPLICATIONS

This application is a Continuation of, and claims priority to, co-pending U.S. patent application Ser. No. 17/538,518 filed Nov. 30, 2021, which is a Continuation of PCT Patent Application Serial No. PCT/US2020/039830, filed Jun. 26, 2020, which claims priority to Provisional Application Ser. No. 62/867,543 filed on Jun. 27, 2019, the contents of which are incorporated herein in their entirety.

FIELD OF INVENTION

The present invention is related to the field of microfluidic cell culture systems. A variety of microfluidic devices and a perfusion manifold assembly are contemplated that limit small-molecule absorption into their material makeup. An absorption kit or compound distribution kit is also contemplated to characterize the movement of a compound within an experimental or clinical system. A gas exchanger is also contemplated to control the rate of gas flow from one area to another, such as from the ambient environment to the interior of a microfluidic device.

BACKGROUND

New microfluidics technology offers useful experimental tools for studying cells ex vivo. Compared with conventional culture systems, a microfluidic device can provide a more physiologically relevant cellular environment, by generating fluid flows which can maintain a more constant and soluble microenvironment, such as described by Breslauer et al. in the publication "Microfluidics-based systems biology." Two-dimensional (2D) monolayer cell culture systems have been used for many years in biological research. The most common cell culture platform is the two-dimensional (2D) monolayer cell culture in petri dishes or flasks. Although such 2D in vitro models are less expensive than animal models and are conducive to systematic, and reproducible quantitative studies of cell physiology (e.g., in drug discovery and development), the physiological relevance of the in vitro systems to the in vivo condition is often questionable and the results from such studies often lack validity. It has now been widely accepted that three-dimensional (3D) cell culture matrix promotes many biological relevant functions not observed in 2D monolayer cell culture. Said another way, 2D cell culture systems do not accurately recapitulate the structure, function, and physiology of living tissues in vivo.

U.S. Pat. No. 8,647,861 describes microfluidic "organ-on-chip" devices comprising living cells on membranes in microchannels exposed to culture fluid at a flow rate. In contrast to static 2D culture, microchannels allow the perfusion of cell culture medium throughout the cell culture during in vitro studies and as such offer a more in vivo-like physical environment. In simple terms, an inlet port allows injection of cell culture medium into a cell-laden microfluidic channel or chamber, thus delivering nutrients and oxygen to cells. An outlet port then permits the exit of remaining medium as well as harmful metabolic by-products.

U.S. patent application Ser. No. 15/248,690 describes a perfusion manifold assembly that retains one or more microfluidic devices, such as "organ-on-chips", that comprise cells that mimic at least one function of an organ in the body, and allow the perfusion and optionally the mechanical actuation of said microfluidic devices, optionally without tubing. The perfusion manifold assembly interacts with a culture module that allows the perfusion and optionally mechanical actuation of one or more microfluidic devices, such as "organ-on-chip" devices. The culture module comprises a pressure manifold that allows for perfusion of microfluidic devices, such as the "organ-on-chip" devices.

The materials oftentimes used to fabricate these microfluidic devices or "organ-on-chip" devices, and their relating infrastructure, such as the perfusion manifold assembly, are oftentimes prone to erroneous distribution of compounds and absorption of small molecule compounds they are designed to non-absorbingly interface with. While the materials used to construct microfluidic devices and their infrastructure, such as polydimethylsiloxane (PDMS) and the styrenic block copolymer (SEBS) manufactured by Kraton, tend to be widely available, inexpensive and amendable to microfluidic device fabrication, they inhibit particular varieties of research they otherwise would be ideal for, such as the drug discovery and development, etc. For the purposes of drug discovery and development, microfluidic device absorbency can lead to variability in drug exposure to subjects in the microfluidic device, such as patient cells, animal cells, microbial cells, small organisms, etc. In order to enable therapeutic prediction, there needs to be a high confidence in the concentration of a compound that specimen is exposed to.

Despite absorbency issues, materials used to fabricate microfluidic devices, such as PDMS, also tend to promote the transport of gasses vital in supporting the viability and function of the subjects inside the microfluidic device. In particular, oxygen from the outside environment is allowed to permeate/pass to the interior of the microfluidic device, supplying the cells with oxygen needed for respiration. Similarly, carbon dioxide, which is released during cellular respiration, is allowed to pass through the material from inside the microfluidic device to the external environment; this prevent this waste product from building-up and becoming toxic to the cells. Non-absorbing or low-absorbing materials, such as many hard plastics, tend to hinder the transport of these gasses into and out of microfluidic devices. What is needed is a solution to decouple gas permeability, which is needed to support biological viability and function, from absorbency, which limits the applications of these devices in the research of pharmaceutical, in the materials used in microfluidic devices.

SUMMARY OF THE INVENTION

The present invention is related to the field of microfluidics. The present invention is related to compound distribution within microfluidic devices and their associated systems. In one embodiment, present invention aims to solve the problem of molecule and compound absorbency into the materials making up laboratory equipment, microfluidic devices and their related infrastructure, without restricted gas transport within microfluidic devices. Compounds, such as pharmaceuticals and chemicals, can absorb into, bind to, or poorly distribute within various components of in vivo and in vitro experimental setups, with frequent offenders including infusion tubing, syringes, tissue-culture labware, and pipette tips. Such absorption binding, and poor distribution often goes unnoticed, thereby contributing to variability and skewing quantitative experimental results (e.g. dose-response curves). Microfluidic devices are no exception. Microfluidic devices fabricated from entirely gas-permeable materials tend to absorb small molecule compounds disrupting data, thereby confounding the data collected using those microfluidic devices. For example, the material polydimethylsiloxane (PDMS) is highly absorptive, which can negatively affect experiments, especially if that absorption is not understood. Absorption of small molecules into the bulk material making up microfluidic devices decreases the concentration of those small molecules that may come into contact with specimen within microfluidic devices, such as cells and small organisms.

It is estimated that small-molecule compounds fall into one of three categories of absorption, (1) compounds that do not absorb at detectable levels, (2) compounds that somewhat absorb at levels that can be detected, and (3) compounds that highly or completely absorb. It is estimated that about 40% of small-molecule compounds do not absorb, falling in the first category. It is estimated that about 40% of small-molecule compounds somewhat absorb, falling into the second category. It is estimated that about 20% of small-molecule compounds completely absorb, falling into the third, most difficult, category. As such, it is estimated that approximately 60% of small-molecule compounds could be potentially problematic not only during scientific experimentation, but also during live patient dosing.

Small molecules may also be known as xenobiotics. Xeno means foreign. Xenobiotics tend to be what is thought of classically as chemicals, which do not typically occur in the human body. Xenobiotics tend to be smaller molecules compared to biologics. Biologics, such as proteins and antibodies, naturally occur in the human body and tend to be larger molecules as compared to xenobiotics. In practice, most xenobiotics are under 1 kDa in molecular weight. For the purpose of the present invention a molecule under 1 kDa in molecular weight may be considered a small molecule.

Some materials are more prone to material absorption than others. Polymers can generally be seen as rigid or elastomeric. Polymers may be gauged as rigid or elastomeric based on their Young's Moduli, also known as flexural modulus, also known as modulus of elasticity. In practice, any polymer with a modulus of elasticity over 0.1 GPa is considered effectively rigid, or non-flexible, certainly for the purposes of microfluidic device fabrication. Rigid polymers may fall in the range of 0.1 GPa to 150 GPa. Metals usually have a modulus of elasticity value of at least 30 GPa or greater. For example, aluminum can have a modulus of elasticity value up to about 69 GPa. In some embodiments, the rigidity or flexibility of materials and/or the biocompatible material can be determined by the material hardness. For example, hardness of a material can be typically measured by its resistance to indentation under a static load. The most commonly used measures are the Shore hardness and Rockwell hardness. Both are empirical relative measures. The Shore hardness is a measure often used as a proxy for flexural modulus of elastomers. The Shore A scale is typically used for softer elastomers while Shore scale D is used for harder elastomers or softer rigid thermoplastic materials. By way of example only, rigid but softer thermoplastic materials such as polypropylenes can have typical values between 75 and 85 on the Shore D scale. Harder rigid thermoplastic materials such as acrylic can be usually characterized on Rockwell M scale. For example, Rockwell M value of acrylic can be 85-105, polycarbonate 72, polystyrene 68-70, and polysulfone 70.

Few materials fall between being flexible or elastomeric and rigid. Said another way, when looking at moduli of elasticity, very few materials fall in a range where it would be ambiguous if they are elastomeric or rigid. Materials that fall may be considered between flexible or elastomeric and rigid, including polytetrafluorethylene (PTFE) or Teflon, and fluorinated ethylene propylene (FEP), have been tested and have been found to be absorbing. Therefore, only rigid materials may generally be considered low-absorbing. Another class of flexible polymers are rubbers, which are different from plastics. Rubbers tend to be flexible as well. Rubbers include natural rubber and liquid silicone rubber. However, it has been found that rubbers generally tend to absorb small molecules as well.

Following an extensive look into both rigid and elastomeric polymers it has generally been seen that rigid polymers are low-absorbing, while elastomeric polymers are prone to absorption of small molecules. Without being bound by theory, molecules or monomers within elastomeric polymers generally have higher mobility than molecules within rigid polymers. Polymers are made up of monomers, or molecules that come together through polymerization to form a polymer. As the molecules or monomers within rigid polymers are not as mobile, it is more difficult for molecules to absorb or diffuse into rigid polymers. Conversely, as the molecules or monomers within elastomeric polymers as more mobile, it is less difficult for molecules to absorb or diffuse into elastomeric polymers. Therefore, when using elastomeric polymers for their other beneficial properties, such as their ability to stretch, one must rely more heavily on chemical rather than physical parameters to stop absorption or diffusion of other molecules into the polymer. Chemical parameters may not only entail coatings, but also the chemical properties of the polymer, such as dispersion, polarity, and hydrogen bonding.

Hansen solubility parameters developed by Charles M. Hansen predicted if one material will dissolve in another. For the uses herein, the Hansen solubility parameters are helpful in predicting the solubility of a molecule into a solid. The three Hansen solubility parameters are dispersion (SD), polarity (SP), and hydrogen bonding (δH). Dispersion forces, also known as Van der Waals forces, are the distance-dependent interactions between molecules, such as attraction and repulsion. Polarity is the uneven partial charge distribution between various atoms in a compound. Hydrogen bonding are the attractive forces between hydrogen atoms covalently bonded to very electronegative atoms, such as nitrogen, oxygen and fluorine and another very electronegative atom. Materials with similar Hansen solubility parameters are more likely to dissolve into each other. The following equation may be used to determine the Hansen solubility parameter of a material:

$$(Ra)^2 = 4(\delta_{D2}-\delta_{D1})^2 + (\delta_{P2}-\delta_{P1})^2 + (\delta_{H2}-\delta_{H1})^2$$

Where Ra is the is the distance between Hansen parameters in Hansen space. The closer the Hansen parameters the more likely the two material are to dissolve into each other. $\delta_{D1}$ is the dispersion force of the first material. $\delta_{P1}$ is the polarity of the first material. $\delta_{H1}$ is the hydrogen bonding of the first material. $\delta_{D2}$ is the dispersion force of the second material. $\delta_{P2}$ is the polarity of the second material. $\delta_{H2}$ is the hydrogen bonding of the second material.

Following a detailed and mathematical look into both elastomeric and rigid polymers, there has not been a polymer found that may make up the body of a multi-purpose microfluidic device. It is desired that the microfluidic device be low-absorbing, able to stretch in order to better emulate in vivo physiology, as well as biocompatible. As stated before, rigid polymers tend not to absorb. Elastomeric polymers are flexible. As such, there has not yet been found any elastomeric nor rigid polymers that, in their own right, both resist molecule absorption and also stretch. As such, as strategic combination of elastomeric and rigid polymers may be able to be used, in one embodiment, to fabricate a flexible, low-absorbing microfluidic device.

Absorption into the body of the microfluidic device negatively impacts experimental readouts, such as cellular metabolism. A challenge when using microfluidic devices is understanding and quantifying the rate of metabolism and the resulting metabolite produced when cells are in contact with candidate compounds. In order to deduce intrinsic clearance of drugs in the case of, say, liver cells, the metabolism, or loss of the parent compound, is often measured. Intrinsic clearance is the ability of the liver to remove drug in the absence of limitations, such as flow or binding to cells or proteins in the blood. Low rates of metabolism can make it difficult to detect loss of the parent compound, even if the microfluidic device is non-absorbing. Most importantly, absorption can make it impossible to deduce whether compound loss should be attributed to metabolism or absorption. In simpler terms, if cells consume low concentrations of a parent compound, it is difficult to quantify that loss. A practical level of sensitivity of detection in an LC/MS instrument is ±25%. As such, a decrease in the concentration of the parent compound needs to be at least 25% and ideally much more in order to effectively quantify metabolism. Quantifying metabolism is made more difficult by absorption of the parent compound. If absorption into the material, such as PDMS, is significant, then the observed apparent rate of metabolism (if all of compound loss is attributed to metabolism) will over-estimate actual cell-mediated metabolism as the decrease in compound concentration will be incorrectly attributed to metabolism. In some cases, all of the parent compound could be depleted by the material. In this case, absorption will prevent even an estimation of the upper possible rate of metabolism, since there will be no data to analyze as all of the compound has been lost. Material absorption can be computationally modeled and accounted for given information on the material-compound properties, such as the rate and extent of absorption in the material, experimental parameters, such as dosing concentration and flow rate, and microfluidic device geometry as long as all of the parent compound is not being depleted by the material. Computational modeling, however, requires extensive studies to characterize the compound—material interaction as well as computationally expensive models of the system to "subtract out" the contribution of material absorption to loss or disappearance of compound. If compound loss is complete, these models cannot account for the contribution of absorption, as compound loss is complete.

The present invention is made up of multiple unique embodiments. One embodiment of the present invention is a method for using a rigid microfluidic device with a high flow rate (e.g. greater than 40 µL/hr) in order to introduce important gases into the channels of the microfluidic device. Another embodiment of the present invention is a method for using a rigid microfluidic device with a recirculated fluid (in one embodiment, flowing at a high flow rate), in order to both reduce the volume of fluid being used and also maintain the important chemical and biological material within the fluid within the fluid for use within the microfluidic device, such as cell signals. Another embodiment of the present invention is a method for using a rigid microfluidic device with a reciprocated fluid (in one embodiment, flowing at a high flow rate), in order simplify the experimental setup, reduce the volume of fluid being used, and also maintain the important chemical and biological material within the fluid for use within the microfluidic device, such as cell signals.

Another embodiment of the present invention is a rigid microfluidic device comprising a gas exchanger in order to introduce gases into the channels of the microfluidic device. Another embodiment of the present invention is a gas exchanger, the gas exchanger made up of a rigid polymer comprising pores, the pores filled with an elastomeric polymer. Another embodiment of the present invention is an elastomeric microfluidic device comprising a gas exchanger and rigid polymer masks. Another embodiment of the present invention is a microfluidic device, also known as a "halo chip," comprising gas channels along the perimeter of the working channels of the microfluidic device in order to encourage gas flow between the gas and working channels. Another embodiment of the present invention is a rigid microfluidic device comprising elastomeric channel walls and an elastomeric membrane between a first channel and a second channel. Another embodiment of the present invention is a rigid microfluidic device comprising an elastomeric membrane between a first channel and a second channel, such that the elastomeric channel stretches when differential pressure is applied across the elastomeric membrane. Another embodiment of the present invention is a low-absorbing perfusion manifold assembly representing fluidic infrastructure around the microfluidic device. Another embodiment of the present invention is a compound distribution kit used to determine compound absorption into materials that make up experimental and clinical systems. The microfluidic devices and the low-absorbing perfusion manifold assembly presented herein aim to minimize small molecule absorption, while the microfluidic devices also aim to allow ambient gases to access experimental regions of the devices, such as microfluidic channels containing living cells. The microfluidic devices, the methods to use them, and the low-absorbing perfusion manifold assembly were all designed following the surprising discovery that many elastomeric materials absorb small-molecules, such as those found in many compounds (drugs, chemicals, cosmetics etc.) U.S. Pat. No. 8,647,861 describes a microfluidic device, or organomimetic device, or device capable of mimicking the functionality of an organ, comprising: a body having a central microchannel therein; and an at least partially porous membrane configured to form a first microchannel and a second microchannel, wherein a first fluid may be applied through the first microchannel and a second fluid may be applied through the second microchannel, the membrane may optionally be coated with at least one attachment molecule that supports adhesion of a plurality of living cells wherein the porous membrane is at least partially flexible. In one embodiment, the device further comprising: a first operating channel separated the first and second central microchannels by a first microchannel wall, wherein the membrane is fixed to the first chamber microchannel wall; and wherein applying a pressure to the first operating channel causes the membrane to flex in a first desired direction to expand or contract along the plane within the first and second central microchannels. The microfluidic device of U.S. Pat. No. 8,647,861 may be fabricated out of elastomeric polymers, such as PDMS.

One embodiment of the present invention is to apply rigid polymer thin films or masks. Thin, rigid polymer films or masks serve to limit gaseous transport into the body of the microfluidic device from the ambient environment. One use of the microfluidic devices in U.S. Pat. No. 8,647,861 are to study seeded cells, such as certain varieties of gut cells that are native to low-oxygen environments. Many elastomeric polymers are highly permeable to gas transport, so much so that some varieties of cells express higher levels of viability with limited gas transport into the microfluidic device housing them. As such, thin films or masks fabricated from rigid polymers may be put into contact with the outside surfaces of the microfluidic devices fabricated from elastomeric polymers in order to limit the transport of gases into the bodies of the microfluidic devices. Rigid polymers include, but are not limited to polyethylene terephthalate (PET), cyclic olefin copolymer (COP), polytetrafluorethylene, polypropylene, polyethylene terephthalate and polyvinyl chloride, acrylic, polystyrene, polycarbonate, glass, epoxy fiberglass, ceramic and metal. A method is contemplated providing an elastomeric microfluidic device comprising outside surfaces and one or more thin films of rigid polymer, and putting said one or more thin films of rigid polymer in contact with said outside surfaces. A method is contemplated providing an elastomeric microfluidic device comprising thin film of rigid polymer and a first channel and a second channel separated by a membrane, and placing said thin film of rigid polymer in contact with an outer surface of said elastomeric microfluidic device. A fluidic device is contemplated comprising an elastomeric body comprising one or more channels separated by a membrane, outer surfaces, and thin films of rigid polymer in contact with at least one of said outer surfaces. A system is contemplated comprising a microfluidic device comprising a first channel and a second channel separated by a membrane, and one or more outer surfaces, said outer surfaces in contact with one or more thin films of rigid polymer. Said thin films may be considered masks. For purposes herein, a mask may be considered a layer of polymer for either restricting or allowing gas or molecule transport.

In one embodiment, the present invention contemplates a fluidic device, said fluidic device comprising (i) a plurality of outer sides, (ii) a first channel disposed within said body, (iii) a second channel disposed within said body, (iv) a membrane disposed between said first channel and second channel, and (iv) one or more gas-impermeable masks contacting one or more of said plurality of outer sides.

In one embodiment, a method of controlling gas transport is contemplated, comprising: a) providing a substantially gas-permeable microfluidic device comprising i) a plurality of outer sides and ii) living cells in an inner channel or chamber, said microfluidic device comprising an elastomeric polymer having a modulus of elasticity below 0.1 GPa; and one or more gas-impermeable masks having a modulus of elasticity between 0.1 and 150 GPa; b) contacting at least one of said plurality of outer sides with a gas-impermeable mask; and c) introducing non-oxygenated culture media into said channel or chamber at a flow rate.

In one embodiment, a fluidic device is contemplated, said fluidic device comprising (i) a plurality of outer sides, (ii) a first channel disposed within said body, (iii) a second channel disposed within said body, (iv) a membrane disposed between said first channel and second channel, (iv) a gas exchanger contacting at least one of said first channel and second channel, and (v) one or more gas-impermeable masks contacting one or more of said plurality of outer sides.

In one embodiment, the present invention contemplates a method of controlling gas transport, comprising: a) providing a substantially gas-permeable microfluidic device comprising i) a plurality of outer sides, ii) a gas exchanger and iii) living cells in an inner channel or chamber, said device comprising an elastomeric polymer having a modulus of elasticity below 0.1 GPa; b) adding a substantially gas-impermeable mask to at least one of said plurality of outer sides without masking the gas exchanger; and c) introducing non-oxygenated culture media into said channel or chamber at a flow rate, wherein the rate of gas transport to said living cells is controlled by said gas exchanger. In one embodiment, said substantially gas-impermeable mask comprises a polyethylene terephthalate (PET) film.

One embodiment of the invention presented herein is an improvement on the microfluidic device presented in U.S. Pat. No. 8,647,861, following the discovery that the materials most commonly used to fabricate the microfluidic devices in U.S. Pat. No. 8,647,861 (e.g. PDMS) have the potential to be highly absorptive to xenobiotics and small molecules.

In one embodiment, a microfluidic device is contemplated comprising a plurality of outer sides comprising substantially gas-permeable polymer having a modulus of elasticity below 0.1 GPa, and a substantially gas-impermeable mask attached to at least one of said plurality of outer sides. In one embodiment, said substantially gas-impermeable mask comprises a polyethylene terephthalate (PET) film.

One embodiment of the present invention is to apply coatings. The microfluidic device, the perfusion manifold assembly, and/or their components may be coated. Coatings may be applied in a variety of methods, such as through films, brushed on, spray coating, spin coating, vapor deposition, rolled on, plating, dip coating, etc. The coating may be all-over, completely covering the substrate, or the coating may only cover parts or portions of the substrate.

Coatings may be applied to change the surface properties of the substrate, such as absorption resistance, gas resistance, wettability, adhesion, corrosion resistance, wettability, electrical conductivity, etc. The coatings may be applied as a specified thickness. Coatings may be applied as liquids, gases or solids.

To overcome the problem of absorption into the body of microfluidic devices such as those disclosed in U.S. Pat. No. 8,647,861, microfluidic devices were redesigned to be built from rigid materials, such as, but not limited to, glass, cyclic olefin copolymer (COP), etc. These rigid microfluidic devices are detailed in PCT/US2014/071570. In one embodiment, the invention presented herein comprises a low-absorbing, gas-impermeable microfluidic device. In simple terms, a microfluidic device that would limit small-molecule absorption, as well as gas flow, into the bulk of the microfluidic device. In one embodiment, this low-absorbing, gas-impermeable microfluidic device is fabricated from a rigid polymer. In one embodiment, the invention presented herein comprises a rigid microfluidic device comprising a first channel and a second channel separated by a membrane. In one embodiment, the low-absorbing, gas-impermeable microfluidic device comprises a solid substrate comprising one or more microfluidic channels. While designed en route to a low-absorbing, gas-permeable microfluidic device, the low-absorbing, gas-impermeable microfluidic device is a unique invention with a variety of useful applications. In one embodiment, the rigid or low-absorbing, gas-impermeable microfluidic device comprises a plurality of microfluidic channels. In an exemplary embodiment, the rigid or low-absorbing, gas-impermeable microfluidic device comprises: a) a substrate comprising a one or more microfluidic channels, and b) a porous membrane separating said one or more microfluidic channel into one or more first chambers and second chambers. It is not intended that the microfluidic device be limited by substrate, membrane, chamber or channel configuration. In one embodiment, said first and second chambers are oriented vertically. In one embodiment, said first and second chambers are oriented horizontally. Said first and second chambers may also be referred to as channels. Said first and second chambers, if oriented horizontally, may be referred to as top and bottom chambers or channels. A first fluid may be applied through said first chamber. A second fluid may be applied through said second chamber.

Low-absorbing, gas-impermeable microfluidic devices may be fabricated using rigid or low-absorbing, gas-impermeable materials such as, but not limited to, glass, cyclic olefin copolymer (COP), etc. Low-absorbing, gas-impermeable microfluidic devices may be considered advantageous to high-absorbing, gas-permeable microfluidic devices, such as those fabricated from elastomeric materials including PDMS, as they are generally resistant to absorption of small molecules, unlike high-absorbing, gas-permeable microfluidic devices. Said another way, rigid microfluidic devices may be considered advantageous to elastomeric microfluidic devices, as rigid microfluidic devices may be considered impermeable to absorption of small molecules or xenobiotics. In some embodiments, the rigid materials can reduce absorption of molecules by at least about 10% or more, including, e.g., at least about 20%, at least about 30%, at least about 40%, at least about 50%, at least about 60%, at least about 70%, at least about 80%, at least about 90% or more, as compared to the extent of molecule absorption into PDMS.

In one embodiment, a microfluidic device is contemplated comprising a plurality of outer sides comprising substantially gas-impermeable polymer having a modulus of elasticity between 0.1 and 150 GPa, and a substantially gas-permeable inner channel wall. In one embodiment, said substantially gas-permeable inner channel wall comprises polydimethylsiloxane (PDMS).

Despite these advantages and the ability to modify experimental protocols to enable these low-absorbing, gas-impermeable microfluidic devices, they do suffer from a lack of ambient gas flow. Some commonly used microfluidic devices are fabricated out of elastomeric or gas-permeable materials, such as PDMS and other gas-permeable or porous or elastomeric materials. Scientists oftentimes rely on the gas-permeable characteristic of these materials, such as PDMS, in order to introduce ambient gases through the bulk material of the microfluidic device. In some cases, entirely gas-impermeable microfluidic devices may cause harm to specimens, such as cells, as they are unable to access ambient gases, such as oxygen. Certain specimen, such as some varieties of cell cultures, require specific levels of particular gases in order to be physiologically relevant or even in order to survive. However, experimental protocols may be adapted such that higher levels of desired gas may be introduced into the low-absorbing, gas-impermeable microfluidic devices, through the use of techniques such as higher flow rates and the use of medias with higher gas concentrations.

There are several methods contemplated to increase gas delivery into microfluidic devices. These methods include increasing the flow rate of media into the microfluidic device to increase the volume of gas-containing media flowing over the cells with time, increasing the dissolved gas content of the media flowing through the microfluidic device, recirculation of media, reciprocation of media from environments with high concentrations of ambient gases to the gas-impermeable/gas-consuming interior of the device and then back again, and delivering gases to the interior of the microfluidic device from the outside ambient environment through the microfluidic device bulk material.

As such, the present invention contemplates several protocols to use these rigid or low-absorbing, gas-impermeable microfluidic devices. A first protocol is to perfuse these rigid or low-absorbing, gas-impermeable microfluidic devices with high flow rates of fluid or media in order to transport gases into the channels of the microfluidic device via the dissolved gasses of the fluid or media. In one embodiment, increased gas transport into the microfluidic device may be achieved by using higher flow rates of media containing the important gases, such as oxygen, into the microfluidic device. In this embodiment, as the flow rate of the media is higher, more media is introduced into the microfluidic device in a set amount of time, and thus more of the desired gas is introduced into the microfluidic device. The use of high flow rates in microfluidic devices to increase gas transport is useful in gas-impermeable microfluidic devices, as gas may not intrinsically diffuse into the microfluidic device otherwise. Increasing flowrate also removes unwanted gasses, such as carbon dioxide produced by the cells as a byproduct of respiration. Interestingly, increased flow rates may also significantly improve compound distribution within a microfluidic device, such that the majority of the small molecules are not absorbed in the first portion of a channel. Those conducting these experiments were surprised by how effective increasing the flow rate, even slightly, was at improving the distribution of the agent, drug, etc. throughout the channel.

Oftentimes these rigid or low-absorbing, gas-impermeable microfluidic devices need to be perfused with media nearly continuously in order to deliver the oxygen required for particular experiments, such as those comprising cells undergoing cellular respiration; the oxygen is delivered via the oxygen dissolved in the media entering the microfluidic device as opposed to what may be considered the more efficient route of a gas-permeable microfluidic device, which is directly through the bulk material. The efficiency is forsaken in order to limit molecule absorption into the body of the microfluidic device. For example, if microfluidic devices comprising cells remain static, that is without perfusion with oxygen carrying media, for an extended period of time, cells contained within loose viability and function, in severe cases apoptosing or necrosing. In a surprising finding, it was discovered that in the case of liver hepatocyte cells cultured within microfluidic devices, the hepatocytes experience the negative consequence of oxygen deprivation within minutes of stopping fluid flow. Hepatocytes are a highly metabolically active cell type. Similarly, it was found that to deliver enough oxygen to ensure cell viability and function in low-absorbing, gas-impermeable microfluidic devices, that it was necessary to perfuse the devices at flow rates that were higher than typically used for the culture of hepatocytes. To mitigate this challenge, higher flow rates than are typically used for the culture of hepatocytes in these microfluidic devices have been utilized and the time that the low-absorbing, gas-impermeable microfluidic devices remained static, that is without media perfusion, was minimized. It was discovered through experimentation that many of the cell seeding steps that typically are performed under no fluid flow or static conditions could be shortened and that higher flow rates than were typically used could be utilized in the devices. For example, it was found that these rigid or low-absorbing, gas-impermeable microfluidic devices do not need to remain static for extended periods of time for adequate cell attachment to the microfluidic device. For example, for certain experiments microfluidic devices may need to be inverted without flow in order to allow cells within the microfluidic device to attach to a membrane. In this case, the cells would need to be without flow, and therefore without oxygen they require. However, even for this case it was found that the microfluidic devices do not necessarily need to be inverted without flow for extended periods of time. Surprisingly, even connecting these low-absorbing, gas-impermeable microfluidic devices to flow, even high flow, immediately following seeding had minimal negative consequences on the cells cultured within the device. Occasional high-flow cycles, which may be used to dispose of bubbles, may also be used on the low-absorbing, gas-impermeable microfluidic devices with no apparent negative consequences to cell layers within. Additionally, it was found that several time-intensive and sequential steps could be combined to save time and minimize the time that microfluidic devices remained static, including seeding endothelial cells and applying extracellular matrix in the same step, condensing the overall seeding protocol, making the use of these microfluidic devices more user-friendly and advantageous over other microfluidic device designs as well.

In one embodiment, a method of controlling gas transport is contemplated, comprising: a) providing a substantially gas-impermeable microfluidic device comprising a rigid polymer and living cells in a channel or chamber, said living cells having a gas consumption rate; and b) introducing culture media into said channel or chamber at a flow rate, said culture media carrying gas, wherein the rate of gas transport to said living cells is controlled by the flow rate, and said rate of gas transport meets or exceeds said gas consumption rate. In one embodiment, said rigid polymer has a modulus of elasticity between 0.1 and 150 GPa. In one embodiment, said rigid polymer is polycarbonate. In one embodiment, said flow rate is greater than 40 uL/hr. In one embodiment, a method further comprises increasing the flow rate in order to increase the rate of gas transport. In one embodiment, a method further comprises introducing a drug or drug candidate into said channel or chamber, wherein said rigid polymer reduces the absorption of said drug or drug candidate by at least about 70% or more, as compared to the extent of absorption into PDMS. In one embodiment, a method further comprises evaluating the viability of said cells via cellular assays and/or visual inspection.

However, increasing the flow rate of media into the microfluidic device may not be physiologically relevant, as fluids in vivo flow at specific flow rates. It is usually desired to expose specimen, such as cells, to similar conditions in vitro as is found in vivo. Fluid flow rate is directly related to shear; increasing the flow rate of media into the microfluidic device may expose specimen, such as cells, to undue levels of shear. Undue levels of shear may have negative impacts, particularly when the high shear is in channels containing cells that typically are exposed to low or no shear/fluid flow. The flow rate of media through the device impacts the ability of cells to communicate with one other via cellular factors secreted into the microfluidic channel. In particular, at excessively high flow rates, these cytokines and other dissolved factors are diluted into the high volume of media passing through the microfluidic device. High flow rates effectively wash out the factors and can prevent the cells form sensing the signals and, therefore, hinder or prevent the proper in vivo response that is attempting to be recapitulated. Similarly, just as signaling factors can be diluted out by the higher flow rates, so too can the various factors that are excreted by cells into the effluent media that are being quantified. For example, if rate of metabolism is being assessed, the concentration of the metabolized form of the dosed compound might be so dilute that it is effectively undetectable in the media as the concentration falls below the lower limit of detection of the analytical instrument. If metabolism is being detected by depletion of the compound being dosed, a high flow rate will decrease the change in concentration of the parent compound as it passes through the microfluidic device, which also can make detection of this change impossible. In other words, high flow rates can decrease the "signal" that is being sensed to the level of the noise of the analytical instrument, making quantification impossible. The principle is similar for cell-to-cell signaling; the released factors are diluted below the concentration that other cells can detect and respond to. Finally, since cells within the low-absorbing, gas-impermeable microfluidic device are supplied with oxygen via media flow a major limitation of this approach is that the cells within the device do not receive oxygen if the low-absorbing, gas-impermeable microfluidic device is removed from fluid flow. Not being able to remove the low-absorbing, gas-impermeable microfluidic device from flow without negative consequences on the cells within presents a major practical limitation, since microfluidic devices often require periodic periods where flow is stopped such that the cells within the device can be imaged under a microscope and also to refill inlet and outlet media reservoirs of perfusion manifold assemblies with media. Indeed, delivery of oxygen to the cell layer is vital to the basic function of the cells and necessary to maintain viability; if media flow is stopped for an extended period of time, the cells within the rigid, low-absorbing, gas-impermeable microfluidic device tend to die.

Considering the disadvantages of running fluid at high flow rates in microfluidic devices seeded with cells other alternatives were developed. Another embodiment of the application herein is a protocol for using the rigid microfluidic devices of U.S. patent application Ser. No. 15/105,388 with recirculated fluid. In this embodiment, fluid that exits the microfluidic device may be recirculated to the inlet of the microfluidic device. Not only does this setup decrease the amount of fluid or media necessary, but also preserves any important chemical or biochemical markers within the media that would be beneficial if reintroduced into the microfluidic device. For example, cells secrete signals, such as paracrine and autocrine signals. It is advantageous to have cell signals not wasted, but instead continuously in contact with the cells.

In one embodiment, one or more microfluidic devices are contemplated comprising i) cells on a surface and ii) inlet and outlet ports, said inlet and outlet ports in fluidic communication with a recirculation pathway, and 2) flowing culture media into said one or more microfluidic devices in a direction, thereby causing fluid to exit said outlet port of said one or more microfluidic devices and enter said recirculation pathway, moving in the direction of said inlet port of said one or more microfluidic devices. In one embodiment, said fluid moves in the direction of said inlet port to reach said inlet port, thereby recirculating said culture media without reversing the direction of fluid flow. Secreted factors and waste products in recirculating cultures are recirculated back to the cells, whereas in non-recirculating culture, the secreted factors and waste products are permanently removed. Where recirculation is desired, a given volume of culture media (e.g. all of it, a portion of it, etc.) is recirculated, whereas in non-recirculating perfusion, the culture media is perfused through the system and sent to directly to waste. Secreted factors and waste products in recirculating cultures are diluted into the total culture media volume (although this can be avoided by the use of a second reservoir, and the second reservoir can be avoided by using tubing). In one embodiment, media flowed through the low-absorbing, gas-impermeable microfluidic device may be collected and recirculated back through the low-absorbing, gas-impermeable microfluidic device. In one embodiment, the media is recirculated once. In another embodiment, the media is recirculated more than one. Recirculating media solves three problems: specimen within microfluidic devices may be further exposed to experimental compounds dosed in the media, the media may be refilled with nutrients in between recirculation, and both cell signaling factors and factors to be analytically quantified as cellular readouts will not be diluted out by the high-volumes required for the single-pass, high flow rate solution. Increasing the flow rate does not solve the practical problem that once the device is removed form fluid flow, the delivery of oxygen and removal of $CO_2$ ceases.

In one embodiment of a recirculation setup or method, it is contemplated that the media would flow through low-absorbing, gas-permeable tubing where it could come into contact with ambient gases before flowing into the microfluidic device. The media, having been depleted of those ambient gases while inside the microfluidic device by the specimen, would then rapidly equilibrate to the ambient environment.

In one embodiment, when the media is flowed past cells, the oxygen concentration in the media is depleted due to cellular respiration. In one embodiment of maintaining both oxygen levels in the desired flow rate within a microfluidic device, a recirculation experimental setup may be used. In one embodiment, a recirculation setup is used such that the media can be re-oxygenated prior to being recirculated through the microfluidic device and $CO_2$ removed from the media. In another embodiment, a recirculation setup is used such that cells within the low-absorbing, gas-impermeable microfluidic device experience prolonged exposure to a dosing compound while maintaining a desired flow rate. In this setup, the low volume enabled by reciprocation enables the long exposure time. In one embodiment, cells requiring a high shear rate are being dosed with a low clearance compound. Low clearance compounds are metabolized slowly be cells. High flow rates may be used to produce high shear force on cells and to increase the amount of oxygen delivered to the cells. However, if a high flow rate is used, the cells are generally not exposed to low clearance compounds long enough for a significant amount of metabolism to take place and quantification of this metabolism, let alone detection, is impossible. The recirculation setup may be used to maintain high flow rates, while still allowing cells to be exposed the low clearance compound long enough to detect and quantify metabolism.

In another embodiment, the dissolved gas content of the media flowing through the microfluidic device may be increased prior to it entering the microfluidic device. In one embodiment, the dissolved gas content of the media may be increased prior to entering the microfluidic device by bubbling gas through the media. The content of this gas mixture can be determined based on the aim attempting to be achieved; if the aim is to increase dissolved oxygen, then a gas mixture containing a high concentration of oxygen can be utilized (e.g. bubbling 100% oxygen through the media increases the media oxygen content by a factor of 5 compared to atmospheric air which is only 21% oxygen). In another embodiment, the dissolved gas content of the media may be increased prior to entering the microfluidic device by pressurizing the media with the desired gas or a carrier of the desired gas. Atmospheric pressure is ~101 kPa—by pressurizing with 202 kPa, as an example, the gas concentration is increased by a factor of two. In one embodiment the concentration of oxygen within a media may be increased by pressurizing the media with a higher oxygen concentration than atmospheric levels or by using an oxygen carrier within the media, such as hemoglobin, perfluorocarbon-based oxygen carriers, hemocyanin, etc. In one embodiment, the gas pressurizing the media may be a gas blanket. However, simply increasing the dissolved gas content of the media may not be physiologically relevant as fluids in vivo contain specific concentrations of gas. It is usually desired to expose specimen, such as cells, to similar conditions in vitro as is found in vivo. Oxygen carriers generally do not suffer from this limitation, since they increase the oxygen carrying capacity without increasing the dissolved oxygen (the additional oxygen is bound to the carrier and not dissolved in the media). Both flowing media at higher flow rates and increasing the dissolved gas content of media also succumb to the following significant shortfall. As the media flows through the microfluidic device, the specimen at the beginning of the channels will experience higher levels of the desired gas. The specimen at the beginning of the channel may then uptake high levels of said gas, leaving lower levels of the desired gas for specimen further in the channels. The spatial gradient in cellular oxygen exposure levels can result in gradients in cellular response, which are difficult to assess since the effluent from the microfluidic devices is a pooled sample of the media as it passes through the microfluidic device. This solution, too, does not solve the practical problem that once perfusion of media stops, so too does the delivery of oxygen and removal of $CO_2$.

However, recirculation systems can be difficult to setup and use. For example, peristaltic pumps are oftentimes necessary for recirculation setups. Peristaltic pumps disadvantages include size limitations and that they oftentimes require flexible tubing. Flexible tubing is oftentimes made of elastomeric polymers. As stated before, elastomeric polymers are prone to material absorption. As such, one embodiment of the present invention is a protocol for using the rigid microfluidic devices of U.S. patent application Ser. No. 15/105,388 with reciprocated fluid. For uses herein, reciprocation is flowing a fluid in one direction through a microfluidic device, collecting that fluid, and then flowing the same fluid in the other direction through the microfluidic device. Reciprocation of fluid or media through a microfluidic device is not obvious or intuitive fluids are not reciprocated through the body. However, surprisingly cells in microfluidic devices experienced high levels of viability when media was reciprocated in the microfluidic devices. When fluid is reciprocated in microfluidic devices, simple two-way pumps may be used, low volumes of media may be used, ambient gas levels may be introduced to the channels of the microfluidic device, and the media retains signals secreted by the cells.

The present invention contemplates, in one embodiment, a method of controlling gas transport, comprising: a) providing a substantially gas-impermeable microfluidic device comprising i) living cells on a surface and ii) inlet and outlet ports, said inlet and outlet ports in fluidic communication with iii) a recirculation pathway, and b) flowing culture media carrying gas at a flow rate into said inlet port of said microfluidic device in a direction, thereby causing fluid to exit said outlet port of said microfluidic device and enter said recirculation pathway, thereby recirculating said culture media without reversing the direction of fluid flow, wherein the rate of gas transport to said living cells is increased by said recirculating. In one embodiment, said rigid polymer has a modulus of elasticity between 0.1 and 150 GPa. In one embodiment, said flow rate is 40 uL/hr or less.

The present invention contemplates, in one embodiment, a method of controlling gas transport, comprising: a) providing a substantially gas-impermeable microfluidic device comprising i) living cells on a surface and ii) inlet and outlet ports, said inlet and outlet ports in fluidic communication with iii) a reciprocation actuator, and b) flowing culture media carrying gas at a flow rate into said inlet port of said microfluidic device in a direction, thereby causing fluid to move in the direction of said outlet port; and c) reciprocating said fluid with said reciprocation actuator, thereby reversing the direction of fluid flow, wherein the rate of gas transport to said living cells is increased by said reciprocating. In one embodiment, said rigid polymer has a modulus of elasticity between 0.1 and 150 GPa. In one embodiment, said flow rate is 40 uL/hr or less.

Despite the benefits of high flow rates, recirculation and reciprocation, occasionally these rigid microfluidic devices need to be removed from flow in order to take samples, image under microscopes, add new cell types, etc. It has been found that even after a few minutes without flow, some cell types within microfluidic devices begin to suffer from a lack of oxygen. Following this discovery, a microfluidic device fabricated from a strategic combination of rigid and elastomeric polymers was developed in order to ensure that both the microfluidic device is able to stretch, but almost more importantly that the channels within the microfluidic device are able to access ambient gases. Reciprocation is taught in International Patent Application No. PCT/US2019/25449, the contents of which are incorporated herein by reference If flow rate flexibility, and controlled, consistent, physiologically-relevant dissolved concentrations of gasses in media, and physically relevant environments are desired, and/or user-friendly workflows that allow for the microdevice to be removed from fluid flow for short periods, then microfluidic devices that are both low-absorbing and gas-permeable would be advantageous. As such, microfluidic devices fabricated that are both low-absorbing, but have controllable gas-permeability would be advantageous compared to completely gas-impermeable microfluidic devices as they as they decrease absorbency of important compounds being tested as well as allow the cells to access ambient gases during the experiment. In one embodiment a microfluidic device fabricated out of a strategic combination of gas-permeable and gas-impermeable materials is contemplated. A low-absorbing, gas-permeable microfluidic device was then desired based on the results gathered using the low-absorbing, gas-impermeable microfluidic device. In some embodiments, the material makeup of this microfluidic device can reduce absorption of molecules by at least about 10% or more, including, e.g., at least about 20%, at least about 30%, at least about 40%, at least about 50%, at least about 60%, at least about 70%, at least about 80%, at least about 90% or more, as compared to the extent of molecule absorption into PDMS.

A resulting low-absorbing, gas-permeable microfluidic device is contemplated in one embodiment, comprising a body having at least one channel therein, said channel having channel walls and a membrane, wherein at least one of said channel walls and membrane are elastomeric. The microfluidic device may be predominantly rigid, while having a channel comprising elastomeric walls and an elastomeric membrane. The membrane may be elastomeric to facilitate gas transport on either side of said membrane. The walls of the channel may be elastomeric to facilitate stretching of the membrane if desired. However, in some embodiments differential pressure may be used to stretch said membrane, and in that case the body and channel walls may be rigid, while simply the membrane is elastomeric. In the embodiment where solely the membrane is elastomeric, the amount of absorbing material may be minimized as the membrane may represent a small volume of the membrane in one embodiment. In one embodiment, the microfluidic device comprises a body having at least one channel therein, said channel having elastomeric walls and an elastomeric membrane, wherein at least a portion of said body is rigid. Furthermore, the embodiment comprising elastomeric channel walls and a membrane may necessitate further fabrication steps than an embodiment wherein the body is entirely rigid. In one embodiment, the microfluidic device comprises a body having at least one channel therein, said channel having rigid walls and an elastomeric membrane, wherein at least a portion of said body is rigid.

The present invention contemplates, in one embodiment, another resulting low-absorbing, gas-permeable microfluidic device such as a microfluidic device comprising a body, said body having a channel therein, and a gas exchanger. A low-absorbing microfluidic device may comprise a rigid body and a gas exchanger, such that the body does not absorb molecules, while gas transport can still take place within the microfluidic device. While the gas exchanger may be in any portion of the microfluidic device, in an exemplary embodiment the gas exchanger is in contact with a channel, such that gas may be exchanged from the ambient environment with a cell culture in the channel.

In one embodiment, the low-absorbing, gas-permeable microfluidic device comprises a low-absorbing body having a channel, said channel having a channel wall, wherein said channel wall comprises a gas exchanger in contact with the ambient environment. In one embodiment, the low-absorbing, gas-permeable microfluidic device comprises a low-absorbing, rigid body having a channel, said channel having a channel wall, wherein said channel wall comprises a gas exchanger having a gas-permeable material in contact with the ambient environment.

In one embodiment, the low-absorbing, gas-permeable microfluidic device comprises a solid substrate comprising one or more microfluidic channels. In one embodiment, the microfluidic device comprises a plurality of microfluidic channels. In an exemplary embodiment, the low-absorbing, gas-permeable microfluidic device comprises: a) a solid substrate comprising a single microfluidic channel, b) a porous membrane separating said single microfluidic channel into a first chamber and a second chamber, and c) a gas exchanger to allow gas transport from the ambient environment outside the microfluidic device into the microfluidic device. It is not intended that the microfluidic device be limited by substrate, membrane, chamber or channel configuration. In one embodiment, said first and second chambers are oriented vertically. In one embodiment, said first and second chambers are oriented horizontally. Said first and second chambers may also be referred to as channels. Said first and second chambers, if oriented horizontally, may be referred to as top and bottom chambers or channels.

In one embodiment, the microfluidic device is fabricated from a first and second channel layers. Said first channel layer may comprise a first surface and a second surface. Said second channel layer may comprise a third surface and a fourth surface. Microfluidic chambers or channels may be disposed upon said surfaces. For example, chambers may be etched, molded, or cut onto substrate surfaces. In one embodiment, said first surface comprises said first chamber. In one embodiment, said third surface comprises said second chamber. Said first channel layer may be referred to as a first layer or first substrate. Said second substrate may be referred to as a second layer or second channel layer. If the first and second chambers or channels are oriented vertically, said first channel layer may be referred to as a top layer or top substrate. If the first and second chambers or channels are oriented vertically, said second channel layer may be referred to as a bottom layer or bottom substrate.

In an exemplary embodiment, the membrane may be sandwiched between the first and second channel layers. The first and second channel layers, the membrane and the gas exchanger may be attached permanently or temporarily. A first fluid may be applied through said first chamber. A second fluid may be applied through said second chamber. In one embodiment the layers are attached through plasma-activated bonding. Unlike the microfluidic device presented in U.S. Pat. No. 8,647,861, the microfluidic device presented here may only optionally contain working channels for mechanical actuation.

In one embodiment, the microfluidic device is used for the characterization of organ microbiomes. In one embodiment, the low-absorbing, gas-permeable microfluidic device may be used to test the effects drugs, foods, chemicals, cosmetics, physiological stimulants stresses etc. have on cellular systems. Different cell types sometimes require different amounts of oxygen in order to thrive. If cellular health is a goal, oxygen entering the device should be greater than oxygen uptake rate within the microfluidic device in order to ensure that cells have access to as much oxygen as they require. For example, liver hepatocytes oftentimes require atmospheric levels of oxygen, whereas some bacteria cultures in the gut require very little oxygen. As such, microfluidic devices, especially those with applications in cellular biology, would benefit by being low-absorbing, while still allowing necessary levels of oxygen to reach cells, experiments, etc. inside the microfluidic device. Oftentimes however, low-absorbing materials tend to be gas-impermeable. In this way, a microfluidic device minimizing the amount of material absorbency may be designed with a combination of gas-permeable and gas-impermeable components.

Another important aspect of microfluidic device material choice to be considered is transparency. Optical transparency is advantageous in microfluidic devices for multiple reasons. Transparency is advantageous for imaging. In one embodiment, the low-absorbing, gas-permeable microfluidic device described here may be used in conjunction with a microscope, such as an inverted microscope, an upright microscope, a confocal microscope, a light microscope, an electron-scanning microscope, etc. Transparency is also advantageous with the use of optogenetically active cells. In one embodiment, the cell layer in the low-absorbing, gas-permeable microfluidic device comprises a layer of optogenetically active cells. In one embodiment, the materials making up the microfluidic devices are also biocompatible. As an exemplary use of the microfluidic devices presented herein is for the use of culturing cells, biocompatibility may be important.

Imaging microfluidic devices on microscopes enables scientists to get an intimate perspective on cellular interactions, phenotypes, and more. Opaqueness offers scientists the ability to protect their experiments from ambient light if necessary. In one embodiment, the low-absorbing, gas-permeable microfluidic device is fabricated from opaque materials. As such, the microfluidic device presented herein may be partially or entirely transparent or entirely opaque depending on the needs of the experiment and the particular embodiment.

First and second channels layers comprise substrates containing one or more channels or pathways for fluid movement and experiment housing. Each channel layer may comprise one or more microfluidic channels. In another embodiment, each channel layer may comprise a plurality of channels. In one embodiment, where the microfluidic device is assembled in a vertical orientation, the first channel layer may be considered the top channel layer and comprises a first or top channel and the second channel layer may be considered the bottom channel layer and comprises a second or bottom channel. In particular embodiments, the first channel may be referred to as the top channel due to its location above a membrane and the second channel may be referred to as the bottom channel due to its location below a membrane. In such an embodiment, a membrane separates the first and second channels.

Experiments contained within the channels include cell growth and testing. In one embodiment, cells are grown in the channels of the low-absorbing, gas-permeable microfluidic device as to form a cell layer. In one embodiment, epithelial cells are grown in the first channel in the top channel layer and endothelial cells are grown in the second channel in the bottom channel layer. In one embodiment, epithelial and endothelial cells cultured within said first and second channels are separated by a membrane.

Channels in the channel layers may be a variety of different heights, including but not limited to equaling the height of the channel layer itself or cutting through the entire channel layer. In one embodiment, the height of the first channel is less than the height of the channel layer comprising the channel. In one embodiment, the height of the second channel is less than the height of the channel layer comprising the channel. The heights of a first channel and a second channel can vary to suit the needs of desired applications. In one embodiment, the channel heights are chosen to suit a particular cell size. In one embodiment, the channel heights are chosen to suit a particular shear force level. In one embodiment, channel heights are between 10 µm and 5000 µm. In one embodiment, the channel heights are between 100 µm and 1000 µm. In one embodiment, a "regular" channel height may be 100 µm, while a "tall" channel height may be 1000 µm. In one embodiment, the height of a first channel is equal to the height of the channel layer comprising the channel. In one embodiment, the height of the second channel is equal to the height of the channel layer comprising the channel. In one embodiment, the height of a first channel and the height of a second channel are the same. In one embodiment, the height of a first channel and the height of a second channel are different. In one embodiment, the height of a first channel is greater than the height of a second channel. In one embodiment, the height of the first channel is 1000 µm and the height of the second channel is 100 µm. In one embodiment, the height of a first channel is greater than the height of a second channel because epithelial cells are seeded in the first channel, while endothelial cells are seeded in the second channel. Some varieties of epithelial cells are larger, and therefore may require more room than endothelial cells. Particular ratios of the first channel and second channel heights are advantageous for particular cell lines and levels of shear force. In one embodiment, the height of a first channel is consistent across the entire first channel. In one embodiment, the height of a second channel is consistent across the entire second channel. In one embodiment, the height of a first channel is inconsistent along the length of the first channel. In one embodiment, the height of a second channel is inconsistent along the length of the second channel. In one embodiment, the height of a first channel is larger in the cell culture area, as compared to non-cell culture areas within the first channel. In one embodiment, the height of a second channel is larger in the cell culture area, as compared to non-cell culture areas of the second channel. For example, the height ratio of the first channel to the second channel is greater than 1:1, including, for example, greater than 1.1:1, 1.5:1, 2:1, 2.5:1, 3:1, 3.5:1, 4:1, 4.5:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1. In some embodiments, the height ratio of a first channel to a second channel can range from 1.1:1 to about 50:1, or from about 2.5:1 to about 50:1, or from 2.5 to about 25:1, or from about 5:1 to about 25:1. In one embodiment, the height ratio of a first channel to a second channel ranges from about 10:1 to about 20:1.

Different embodiments comprise microfluidic devices with different channel alignments. Channels may be aligned differently to achieve various levels of cellular interaction. For example, if cells are cultured in channels one two opposing sides of a membrane, the channels on either side of the membrane may be aligned such that they only overlap 50%, such that only 50% of the cells may interact with each other. In one embodiment, a first channel on a first side of a membrane and a second channel on a second side of a membrane are aligned. In one embodiment, the first and second channels, on opposing sides of a membrane, are not aligned. In one embodiment, the first and second channels are partially aligned. In one embodiment, there is a port or via at both ends of a first or second channel so that fluids may be introduced into the microfluidic device. In one embodiment, microfluidic device infrastructure may be made to be in fluidic communication with the microfluidic device through these ports. First and second channel layers may be fabricated from the same or different materials. In one embodiment, the first, or top, channel layer and second, or bottom, channel layers are fabricated from the same material. In one embodiment, the first channel layer and second channel layer are fabricated from different materials. In one embodiment, the first channel layer is made up of a single material. In one embodiment, the second channel layer is made up of a single material. In one embodiment, the first channel layer is made up of multiple materials. In one embodiment, the second channel layer is made up of multiple materials. In one embodiment the first channel layer is fabricated from one or more gas-permeable materials. In one embodiment, the first channel layer is fabricated from one or more gas-impermeable materials. In one embodiment, the second channel layer is fabricated from one or more gas-permeable materials. In one embodiment, the second channel layer is fabricated from one or more gas-impermeable materials. Gas-impermeable materials that have also been shown to be low absorbing include cyclic olefin copolymer (CCP), cyclic olefin polymer (COP), polycarbonate, polyethylene (PE), polyethylene Terephthalate, polystyrene (PS), (PET) glass, etc. In one embodiment, the first and second channel layers are fabricated fully or partially from gas-permeable materials and are modified in such as a way as to limit absorbency. In one embodiment, the first and second channel layers may achieve low-absorbency by being fabricated partially from gas-impermeable materials. In one embodiment, the first and second channel layers may achieve low-absorbency by being coated with a substance. In one embodiment, the first and second channel layers may achieve low-absorbency by having their surfaces modified to reach impermeability.

The membrane provides a diffusive barrier between first and second channels on opposing sides of the membrane. While the membrane may be gas-impermeable, oftentimes it is beneficial to allow oxygen diffusion through the membrane. As such, in one embodiment, the membrane is gas-permeable. In one embodiment, the membrane is fabricated from PDMS. However, one embodiment, the membrane is gas-impermeable. For example, cell types in the top and bottom channel may benefit from exchanging gases. Gas-permeability may be prioritized over low-absorbency in the membrane layer for this diffusivity reason. In some embodiments, the membrane may be a smaller volume as compared to the volumes of other components of the microfluidic device, such as the top and bottom channel layers and the gas exchanger. If the membrane has a smaller volume than other components it would not absorb as much of the experimental compound, minimizing absorbency impacts. In other embodiments, the membrane is non-porous in order to limit physical contact between top and bottom channel environments and inhabitants. In some embodiments, the membrane is porous in order to allow contact between top and bottom channel environments and inhabitants. In one embodiment, the membrane layer is homogenous, such as being evenly/porous across the entire layer. In another embodiment, the membrane layer is heterogenous, such as being porous only in the regions that overlap top and bottom channels. In some embodiments, the membrane is flexible as to allow it to stretch. In this embodiment, the ability to stretch, or achieve actuation, is beneficial for experiments involving cells attached to the membrane, as it is able to replicate mechanical strain on in-vivo cells. In some embodiments, stretch, or actuation, is achieved by using vacuum in optional working channels in the microfluidic device. In some embodiments stretch, or actuation, is achieved by having a pressure differential in the top and bottom channels, as to push the membrane in the direction of the lower pressure channel. Stretch or actuation achieved by a pressure differential may be advantageous as it may be more physiology relevant than actuation of the membrane by vacuum channels which applies no pressure to the cell layer. Indeed, this stretching mechanism better recapitulates the physiologic mechanisms for mechanical stretching of cells and tissues, which include pressure differentials. For example, arteries tend to expand as the heart beats and expels blood from within the ventricles and into the artery lumen. This expansion (and resulting strain on the cells composing the vasculature walls) occurs because of the pressure generated by the beating heart, much like a balloon expands when pressurized with air. The pressures needed to flex the membrane and create these in vivo relevant strains is, in one embodiment, a similar pressure as would be seen in the capillary beds of the lungs. Stated more simply, in one embodiment both the pressures that the cell layers are exposed to and the stretch are tuned to be simultaneously physiologically relevant. Additionally, the shape of this stretch better emulates the shape of the expansion seen in blood vessels and the alveolar sacs, since in this embodiment the membrane is physically displaced into a channel and assumes the shape of an arc as opposed to a linear displacement (i.e. the membrane moves up and down as it stretches).

As previously stated, in order to overcome low levels of important gases in microfluidic devices, as well as avoid the use of high, continuously applied, flow rates and high dissolved gas concentrations in the media, a gas exchanger may be built into the microfluidic device in such a way as to not promote molecule, substance and/or experimental compound absorbency while still allowing important gases, such as oxygen, to diffuse through the microfluidic device. In one embodiment, the low-absorbing, gas-permeable microfluidic device comprises a gas-exchanger. In one embodiment, the purpose of the gas-exchanger is to introduce ambient gases into the microfluidic device. In one embodiment, the purpose of the gas-exchanger is to introduce selected gases into the microfluidic device.

In one embodiment, a gas exchanger may be incorporated into the microfluidic device as a structural element of the microfluidic device in contact with the ambient environment or a desired gas source. In one embodiment, the gas exchanger may be channel capping layer, such that the gas exchanger encloses one or more channels within the microfluidic device. As such, in one embodiment, the gas exchanger caps one or more channels. In one embodiment, the gas exchanger is attached to the bottom of the microfluidic device, such as to form a floor to the bottom channel layer. In this embodiment, the ceiling of the bottom channel would be the membrane and the base of the bottom channel would be the gas exchanger.

In one embodiment, the gas exchanger may comprise a single material or a combination of materials. Materials used to fabricate the gas exchanger may be selected from polydimethylsiloxane (PDMS), room temperature vulcanizing (RTV) silicone, TeflonAF2400, polymethylpentene (PMP), polyethylene terephthalate (PET), polycarbonate (PC), cyclic olefin polymer (COP), etc.

In one embodiment, room temperature vulcanizing (RTV) silicone may be used for the gas exchanger. In one embodiment, RTV silicone may be sprayed onto the body of the microfluidic device to fabricate a gas exchanger.

In another embodiment, TeflonAF2400 may be used as a gas exchanger material. TeflonAF2400 is an exceptional material, as it is transparent, gas-permeable and low-absorbing to non-absorbing. In one embodiment, the gas exchanger may be fabricated out of a gas-permeable and/or gas-impermeable material and then coated with TeflonAF2400.

In another embodiment, polymethylpentene (PMP), commonly called TPX, a trademarked name of Mitsui Chemicals, may be used as a gas exchanger material. PMP or TPX is another exceptional material, as it is transparent, gas-permeable and low-absorbing. Polymethylpentene (PMP) has several other advantageous properties, such as favorable optical properties, a low cost, injection moldable, and resistant to many solvents. Resistance to solvents may be important if the microfluidic device is to be used during assays, as assays often use harsh solvents. A resistance to solvents may allow the microfluidic device to be used in a greater range of assays. Both TeflonAF2400 and PMP have the added advantage of being rigid materials and are stable/robust to the manual handling typically associated with microdevices. PMP may be fabricated in both liquid and solid form.

In some embodiments the inventors found that TPX or PMP can prove difficult to bond. As such, in other embodiments, the gas exchanger comprises PDMS. PDMS is advantageous as it is simple to use in fabrication and bonds well. In one embodiment the gas exchanger may be a layer of PDMS. The PDMS may be applied using a variety of methods. In one embodiment, a sheet or layer of PDMS may be applied to the body of a microfluidic device. In one embodiment, the sheet or layer of PDMS may be spin-coated. In one embodiment, the sheet of PDMS may be 2 µm±0.4 µm. In one embodiment, the PDMS may be coated onto said microfluidic device. In one embodiment, the PDMS may be spray coated on. With regard to this method, the inventors dissolved PDMS in a solvent and spray coated the body of the microfluidic device. In one embodiment the gas exchanger is a thin layer of PDMS, such as to minimize molecule absorbance. However, the inventors found a thin layer of PDMS to be fragile in some instances. In one embodiment, the gas exchanger is a thick layer of PDMS, such as to be more durable. However, the inventors found a thicker layer of PDMS to be more absorbent.

In one embodiment, the gas exchanger may be a combination of different materials in order to overcome the above disadvantages. In an exemplary embodiment of a gas exchanger, the gas exchanger may comprise a combination of a low-absorbing material with a gas-permeable material. The low-absorbing material may be porous, such that gas may flow from the ambient environment, through the gas-permeable material, and then through the pores of the low-absorbing material.

In one embodiment, the gas exchanger is a two-layer combination of PDMS and polyethylene terephthalate (PET) or polycarbonate (PC). PDMS is gas-permeable and absorbent. PET is gas-impermeable and non-absorbent. In one embodiment, the PET may be porous.

In one embodiment, a gas exchanger may be fabricated and bonded to the body of a microfluidic device in the exemplary protocol as follows. A sheet of PDMS may be spun coat to a thickness of 2 µm±0.4 µm. The appropriate size may be cut out of the PDMS sheet. The sheet of PDMS may then be bonded to a corresponding size of porous film, such as PET or PC. The bonding may be done via silane bonding. The compound (bis(3-triethoxysilypropyl)amine) may be mixed with 100% isopropyl alcohol (IPA), which is then coated on the porous membrane before being let to dry. Once the mixture is dry, the PDMS may be plasma treated. The two layers may then be adhered by contact.

In one embodiment one layer or material of the gas exchanger may be porous, as discussed above. In one embodiment, the porosity is created through track etching. In one embodiment, the porosity of a component of the gas exchanger (such as PET or PC) is between 1% and 50%. In one embodiment, the porosity is between 1% and 40%. In one embodiment, the porosity is between 1% and 5%. In one embodiment, the porosity is 1%. In one embodiment, the porosity is 3%. In one embodiment, the porosity is 11.4%. In one embodiment, the porosity is 40%. Porosities of 1%, 3%, 11.4%, and 40% have all been explored with the microfluidic devices herein. Porosities including but not limited to 0.3%, 1.6%, 3%, 5%, 5.7%, 7.9%, 11%, 12.5%, 14.1%, 18.8%, 21.2% are commercially available as well. Furthermore, porosities of any percentage may be fabricated and used. The porosity of the membrane may be tuned for the experiment. The porosity of the membrane may be used to control the rate of oxygen transport within the microfluidic device. For example, based on the oxygen uptake rate of the cells within a microfluidic device, a membrane with a specific porosity may be used.

In the embodiment discussed above, track-etched PET serves as a transparent scaffold to give the gas exchanger mechanical stability and low-absorbency, while the thin layer of gas-permeability PDMS seals the PET pores to leakage of fluid from inside the device to outside the device. The combination of PDMS and porous PET provides gas exchanging properties, while having minimal absorption. In this embodiment, some of the small molecule compounds may absorb into the PDMS through the pores in the PET, however compared to the gas exchanger being fabricated from an entirely absorbent material, this absorbency may be considered negligible in many cases. Further in this embodiment of the gas exchanger, the porous, track-etched PET and PDMS gas exchanger would not only be able to increase gas transport compared to a completely gas-impermeable microfluidic device, but also decouples gas transport from fluid flow.

A gasket may be defined as a mechanical seal, which fills the space between two mating surfaces, in order to, for example, prevent leaks or provide compression. In one embodiment, the microfluidic device has a gasket layer. In one embodiment, the gasket layer on the top surface of the microfluidic device. In one embodiment, the gasket layer has four ports to interact with the ports exiting a first channel of a first channel layer. In a particular embodiment, the gasket layer has four ports to interact with the ports exiting a top channel of a top channel layer. The gasket may be used to ensure a tight fluidic connection between the microfluidic device and relating infrastructure. The inclusion of a gasket layer is advantageous as it decreases the chance of leakage compared to microfluidic devices not comprising a gasket layer. In one embodiment the gasket is made out of a compressible material. In another embodiment the gasket is made out of an adhesive material. The gasket may be used to keep the microfluidic device the same size as it's absorbent predecessor in order to fit into existing microfluidic device accessories, such as a perfusion manifold. The gasket may be embodied in multiple heights in order to raise the height of the microfluidic device to a desired level such that it fits into a compression fit snugly. The gasket is not required to be gas-permeable and, therefore, may also be more easily made non-absorbent so that it does not absorb any small molecule compounds into the walls of its ports. The gasket may achieve non-absorbency by being fabricated from a partially or entirely gas-impermeable material, coated with a gas-impermeable, non-absorbing substance, having its surface modified to reach impermeability (such as plasma treatment), etc. In one embodiment the gasket covers the entire surface of the microfluidic device. In another embodiment the gasket only covers a portion of the surface of the microfluidic device.

In one embodiment the low-absorbing, gas-permeable microfluidic device featuring a gas exchanger may be used to introduce and sustain a gas concentration gradient in the microfluidic device. In this embodiment a specific concentration of gas could be introduced to the gas exchanger. The gas is then depleted by the cell layers, such as endothelial and epithelial cell layers, resulting in a hypoxic first channel, top channel, or luminal channel. In one exemplary embodiment the gas is oxygen. In another embodiment the gas is carbon dioxide. In another embodiment the gas is nitrogen. The gas gradient may be altered by introducing cell layers of various permeability. The vertical gradient of gas through the microfluidic device maintains the longitudinal concentration of gas along the entire length of the microfluidic device. In the embodiment where an oxygen gradient is introduced in the low-absorbing, gas-permeable microfluidic device with a gas exchanger, the longitudinal oxygen concentration along the entire length of the microfluidic device is maintained. In one embodiment, a gas-gradient is introduced into the low-absorbing, gas-permeable microfluidic device by flowing the selected gas through adjacent working channels. In one embodiment, a gas gradient is introduced into the low-absorbing, gas-permeable microfluidic device with a gas-exchanger using chemical reactions. In another embodiment, the porosity of the PET scaffold is varied to supply a greater flux of gas into and out of the microfluidic device.

In one embodiment, one or more sensors may be used to measure the gas gradient in the low-absorbing, gas-permeable microfluidic device. In the exemplary oxygen gradient embodiment, one or more oxygen sensors may be used to measure the oxygen gradient in the low-absorbing, gas-permeable microfluidic device. In one embodiment, the sensors are electrical sensors. In one embodiment the sensors are optical sensors. In one embodiment, the one or more sensors are external to the microfluidic device. In one embodiment, the one or more sensors are inserted into ports or vias of the microfluidic device. In one embodiment, the one or more sensors are embedded in the microfluidic device. In one embodiment, the one or more sensors are inserted into the material making up the body of the microfluidic device. In one embodiment, the one or more sensors are in a first channel. In one embodiment, the one or more sensors are in a second channel. In one embodiment, the one or more sensors are in both a first channel and a second channel. In one embodiment, the one or more sensors are in both a top channel and a bottom channel. A plurality of sensors may be used in the microfluidic devices presented herein, in order to measure gradients within said microfluidic devices. A plurality of sensors may be used to measure an oxygen gradient. In one embodiment, sensors may be found along the length of one or more channels within the microfluidic device, making measurements, such as oxygen concentration measurements, along the length of the channels.

The gas exchanger itself may be considered a unique invention. Gas exchangers have many uses, even outside the field of microfluidics. Gas exchangers may be helpful in transporting gases from one region another, or controlling the rate of gas exchange or flow. Gas exchangers may be used to maintain the rate of gas flow, decrease the rate of gas flow, or increase the rate of gas flow.

A gas exchanger may be, in one embodiment, a gas-impermeable substrate comprising pores, wherein the pores are filled with a gas-permeable material. In an exemplary embodiment, the gas exchanger is fabricated from a strategic combination of gas-impermeable and gas-permeable polymers. The relative volumes of gas-permeable and gas-impermeable polymers may be adapted in order to fabricate a gas exchanger of desirable characteristics. For example, if the gas exchanger is used to increase the gas flow rate from, say, the ambient environment into a microfluidic device, then a larger volume of gas-permeable polymer may be used. For example, if the gas exchanger is used to decrease the gas flow rate from, say, the ambient environment into a microfluidic device, then a smaller volume of gas-permeable polymer may be used.

In one embodiment, a device is contemplated comprising a gas-impermeable substrate, said gas-impermeable substrate comprising (i) a first surface, (ii) a second surface, and (iii) one or more gas-permeable regions. In one embodiment, said substrate is a film. In one embodiment, said substrate is a sheet. In one embodiment, said substrate is a lamination. In one embodiment, said substrate is a composite. In one embodiment, said substrate is a gas-exchange membrane. In one embodiment, said substrate is a gas-exchange membrane. In one embodiment, said substrate is a pore-filled substrate. In one embodiment, said substrate is a pore-filled film. In one embodiment, said substrate is a pore-filled gas-exchange membrane. In one embodiment, said substrate is a pore-filled composite. In one embodiment, said regions are pores. In one embodiment, said regions are conduits. In one embodiment, said regions are indentations. In one embodiment, said regions contact at least one of said first surface and said second surface. In one embodiment, said regions bridge said first surface and said second surface. In one embodiment, said polymer comprises polyethylene terephthalate (PET) and said pores comprises polydimethylsiloxane (PDMS).

In one embodiment, a rigid polymer film is contemplated comprising elastomeric pores. In one embodiment, said rigid polymer film comprises polyethylene terephthalate (PET) and said elastomeric pores comprises polydimethylsiloxane (PDMS).

In one embodiment, the gas exchanger is a gas-impermeable substrate comprising one or more gas-permeable regions. In one embodiment, the gas exchanger is a rigid substrate comprising one or more flexible or elastomeric regions. In one embodiment, the gas exchanger is a gas-impermeable substrate comprising a first surface, a second surface, and one or more gas-permeable regions. In one embodiment, the gas exchanger is a rigid substrate comprising a first surface, a second surface, and one or more elastomeric regions. In one embodiment, the gas exchanger is a gas-impermeable substrate comprising a first surface, a second surface, and a one or more gas-permeable regions between said first surface and said second surface. In one embodiment, the gas exchanger is a rigid substrate comprising a first surface, a second surface, and a one or more elastomeric regions between said first surface and said second surface. In one embodiment, the gas exchanger is a gas-impermeable substrate comprising a first surface, a second surface, and one or more gas-permeable regions contacting at least one of said first surface and said second surface. In one embodiment, the gas exchanger is a rigid substrate comprising a first surface, a second surface, and one or more elastomeric regions contacting at least one of said first surface and said second surface.

In one embodiment, said gas-exchanger is a gas-impermeable membrane comprising pores, wherein said pores are at least partially filled with a gas-permeable material. In one embodiment, said gas-exchanger is a gas-impermeable film comprising pores, wherein said pores are at least partially filled with a gas-permeable material. In one embodiment, said gas-exchanger is a rigid membrane comprising pores, wherein said pores are at least partially filled with an elastomeric material. In one embodiment, said gas-exchanger is a gas-impermeable film comprising pores, wherein said pores are at least partially filled with a gas-permeable material. In one embodiment, said gas-exchanger is a rigid film comprising pores, wherein said pores are at least partially filled with an elastomeric material. In one embodiment, said gas-exchanger is a gas-impermeable polymer membrane comprising pores, wherein said pores are at least partially filled with a gas-permeable polymer. In one embodiment, said gas-exchanger is a rigid polymer membrane comprising pores, wherein said pores are at least partially filled with an elastomeric polymer. In one embodiment, said gas-exchanger is a gas-impermeable polymer film comprising pores, wherein said pores are at least partially filled with a gas-permeable polymer. In one embodiment, said gas-exchanger is a rigid polymer film comprising pores, wherein said pores are at least partially filled with an elastomeric polymer.

In one embodiment, the gas exchanger is a gas-impermeable substrate comprising a first surface, a second surface, and one or more gas-permeable pores. In one embodiment, the gas exchanger is a rigid substrate comprising a first surface, a second surface, and one or more elastomeric pores. In one embodiment, the gas exchanger is a gas-impermeable substrate comprising a first surface, a second surface, and a one or more gas-permeable pores between said first surface and said second surface. In one embodiment, the gas exchanger is a rigid substrate comprising a first surface, a second surface, and a one or more elastomeric pores between said first surface and said second surface. In one embodiment, the gas exchanger is a gas-impermeable substrate comprising a first surface, a second surface, and one or more gas-permeable pores contacting at least one of said first surface and said second surface. In one embodiment, the gas exchanger is a rigid substrate comprising a first surface, a second surface, and one or more elastomeric pores contacting at least one of said first surface and said second surface.

In one embodiment, the gas exchanger is a gas-impermeable membrane comprising a first surface, a second surface, and one or more gas-permeable regions. In one embodiment, the gas exchanger is a rigid membrane comprising a first surface, a second surface, and one or more elastomeric regions. In one embodiment, the gas exchanger is a gas-impermeable membrane comprising a first surface, a second surface, and a one or more gas-permeable regions between said first surface and said second surface. In one embodiment, the gas exchanger is a rigid membrane comprising a first surface, a second surface, and a one or more elastomeric regions between said first surface and said second surface. In one embodiment, the gas exchanger is a gas-impermeable membrane comprising a first surface, a second surface, and one or more gas-permeable regions contacting at least one of said first surface and said second surface. In one embodiment, the gas exchanger is a rigid membrane comprising a first surface, a second surface, and one or more elastomeric regions contacting at least one of said first surface and said second surface.

In one embodiment, the gas exchanger is a gas-impermeable sheet comprising a first surface, a second surface, and one or more gas-permeable regions. In one embodiment, the gas exchanger is a rigid sheet comprising a first surface, a second surface, and one or more elastomeric regions. In one embodiment, the gas exchanger is a gas-impermeable sheet comprising a first surface, a second surface, and a one or more gas-permeable regions between said first surface and said second surface. In one embodiment, the gas exchanger is a rigid sheet comprising a first surface, a second surface, and a one or more elastomeric regions between said first surface and said second surface. In one embodiment, the gas exchanger is a gas-impermeable sheet comprising a first surface, a second surface, and one or more gas-permeable regions contacting at least one of said first surface and said second surface. In one embodiment, the gas exchanger is a rigid sheet comprising a first surface, a second surface, and one or more elastomeric regions contacting at least one of said first surface and said second surface.

In one embodiment, the gas exchanger is a gas-impermeable substrate comprising a first surface, a second surface, and one or more gas-permeable film. In one embodiment, the gas exchanger is a rigid film comprising a first surface, a second surface, and one or more elastomeric regions. In one embodiment, the gas exchanger is a gas-impermeable film comprising a first surface, a second surface, and a one or more gas-permeable regions between said first surface and said second surface. In one embodiment, the gas exchanger is a rigid film comprising a first surface, a second surface, and a one or more elastomeric regions between said first surface and said second surface. In one embodiment, the gas exchanger is a gas-impermeable film comprising a first surface, a second surface, and one or more gas-permeable regions contacting at least one of said first surface and said second surface. In one embodiment, the gas exchanger is a rigid film comprising a first surface, a second surface, and one or more elastomeric regions contacting at least one of said first surface and said second surface.

In one embodiment, the gas exchanger is a gas-impermeable membrane comprising a first surface, a second surface, and one or more gas-permeable pores. In one embodiment, the gas exchanger is a rigid membrane comprising a first surface, a second surface, and one or more elastomeric pores. In one embodiment, the gas exchanger is a gas-impermeable membrane comprising a first surface, a second surface, and a one or more gas-permeable pores between said first surface and said second surface. In one embodiment, the gas exchanger is a rigid membrane comprising a first surface, a second surface, and a one or more elastomeric pores between said first surface and said second surface. In one embodiment, the gas exchanger is a gas-impermeable membrane comprising a first surface, a second surface, and one or more gas-permeable pores contacting at least one of said first surface and said second surface. In one embodiment, the gas exchanger is a rigid membrane comprising a first surface, a second surface, and one or more elastomeric pores contacting at least one of said first surface and said second surface.

In one embodiment, the gas exchanger is a gas-impermeable film comprising a first surface, a second surface, and one or more gas-permeable pores. In one embodiment, the gas exchanger is a rigid film comprising a first surface, a second surface, and one or more elastomeric pores. In one embodiment, the gas exchanger is a gas-impermeable film comprising a first surface, a second surface, and a one or more gas-permeable pores between said first surface and said second surface. In one embodiment, the gas exchanger is a rigid film comprising a first surface, a second surface, and a one or more elastomeric pores between said first surface and said second surface. In one embodiment, the gas exchanger is a gas-impermeable film comprising a first surface, a second surface, and one or more gas-permeable pores contacting at least one of said first surface and said second surface. In one embodiment, the gas exchanger is a rigid film comprising a first surface, a second surface, and one or more elastomeric pores contacting at least one of said first surface and said second surface.

In one embodiment, the gas exchanger is a gas-impermeable sheet comprising a first surface, a second surface, and one or more gas-permeable pores. In one embodiment, the gas exchanger is a rigid sheet comprising a first surface, a second surface, and one or more elastomeric pores. In one embodiment, the gas exchanger is a gas-impermeable sheet comprising a first surface, a second surface, and a one or more gas-permeable pores between said first surface and said second surface. In one embodiment, the gas exchanger is a rigid sheet comprising a first surface, a second surface, and a one or more elastomeric pores between said first surface and said second surface. In one embodiment, the gas exchanger is a gas-impermeable sheet comprising a first surface, a second surface, and one or more gas-permeable pores contacting at least one of said first surface and said second surface. In one embodiment, the gas exchanger is a rigid sheet comprising a first surface, a second surface, and one or more elastomeric pores contacting at least one of said first surface and said second surface.

In one embodiment, the gas exchanger is a gas-impermeable membrane comprising a first surface, a second surface, and one or more gas-permeable pores, wherein said membrane comprises cyclic olefin copolymer (COP) and said pores comprise polydimethylsiloxane (PDMS). In one embodiment, the gas exchanger is a gas-impermeable membrane comprising a first surface, a second surface, and a one or more gas-permeable pores between said first surface and said second surface, wherein said membrane comprises cyclic olefin copolymer (COP) and said pores comprise polydimethylsiloxane (PDMS). In one embodiment, the gas exchanger is a gas-impermeable membrane comprising a first surface, a second surface, and one or more gas-permeable pores contacting at least one of said first surface and said second surface, wherein said membrane comprises cyclic olefin copolymer (COP) and said pores comprise polydimethylsiloxane (PDMS).

Furthermore, the gas exchanger may be coated with or have a film of a particular material in order to enhance bonding. For example, the present invention contemplates, in one embodiment, a gas exchanger comprising a porous, gas-impermeable substrate may not only have the pores filled with a gas-permeable material, but may also have a layer or coating or film of the gas-permeable material on top of it.

"Like dissolves like" is a common expression used by chemists to remember how some solvents interact with solutes. It refers to "polar" and "nonpolar" solvents and solutes. For example, water is polar and oil is non polar. Like does not dissolve like well, meaning that water will not dissolve oil. For example, water is polar and salt (NaCl) is ionic (which is considered extremely polar). Like dissolves like, that means polar dissolves polar, so water dissolves salt. Much the same, "like bonds to like." It has been found that materials bond more easily, such as through chemical treatment, plasma treatment, etc. For example, PDMS bonds easily to PDMS as compared to other polymers. As such, in one embodiment, the gas exchanger may have a coating, or film, or layer, which allows it to more easily bond to other structures.

In one embodiment, the gas exchanger is a gas-impermeable substrate comprising a first surface, a second surface, one or more gas-permeable regions, and a gas-permeable coating on said first surface. In one embodiment, the gas exchanger is a gas-impermeable substrate comprising a first surface, a second surface, a one or more gas-permeable regions between said first surface and said second surface, and a gas-permeable coating on said first surface. In one embodiment, the gas exchanger is a gas-impermeable substrate comprising a first surface, a second surface, one or more gas-permeable regions contacting at least one of said first surface and said second surface, and a gas-permeable coating on said first surface.

In one embodiment, the gas exchanger is a gas-impermeable substrate comprising a first surface, a second surface, one or more gas-permeable regions, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable substrate comprising a first surface, a second surface, a one or more gas-permeable regions between said first surface and said second surface, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable substrate comprising a first surface, a second surface, one or more gas-permeable regions contacting at least one of said first surface and said second surface, and a gas-permeable coating on said first surface, wherein said membrane comprises cyclic olefin copolymer (COP) and said regions and coating comprise polydimethylsiloxane (PDMS).

In one embodiment, the gas exchanger is a gas-impermeable membrane comprising a first surface, a second surface, one or more gas-permeable regions, and a gas-permeable coating on said first surface. In one embodiment, the gas exchanger is a gas-impermeable membrane comprising a first surface, a second surface, a one or more gas-permeable regions between said first surface and said second surface, and a gas-permeable coating on said first surface. In one embodiment, the gas exchanger is a gas-impermeable membrane comprising a first surface, a second surface, one or more gas-permeable regions contacting at least one of said first surface and said second surface, and a gas-permeable coating on said first surface.

In one embodiment, the gas exchanger is a gas-impermeable membrane comprising a first surface, a second surface, one or more gas-permeable regions, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable membrane comprising a first surface, a second surface, a one or more gas-permeable regions between said first surface and said second surface, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable membrane comprising a first surface, a second surface, one or more gas-permeable regions contacting at least one of said first surface and said second surface, and a gas-permeable coating on said first surface, wherein said membrane comprises cyclic olefin copolymer (COP) and said regions and coating comprise polydimethylsiloxane (PDMS).

In one embodiment, the gas exchanger is a gas-impermeable sheet comprising a first surface, a second surface, one or more gas-permeable regions, and a gas-permeable coating on said first surface. In one embodiment, the gas exchanger is a gas-impermeable sheet comprising a first surface, a second surface, a one or more gas-permeable regions between said first surface and said second surface, and a gas-permeable coating on said first surface. In one embodiment, the gas exchanger is a gas-impermeable sheet comprising a first surface, a second surface, one or more gas-permeable regions contacting at least one of said first surface and said second surface, and a gas-permeable coating on said first surface.

In one embodiment, the gas exchanger is a gas-impermeable sheet comprising a first surface, a second surface, one or more gas-permeable regions, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable sheet comprising a first surface, a second surface, a one or more gas-permeable regions between said first surface and said second surface, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable sheet comprising a first surface, a second surface, one or more gas-permeable regions contacting at least one of said first surface and said second surface, and a gas-permeable coating on said first surface, wherein said membrane comprises cyclic olefin copolymer (COP) and said regions and coating comprise polydimethylsiloxane (PDMS).

In one embodiment, the gas exchanger is a gas-impermeable film comprising a first surface, a second surface, one or more gas-permeable regions, and a gas-permeable coating on said first surface. In one embodiment, the gas exchanger is a gas-impermeable film comprising a first surface, a second surface, a one or more gas-permeable regions between said first surface and said second surface, and a gas-permeable coating on said first surface. In one embodiment, the gas exchanger is a gas-impermeable film comprising a first surface, a second surface, one or more gas-permeable regions contacting at least one of said first surface and said second surface, and a gas-permeable coating on said first surface.

In one embodiment, the gas exchanger is a gas-impermeable film comprising a first surface, a second surface, one or more gas-permeable regions, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable film comprising a first surface, a second surface, a one or more gas-permeable regions between said first surface and said second surface, and a gas-permeable coating on said first surface, wherein said membrane comprises cyclic olefin copolymer (COP) and said regions and coating comprise polydimethylsiloxane (PDMS). In one embodiment, the gas exchanger is a gas-impermeable film comprising a first surface, a second surface, one or more gas-permeable regions contacting at least one of said first surface and said second surface, and a gas-permeable coating on said first surface, wherein said membrane comprises cyclic olefin copolymer (COP) and said regions and coating comprise polydimethylsiloxane (PDMS).

In one embodiment, the gas exchanger is a gas-impermeable substrate comprising a first surface, a second surface, one or more gas-permeable pores, and a gas-permeable coating on said first surface. In one embodiment, the gas exchanger is a gas-impermeable substrate comprising a first surface, a second surface, a one or more gas-permeable pores between said first surface and said second surface, and a gas-permeable coating on said first surface. In one embodiment, the gas exchanger is a gas-impermeable substrate comprising a first surface, a second surface, one or more gas-permeable pores contacting at least one of said first surface and said second surface, and a gas-permeable coating on said first surface.

In one embodiment, the gas exchanger is a gas-impermeable substrate comprising a first surface, a second surface, one or more gas-permeable pores, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable substrate comprising a first surface, a second surface, a one or more gas-permeable pores between said first surface and said second surface, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable substrate comprising a first surface, a second surface, one or more gas-permeable pores contacting at least one of said first surface and said second surface, and a gas-permeable coating on said first surface, wherein said membrane comprises cyclic olefin copolymer (COP) and said pores and coating comprise polydimethylsiloxane (PDMS).

In one embodiment, the gas exchanger is a gas-impermeable membrane comprising a first surface, a second surface, one or more gas-permeable pores, and a gas-permeable coating on said first surface. In one embodiment, the gas exchanger is a gas-impermeable membrane comprising a first surface, a second surface, a one or more gas-permeable pores between said first surface and said second surface, and a gas-permeable coating on said first surface. In one embodiment, the gas exchanger is a gas-impermeable membrane comprising a first surface, a second surface, one or more gas-permeable pores contacting at least one of said first surface and said second surface, and a gas-permeable coating on said first surface.

In one embodiment, the gas exchanger is a gas-impermeable membrane comprising a first surface, a second surface, one or more gas-permeable pores, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable membrane comprising a first surface, a second surface, a one or more gas-permeable pores between said first surface and said second surface, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable membrane comprising a first surface, a second surface, one or more gas-permeable pores contacting at least one of said first surface and said second surface, and a gas-permeable coating on said first surface, wherein said membrane comprises cyclic olefin copolymer (COP) and said pores and coating comprise polydimethylsiloxane (PDMS).

In one embodiment, the gas exchanger is a gas-impermeable sheet comprising a first surface, a second surface, one or more gas-permeable pores, and a gas-permeable coating on said first surface. In one embodiment, the gas exchanger is a gas-impermeable sheet comprising a first surface, a second surface, a one or more gas-permeable pores between said first surface and said second surface, and a gas-permeable coating on said first surface. In one embodiment, the gas exchanger is a gas-impermeable sheet comprising a first surface, a second surface, one or more gas-permeable pores contacting at least one of said first surface and said second surface, and a gas-permeable coating on said first surface.

In one embodiment, the gas exchanger is a gas-impermeable sheet comprising a first surface, a second surface, one or more gas-permeable pores, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable sheet comprising a first surface, a second surface, a one or more gas-permeable pores between said first surface and said second surface, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable sheet comprising a first surface, a second surface, one or more gas-permeable pores contacting at least one of said first surface and said second surface, and a gas-permeable coating on said first surface, wherein said membrane comprises cyclic olefin copolymer (COP) and said pores and coating comprise polydimethylsiloxane (PDMS).

In one embodiment, the gas exchanger is a gas-impermeable film comprising a first surface, a second surface, one or more gas-permeable pores, and a gas-permeable coating on said first surface. In one embodiment, the gas exchanger is a gas-impermeable film comprising a first surface, a second surface, a one or more gas-permeable pores between said first surface and said second surface, and a gas-permeable coating on said first surface. In one embodiment, the gas exchanger is a gas-impermeable film comprising a first surface, a second surface, one or more gas-permeable pores contacting at least one of said first surface and said second surface, and a gas-permeable coating on said first surface.

In one embodiment, the gas exchanger is a gas-impermeable film comprising a first surface, a second surface, one or more gas-permeable pores, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable film comprising a first surface, a second surface, a one or more gas-permeable pores between said first surface and said second surface, and a gas-permeable coating on said first surface, wherein said membrane comprises cyclic olefin copolymer (COP) and said pores and coating comprise polydimethylsiloxane (PDMS). In one embodiment, the gas exchanger is a gas-impermeable film comprising a first surface, a second surface, one or more gas-permeable pores contacting at least one of said first surface and said second surface, and a gas-permeable coating on said first surface, wherein said membrane comprises cyclic olefin copolymer (COP) and said pores and coating comprise polydimethylsiloxane (PDMS).

One embodiment of the present invention is a fluidic device for monitoring biological function is contemplated, said fluidic device comprising (i) a first channel, (ii) a second channel, (iii) a membrane disposed between said first channel and second channel, and (iv) a gas exchanger contacting at least one of said first and second channel configured to be able to control the rate of gas transport into said fluidic device. In one embodiment, said fluidic device is a microfluidic device. In one embodiment, the first and second channel layers are gas impermeable. In one embodiment, said first and second channel layers are resistant to absorption of small molecules. In one embodiment, at least one of said first and second channel layers comprise (cyclic olefin copolymer) COP. In one embodiment, at least one of said first and second channels comprise cells. In one embodiment, said cells are human cells. In one embodiment, said gas exchanger provides mechanical stability to said fluidic device. In one embodiment, said gas exchanger at least partially encloses at least one of said first channel or said second channel. In one embodiment, said gas exchanger at least partially borders at least one of said first channel or said second channel. In one embodiment, said gas exchanger comprises two polymer layers. In one embodiment, said gas exchanger comprises polymethylpentene (PMP). In one embodiment, said gas exchanger comprises polydimethylsiloxane (PDMS). In one embodiment, said gas exchanger comprises polyethylene terephthalate (PET). In one embodiment, said gas exchanger comprises polytetrafluoroethene (PTFE or Teflon). In one embodiment, said gas exchanger comprises poly[4,5-difluoro-2,2-bis(trifluoromethyl)-1,3-dioxole-co-tetrafluoroethylene] (TeflonAF2400). In one embodiment, said gas exchanger comprises a polymer film comprising a plurality of pores, said plurality of pores defining a porosity. In one embodiment, said porosity is between 0.05% and 15%. In one embodiment, said porosity regulates a rate of gas transport. In one embodiment, said plurality pores are filled with a gas-permeable polymer. In one embodiment, said gas-permeable polymer comprises polydimethylsiloxane (PDMS). In one embodiment, said polymer film is polyethylene terephthalate (PET). In one embodiment, said gas exchanger comprises a gas impermeable film comprising a plurality of gas-permeable pores, said plurality of pores defining a porosity. In one embodiment, said gas exchanger is less gas-permeable than polydimethylsiloxane (PDMS). In one embodiment, said gas-exchanger comprises less than 0.025-1 µL by volume of porosity. In one embodiment, said gas exchanger runs along the length of at least one of said first channel or said second channel. In one embodiment, said gas exchanger is configured for providing a constant rate of gas transport along the length of at least one of said first channel and said second channel. In one embodiment, said membrane comprises a gas-permeable polymer. In one embodiment, said membrane comprises polydimethylsiloxane (PDMS). In one embodiment, said membrane comprises a plurality of pores, said plurality of pores defining a porosity. In one embodiment, said porosity of said membrane is between 5% and 10%. In one embodiment, said porosity regulates a rate of gas transport through the membrane. In one embodiment, said device further comprises one or more sensors. In one embodiment, at least one sensor is an oxygen sensor. In one embodiment, said fluidic device comprises a hypoxic environment in said at least one of said first and second channels.

In one embodiment, a fluidic device is contemplated for monitoring biological function, said fluidic device comprising (i) a first channel layer including a first channel, (ii) a second channel layer including a second channel, (iii) a membrane located between said first channel layer and second channel layer, and (iv) a gas exchanger contacting at least one of said first and second channels configured to be able to introduce gas flow into said fluidic device. In one embodiment, said fluidic device is a microfluidic device. In one embodiment, the first and second channel layers are gas impermeable. In one embodiment, said first and second channel layers are resistant to absorption of small molecules. In one embodiment, at least one of said first and second channel layers comprise (cyclic olefin copolymer) COP. In one embodiment, at least one of said first and second channels comprise cells. In one embodiment, said cells are human cells. In one embodiment, said gas exchanger provides mechanical stability to said fluidic device. In one embodiment, said gas exchanger at least partially encloses at least one of said first channel or said second channel. In one embodiment, said gas exchanger at least partially borders at least one of said first channel or said second channel. In one embodiment, said gas exchanger comprises two polymer layers. In one embodiment, said gas exchanger comprises polymethylpentene (PMP). In one embodiment, said gas exchanger comprises polydimethylsiloxane (PDMS). In one embodiment, said gas exchanger comprises polyethylene terephthalate (PET). In one embodiment, said gas exchanger comprises polytetrafluoroethene (PTFE or Teflon). In one embodiment, said gas exchanger comprises poly[4,5-difluoro-2,2-bis(trifluoromethyl)-1,3-dioxole-co-tetrafluoroethylene] (TeflonAF2400). In one embodiment, said gas exchanger comprises a polymer film comprising a plurality of pores, said plurality of pores defining a porosity. In one embodiment, said porosity is between 0.05% and 15%. In one embodiment, said porosity regulates a rate of gas transport. In one embodiment, said plurality pores are filled with a gas-permeable polymer. In one embodiment, said gas-permeable polymer comprises polydimethylsiloxane (PDMS). In one embodiment, said polymer film is polyethylene terephthalate (PET). In one embodiment, said gas exchanger comprises a gas impermeable film comprising a plurality of gas-permeable pores, said plurality of pores defining a porosity. In one embodiment, said gas exchanger is less gas-permeable than polydimethylsiloxane (PDMS). In one embodiment, said gas-exchanger comprises less than 0.025-1 µL by volume of porosity. In one embodiment, said gas exchanger runs along the length of at least one of said first channel or said second channel. In one embodiment, said gas exchanger is configured for providing a constant rate of gas transport along the length of at least one of said first channel and said second channel. In one embodiment, said membrane comprises a gas-permeable polymer. In one embodiment, said membrane comprises polydimethylsiloxane (PDMS). In one embodiment, said membrane comprises a plurality of pores, said plurality of pores defining a porosity. In one embodiment, said porosity of said membrane is between 5% and 10%. In one embodiment, said porosity regulates a rate of gas transport through the membrane. In one embodiment, the method further comprises one or more sensors. In one embodiment, at least one sensor is an oxygen sensor. In one embodiment, said fluidic device comprises a hypoxic environment in said at least one of said first and second channels.

Another embodiment of the present invention is an upgraded perfusion manifold assembly that minimizes the amount of small molecule compound to absorb into its materials. In one embodiment, the perfusion manifold assembly comprises i) a cover or lid assembly configured to serve as the top of ii) one or more fluid reservoirs, iii) a gasketing layer under said fluid reservoir(s), iv) a fluidic backplane under, and in fluidic communication with, said fluid reservoirs, v) a capping layer over said fluidic backplane, and vi) a projecting member or skirt for engaging the microfluidic device or a carrier containing a microfluidic device.

One embodiment of the present invention is a method of fabricating a microfluidic device, comprising: a) providing a microfluidic device comprising a channel; b) selecting a gas exchanger of a porosity, wherein said porosity determines a rate of gas transport; and c) capping said channel with said gas exchanger. In one embodiment, said channel comprises a first chamber and a second chamber separated by a membrane. In one embodiment, said microfluidic device is able to maintain a constant rate of gas transport with and without fluid flow. In one embodiment, said gas comprises oxygen. In one embodiment, said gas exchanger comprises polyethylene terephthalate (PET). In one embodiment, said gas exchanger comprises polydimethylsiloxane (PDMS). In one embodiment, wherein said gas exchanger is a device comprising a first gas impermeable substrate, said first gas impermeable substrate having (i) a first side, (ii) a second side, and (iii) one or more gas-permeable regions are between said first side and said second side. In one embodiment, said gas exchanger is a film. In one embodiment, said regions are pores. In one embodiment, said regions contact at least one of said first side and said second side. In one embodiment, said channel is an open channel. In one embodiment, said gas exchanger comprises pores filled with a gas-permeable material, said pores defining said porosity. In one embodiment, said gas exchanger comprises gas impermeable regions and gas-permeable regions, wherein said gas-permeable regions represent less than 10% by volume of the gas exchanger. In one embodiment, said microfluidic device further comprises cells, and said rate of gas transport is selected to maintain the viability of said cells. In one embodiment, said rate of gas transport creates a gas concentration profile within said microfluidic device. In one embodiment, said microfluidic device further comprises liver cells, and said gas concentration profile is liver oxygen zonation. In one embodiment, said microfluidic device further comprises cancer cells, and said gas concentration profile is a hypoxic environment. In one embodiment, said microfluidic device further comprises colon cells, and said gas concentration profile is a hypoxic lumen environment. In one embodiment, said gas exchanger limits the flow of gas into the microfluidic device. In one embodiment, said gas exchanger increases the flow of gas into the microfluidic device.

One embodiment of the present invention is a fluidic device comprising a first substrate having an open channel and a second substrate comprising a gas exchanger, wherein said second substrate caps the first substrate forming an at least partially enclosed channel. In one embodiment, said gas exchanger comprises polyethylene terephthalate (PET). In one embodiment, said gas exchanger comprises polydimethylsiloxane (PDMS). In one embodiment, said gas exchanger is a device comprising a gas impermeable material, said gas impermeable material having (i) a first side, (ii) a second side, and (iii) one or more gas-permeable regions are between said first side and said second side. In one embodiment, said material is a film. In one embodiment, said regions are pores. In one embodiment, said regions contact at least one of said first side and said second side. In one embodiment, said regions represent less than 10% by volume of the gas exchanger. In one embodiment, said device is a microfluidic device. In one embodiment, said gas exchanger comprises a composite of a gas-permeable material and a gas-impermeable material. In one embodiment, said gas exchanger comprises a first gas-permeable substrate and a second gas-impermeable substrate.

One embodiment of the present invention is a method of controlling gas transport, comprising: a) providing a fluidic device comprising body and a gas exchanger contacting said body, said gas exchanger comprising a gas-impermeable polymer substrate with gas-permeable regions, said substrate comprising first and second sides, said regions creating a porosity; and b) introducing gas on said first side of said substrate, wherein the rate of gas transport to said second side is controlled by said porosity. In one embodiment, said polymer comprises polyethylene terephthalate (PET) and said regions comprises polydimethylsiloxane (PDMS). In one embodiment, said fluidic device body is gas-permeable. In one embodiment, said fluidic device body is gas-impermeable. In one embodiment, said gas exchanger comprises a gas-permeable polymer layer in contact with said first side of said substrate. In one embodiment, said fluidic device comprises at least one channel. In one embodiment, said gas exchanger comprises at least one wall of said at least one channel. In one embodiment, said fluidic device contains cells. In one embodiment, said gas comprises oxygen. In one embodiment, said gas exchanger reduces the rate of gas transport into said microfluidic device. In one embodiment, said gas exchanger increases the rate of gas transport into said microfluidic device. In one embodiment, said gas exchanger maintains a rate of gas transport into said microfluidic device with and without fluid flow in said channel. In one embodiment, said gas exchanger is selected from the list comprising a film, a sheet, a composite, a gas-exchange membrane, a lamination, a pore-filled substrate, a pore-filled film, a pore-filled membrane, and a pore-filled composite. In one embodiment, said regions are selected from the list comprising pores, conduits, indentations, holes, and channels. In one embodiment, said regions contact at least one of said first side and said second side. In one embodiment, said regions represent less than 10% by volume of the gas exchanger.

One embodiment of the present invention is a method of fabricating a gas exchanger comprising: a) providing a gas impermeable polymer substrate with pores, said substrate comprising first and second surfaces, said pores creating a porosity; b) coating said first surface with an uncured gas-permeable polymer, such that said uncured gas-permeable polymer penetrates said pores; c) removing excess uncured polymer from said first and second surfaces, such that said first and second surfaces are substantially free of said uncured polymer, while said pores are filled with said uncured gas-permeable polymer; and d) curing said uncured gas-permeable polymer in said pores to fabricate a substantially gas impermeable gas exchanger. One embodiment of the present invention is a microfluidic device comprising said fabricated gas exchanger. In one embodiment, said gas-impermeable polymer substrate comprises polyethylene terephthalate (PET). In one embodiment, said gas-permeable polymer comprises polydimethylsiloxane (PDMS). In one embodiment, said pores comprises less than 100 µL by volume of gas-permeable polymer. In one embodiment, said pores comprises less than 50 µL by volume of said gas-permeable polymer. In one embodiment, said pores comprises less than 10 µL by volume of said gas-permeable polymer. In one embodiment, said pores comprises less than 1 µL by volume of said gas-permeable polymer. In one embodiment, the method further comprises the step of degassing said uncured gas-permeable polymer.

One embodiment of the present invention is a method of fabricating a gas exchanger comprising: a) providing (i) a first gas-impermeable polymer substrate with pores, said substrate comprising first and second surfaces, said pores creating a porosity, and (ii) a second gas-permeable polymer substrate; and b) laminating said first surface with said second gas-permeable polymer substrate, such that said gas-permeable polymer substrate covers said pores. In one embodiment, said first gas-impermeable polymer substrate comprises polyethylene terephthalate (PET). In one embodiment, said second gas-permeable polymer substrate comprises polydimethylsiloxane (PDMS). In one embodiment, said first or second substrate is a film. In one embodiment, first or second substrate is a membrane.

One embodiment of the present invention is a method of fabricating a gas exchanger comprising: a) providing (i) a first gas-impermeable polymer substrate with pores, said substrate comprising first and second surfaces, said pores creating a porosity, and (ii) a second gas-permeable polymer substrate; and b) contacting said first surface with said second gas-permeable polymer substrate, such that said gas-permeable polymer substrate forms to said gas-impermeable polymer substrate, covering said pores. In one embodiment, said first gas-impermeable polymer substrate comprises polyethylene terephthalate (PET). In one embodiment, said second gas-permeable polymer substrate comprises polydimethylsiloxane (PDMS). In one embodiment, said first or second substrate is a film. In one embodiment, said first or second substrate is a membrane.

The present invention contemplates, in one embodiment, a method of controlling gas transport, comprising: a) providing a substantially gas-impermeable microfluidic device comprising i) a gas exchanger and ii) living cells in a channel or chamber, said device comprising a rigid polymer; and b) introducing culture media into said channel or chamber at a flow rate, said culture media carrying gas, wherein the rate of gas transport to said living cells is controlled by said gas exchanger. In one embodiment, said rigid polymer is polycarbonate. In one embodiment, said rigid polymer has a modulus of elasticity between 0.1 and 150 GPa. In one embodiment, said gas exchanger comprises a film of polydimethylsiloxane (PDMS) positioned below said channel or chamber. In one embodiment, said gas exchanger comprises a film of a non-permeable polymer with gas-permeable pores, said film positioned below said channel or chamber.

The present invention contemplates, in one embodiment, a method of controlling gas transport in a microfluidic device, comprising: a) providing a substantially gas-impermeable microfluidic device comprising a plurality of outer sides comprising substantially gas-impermeable polymer having a modulus of elasticity between 0.1 and 150 GPa, and a substantially gas-permeable inner membrane disposed between a first channel and a second channel; and b) introducing a fluid into said at least one of said first channel or said second channel at a flow rate, wherein said substantially gas-permeable inner membrane is configured to allow gas transport between said first channel and said second channel.

In one embodiment, a microfluidic device is contemplated comprising a plurality of outer sides comprising substantially gas-impermeable polymer having a modulus of elasticity between 0.1 and 150 GPa, and a substantially gas-permeable inner membrane. In one embodiment, said substantially gas-permeable inner membrane comprises polydimethylsiloxane (PDMS). In one embodiment, wherein said polydimethylsiloxane (PDMS) membrane is configured for stretching.

In one embodiment, a method is contemplated comprising: a) providing a microfluidic device comprising a plurality of outer sides comprising substantially gas-impermeable polymer having a modulus of elasticity between 0.1 and 150 GPa, and a substantially gas-permeable inner membrane; and b) stretching said membrane. In one embodiment, wherein said substantially gas-permeable inner membrane comprises polydimethylsiloxane (PDMS). In one embodiment, wherein said stretching is achieved by applying differential pressure across said membrane. In one embodiment, wherein said microfluidic device further comprises a gas exchanger.

In one embodiment, a microfluidic device is contemplated comprising: (i) a first channel and a second channel, each of said first channel and second channel comprising a plurality of walls, wherein at least one of said walls are gas-permeable having a modulus of elasticity below 0.1 GPa and at least one of said walls are gas-impermeable having a modulus of elasticity between 0.1 and 150 GPa, and (ii) a gas-permeable membrane disposed between said first and second channel, said membrane having a modulus of elasticity less than 0.1 GPa.

Another embodiment of the present invention is applying the presently described embodiments gas exchangers or gas transport membranes to any microfluidic cell culture system. It may be desirable to better control the gas exchange into various microfluidic devices on the market depending on the unique needs of the scientist. Oxygen delivery to the cells in microfluidic culture is an industry-wide problem, particularly as manufacturers adopt thermoplastics due to their easier manufacturing and/or lower gas absorption. The idea of replacing one of the walls (e.g. the device's bottom) with a gas exchanger as described herein is a brilliant solution to this major problem.

For example, the embodiments of gas exchangers described herein may be applied to the Mimetas's microfluidic device of U.S. Pat. No. 10,532,355, which is incorporated by reference herein in its entirety. The bottom of the Mimeta's microfluidic products such as the OrganoPlate® 2-lane, OrganoPlate® 3-lane, etc. may be replaced with a gas exchanger in order to achieve better control over the gas concentrations within the microfluidic device. The gas exchanger may replace any structural elements of the microfluidic device. In particular, the gas exchanger may replace structural elements in contact with channels within the microfluidic device. In cases wherein the microfluidic device has more than one channel, the gas exchanger may be placed between the channels of the microfluidic device. Other exemplary embodiments of microfluidic devices that may be advantageously combined with the microfluidic devices of Aim Biotech (e.g. U.S. Patent Publication No. 20180327700A1) and the microfluidic devices of the Massachusetts Institute of Technology's Mechanobiology Lab (e.g. U.S. Pat. Nos. 9,121,847 and 9,261,496). These three patent applications are incorporated in their entirety herein.

In one embodiment, a method is contemplated, comprising: (i) providing a microfluidic device and a gas exchanger; and (ii) applying said gas exchanger to said microfluidic device, altering the gas-permeability of said microfluidic device. A method is contemplated, comprising: (i) providing a microfluidic device and a gas exchanger; (ii) removing a substrate of said microfluidic device; and (iii) replacing said substrate with said gas exchanger, altering the gas-permeability of said microfluidic device. A method is contemplated, comprising: (i) providing a microfluidic device comprising at least one channel and a membrane within said channel; and (ii) applying a gas exchanger to said at least one channel. In one embodiment, said channel comprises cells.

It is not intended that the microfluidic device be limited by the number of channels; the microfluidic device to have a gas exchanger applied thereto may have one, two, three, four, five, six, etc. channels.

Another embodiment of the present invention is an upgraded perfusion manifold assembly that minimizes the amount of small molecule compound to absorb into its materials. In one embodiment, the perfusion manifold assembly comprises i) a cover or lid configured to serve as the top of ii) one or more fluid reservoirs, iii) a gasketing layer under said fluid reservoir(s), iv) a fluidic backplane under, and in fluidic communication with, said fluid reservoirs, v) a capping layer over said fluidic backplane, and vi) a projecting member or skirt for engaging the microfluidic device or a carrier containing a microfluidic device.

The cover or lid assembly may aid in protecting the reservoirs from both spilling and contamination. In one embodiment, the lid assembly comprises a lid, filter(s), and a lid gasket. Filters may be configured into the lid assembly in order to aid in sterility of the fluid within the reservoirs. In one embodiment the filters are flat filters. These thin filters may be cut from a flat substrate material. In one embodiment the filters are thick filters. These thick filters may be cut from a thick substrate material. In the embodiment wherein, the lid assembly comprises a lid gasket, the lid gasket may take on a variety of embodiments. In one embodiment, the lid gasket is compressible. In one embodiment, the lid gasket is adhesive. The lid gasket may vary in thickness in order to best seal the reservoirs off from the external environment. Alternatively, in other embodiment, the lid gasket comprises the filters, instead of having separate filters. In one embodiment, the lid gasket is porous. In another embodiment the lid gasket is non-porous. In one embodiment, the lid gasket permanently conforms to the shape of the reservoirs after the first time the reservoirs is pressed into it. In another embodiment the lid gasket temporarily conforms to the shape of the reservoirs after each time the lid gasket is pressed onto them. In yet another embodiment, the lid gasket does not conform to the shape of the reservoirs. The cover or lid assembly can be removed and the perfusion manifold assembly can still be used. In one embodiment, the lid assembly is held onto the reservoir using a radial seal. An applied pressure is not necessarily required to create a seal. In another embodiment, the lid assembly is held onto the reservoir using one or more clips, screws or other retention mechanisms.

The fluid backplane may be used to route fluid from the reservoirs to the microfluidic devices, such as a microfluidic device. In one embodiment, the assembly further comprises fluid ports positioned at the bottom of the fluidic backplane. In one embodiment the fluidic backplane comprises one or more fluidic resistors. Without being bound by theory of any particular mechanism, it is believed that these resistors serve to stabilize the flow of fluid coming from the reservoirs so that a stable flow can be delivered to the microfluidic device, and/or they serve to provide a means for translating reservoir pressure to perfusion flow rate.

In previous renditions of this invention there has been a single layer responsible for both capping and gasketing. The invention presented here suggests two separate layers, i.e. one for gasketing and one for capping the fluidic backplane. In one embodiment both the fluid reservoirs and fluid backplane are fabricated from hard plastics, and as such may need a compressible gasket between them to protect from leaks at the sites of fluid connections. Having two separate layers is advantageous as capping the fluidic backplane and gasketing between the fluidic backplane and reservoirs may be decoupled. Oftentimes materials having the characteristics necessary to be used as gaskets, especially transparent gaskets, have absorbency issues. By decoupling the functions of the previous single layer, the amount of absorbing material may be minimized in the perfusion manifold assembly and segregated/isolated to the layer responsible for gasketing. In one embodiment both the capping and gasketing layers are transparent. It may advantageous to have transparent capping and gasketing layers so that the fluidic backplane may be imaged on a microscope if necessary. In one embodiment of the new invention, the gasketing layer is made up of a compressible material, such as SEBS, while the capping layer is made up of an incompressible material, such as COP. In another embodiment, the gasketing layer made up of a compressible material may be coated with a thin layer of an incompressible material, such as with parylene, in order to make it non-absorbent while still maintaining bulk flexibility and, therefore, the ability to seal or gasket the fluid layer to the reservoirs. The capping layer may be partially or completely coated in Parylene. In an exemplary embodiment, a partially coated capping layer fabricated out of COP is used in conjunction with a gasketing layer fabricated out of SEBS. The combination of a partially Parylene-coated COP capping layer and SEBS gasketing layer is advantageous over a single, completely Parylene coated COP layer. Parylene is difficult to bond, whereas COP bonds well to other materials, including other parts made out of COP. By using two layers, one may seal the fluidic backplane to the Parylene-coated COP capping layer by material bonding, and seal the capping layer to the reservoirs with the SEBS gasketing layer. Further, when using two layers only a small piece of SEBS needs to be coated with Parylene to successfully prevent absorption. If a single layer is used, any fluid-contacting surface may need to be coated with Parylene, which means that the ports, the face of the components being sealed (such as the reservoirs), and the entire length of the fluid routing channels in the perfusion manifold assembly would need to be coated. Coating that much of the COP capping layer is difficult. When Parylene is coated, the part needs to be held somewhere, much like Achille's heel.

In one embodiment the perfusion manifold assembly comprises a projecting member or skirt. In one embodiment, the projecting member or skirt is engaged with a microfluidic device. In one embodiment, the microfluidic device comprises a first channel, a second channel and a membrane separating at least a portion of said first and second channels. In another embodiment, wherein the microfluidic device is oriented vertically, the microfluidic device comprises a top channel, a bottom channel, and a membrane separating at least a portion of said top channel and bottom channel. In one embodiment, the microfluidic device comprises cells on the membrane and/or in or on the channels. The projecting member or skirt may be designed so that the fluidic backplane is able to easily align with a connecting microfluidic device. In one embodiment, the projecting member or skirt may be designed in order to interact with a culture system.

The perfusion manifold assembly may be attached together via several methods. In one embodiment, screws may be used to secure the perfusion manifold assembly. In another embodiment, clips are used to secure the perfusion manifold assembly. In another embodiment, adhesives are used to secure the perfusion manifold assembly. In another embodiment, surface modification is used to secure the perfusion manifold assembly. In one embodiment, the perfusion manifold assembly is permanently bonded together. In one embodiment, the perfusion manifold assembly is temporarily bonded together.

If these above described perfusion manifold assemblies are to be used with low-absorbing, gas-impermeable microfluidic devices, the design of the perfusion manifold assembly may be used to introduce a desired gas concentration into the microfluidic device. In one previously described embodiment, the dissolved gas content of the media may be increased prior to entering the microfluidic device by pressurizing the media with the desired gas or by adding a carrier of the desired gas to the media. In one previously described embodiment, the concentration of oxygen within a media may be increased by pressurizing the media with a concentration of oxygen or by increasing the concentration of oxygen in the pressurized gas mixture or by adding an oxygen carrier, such as hemoglobin or hemocyanin, to the media. In one previously described embodiment, the gas pressurizing the media may be a gas blanket. In one embodiment, the dissolved gas content of the media in the perfusion manifold assembly reservoirs may be increased prior to entering the microfluidic device by pressurizing the media in the reservoirs with the desired gas or a carrier of the gas in the headspace of the reservoir. In one embodiment, the concentration of oxygen within the media in the perfusion manifold assembly reservoirs may be increased by pressurizing the media in the headspace of the reservoirs with oxygen or by adding an oxygen carrier, such as hemoglobin, to the media.

A perfusion manifold assembly is contemplated comprising (i) a lid configured to serve as the top of (ii) one or more fluid reservoirs, (iii) a gasketing layer resistant to absorption of small molecules under said fluid reservoir(s), (iv) a fluidic backplane under, and in fluidic communication with, said fluid reservoirs, (v) a capping layer resistant to the absorption of small molecules over said fluidic backplane, and (vi) a projecting member for engaging the microfluidic device. In one embodiment, said gasketing layer comprises parylene-coated SEBS. In one embodiment, said capping layer is fabricated from COP.

In both in vitro and in vivo experiments, researchers should consider compound distribution within the biological model and experimental setup, as distribution determines exposure—the concentration of compound that cells truly experience. Volume of distribution is typically assessed and accounted for in in vivo studies, but the effects of system components such as infusion tubing, syringes, tissue-culture plates and pipette tips are often missed. While absorption is a major component of erroneous compound distribution, undesired compound distribution also includes compound pooling in one region of an experimental setup, adsorption, and other situations where a compound is not where it theoretically should be or where the user would like it to be. For example, erroneous compound distribution may be when a compound is not uniformly distributed throughout a system. For example, erroneous compound distribution may be when cells in the former portion of a cell culture channel metabolize the compound, such that cells in the latter portion of a cell culture channel are unable to be contacted by the compound.

With microfluidic device experiments, compound distribution may be addressed in a number of ways. Several of these are captured herein, where experimental conditions have been selected to optimize compound exposure. Additionally, a compound distribution kit has been developed directly evaluate distribution and compound exposure. In analogy with in vivo distribution studies, it may be recommended to use this kit to assess distribution for certain classes of compounds. Small molecules with a molecular weight below 1 kDa should be evaluated using the compound distribution kit; molecules larger than 1 kDa are typically not a concern, unless they already proved "sticky" or prone to absorbing or adsorbing to materials used in the experiment during development. Biologics, such as monoclonal antibodies, although less likely to be a concern, may also be evaluated especially if they are known to be "sticky" or likely to absorb or adsorb to materials used in the experiment.

In addition to helping assess distribution, the compound distribution kit can also be used to quantitatively account for distribution effects. The quantitative accounting of distribution effects is done using calculators that are included in the kit, which can be applied to each experiment's results.

The compound distribution kit, in one embodiment, is a kit that allows users to approximate the range of possible bio-model exposure concentrations to a dosed compound over time. The compound distribution kit may be used to determine the absorption of compounds in experimental or clinical equipment, such as, for example, microfluidic devices. In one embodiment, the compound distribution kit is intended to be used as a specialized control experiment—the absorption control experiment—prior to an intended study. As such, the contents of the absorption kit may, in one embodiment, mirror the components of an intended study, and the method of use may be a simplified version of the intended study. For example, the compound distribution kit may use the same dosing, perfusion, and sampling design as an intended study or experiment. In an embodiment where these guidelines are followed the compound distribution kit would be able to assess compound distribution (e.g. compound loss or gain) at the same timepoints and under the same experimental conditions that are relevant for the intended experiment.

Not only the materials making up microfluidic devices are prone to absorption. Many materials used in experimental and clinical applications absorb small-molecules. For example, infusion tubing used to administer intravenous fluids and/or drugs may absorb high quantities of small-molecule compounds. As another example, the rubber gaskets of syringes are also known to absorb small-molecule compounds. The absorption of small-molecule compounds into the materials of the infrastructure used to transport them is especially problematic when the small-molecule compounds are, for example, drugs being tested for or even actively used treat patients. The problem worsens if the patient is pediatric. Pediatric patients receive lower doses or concentrations of drugs. If the same fluid transport setup (i.e. the length of infusion tubing) is being used to treat both adult and pediatric patients, then the pediatric patients are receiving even less of the drug than the adults. Oftentimes scientists and clinicians are not aware of small-molecule absorption. Physicians and clinical scientists need to be able to both understand if their compound is prone to material absorption, and if so, be able to quantify the amount of compound being absorbed into their system. In one embodiment, it is recommended that the compound distribution kit is used ahead of experiments that involve compounds that are smaller than 1000 Da. However, if there is an indication that the compound in question suffers from absorption or adsorption in plate-based systems, the compound distribution kit should be used for biologics and small-molecules larger than 1000 Da.

Drug concentration is related to assay results. Generally, when experiments are run many compound doses are used. For example, in an experiment using a drug compound, many drug compound doses may be tried. Following the experiment and relevant assaying, a curve is generated based on the system response to the compound. The curve generally has a sigmoid. The sigmoid may be upward or downward pointing based on whether the compound results in more or less excretion from, for example, cells. As such, the percentage of the compound that is absorbing into the system directly affects assay results.

Currently, the primary method of estimating or quantifying compound absorption into systems is to do computational modeling of the system, such as with the program COMSOL Multiphysics (COMSOL). However, computational models are oftentimes not an ideal solution. Computational models may not work, as some compounds absorb completely. That is to say, if systems are exposed to a very low concentration of compound, even if the exposure level can be predicted, it may be too low to be a useful correction. Regardless of the ability to correct data in only some situations, computational models also may require a complicated workflow.

In order for computational modeling to be functional, absorption of every compound introduced into the system should be quantified first in material characterization studies. Material characterization studies can be very time consuming. Furthermore, fully characterizing systems is not feasible for large scale experiments or clinical setups is not always feasible. As well, computational models may not be able to accurately deconvolute data in many experiments due to high numbers of variables, including those introduced by the cells. Even with the aid of computational models to account for many of these variables, in the presence of absorption there is still a decreased overall confidence in results in in vitro to in vivo extrapolation (IVIVE).

As such, a compound distribution kit is presented herein that may not only easily inform scientists and clinicians of compound absorption into systems, but may also, in some embodiments, recommend improvements to reduce absorption. The invention presented herein may be able to save scientists and clinicians valuable time and money over using computational modeling.

Several levels of the compound distribution kit are contemplated. On the simplest level, the compound distribution kit may offer scientists and clinicians either an affirmative or negative result, alerting them whether or not the absorption in a system is tolerable. On a slightly more detailed level, the compound distribution kit may be able to offer a range compound absorption. On the most comprehensive level, the compound distribution kit may be able to fully characterize the system, quantifying the concentration of the compound that is absorbed into the scientist or clinician's system.

In one embodiment, the compound distribution kit characterizes the system the scientist or clinician is to use. In a preferred embodiment, however, the compound distribution kit characterizes a simplified system. A simplified system may be preferable, such that the user does not have to spend valuable time or money setting up what may be a very costly experimental or clinical system. As an example, a holding tank may be used in the place of a human body if testing the fluidic infrastructure of a dialysis machine. As another example, a microfluidic device with a pore-less membrane separating two channels may be used instead of a microfluidic device comprising cultured cells overlaying a porous membrane. If in this example the scientists aim to find if a compound is toxic to the cells within the microfluidic device, they may use the same media, take samples at the same time points, etc. In some cases, only portions of a clinical or experimental setup would need to be understood, and therefore the other components of that system could be simplified for use with the compound distribution kit. In one embodiment, sampling taken for assays may be replaced with sampling taken for compound concentration analysis.

In one embodiment, a user would design their ideal protocol or experiment and then modify it accordingly for use with the compound distribution kit. In one embodiment, the user may use the results of the compound distribution kit to decide whether the experiment is worthwhile. In one embodiment, the results of the compound distribution kit to modify the experiment, such as to change fluid flow rate, use lower volumes of absorbing material, etc. In one embodiment, the results of the compound distribution kit may be used to influence error bars on the results of the actual protocol. For example, the percent of a compound absorbed may be calculated from the compound distribution kit and those percentages may contribute to error bars following an actual experiment using the unmodified protocol.

As previously stated, compound concentration is directly related to assay results. Assay results are used to generate half maximal inhibitory concentration calculations $IC_{50}$. In one embodiment, the results of the compound distribution kit may be used to influence the $IC_{50}$ following the completion of an actual protocol. The $IC_{50}$ is a measure of the potency of a compound in inhibiting a specific biological or biochemical function. In other words, the $IC_{50}$ is a quantitative measure of how much of a compound is needed to inhibit a biological process. The $IC_{50}$ represents the concentration of a compound that is needed for 50% inhibition or maximum effect in vitro, such as in a microfluidic device. For example, if the intended study shows an $IC_{50}$ at a dosing concentration of 1 µM, the results of the compound distribution kit may indicate that the actual $IC_{50}$ is at an exposure concentration in the range of 0.6 µM to 1 µM.

For example, for a particular protocol using cells within a microfluidic device the $IC_{50}$ at the 24-hour point may be 1 µM. In a worst case all 50% of the loss of the compound comes upstream of a microfluidic device. In that worst-case cells within that microfluidic device would only have seen 0.5 µM of the compound at the $IC_{50}$. Knowing that the 50% compound loss happened before the compound entered the microfluidic device would aid in adjusting the $IC_{50}$ graph. In a best-case all of the absorption happens downstream of a microfluidic device. In that best-case cells within that microfluidic device would have seen 100% of the compound dose. Knowing that all of the absorption happens downstream of the microfluidic device would mean that the $IC_{50}$ graph would not need to be adjusted. In another case, the compound is absorbed into the microfluidic device itself. The case of the compound absorbing into the microfluidic device itself would lead to the $IC_{50}$ graph being adjusted somewhere in between the before mentioned worst-case and best-case. Error bars may also be added to the $IC_{50}$ graph using the results of the compound distribution kit. Likewise, the results of the compound distribution kit may be used to adjust or add error bars to the graphs of assays, such as albumin, lactate dehydrogenase, etc.

In one embodiment, a workflow or method of use for an compound distribution kit may comprise the steps of (1) prepare experimental setup, (2) prepare dosing solutions, (3) dose experimental setup, (4) collect effluent at one or more time points, (5) determine effluent sample concentration, and (6) assess absorption of dosing solution into the materials making up the experimental setup.

The compound distribution kit may be used with any of the microfluidic devices presented herein. The compound distribution kit may be used to determine compound absorption into systems or experiments comprising the high-absorbing, gas-permeable microfluidic device, the low-absorbing, gas-impermeable microfluidic device, and the low-absorbing, gas-permeable microfluidic device. The compound distribution kit may also be used to determine compound absorption into low-absorbing and high-absorbing perfusion manifold assemblies. While the compound distribution kit may be used by any scientist interested in absorption of a compound into any system, embodiments particular to the microfluidic devices and perfusion manifold assemblies discussed herein will be presented.

The compound distribution kit for microfluidic device use may comprise physical and/or digital components. In one embodiment, the physical component of the compound distribution kit comprises one or more microfluidic devices, one or more perfusion manifold assemblies, one or more filters (such as Millapore brand Steriflip® filters), and a quick start guide. In one embodiment, the user of the compound distribution kit may also need any of the following: a culture module, a gas mixer, an incubator, a biosafety cabinet, a liquid chromatography-mass spectrometer (LCMS), ethanol (such as 70% ethanol), at least one 150 mm Petri dish, at least one 50 mL conical tubes, at least 10 Eppendorf® tubes, pipette tips, a pipette aid or gun, an aspirator, aspirator tips, media, wipes, and dimethyl sulfoxide (DMS)). In one embodiment, said microfluidic device comprises: a) a solid substrate comprising a single microfluidic channel, and b) a non-porous membrane separating said single microfluidic channel into a first chamber and a second chamber. A quick start guide may be instructions for a user, such that if followed the user may be able to easily use the compound distribution kit. Filters may be used to equilibrate fluids used in the compound distribution kit. In an exemplary embodiment, the digital component of the compound distribution kit comprises a calculator and a library of digital protocols on a community portal. The library of digital protocols may comprise one or more protocols.

It is not intended that the present invention be limited by media or stock solution type. The non-dosed media or stock solution may be dimethylsulfoxide (DMSO), water, Eagle's minimal essential medium (EMEM), Dulbecco's modified Eagle's medium (DMEM), etc. Any solvent or cell culture media is imagined. In one embodiment, the microfluidic devices are washed with 200 μL per channel. In one embodiment, said perfusion manifold assemblies are primed with 3 mL of media in the inlet reservoirs and 200 μL of media in the outlet reservoirs.

In the embodiment in which perfusion manifold assemblies are fluidically connected to at least one culture module, it is recommended a regulation cycle is run immediately before starting an experiment in order to decrease the volume of bubbles in the system. A regulate cycle or bubble removal cycle is encompassed in U.S. patent application Ser. No. 15/647,727 and is referenced herein in its entirety.

Samples may be taken at any time point the user desires. In an exemplary timepoint, samples are taken at six time points, including a sample taken at the beginning of the experiment from each of the perfusion manifold assembly inlet and outlet reservoirs. For example, if six samples are taken from a perfusion manifold assembly comprising two inlet reservoirs and two outlet reservoirs, there would be a total of 24 samples taken for that perfusion manifold assembly. In an exemplary embodiment, at least three perfusion manifold assemblies are used in order to achieve better experimental results. For example, if six samples are taken from each of three perfusion manifold assemblies each comprising two inlet reservoirs and two outlet reservoirs, there would be a total of 72 samples taken for that experiment. When preparing a dosing solution portions of both the stock (or blank) solution should be set aside for later solution analysis. In a preferred embodiment, 200 μL of stock and dosing solutions are set aside for later analysis.

A calibration curve, also known as a standard curve, is a general method for determining the concentration of a substance in a sample by comparing the unknown to a set of standard samples of known concentration, such as dilutions of 1:10, 1:100, 1:1000, as well as non-dosed and fully dosed samples. In an exemplary embodiment, sample solutions are prepared for a five-point standard curve. In an exemplary embodiment, sample solutions include undiluted dosing solution, a 1:10 dosing solution to sample solution dilution, a 1:100 dosing solution to sample solution dilution, a 1:1000 dosing solution to sample solution dilution, and stock solution. In one embodiment, there are multiple of each sample solution in order to decrease experimental error. In one embodiment, a standard curve is created for each channel of a microfluidic device. In one embodiment, each perfusion manifold assembly has one inlet and one outlet reservoir corresponding to each channel of a microfluidic device. For example, if a five-point calibration is done for a single two-channel microfluidic device and corresponding perfusion manifold assembly with one inlet and one outlet reservoir for each microfluidic device channel, and there are two replicates of each sample, then 20 total samples would be needed to complete the calibration curve.

The compound distribution kit may require high numbers of samples, between samples needed for standard curves and samples needed for system absorption analysis. For example, in an experiment using three two-channel microfluidic devices and three perfusion manifold assemblies, each with one inlet reservoir and one outlet reservoir, up to 92 samples would be necessary when doing a five-point, two replicate calibration and taking six timepoint samples at each of the two inlet reservoirs and two outlet reservoirs per perfusion manifold assembly. If samples are not used immediately, they should be kept in cold storage, such as a freezer.

Running (or flushing) a culture module at a high flow rate during experimentation may be used to prime perfusion manifold assemblies. In one embodiment, a culture module is run at 600 μL/hr for five minutes to completely flush or prime one or more perfusion manifold assembly.

Sample compound concentration quantification may be done in any method known in the art. In one embodiment, sample compound concentrations may be quantified using spectrometry, chromatography, or other separation techniques. Spectrometry may include mass spectrometry (MS), liquid chromatography-mass spectrometry (LCMS), etc. Chromatography may include high performance liquid chromatography (HPLC), thin-layer chromatography (TLC), gas chromatography (GC), counter-current chromatography (CCC), ion chromatography, paper chromatography, etc. Other separation techniques include centrifugation, electrophoresis, liquid-liquid extraction, solid phase extraction, crystallization, distillation, field flow fractionation, drying, decantation, etc.

The calculator may alternatively be known as the absorption calculator. In one embodiment, the calculator outputs the final results of the compound distribution kit. In one embodiment, the calculator outputs result that may be able to guide users toward higher accuracy in their experiments. The calculator may be used to analytically assess compound absorption by comparing the concentration of compound in a plurality of said calibration solutions to the concentration of a compound in one or more sample solutions. The calculator may be a calculation program or software, such as a Microsoft Excel calculator, a MATLAB calculator, etc. The calculator may also be a script of code, such as Python, C, C++, Java, etc. For example, LCMS results and dosing method may be entered into a "user input" section of a calculator to generate a compound distribution result. In one embodiment, the calculator outputs a graph. In one embodiment, recovered (effluent) concentrations are plotted against time for both top and bottom channels. A recovered concentration close to 1 at any given time point, may mean that little compound was absorbed by the system. The curves may rise with time as the gradients that drive absorption and adsorption processes diminish. The range of potential cellular exposure concentrations may be plotted for each collection time period for one or more channels. For example, if all compound loss occurred upstream of the cells, the cells would experience a lower compound concentration than if the compound loss occurred entirely downstream of the cells (in which case the cells would experience the full dosing concentration). If a compound is minimally absorbed, a user may observe a tighter range near the top of the graph, which means that the cells are expected to be exposed to most of the dosed compound. The calculator may also export a table of results, such as indicating range of cellular exposure in one or more channels or fraction of dosing values.

Based on the calculator results, a user can choose to proceed with, say, a drug study as is, make a modification to the study (such as change the flowrate or dosing time), or drop the study all together. Based on the results of the of the compound distribution kit a user might choose to modify any number of drug study experimental conditions either individually or in combination, depending on the desired impact. For example, the user might adjust flowrate in order to create more consistent compound exposure concentrations along the length of the microfluidic device or over time. Indeed, increasing flow rate would minimize the time the media, which contains compound, is exposed to the absorbing material, which in turn minimizes loss of the compound along the length of the microfluidic device and creates a more uniform exposure of the cells to the compound. A user might also choose to increase dosing concentration for a highly absorbing compound, either alone or in concert with increasing flow rates. Similarly, a user may decide to throw out the results from early time points, since this is when the extent of compound loss due to absorption is at its highest and, therefore, its effects most impactful. Thus, at later time points, after the system has possibly started to saturate with compound, depending on the absorption characteristics of the particular compound of interest, and the concentration of the dosed compound begins to rise, the data coming from the system will be more reliable, accurate, and consistent. For example, for a ±18% uncertainty in a 6 to 24-hour time period may be acceptable for some studies but not others. As a note, if a user is proceeding with a biological study, the user should measure effluent compound concentration as well. The calculator is envisioned to output varying levels of absorption data depending on the user. At the broadest end, the calculator would output whether or not the level of absorption in a study is allowable, i.e. whether the level of absorption was high enough that it would negatively impact the experimental data. Allowable levels of absorption would not be significant in the study. The broad end of calculator output may be considered a go/no-go decision maker for experiments for compounds based on results of a simple or small-scale experiment. At a slightly more detailed level, the calculator could report confidence intervals for exposure concentrations. At an even more detailed level, the calculator would output quantified absorption levels at the different timepoints, such that the user would be able to visualize the absorption of the compound into the system for the duration of the experiment. In another embodiment, the calculator would tell the user the potential compound exposure concentration at different time points. Results from absorption tests, without biologics for example, may be used to put error bars, or confidence intervals, on exposure concentrations in actual drug studies, comprising biologicals for example. Exposure concentration confidence intervals decrease with experiment duration, with lower confidence at later time points. The calculator may output charts for the user to see. Examples of charts include minimal absorption charts, nearly complete absorption charts, outlet concentration of compound charts, cellular exposure range ranges, dose-response confidence interval charts, etc. For example, the user would enter system input and output concentrations of a compound and the calculator would then output approximate ranges of cell exposure to a drug.

The calculator may also output experimental suggestions to lower absorbency. In one embodiment, the calculator outputs modified experimental protocols to minimize absorption, such as increased flow rate or waiting until later time points to sample, such as when the system has reached steady state.

Again, the digital component of the compound distribution kit may comprise one or more protocols for the user. In one embodiment, the digital component of the compound distribution kit comprises protocols for running drug studies on a culture module, that defines dosing solution preparation processes, sampling directions, suggested time points for experimental duration. For example, for an experiment of less than three hours it may be suggested to sample the system at 0.5, 1, 1.5, 2, and 3 hours. For example, for an experiment of six hours it may be suggested to sample the system at 0.5, 1, 2, 4, and 6 hours. For example, for an experiment of 12 hours it may be suggested to sample the system at 1, 3, 6, 9, and 12 hours. For example, for an experiment of 24 hours it may be suggested to sample the system at 1, 3, 6, 12, and 24 hours. For example, for an experiment of 48 hours it may be suggested to sample the system at 1, 3, 6, 24, and 48 hours. For example, for an experiment of more than 72 hours it may be suggested to sample the system at 1, 6, 24, 48, and 72 hours. The digital component of the compound distribution kit may also comprise a catalog of frequently asked questions.

An exemplary method may follow the method of an intended experiment or study. As an example, the compound distribution kit may be used with microfluidic devices. An exemplary method for use with microfluidic devices may follow an intended study method with the following changes: no coatings, no cell seeding, and reduced number of compound doses. In one embodiment, there may not be a need to perform coatings on the microfluidic device that are related to biological aspects of the experiment. Some coatings, such as those that change the chemistry of the microfluidic device material makeup, may need to be done, especially if they may affect compound absorbency. It one embodiment, coatings are done with the compound distribution kit at the discretion of the user. In one embodiment, cell seeding is not needed. In one embodiment, if the intended-study protocol compares several concentrations of a test compound, the absorption control experiment need only be run for one of these concentrations. In one embodiment, it is recommended to use the highest compound concentration planned for the intended study, in order to maximize quantification (e.g. LCMS) sensitivity. However, a lower concentration of test compound may be selected if there are concerns about the compound's solubility limits or it crashing out of solution at the higher concentration. Crashing out of solution is when the concentration of a solute in a solution reaches a point where the solute precipitates. In one embodiment, the compound is dosed for the same duration, at the same flow rate, in the same microfluidic channel(s) as per the intended protocol, experiment or study. That is, if the intended study specifies dosing only in a first channel, with no compound in a second channel, then the same method would be applied during the use of the compound distribution kit. In one embodiment, media and solution should be the same during use of the compound distribution kit as in the intended study. In one embodiment, the same media or solution, as well as any additives or supplements, as medium composition and additives can interact with test compounds (e.g. protein binding). In one embodiment, media or solutions should also be equilibrated in the same manner, such as degassing and preheating. In one embodiment, effluent samples taken during use of the compound distribution kit should be collected at the same time as the intended study. Compound distribution can be a highly dynamic process, and as such matching time points may be able to ensure that the results of the compound distribution kit correspond closely to the intended study. In an embodiment where perfusion manifold assemblies are being used, samples may also be taken from each of the input reservoirs once per input media exchanger, at the same time as effluent samples are collected right before exchanging media, aiding in ensuring that no compound is disappearing from the system through an unexpected means, such as compound crashing or photodegradation. In an exemplary embodiment, it is recommended to generate standard curves for LCMS analysis. In one embodiment, a 5-point standard curve in triplicate using a volume of at least 50 μL per sample may be used. Serial dilutions of media used in a first channel and a second channel may be prepared. LCMS may be used to analyze inlet, effluent, blank media and standard curve samples. The results may, in one embodiment, be put into a compound distribution or absorption calculator.

In one embodiment, it may be possible to include the modifications additively to the first experimental protocol, so that the results of the absorption experiment are collected during the intended experiment. This alternative embodiment is still quite useful: it still allows correcting the results of the intended study using the added measurements of compound concentration. It may be considered more efficient to run one experiment instead of two.

An exemplary method of use for the compound distribution kit follows:
1. Media Gas Equilibration
    1. Warm first channel medium and second channel medium in 50 mL conical tubes at 37° C. in a water or bead bath for at least 1 hour
        a. Prepare at least 4 mL of each media type to per microfluidic device—it is recommended to test at least 3 microfluidic devices per compound
        b. Media should be prepared in the same way as the media used when dosing cells with compound, matching all media components/supplements, with the exception of the compound to be tested at this stage
    2. Transfer conical tubes to the biosafety cabinet (BSC) and immediately Steriflip medium:
        a. Connect the 0.45 µm Steriflip unit to the conical tube and apply vacuum to assembled unit for 10 seconds prior to inverting
        b. Invert the assembled Steriflip and ensure that medium passes through the filter in a continuous stream
        c. It should take approximately 2 seconds for each 10 mL of medium to pass through the filter—if it takes longer, stop and see troubleshooting protocol as medium will not be equilibrated properly
    3. Leave the filtered medium under vacuum for 5 minutes
    4. Remove conical tube with medium from Steriflip unit while still under vacuum and then turn off pump. Replace the lid inside the BSC, and immediately place in an incubator or bath to maintain temperature
    5. Store this media with cap slightly loose in the incubator prior to use
2. Microfluidic Device Washing
    1. Unpackage gamma irradiated microfluidic devices in the BSC and place in a 150 mm culture dish
    2. Wash each channel with 200 µL of equilibrated media
        a. Place the pipette tip perpendicular to channel Inlet
        b. Ensure tip is snug in port and introduce media into top and bottom channel
        c. Aspirate outflow liquid from the outlet of the microfluidic device
    3. Aspirate and discard any excess media from the surface of the microfluidic device, but keep channels filled with media
    4. If bubbles are observed anywhere in the microfluidic device channels or ports, aspirate each microfluidic device port to remove media from channels, then reintroduce media.
    5. Place small equilibrated medium droplets on each inlet and outlet
    6. Cover the culture dish and place in the incubator until Pods are primed
3. Perfusion Manifold Assembly Priming
    1. Sanitize the exterior of perfusion manifold assembly packaging with 70% ethanol and transfer perfusion manifold assemblies into the BSC
    2. Retrieve trays from the culture module and sanitize with ethanol before transferring into the BSC
        a. Orient the trays with the handle to the user's left inside the BSC
    3. Open perfusion manifold assembly package in the BSC, and place the perfusion manifold assemblies into the trays
    4. Add 3 mL of equilibrated medium to the appropriate inlet reservoir
    5. Add 300 µL of equilibrated medium to the appropriate outlet reservoir, directly over each outlet via
    6. Prime perfusion manifold assemblies in the culture module
        a. Use the rotary dial to highlight a priming cycle
        b. Press the dial to select a prime cycle
        c. Rotate the dial to a start option and press the dial again to begin the cycle
        d. Close the incubator door and wait 1 minute for the cycle to complete
        e. The status bar will read 'Ready', confirming the cycle is finished
    7. Transfer trays to the BSC
    8. Inspect the underside of each perfusion manifold assembly—observe droplets have formed on all four ports
        a. If any perfusion manifold assembly does not show droplets, re-run a prime cycle on those perfusion manifold assemblies
    9. Set perfusion manifold assemblies aside and retrieve microfluidic devices from the incubator
4. Microfluidic Device to Culture Module and Regulate
    1. Hold perfusion manifold assembly with non-dominant hand
    2. With microfluidic device in dominant hand, slide the arms of microfluidic device carrier into the tracks on the underside of the perfusion manifold assembly until the microfluidic device Carrier is fully seated in the Perfusion manifold assembly
    3. Place thumb on the carrier tab and gently depress tab in and up to engage the tab with the perfusion manifold assembly
    4. Aspirate any excess medium from perfusion manifold assembly window
    5. Place the perfusion manifold assembly with microfluidic device into the tray, with the reservoirs along the back wall
    6. Repeat for each perfusion manifold assembly and microfluidic device Carrier and transfer loaded Tray to Zoë
    7. Select flow rate settings on Zoë
        a. Flow Rate: 30 µL/hr for the top and bottom channel
    8. Run a regulate cycle to reduce bubble formation
        a. The cycle will take 2 hours to complete, after which the culture module switches to the set flowrate
5. Second Regulate Cycle
    1. The following morning of running the regulate cycle, pause the culture module by pressing the silver activation button located over the bays
    2. Slide tray out and transfer to the BSC
    3. Remove perfusion manifold assembly lids and using a 200 µL pipette, perform a via wash on each inlet and outlet perfusion manifold assembly reservoir:
        a. Using media within the perfusion manifold assembly reservoir, pipette 200 µL of media directly over the top of the via to dislodge any bubbles that may be present
        b. Repeat this wash step for each of the four perfusion manifold assembly reservoirs 4. Replace perfusion manifold assembly lids and return the Trays to the culture
5. Run the regulate cycle again
6. Dosing is ready to commence following completion of the second regulate cycle
6. Preparation of Dosing Solution
Note 1: Use the same media with supplements that will be used for running the microfluidic device study for the system absorption test.
1. Refer to the Calculator for Study Design and Data Handling for this portion of the protocol
   a. In a "USER INPUTS" tab, add details of the planned dosing experiment in the designated space (flowrate, duration of study, units of concentration, channel to be dosed with compound).
   b. Use the dropdown menu to select the channel to be dosed with compound
      i. First
      ii. Second
      iii. First and second
2. Prepare the stock solution of compound by dissolving in vehicle of choice, based on the dosing volume indicated in the calculator
3. Dilute stock solution in the appropriate gas-equilibrated media
7. Dosing and Sample Collection
1. Pause the culture module
2. Take trays to the BSC
3. Aspirate the media out of the inlets and outlets making sure to avoid bringing the aspirator tip too close to the vias (there will be a small amount of media remaining near the via and this is acceptable).
4. Refer to the calculator and add total media volume needed to run the study to completion into the top and bottom inlet reservoirs of the perfusion manifold assembly.
5. Sample 50 µL from the top and bottom inlet reservoir of each perfusion manifold assembly to capture the t=0 dosing media concentration.
6. Reserve 200 µL dosing media from the conical as well as "blank" media with no compound for standard curve preparation
   a. Store these samples according to user standard practices
7. Return the tray into the culture module and prime the system with dosing media by setting the flow rate to 600 µL/hr and run for 5 minutes. This replaces the media in the microfluidic device with dosing solution.
8. Pause the culture module and transport trays to the BSC
9. Completely aspirate the effluent collected in the outlet reservoir so as not to dilute the compound effluent collected in the later timepoints.
10. Return the tray to the culture module and set the flow rate as directed in the study. Begin timing for sample collection once flow is initiated on the culture module
11. Use the remaining dosing solution to prepare serial dilutions as samples for a standard calibration curve
    a. It is recommend to generate samples for a 5-point standard curve in a triplicate of volume 50 µL using serial dilutions of the top and bottom media using the following ratios (Dosing solution: Media)
       i. Undiluted media with compound
       ii. 1:10 dilution
       iii. 1:100 dilution
       iv. 1:1000 dilution
       v. Blank (media without compound)
    b. Store these samples according to user standard practices
12. Sample 50 µL from inlet and outlet reservoir at the remaining timepoints until the conclusion of the study
    a. With the exception of the first and last timepoints, subsequent sample times do not require sampling the inlet reservoirs
    b. Handle and process samples per user standard practices
    c. Aspirate outlets completely before returning perfusion manifold assemblies to the culture module
NOTE: In case the volume collected is less than 50 µL, record the volume collected.
13. Send samples to LCMS upon completion of the dosing experiment.
8. Data Analysis
14. Upon sample analysis by LCMS, enter the concentration data into the "User Inputs" sheet in columns D, E, F of the calculator into the appropriate cells
15. View the results in the appropriate tab marked.
    a. Recovered concentrations are plotted with time for both top and bottom channels.
    b. The range of potential cellular exposure concentrations are plotted for each collection time period and both channels.
    c. Tables indicate the range (max and min) cellular exposure concentrations in both channels with time as well as the exposure expressed as a fraction of the dosing concentration.

One embodiment of the present invention is a method of analyzing compound distribution in a system, comprising: a) providing a system and a first experimental protocol for use with said system, said first experimental protocol comprising introducing a compound into said system and taking actions at one or more timepoints; b) modifying said first experimental protocol to generate a first modified experimental protocol; c) measuring compound concentration at one or more of said timepoints from said first experimental protocol; d) performing said first modified experimental protocol; and e) using said measurement of concentration of said compound to analyze compound distribution across said system. In one embodiment, the method further comprises the step of f) performing said first experimental protocol. In one embodiment, said system comprises one or more microfluidic devices. In one embodiment, said system comprises infusion tubing. In one embodiment, said system comprises syringes. In one embodiment, said system comprises one or more biological elements and said first experimental protocol is modified to exclude at least one of said one or more biological elements. In one embodiment, said first experimental protocol comprises compound testing on said biological elements. In one embodiment, said first experimental protocol comprises cells and said first modified experimental protocol does not comprise cells. In one embodiment, said system comprises coatings and said first experimental protocol is modified by excluding coatings. In one embodiment, said first modified experimental protocol does not comprise taking actions at one or more timepoints of said first experimental protocol. In one embodiment, said performing a measurement of the concentration replaces said taking actions at one or more timepoints. In one embodiment, said first modified experimental protocol is modified in that only a subset of input compound concentrations are included in said modified experimental protocol as compared to said first experimental protocol. In one embodiment, said first modified experimental protocol in that porous elements are excluded as compared to said first experimental protocol. In one embodiment, said system includes a first microfluidic device comprising a first membrane with pores. In one embodiment, said system is replaced with a second system in said modified experimental protocol, said second system including a second microfluidic device not comprising a membrane without pores in at least one region in which said first membrane comprises pores. In one embodiment, said first experimental protocol comprises flowing fluid in said system. In one embodiment, said system comprises an input port configured to permit fluid input to the system. In one embodiment, the system comprises an output port configured to permit fluid output from the system. In one embodiment, said first experimental protocol comprises flowing into said input port. In one embodiment, said first experimental protocol comprises collecting a first sample from said output port. In one embodiment, said measuring of the concentration of said compound comprises collecting a sample from said output port and quantifying said concentration of said compound in said sample. In one embodiment, said first modified experimental protocol further quantifies the percentage of said compound that is absorbed into said system. In one embodiment, the method further comprises introducing fluid flow to said system. In one embodiment, said taking actions comprises sampling effluent. In one embodiment, said first experimental protocol further comprises assaying said effluent to achieve an apparent metabolite value. In one embodiment, the method further comprises using said measurement of concentration of said compound to correct said apparent metabolite value. In one embodiment, the method further comprises using said measurement of concentration of said compound to determine variability of said apparent metabolite value. In one embodiment, the method further comprises using said measurement of concentration to determine whether to perform said first experimental protocol. In one embodiment, the method further comprises (i) using said measurement of concentration of said compound to generate a second modified experimental protocol; and (ii) performing said second modified experimental protocol. In one embodiment, said first experimental protocol comprises living cells.

The present invention contemplates, in one embodiment, a method of determining compound distribution in a system, comprising: a) providing a first system and a first experimental protocol for said first system, said first system comprising: i) first fluidic channel; ii) a second fluidic channel; and iii) a first membrane disposed between said first fluidic channel and said second fluidic channel, said first membrane comprising pores; wherein said first experimental protocol comprises introducing a compound into said first system and taking actions at one or more timepoints; b) modifying said first experimental protocol to generate a first modified experimental protocol, by substituting said first membrane with a second membrane, said second membrane lacking pores; c) performing said modified experimental protocol; d) performing a measurement of the concentration of said compound at one or more of said timepoints of said first experimental protocol; and e) comparing said measurement of concentration of said compound to the concentration of said compound to determine compound distribution in said system. In one embodiment, said taking actions comprises sampling an effluent. In one embodiment, the method further comprises said effluent. In one embodiment, said experimental protocol comprises one or more biological elements. In one embodiment, said first experimental protocol is modified by excluding at least one of said biological elements. In one embodiment, said biological elements comprise cells. In one embodiment, said biological elements comprise biological coatings. In one embodiment, said modified experimental protocol determines the compound absorption into said system by calculating the percentage of said compound that is absorbed into the setup of said experimental protocol. In one embodiment, said experimental protocol comprises contacting said one or more biological elements with said compound.

The present invention contemplates, in one embodiment, a method of determining compound distribution in a system, comprising: a) providing a system and an experimental protocol for said system comprising one or more biological elements; wherein said one or more biological elements are contacted by a compound; b) modifying said experimental protocol by excluding at least one of said one or more biological elements; c) performing said modified experimental protocol; and d) determining the distribution of said compound in said system using by measuring the concentration of said compound in said system. In one embodiment, said experimental protocol comprises introducing fluid flow into said system. In one embodiment, the method further comprises collecting effluent. In one embodiment, said experimental protocol comprises assaying said effluent. In one embodiment, said biological elements comprise cells. In one embodiment, said biological elements comprise biological coatings. In one embodiment, said system comprises one or more microfluidic devices. In one embodiment, said distribution of said compound is used to calculate error bars for results from said experimental protocol. In one embodiment, percent distribution of said compound is used to calculate half maximal inhibitory concentration ($IC_{50}$) for said experimental protocol The present invention contemplates, in one embodiment, a method of assessing compound distribution in a system, comprising: a) providing a system and a first experimental protocol for said system, said first experimental protocol comprising introducing a compound into said system; b) modifying said first experimental protocol to generate a modified experimental protocol, said modified experimental protocol comprising: i) introducing said compound using a first concentration; and ii) performing a first measurement of the concentration of said compound; c) performing said modified experimental protocol; d) comparing said measurement of the concentration of said compound to a threshold; e) performing said first experimental protocol if said measurement of concentration surpasses said threshold. In one embodiment, said first experimental protocol further comprises introducing fluid flow into said system. In one embodiment, the first experimental protocol further comprises collecting effluent at one or more time points. In one embodiment, said first experimental protocol comprises assaying said effluent. In one embodiment, said biological elements comprise cells. In one embodiment, said biological elements comprise biological coatings. In one embodiment, said system comprises one or more microfluidic devices. In one embodiment, said first measurement is performed at least one of said one or more time points of said first experimental protocol. In one embodiment, said measurement of the concentration of said compound to a threshold are compared by dividing said first measurement by said first concentration to obtain a first ratio. In one embodiment, the said threshold is a first ratio value above one of 10%, 20%, 33%, 50%, 66%, and 75%. In one embodiment, said modified experimental protocol further comprises measuring an input compound concentration, and wherein the said first measurement is divided by the measured said input concentration to obtain a measured ratio.

One embodiment of the present invention is a method of assessing compound distribution, comprising: a) introducing a flow to a fluidic circuit, said flow comprising an initial concentration of a compound; b) collecting one or more effluent samples from said fluidic circuit; c) determining the concentration of said compound in said one or more effluent samples so as to generate measured concentrations; and d) comparing said measured concentrations with the initial concentration of said compound, thereby assessing compound absorption in said fluidic circuit. In one embodiment, said fluidic circuit comprises one or more microfluidic devices. In one embodiment, said one or more microfluidic devices comprise at least one inlet and/or one outlet. In one embodiment, the fluidic circuit further comprises one or more perfusion manifold assemblies in fluidic communication with said one or more microfluidic devices. In one embodiment, said fluidic circuit comprises infusion tubing. In one embodiment, said fluidic circuit comprises one or more syringes. In one embodiment, said fluidic circuit comprises a polymer that absorbs small-molecules. In one embodiment, said concentrations of said compound in one or more effluent samples are determined using chromatography and/or spectrometry. In one embodiment, said concentrations of said compound in one or more effluent samples are determined using liquid chromatography-mass spectrometry (LCMS). In one embodiment, said compound is a small-molecule compound. In one embodiment, said compound is a drug.

In one embodiment, a method of assessing compound absorption into a system is contemplated, comprising: a) defining an experimental protocol for a system; b) modifying said experimental protocol to exclude biological elements; c) performing said modified experimental protocol to assess compound absorption into said system. A method of assessing compound absorption into a system is contemplated, comprising: a) defining an experimental protocol for a system comprising one or more microfluidic devices comprising one or more porous elements; b) modifying said experimental protocol to substitute said one or more microfluidic devices comprising one or more porous element with one or more microfluidic devices comprising non-porous elements; c) performing said modified experimental protocol to assess compound absorption into said system. A method of assessing compound absorption into a system is contemplated, comprising: a) defining an experimental protocol for a system; b) modifying said experimental protocol by excluding biological elements; c) performing said modified experimental protocol to assess the percent absorption of a compound into said system over time, wherein said percent absorption of said compound is used to calculate error bar calculations for said experimental protocol over the duration of the experiment.

In one embodiment, a method of assessing compound absorption is, contemplated, comprising: a) defining an experimental protocol for a system comprising the use of a compound; b) modifying said experimental protocol to exclude biological elements; c) performing said modified experimental protocol to assess the absorption of said compound into said system; and d) performing said experimental protocol if less than 50% of said compound is absorbed into said system at a time point of interest. In one embodiment, said experimental protocol comprises collecting effluent. In one embodiment, said experimental protocol comprises assaying said effluent. In one embodiment, said biological elements comprise cells. In one embodiment, said biological elements comprise biological coatings. In one embodiment, said system comprises one or more microfluidic devices. In one embodiment, compound absorption into said system is less than 40%. In one embodiment, compound absorption into said system is less than 30%. In one embodiment, compound absorption into said system is less than 20%. In one embodiment, compound absorption into said system is less than 10%. In one embodiment, compound absorption into said system is less than 5%.

In one embodiment, a method of assessing compound distribution in a system is contemplated, comprising: a) providing an experimental or clinical system, b) defining a first experimental protocol for a system, said first experimental protocol comprising introducing a compound into said system and taking actions at one or more timepoints; c) modifying said first experimental protocol to generate a modified experimental protocol, said modified experimental protocol comprising performing a measurement of the concentration of said compound at one or more of said timepoints from said first experimental protocol; d) performing said modified experimental protocol; and e) using said measurement of concentration of said compound to assess compound distribution. In one embodiment, the method further comprises the step of f) performing said first experimental protocol. In one embodiment, said system comprises one or more microfluidic devices. In one embodiment, said system comprises infusion tubing. In one embodiment, said system comprises syringes. In one embodiment, said system further comprises pipette tips. In one embodiment, said system further comprises culture plates. In one embodiment, said system comprises biological elements and said first experimental protocol is modified to exclude biological elements. In one embodiment, said experimental protocol comprises compound testing on said biological elements. In one embodiment, said system comprises cells and said first experimental protocol is modified by excluding cells. In one embodiment, said system comprises coatings and said first experimental protocol is modified by excluding coatings. In one embodiment, said experimental protocol is modified by removing said taking actions at one or more time points. In one embodiment, said performing a measurement of the concentration of said taking actions. In one embodiment, said experimental protocol is modified by selecting only a subset of input compound concentrations to include in said modified experimental protocol. In one embodiment, said experimental protocol is modified by excluding porous elements. In one embodiment, said system includes a first microfluidic device comprising a first membrane with pores; and further comprising replacing said system with a second system, said second system including a second microfluidic device not comprising a membrane without pores in at least one region in which said first membrane comprises pores. In one embodiment, said first experimental protocol comprises flowing fluid in said system. In one embodiment, said system comprises an input port configured to permit fluid input to the system. In one embodiment, the system comprises an output port configured to permit fluid output from the system. In one embodiment, said first experimental protocol comprises flowing into said input port. In one embodiment, said first experimental protocol comprises collecting a first sample from said output port. In one embodiment, said performing a measurement of the concentration of said compound of the said modified experimental protocol comprises collecting a concentration sample from said output port. In one embodiment, said modified experimental protocol further assesses the percentage of said compound that is absorbed into said system. In one embodiment, said taking actions comprises sampling effluent. In one embodiment, said first experimental protocol further comprises assaying said effluent to achieve a result. In one embodiment, said measurement of concentration of said compound to correct said result. In one embodiment, said measurement of concentration of said compound to determine variability of said result. In one embodiment, said measurement of concentration to determine whether to perform said first experimental protocol. In one embodiment, the method further comprises (i) using said measurement of concentration of said compound to generate a second modified experimental protocol; and (ii) performing said second modified experimental protocol. In one embodiment, said system comprises living cells.

In one embodiment, a method of assessing compound distribution in a system is contemplated, comprising: a) defining a first experimental protocol for a first system, said first system comprising: i) first fluidic channel; ii) a second fluidic channel; and iii) a first membrane interspersed in at least one region between said first fluidic channel and said second fluidic channel, said first membrane comprising pores; wherein said first experimental protocol comprises introducing a compound into said first system and taking actions at one or more timepoints; b) modifying said first experimental protocol to generate a modified experimental protocol, by substituting said first membrane with a second membrane, said second membrane lacking pores in at least one corresponding region in which said first membrane comprises pores; wherein said modified experimental protocol comprises performing a measurement of the concentration of said compound at one or more of said time points of said first experimental protocol; c) performing said modified experimental protocol; and d) using said measurement of concentration of said compound to assess compound absorption. In one embodiment, said taking actions comprises sampling an effluent. In one embodiment, the method further comprises assaying said effluent. In one embodiment, said experimental protocol is modified by excluding biological elements. In one embodiment, said biological elements comprise cells. In one embodiment, said biological elements comprise biological coatings. In one embodiment, said modified experimental protocol assesses the compound absorption into said system by assessing the percentage of said compound that is absorbed into the setup of said experimental protocol. In one embodiment, said experimental protocol comprises compound testing on said biological elements.

In one embodiment, a method of assessing compound distribution in a system is contemplated, comprising: a) defining an experimental protocol for a system; b) modifying said experimental protocol by excluding biological elements; c) performing said modified experimental protocol to assess the percent absorption of a compound into said system, wherein said percent absorption of said compound to calculate results for said experimental protocol. In one embodiment, said experimental protocol comprises collecting effluent. In one embodiment, said experimental protocol comprises assaying said effluent. In one embodiment, said biological elements comprise cells. In one embodiment, said biological elements comprise biological coatings. In one embodiment, said system comprises one or more microfluidic devices. In one embodiment, said experimental protocol comprises a compound. In one embodiment, said experimental protocol comprises testing compound on said biological elements. In one embodiment, said percent absorption of said compound is used to calculate error bars for said results from said experimental protocol. In one embodiment, said percent absorption of said compound is used to calculate half maximal inhibitory concentration (IC50) for said experimental protocol The present invention contemplates, in one embodiment, a method of assessing compound distribution in a system, comprising: a) defining a first experimental protocol for a system, said first experimental protocol comprising introducing a compound into said system; b) modifying said first experimental protocol to generate a modified experimental protocol, said modified experimental protocol comprising: i) introducing said compound using a first concentration; and ii) performing a first measurement of the concentration of said compound; c) performing said modified experimental protocol; d) comparing said measurement of the concentration of said compound to a threshold; and e) performing first experimental protocol if said measurement of concentration surpasses said threshold. In one embodiment, said first experimental protocol comprises collecting effluent. In one embodiment, said first experimental protocol comprises assaying said effluent. In one embodiment, said biological elements comprise cells. In one embodiment, said biological elements comprise biological coatings. In one embodiment, said system comprises one or more microfluidic devices. In one embodiment, said first measurement is performed at one or more of the same timepoints as in the first experimental protocol. In one embodiment, said comparing in (d) comprises dividing said first measurement by said first concentration to obtain a first ratio. In one embodiment, said threshold is a first ratio value above one of 10%, 20%, 33%, 50%, 66%, and 75%. In one embodiment, said modified experimental protocol further comprises measuring an input compound concentration, and wherein the said first measurement is divided by the measured said input concentration to obtain a measured ratio.

In one embodiment, a method of assessing compound absorption is contemplated, comprising: a) introducing a compound to a fluidic circuit; b) collecting one or more effluent samples from said fluidic circuit; c) determining the concentration of said compound in said one or more effluent samples so as to generate measured concentrations; and d) comparing said measured concentrations with the concentration of said compound, thereby assessing compound absorption in said fluidic circuit. In one embodiment, said fluidic circuit comprises one or more microfluidic devices. In one embodiment, each of said one or more microfluidic devices comprise at least one inlet. In one embodiment, each of said one or more microfluidic devices comprise at least one outlet. In one embodiment, said fluidic circuit comprises one or more perfusion manifold assemblies in fluidic communication with said one or more microfluidic devices. In one embodiment, said fluidic circuit comprises infusion tubing. In one embodiment, said fluidic circuit comprises one or more syringes. In one embodiment, said fluidic circuit comprises a polymer that absorbs small-molecules. In one embodiment, said concentrations of said compound in one or more effluent samples are determined using chromatography and/or spectrometry. In one embodiment, said concentrations of said compound in one or more effluent samples are determined using liquid chromatography-mass spectrometry (LCMS). In one embodiment, said compound is a small-molecule compound. In one embodiment, said compound is a drug. In one embodiment, said fluidic circuit further comprises one or more perfusion manifold assemblies. In one embodiment, said fluidic circuit further comprises at least one inlet.

In one embodiment, a workflow or method of use for an compound distribution kit may comprise the steps of (1)

prepare microfluidic devices and perfusion manifold assemblies for use with a culture module, (2) prepare one or more dosing solutions for calibration, (3) dose microfluidic devices and perfusion manifold assemblies, (4) collect effluent at desired time points, (5) quantify effluent compound concentration, and (6) assess system absorption of compound. A method of assessing compound absorption is contemplated, comprising: a) providing a compound, a stock solution and a fluidic circuit comprising a fluidic device and at least one inlet and at least one outlet; b) combining said compound and said stock solution so as to prepare a dosing solution and a plurality of calibration solutions; c) introducing at least a portion of said dosing solution into said fluidic device at one or more of said at least one inlet; d) collecting one or more effluent samples from one or more of said at least one outlet; e) determining the concentration of said compound in said one or more effluent samples so as to generate measured concentrations; and f) comparing said measured concentrations with the concentration of said compound in said plurality of calibration solutions, thereby assessing compound absorption in said fluidic circuit. In one embodiment, said concentrations of said compound in one or more effluent samples are determined using chromatography and/or spectrometry. In one embodiment, said concentrations of said compound in one or more effluent samples are determined using liquid chromatography-mass spectrometry (LCMS). In one embodiment, said compound is a small-molecule compound. In one embodiment, said compound is a drug. In one embodiment, said calibration solutions comprise a five-point calibration. In one embodiment, said fluidic circuit further comprises one or more perfusion manifold assemblies.

In one embodiment, a method of assessing compound absorption into a flow system is contemplated comprising: a. providing one or more microfluidic devices, one or more perfusion manifold assemblies, one or more culture modules, a compound, and a stock solution; b. preparing one or more dosing solutions and one or more calibration solutions by dosing said stock solution with said compound; c. priming said one or more microfluidic devices and said one or more perfusion manifold assemblies with said stock solution; d. fluidically connecting said one or more microfluidic devices, said one or more perfusion manifold assemblies, and said one or more culture modules as to create a flow system; e. replacing said stock solution with said dosing solution in said one or more microfluidic devices and said one or more perfusion manifold assemblies; f. collecting a plurality of effluent solutions at one or more time points; g. determining the concentration of said compound in said plurality effluent solutions; and h. comparing the concentration of said compound in said plurality of effluent solutions and said one or more calibration solutions, thereby assessing compound absorption into said flow system. In one embodiment, said one or more microfluidic devices each comprise at least one inlet and at least one outlet. In one embodiment, said one or more perfusion manifold assemblies each comprise at least one inlet and at least one outlet. In one embodiment, said concentrations of said compound in said plurality of effluent samples are determined using chromatography and/or spectrometry. In one embodiment, said concentrations of said compound in said plurality of effluent samples are determined using liquid chromatography-mass spectrometry (LCMS). In one embodiment, said compound is a small-molecule compound. In one embodiment, said compound is a drug. In one embodiment, said one or more calibration solutions comprise a five-point calibration.

In one embodiment, a method of assessing compound absorption into a flow system is contemplated comprising: a. providing one or more microfluidic devices, one or more perfusion manifold assemblies, at least one culture module, a compound, and a stock solution; b. preparing said one or more microfluidic devices and said one or more perfusion manifold assemblies for use with said one or more culture modules by: i. priming said one or more microfluidic devices with said stock solution; and ii. fluidically connecting said one or more microfluidic devices to said one or more perfusion manifold assemblies, and said one or more perfusion manifold assemblies to said at least one culture module as to create a flow system; c. preparing a dosing solution and one or more calibration solutions by dosing said stock solution with said compound; d. introducing said dosing solution into said one or more microfluidic devices by: i. fluidically disconnecting said one or more perfusion manifold assemblies from said at least one culture module; ii. replacing said stock solution with said dosing solution; and iii. fluidically connecting said one or more perfusion manifold assemblies to said at least one culture module; e. sampling effluent from said flow system at one or more time points to create one or more effluent samples; d. determining the concentration of said compound in said one or more calibration solutions, said one or more effluent samples, said dosing solution, and said stock solution; and e. comparing the concentration of said compound in said one or more calibration solutions, said one or more effluent samples, said dosing solution, and said stock solution, thereby assessing compound absorption into said flow system.

In another embodiment, a method of assessing compound absorption into a flow system is contemplated comprising: a. providing one or more microfluidic devices, one or more perfusion manifold assemblies each comprising at least one inlet reservoir and at least one outlet reservoir, at least one culture module, a compound, and a stock solution; b. preparing microfluidic devices and perfusion manifold assemblies for use with said at least one culture module by: i. degassing said stock solution using a filter; ii. washing said one or more microfluidic devices with said stock solution; iii. priming one or more perfusion module assemblies by partially or completely filling said at least one inlet reservoir and said at least one outlet reservoir with said degassed stock solution; and iv. fluidically connecting said one or more microfluidic devices with said one or more perfusion manifold assemblies and fluidically connecting said one or more perfusion manifold assemblies with said at least one culture module as to create a flow system; c. preparing a dosing solution by dosing said stock solution with said compound; d. introducing said dosing solution into said one or more microfluidic devices and said one or more perfusion manifold assemblies by: i. fluidically disconnecting said one or more perfusion manifold assemblies from said at least one culture module and removing any of said stock solution left in said at least one inlet reservoir; ii. partially or completely filling said at least one inlet reservoir with said dosing solution and setting aside a portion of each of said dosing solution and said stock solution; iii. fluidically connecting said one or more perfusion manifold assemblies to said at least one culture module and flushing said at least one culture module at a high flow rate for at least five minutes; iv. stopping said at least one culture module from running, fluidically disconnecting said one or more perfusion manifold assemblies from said at least one culture module, and aspirating the resulting effluent from said at least one outlet reservoir; v. fluidically connecting said one or more perfusion manifold assemblies to said at least one culture module, running said at least one culture module at a low flow rate for a desired period of time; and vi. sampling from said at least one inlet reservoir and said at least one outlet reservoir at planned time points to yield one or more samples; e. preparing a plurality of calibration solutions for a five-point standard curve, said plurality of calibration solutions comprising i. at least one sample of undiluted dosing solution, ii. at least one sample of a 1:10 dilution of said dosing solution to said stock solution, iii. at least one sample of a 1:100 dilution of said dosing solution to said stock solution, iv. at least one sample of a 1:1000 dilution of said dosing solution to said stock solution, and v. at least one sample of said stock solution, f. determining the concentration of said compound in said plurality of calibration solutions, said one or more samples, said dosing solution, and said stock solution through using chromatography and/or spectrometry; and g. comparing the concentration of said compound in said one or more calibration solutions, said one or more samples, said dosing solution, and said stock solution, thereby assessing compound absorption into said flow system.

In one embodiment, a workflow or method of use for an compound distribution kit may comprise the steps of (1) prepare one or more microfluidic devices and perfusion manifold assemblies for use with a culture module by (a) washing said one or more microfluidic devices with a media and (b) fluidically connecting said one or more microfluidic devices with at least culture module, (2) prepare one or more dosing solutions by (a) preparing stock solutions and (b) dosing said stock solution with a compound, (3) dose microfluidic devices and perfusion manifold assemblies by (a) fluidically disconnecting said one or more perfusion manifold assemblies from said at least one culture module, (b) replacing said media with said at least one dosing solution, and (c) fluidically connecting said one or more perfusion manifold assemblies from said at least one culture module, (4) quantifying sample compound concentration by (a) taking sample solutions from said outlet reservoirs at one or more timepoints (b) preparing a plurality of calibration solutions for a calibration curve and (c) analytically quantifying the concentration of said compound in all of said sample solutions and said plurality of calibration solutions and (5) analytically assessing compound absorption by comparing the concentration of said compound in said plurality of said calibration solutions to the concentration of said compound in said one or more sample solutions.

In one embodiment, a workflow or method of use for an compound distribution kit may comprise the steps of (1) prepare microfluidic devices and perfusion manifold assemblies, comprising at least one inlet reservoir and at least one outlet reservoir, for use with a culture module by (a) degassing media using a filter and (b) washing said one or more microfluidic devices with said degassed media, and (c) fluidically connecting said one or more microfluidic devices with said culture module by (i) priming one or more perfusion module assemblies with said degassed media by filling said at least one inlet reservoir and at least one outlet reservoir with media, (ii) fluidically connecting said one or more microfluidic devices with said one or more perfusion manifold assemblies, and (iii) placing said one or more perfusion manifold assemblies in fluidic communication with at least one culture module, (2) prepare a dosing solution by (a) preparing a stock solution and (b) dosing said stock solution with a compound as to create a dosing solution, (3) dose microfluidic devices and perfusion manifold assemblies by (i) fluidically disconnecting said one or more perfusion manifold assemblies from said at least one culture module and removing any media left in said at least one inlet reservoir, (ii) filling said at least one inlet reservoir with said dosing solution and setting aside a portion of each of said dosing solution and said stock solution, (iii) fluidically connecting said perfusion manifold assemblies to said at least one culture module and flushing said at least one culture module at a high flow rate for five minutes, (iv) stopping said at least one culture module from running, removing said one or more perfusion manifold assemblies from said at least one culture module and aspirating the resulting effluent from said at least one outlet reservoir, (v) fluidically connecting said one or more perfusion manifold assemblies to said at least one culture module, and (vi) sampling from said inlet and outlet reservoirs at planned timepoints to yield one or more sample solutions, (4) quantifying sample compound concentration by (a) preparing a plurality of calibration solutions for a five point standard curve, said plurality of calibration solutions comprising (i) at least one sample of undiluted dosing solution, (ii) at least one sample of a 1:10 dilution of said dosing solution to said stock solution, (iii) at least one sample of a 1:100 dilution of said dosing solution to said stock solution, (iv) at least one sample of a 1:1000 dilution of said dosing solution to said stock solution, and (v) at least one sample of said stock solution, (b) analytically quantifying the concentration of said compound across said plurality of calibration solutions and said one or more sample solutions, and (5) analytically assessing compound absorption by comparing the concentration of said compound in said plurality of said calibration solutions to the concentration of said compound in said one or more sample solutions using an absorption calculator.

The present invention is also related to gas distribution within microfluidic devices. Several methods are contemplated for controlling gas distribution within microfluidic devices.

One embodiment contemplated to control gas is a microfluidic device comprising one or more gas-exchange channels to flow a fluid, either a gas or liquid, and exchange gas between a gas source and another one or more channels within a microfluidic device. The gas-control microfluidic device allows the gas concentration within a gas-permeable microfluidic device to be controllable. A gas, such as oxygen, nitrogen, helium, carbon dioxide, a mixture thereof, a smoke, a vapor, etc., may be introduced into the gas channels of the microfluidic device. The body of the microfluidic device comprises a permeable material, such as PDMS. The gas may transport through the body of the microfluidic device into the working or cell channels of the microfluidic device. Cell viability may be improved when the cells are cultured in similar environments that they experience in vivo. As such, the ability to introduce in vivo relevant gas concentrations to the cells within the microfluidic device allows scientists to achieve better experimental results. For example, if an anaerobic environment is desired for the channels, nitrogen may be flowed through the gas channels. For another example, if a highly oxygenated environment is desired for the channels, oxygen may be flowed through the gas channels.

In one embodiment, a microfluidic device comprises a body having a culture channel, a gas-exchange channel, and a gas exchanger between said culture channel and said gas-exchange channel. In one embodiment, said gas-exchange channel comprises a gas. In one embodiment, said gas-exchange channel comprises a fluid or liquid.

Another embodiment contemplated to control gas is a "halo chip," a microfluidic device with the capability of creating a desired gaseous environment within the channels of the microfluidic device. The "halo chip" or gas control microfluidic device has a gas channel or gas-exchange channel that runs around the perimeter of the working or cell channels of the microfluidic device. In one embodiment, said gas-exchange channel comprises a gas. In one embodiment, said gas-exchange channel comprises a fluid.

In one embodiment, the gas control microfluidic device may also comprise a check valve to allow the gas to leave the microfluidic device. Further, the gas control microfluidic device may also comprise vacuum channels. When vacuum is applied to the vacuum channels the microfluidic device may stretch to emulate cellular physiology in vivo. The gas control may also comprise sensors, such as oxygen sensors, in order to monitor the gas levels within the microfluidic device.

In one embodiment, a microfluidic device is contemplated, comprising: a) one or more fluidic channels; b) gas channels around at least a portion of the perimeter of said one or more fluidic channels, separated from said one or more fluidic channels by a gas-permeable wall. In one embodiment, said microfluidic device comprises polydimethylsiloxane (PDMS). In one embodiment, said microfluidic device further comprises a valve in contact with said gas channels. In one embodiment, said microfluidic device further comprises sensors. In one embodiment, said gas channels are around the entire perimeter of said working channels.

The present invention contemplates, in one embodiment, a method of controlling gas transport, comprising: a) providing a microfluidic device comprising i) one or more fluidic channels, and (ii) gas channels around at least a portion of the perimeter of said one or more fluidic channels, separated from said fluidic channels by a gas-permeable wall; c) introducing a fluid into said one or more fluidic channels at a flow rate; b) introducing a non-oxygen gas into said gas channels as to control the gas transport into said fluid. In one embodiment, said microfluidic device comprises polydimethylsiloxane (PDMS). In one embodiment, said microfluidic device further comprises a valve in contact with said gas channels. In one embodiment, said microfluidic device further comprises sensors. In one embodiment, said gas channels are around the entire perimeter of said working channels.

Another embodiment contemplated to control gas within microfluidic devices is using anaerobic cell culture incubators. A gas-permeable microfluidic device, may be controlled using a gas-controlled or anerobic cell culture incubator, in some embodiments in conjunction with perfusion manifold assemblies and culture modules. A silicone material, such as PDMS, allows rapid gas exchange between the channels within the microfluidic device and the external environment of the microfluidic device, since the incubator volume/gas supply may be considered infinite compared to the small volume of a microfluidic device. The incubator conditions, in most instances, will define the gas microenvironment experienced by the cells within the microfluidic device, regardless of fluid flow rate. There are generally three major sources for gas transport within a microfluidic device: incubator/environment air, dissolved gas in flowing fluid/media entering the microfluidic device, and cellular metabolism/processes.

Cellular gas uptake and release is an important factor of the gas microenvironment and differs between cell types. Oxygen delivery through cell culture media alone is insufficient to maintain many cell types, thus the main oxygen source is the transport through a gas-permeable material. The maximum hepatocyte uptake rate in microfluidic devices, based on literature values and scaled to the cell culture area of microfluidic device of U.S. Pat. No. 8,647,861, may be considered to be 88 nmol/hr. Colonic oxygen uptake rate in microfluidic devices may be considered to be 2,020 nmol/hr, based on literature values and scaled to the culture area of the microfluidic device of U.S. Pat. No. 8,647,861. However, oxygen delivery through media flow alone is only 5.8 nmol/hr, calculated based on the carrying capacity of water for oxygen and a flow rate of 304/hr. Oxygen delivery through a PDMS microfluidic device, such as that present in U.S. Pat. No. 8,647,861, may be considered to be 574 nmol/hr, which is a significant improvement on the oxygen delivery rate of media flow alone. A system is contemplated, comprising a gas-permeable microfluidic device having at least one channel, wherein said gas-permeable microfluidic device is disposed in a gaseous environment. In one embodiment, said gaseous environment is controlled by an incubator. In one embodiment, said gaseous environment is controlled by a hypoxic incubator. In one embodiment, said gaseous environment is a hypoxic environment. In one embodiment, said gaseous environment is a hyperoxic environment. In one embodiment, said system is configured such that said gaseous environment controls the gas concentration in said gas-permeable microfluidic device. In one embodiment, said channel comprises a membrane. In one embodiment, said channel comprises cells.

In another embodiment, a method is contemplated of controlling the gas concentration within a microfluidic device comprising: (i) providing a microfluidic device comprising at least one channel; (ii) placing said microfluidic device in a gaseous environment, such that said at least one channel assumes the gas concentration of said gaseous environment. In one embodiment, said method further provides an incubator, and wherein said gaseous environment is controlled by said incubator. In one embodiment, said incubator is a gas-controlled incubator. In one embodiment, said gaseous environment is a hypoxic environment. In one embodiment, said gaseous environment is a hyperoxic environment. In one embodiment, said microfluidic device is gas-permeable. In one embodiment, said channel comprises a membrane. In one embodiment, said channel comprises cells. In one embodiment, said cells comprise epithelial cells. In one embodiment, said cells comprise endothelial cells.

DEFINITIONS

The term "microfluidic" as used herein, relates to components where moving fluid is constrained in or directed through one or more channels wherein one or more dimensions are 1 mm or smaller (microscale). Microfluidic devices are described in the U.S. Pat. No. 8,647,861, and the International Patent App. No. PCT/US2014/071611, the contents of each are incorporated herein by reference (such microfluidic devices are also referred to herein as "chips"). Microfluidic channels may be larger than microscale in one or more directions, though the channel(s) will be on the microscale in at least one direction. In some instances, the geometry of a microfluidic channel may be configured to control the fluid flow rate through the channel (e.g. increase channel height to reduce shear). Microfluidic channels can be formed of various geometries to facilitate a wide range of flow rates through the channels.

The phrases "connected to," "coupled to," "in contact with," and "in communication with" as used herein, refer to any form of interaction between two or more entities, including mechanical, electrical, magnetic, electromagnetic, fluidic, and thermal interaction. For example, in one embodiment, channels in a microfluidic device are in fluidic communication with a fluid source such as a fluid reservoir. Two components may be coupled to each other even though they are not in direct contact with each other. For example, two components may be coupled to each other through an intermediate component (e.g. tubing or other conduit). Thus, a working fluid in a rigid container can be in fluidic communication with a working fluid reservoir via tubing or other conduit.

The term "channels" as used herein, are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

"Microchannels" are channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances, the geometry of a microfluidic channel may be configured to control the fluid flow rate through the channel (e.g. increase channel height to reduce shear). Microfluidic channels can be formed of various geometries to facilitate a wide range of flow rates through the channels.

The present invention contemplates a variety of "microfluidic devices," including but not limited to microfluidic device, perfusion manifold assemblies (without microfluidic devices), and perfusion manifold assemblies engaged with microfluidic devices. However, the methods described herein for engaging microfluidic devices (e.g. by drop-to-drop connections), and for perfusing microfluidic devices are not limited to the particular embodiments of microfluidic devices described herein, and may be applied generally to microfluidic devices, e.g. devices having one or more microchannels and ports.

A surface or a region on a surface is "hydrophobic" when it displays (e.g. advancing) contact angles for water greater than approximately ninety (90) degrees (in many cases, it is preferable that both advancing and receding contact angles are greater than approximately 90 degrees). In one embodiment, the hydrophobic surfaces of the present invention display advancing contact angles for water between approximately ninety (90) and approximately one hundred and ten (110) degrees. In another embodiment, hydrophobic surfaces have regions displaying advancing contact angles for water greater than approximately one hundred and ten (110) degrees. In another embodiment, hydrophobic surfaces have regions displaying receding contact angles for water greater than approximately 100 degrees. It is important to note that some liquids, and particularly some biological liquids, contain elements that may coat a surface after wetting it, thereby affecting its hydrophobicity. In the context of the present invention, it may be important that a surface resists such coating from a liquid of intended use, for example, that such coating does not create an advancing and/or receding contact angle that is less than 90 degrees over the duration that the surface remains wetted by the said liquid.

A surface or a region on a surface is "hydrophilic" when it displays (e.g. advancing) contact angles for water less than approximately ninety (90) degrees, and more commonly less than approximately seventy (70) degrees (in many cases it is preferable that both the advancing and receding contact angles are less than approximately 90 degrees or approximately 70 degrees).

Measured "contact angles" can fall in a range, i.e. from the so-called advancing (maximal) contact angle to the receding (minimal) contact angle. The equilibrium contact is within those values, and can be calculated from them.

Hydrophobic surfaces "resist wetting" by aqueous liquids. A material is said to resist wetting by a first liquid where the contact angle formed by the first liquid on the material is greater than 90 degrees. Surfaces can resist wetting by aqueous liquids and non-aqueous liquids, such as oils and fluorinated liquids. Some surfaces can resist wetting by both aqueous liquids and non-aqueous liquids. Hydrophobic behavior is generally observed by surfaces with critical surface tensions less than 35 dynes/cm. At first, the decrease in critical surface tension is associated with oleophilic behavior, i.e., the wetting of the surfaces by hydrocarbon oils. As the critical surface tensions decrease below 20 dynes/cm, the surfaces resist wetting by hydrocarbon oils and are considered oleophobic as well as hydrophobic.

Hydrophilic surfaces "promote wetting" by aqueous liquids. A material is said to promote wetting by a first liquid where the contact angle formed by the first liquid on the material is less than 90 degrees, and more commonly less than 70 degrees.

As used herein, the term "shear stress" in general refers to an applied force per unit area, acting parallel to a surface element. "Shear" or "shear stress" refers to a force on an object parallel to the face of an object. Shear stress is primarily caused by friction between fluid particles, related to fluid viscosity, and a component of shear strain. t (Greek: tau) refers to a combined effect of viscosity and relative velocities where the stress is parallel to the surface of the material, as opposed to normal stress when the stress is perpendicular to the surface. Shear stress is relevant to the motion of fluids upon surfaces, which result in the generation of shear stress. the shear stress (o). As an example, fluid flow across the surface of a cell may exert shear stress on said cell.

As used herein, the term "shear rate" or "shear strain" refers to the rate of change of velocity at which one layer of fluid passes over an adjacent layer. "Shear rate" is also referred to as y, (Greek: gamma G) or "rate of shear". In a non-Newtonian fluid, such as blood, the relationship between shear stress and shear rate is different.

A "gas exchanger" refers to a mechanical or chemical component, such as comprised within a microfluidic device, which allows the transport of gas. The gas exchanger may alternatively be known as a "gas transport membrane," "gas exchange membrane," or "gas control membrane."

"Metabolism" is a chemical process that occurs within a living organism, such as a cell, in order to maintain life. "Cellular metabolism" is "metabolism" specific to cells. For example, a cell may metabolize a pharmaceutical compound.

A "manifold" is a physical component of a system that takes in a fluid (gas or liquid) and splits the flow of that fluid into multiple flow routes. An example of a "manifold" is a pipe, chamber, or channel that branches into several new openings.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result. It may be advantageous to use reciprocating flow, meaning that a volume of fluid is alternately introduced into and then withdrawn from the microfluidic device or from a portion of the microfluidic device, such as a channel or chamber. In such cases, the reciprocating flow may be driven by a device that is connected or in fluidic communication with the microfluidic device or with a portion of the microfluidic device.

As used herein, the terms "molecules," "particles," and "particulates" refers broadly to a constituent of matter, both viable and non-viable. As one example, a particle refers to a cell, such as a cell within a fluid, including both cells normally present in the blood of healthy patient (white cell, red cell, platelets, etc.), cells not normally present into the bloodstream such as circulating tumor cells. However, the fluid is not limited to blood, i.e. cells are found in fluids, such as macrophages found in lung fluid, etc. As another example, a particle refers to microorganisms, e.g., spores, virions, bacterium, such as found in normal flora or present in diseased states, and microscopic physical particles/particulates, including but not limited to pollutants, as well as any physical particles/particulates that could enter the blood stream or other bodily fluid. Particles also include beads and the like, which can be conveniently used in some embodiments in place of cells in order to take measurements or otherwise evaluate a parameter, e.g. flow rate, buoyancy, viscosity, shear, etc.

The term "small molecule" refers to a molecule below the molecular weight of 1 kDa.

A "xenobiotic" is a molecule that does not typically occur in the human body, and may be considered a chemical. Xenobiotics are typically smaller than biologics, which are typically found to be naturally occurring the human body. A xenobiotic is generally below the size of 1 kDa.

The term "rigid," when applied to polymers, refers to a polymer with a modulus of elasticity, or Young's Modulus, or flexural modulus, above 0.1 GPa.

The term "elastomeric" or "flexible," when applied to polymers, refers to a polymer with a modulus of elasticity, or Young's Modulus, or flexural modulus, below 0.1 GPa.

The term "gas-permeable" refers to a polymer which largely allows the transport of gases through its material makeup.

The term "gas-impermeable" refers to a polymer which does not largely allow the transport of gases through its material makeup.

The term "low-absorbing" refers to a polymer which does not largely allow for the absorption of xenobiotics or small molecules into its material makeup.

The term "absorbing" refers to a polymer which does largely allow for the absorption of xenobiotics or small molecules into its material makeup. The term "solid substrate" as used herein, refers to a substrate that may be biological, nonbiological, organic, inorganic, or a combination of any of these, existing as particles, strands, precipitates, gels, sheets, tubing, spheres, containers, capillaries, pads, slices, films, plates, slides, etc. The solid substrate is preferably flat but may take on alternative surface configurations. For example, the solid substrate may contain raised or depressed regions, such as microfluidic channels and/or inlet and outlet ports. For example, the substrate may be functionalized glass, Si, Ge, GaAs, GaP, Sioxygen, SiN4, modified silicon, nitrocellulose and nylon membranes, or any one of a variety of gels or polymers such as (poly) tetrafluoroethylene, (poly)vinylidendifluoride, polystyrene, polycarbonate, or combinations thereof. Other suitable solid substrate materials are be readily apparent to those of skill in the art. The surface of the solid substrate may also contain reactive groups, which could be carboxyl, amino, hydroxyl, thiol, or the like. More preferably, the surface will be optically transparent and will have surface Si—OH functionalities, such as are those found on silica surfaces.

The term "porous membrane" as used herein, refers to a material that is flexible, elastic, or a combination thereof with pores large enough to only permit exchange of gases and small chemicals, or large enough to permit migration and transchannel passage of large proteins, and/or portions thereof. The membrane may also be designed or surface patterned to include micro and/or nanoscopic patterns therein such as grooves and ridges, whereby any parameter or characteristic of the patterns may be designed to desired sizes, shapes, thicknesses, filling materials, and the like.

The term "chamber" as used herein, refers to an isolated region of a microchannel that is separated by a porous membrane. For example, the porous membrane may extend longitudinally down the midpoint of a microchannel thereby providing an upper chamber and a lower chamber.

The term "media" refers to a liquid for conveying a substance. In one embodiment, the substance is nutritive, such as in a culture medium.

The term "valve" refers to a mechanical component that can control fluid flow. Diaphragm valves (or membrane valves) consists of a valve body with two or more ports, a diaphragm, and a "weir or saddle" or seat upon which the diaphragm closes the valve.

As used herein, the term "rheology" refers to the flow and deformation of fluids, gases and solids under the influence of mechanical forces. In other words, rheology may be referred to as physics relating to non-Newtonian flow and Newtonian flow of liquids, soft solids, solids and gases.

As used herein, the term "biomimetic" or "biomimicry" refers to materials, e.g. fluids, membranes, etc., synthetic systems, synthetic devices, machines etc., that have functions that mimic a biological process or biological component, e.g. blood, intestinal contents, lung fluid, etc.

The term "transparent," generally refers to the ability of light to pass through. For example, a microfluidic device may be considered transparent if light is able to pass through the body of the microfluidic device and the contents of the channels may be able to be seen by a standard light microscope.

The term "crash out" or "crashing out of solution" refers to when the concentration of a solute or compound in a solution reaches a point where the solute or compound precipitates out of the solution, forming a solid.

It is not intended that the present invention be limited by the nature of the indentations. The term "indentation" as used herein, refers to a space, cavity, dent, crater, well, depression, hollow, recess or impression that is formed in the surface. In a preferred embodiment, indentations do not extend through the entire thickness of a surface. While a hole can be an indentation, the hole preferably does not extend completely through the surface. In one embodiment, each of said indentations has a depth that extends up to the midpoint of said first or second element (i.e. the depth of the indentation is equal to or less than one-half the thickness of the surface). In one embodiment, said second surface is crenellated and the gaps comprise said indentations. In another embodiment, the indentations have raised edges. The term "raised edge" means that the edge of the indentation rises above the plane of the surface. In one embodiment, there are particles in the indentations (e.g. beads). It is not intended that the present invention be limited by the manner in which the indentations are manufactured. In one embodiment, the indentations are introduced into the surface by treating the surface (e.g. etching a surface of glass, silicon or otherwise etchable surface). In another embodiment, the indentations are introduced by casting or molding. In a preferred embodiment, the indentations are integrally molded using a polymeric surface (e.g. plastic). The term "integrally molding" as used herein refers to the method of casting such that features are of unitary construction. The term "unitary construction" refers to an association of elements (e.g. the surface and the indentations) such that they are formed from the same piece of raw material without the need for further integration. In one embodiment, the first surface comprises plastic and has indentations. In one embodiment, said first surface is elastomeric.

As used herein, the term "gas transport" refers to the passage of a gas through a material or the passage of gas from one area to another. The "rate of gas transport" refers the measure of flow of gas through a material or from one area to another. The rate may refer to either volumetric flow rate or mass flow rate. Volumetric flow rate is the volume of fluid which passes per unit time. Mass flow rate is the mass of a substance which passes per unit of time.

The term "diffusion" refers to the movement of molecules or atoms from a region of higher concentration to a region of lower concentration.

The term "gradient" refers to an increase or decrease in the magnitude of a property. For example, a chemical potential gradient would be the change in chemical potential across a system.

The term "adsorption" refers to the process by which a solid holds the molecules of a gas or liquid or solute as a film on its surface.

As used herein, the term "fluid" refers to either a liquid or gas, which is unable to hold a fixed shape and yields easily to external pressure. As used herein, the term "fluid flow" refers to the movement of a fluid. As used herein, the term "fluid flow rate" refers to the measure of flow of a fluid.

A channel may be considered "open" if it lacks at least one wall in at least one portion of the channel. Likewise, an open channel may be "capped" or covered with another object or material.

As used herein, the term "porosity" refers to the quality of being porous, or comprising holes. The term "pores" refers to those holes. The term "porous elements" refers to components of a system which comprise pores, and therefore have a porosity.

A "cap" is an object or material that covers or "caps" another. A "capping layer" is a sheet or film which covers an invention component.

A "wall," such as a "channel wall," is a barrier or enclosure of a hollow area.

As used herein, the term "surface" refers to the outermost portion of an object, such as the portion of an object in contact with another component. For example, a fluid may contact the surface of a channel, wherein that surface is a wall of the channel.

As used herein, the term "layer" refers to a flat or thin component, material, or object. For example, a sheet or film may be referred to as a layer.

As used herein, the term "side" refers to a surface which generally opposes another surface. A "surface" may also be a position to the left or right of an object or central point.

As used herein, the term "membrane" refers to a component or material which allows the passage of molecules, fluids, cells, etc. through it As used herein, the term "sheet" refers to a thin material. As used herein, the term "film" also may refer to a thin material. The terms sheet and film are interchangeable herein. The term "film" may also refer to a very thin liquid or layer of biological material, such as bacteria. The term "thin film" refers to a film of remarkable thinness, such as below 10 µm.

The term "maintain" refers to keeping a commodity or variable, such as a rate of gas transport or a flow rate of media, relatively constant.

The term "resistant" refers to a material or component that is generally impervious to manipulation by another substance. However, the term resistant is qualified as largely impervious, such that the material or component is not manipulated by the majority of another substance. There exists no entirely perfect material or structure. For example, a polymer may be resistant to small molecule absorption. The resistance of that polymer is compared to polymers that are known to absorb.

The term "cells" refers to the smallest structural and functional unit of an organism, such as a human. Cells may be "cultured" or grown on a surface or in an environment, such as within a microfluidic device.

A "gas concentration profile" refers to the gradient of gas molecules in volume or the curve that results when the concentration of a gas is plotted versus position in that volume.

Liver oxygen zonation is the gradient of oxygenation within a liver environment. That gradient may be divided or designated to levels, such that some are considered aerobic and some are considered anaerobic.

As used herein, the term "hypoxic" refers to an environment that is low in oxygen.

As used herein, the term "lumen" refers to the inside space of a tubular structure.

As used herein, the term "contact" refers to one material, substance, fluid, object, etc. touching another. For example, a fluid in a channel contacts the walls of the channel. For example, a tube may contact the inlet of a microfluidic device.

As used herein, the term "substantially free" refers to an environment that has a low concentration of a substance, such as a molecule, fluid, a particular gas, etc.

As used herein, the term "penetrate" refers to one material filling or entering another.

As used herein the term "cure" or "cured" refers to the solidification, toughening, hardening, and/or cross-linking of a material, such as a polymer. Curing may be initiated by heat, radiation, electron beams, chemical additives, the absence of a particular compound or gas, etc. Conversely, the term "uncured" refers to a material that has not yet been cured, solidified, toughened, hardened, and/or cross-linked.

The term "coating" refers to one material or substance that covers another. The term "biological coating" refers to a coating that is biological in nature or serves a biological purpose, such as interacts with cells, etc.

The term "excess" refers to a surplus of a material, component or substance.

The term "fabricate" refers to the creation, building, construction or manufacturing of a component, such as to fabricate a microfluidic device.

As used herein, the term "by volume" or "percent by volume" refers to a measure of a value, such as concentration, with regards to the total volume of a body or solution.

As used herein, the term "experimental protocol" refers to the directions on how to set up and conduct an experiment.

As used herein, the term "modified experimental protocol" refers to an experimental protocol that has been altered from its original form.

As used herein, the term "setup" refers to the way in which equipment or experiments are organized, planned and/or arranged.

As used herein, the term "intended study" refers to an experimental protocol, also known as a study, as it is proposed to be run or executed.

As used herein, the term "infusion tubing" refers to tubing used to administer intravenous drugs.

As used herein, the term "syringe" refers to a piece of medical and experimental equipment comprising a nozzle and piston or bulb used suck in and eject liquid in a stream.

As used herein, the term "biological elements" refers to components of an invention which are biological in nature such as cells or extracellular matrix.

As used herein, the term "taking actions" refers to active steps taken by the user of a method.

As used herein, the term "concentration" refers to the amount of a substance, such as a compound or drug, per defined space. The term "apparent concentration" refers to the concentration of a substance without taking into account variability, such as absorption into the system.

As used here, the term "input" refers to the inlet of a system or that which is put into a system.

As used herein, the term "output" refers to the outlet of a system or that which exits a system.

As used herein, the term "sample" refers to a small quantity intended to extract information about that which the sample was removed from. As an example, a sample may be taken from a fluidic experiment to be assayed.

As used herein, the term "effluent" refers to fluid which has flowed out of a system. The term "effluent sample" refers to a sample taken from effluent. The terms "effluent" and "effluent sample" may be interchangeable.

The term "influent" refers to fluid which is to be flowed into a system. The term "influent sample" refers to a sample taken from influent. The terms "influent" and "influent sample" may be interchangeable.

The term "quantification" refers to the counting and measuring of observations into quantities. For example, the concentration of a compound in a fluid may be quantified to make a quantification.

The term "percent absorption" refers to the percent of a compound or substance that absorbs into the system which it contacts.

As used herein, the term "assay" refers to the qualitative or quantitative measuring of the presence, amount, or function activity of a target entity, such as an analyte. The term "assaying" refers to the action of taking an assay of a target entity.

The term "analyte" refers to a substance whose chemical constituents may be identified and/or measured.

As used herein, the term "metabolite" refers to a substance formed in or necessary for metabolism. The term "apparent metabolite" refers to a metabolite as it seems to be, without taking into account variability, such as absorption into a system.

As used herein, the term "metabolism" refers to the chemical processes that occur within a living organism in order to maintain life.

The term "scaffold" refers to a material that have been engineered to positively interact with biology, whether that biology is in vivo or in vitro. For example, a membrane may be considered a scaffold.

As used herein, the term "variability" refers to the total variation seen in an experiment and can come from a variety of sources, including, but not limited to, process and biological population inconsistency.

As used herein, the term "introduce" refers to the input of a fluid or material or biological element, etc., into a system.

As used herein, the term "determine" refers to the active step of ascertaining or establishing a next step, result, etc.

As used herein, the term "error bars" refer to the line through a point on a graph, parallel to one of the axes, which represents the uncertainty or error of that data. The inventions presented herein may be able to either reduce error bars or aid scientists in making them for accurate.

As used herein, the term "half maximal inhibitory concentration (IC50)" refers to a measure of the potency of a compound in inhibiting a specific biological or biochemical function. In other words, the IC50 is a quantitative measure of how much of a compound is needed to inhibit a biological process. The IC50 represents the concentration of a compound that is needed for 50% inhibition or maximum effect in vitro, such as in a microfluidic device. For example, if the intended study shows an IC50 at a dosing concentration of 1 µM, the results of the compound distribution kit may indicate that the actual IC50 is at an exposure concentration in the range of 0.6 µM to 1 µM.

As used herein, the term "threshold" refers to a magnitude that the result of a certain reaction, phenomenon, result or condition may be compared to. For example, if compound absorption is over a certain threshold, the intended study may not be worth completing.

As used herein, the term "time point" refers to a point during an experiment or clinical procedure when an action is taken.

As used herein, the term "measurement" refers to the assignment of a numerical characteristic to an object or event. For example, a measurement of system absorption or compound distribution in a system may be taken.

As used herein, the term "ratio" refers to the quantitative relation between two amounts showing the number of times one value contains or is contained in the other. Ratios are helpful in comparison.

As used herein, the term "fluidic circuit" refers to a system of connections, including tubing, channels, conduits, arteries, veins, chambers, tanks, ducts, grooves, mains, passages, troughs, pipes, conduits, inlets, outlets, etc. that a fluid may flow through. Is not intended that a fluidic circuit is limited to a continuous system. A fluidic circuit may comprise breaks in flow, such as valves, bubbles, or empty spaces.

As used herein, the term "chromatography" refers to the separation of a mixture by passing it through in solution or as a vapor through a medium in which the components move at different rates.

The term "spectrometry" refers to the separation and measurement of spectral components of a physical phenomenon. As used herein, spectrometry may be used to quantify analytes and/or metabolites in a system.

As used herein, the term "drug" refers to a medicine or other substance which has physiological effects when introduced to a biological system. The term "pharmaceutical" refers to drugs for medical purposes. The term "drug candidate" refers to a molecule that has been shown to have sufficient target selectivity and potency, and favorable medicine-line properties and justifies further development.

As used herein, the term "compound" may refer to any chemical, biological and/or pharmaceutical substance composed of many molecules in gaseous, liquid, or solid form.

Herein, the terms "substance" refers to a matter with uniform properties.

As used herein, the term "compound distribution" refers to the concentration of a compound across a system.

As used herein, the term "polymer" refers to a substance that has a molecular structure consisting chiefly or entirely of a large number of similar units bonded together.

As used herein, the term "plastic" refers to a synthetic material made up polymers. A plastic is a type of polymer.

As used herein, the term "regulate" refers to the control or coordination of a process and/or system.

As used herein, the term "fill" refers to when an empty space is occupied by matter.

As used herein, the term "runs along the length" refers to when one material, substance, component, etc. is placed in coordination with the length of another material, substance, component, etc. For example, a channel may run along the length of a substrate.

As used herein, the term "constant" refers to an action and/or process that occurs continuously over a period of time.

As used herein, the term "sensor" refers to a component which detects or measures a physical property. Example of sensors include flow rate sensors, gas sensors, fluorescent sensors, etc.

The term "oxygen sensor" refers to a sensor which detects the presence or measures the concentration of oxygen.

As used herein, the term "mechanical stability" refers to the physical strength of a material and/or component.

As used herein, the term "at least partially" refers to an extent which ranges from only in part to full.

As used herein, the term "border" refers to the edge or boundary or part near. A component may border another component. A component may also have a border.

As used herein, the term "enclose" refers to a component or material or substance which surrounds another. A component may be partially enclosed, or not entirely surrounded.

The term "reservoir" or "fluidic reservoir" refers to a container where fluid collects.

The term "fluidic communication" refers to continuous fluid contact in a system. For example, two components may be in fluidic communication if they each comprise a fluid, and those fluids are in contact.

The term "backplane" refers to a material or component used for mechanical stability. A backplane may have additional features supported on it, such as protrusions or channels.

The term "gasket" or "gasketing layer" refers to a material or component used for sealing a junction between two surfaces. For example, a gasketing layer may be used between a fluidic backplane and a reservoir.

The term "projecting member" refers to a component that protrudes from the body of a system or device.

The term "cap" or "capping layer" refers to a material or component used for topping or covering. For example, channels in a backplane may be capped or covered with a capping layer.

The term "media" refers to a liquid for use in a biological system. For example, when cell media is oftentimes needed when culturing cells. The term "culture media" refers to media being used to culture biologics, such as cells or bacteria. The term "cell media" or "cell culture media" refers to media used for culturing cells in particular.

As used herein, the term "additives" refers to a substance added to something in order to improve it, preserve it, or otherwise. For example, additives may be added to culture media in order to have better growth.

The term "solvent" refers to a fluid that may be used to dissolve other substances or fluids or solutes.

The term "solute" refers to a substance, such as an additive, that may be dissolved in a solute.

The term "modulus of elasticity", also known as flexural modulus, also known as Young's Moduli, refers to the measurement of an object or material or substance's resistance to being deformed elastically (non-permanently) when a stress is applied to it. Polymers may be gauged as rigid or elastomeric based on their modulus of elasticity. Herein, any polymer with a modulus of elasticity over 0.1 GPa is considered effectively rigid, or non-flexible, certainly for the purposes of microfluidic device fabrication. Rigid polymers may fall in the range of 0.1 GPa to 150 GPa. Metals usually have a modulus of elasticity value of at least 30 GPa or greater. For example, aluminum can have a modulus of elasticity value up to about 69 GPa.

Herein, the term "recirculation" refers to the process of circulating a fluid again through a system, such as a fluidic circuit.

The term "recirculation pathway" refers to a fluidic circuit or fluidic pathway or system of tubing and/or channels used for recirculation.

Herein, the term "reciprocation" refers to a process in a fluidic system where the fluid is flowed back and forth through said system.

The term "reciprocation pathway" refers to a fluidic circuit or fluidic pathway or system of tubing and/or channels used for reciprocation.

The term "reciprocation actuator" refers to a mechanical component or actuator used to change the direction of a fluid during reciprocation and/or in reciprocation pathway.

Herein, the term "actuator" refers to mechanical component that is responsible for moving and controlling a mechanism of a system.

Herein, the term "body" refers to the physical structure of a system or device. For example, the body of a microfluidic device is the main structure of the device, for example built out of a polymer.

Herein, the term "viability" refers to the ability to function or work correction. For example, the viability of culture cells may be qualified by the cells having the correct morphology, forming uniform monolayers, expressing the correct genes and markers, outputting correct levels of metabolites, etc.

The term "oxygen-carrying component" refers broadly to a substance capable of carrying oxygen. In one embodiment, the oxygen-carrying component is native or modified hemoglobin. As used herein, the term "hemoglobin" refers to the respiratory protein generally found in erythrocytes that is capable of carrying oxygen. Modified hemoglobin includes, but is not limited to, hemoglobin altered by a chemical reaction such as cross-linking, polymerization, or the addition of chemical groups (e.g., polyethylene glycol, polyoxyethylene, or other adducts). Similarly, modified hemoglobin includes hemoglobin that is encapsulated in a liposome. For example, the hemoglobin may be derived from animals and humans; preferred sources of hemoglobin are cows and humans. In addition, hemoglobin may be produced by other methods, including recombinant techniques. A most preferred oxygen-carrying-component of the present invention is "polyethylene glycol-modified hemoglobin." The term "polyethylene glycol-modified hemoglobin" refers to hemoglobin that has been modified such that it is associated with polyethylene glycol; generally speaking, the modification entails covalent binding of polyethylene glycol (PEG) to the hemoglobin.

The term "non-oxygen-carrying component" refers broadly to substances like plasma expanders that can be administered, e.g., for temporary replacement of red blood cell loss. In preferred embodiments of the invention, the non-oxygen-carrying component is a colloid (i.e., a substance containing molecules in a finely divided state dispersed in a gaseous, liquid, or solid medium) which has oncotic pressure (colloid osmotic pressure prevents, e.g., the fluid of the plasma from leaking out of the capillaries into the interstitial fluid). Examples of colloids include hetastarch, pentastarch, dextran-70, dextran-90, and albumin.

Other than in the operating examples, or where otherwise indicated, all numbers expressing quantities of ingredients or reaction conditions used herein should be understood as modified in all instances by the term "about." The term "about" when used to describe the present invention, in connection with percentages means±5%.

As used herein, the term "substantially" is a relative term that can be used to indicate similar dimensions (e.g. height, width, etc.) or similar features (e.g. porosity, linearity, etc.) that need not be identical to a reference, e.g. preferably at least 80% of the dimension or feature, more typically, at least 90%, or at least 95%, or at least 97% or at least 99% or more.

BRIEF DESCRIPTION OF THE FIGURES

FIG. 11 depicts the compound distribution profile in a high-absorbing, gas-permeable microfluidic device fabricated out of PDMS. The model depicts a highly absorbing compound, midazolam, being perfused through both the top and bottom channels of the microfluidic device at 150 uL/hr.

FIG. 23, 23.1-23.4 shows a table of polymers and a listing of their characteristics, most notably their flexural modulus or modulus of elasticity. A number of polymers in the table have been highlighted as exhibiting elastomeric properties. Those polymers that may be considered elastomeric have a modulus of elasticity under 0.1 GPa. Chlorinated (polyvinyl chloride) PVC has also been marked as elastomeric due to its surface hardness.

FIG. 25A depicts the resulting fluorescence in a combined gasketing and capping layer following exposure to the fluorescent small molecule, rhodamine, which is known to absorb. FIG. 25B depicts the resulting fluorescence in a fluidic layer assembly comprising separate low-absorbing gasketing and low-absorbing capping layer.

FIG. 28A depicts liver cells in a low-absorbing, gas-impermeable microfluidic device fabricated from COP on day 7 of culture. FIG. 28B shows comparable albumin production, a readout of liver function, in the liver cells in both the low-absorbing microfluidic device and the absorbing microfluidic device.

FIG. 29A depicts, with a black solid line, an expected depletion model of the drug Diazepam in a plate culture calculated from in vivo drug clearance data (liver metabolism). The data points depict concentration decline in a plate experiment, with the dotted yellow line being a best-fit line to the data. As would be expected, the decline is log-linear with respect to time, indicating metabolism as the primary driver for compound loss. The slope of this line indicates the rate of metabolism, or intrinsic clearance. Since the data has a lower slope than the model predicted, we can see from the graph that the measure rate of metabolism in the plate was much lower than in vivo. FIG. 29B similarly depicts an expected depletion model of the drug Diazepam in an embodiment of a microfluidic device based on in vivo data from the literature. Data from actual cell-based experiments is shown for both a device fabricated from a highly absorbing PDMS device and a low-absorbing microfluidic device fabricated from COP. Best-fit lines are drawn through both data sets, with the slope indicating the rate of metabolism. As is readily apparent, the COP microfluidic device (here designated as "New Liver-Chip") matches the in vivo predicted value much more closely than the PDMS device. However, the PDMS device appears to have a higher rate of metabolism based on the steeper slope. It is also important to note that the PDMS Liver-Chip data is not well approximated by a line on the log scale, as would be expected if metabolism was the only driver for compound loss. Indeed, taken together (that is to say, knowing that diazepam absorbs into PDMS, seeing the poor fit of the data to a metabolism curve, and observing the higher than expected rate of compound loss), this clearly demonstrates an over-prediction of metabolism in the PDMS device and accurate prediction in the non-absorbing system.

FIG. 33A depicts the fraction of Coumarin recovered from the solutions. FIG. 33B depicts the fraction of Rhodamine B recovered from the solutions for coatings of varying thicknesses on two materials known to absorb. FIG. 33A shows that some Coumarin was absorbed by both the coated PDMS and SEBS with different coating thicknesses. FIG. 33B shows that minimal Rhodamine B was absorbed by the PDMS and SEBS at the different coating thicknesses.

FIG. 35A demonstrates deformation of the channel due to engagement with the perfusion manifold assembly, even before stretching the membrane. FIG. 35B shows this same device under stretch. It can be seen that in the absorbing microfluidic device that is actuated in this manner, that there is a non-uniform stretch profile along the channel length, especially but not limited to, the area toward the edges of the working channels and far away from the working channels.

FIG. 45A shows a gas-permeable, low-absorbing microfluidic device comprising an 11% porous PET and PDMS thin-film gas exchanger. FIG. 45B depicts a low-absorbing, gas-permeable microfluidic device comprising a PDMS thin-film gas exchanger.

FIGS. 46A, 46B, 46C, and 46D depict liver cell (hepatocyte) layer morphology in an absorbing microfluidic device fabricated from PDMS on successive days. FIG. 46A shows the monolayer on Day 1. FIG. 46B shows the monolayer on Day 3. FIG. 46C shows the monolayer on Day 6. FIG. 46D shows the monolayer on Day 10. The monolayer appeared to be maintained through Day 10, with slight morphological decline.

FIGS. 47A, 47B, 47C, and 47D depict the morphology of the cell monolayer (33) in a low-absorbing, gas-impermeable microfluidic device (13) constructed from COP. FIG. 47A shows the monolayer (33) on Day 1. FIG. 47B shows the monolayer (33) on Day 3. FIG. 47C shows the monolayer (33) on Day 6. FIG. 47D shows the monolayer (33) on Day 10. The monolayer (33) appeared to be declining rapidly over the course of the 10 days, with most cells completely dead or dying by Day 10.

FIGS. 48A, 48B, 48C, and 48D depict the morphology of the cell monolayer (33) in a low-absorbing, gas-permeable microfluidic device (1) with a porous PET and thin film PDMS gas exchanger (9). FIG. 48A shows the monolayer (33) on Day 1. FIG. 48B shows the monolayer (33) on Day 3. FIG. 48C shows the monolayer (33) on Day 6. FIG. 48D shows the monolayer (33) on Day 10. The monolayer (33) appeared to be maintained through Day 10, with slight morphological decline (similar to the gas-permeable, but absorbing device in FIG. 46A-D).

FIGS. 49A, 49B, 49C, and 49D depict the morphology of the cell monolayer (33) in a low-absorbing, gas-permeable microfluidic device (1) with a thin film PDMS gas exchanger (9). FIG. 49A shows the monolayer (33) on Day 1. FIG. 49B shows the monolayer (33) on Day 3. FIG. 49C shows the monolayer (33) on Day 6. FIG. 49D shows the monolayer (33) on Day 10. The monolayer (33) appeared to be maintained through Day 10, with slight morphological decline (similar to the gas-permeable, but absorbing device in FIG. 46A-D).

FIG. 50A shows the Bile Canaliculi MRP2 signal on an absorbing microfluidic device (12) constructed from PDMS on Day 14. FIG. 50B shows the Bile Canaliculi MRP2 signal on a low-absorbing, gas-impermeable microfluidic device (13) constructed from COP on Day 14. FIG. 50C shows the Bile Canaliculi MRP2 signal on a low-absorbing, gas-permeable microfluidic device (1) with a porous PET and thin film PDMS gas exchanger (9) on Day 14. FIG. 50D shows the Bile Canaliculi MRP2 signal on a low-absorbing, gas-permeable microfluidic device (1) with a thin film PDMS gas exchanger (9) on Day 14. There was no MRP2 signal for any of the conditions on Day 14.

FIGS. 55A, B, C and 56A, B, C show hepatocyte attachment and morphology in both a low-absorbing, gas-impermeable microfluidic device fabricated from COP and a high-absorbing, gas-permeable microfluidic device fabricated from PDMS on day 1, day 2 and day 3 of cell layer growth. FIG. 55A shows hepatocyte attachment and morphology in a low-absorbing, gas-impermeable microfluidic device fabricated from COP on day 1. FIG. 55B shows hepatocyte attachment and morphology in a low-absorbing, gas-impermeable microfluidic device fabricated from COP on day 2. FIG. 55C shows hepatocyte attachment and morphology in a low-absorbing, gas-impermeable microfluidic device fabricated from COP on day 3. FIG. 56A shows hepatocyte attachment and morphology in a high-absorbing, gas-permeable microfluidic device fabricated from PDMS on day 1. FIG. 56B shows hepatocyte attachment and morphology in a high-absorbing, gas-permeable microfluidic device fabricated from PDMS on day 2. FIG. 56C shows hepatocyte attachment and morphology in a high-absorbing, gas-permeable microfluidic device fabricated from PDMS on day 3.

FIGS. 57A and 57B show hepatocyte and LSEC morphologies on day 9 in a high-absorbing, gas-permeable microfluidic device fabricated from PDMS. FIG. 57A shows hepatocyte morphology on day 9 in a high-absorbing microfluidic device fabricated from PDMS. FIG. 57B shows LSEC morphology on day 9 in a high-absorbing microfluidic device fabricated from PDMS.

FIGS. 58A and 58B show hepatocyte and LSEC morphologies on day 9 in a low-absorbing, gas-impermeable microfluidic device fabricated from COP. FIG. 58A shows hepatocyte morphology on day 9 in a low-absorbing, gas-impermeable microfluidic device fabricated from COP. FIG. 58B shows LSEC morphology on day 9 in a low-absorbing, gas-impermeable microfluidic device fabricated from COP. Both hepatocytes and LSECs showed comparable morphologies and maintained monolayers in both the low-absorbing, gas-impermeable microfluidic device and the high-absorbing, gas-permeable microfluidic device on day 9.

FIGS. 59A and 59B show bile canaliculi fluorescence staining via MRP2 at day 9 of cell layer culture on two different microfluidic devices. FIG. 59A shows bile canaliculi fluorescence staining via MRP2 on a high-absorbing, gas-permeable microfluidic device fabricated from PDMS using a 20× microscope objective on day 9 of cell layer culture. FIG. 59B shows bile canaliculi fluorescence staining via MRP2 on a high-absorbing, gas-permeable microfluidic device fabricated from COP using a 20× microscope objective on day 9 of cell layer culture.

FIG. 64 shows an experimental matrix in which all the experimental conditions may be seen for an optimization study aimed at sustaining Liver-Chip viability and function. The microfluidic devices comprised: three low-absorbing, gas-impermeable microfluidic devices fabricated from COP with media equilibrated with 100% oxygen (i.e. 100 kPa, no CO2 equilibration, with a 150 µL/hr flow rate in the top channel and a 150 µL/hr flow rate in the bottom channel being run on a culture module; three low-absorbing, gas-impermeable microfluidic devices fabricated from COP, with 21% oxygen media equilibration and 5% carbon dioxide, a 150 µL/hr flow rate in the top channel and a 150 µL/hr flow rate in the bottom channel being run on a culture module; three low-absorbing, gas-impermeable microfluidic devices fabricated from COP, with media equilibrated to 21% oxygen and 5% carbon dioxide, a 150 µL/hr flow rate in the top channel and a 150 µL/hr flow rate in the bottom channel, and additionally having 15 mM HEPES in the media to pH buffer the media, being run on a culture module; low-absorbing, gas-impermeable microfluidic devices fabricated from COP, with media equilibrated to 21% oxygen and 5% carbon dioxide, at a 300 µL/hr flow rate in the top channel and a 300 µL/hr flow rate in the bottom channel being run on a syringe pump; two high-absorbing, gas-permeable microfluidic devices fabricated from PDMS, with media equilibrated to 21% oxygen and 5% carbon dioxide, with a 300 µL/hr flow rate in the top channel and a 300 µL/hr flow rate in the bottom channel being run on a syringe pump; and two high-absorbing, gas-permeable microfluidic devices, fabricated from PDMS, with media equilibrated with 21% oxygen and 5% carbon dioxide, with a 30 µL/hr flow rate in the top channel and a 30 µL/hr flow rate in the bottom channel being run on a culture module.

In FIG. 67, the media is first drawn from the external reservoir, through the microfluidic device, into the syringe. The media is then optionally held static in the syringe in the middle panel of the figure. The media is then pushed out of the syringe, back through the microfluidic device, into the external reservoir. The external reservoir may alternatively be known as a reservoir or fluid reservoir.

FIG. 72 illustrates one of the challenges with absorption; even though both the top and bottom channel were dosed with compound and even though flow rate (150 uL/hr) is higher than is typically run in these microfluidic device (i.e. "best case scenario") only the cells at the beginning of the cell culture channel are contacted by the drug before it is absorbed into the PDMS. The latter half of the microfluidic devices are exposed to a concentration of compound that is nearly "0".

FIG. 76 shows a listing of compounds tested for absorption, their molecular weight (MW), one of their physicochemical parameters (log P), and the partition coefficient for the level of absorption into PDMS and the material of the perfusion manifold assembly (pod).

FIG. 77A shows three microfluidic devices in microfluidic device holders or carriers and three open sterility bags, which had originally contained the three microfluidic devices. FIG. 77B shows three perfusion manifold assemblies in a sterile container. FIG. 77C shows two filters in sterile packaging.

Figure 78:
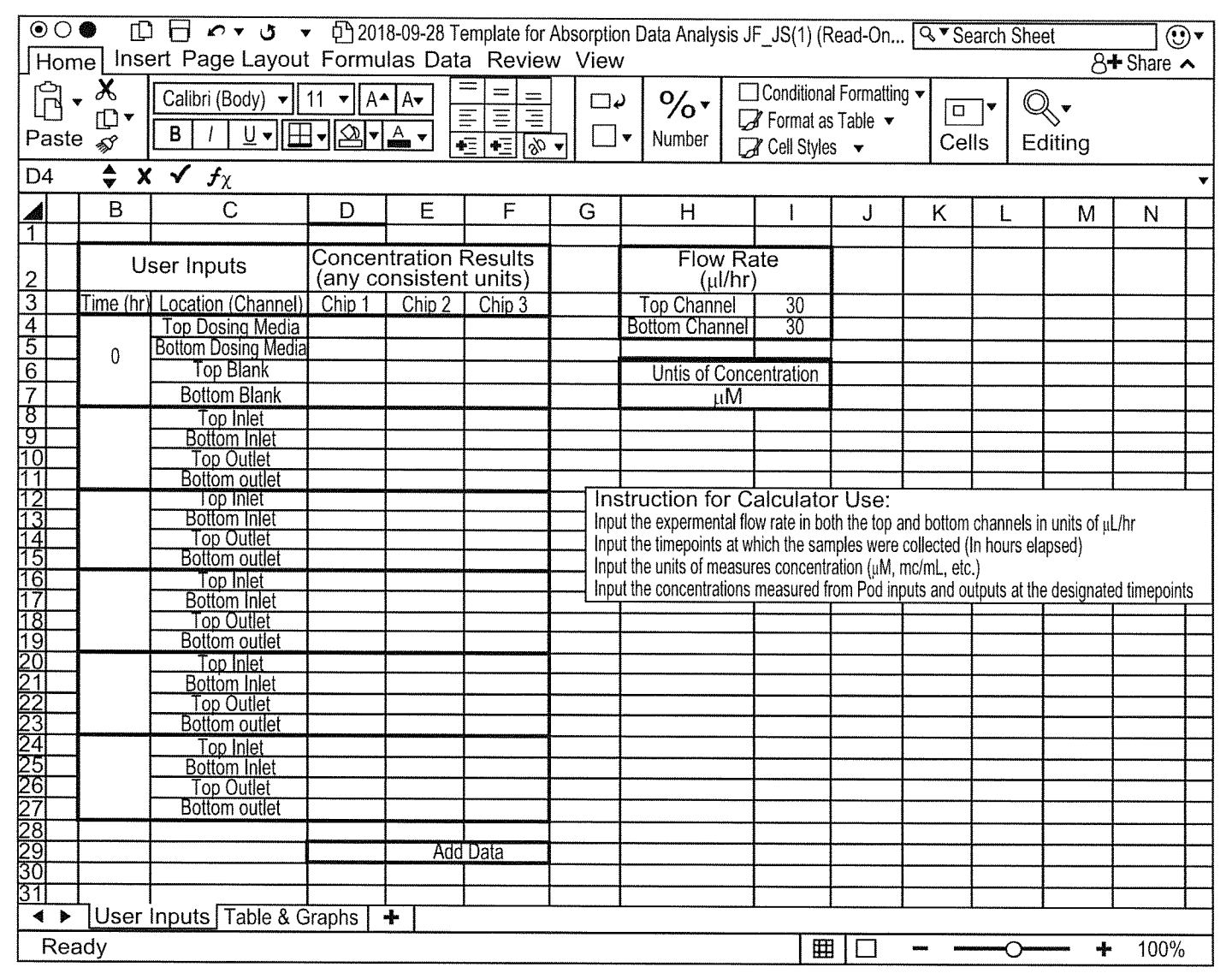

FIG. 78 shows an example of a calculator or absorption calculator. FIG. 78 shows one embodiment where the calculator is a Microsoft Excel calculator. The calculator is part of the digital component of the compound distribution kit.

FIG. 79 also shows perfusion manifold assemblies preparing to be fluidically connected to a culture module, two tubes of solution, and examples of a calculator and graphical calculator results.

In FIG. 81 the perfusion manifold assemblies each have two inlet and two outlet reservoirs and the two inlet reservoirs are shown filled with a fluid.

FIG. 85 first shows perfusion manifold assemblies and microfluidic devices (in carriers or holders) either in sterile packaging or recently removed from sterile packaging. FIG. 85 then shows the microfluidic devices in an orientation to be fluidically connected to the perfusion manifold assemblies. FIG. 85 then shows the microfluidic devices fluidically connected to the perfusion manifold assemblies and the inlet reservoirs of the perfusion manifold assemblies filled with fluid. Finally, FIG. 85 shows perfusion manifold assemblies in an orientation to be fluidically connected to a culture module.

FIGS. 86A and 86B show examples of compound distribution kit output for minimal absorption. FIG. 86A shows a graph of the outlet concentration in one channel of a microfluidic device for a case of minimal exposure. FIG. 86B shows a graph of the cellular exposure range in one channel of a microfluidic device for a case of minimal absorption, which uses the data in FIG. 86A to compute a minimum and maximum possible concentration of compound "seen" by the cells inside the microfluidic device.

FIGS. 87A and 87B show examples of compound distribution kit output for nearly complete absorption of a compound. FIG. 86A shows a graph of the outlet concentration in one channel of a microfluidic device for a case of nearly complete absorption. FIG. 86B shows a graph of the cellular exposure range in one channel of a microfluidic device for a case of nearly complete absorption.

FIGS. 88A, 88B, 88C, and 88D show example calculator outputs for the compound Rhodamine. FIG. 88A shows the outlet concentration of Rhodamine in a first channel of one or more microfluidic devices. FIG. 88B shows the cellular exposure concentration range of Rhodamine in a first channel of one or more microfluidic devices. FIG. 88C shows the outlet concentration of Rhodamine in a second channel of one or more microfluidic devices. FIG. 88D shows the cellular exposure concentration range of Rhodamine in a second channel of one or more microfluidic devices.

FIG. 89 shows the results from absorption testing microfluidic devices and perfusion manifold assemblies without cells. The results can be used to put error bars, or confidence intervals, on exposure concentrations in actual drug studies with cells. Exposure concentration confidence intervals decrease with experiment duration, as the recovered concentration rises, with tighter confidence intervals at later timepoints.

FIG. 90A shows a dose-response confidence interval chart for Rhodamine for a six-hour timepoint. FIG. 90*b* shows a dose-response confidence interval chart for Rhodamine for a 72-hour timepoint.

FIG. 91 shows a chart detailing recommended media collection time points given an experiment duration, which would be defined by the particulars of the compound study of interest.

FIG. 95 shows that the flow results fit the COMSOL model for the outlet concentrations of the compound. Rhodamine tends to have a lower rate of absorption, but higher extent of absorption, which results in it saturating its surroundings over time. The importance of this is that despite initially seeing huge losses of rhodamine, after a period of time, the rate of rhodamine loss diminishes significantly.

FIG. 96A shows experimental results of the cellular exposure range of the small-molecule compound Rhodamine for a first channel of a microfluidic device. FIG. 96B shows computational (COMSOL) model results of the cellular exposure range of the small-molecule compound Rhodamine for a single channel of a microfluidic device. The charts in FIGS. 96A and 96B show that the computational (COMSOL) model accurately predicted Rhodamine absorption into the materials making up microfluidic devices, particularly PDMS.

FIGS. 97A and 97B show a comparison between computational (COMSOL) model results and actual experimental results for cellular exposure ranges of the small-molecule compound Rhodamine. FIG. 97A shows experimental results of the cellular exposure range of the small-molecule compound Rhodamine for a second channel of a microfluidic device. FIG. 97B shows computational (COMSOL) model results of the cellular exposure range of the small-molecule compound Rhodamine for a second channel of a microfluidic device. The charts in FIGS. 97A and 97B show that the computational (COMSOL) model accurately predicts small-molecule absorption into the materials making up microfluidic devices, particularly PDMS.

FIGS. 98A and 98B show a comparison between a computational (COMSOL) model results and actual experimental results for cellular exposure ranges of the small-molecule compound Coumarin. FIG. 98A shows experimental results of the cellular exposure range of the small-molecule compound Coumarin for a first channel of a microfluidic device. FIG. 98B shows computational (COMSOL) model results of the cellular exposure range of the small-molecule compound Coumarin for a first channel of a microfluidic device. It was found that the computational (COMSOL) model did not accurately predict the absorption, because the model did not take into account the rest of the flow system outside the microfluidic device. For this experiment the microfluidic device was in fluidic communication with a perfusion manifold assembly. The compound Coumarin was especially susceptible to absorption into one of the materials making up the perfusion manifold assembly, SEBS. As such, the computational (COMSOL) model did not accurately predict the absorption into the entire flow system.

FIG. 99A shows experimental results of the cellular exposure range of the small-molecule compound Coumarin for a second channel of a microfluidic device. FIG. 99B shows computational (COMSOL) model results of the cellular exposure range of the small-molecule compound Coumarin for a second channel of a microfluidic device. It was found that the computational (COMSOL) model did not accurately predict the absorption, because the model did not take into account the rest of the flow system outside the microfluidic device. For this experiment the microfluidic device was in fluidic communication with a perfusion manifold assembly. The compound Coumarin was especially susceptible to absorption into one of the materials making up the perfusion manifold assembly, SEBS. As such, the computational (COMSOL) model did not accurately predict the absorption into the entire flow system.

FIG. 106A shows the outlet concentration of Drug X over time. FIG. 106B shows cellular exposure ranges in the first channel. FIGS. 106A and 106B show that Drug X was absorbed into the system. The loss of Drug X is consistent with a lower absorbing molecule as nearly all of the compound is recoverable at 72 hours, showing that the microfluidic device material became saturated. FIGS. 106A and 106B show that over time cell exposure to Drug X would reach between 80-100%. The media carrying Drug X in FIGS. 106A and 106B also contained 2% fetal bovine serum (FBS).

FIGS. 107A and 107B show a summary of flow studies of Drug X in a second channel of a two-channel microfluidic device. FIG. 107A shows the outlet concentration of Drug X over time. FIG. 107B shows cellular exposure ranges in the first channel. FIGS. 107A and 107B show that Drug X was completely absorbed into the system. The second channel flow rate may possibly be increased in order to lessen the amount of compound absorption.

FIG. 108A shows the outlet concentration of Drug Y over time. FIG. 108B shows the range of cellular exposure in the first channel of the microfluidic device over time. The compound loss is consistent with a moderately absorbing molecule as nearly all of the compound is recovered over 72 hours in the effluent, as the material making up the microfluidic device becomes saturated. Over time cellular exposure of Drug Y would be between 80-100%. The media carrying Drug Y in FIGS. 108A and 108B also contained 2% fetal bovine serum (FBS).

FIG. 109A shows the outlet concentration of Drug Y over time. FIG. 109B shows the range of cellular exposure in the second channel of the microfluidic device over time. The compound loss in the second channel of the microfluidic device points towards absorption. The flow rate may be increased to perhaps decrease compound absorption.

FIGS. 111A-G demonstrate the effectiveness of silicon valves. FIG. 111A shows an embodiment of a recirculation setup using an umbrella valve. FIG. 111B shows an embodiment of a recirculation setup using a duck-billed valve. FIG. 111C-E show multiple embodiments of recirculation setups using tubes and duck billed valves. FIG. 111F shows an embodiment of a recirculation setup using a tube and a duck-billed valve. FIG. 111G shows an embodiment of a recirculation setup using a tube and an umbrella valve.

FIG. 114 shows a microfluidic device comprising a low-absorbing body having a main channel, a flexible membrane, working or gas channels, and flexible walls between said main channel and said working or gas channels. Alternatively, FIG. 114 shows a microfluidic device comprising a substantially rigid body having a channel, said channel comprising a flexible membrane, wherein said membrane may be stretched by working or gas channels separated from said channel by one or more flexible walls.

FIG. 115A shows nearly complete absorption of Compound Z at low flow rates, such as 30 uL/hr. FIG. 115B shows that significant absorption (nearly 80% loss) of Compound Z at high flow rates, such as 150 uL/hr. FIG. 115C shows cellular exposure of Compound Z in said first channel of the compound at 30 uL/hr. FIG. 115D shows cellular exposure of Compound Z in said first channel of the compound at 150 uL/hr. Experiments were also run at a higher concentration to compensate for compound loss. Increased dosing concentration of Compound Z was conducted and the recovered outlet concentration was used as the effective "cellular exposure concentration." Increasing the dosing concentration increases the likelihood of a false positive (compound is not toxic, but a toxic effect is seen in the microfluidic device), but eliminates the possibility of a false negative (compound is actually toxic, but the microfluidic device does not show any toxic response).

As seen in FIG. 118 the incubator starts at atmospheric oxygen levels (18.5% in a humidified incubator), reaches 1% oxygen setpoint (seen with a long tail-end), and returns to atmospheric oxygen upon the incubator being opened to the atmosphere.

Figure 122:
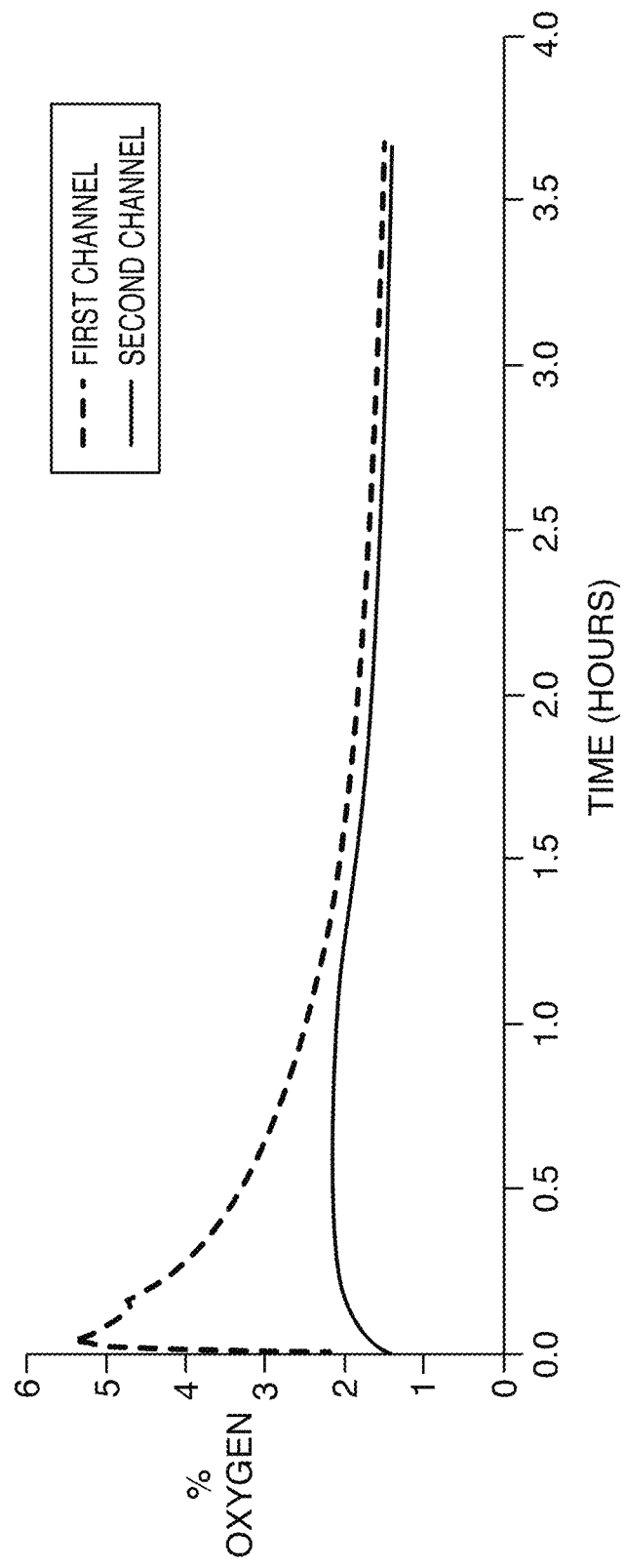

FIG. 122 shows a diagram of results of recovery time when opening an incubator door. Oxygen measurements were taken at the outlet of a microfluidic device under 100 µL/hr water flow in a culture module inside an incubator set to 1% oxygen. The microfluidic device, culture module, and remainder of system were equilibrated to the incubator environment for 12 hours prior. The incubator door was opened for five seconds before starting measurements.

Figure 123:
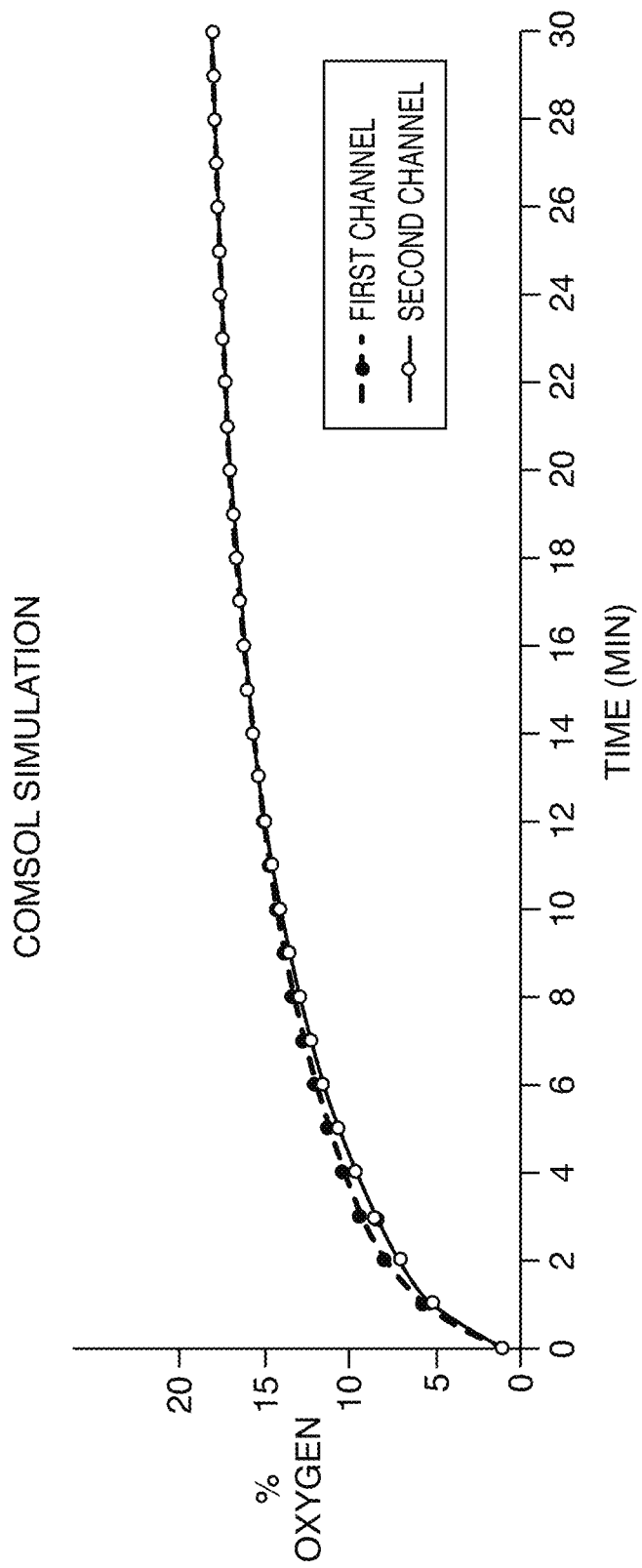

FIG. 123 shows a diagram of results of a COMSOL Multiphysics simulation plot of PDMS microfluidic device first and second channel volume averages of a static PDMS microfluidic device equilibrated to 1% oxygen and exposed to atmospheric oxygen.

Figure 124:
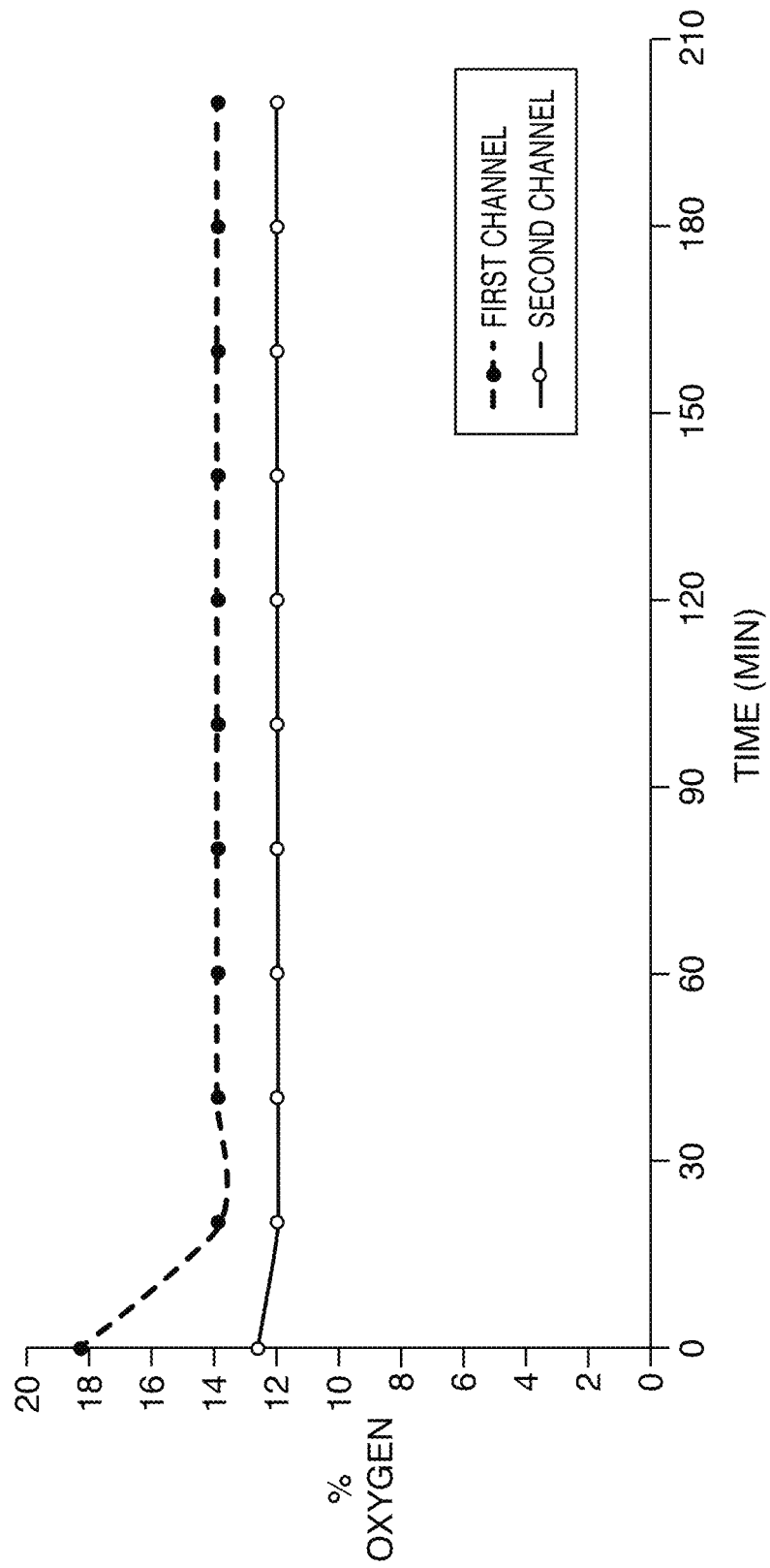

FIG. 124 shows a diagram of results of a COMSOL Multiphysics simulation plot of PDMS microfluidic device first and second channel volume averages of a microfluidic device with seeded Caco-2 cells in culture conditions or 18.5% oxygen incubator and 18.5% oxygen inlet water at 100 µL/hr water flow rate.

Figure 125:
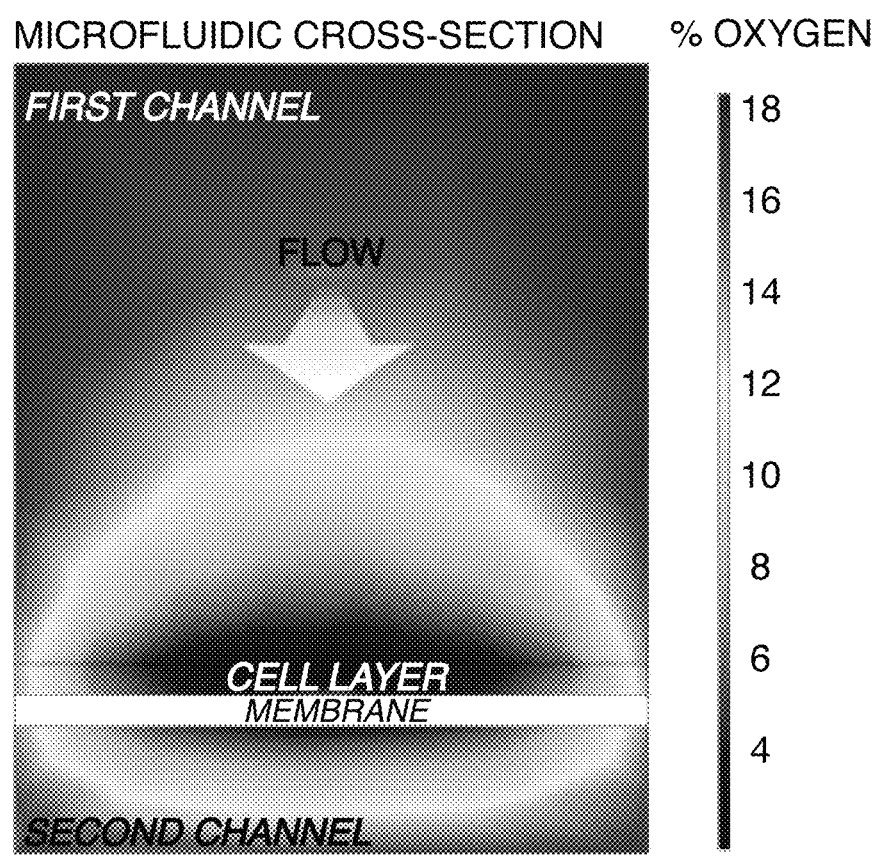

FIG. 125 shows a diagram of a PDMS microfluidic device oxygen microenvironment with the addition of Caco-2 cells. FIG. 125 shows a cross-sectional surface pot of water oxygen concentrations in the center of the microfluidic device.

Figure 126:
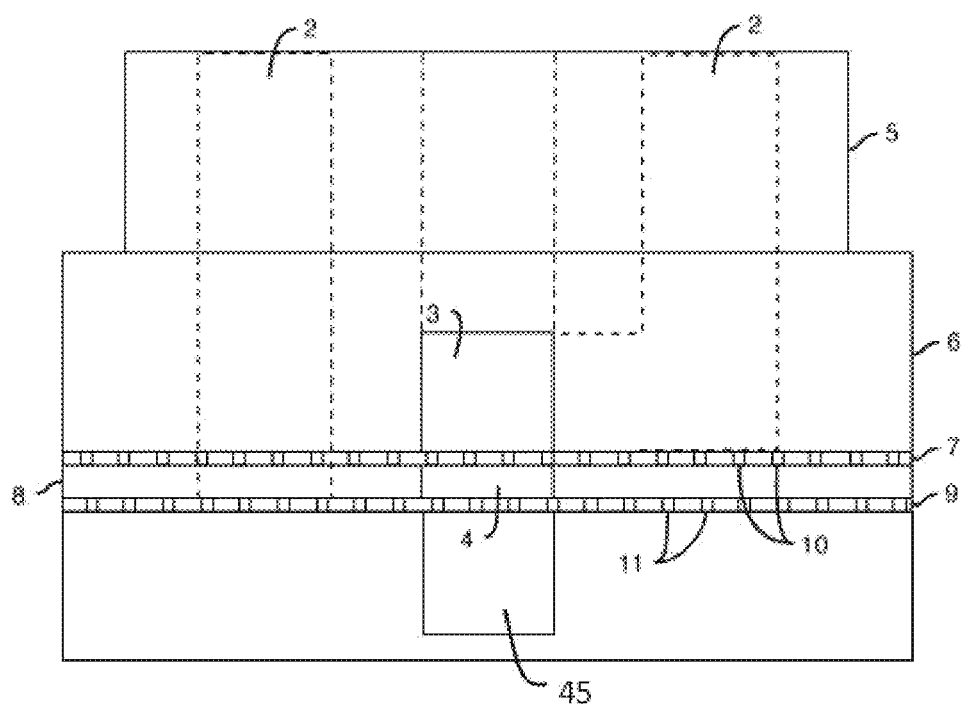

FIG. 126 shows a diagram of one embodiment of a gas-exchange microfluidic device, comprising a gas-exchange channel used to introduce gas into the body of the microfluidic device. The embodiment in FIG. 126 comprises a body having a culture channel, a gas-exchange channel, and a gas exchanger between said culture channel and said gas-exchange channel. The embodiment in FIG. 126 is much like the device in FIG. 3, but also comprises a gas-exchange channel in contact with the gas exchanger in order to exchange a gas of a desired concentration with the channels of the microfluidic device.

DESCRIPTION OF THE INVENTION

Several embodiments to improve compound distribution and absorbency within microfluidic devices are presented herein.

One exemplary embodiment of the present invention is a low-absorbing microfluidic device to conduct experiments, cellular and otherwise. Another exemplary embodiment of the present invention is a low-absorbing perfusion manifold assembly representing fluidic infrastructure around the microfluidic device. Both the low-absorbing microfluidic device and the low absorbing perfusion manifold assembly aim to minimize small molecule absorption, while allowing ambient gases to access experimental regions of the devices, such as microfluidic channels.

U.S. Pat. No. 8,647,861 describes a microfluidic device, or organomimetic device, or microfluidic device for the use of mimicking organ function, comprising: a body having a central microchannel therein; and an at least a partially porous membrane positioned within the central microchannel and along a plane, the membrane configured to separate the central microchannel to form a first central microchannel and a second central microchannel, wherein a first fluid is applied through the first central microchannel and a second fluid is applied through the second central microchannel, the membrane coated with at least one attachment molecule that supports adhesion of a plurality of living cells wherein the porous membrane is at least partially flexible, the device further comprising: a first operating channel separated the first and second central microchannels by a first microchannel wall, wherein the membrane is fixed to the first chamber microchannel wall; and wherein applying a pressure to the first operating channel causes the membrane to flex in a first desired direction to expand or contract along the plane within the first and second central microchannels. Many embodiments of the present invention may be considered improvements on the microfluidic device presented in U.S. Pat. No. 8,647,861, following the surprising discovery that the materials most commonly used to fabricate the microfluidic devices in U.S. Pat. No. 8,647,861 are absorptive. In the process of fabricating a low-absorbing microfluidic device, both gas-impermeable and a gas-permeable option were designed and fabricated.

In some instances, such as when anaerobic bacteria are being cultured, a microfluidic device fabricated from highly permeable materials may not be desired. As such, one embodiment of the present invention is to mask the microfluidic device with films of non-permeable materials.

One embodiment contemplated to control gas is a microfluidic device comprising one or more gas-exchange channels to flow a fluid, either a gas or liquid, and exchange gas between a gas source and another one or more channels within a microfluidic device. The gas-control microfluidic device allows the gas concentration within a gas-permeable microfluidic device to be controllable. A gas, such as oxygen, nitrogen, helium, carbon dioxide, a mixture thereof, a smoke, a vapor, etc., may be introduced into the gas channels of the microfluidic device. The body of the microfluidic device comprises a permeable material, such as PDMS. The gas may transport through the body of the microfluidic device into the working or cell channels of the microfluidic device. Cell viability may be improved when the cells are cultured in similar environments that they experience in vivo. As such, the ability to introduce in vivo relevant gas concentrations to the cells within the microfluidic device allows scientists to achieve better experimental results. For example, if an anaerobic environment is desired for the channels, nitrogen may be flowed through the gas channels. For another example, if a highly oxygenated environment is desired for the channels, oxygen may be flowed through the gas channels.

In one embodiment, the gas-exchange channel may be used in conjunction with a gas exchanger. In one embodiment, a microfluidic device is contemplated comprising a body having a culture channel, a gas-exchange channel, and a gas exchanger between said culture channel and said gas-exchange channel, as shown in FIG. 126. The embodiment in FIG. 126 is much like the device in FIG. 3, but also comprises a gas-exchange channel (45) in contact with the gas exchanger (9) in order to exchange a gas of a desired concentration with the channels (3, 4) of the microfluidic device.

Figure 93:
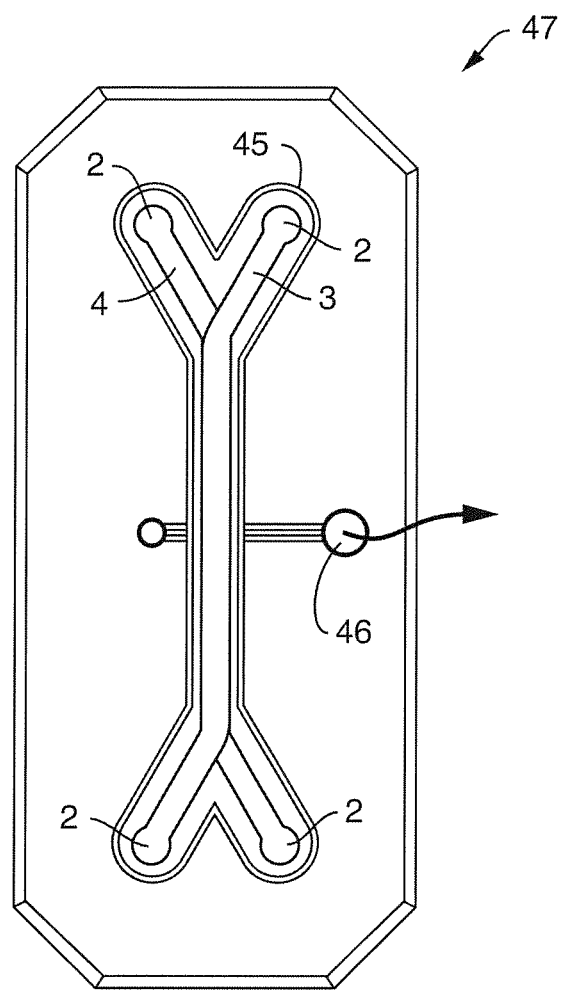
FIG. 93 shows a diagram of a "halo chip" or microfluidic device with the capability of creating a desired gaseous environment within the channels of the microfluidic device. The microfluidic device shown in FIG. 93 has a gas channel that runs around the perimeter of the working or cell channels of the microfluidic device. A gas, such as nitrogen or oxygen, may be flowed into the gas channels of the microfluidic device. The body of the microfluidic device comprises a permeable material, such as PDMS. The gas may transport through the body of the microfluidic device into the working or cell channels of the microfluidic device. For example, if an anaerobic environment is desired for the channels, nitrogen may be flowed through the gas channels. For another example, if a highly oxygenated environment is desired for the channels, oxygen may be flowed through the gas channels. The microfluidic device shown in FIG. 93 may also comprise a check valve to allow the gas to leave the microfluidic device. Further, the microfluidic device in FIG. 93 may also comprise vacuum channels. When vacuum is applied to the vacuum channels the microfluidic device may stretch to emulate cellular physiology in vivo. The microfluidic device in FIG. 93 may also comprise sensors, such as oxygen sensors, in order to monitor the gas levels within the microfluidic device.
Figure 94:
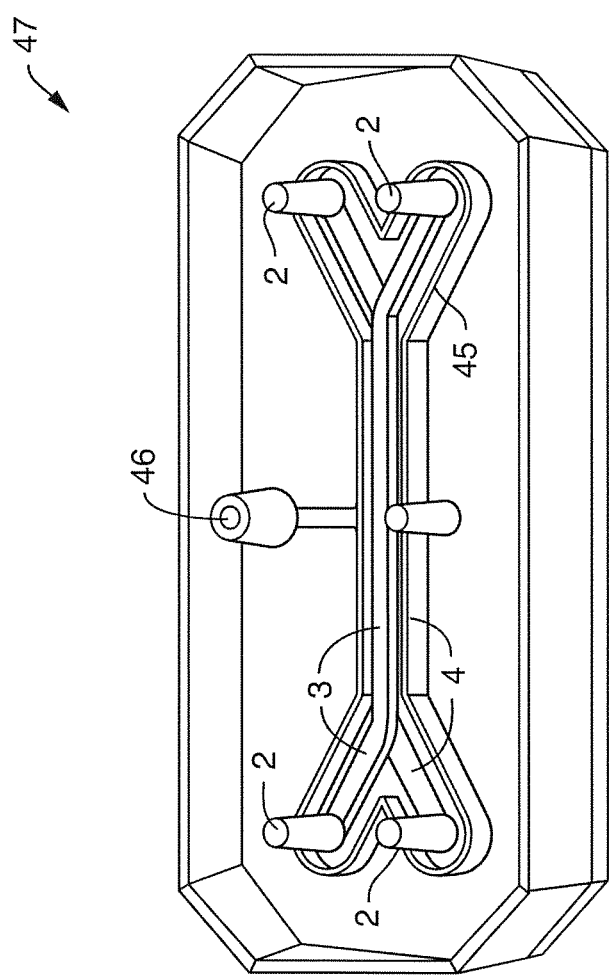
FIG. 94 shows a diagram of the fabricated "halo chip" or microfluidic device shown in the diagram of FIG. 93. The microfluidic device shown in FIG. 94 comprises gas channels in order to introduce a gaseous environment to the working or cell channels within the microfluidic device. A gas, such as oxygen, nitrogen, helium, carbon dioxide, a mixture thereof, a smoke, a vapor, etc., may be introduced into the gas channels of the microfluidic device. That gas may then diffuse through the body of the microfluidic device into the working or cell channels of the microfluidic device. Cell viability may be improved when the cells are cultured in similar environments that they experience in vivo. As such, the ability to introduce in vivo relevant gas concentrations to the cells within the microfluidic device allows scientists to achieve better experimental results. The microfluidic device shown in FIG. 94 may also comprise vacuum channels for stretching the microfluidic device, valves, sensors, channel inlets, channel outlets, etc.

Another embodiment contemplated to control gas is a "halo chip," a microfluidic device with the capability of creating a desired gaseous environment within the channels of the microfluidic device, as shown in FIGS. 93 and 94. The "halo chip" or gas control microfluidic device has a gas channel that runs around the perimeter of the working or cell channels of the microfluidic device. FIG. 93 shows a diagram of a "halo chip" or microfluidic device (47) with the capability of creating a desired gaseous environment within the channels of the microfluidic device. The microfluidic device shown in FIG. 93 has a gas channel (45) that runs around the perimeter of the working or cell channels (3, 4) of the microfluidic device. A gas, such as nitrogen or oxygen, may be flowed into the gas channels of the microfluidic device. The body of the microfluidic device comprises a permeable material, such as PDMS. The gas may transport through the body of the microfluidic device into the working or cell channels (3, 4) of the microfluidic device (47). For example, if an anaerobic environment is desired for the channels (3, 4), nitrogen may be flowed through the gas channels (45). For another example, if a highly oxygenated environment is desired for the channels, oxygen may be flowed through the gas channels. The microfluidic device (47) shown in FIG. 93 may also comprise a check valve (46) to allow the gas to leave the microfluidic device. Further, the microfluidic device (47) in FIG. 93 may also comprise vacuum channels. When vacuum is applied to the vacuum channels the microfluidic device (47) may stretch to emulate cellular physiology in vivo. The microfluidic device in FIG. 93 may also comprise sensors, such as oxygen sensors, in order to monitor the gas levels within the microfluidic device.

FIG. 94 shows different view of the "halo chip" or microfluidic device (47) shown in FIG. 93. The microfluidic device (47) shown in FIG. 94 comprises gas channels (45) in order to introduce a gaseous environment to the working or cell channels (3, 4) within the microfluidic device. A gas, such as oxygen, nitrogen, helium, carbon dioxide, a mixture thereof, a smoke, a vapor, etc., may be introduced into the gas channels (45) of the microfluidic device (47). That gas may then diffuse through the body of the microfluidic device into the working or cell channels (3, 4) of the microfluidic device (47). Cell viability may be improved when the cells are cultured in similar environments that they experience in vivo. As such, the ability to introduce in vivo relevant gas concentrations to the cells within the microfluidic device allows scientists to achieve better experimental results. The microfluidic device (47) shown in FIG. 94 may also comprise vacuum channels for stretching the microfluidic device, valves, sensors, channel inlets, channel outlets, etc.

Figure 1:
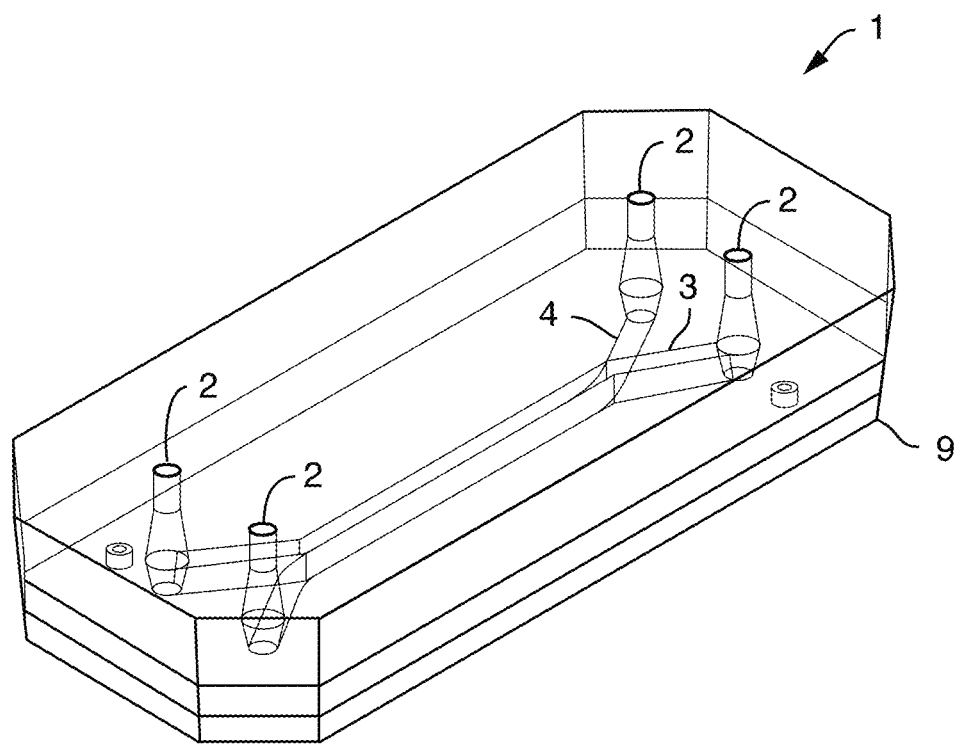
FIG. 1 depicts one embodiment of a low-absorbing, gas-permeable microfluidic device comprising a gas exchanger.
Figure 5:
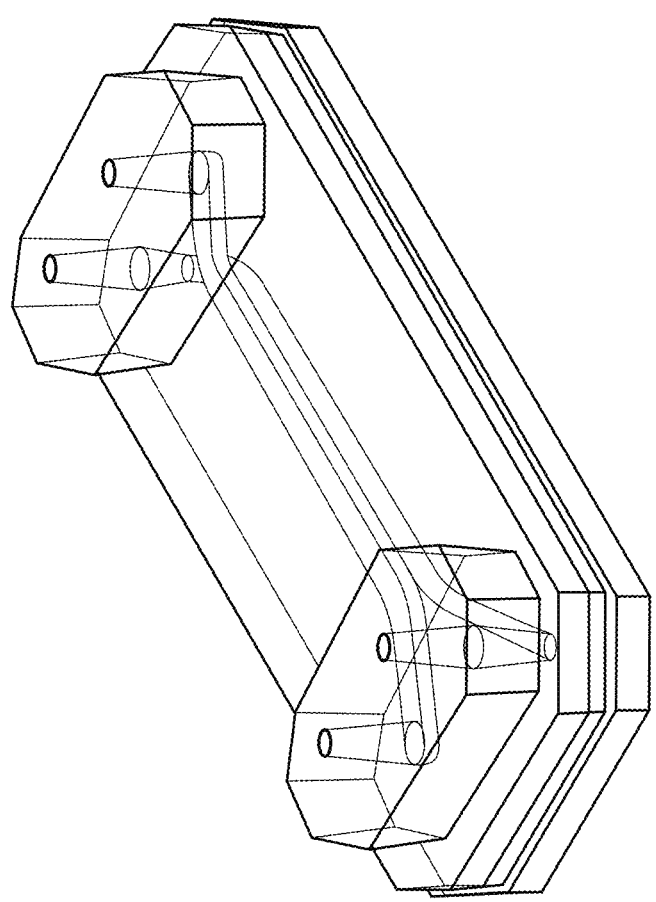
FIG. 5 shows a low-absorbing, gas-impermeable microfluidic device fabricated from COP and SEBS gasketing layers.
Figure 6:
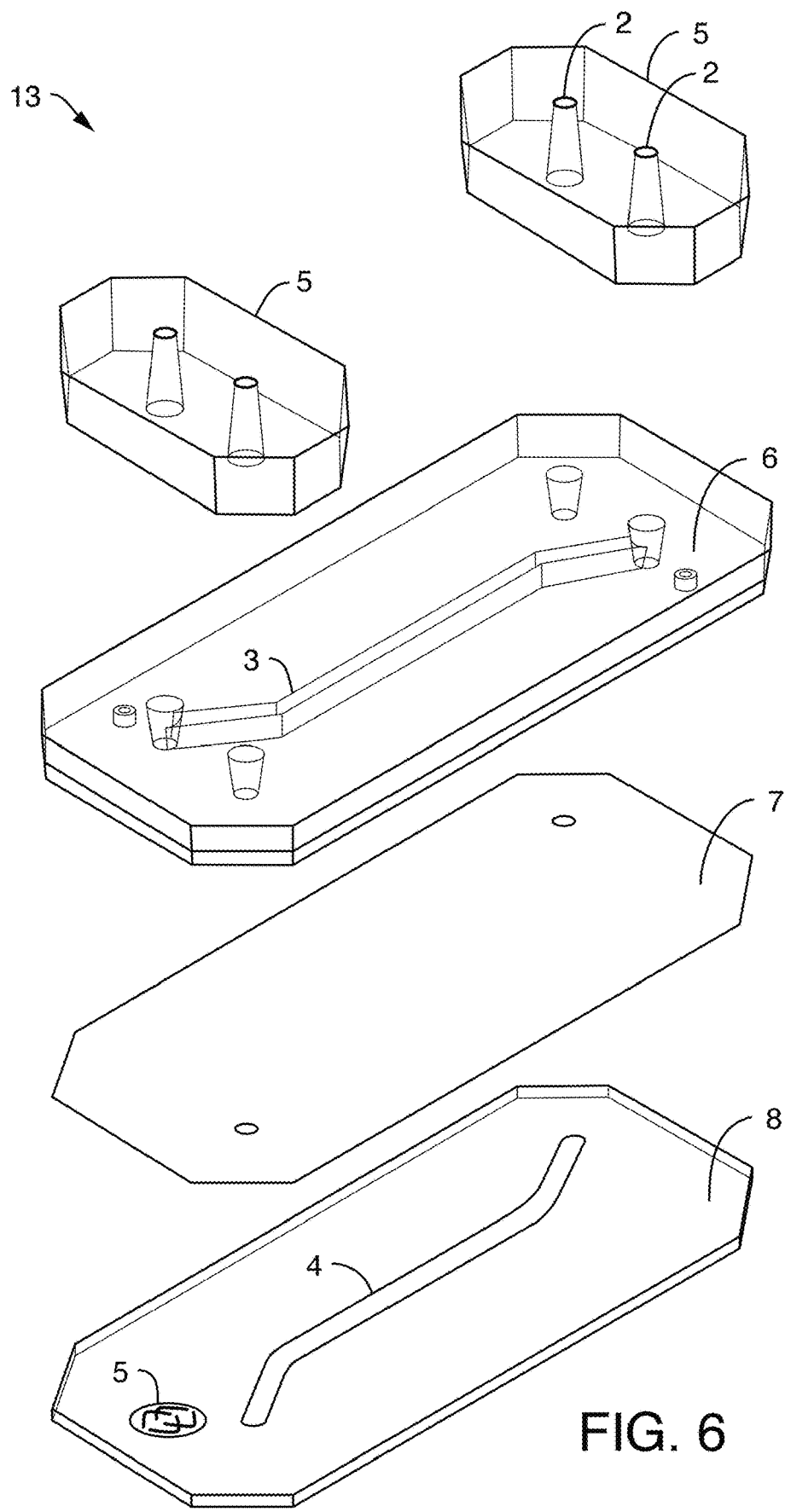
FIG. 6 shows an exploded view of a low-absorbing, gas-impermeable microfluidic device fabricated from COP and SEBS comprising gaskets, a top channel layer, a cell culture membrane, and a bottom channel layer.

In some instances, especially those involving small molecule agents, absorbency into PDMS is problematic. One of the first iterations of the invention presented herein in order to overcome said absorbency is a gas-impermeable, low-absorbing microfluidic device. The gas-impermeable microfluidic device comprising: a body having at least one channel therein, and a membrane positioned in that channel. The gas-impermeable microfluidic device comprising: a body having a central microchannel therein; and an at least partially porous membrane positioned within the central microchannel and along a plane, the membrane configured to separate the central microchannel to form a first central microchannel, or bottom channel, and a second central microchannel, or top microchannel, wherein a first fluid is applied through the first central microchannel and a second fluid is applied through the second central microchannel. FIG. 5 depicts an embodiment of a microfluidic device entirely fabricated out of gas-impermeable materials, such as COP and SEBS gasketing layers. The gas-impermeable microfluidic device (13) has a body fabricated out of COP in order to be low-drug absorbing. FIG. 6 depicts the same embodiment of a microfluidic device fabricated out of entirely gas-impermeable materials exploded as to see the different layers. The gas-impermeable microfluidic device may include similar layers as the absorbent microfluidic device (12) above mentioned or the low-absorbent microfluidic device (1) presented herein. These elements include, but are not limited to, the top channel layer (6) comprising a top channel (3), the bottom channel layer (8) comprising a bottom channel (4), and a membrane (7) between the top channel layer (6) and the bottom channel layer (8). The embodiment depicted in FIG. 6 contains two gaskets (5) instead of one gasket (5) covering the entire top surface of the microfluidic device (13) as depicted in FIG. 1. The format of the gas-impermeable microfluidic device (13) is compatible with the infrastructure of the absorbent microfluidic device (12) described in U.S. Pat. No. 8,647,861. The embodiment of the gas-impermeable microfluidic device (13) in FIG. 5 is more amenable to large scale manufacturing than the absorbent microfluidic device (12) described in U.S. Pat. No. 8,647,861, the reason being that the gas-impermeable microfluidic device is amenable to thermoplastic injection molding processes. Notably missing from this design are working channels, as microfluidic device fabricated from rigid materials cannot be stretched using working channels, as the culture channel walls are also rigid. If the membrane is elastomeric, then differential stretching is a possibility. The latter embodiment is discussed in further detail later.

Figure 114:
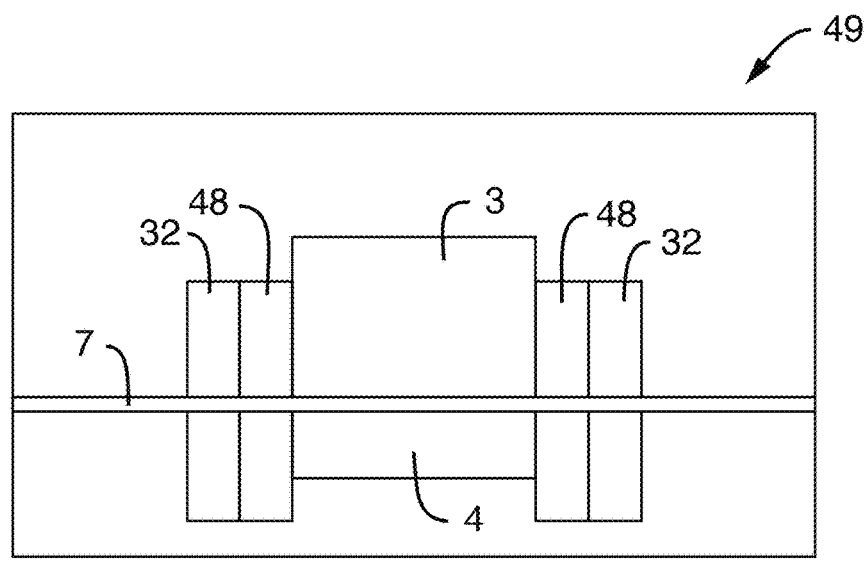
FIG. 114 comprises an embodiment of a low-absorbing microfluidic device comprising a rigid body having a main channel, an elastomeric membrane positioned in that channel, working or gas channels, and elastomeric walls between said main channel and said working or gas channels. Alternatively.

In some experimental pursuits stretching of the microfluidic device using is advantageous. The microfluidic device fabricated from entirely rigid materials was modified to allow the membrane to be stretched through working channels. An embodiment of the low-absorbing microfluidic device was fabricated in order to include working or gas channels, and have the membrane be able to be stretched with said working or gas channels. FIG. 114 shows one embodiment of this low-absorbing microfluidic device (49) comprising an elastomeric membrane (7) and elastomeric channel walls (48). The low-absorbing microfluidic device (49) may be predominantly rigid, while having a main channel comprising elastomeric walls and an elastomeric membrane (7). The main channel may comprise a first channel (3) and a second channel (4). The membrane (7) may be elastomeric to facilitate gas transport on either side of said membrane. The walls of the channel (48) may be elastomeric to facilitate stretching of the membrane (7) if desired through the use of gas or working channels (32). However, in some embodiments differential pressure may be used to stretch said membrane (7), and in that case the body and channel walls may be rigid, while simply the membrane (7) is elastomeric. In the embodiment where solely the membrane is elastomeric, the amount of absorbing material may be minimized as the membrane may represent a small volume of the membrane in one embodiment. In one embodiment, the microfluidic device comprises a body having at least one channel (3, 4) therein, said channel having elastomeric walls (48) and an elastomeric membrane (7), wherein at least a portion of said body is rigid. Furthermore, the embodiment comprising elastomeric channel walls (48) and a membrane (7) may necessitate further fabrication steps than an embodiment wherein the body is entirely rigid. In one embodiment, the microfluidic device comprises a body having at least one channel (3, 4) therein, said channel having rigid walls and an elastomeric membrane (7), wherein at least a portion of said body is rigid. However, a substantially rigid microfluidic device fabricated with elastomeric channel walls requires further fabricate steps, and lamination fabrication would not be able to be as effectively used.

Figure 37A:
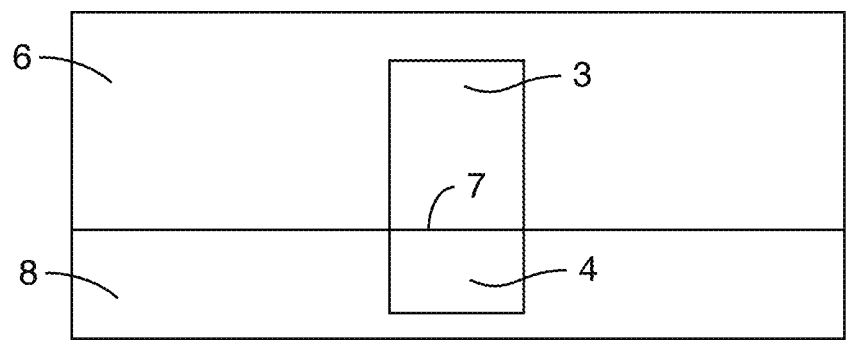
FIG. 37A-B display the membrane before and after the pressure differential is applied across the top and bottom channels. In some embodiments stretch is achieved by having a pressure differential across the top channel and bottom channel, as to push the membrane in the direction of the lower pressure channel.
Figure 37B:
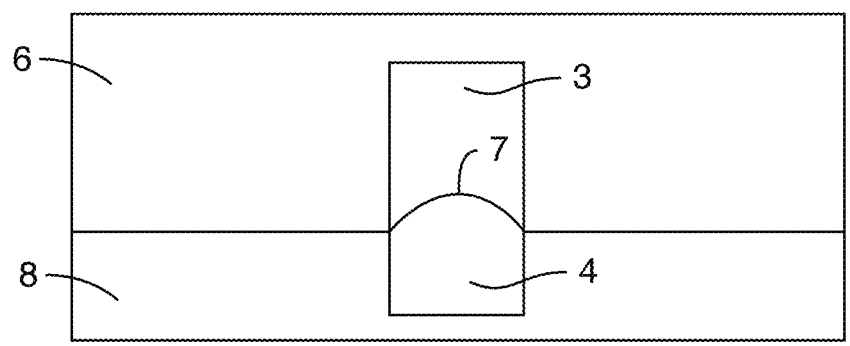

As previously stated, the microfluidic device fabricated out of entirely rigid materials may be modified to have an elastomeric membrane in order to facilitate differential stretching. Differential stretching is shown in FIGS. 37A and 37B. The microfluidic device shown in FIGS. 37A and 37B may have a body (6, 8) of any material as long as the membrane (7) is elastomeric.

In some cases, these entirely gas-impermeable microfluidic devices cause death of specimens, such as cells, as they are unable to access ambient gases, such as oxygen, which are required for essential biological functions, like respiration.

In order to overcome low oxygen levels in microfluidic devices, made both from rigid and elastomeric materials, several new techniques were contemplated and then employed. One embodiment to overcome the gas-impermeability was to add supplements, such as hemoglobin, to the media or fluid, such as to augment (e.g. increase) the gas carrying capacity of the media or fluid. It was found, however, that these supplements are sometimes difficult to work with.

Another embodiment to overcome the gas-impermeability was to flow fluids or media at high flow rates in order to introduce a higher concentration of dissolved oxygen into the channels of the microfluidic device. Unfortunately, there are some disadvantages to high flow rates including fluid or media waste. In the cases that cells are cultured in the microfluidic device, important cellular signals can be washed away. Further, higher flow rates result in higher levels of shear which may not always be favorable.

Figure 111A:
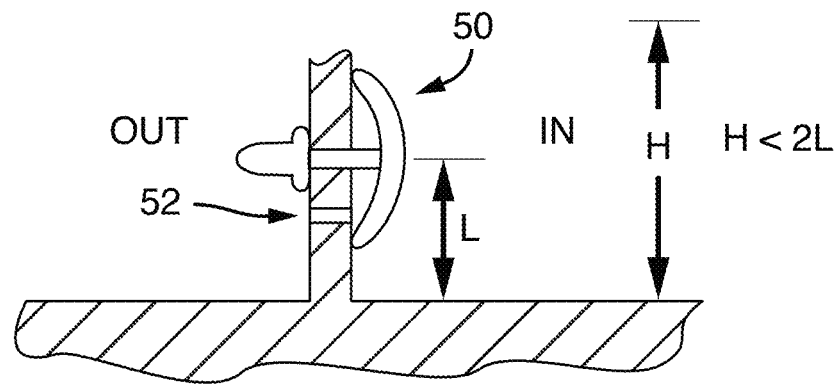
FIGS. 111A-G show multiple embodiments of recirculation methods between two reservoirs, in the figures being an "in" reservoir and an "out" reservoir.
Figure 111B:
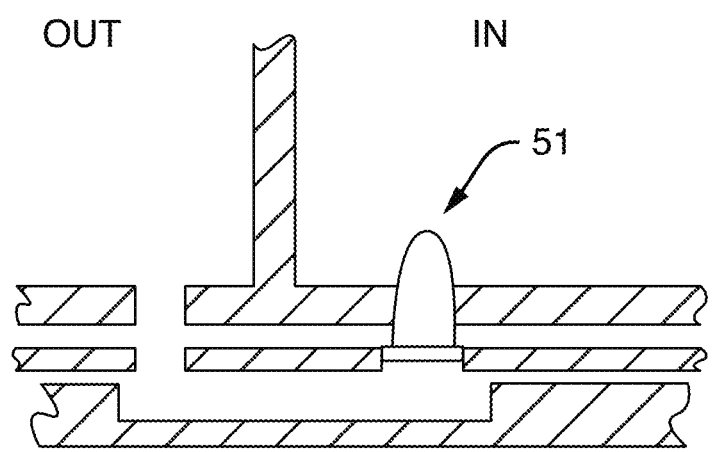
Figure 111C:
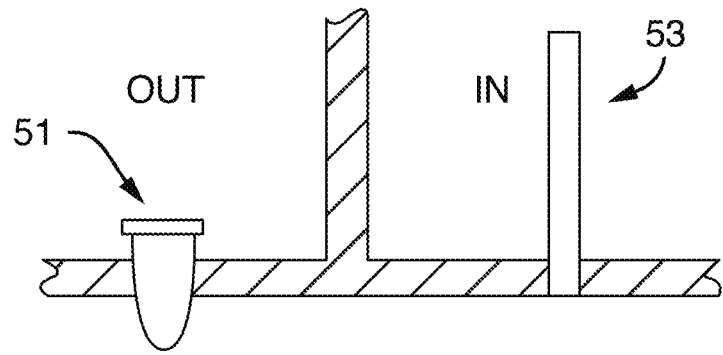
Figure 111D:
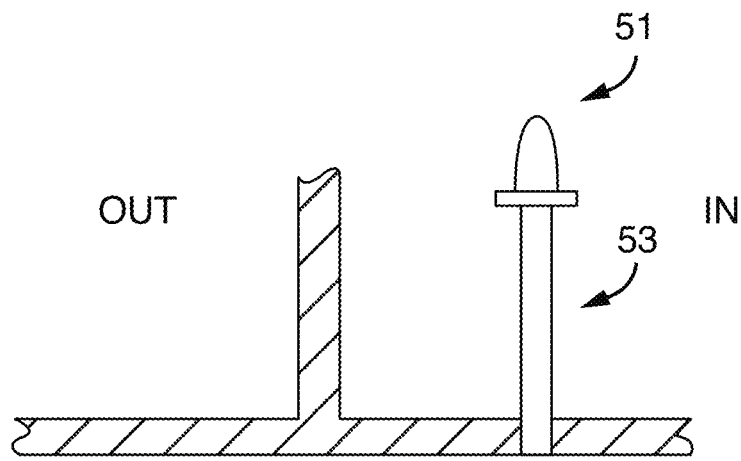
Figure 111E:
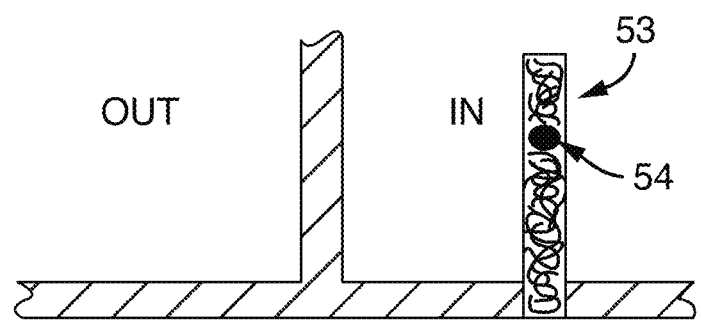
Figure 111F:
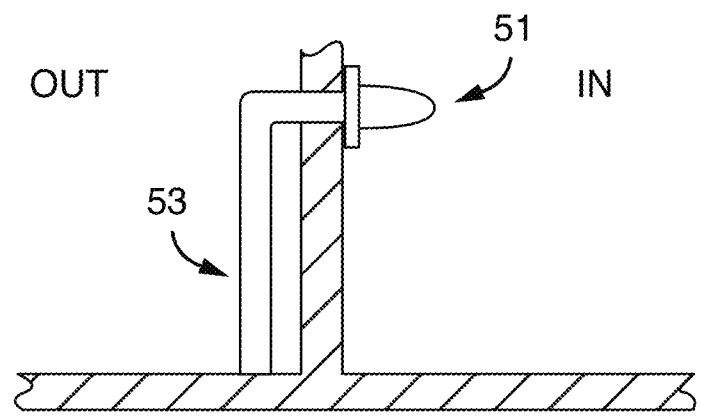
Figure 111G:
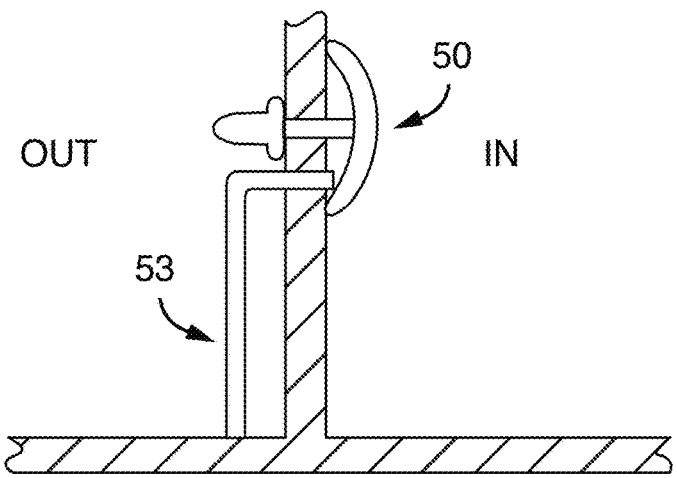

In order to overcome these disadvantages, fluid or media may be recirculated. Recirculation involves circulating substantially the same media through a microfluidic device at least twice. The media may be oxygenated between each circulation. Further, some experiments require high-shear. For example, vascular cells may need to be exposed to high-shear flow in some experiments. High-shear applications require "rapid-recirculation," and therefore large volumes of fluid. FIGS. 111A-G show several embodiments proposed for recirculating media through a microfluidic device, such as that depicted in FIG. 5, using a perfusion manifold assembly, such as that depicted in FIG. 7. FIGS. 111A-G show multiple embodiments of recirculation methods between two reservoirs, in the figures being an "in" reservoir and an "out" reservoir. The general technique contemplated is to have valves and tubes connecting an inlet reservoir to an outlet reservoir, such as those (19) in FIG. 7. Two reservoirs, separated by a wall are shown in FIGS. 111A-G. These reservoirs may be the reservoirs (19) in the perfusion manifold assembly (14). The reservoirs have fluid/liquid/media in them. FIG. 111A shows an embodiment of a recirculation setup using an umbrella valve (50). During flow through the microfluidic device, the valve remains closed and the "OUT" fills with fluid via flow through the microfluidic device. This is a discontinuous, albeit rapid, refilling of the inlet reservoir with media from the "OUT" reservoir, through a hole or channel between the reservoirs, that is normally blocked by the one-way (check) valve It is contemplated that a larger check valve, such as a umbrella valve (50), may be used during recirculation, as small valves are known to leak. FIG. 111B shows an embodiment of a recirculation setup using a duck-billed valve (51). FIG. 111C-E show multiple embodiments of recirculation setups using tubes (53) and duck billed valves (51). FIG. 111F shows an embodiment of a recirculation setup using a tube (53) and a duck-billed valve (51). The recirculation setup shown in FIG. 111F was tested and showed favorable compatibility and success with the culture module (82) and perfusion manifold assemblies (14). FIG. 111G shows an embodiment of a recirculation setup using a tube (53) and an umbrella valve (50). FIGS. 111A-G demonstrate the effectiveness of silicon valves. As well, it was contemplated to use lower resistance resistors to enable higher flow rates and lower shear if desired. Recirculation may be achieved using a mini-valve in a vestigial channel of a perfusion manifold assembly. Recirculation may also be achieved using discontinuous application of pressure to outlets to "burst" the valve leading to recirculation. When the valve "bursts" it allows fluid from the outlet reservoir into the inlet reservoir.

Potential use cases for recirculation include physiologically-relevant capillary-gel shear rates, neutrophil recruitment, with low perfusion manifold assembly shear, but high microfluidic device shear, and thrombosis recapitulation in a microfluidic device, with low perfusion manifold assembly shear, but high shear in the microfluidic device.

Figure 82:
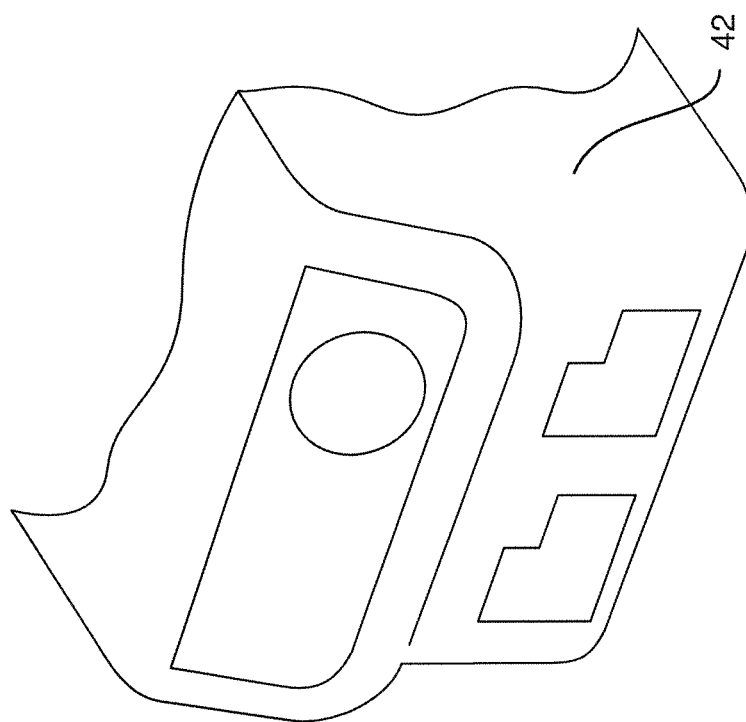
FIG. 82 shows an exemplary embodiment of a culture module.
Figure 83:
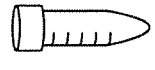
FIG. 83 shows two sets of dilutions acceptable for a five-point calibration.
Figure 84:
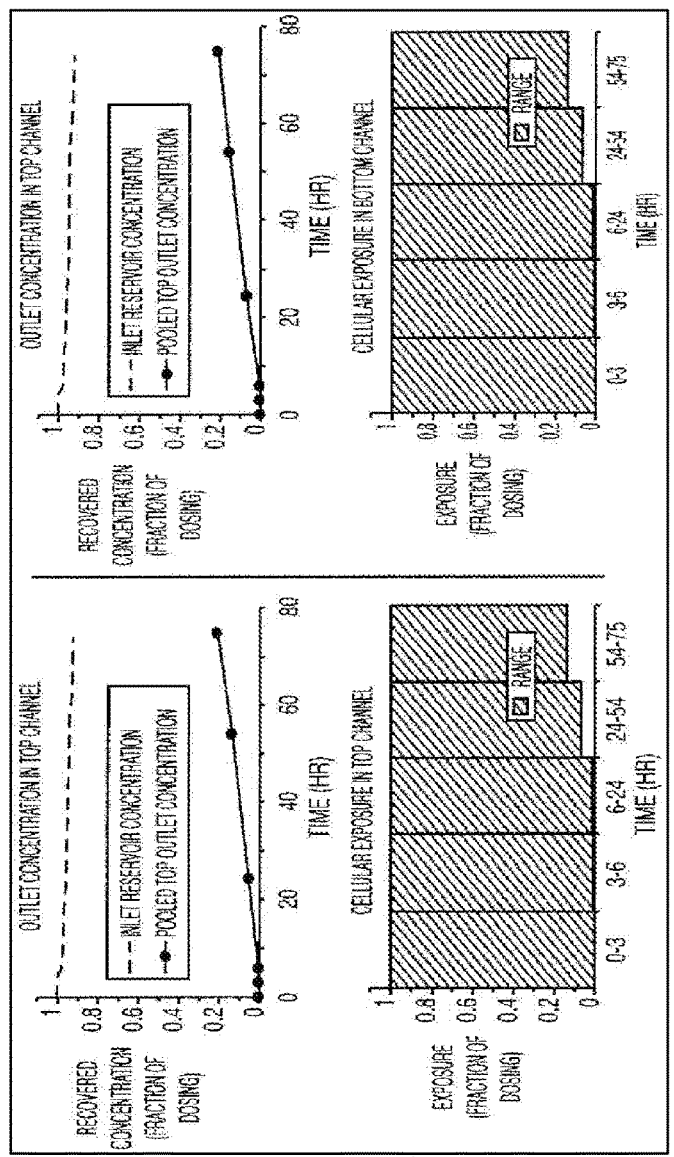
FIG. 84 shows a Microsoft Excel calculator outputting absorption data as part of the digital component of the compound distribution kit.
Figure 85:
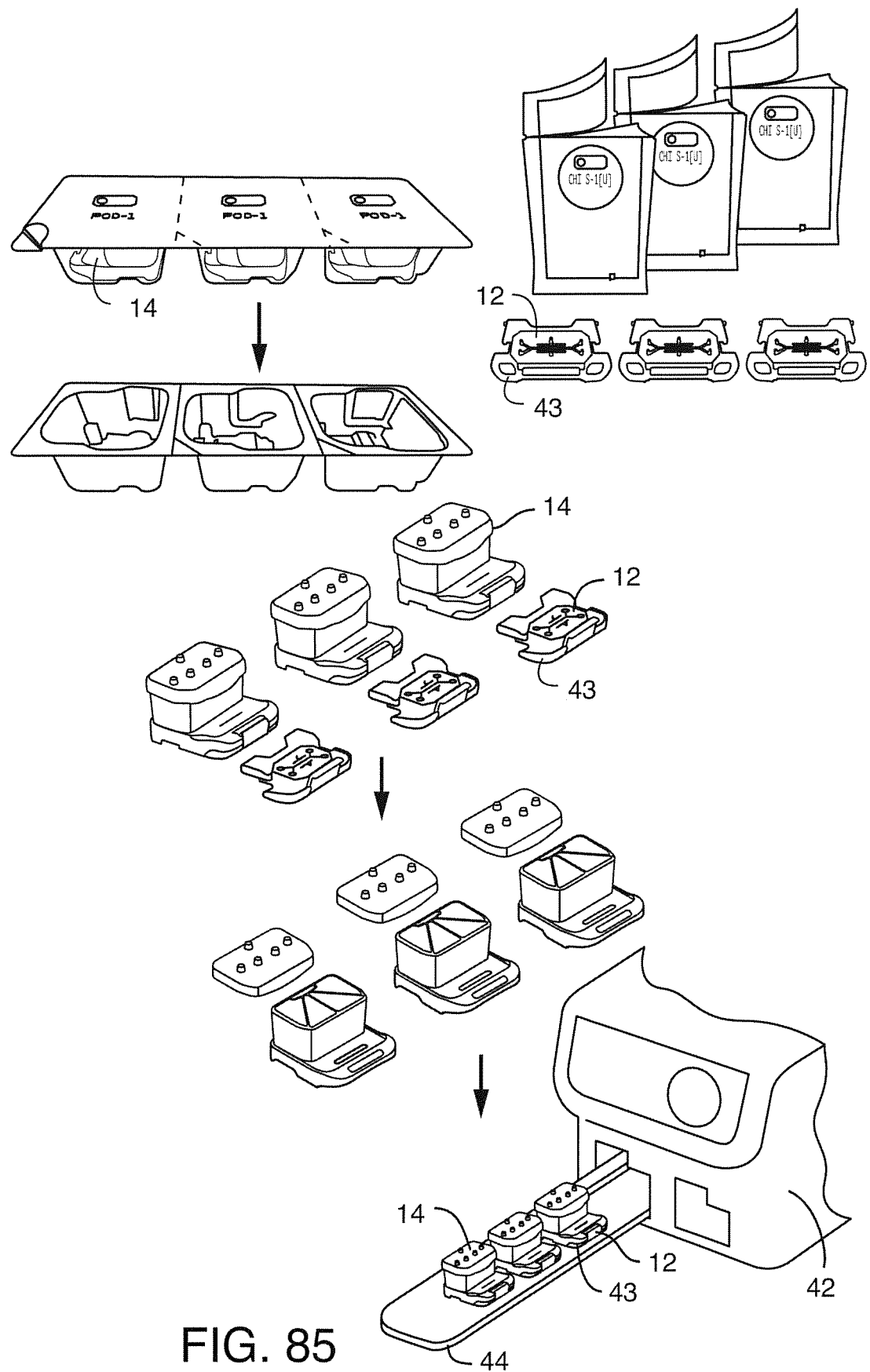
FIG. 85 shows a flow chart of preparing microfluidic devices and perfusion manifold assemblies for use with a culture module.
Figure 86B:
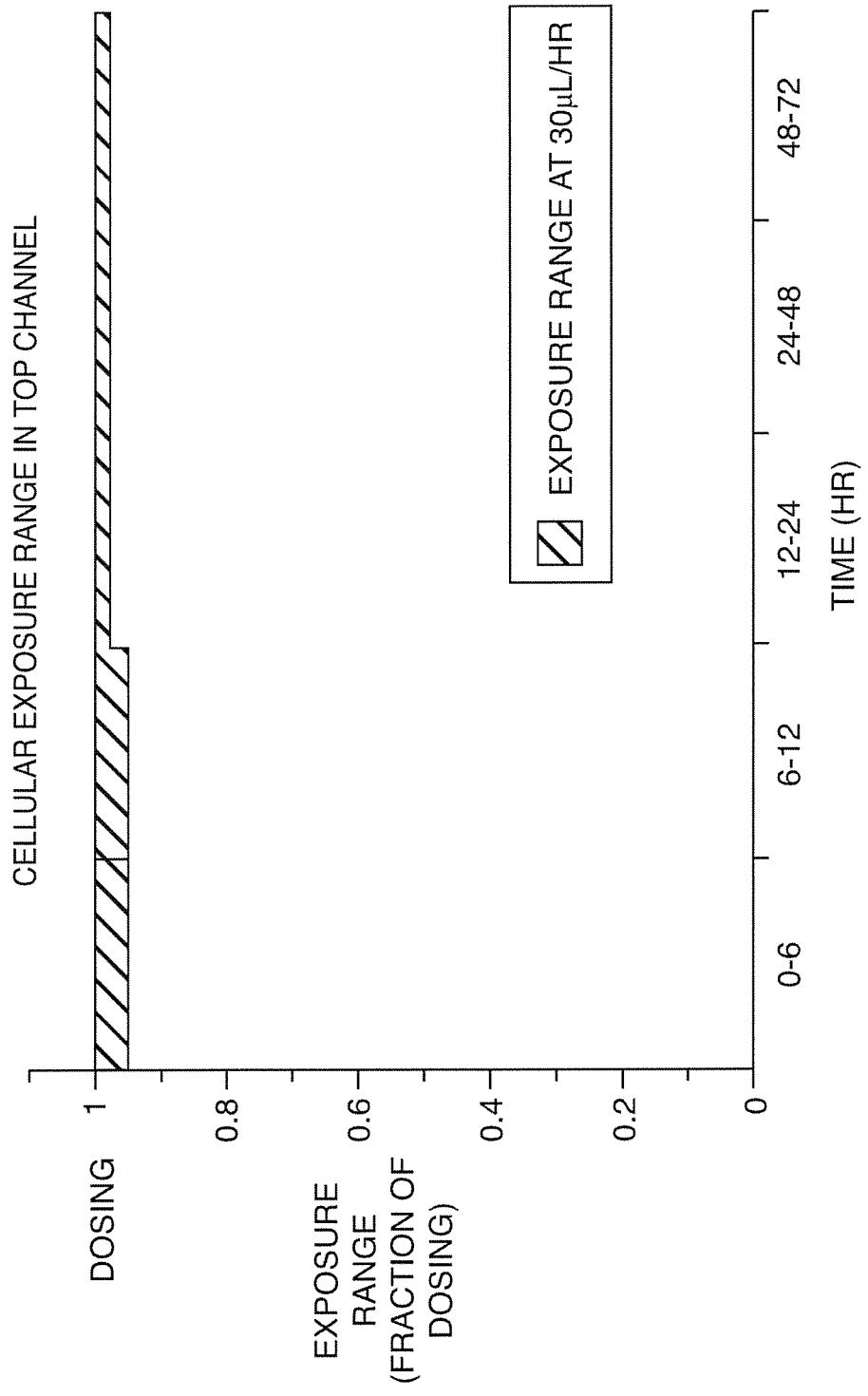
Figure 87A:
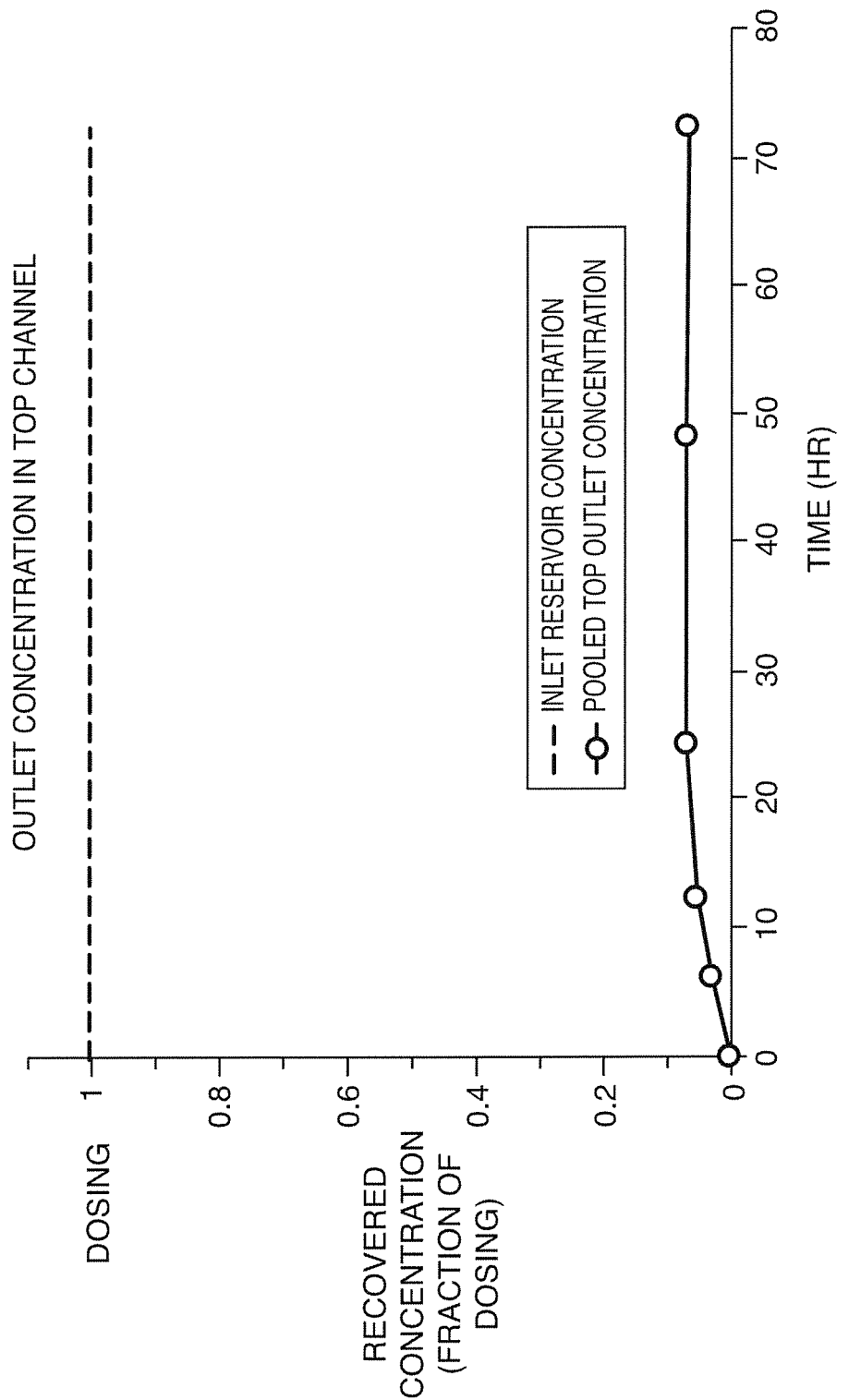
Figure 88A:
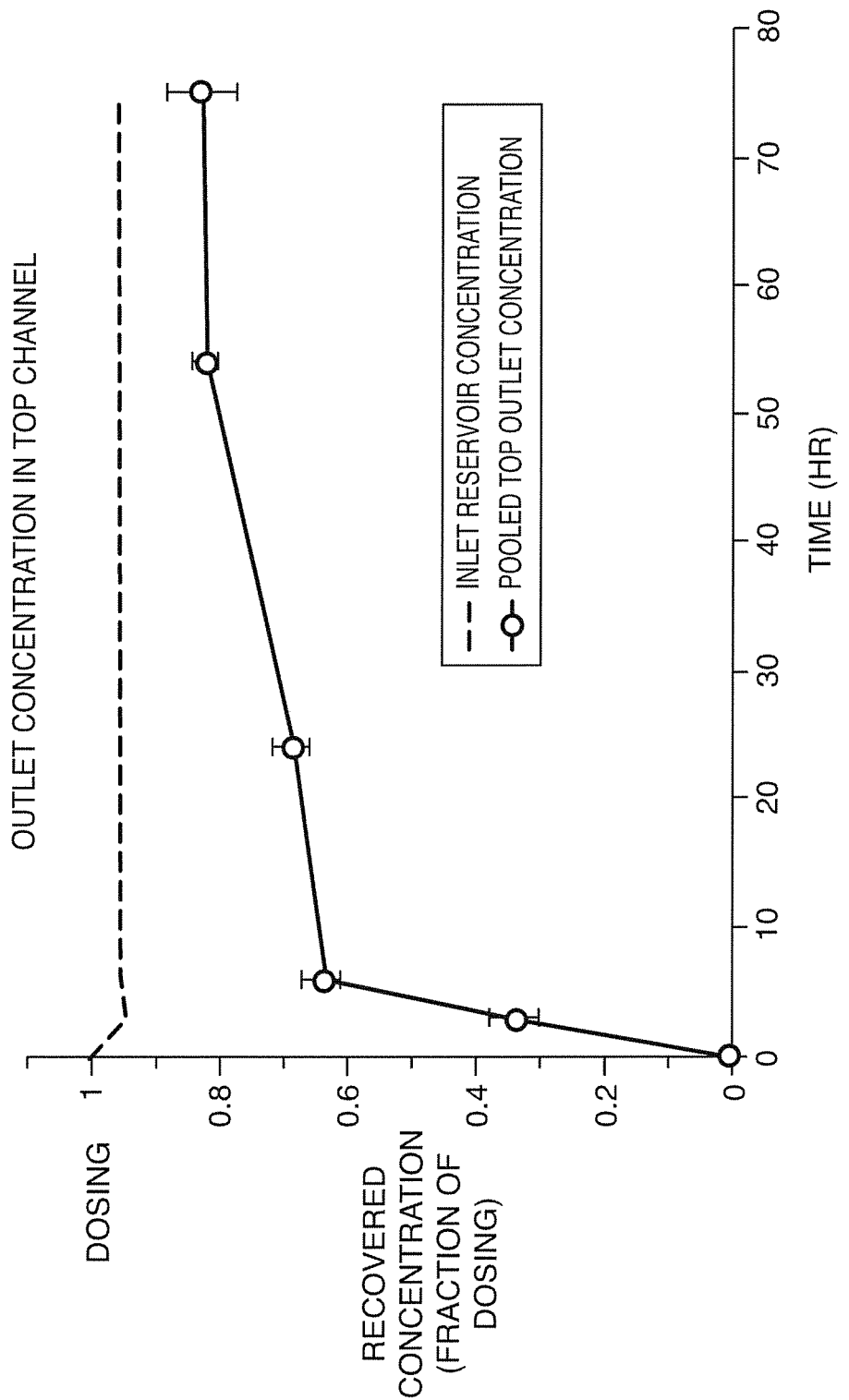
Figure 88C:
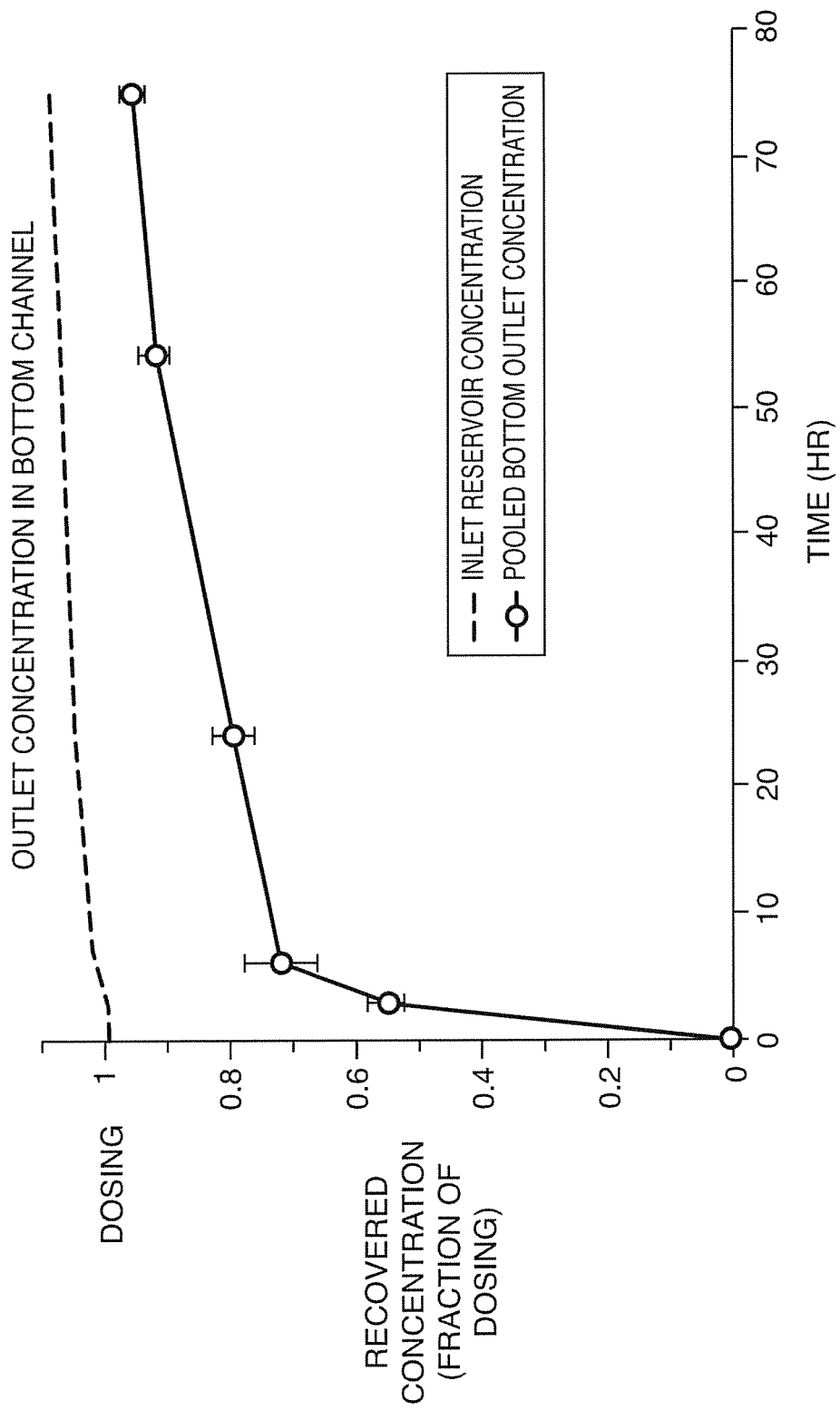
Figure 88D:
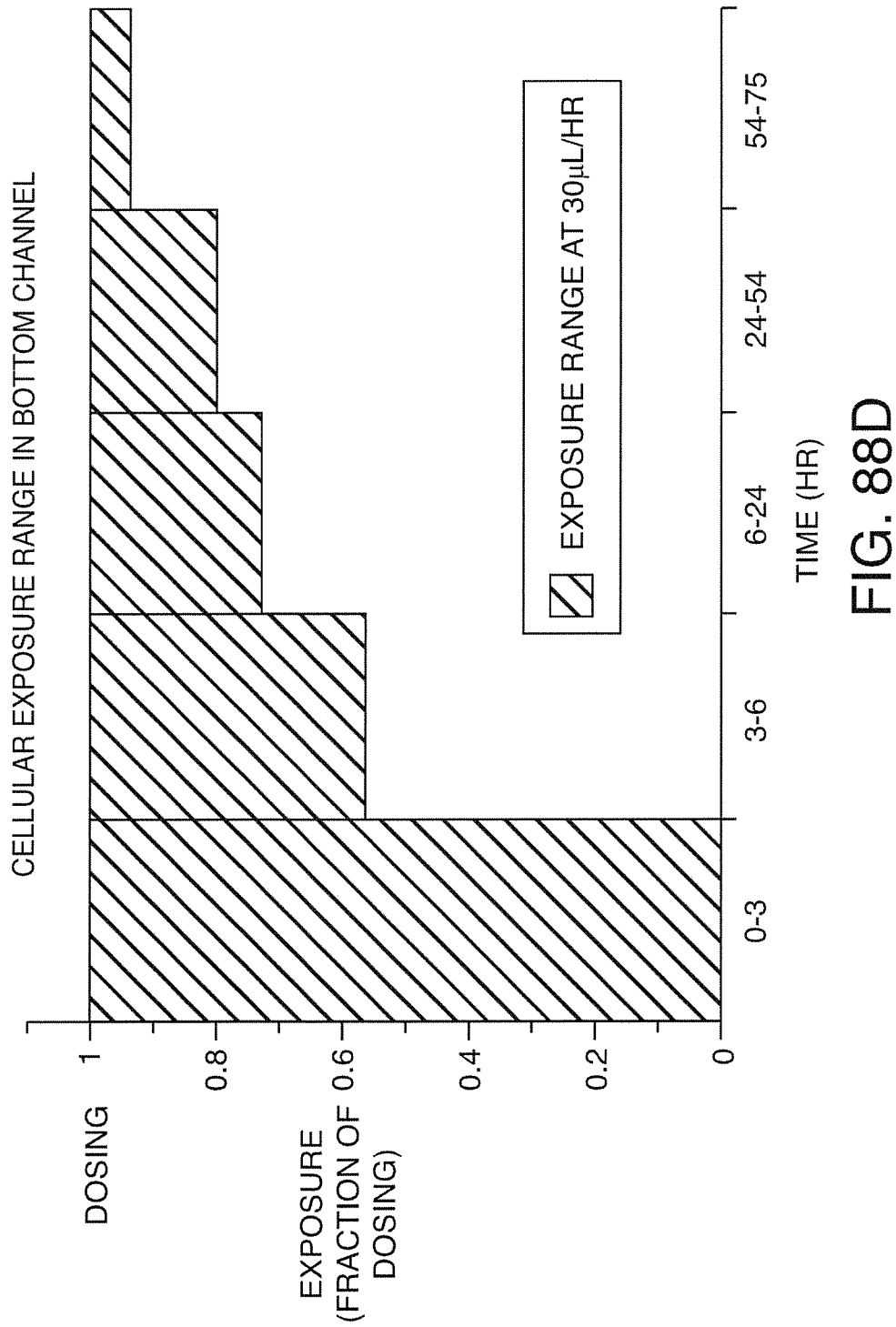
Figure 90A:
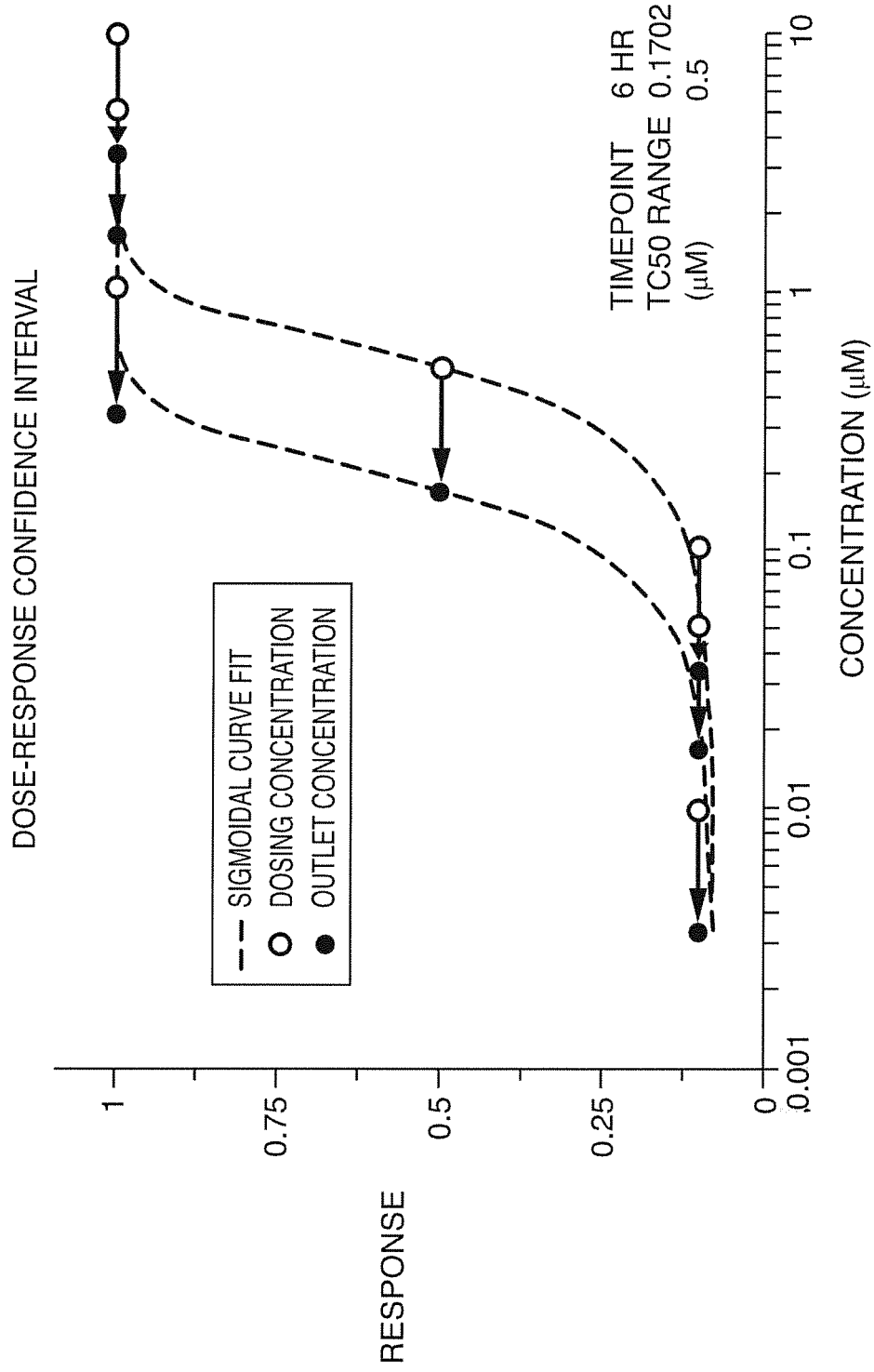
FIGS. 90A and 90B show an example dose-response curve for Rhodamine for a compound distribution kit calculator.
Figure 90B:
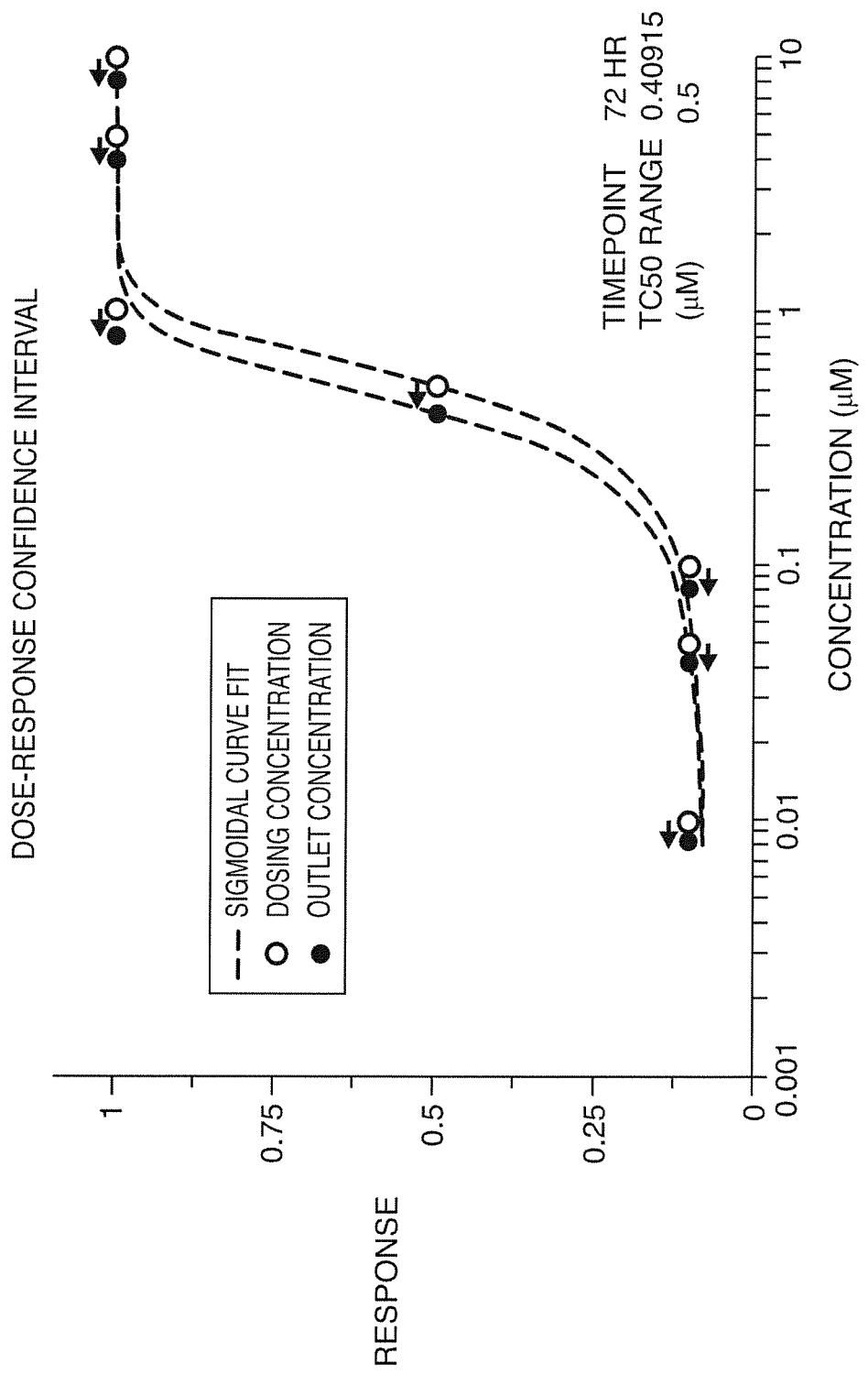

Sometimes, though, recirculation setups can be bulky and require equipment that is difficult to use. In those cases, fluid may be reciprocated, or flowed back and forth through the device. Reciprocation is non-obvious in the case of studying cells in vitro as fluid in vivo does not flow two ways. A surprising discovery was that cells in vitro displayed high levels of viability and organ-specific function with reciprocated media. Reciprocation can also be performed on microfluidic devices in the culture module (42), as seen in FIG. 82, and has been tested as part of experiments to evaluate the rate of metabolism of liver cells to low clearance compounds on the culture module (42). In the experiment, a "low volume" (200 uL) was rapidly reciprocated "back and forth" through the microfluidic device, in order to maximize contact time between media-containing-compound and the cell layer in the microfluidic device. This was achievable for more than 24 hours in a microfluidic device without cells.

Different cell types may require different amounts of oxygen in order to thrive. If cellular health is a goal/requirement, the rate of oxygen entering the microfluidic device should be greater than oxygen uptake rate within the microfluidic device in order to ensure that cells have access to as much oxygen as they require. For example, liver hepatocytes may require atmospheric levels of oxygen, whereas some bacteria cultures in the gut may require very low oxygen concentrations, with atmospheric levels being toxic. As such, microfluidic devices, especially those with applications in cellular biology, would benefit by being low-absorbing, while still allowing necessary levels of oxygen to reach cells, experiments, etc. inside the microfluidic device. Oftentimes however, low-absorbing materials tend to be gas-impermeable. In this way, a microfluidic device minimizing the amount of material absorbency may be designed with a combination of gas-permeable and gas-impermeable components to simultaneously minimize absorption and supply required gas to the cell layer.

An application for using microfluidic devices for Organ-Chips is understanding the resulting metabolite produced when cells are in contact with candidate compounds. In order to deduce intrinsic clearance of drugs, for example, the metabolism or loss of the parent compound oftentimes will need to be quantified. A first challenge in quantifying metabolism is if the metabolism is low. Low rates of metabolism can make it difficult to detect loss of the parent compound, even if the microfluidic device is non-absorbing. A practical limit of detection in an LC/MS instrument is ±25%. As such, a decrease in the concentration of the parent compound needs to be around 25% in order to detect/quantify metabolism with confidence. Another challenge in quantifying metabolism is material absorption of the parent compound. If absorption into the material, such as PDMS, is significant, then the observed apparent rate of metabolism (if all of compound loss is attributed to metabolism) will over-estimate actual cell-mediated metabolism as the decrease in compound concentration will be incorrectly attributed to metabolism. In some cases, all of the parent compound could be depleted by the material. In this case, absorption will prevent even an estimation of the upper possible rate of metabolism, since there will be no data to analyze as all of the compound has been lost. Material absorption can be computationally modeled and accounted for given information on the material-compound properties, like the rate and extent of absorption in the material, experimental parameters, like dosing concentration and flow rate, and microfluidic device geometry as long as all of the parent compound is not being depleted by the material. This however, requires extensive studies to characterize the compound—material interaction as well as computationally expensive models of the system to "subtract out" the contribution of material absorption to loss or disappearance of compound. To reiterate, though, if compound loss is complete, these models cannot account for the contribution of absorption, as compound loss is complete.

Figure 15A:
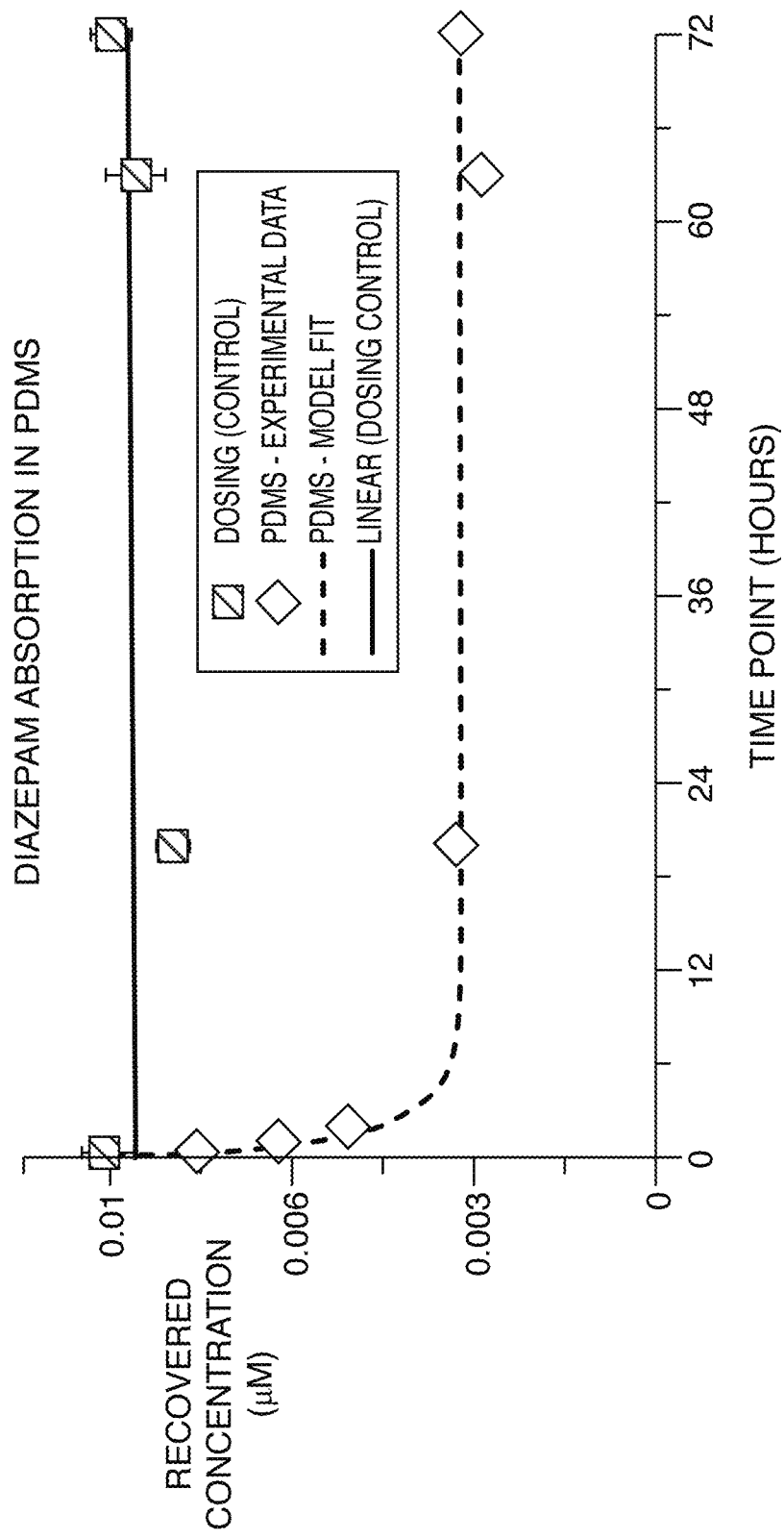
FIGS. 15A and 15B depicts the absorption of the drug Diazepam into both materials PDMS and COP over time, based on the recovered concentration of Diazepam remaining in the fluid contained in the glass vials where the material is contained. This depicts compound "loss" to the material over time.
Figure 15B:
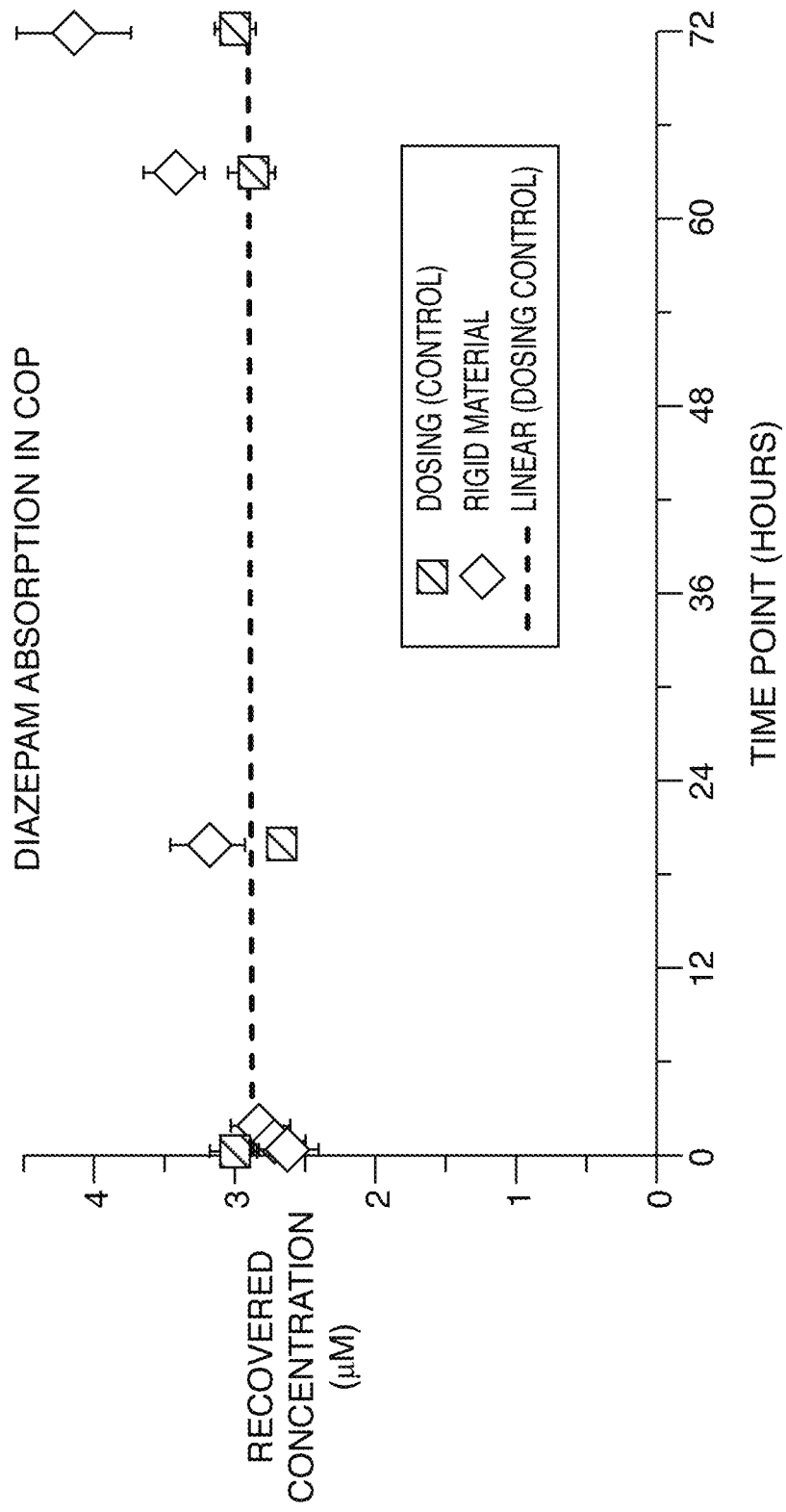
Figure 29A:
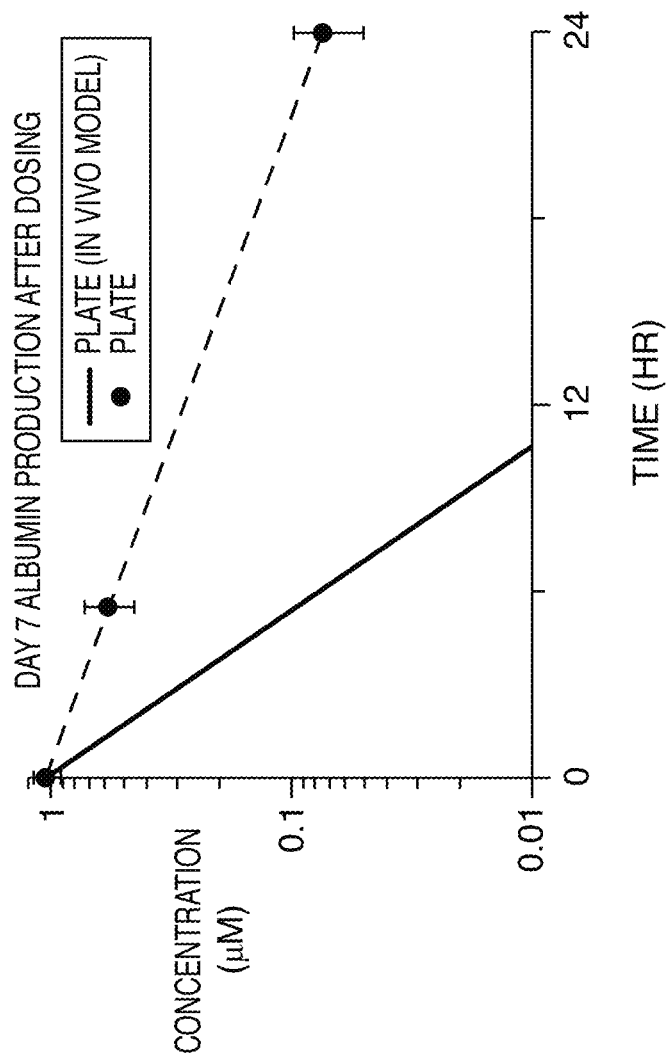
FIGS. 29A and 29B depict depletion of the drug Diazepam, which is known to absorb highly in PDMS, in both a plate and low-absorbing, gas-impermeable microfluidic device fabricated from COP.
Figure 29B:
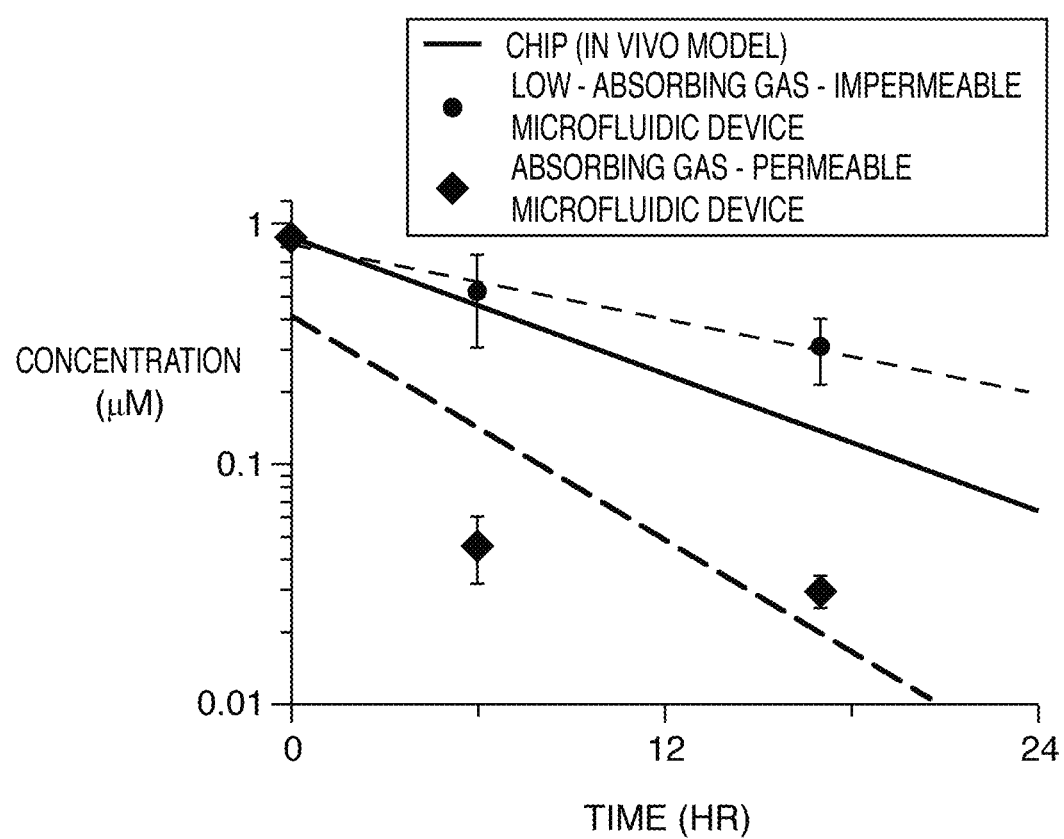
Figure 30:
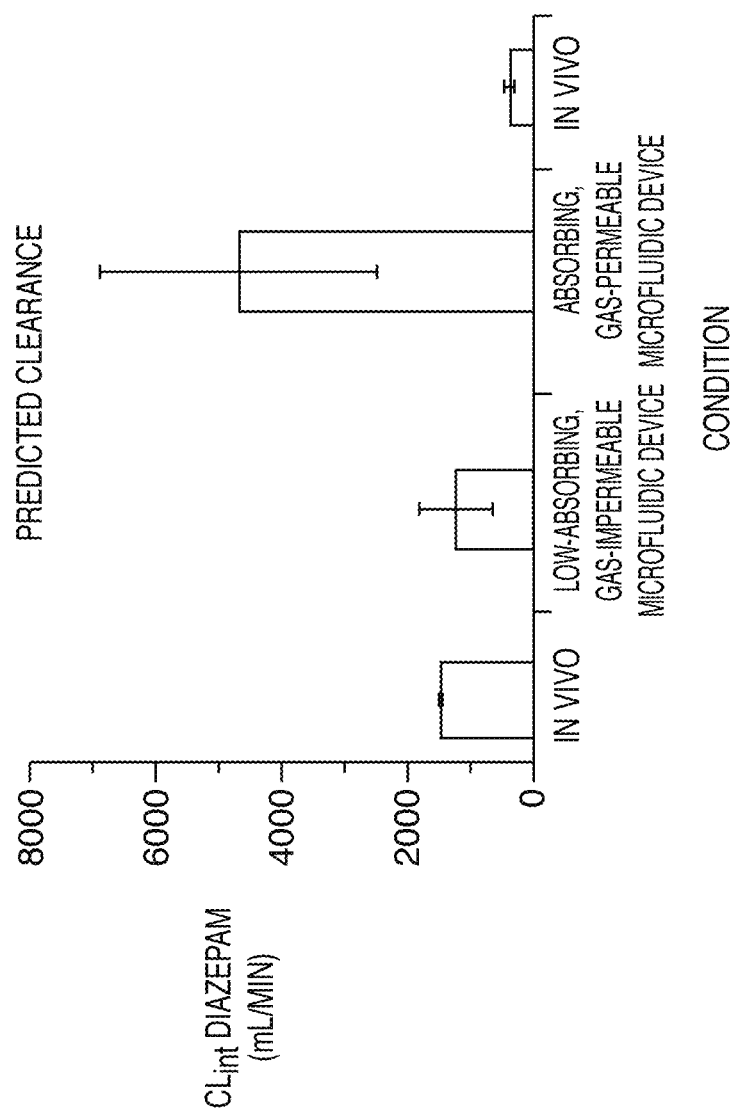
FIG. 30 shows the predicated clearance of Diazepam in vivo, the clearance measured on a plate, measured in an absorbing microfluidic device (12) fabricated from PDMS, and a low-absorbing, gas-impermeable microfluidic device (13) fabricated from COP. As can be seen in the graph, the low-absorbing device, here termed "New Liver-Chip", most closely matches the in vivo rate, and therefore is most predictive.

For example, quantifying the metabolism of Diazepam and amitriptyline in any system is difficult. Both Diazepam and amitriptyline are low clearance compounds, meaning that they are slowly metabolized by the liver. A first challenge is that both Diazepam and amitriptyline oftentimes need long exposure times in microfluidic devices, such as a Liver-Chip. Long exposure times are needed in order to see appreciable compound depletion in order to quantify metabolism. Long exposure times oftentimes mean that very little media volume is provided to the cells, which also provides nutrients and carries away waste. If media nutrients, such as carbon components and dissolved oxygen, are depleted and waste is not sufficiently removed, cells may be damaged or even die. A second challenge is that both Diazepam and amitriptyline absorb into PDMS, a common microfluidic device fabrication material. Long exposure times also mean that the drugs are in contact longer with the PDMS, which exacerbates compound loss due to absorption. PDMS absorption of the compounds can mask quantification of metabolism. FIGS. 15A and 15B depict the seriousness of Diazepam absorption into PDMS. As seen in FIG. 15A, when media containing a compound is exposed to a sample of PDMS material, which comprises the high-absorbing, gas-permeable microfluidic device (12) the decrease in compound concentration is significant in magnitude and speed. Within 12 hours of exposure, nearly the concentration of Diazepam has decreased by nearly ⅔. To contrast, it may be seen in FIG. 15B that none of the dosing concentration of Diazepam was lost to the bulk material of the low-absorbing, gas-impermeable microfluidic device (13) fabricated from COP. The experiments emphasize the large absorbance difference between PDMS and COP. Experiments using Diazepam were also run in microfluidic devices. FIG. 29A depicts an expected depletion model of the drug Diazepam in a plate culture calculated from in vivo drug clearance data versus actual data collected from a plate culture. FIG. 29B depicts an expected depletion model of the drug Diazepam in a microfluidic device when no absorption is present (theoretical) (12) compared to the results from a microfluidic device fabricated from an absorbing material—PDMS, and a low-absorbing microfluidic device (13) fabricated from COP. Both the COP microfluidic device (13) and the plate culture have depletion kinetics that are log-linear as would be expected, but only in the non-absorbing microfluidic device are the values close to those predicted by literature in vivo values. The results from the absorbing microfluidic device, fabricated out of PDMS, are not only off from those predicted from literature values, but the shape of the graph is not log-linear, as would be expected if metabolism was the only driver for compound loss. Indeed, the non-log-linear depletion of diazepam is a clear indication of another dynamic for compound loss, namely the material absorption that is known to occur. FIG. 30 shows the predicated clearance of Diazepam in vivo, on a plate, measured in an absorbing microfluidic device (12) fabricated from PDMS, and a low-absorbing, gas-impermeable microfluidic device (13) fabricated from COP. In summary, the plate culture underpredicts clearance, the absorbing microfluidic device overpredicts clearance, and the non-absorbing microfluidic device, here termed the "New Liver-Chip" accurately predicts intrinsic clearance.

As such, microfluidic devices fabricated out of a strategic combination of gas-permeable and gas-impermeable materials are advantageous compared to previously fabricated microfluidic devices as they decrease absorbency of important compounds being tested as well as allow the experiments to access ambient gases.

Figure 2:
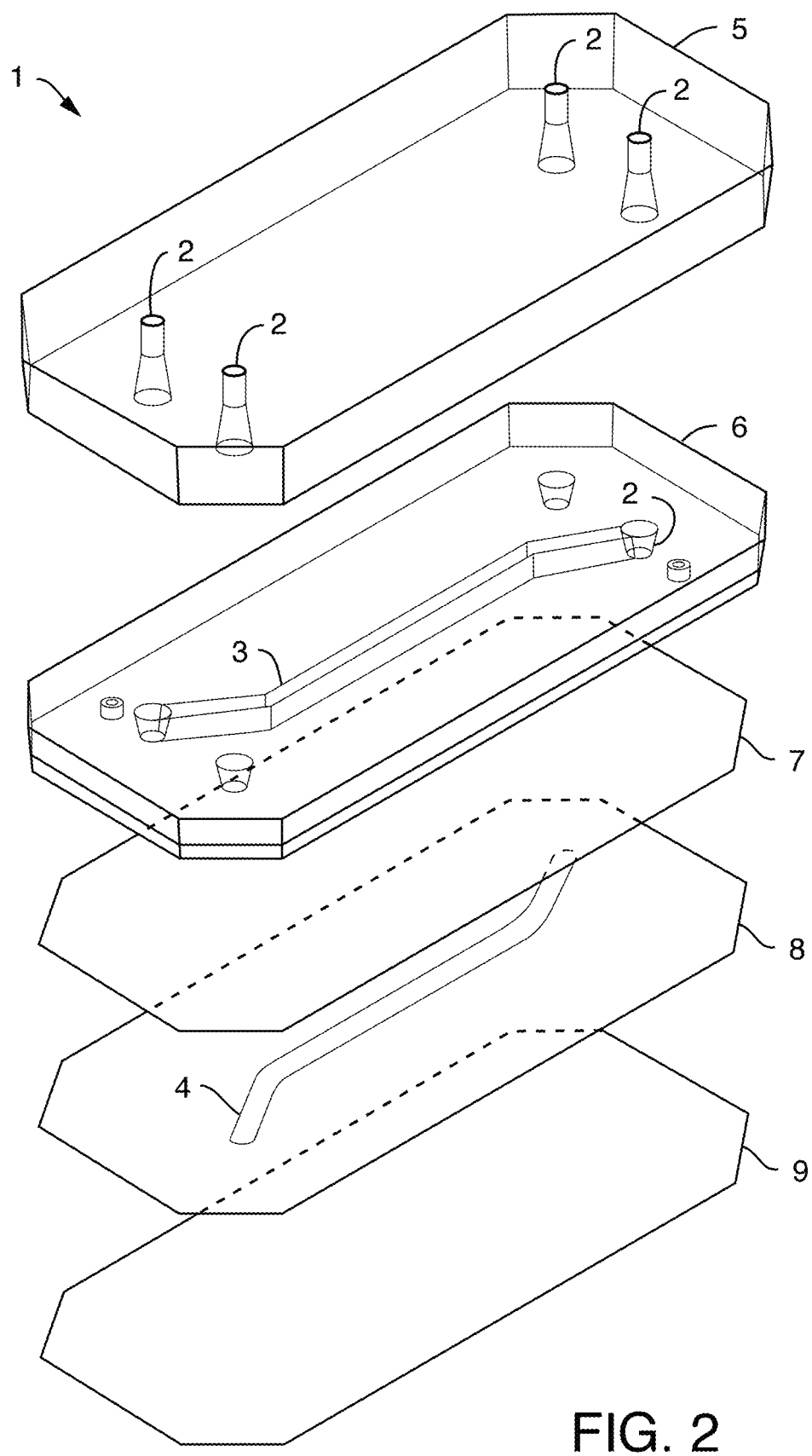
FIG. 2 depicts an exploded view of one embodiment of a low-absorbing, gas-permeable microfluidic device. The exploded view shows that the microfluidic device comprise a gasket, a top channel layer, a membrane, a bottom channel layer, a top channel, a bottom channel and a gas-exchanger.
Figure 3:
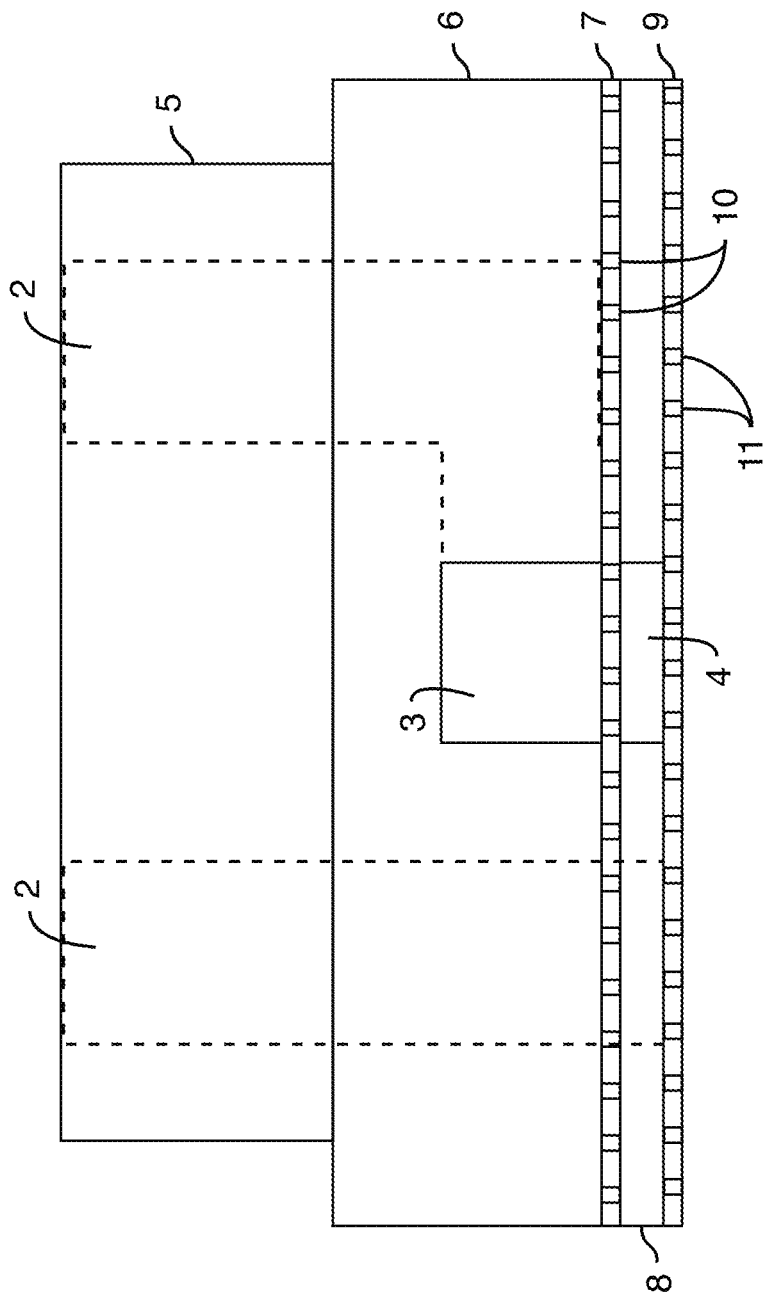
FIG. 3 shows a cross-sectional view of one embodiment of a low-absorbing, gas-permeable microfluidic device comprising a gasket, a top layer, a membrane, a bottom layer, a top channel, a bottom channel, and a gas-exchanger.

The first component of the resulting invention, is a low-absorbent two-channel microfluidic device (1) comprising a gas-permeable membrane (7) between top (6) and bottom (8) channel layers, as well as a gas-exchanger (9) to allow gas transport from the ambient environment outside the microfluidic device into the microfluidic device, in order to meet the needs of the experiment. One embodiment of this invention is depicted in FIG. 1, where a bonded, low-absorbent microfluidic device (1) may be seen. FIG. 2 depicts one embodiment of a possible configuration of the layers, with the gas exchanger (9) on the bottom of the device, bonded to the bottom channel layer (8), bonded to the membrane (7), bonded to the top channel layer (6), bonded to the gasket (5). The organization seen in FIG. 2 is just one possible configuration. Any organization of the layers is considered, as long as the bottom and top layers are separated by the membrane. The top (6) and bottom (8) channel layers, the membrane (7) and the gas exchanger (9) may be attached permanently or temporarily. In one embodiment the layers are attached through plasma-activated bonding. In one embodiment the microfluidic device (1) is bonded permanently by coating the microfluidic device (1) components with silane. In one embodiment, the microfluidic device (1) is used for the characterization of organ microbiomes. FIG. 3 depicts a cross-sectional view of one embodiment of a low-absorbent microfluidic device contemplated herein. In FIG. 3 depicts how in this embodiment the ports (2) in the gasket (5) line up with the ports in the top channel layer (6). As well, FIG. 3 depicts how in this embodiment the top channel (3) in the top channel layer (6) is directly on top of the bottom channel (4) in the bottom channel layer (8), separated by the membrane (7). FIG. 3 also depicts an embodiment in which the membrane has membrane pores (10) and the gas exchanger has gas exchanger pores (11).

Figure 9:
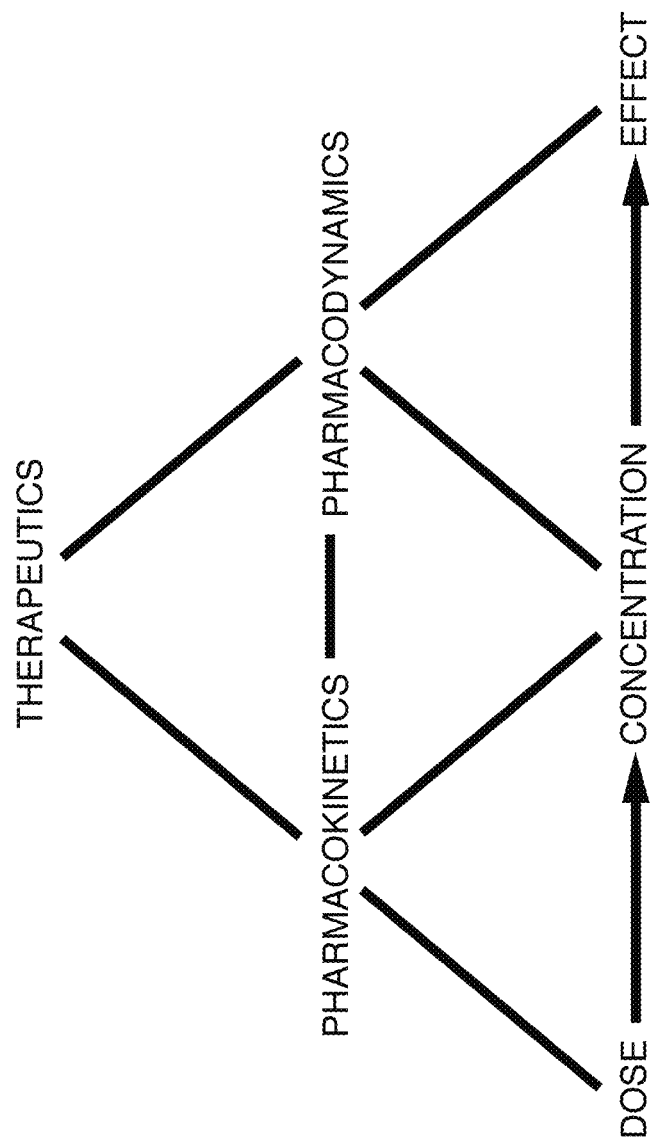
FIG. 9 depicts the drug development triangle, comprising important aspects of developing an understanding of how a therapeutic is going to interact with the body. In summary, the study of pharmacokinetics aims to understand how and quantitatively predict how a particular dose or mass of compound is processed by the various organs in the body to produce and exposure concentration. Pharmacodynamics aims to understand and predict how that exposure concentration results in a given effect (either efficacy or toxicity). Organ-Chips can, have, and are being used to study both pharmacokinetics and pharmacodynamics, which underscores the importance of understanding and controlling the concentration of compounds in microfluidic devices since concentration it is vital for both fields, and, therefore, vital for understanding and predicting how a pharmaceutical is going to interact with the human body.

Microfluidic devices may be used to test the effects drugs, foods, chemicals, cosmetics, physiological stimulants stresses etc. have on cellular systems. In order to quantify metabolism of compounds in cells, such as liver cells, several factors should be understood, such as compound interaction with biology, loss to materials, gradients across the device, protein binding, update/efflux of transporters, passive diffusion through the membrane (7), as well as other possible parameters. FIG. 9 depicts the drug development triangle.

FIG. 9 depicts the drug development triangle, comprising important aspects of developing an understanding of how a therapeutic is going to interact with the body. In summary, the study of pharmacokinetics aims to understand how and quantitatively predict how a particular dose or mass of compound is processed by the various organs in the body to produce and exposure concentration. Quantitative pharmacokinetics focuses on the movement of pharmaceuticals in vivo and in vitro, such as pharmaceutical absorption, distribution, metabolism and excretion. Pharmacodynamics aims to understand and predict how that exposure concentration results in a given effect (either efficacy or toxicity). Quantitative pharmacodynamics focuses on the effects of pharmaceuticals in vivo and in vitro and the mechanism of their action. Examples of pharmacodynamic studies include parent compound dose-response and metabolite dose-response, focusing then on toxicity and efficacy of the pharmaceutical. Microfluidic devices can, have, and are being used to study both pharmacokinetics and pharmacodynamics, which underscores the importance of understanding and controlling the concentration of compounds in microfluidic devices since concentration it is vital for both fields, and, therefore, vital for understanding and predicting how a pharmaceutical is going to interact with the human body. Indeed, the base of the drug development triangle, or the most basic data that should be collected during experimentation, is concentration—both in terms of the effects the cells had on the concentration (pharmacokinetics) and the concentration the cells were exposed to (pharmacodynamics). To reiterate, to enable therapeutic prediction using microfluidic devices and in vitro systems in general, there needs to be a high confidence in the concentrations of compound in the system and an understanding of how and why that concentration is changing.

Figure 12:
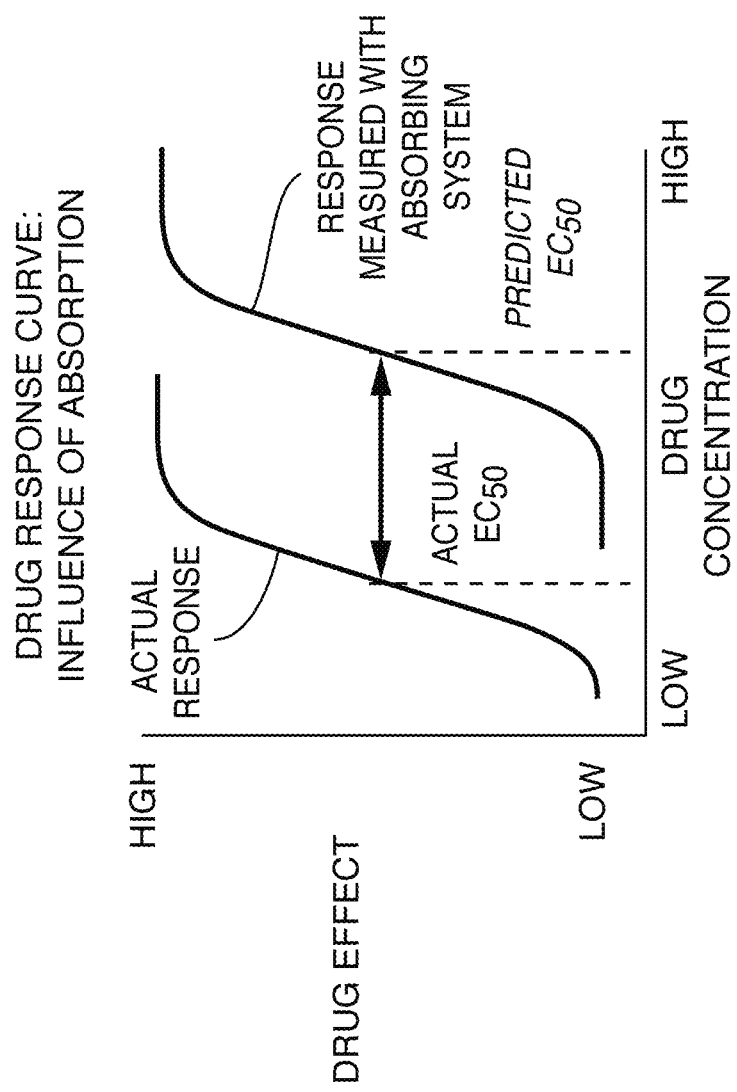
FIG. 12 depicts a drug response curve and the influence of absorption on it. Absorption causes the observed dose response curve to shift as the exposure concentration of the drug to the cells (X-axis) is modulated due to absorption.

Typical microfluidic devices for the use of studying cells are often fabricated out of entirely gas-permeable materials. These entirely gas-permeable microfluidic devices have the possibility of causing serious result variability, as gas-permeable materials tend to absorb small molecule compounds disrupting data. FIG. 11 depicts the signature-compound distribution profile in an absorbing, gas-permeable microfluidic device (12), fabricated out of PDMS. The model depicts a highly absorbing compound, midazolam, being perfused through both the top and bottom channels of the microfluidic device 150 ul/hr. As seen in FIG. 11, only the cells closest to the port (2) where a compound, such as a small-molecule pharmaceutical, is being introduced see the expected concentration or "dosed" concentration. The average concentration impinging on the cells differs from the input concentration, resulting from a concentration gradient along the length of the microfluidic device (12). As such, it is difficult to evaluate the compound pharmacodynamics (e.g., $EC_{50}$, the concentration of drug that gives the half-maximal response from specimen) in the presence of flow and absorption. To further complicate matters, the rate and level of absorption changes with exposure time. As such, spatio-temporal gradients will develop, which are extraordinarily difficult to characterize and account for. Indeed, it is as if a moving target (concentration changes along the length) is trying to be hit while the target is also changing in size (concentration changes with time). Absorption, especially, diminishes the ability of the system to accurately predict toxicity and efficacy. FIG. 12 depicts a stereotypical sigmoidal drug response curve and the influence of absorption on it. If it is assumed that the cells are in contact with all of the drug (or enzyme, etc.) entering the system, then it is assumed that the cells are metabolizing a resulting compound based on the dose entering the system. However, if the cells are actually only in contact with lower levels of the drug (due to absorption or loss of the compound to system components) then the effective concentration of drug (or enzyme, etc.) will be over-predicted. In other words, scientists will believe that a higher than necessary amount of the drug (or enzyme, etc.) may be advantageous in order to produce a given effect. The overuse of the drug (or enzyme, etc.) due to microfluidic device absorbency not only skews data and makes prediction unreliable, but also adds unnecessary costs for drug development and discovery. More importantly, however, inaccurate predictions of $EC_{50}$ or $TC_{50}$, or the concentration where 50% of a toxic effect is seen, could result in the poor decisions on dosing concentrations for in vivo studies, including clinical trials (based on the in vitro data). The basic principle of toxicology is Sola dosis facit venenum or "the dose [is what] makes the poison". In other words, at a high enough concentration, most compounds will become toxic; over-estimating the concentration that causes toxicity ($TC_{50}$) could result in erroneously dosing a patient with a toxic concentration of a compound. Safety assessment of absorbing compounds, therefore, is seriously hampered by absorption.

Figure 4:
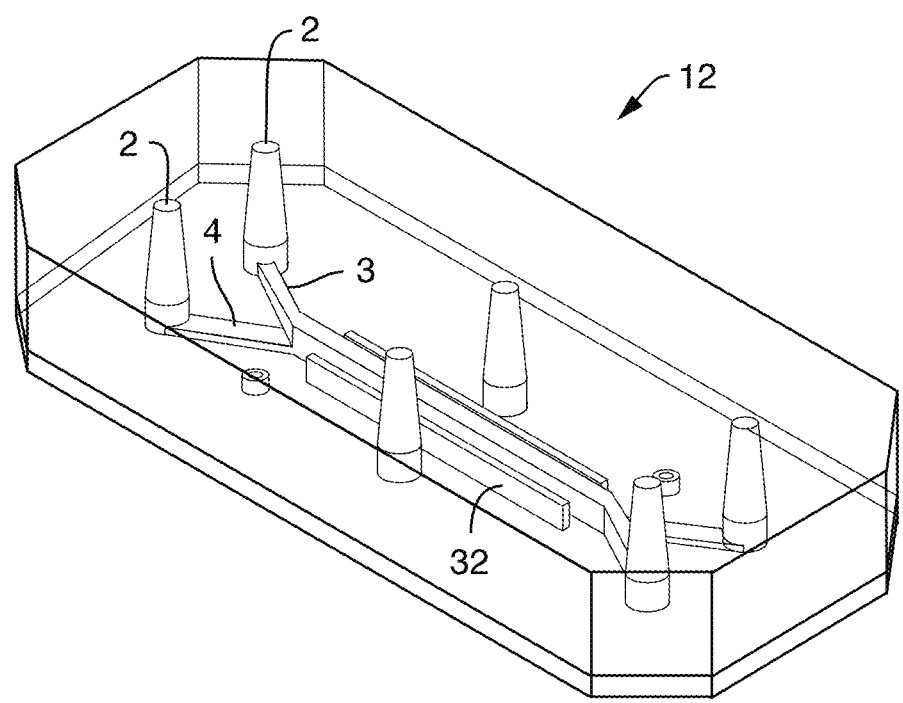
FIG. 4 shows an absorbing, gas-permeable microfluidic device fabricated from PDMS.

FIG. 4 depicts an embodiment of a microfluidic device described in U.S. Pat. No. 8,647,861. The absorbent microfluidic device (12) was fabricated with PDMS in one embodiment. PDMS, and similar fabrication materials, absorb highly many compounds that pharmaceutical scientists desire to test within the microfluidic devices.

Another important aspect of microfluidic device material choice is transparency. Transparency offers scientists the ability to image microfluidic devices on microscopes and be able to get an intimate perspective on cellular interactions, phenotypes, and more. Opaqueness offers scientists the ability to protect their experiments from ambient light if necessary. As such, the microfluidic device may be partially or entirely transparent or entirely opaque depending on the requirements of the experiment.

The top channel layer (6) and bottom channel layer (8) comprise substrates containing channels, such as the top channel (3) and the bottom channel (4), or pathways for fluid movement and experiment housing. Experiments contained within the channels include cell growth and testing. Channels, such as the top channel (3) and the bottom channel (4), in the channel layers may be a variety of different heights, including but not limited to equaling the height of the channel layer itself or cutting through the entire channel layer. At each end of the top channel is a port (2) or via so that fluids may be introduced into the microfluidic device. As well, microfluidic device infrastructure may be made to be in fluidic communication with the microfluidic device through these ports (2). The top channel layer (6) and bottom channel layer (8) may be fabricated from the same or different materials. In some embodiments these materials are gas-impermeable in order to limit compound absorbency. Gas-impermeable materials that have also been shown to be low absorbing include cyclic olefin copolymer (CCP), cyclic olefin polymer (COP), polycarbonate, polyethylene (PE), polyethylene Terephthalate, polystyrene (PS), (PET) glass, etc. The top channel layer (6) and bottom channel layer (8) may also achieve gas-impermeability, and by default low absorption, by being fabricated from a partially gas-impermeable material, coated with a gas-impermeable substance, having its surface modified to reach impermeability, etc.

Figure 35A:
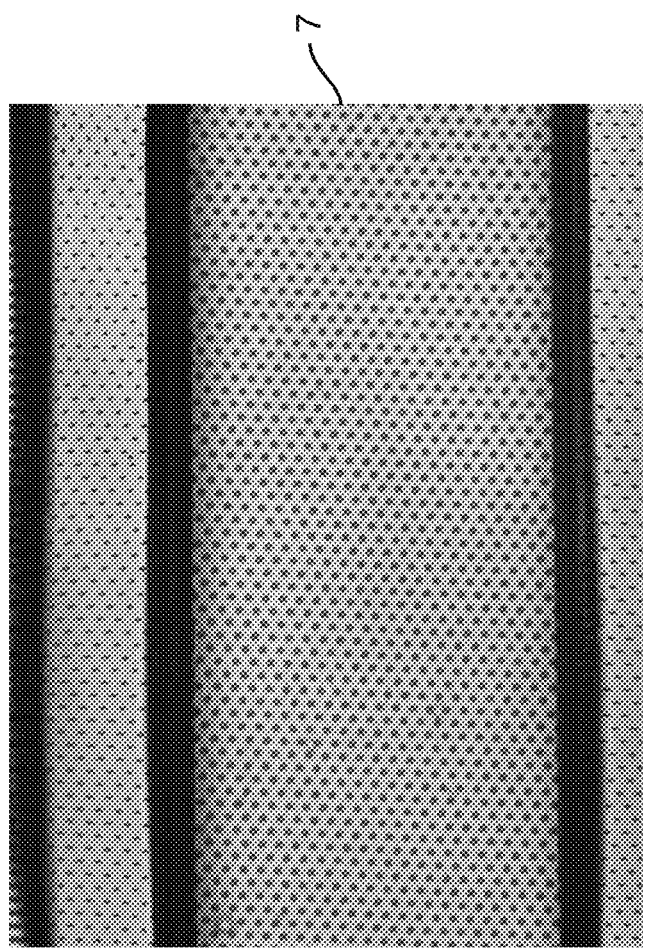
FIGS. 35A and 35B illustrate the difference in stretch between the center of the membrane and a section of the membrane close to the ports in a completely flexible absorbing microfluidic device that is stretched via vacuum application to the working channels.
Figure 35B:
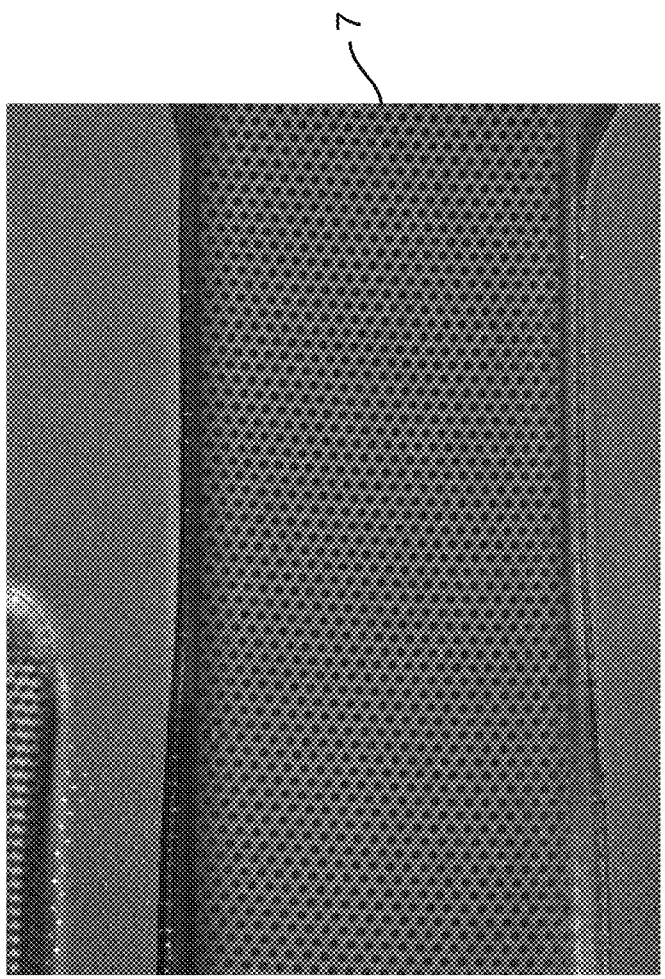

The membrane (7) provides a diffusive barrier between the top channel (3) and bottom channel (4). While the membrane (7) may be gas-impermeable, oftentimes it is beneficial to allow oxygen diffusion through the membrane (7). As such, in some embodiments, it is beneficial to have a gas-permeable membrane (7). For example, cell types in the top channel (3) and bottom channel (4) may benefit from exchanging gases. Gas-permeability may be prioritized over low-absorbency in the membrane layer (7) for this diffusivity reason. In some embodiments, the membrane (7) may be a smaller volume as compared to the volumes of other components of the microfluidic device (1), such as the top channel layer (6) and bottom channel layer (8) and the gas exchanger (9). If the membrane (7) has a smaller volume than other components it would not absorb as much of the experimental compound, minimizing absorbency impacts. In other embodiments the membrane (7) is non-porous in order to limit physical contact between top channel (3) and bottom channel (4) environments and inhabitants. In some embodiments, the membrane (7) may be considered porous, containing membrane pores (10), in order to allow contact between top channel (3) and bottom channel (4) environments and inhabitants. In one embodiment the membrane layer (7) is homogenous, such as being evenly porous across the entire layer. In another embodiment the membrane layer (7) is heterogenous, such as being porous only in the regions that overlap top channel (3) and bottom channel (4) on the top channel layer (6) and bottom channel layer (8). In some embodiments the membrane (7) is flexible as to allow it to stretch. In this embodiment the ability to stretch is beneficial for experiments involving cells attached to the membrane (7), as it is able to replicate mechanical strain on cells as seen in vivo. In some embodiments this stretch is achieved by using vacuum in optional working channels (15), in the microfluidic device, such as those seen in FIG. 4 of the absorbent microfluidic device. In one embodiment the working channels (32) have their own entrance ports (14). Using working channels (32) to induce mechanical actuation and stretch of the membrane (7) creates a strain differential across the membrane (7) where strain in the center of the microfluidic device (12) is significantly greater than the strain near the ports (2). FIGS. 35A and 35B illustrate the difference in stretch between the center of the membrane (7) and a section of the membrane (7) close to the ports (2) in a flexible absorbing microfluidic device that is stretched via vacuum application to the working channels. FIG. 35A demonstrates deformation of the channel due to engagement with a perfusion manifold assembly, even before stretching the membrane. FIG. 35B shows this same device under stretch. It can be seen that in an absorbing microfluidic device that is actuated in this manner, that there has is a non-uniform stretch profile along the channel length, especially but not limited to, the area toward the edges of the working channels and far away from the working channels.

Figure 36:
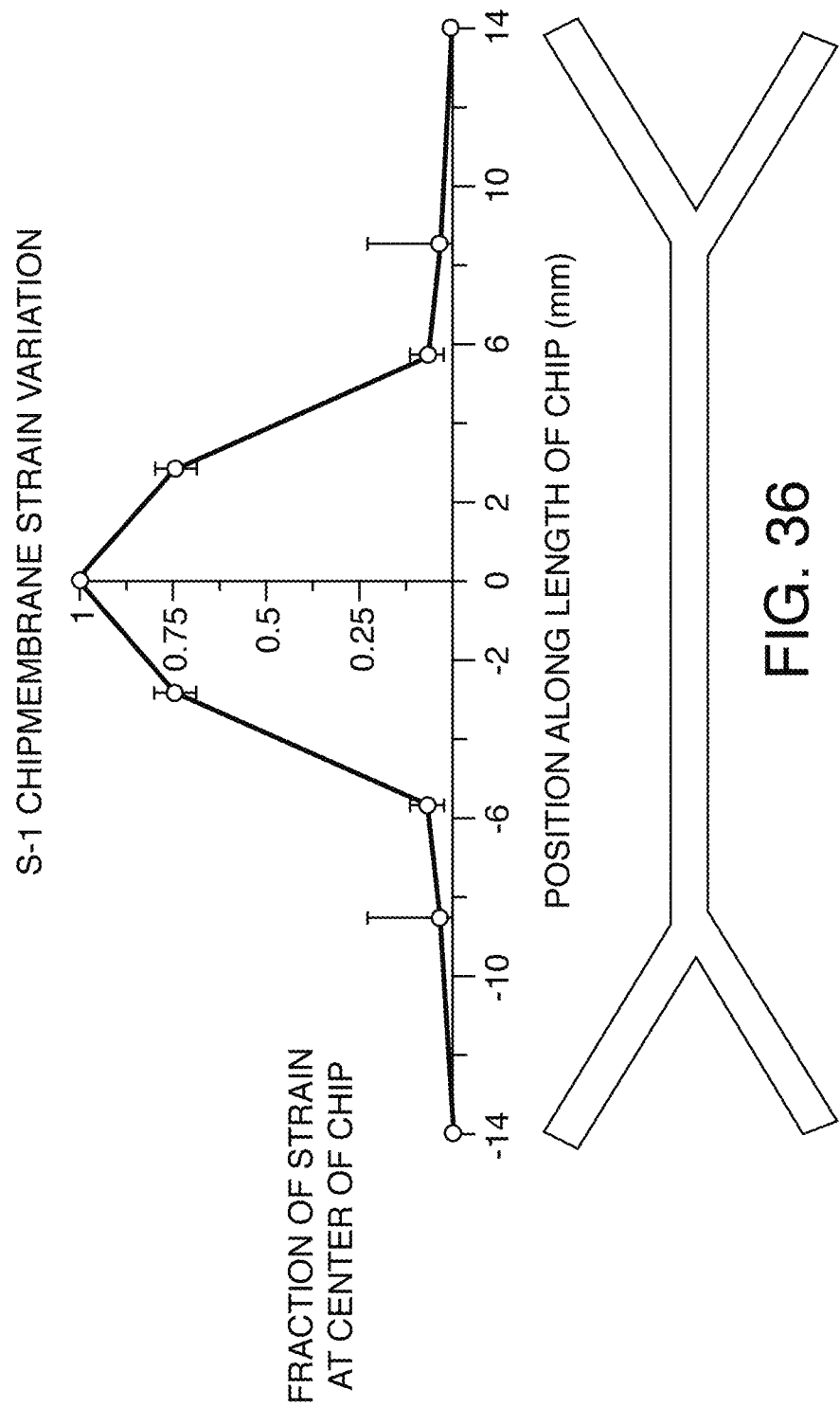
FIG. 36 depicts the difference in stretch over the length of the absorbing microfluidic device. In this embodiment of stretch, only approximately 20% of the culture area is under the applied stretch based on a preliminary study.

FIG. 36 depicts the difference in stretch over the length of the absorbing microfluidic device. In this embodiment of stretch, only approximately 20% of the culture area is under the applied stretch based on a preliminary study.

Figure 38:
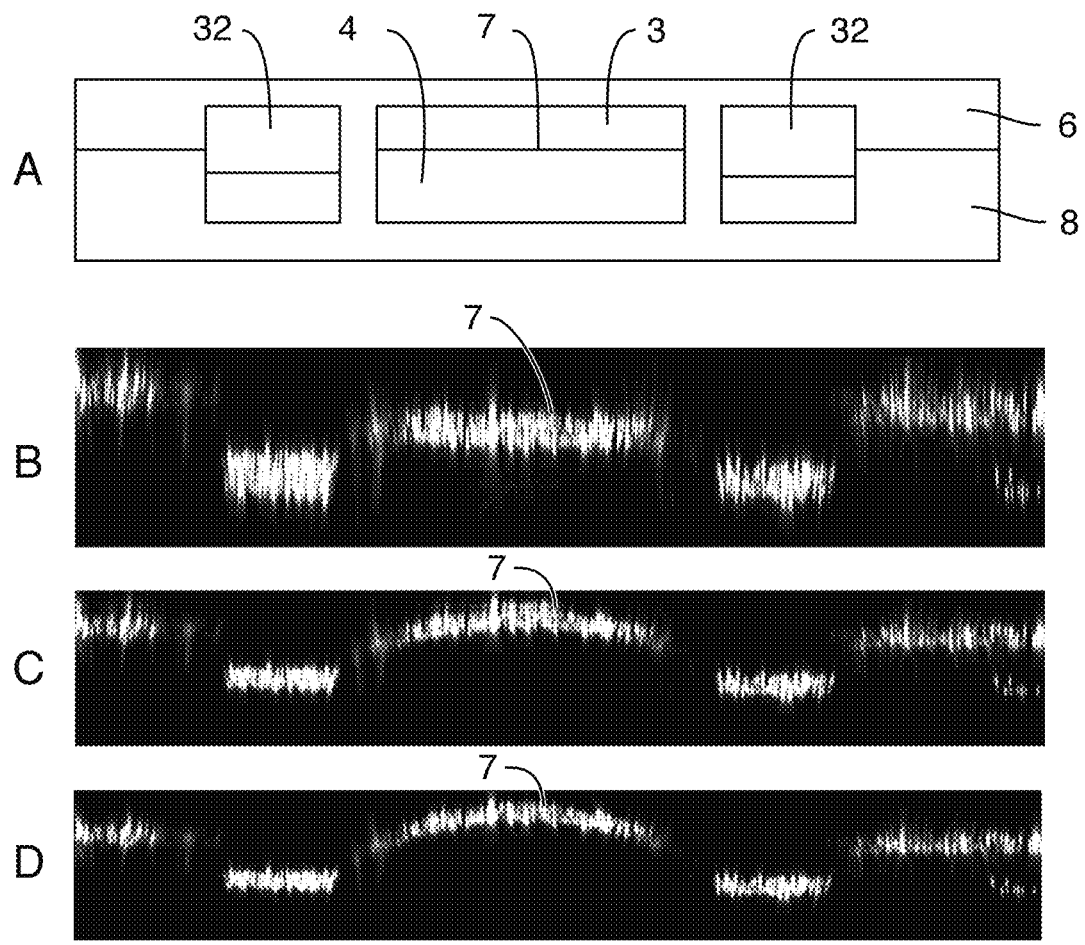
FIG. 38 shows a side view of a 50 µm thick PDMS membrane, having had fluorescent beads embedded in it, imaged on a confocal microscope at different pressure differentials. The membrane deflects into the upper chamber of the device. The fluorescent membrane was fabricated by spin coating a layer of PDMS with fluorescent beads. It may be seen in FIG. 38 that the greater the pressure differential the greater the level of stretch of the membrane.
Figure 39:
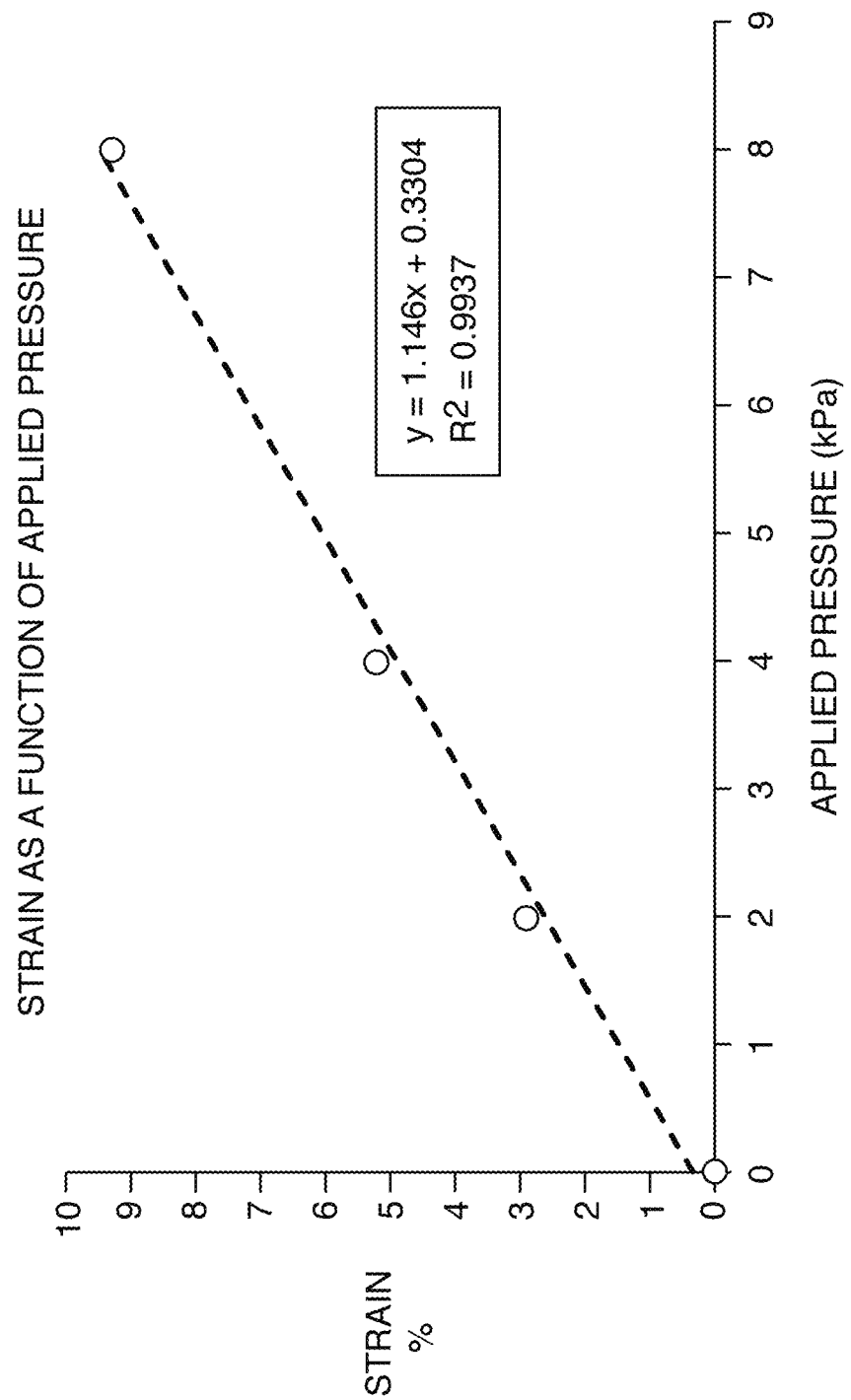
FIG. 39 shows a scatter plot for various levels of applied differential pressure across a 50 µm thick PDMS membrane vs. measured strain, fit with a curve to get the relationship between applied pressure and strain. As expected, in the pressure regime tested, the relationship is linear.
Figure 40:
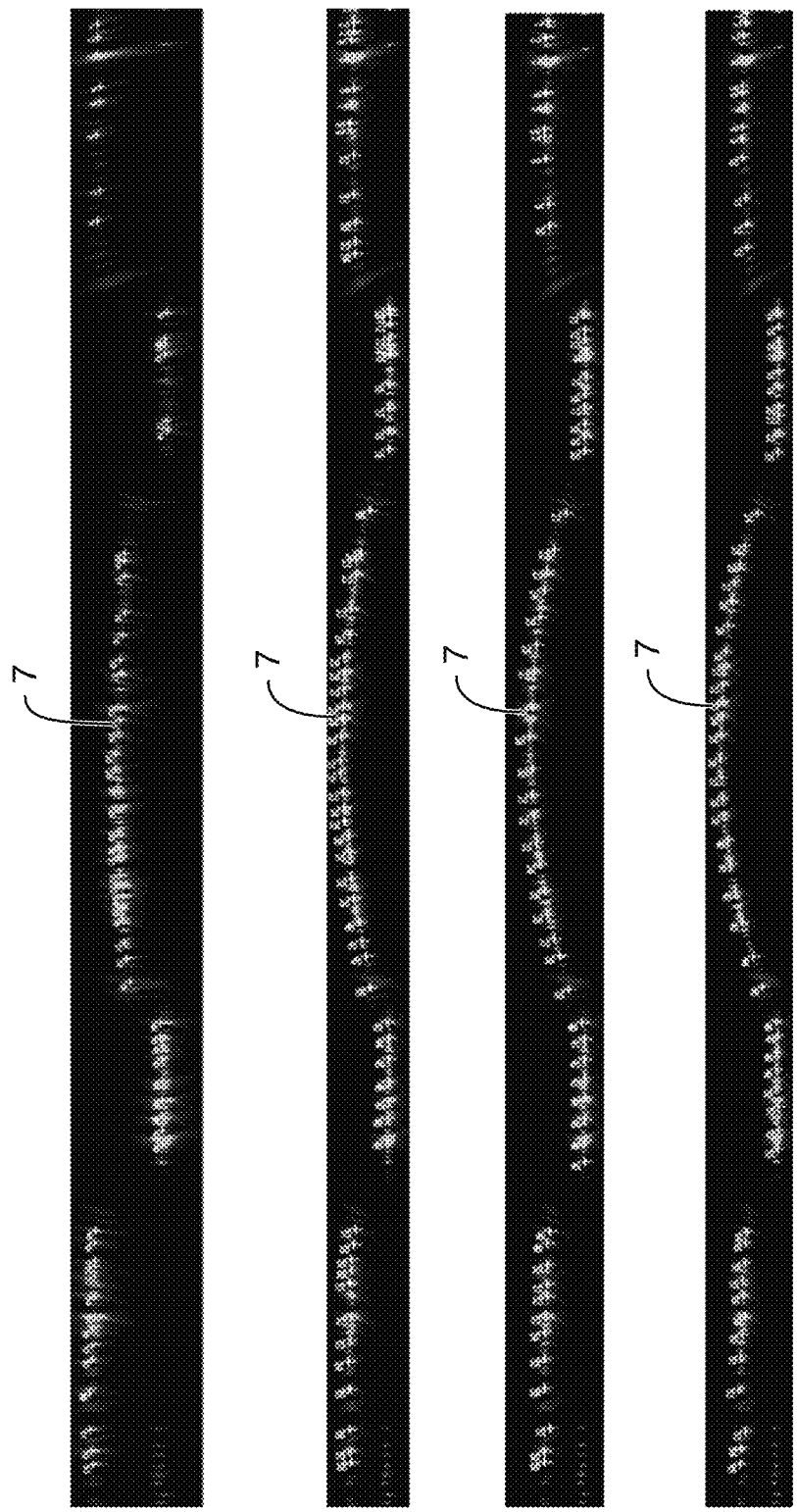
FIG. 40 shows 20 µm thick PDMS membrane actuation resulting from a pressure differential across the PDMS membrane imaged on a confocal microscope.
Figure 41:
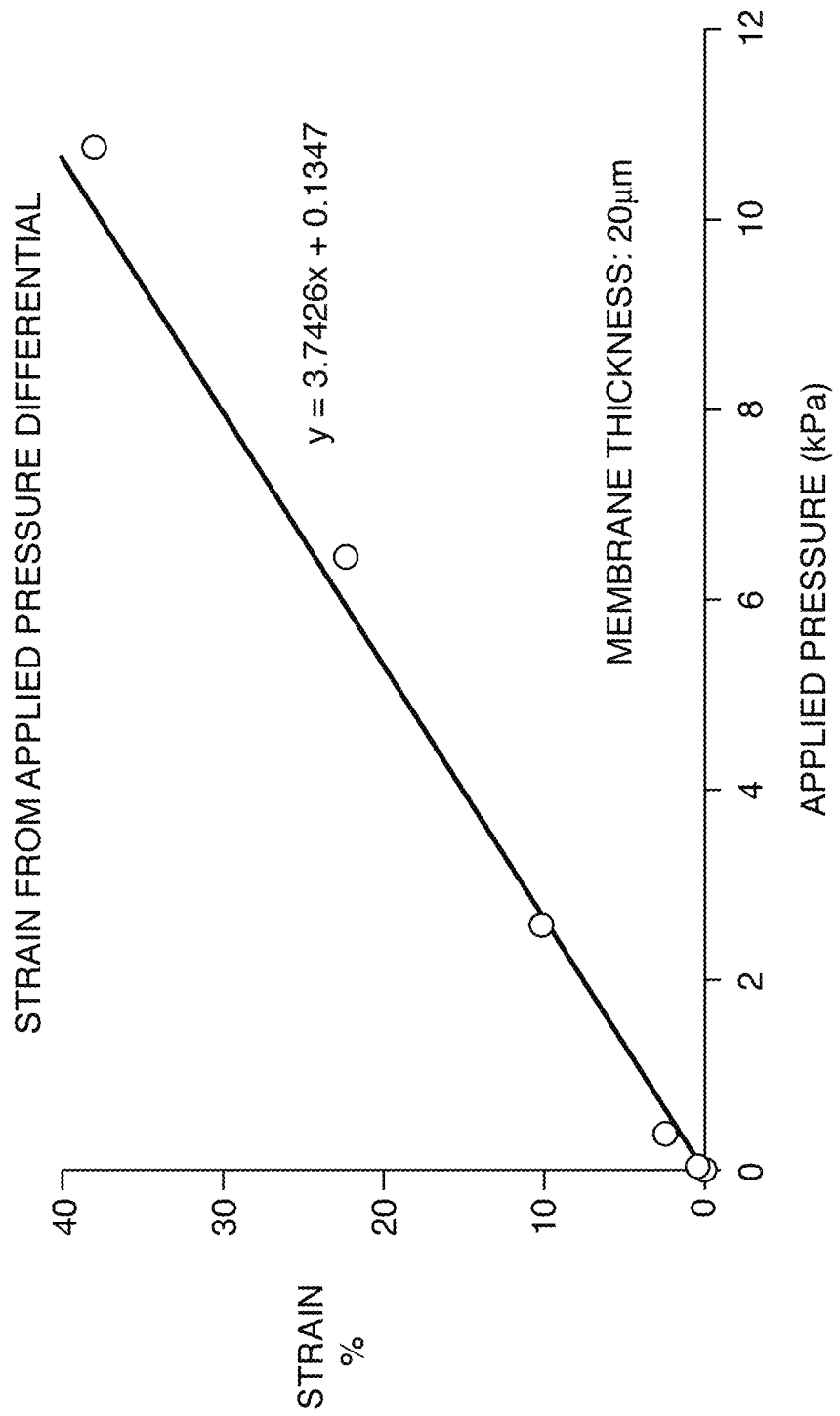
FIG. 41 shows a scatter plot for various levels of applied differential pressure across a 20 µm thick PDMS membrane vs. measured strain, fit with a curve to get the relationship between applied pressure and strain. As expected, in the pressure regime tested, the relationship is linear.
Figure 42:
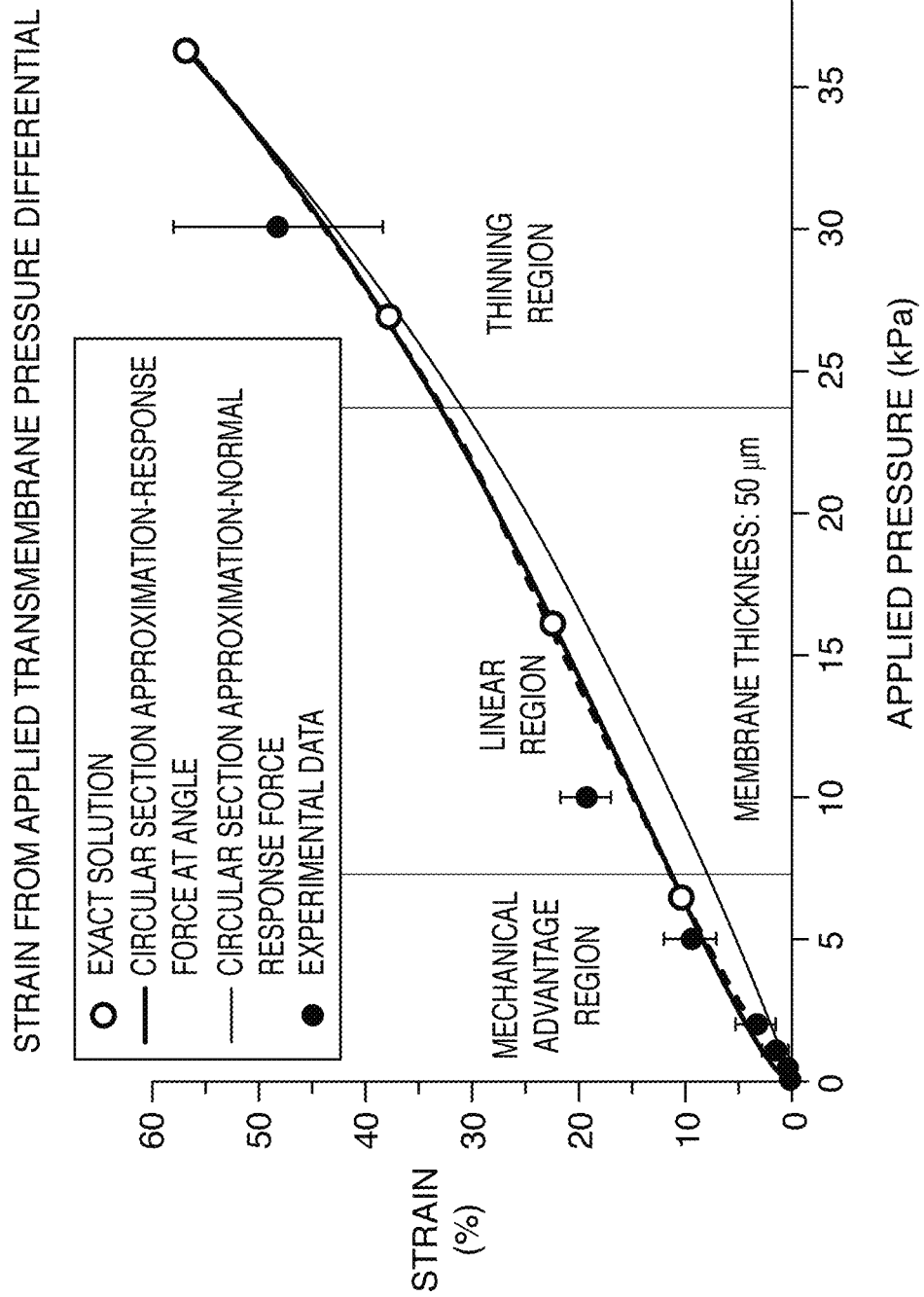
FIG. 42 depicts strain from applied transmembrane pressure differentials along with model predictions and an indication of different stretch regimes based on the dominating physics.
Figure 43:
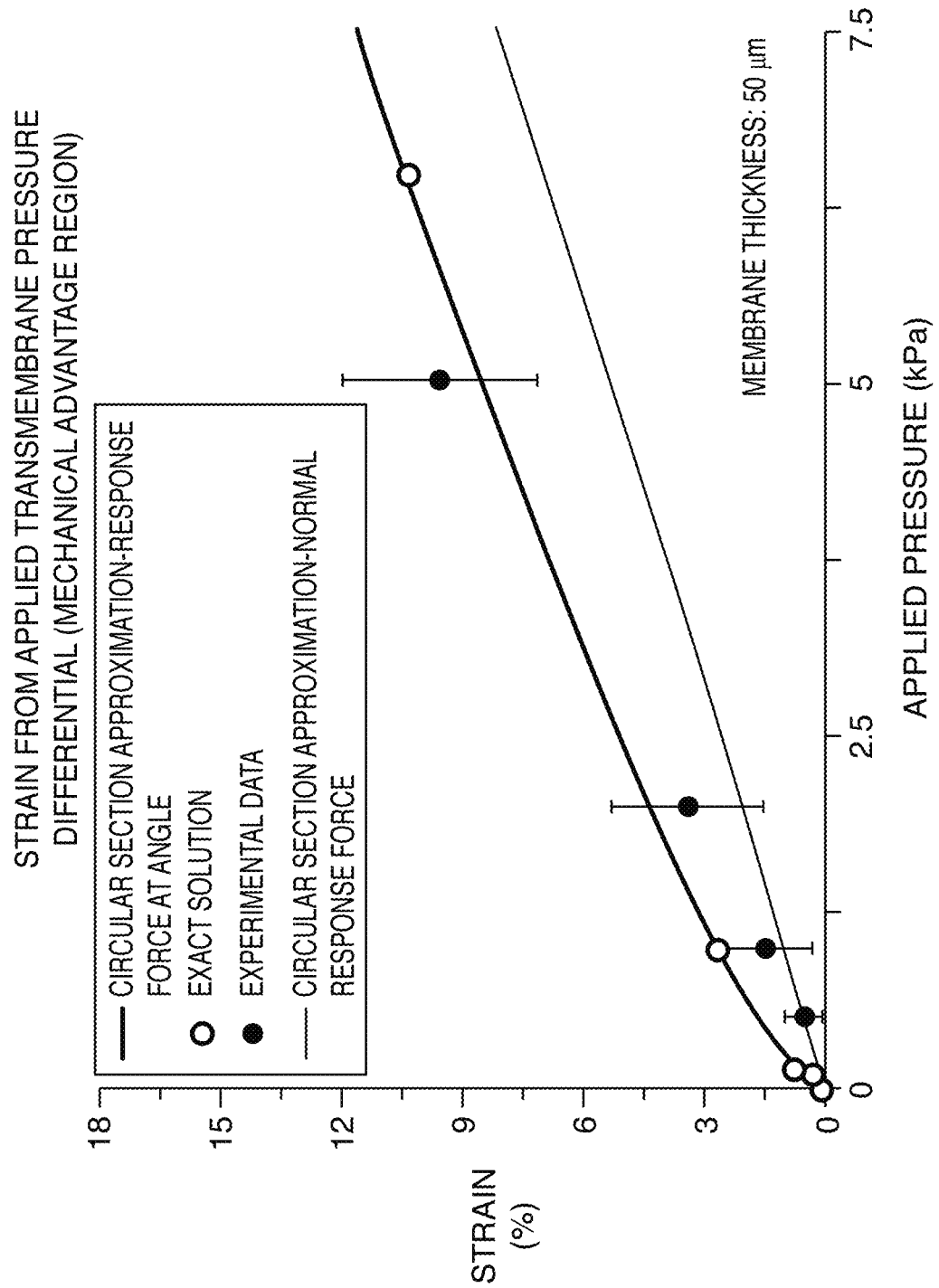
FIG. 43 depicts strain from applied transmembrane pressure differential in the mechanical advantage region/regime, which is the pressure range where the pressure range that is most physiologically relevant (i.e. pressure seen in vivo).

In some embodiments stretch is achieved by having a pressure differential across the top channel (3) and bottom channel (4), as to push the membrane (7) in the direction of the lower pressure channel. FIGS. 37A and 37B display the membrane (7) before and after the pressure differential is applied, in this case the pressure is applied to the bottom channel, causing the channel to deflect into the top channel. When stretch is not desired the inlet ports (2) may be pressurized and the outlet ports (2) may not be pressurized. When stretch is desired the bottom ports (2) may then be pressurized so that the pressure in the bottom channel (4) is greater than that of the top channel (3). FIG. 38 shows a side view of a 50 μm thick PDMS membrane (7), having had fluorescent beads embedded in it, imaged on a confocal microscope at different pressure differentials. The membrane deflects into the upper chamber of the microfluidic device. The fluorescent membrane was fabricated by spin coating a layer of PDMS with fluorescent beads. It may be seen in FIG. 38 that the greater the pressure differential the greater the level of stretch of the membrane (7). Confocal imaging of the beads showed a scatter plot for various levels of applied pressure. A curve was fit to the plot and compared to theoretical values. The results may be seen in FIG. 39, which indicates that a pressure of 3 kPa corresponds to a strain of about 4% for a PDMS membrane thickness of 50 μm. The experiment was repeated for a 20 μm thick PDMS membrane (7). FIG. 40 shows 20 μm thick PDMS membrane (7) actuation imaged on a confocal microscope. FIG. 41 shows a scatter plot for various levels of applied pressure versus measured strain across a 20 μm thick PDMS membrane, with an expected linear curve fit for the pressure regime tested. FIG. 41, indicates that 3 kPa of applied pressure corresponds to a strain of about 11% for a membrane with a thickness of 20 μm. FIG. 42 depicts strain from applied transmembrane pressure differentials using various mathematical models to predict percent strain vs applied pressure and plots vs actual data of different stretch regimes based on the dominating physics. The model and data agree well, indicating a thorough understanding of mechanism and forces experienced at the membrane. FIG. 43 depicts strain from applied transmembrane pressure differential in the "mechanical advantage region"—which is the pressure range where the pressure range that is most physiologically relevant (i.e. pressure seen in vivo)—a zoomed in version of FIG. 42. These graphs, taken together, indicate diminishing returns in regards to strain achieved in the membrane for an applied pressure; as pressure increases linearly, the additional amount of stretch begins to diminish. In the low-pressure regime, even small pressure yields a large change in strain. The range of expected data extracted from models and the experiment data fit well as depicted in both FIGS. 42 and 43. This embodiment of actuation is compatible with the culture module previously mentioned.

Figure 44:
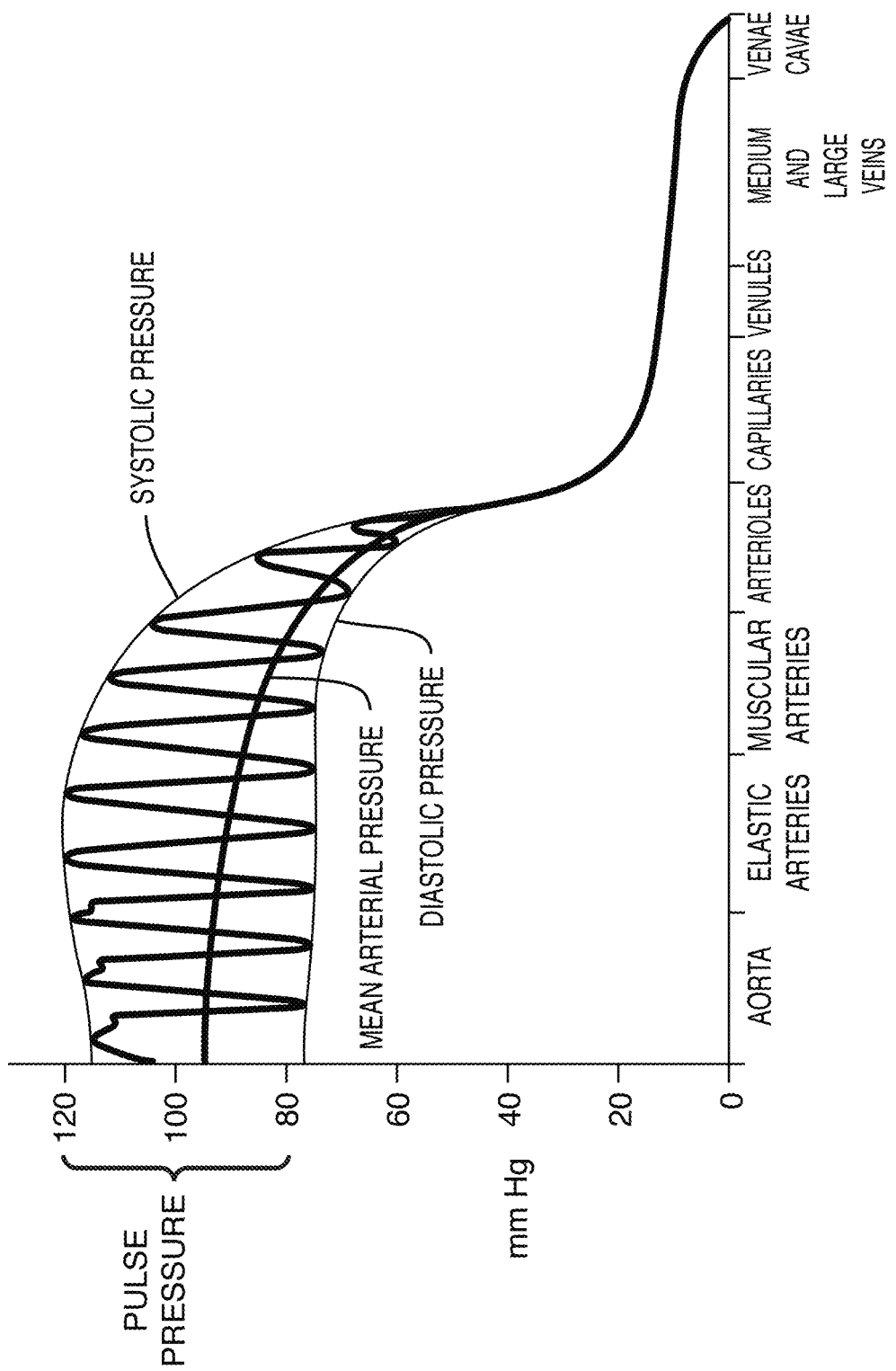
FIG. 44 depicts the physiologically relevant pressures seen in the vasculature. Indeed, within the capillaries, which many Organ-Chips seek to emulate, the in vivo relevant pressure is between 2.5-4 kPa.

Actuating the membrane (7) via pressure differentials have several advantages over mechanically actuating the membrane via vacuum in the working channels (32). First, microfluidic devices not containing working channels are easier to fabricate. This embodiment of actuation in microfluidic devices may also be advantageous as it may be more physiology relevant than other methods, which apply no pressure to the cell layer. Indeed, this stretching mechanism better recapitulates the physiologic mechanisms for mechanical stretching of cells and tissues, which include pressure differentials. For example, arteries tend to expand as the heart beats and expels blood from within the ventricles and into the artery lumen. This expansion (and resulting strain on the cells composing the vasculature walls) occurs because of the pressure generated by the beating heart, much like a balloon expands when pressurized with air. The pressures needed to flex the membrane and create these in vivo relevant strains is, in one embodiment, a similar pressure as would be seen in the capillary beds of the lungs. Stated more simply, in one embodiment both the pressures that the cell layers are exposed to and the stretch are tuned to be simultaneously physiologically relevant. Additionally, the shape of this stretch better emulates the shape of the expansion seen in blood vessels and the alveolar sacs, since in this embodiment the membrane is physically displaced into a channel and assumes the shape of an arc as opposed to a linear displacement (i.e. the membrane move up and down as it stretches). FIG. 44 depicts the physiologically relevant pressure differentials experienced at the endothelial-epithelial barriers as blood flows from large arteries, down to small capillaries, and then into the larger venous vessels returning blood back to the heart. Since many Organ-Chips seek to model or mimic this epithelial-endothelial interface, capturing the pressure differential that is experienced in vivo can be quite advantageous for further recapitulating the mechanical microenvironment. According to various sources, arteriolar capillary pressure in the pulmonary vasculature is approximately 3.3 kPa, with the interstitial pressure being close to −0.8 kPa. In a particular embodiment of an Organ-Chip where the alveolus is modeled, the top channel represents the alveolar interstitial with the bottom channel representing the lung capillary beds. At an applied pressure of 3 kPa to the bottom channel, not only is the pressure differential seen in vivo accurately applied, but the resulting stretch of the membrane (~11%) also accurately recapitulates the type of mechanical strain that would be experienced in the alveolus due to the expansion of the lungs during respiration.

There are several methods to increase gas transport into microfluidic devices. These methods include increasing fluid/media flow rate into the microfluidic device, increasing dissolved gas content of the media flowing through the microfluidic device, and delivering gases to the interior of the microfluidic device through the microfluidic device bulk material.

In one embodiment, increased gas transport into the microfluidic device may be achieved by using higher flow rates of media containing the important gases, such as oxygen, into the microfluidic device. In this embodiment, as the flow rate of the media is increases, more media is introduced into the microfluidic device in a set amount of time, and thus more of the desired gas is introduced into the microfluidic device. The use of high flow rates in microfluidic devices to increase gas transport is useful in gas-impermeable microfluidic devices (13), as gas may not diffuse into the microfluidic device otherwise. However, increasing the flow rate of media into the microfluidic device may not be physiologically relevant, as fluids in vivo flow at specific flow rates and velocities depending on the vessel. It is usually desired to expose specimen, such as cells, to similar conditions in vitro as is found in vivo. Increasing the flow rate of media into the microfluidic device may expose specimen, such as cells, to undue levels of shear, for example. It is extraordinarily disadvantageous in a microfluidic Organ-Chip to be constrained to a certain flowrate by oxygen transport, as this is just one of a whole host of conditions that are trying to be recapitulated and may be at least in part controlled by flow rate.

In another embodiment, the dissolved gas content of the media flowing through the microfluidic device may be increased prior to it entering the microfluidic device. In one embodiment, the dissolved gas content of the media may be increased prior to entering the microfluidic device by bubbling gas through the media. In another embodiment, the dissolved gas content of the media may be increased prior to entering the microfluidic device by pressurizing the media under a blanket of the desired gas to a pressure higher than atmospheric pressure or with a concentration of a specific gas that is higher than it is normally found in the ambient atmospheric environment. However, increasing the dissolved gas content of the media may not be physiologically relevant as fluids in vivo contain specific concentrations of gas. Indeed, it has been demonstrated in the literature that exposure to excess oxygen concentrations can cause significant damage to tissues, due to the formation of reactive oxygen species. It is usually desired to expose specimen, such as cells, to similar conditions in vitro as is found in vivo. Both of the prior embodiments, flowing media at higher flow rates and increasing the dissolved gas content of media, also succumb to a significant shortfall. As the media flows through the microfluidic device, the specimen at the beginning of the channels will experience higher levels of the desired gas than specimen at the outlet, since specimen at the beginning of the device will consume at least some, if not all of the gas flowing through the device. The specimen at the beginning of the channel may then uptake high levels of said gas, leaving lower levels of the desired gas for specimen further downstream in the channels.

In order to overcome low levels of important gases in microfluidic devices, as well as avoid the use of high flow rates and gas concentrations of media, a gas exchanger (9) may be built into the microfluidic device in such a way as to not promote small molecule compound absorbency while still allowing important gases, such as oxygen, to diffuse uniformly through the microfluidic device. In one embodiment the gas exchanger (9) is attached to the bottom of the microfluidic device (1), such as to form a floor to the bottom channel layer. In this embodiment the ceiling of the bottom channel (4) would be the cell culture membrane (7) and the base of the bottom channel (4) would be the gas exchanger (9). In one embodiment the gas exchanger (9) is a two-layer combination of PDMS and polyethylene terephthalate (PET). PDMS is gas-permeable and absorbent. PET is gas-impermeable and non-absorbent. In one embodiment the PET may be porous, such as containing gas exchanger pores (11). In one embodiment the porosity is created through track etching. In one embodiment the porosity of the PET is between 0.1% and 50%. In this embodiment, track-etched PET or PC serves as a transparent scaffold to give the gas exchanger (9) mechanical stability and low-absorbency, while the thin layer of gas-permeable PDMS seals the PET pores.

In another embodiment, a track-etched scaffold, conversely known as a gas exchanger membrane, fabricated from a rigid polymer may be "silk-screened" with an elastomeric polymer. A track-etched scaffold or gas exchanger membrane fabricated from a rigid polymer, such as PET, may be coated with an elastomeric polymer, such as PDMS, such that the elastomeric polymer permeates or impregnates the pores of the track. The track-etched scaffold or gas exchange membrane may then be "squeegeed" or wiped to remove the excess elastomeric polymer. The elastomeric polymer may then be cured into the pores, such as to create a substantially rigid gas exchanger with gas-permeable pores. The advantage here is that the volume of elastomeric polymer is minimized, and therefore absorption is minimized. The gas exchanger would almost be a composite material of the rigid polymer. The rigid material would comprise a scaffold for holding small volumes of the elastomeric polymer.

Furthermore, the gas exchanger may be coated with or have a film of a particular material in order to enhance bonding. For example, a gas exchanger comprising a porous, gas-impermeable substrate may not only have the pores filled with a gas-permeable material, but may also have a layer or coating or film of the gas-permeable material on top of it.

Figure 110:
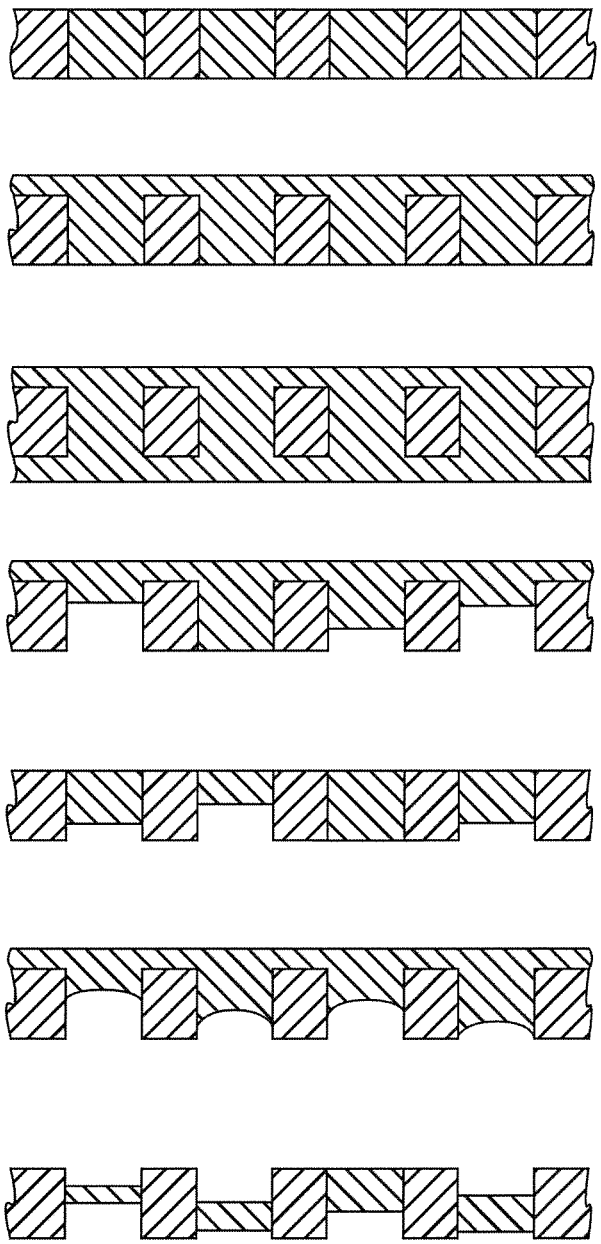
FIG. 110 shows multiple embodiments of a gas exchanger. In the embodiments shown, a substrate comprises regions which are filled by another material. The regions may be pores. The pores may be entirely or partially filled. Further, the pores may be filled as well as covered. The pores may be covered on one or both sides.

"Like dissolves like" is a common expression used by chemists to remember how some solvents interact with solutes. It refers to "polar" and "nonpolar" solvents and solutes. For example, water is polar and oil is non polar. Like does not dissolve like well, meaning that water will not dissolve oil. For example, water is polar and salt (NaCl) is ionic (which is considered extremely polar). Like dissolves like, that means polar dissolves polar, so water dissolves salt. Much the same, "like bonds to like." It has been found that materials bond more easily, such as through chemical treatment, plasma treatment, etc. For example, PDMS bonds easily to PDMS as compared to other polymers. As such, in one embodiment, the gas exchanger may have a coating, or film, or layer, which allows it to more easily bond to other structures. FIG. 110 shows multiple embodiments of a gas exchanger, some of which show said coating. In the embodiments shown, a substrate comprises regions which are filled by another material. The regions may be pores. The pores may be entirely or partially filled. Further, the pores may be filled as well as covered, such as with a coating. The pores may be coated or covered on one or both sides.

Figure 34:
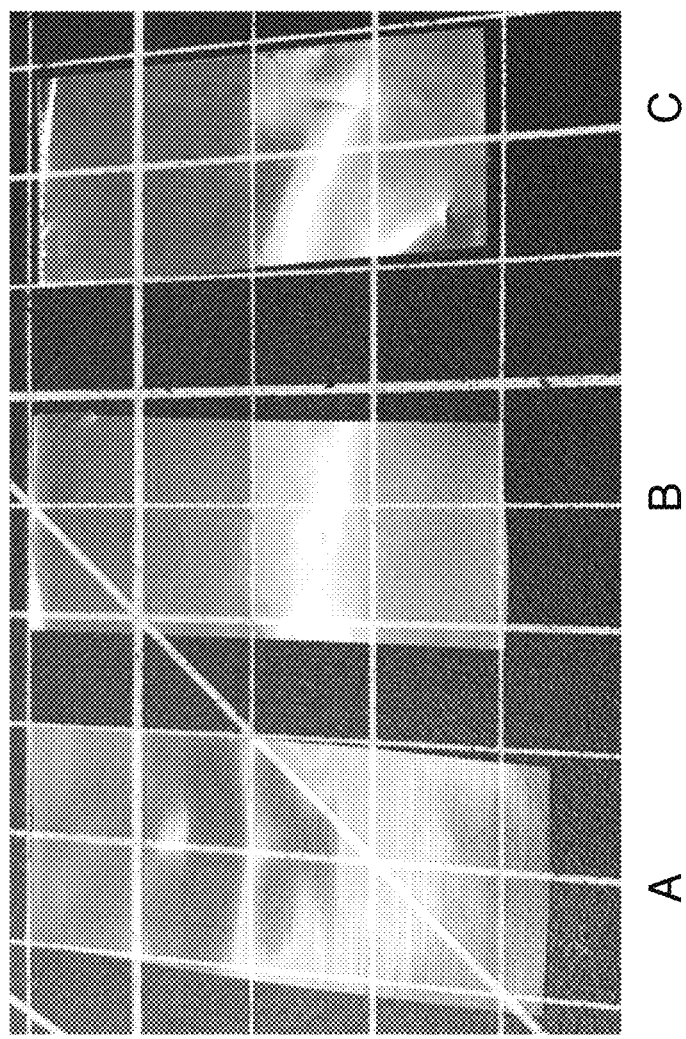
FIG. 34 depicts some different varieties of gas-exchangers, including Teflon AF2400, TPX, and porous PET.

The combination of PDMS and porous PET provides gas exchanging properties while having minimal absorption. In this embodiment some of the small molecule compounds may absorb into the PDMS through the pores in the PET, however compared to the gas exchanger (9) being fabricated from an entirely absorbent material, this absorbency may be considered negligible in many cases. Further in this embodiment of the gas exchanger (9), the porous, track-etched PET and PDMS gas exchanger (9) would not only be able to increase gas transport compared to a completely gas-impermeable microfluidic device (13), but also decouples gas transport from fluid flow. In another embodiment TeflonAF2400 may be used as a gas exchanger (9) material. TeflonAF2400 is an exceptional material, as it is transparent, gas-permeable and low-absorbing to non-absorbing. In one embodiment, the gas exchanger (9) may be fabricated out of a gas-permeable and/or gas-impermeable material and then coated with TeflonAF2400. In another embodiment polymethylpentene (PMP), commonly called TPX, a trademarked name of Mitsui Chemicals, may be used. TPX is another exceptional material, as it is transparent, gas-permeable and low-absorbing. Polymethylpentene (PMP) has several other advantageous properties, such as favorable optical properties, a low cost, injection moldable, and resistant to many solvents. Resistance to solvents may be important if the microfluidic device is to be used during assays, as assays often use harsh solvents. A resistance to solvents may allow the microfluidic device to be used in a greater range of assays. FIG. 34 depicts some different varieties of gas-exchangers (9), including Teflon AF2400, TPX, and porous PET.

The theoretical delivery of oxygen to a microfluidic device via media flow alone, calculated based on the carrying capacity of water for oxygen at a flow rate of 30 µL/h, is 5.8 nmol/h. The theoretical maximum hepatocyte uptake rate of oxygen, calculated via literature values scaled to a microfluidic device seeded with liver cells, is 88 nmol/h. There is a discrepancy between these two values of 83.2 nmol/h, meaning that the fluid flow does not provide sufficient oxygen to support hepatocyte maintenance, metabolism, or other functions. If the hepatocytes do not receive enough oxygen, they will undergo apoptosis or necrosis—they will die.

The theoretical oxygen flow rate in an absorbing microfluidic device (12) fabricated from PDMS is 574 nmol/h and was measured to be 225 nmol/h±9.43 nmol/h, which is more than sufficient to supply even the highly oxygen consuming hepatocyte cell type with sufficient oxygen. The theoretical oxygen flow rate through the bulk material in a low-absorbing, gas-impermeable microfluidic device (13) fabricated primarily from COP is 0 nmol/h and was confirmed via measurement of oxygen transport to be 0 nmol/h±0.63 nmol/h. The theoretical oxygen flow rate in a low-absorbing, gas-permeable microfluidic device (1) fabricated from a strategic combination of gas-impermeable and gas-permeable materials and comprising a gas exchanger made from 11.3% porous PET is 65.2 nmol/h and was measured to be 21.8 nmol/h±6.74 nmol/h, which is well-above the oxygen uptake rate of hepatocytes. The theoretical oxygen flow rate in a low-absorbing, gas-permeable microfluidic device (1) fabricated from a strategic combination of gas-impermeable and gas-permeable materials and comprising a gas exchanger made from 40% porous PET is 231 nmol/h. The measured oxygen flow rate in a low-absorbing, gas-permeable microfluidic device (1) fabricated from a strategic combination of gas-impermeable and gas-permeable materials and comprising a gas exchanger made from TeflonAF2400 was 48 nmol/h±1.80 nmol/h. The theoretical oxygen flow rate in a low-absorbing, gas-permeable microfluidic device (1) fabricated from a strategic combination of gas-impermeable and gas-permeable materials and comprising a gas exchanger made from TPX is 241 nmol/h and was measured to be 265 nmol/h±40.9 nmol/h. All these delivery rates are well in excess of the required oxygen delivery rate, as defined by the cellular oxygen uptake rate. The implication of this is that, oxygen delivery through the bulk material will not only supply a sufficient amount of oxygen as required for cellular function, but also will maintain an oxygen saturated environment that is consistent along the full length of the device.

The gas exchanger (9) may be built into other portions of the microfluidic device (1) in other embodiments. In one embodiment the gas exchanger (9) is configured around the outer walls of the microfluidic device (1). In another embodiment the gas exchanger (9) interfaces with the top channel layer (6) instead of the bottom channel layer (8) as described in an above embodiment. In yet another embodiment, there are multiple gas exchangers (9) configured in various locations in the microfluidic device (1). Gas exchangers (9) may be built such that they may be switched from gas-permeable to gas-impermeable at the scientists liking in order to make the microfluidic device (1) more customizable.

Indeed, in embodiments where a porous PET scaffold is utilized, the porosity of the scaffold in large part defines the oxygen delivery rate through the bulk material. Therefore, by choosing a specific porosity, the oxygen delivery rate can not only be turned on and off in a binary fashion, but also "tuned" to a variety of delivery rates depending on the specifics of the application. Similarly, the location of the PET membrane in a particular embodiment, can be chosen to selectively tuned gas exposure in each channel with a certain level of independence. For example, for Zone 1 of the human liver is exposed to high levels of oxygen in vivo. A user might be advised to select a PET membrane of high porosity in this case. Conversely, Zone 3 in the liver is known to be poor in blood oxygen levels. Here, the advisement would be to select a membrane with very low porosity to throttle oxygen delivery to the low levels seen in vivo. Similarly, cancerous tumors tend to create low oxygen environments and a low porosity PET membrane might be advised adhered to the top of the top channel component and the bottom of the bottom channel component. Conversely, to imitate the hypoxic environment seen in the intestine, and specifically the colon, a high oxygen concentration might be desired in the bottom channel, which represents the vasculature, whereas a low oxygen environment would be advantageous in the top channel, which represents the intestinal lumen. To achieve this, a moderate porosity PET membrane might be chosen to be adhered to the bottom of the bottom channel to delivery oxygen to the vasculature, and a non-permeable membrane chosen for the top of the top channel, to minimize oxygen transport through the bulk material and create the desired hypoxic environment.

In some embodiments the microfluidic device has a gasket layer (5) on the top with four ports (2) to interact with the ports (2) exiting the top channel (3). The gasket (5) may be used to ensure a tight fluidic connection between the microfluidic device (1) and relating infrastructure. In one embodiment the gasket (5) is made out of a compressible material. In another embodiment the gasket (5) is made out of an adhesive material. The gasket (5) may be used to keep the microfluidic device (1) the same size as it's absorbent predecessor (12) in order to fit into existing microfluidic device accessories, such as a perfusion manifold. The gasket (5) may be embodied in multiple heights in order to raise the height of the microfluidic device (1) to a desired level such that it fits into a compression fit snugly. The gasket (5) may also be gas-impermeable so that it does not absorb any small molecule compounds into the walls of its ports (2). The gasket (5) may achieve gas-impermeability and therefore, low absorbance, by being fabricated from a partially or entirely gas-impermeable material, coated with a gas-impermeable substance, having its surface modified to reach impermeability and low absorbance (such as plasma treatment), etc. In one embodiment the gasket (5) covers the entire surface of the microfluidic device (1). In another embodiment the gasket (5) only covers a portion of the surface of the microfluidic device (1).

Figure 52:
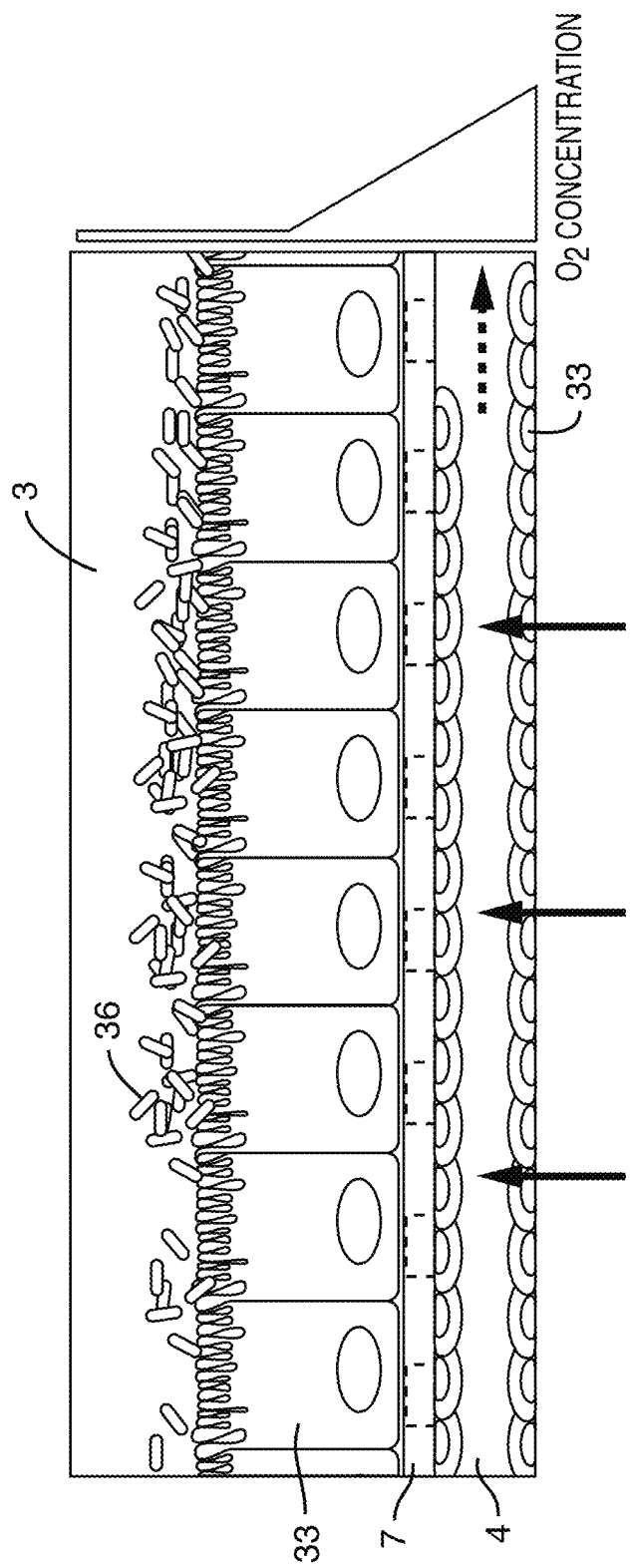
FIG. 52 depicts the method of introducing an oxygen gradient into the low-absorbing, gas-permeable microfluidic device comprising a gas exchanger, using said gas exchanger to selectively introduce a gas into the microfluidic device from the vasculature channel only, while creating a diffusive barrier to the oxygen-rich ambient environment.

In one embodiment the low-absorbing, gas-permeable microfluidic device (1) featuring a gas exchanger (9) may be used to introduce and sustain a gas gradient in the microfluidic device (1). In this embodiment a specific concentration of gas could be introduced to the gas exchanger (9). The gas is then depleted by the cell layers (33), such as endothelial and epithelial cell layers, resulting in a hypoxic top channel (3) or luminal channel—or a gradient in gas from the bottom to the top of the microfluidic device, which is consistent along the entire length of the microfluidic device. In one exemplary embodiment the gas is oxygen. In another embodiment the gas is carbon dioxide. In another embodiment the gas is nitrogen. The gas gradient may be altered by introducing cell layers (33) of various permeability. The vertical gradient of gas through the microfluidic device (1) maintains the longitudinal concentration of gas along the entire length of the microfluidic device (1). In the embodiment where an oxygen gradient is introduced in the low-absorbing, gas-permeable microfluidic device (1) with a gas exchanger (9), the longitudinal oxygen concentration along the entire length of the microfluidic device (1) is maintained. FIG. 52 depicts the method of introducing an oxygen gradient into the low-absorbing, gas-permeable microfluidic device (1) comprising a gas exchanger (9), using said gas exchanger (9) to selectively introduce a gas into the microfluidic device (1) from the vascular channel only, while creating a diffusive barrier to the oxygen-rich ambient environment. The channel comprising the organ specific cells may then have a lower, even anaerobic environment, such that bacteria (36), such as *clostridium symbiosum*, may thrive. In one embodiment, a gas-gradient is introduced into the low-absorbing, gas-permeable microfluidic device (1) by flowing the selected gas through adjacent working channels (32). In one embodiment, a gas gradient is introduced into the low-absorbing, gas-permeable microfluidic device (1) with a gas-exchanger (9) using chemical reactions.

The advantage of the gas exchanger, as depicted in FIG. 52, is that the gas concentration within a microfluidic device may be done in a normal cell culture incubator, without the need for a specialized gas-control incubator. While gas-control incubators may be used to control the gas concentration of gas-permeable microfluidic devices, as shown in FIGS. 117-125, many more laboratories solely have access to normal cell culture incubators, without gas-control. Therefore, the gas exchanger herein presented is highly enabling for those culturing cells that need gas environments other than atmospheric.

In one embodiment sensors may be used to measure the gas gradient in the low-absorbing, gas-permeable microfluidic device (1). In the exemplary oxygen gradient embodiment, oxygen sensors may be used to measure the oxygen gradient in the low-absorbing, gas-permeable microfluidic device (1). In one embodiment, the sensors are electrical sensors. In one embodiment the sensors are optical sensors.

In one embodiment, the sensors comprise a gas sensitive dye. In one embodiment, the gas sensitive dye is an oxygen sensitive dye. In one embodiment the sensors are external to the microfluidic device (1). In one embodiment, the sensors are embedded in the microfluidic device (1). In one embodiment, the sensors are in the top channel (3). In one embodiment, the sensors are in the bottom channel (4). In one embodiment, the sensors are in both the top channel (3) and the bottom channel (4).

Another embodiment of the present invention is an upgraded perfusion manifold assembly (14) that minimizes the amount of small molecule compound to absorb into its materials. The perfusion manifold assembly (14) may be seen in FIG. 7. In one embodiment, the perfusion manifold assembly (14) comprises i) a cover or lid assembly (25) configured to serve as the top of ii) one or more fluid reservoirs (19), iii) a gasketing layer (20) under said fluid reservoir(s) (19), iv) a fluidic backplane (22) under, and in fluidic communication with, said fluid reservoirs (19), v) a capping layer (21) over said fluidic backplane (22), and vi) a projecting member or skirt (23) for engaging the microfluidic device (1) or a carrier containing a microfluidic device (1).

Another embodiment of the present invention is an upgraded perfusion manifold assembly that minimizes the amount of small molecule compound to absorb into its materials. In one embodiment, the perfusion manifold assembly comprises i) a cover or lid configured to serve as the top of ii) one or more fluid reservoirs, iii) a gasketing layer under said fluid reservoir(s), iv) a fluidic backplane under, and in fluidic communication with, said fluid reservoirs, v) a capping layer over said fluidic backplane, and vi) a projecting member or skirt for engaging the microfluidic device or a carrier containing a microfluidic device.

The cover or lid assembly (25) may aid in protecting the reservoirs from both spilling and contamination. In one embodiment, the lid assembly (25) comprises a lid (15), filter(s), and a lid gasket (18). Filters may be configured into the lid assembly (25) in order to aid in sterility of the fluid within the reservoirs (19). In one embodiment the filters are flat filters (16). These thin filters (16) may be cut from a flat substrate material. In one embodiment the filters are thick filters (17). These thick filters (17) may be cut from a thick substrate material. In the embodiment wherein, the lid assembly (25) comprises a lid gasket (18), the lid gasket may take on a variety of embodiments. In one embodiment, the lid gasket is compressible. In one embodiment, the lid gasket is adhesive. The lid gasket may vary in thickness in order to best seal the reservoirs (19) off from the external environment. Alternatively, in other embodiment, the lid gasket (18) comprises the filters, instead of having separate filters. In one embodiment, the lid gasket (18) is porous. In another embodiment the lid gasket (18) is non-porous. In one embodiment, the lid gasket (18) permanently conforms to the shape of the reservoirs (19) after the first time the reservoirs (19) is pressed into it. In another embodiment the lid gasket (18) temporarily conforms to the shape of the reservoirs after each time the lid gasket (18) is pressed onto them. In yet another embodiment, the lid gasket (18) does not conform to the shape of the reservoirs (19). The cover or lid assembly (25) can be removed and the perfusion manifold assembly (14) can still be used. In one embodiment, the lid assembly (25) is held onto the reservoir using a radial seal. An applied pressure is not necessarily required to create a seal. In one embodiment, the lid assembly (25) is held onto the reservoir using one or more clips, screws or other retention mechanisms.

The fluid backplane (22) may be used to route fluid from the reservoirs to the microfluidic devices, such as a microfluidic device. In one embodiment, the perfusion manifold assembly (14) further comprises perfusion manifold assembly ports (28) positioned at the bottom of the fluidic backplane. In one embodiment the fluidic backplane (22) comprises one or more fluidic resistors (27). In one embodiment, the one or more fluidic resistors (27) are comprised of elongated, serpentine channels. Without being bound by theory of any particular mechanism, it is believed that these resistors (27) serve to stabilize the flow of fluid coming from the reservoirs (19) so that a stable flow can be delivered to the microfluidic device (1), and/or they serve to provide a means for translating reservoir (19) pressure to perfusion flow rate.

Figure 8:
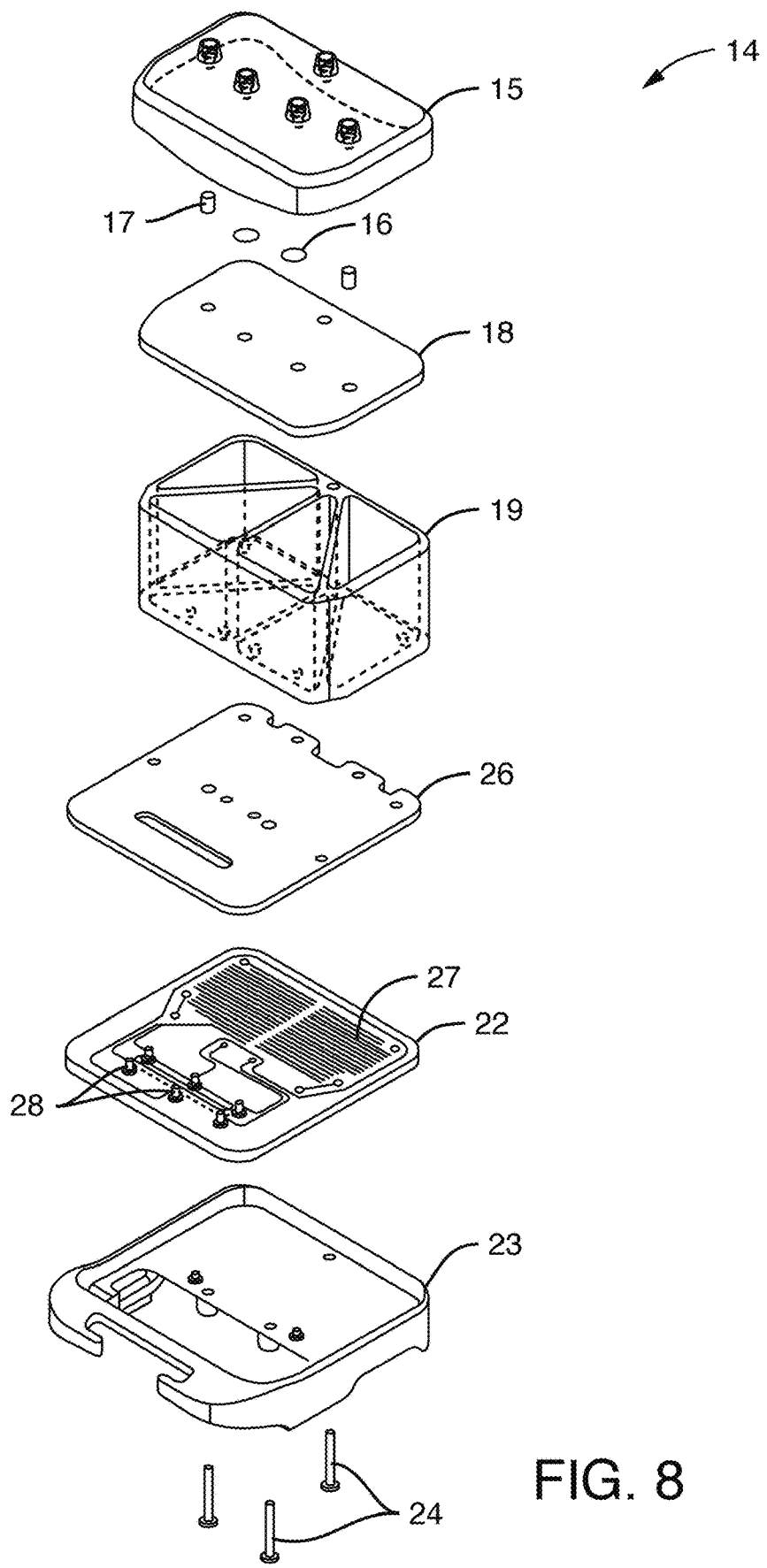
FIG. 8 shows a perfusion manifold assembly comprising one gasketing and capping layer. The perfusion manifold assembly also comprises a lid, different varieties of filters, a lid gasket, reservoirs, a fluidic backplane, a skirt and screws.
Figure 69:
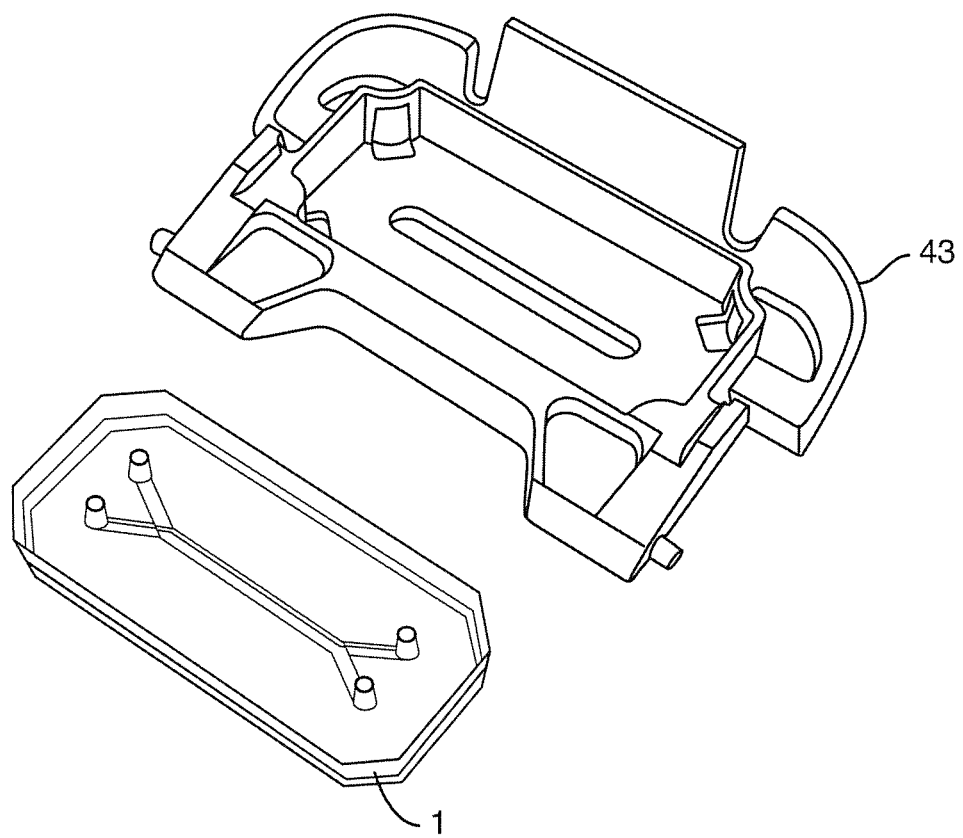
FIG. 69 depicts one embodiment of a low-absorbing, gas-permeable microfluidic device where the channel components are fabricated out of COP (which is known not to absorb), the gasketing material is fabricated from PDMS with a Parylene coating (which the coating is known not to absorb). Also pictured is one embodiment of a perfusion manifold assembly microfluidic device carrier for the use of interfacing the microfluidic device with a perfusion manifold assembly. This embodiment of the microfluidic device is compatible with the face-sealing gasketing method in one preferred embodiment of the device/perfusion manifold assembly.

In previous renditions of this invention there has been a single capping and gasketing layer (26) responsible for both capping and gasketing. A previous rendition may be seen in FIG. 8, which the invention presented herein improves on. The invention presented here suggests two separate layers. One for gasketing (20) and one for capping (21) the fluidic backplane. In one embodiment both the fluid reservoirs (19) and fluid backplane (22) are fabricated from hard plastics, and as such may need a compressible gasket (20) between them to protect from leaks at the sites of fluid connections. Having two separate layers is advantageous as sealing and compression may be decoupled—sealing does not require compression and likely does not require absorptive materials. Conversely, oftentimes materials having the characteristics necessary to be used as gaskets, especially transparent gaskets, have absorbency issues. In one embodiment both the capping (21) and gasketing (20) layers are transparent. It may advantageous to have transparent capping (21) and gasketing (20) layers so that the fluidic backplane (22) may be imaged on a microscope if necessary. In one embodiment of the new invention, the gasketing layer (20) is made up of a compressible material, such as SEBS, while the capping layer (21) is made up of an incompressible material, such as COP. In another embodiment, the gasketing layer (20) made up of a compressible material may be coated, such as with Parylene, in order to make it gas-impermeable. The capping layer may be partially or completely coated in Parylene. In an exemplary embodiment, a partially coated capping layer fabricated out of COP is used in conjunction with a gasketing layer fabricated out of SEBS. The combination of a partially Parylene-coated COP capping layer and SEBS gasketing layer is advantageous over a single, completely Parylene coated COP layer. Parylene is difficult to bond, whereas COP bonds well to other materials, including other parts made out of COP. By using two layers, one may seal the fluidic backplane to the Parylene-coated COP capping layer by material bonding, and seal the capping layer to the reservoirs with the SEBS gasketing layer. Further, when using two layers only a small piece of SEBS needs to be coated with Parylene to successfully prevent absorption. If a single layer is used, any fluid-contacting surface may need to be coated with Parylene, which means that the ports, the face of the components being sealed (such as the reservoirs), and the entire length of the fluidic routing channels in the perfusion manifold assembly would need to be coated. Coating that much of the COP capping layer is difficult. When Parylene is coated, the part needs to be held somewhere, much like Achilles's heel. FIG. 69 depicts a low-absorbing, gas-permeable microfluidic device where the channel components are fabricated out of COP (which is known not to absorb), the gasketing material is fabricated from PDMS with a Parylene coating (which the coating is known not to absorb). In another embodiment, a perfusion manifold assembly microfluidic device carrier for the use of interfacing the microfluidic device with a perfusion manifold assembly is preferred. This embodiment of the microfluidic device is compatible with the face-sealing gasketing method in one preferred embodiment of the device/perfusion manifold assembly.

In one embodiment the perfusion manifold assembly (14) comprises a projecting member or skirt (23). In one embodiment, the projecting member or skirt (23) is engaged with a microfluidic device (1). In one embodiment, the microfluidic device (1) comprises a top channel (3), a bottom channel (4), and a membrane (7) separating at least a portion of said top channel (3) and bottom channel (4). In one embodiment, the microfluidic device (1) comprises cells on the membrane (7) and/or in or on the channels. The projecting member or skirt (23) may be designed so that the fluidic backplane (22) is able to easily align with a connecting microfluidic device (1). In one embodiment, the projecting member or skirt (23) may be designed in order to interact with a culture system.

The perfusion manifold assembly (14) may be attached together via several methods. In one embodiment, screws (24) may be used to secure the perfusion manifold assembly (14). In another embodiment, clips are used to secure the perfusion manifold assembly (14). In another embodiment, adhesives are used to secure the perfusion manifold assembly (14). In another embodiment, surface modification is used to secure the perfusion manifold assembly (14). In one embodiment, the perfusion manifold assembly (14) is permanently bonded together. In one embodiment, the perfusion manifold assembly (14) is temporarily bonded together.

EXPERIMENTAL

1. Absorbency Experiments on Materials

Figure 13A:
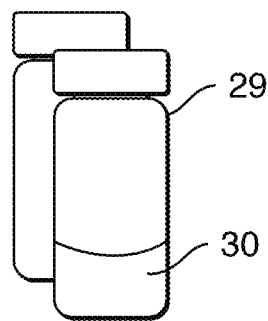
FIG. 13A-B illustrates the test protocol for a time-dependent material absorption test (including absorbing materials such as PDMS). This study aims to determine the intrinsic material-compound interaction properties of drug-absorbing materials, PDMS or otherwise.
Figure 13B:
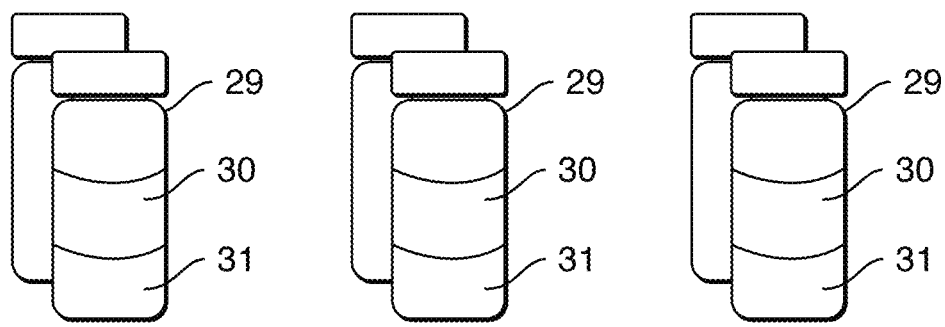

A method for ascertaining the absorption of a specific small-molecule into a polymer was developed. The output of this method are the fundamental parameters that fully define the absorption of a specific compound into the material tested; specifically, the diffusivity and partition coefficient are ascertained. The test set-up is depicted in FIGS. 13A and 13B. The steps for ascertaining this absorption is as follows:
1. Dissolve the small molecule in an aqueous phase (medium) and incubate the solution (30) with the tested material (31), such as in a vial (29). The incubation should be long enough so that diffusion is not limiting absorption and the transport into the material is at equilibrium with the transport of the compound out of the material and into the aqueous phase.
2. Sample media from the vials at a number of time points.
3. Measure the concentration of the small molecule remaining in the aqueous phase (30) using a mass spectrometer, plate reader, etc. from the media sampled.
4. Curve-fit the measured data to quantify the absorption and diffusion parameters.

Each experiment includes a number of controls and test conditions. Using multiple controls and test conditions allows absorption to the vial and well-plate to be characterized, as well as absorption versus adsorption to the tested material, as well as yielding the time-dependent nature of absorption into the material. Controls comprise vials (29) filled with solely the small molecule dissolved in an aqueous phase (30) in order to quantify the loss of compound caused by adsorption to the glass of the vial (29). The goals of the experiments are to directly quantify partitioning of the compound, or compound loss at equilibrium (kinetics), and to directly quantify diffusion of the compound, or time-dependent compound loss (dynamics). The developed method is robust in regards to quantifying the drug-specific progression and extent of compound loss.

Figure 14:
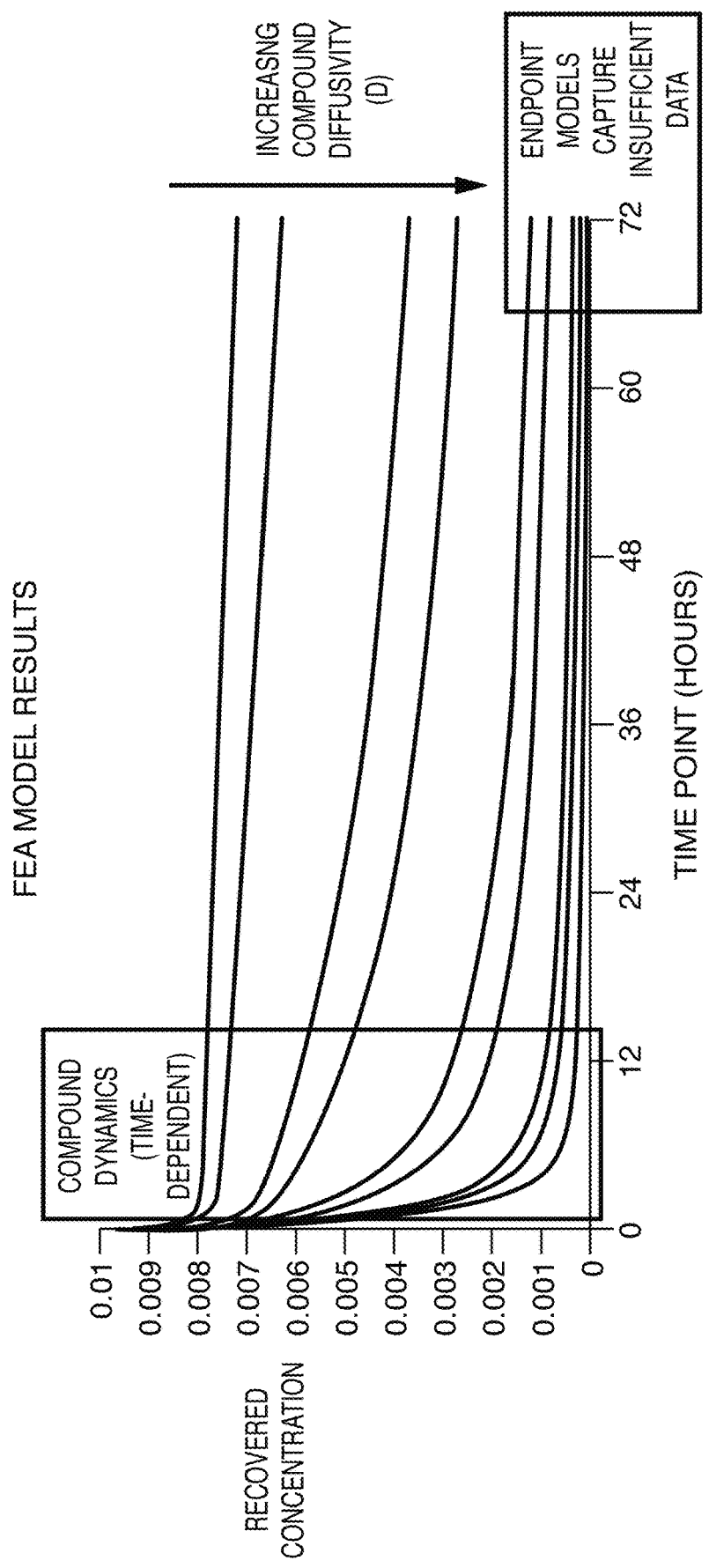
FIG. 14 depicts a fine element analysis, or a computational model, of recovered compound concentration from a set volume of PDMS after different time points for compounds of varying diffusivity. Data from time-dependent material absorption tests, like those depicted in FIG. 13A-B, is compared to graphs like the one depicted here and used to determine the fundamental parameters defining compound-specific absorption into the material tested; here, a determination of diffusivity, or speed of compound loss.

Single time point experiments are only capable of extracting kinetics, not dynamics. Time-dependent studies capture not only equilibrium endpoints (K), but also time-dependent changes/dynamics (D). One-dimensional computational models are used to fit experimental results of time-dependent studies. FIG. 14 depicts a finite element analysis model, or a computational model that is solved incrementally, of recovered compound concentration from a set volume of PDMS after different time points for compounds of varying diffusivity. The higher the diffusivity the faster the compound absorbs into the surrounding permeable material. The results show that the higher the diffusivity of the compound the lower the recovered concentration of the compound after any time spent with a permeable material, such as PDMS. The results also demonstrate that the longer the time spent with a permeable material, such as PDMS, the lower the recovered concentration of the compound. Using a graph, like the one pictured in FIG. 14, experimental data can be matched to one of the curves. Once the particular curve is known, the parameters which defined that curve are taken as the fundamental parameters defining the material-compound absorptive interaction.

Figure 20A:
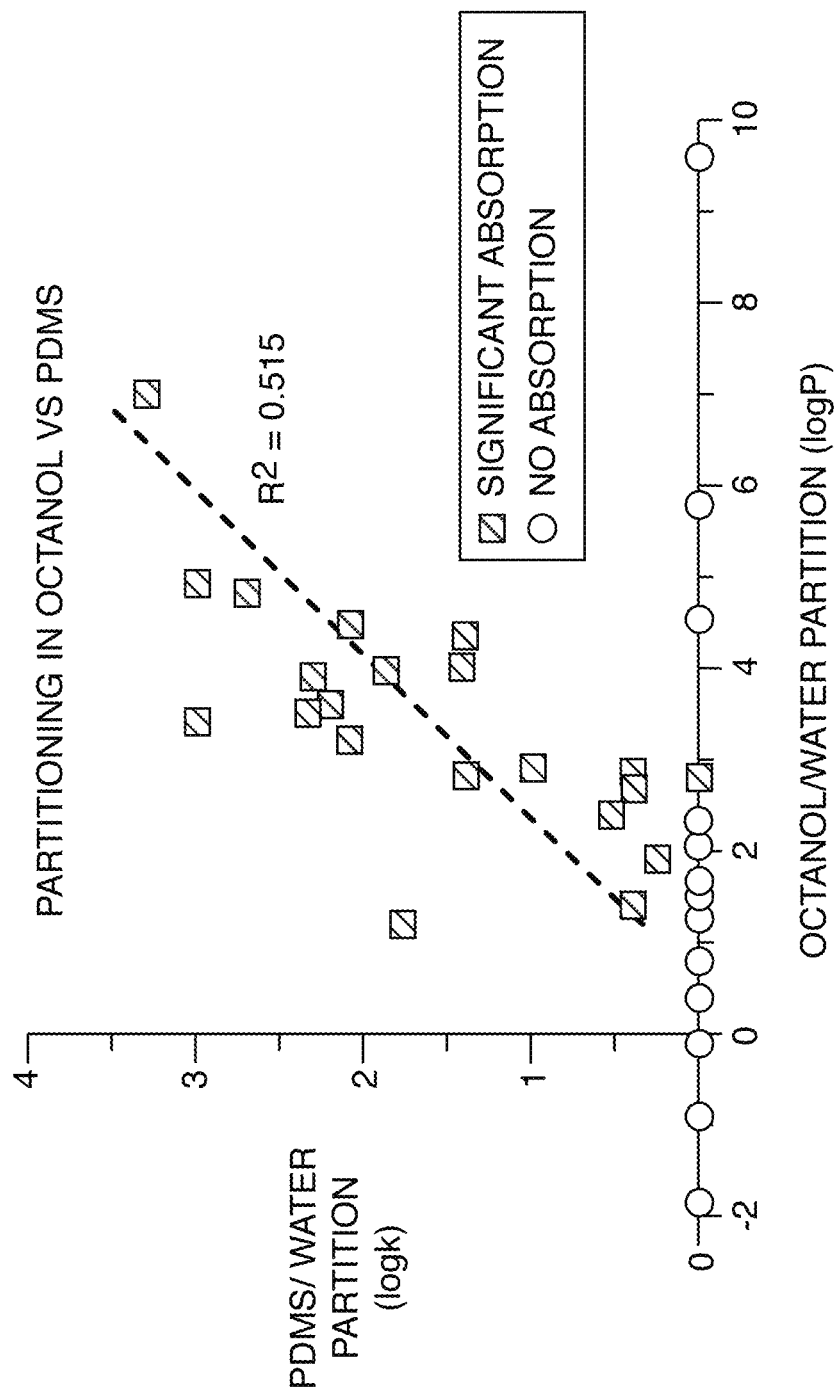
FIGS. 20A and 20B depict the results of absorption testing of many different small molecule compounds and the relationship between the physicochemical parameter "log P" or octanol partitioning and "log K" or PDMS partitioning. Note that an $R^2$ value of 0.515 indicates a weak correlation between the two parameters. Taken alone, log P cannot be used to predict PDMS partitioning. When absorption is considered with respect to both log P and molecular weight simultaneously, we see even less of a correlation between a binary "will/will not" absorb and these two parameters.
Figure 20B:
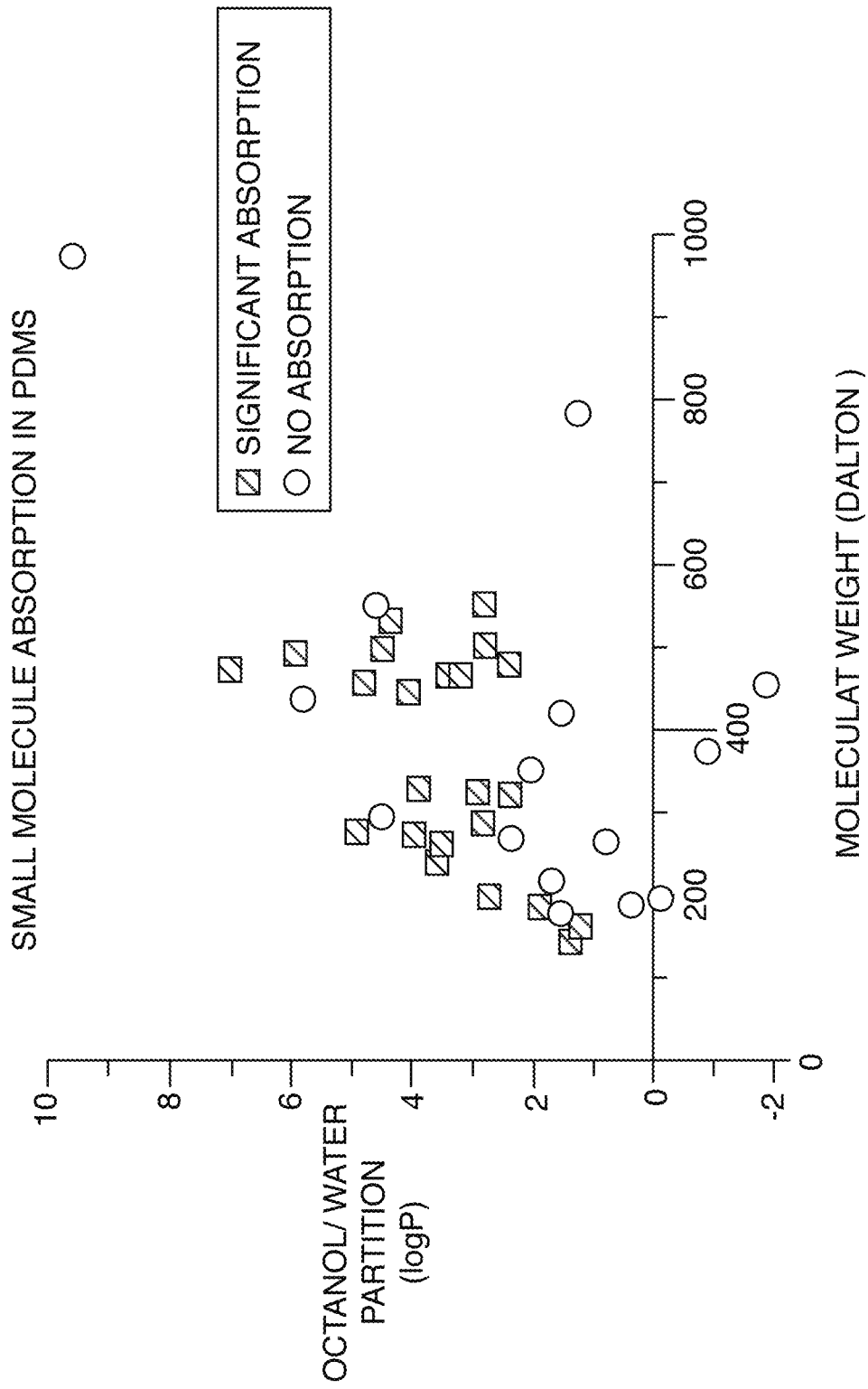
Figure 21A:
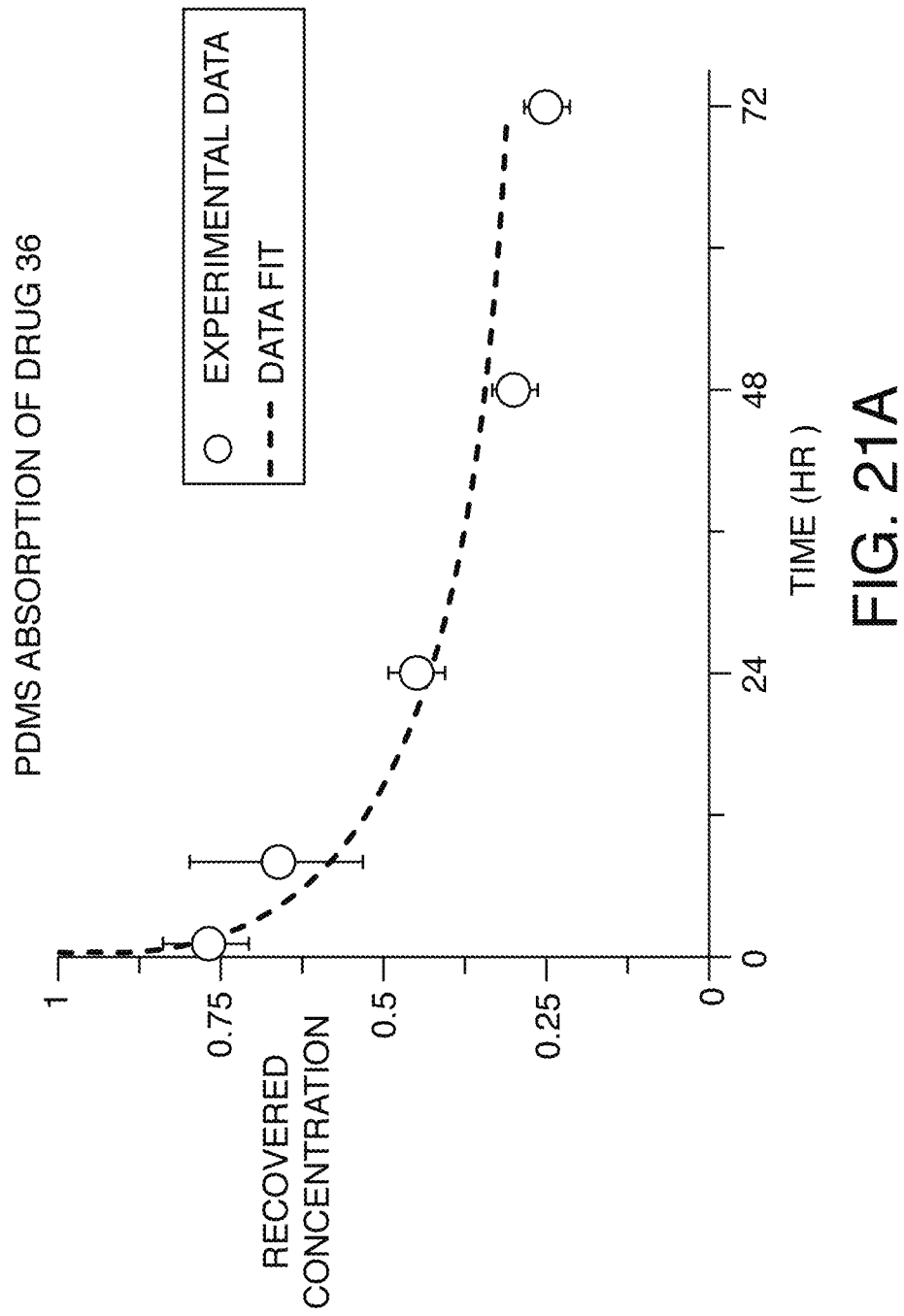
FIGS. 21A and 21B depict the results of absorption testing of individual drug molecules, Drug 36 and Drug 48, respectively.
Figure 21B:
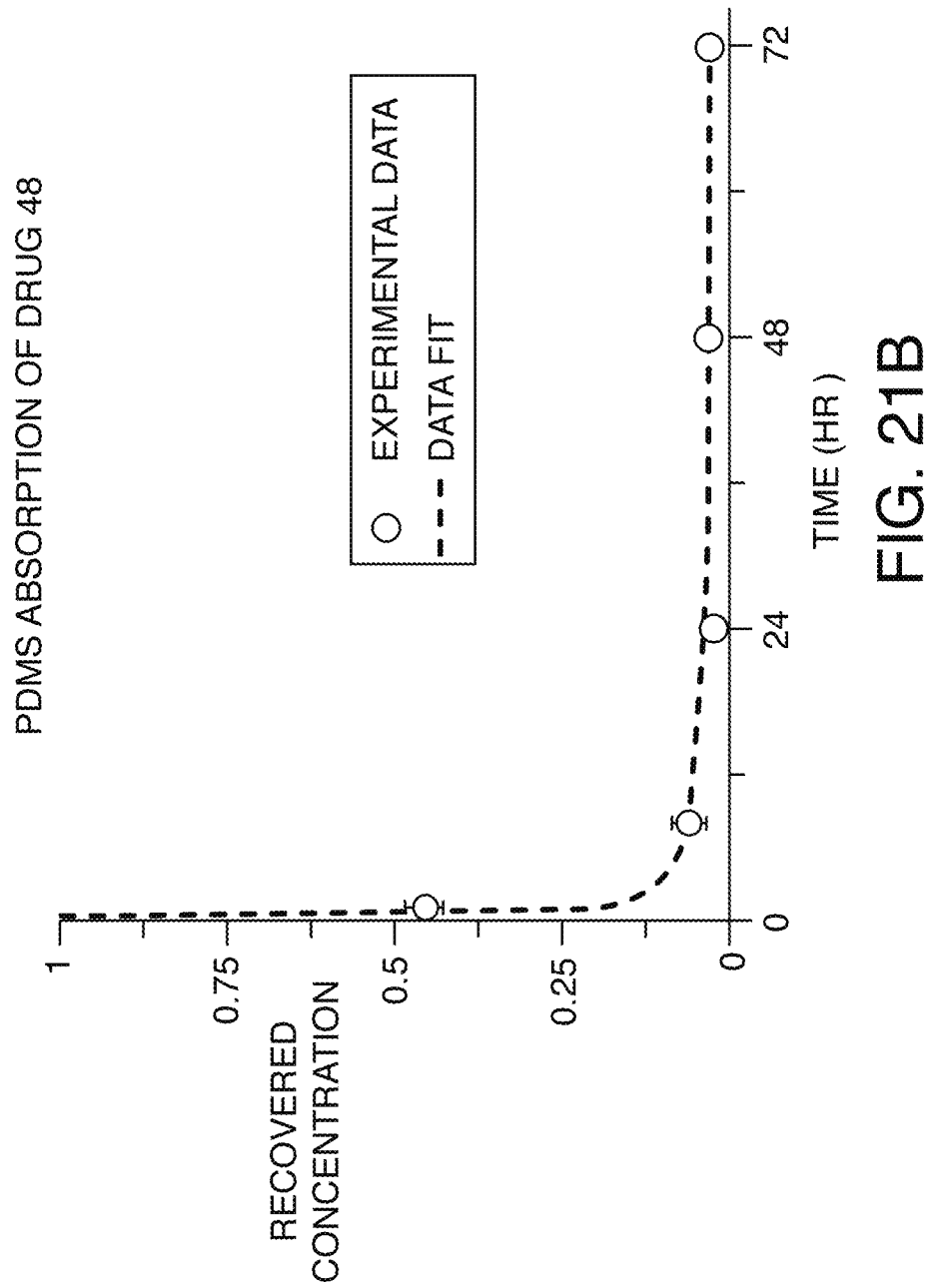

FIGS. 20A and 20B depict the results of absorption testing on many different small molecule compounds such as pharmaceuticals, specifically for the parameter partition coefficient in PDMS. Many compounds were tested from multiple industry collaborators. Results in FIG. 76 depict the level of absorption into PDMS and the material of the perfusion manifold assembly (pod). Tested compounds include both approved compounds already on the market, as well as candidates still in the pharmaceutical development pipeline. The compounds cover a range of molecular weights and lipophilicity (log P), which are two physicochemical parameters that indicate absorption. The results of the material testing were then plotted versus these parameters. The results showed that the majority of small-molecules are at risk for significant PDMS absorption. However, the extent of absorption is not well-predicted by log P or molecular weight mathematical models alone, only strongly indicative. It was found that approximately 60% of the compounds tested absorb into PDMS, while none of the compounds absorb into COP. Surprisingly, it was found that approximately 50% of the compounds also absorb into SEBS to some extent, a preferred material in one embodiment of the previously presented perfusion manifold assembly (14). Large molecules, above about 1 kDa, have a low risk of absorption.

Figure 70:
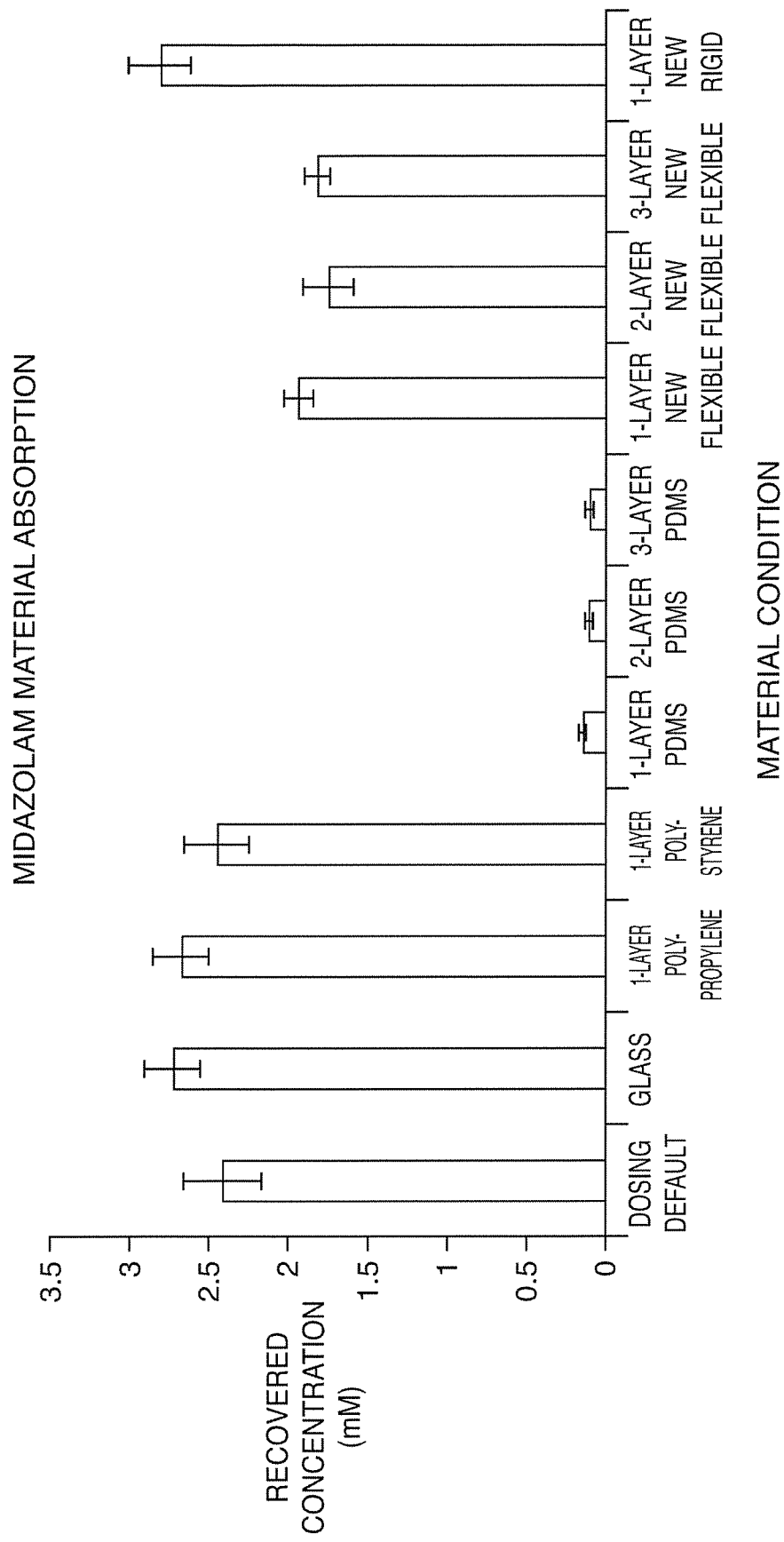
FIG. 70 shows the recovered concentration of Midazolam, a small molecule known to absorb, from a solution that had been in contact with various materials, including glass, polypropylene, polystyrene, PDMS, SEBS and COP.
Figure 72:
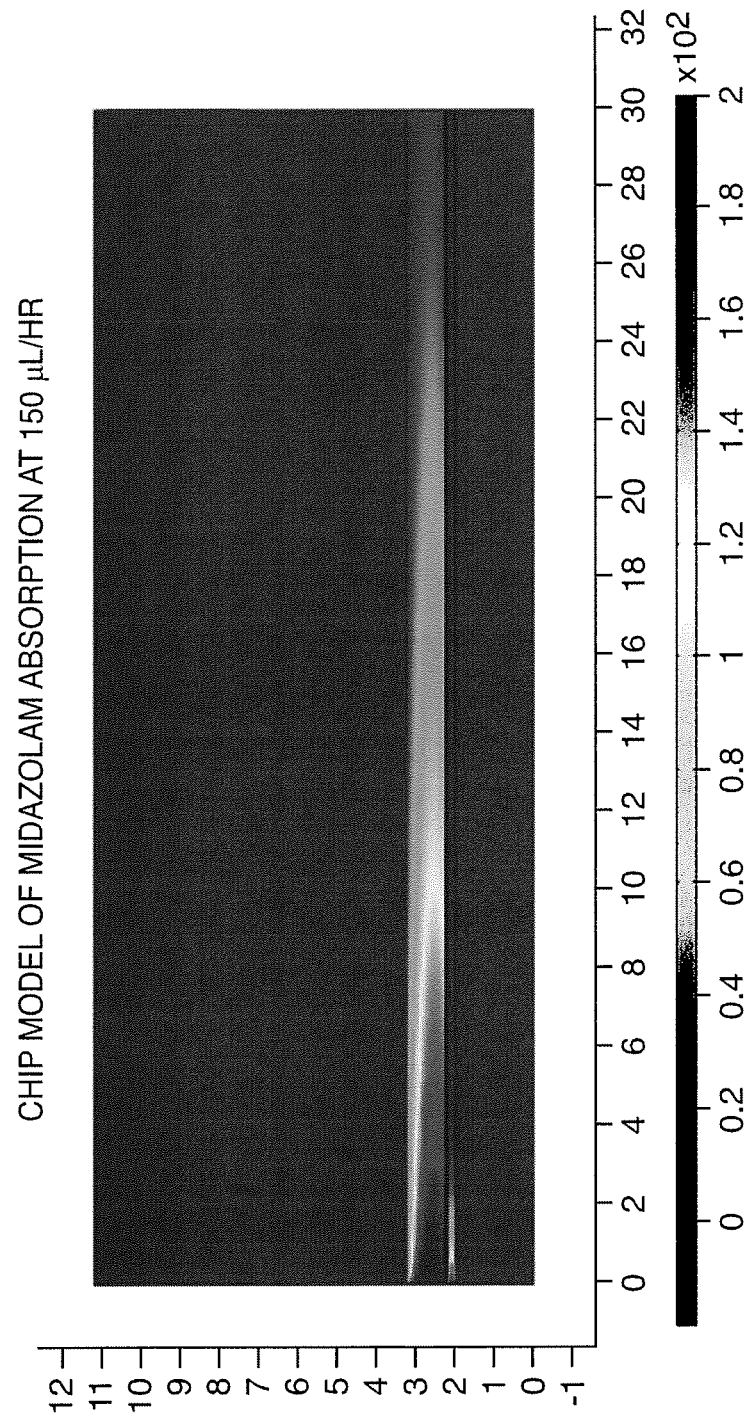
FIG. 72 shows a computational model of Midazolam absorbing into a high-absorbing, gas-permeable microfluidic device fabricated from PDMS.
Figure 73:
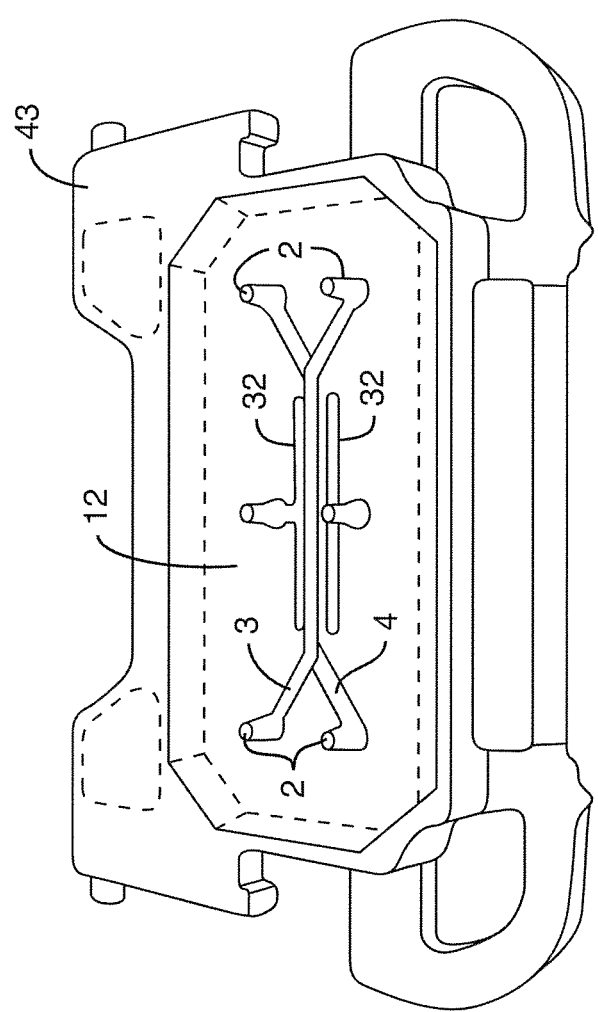
FIG. 73 shows an exemplary embodiment of a high-absorbing, gas-permeable microfluidic device in a microfluidic device holder or clip, such that the high-absorbing, gas-permeable microfluidic device may be fluidically connected to a perfusion manifold assembly.
Figure 74:
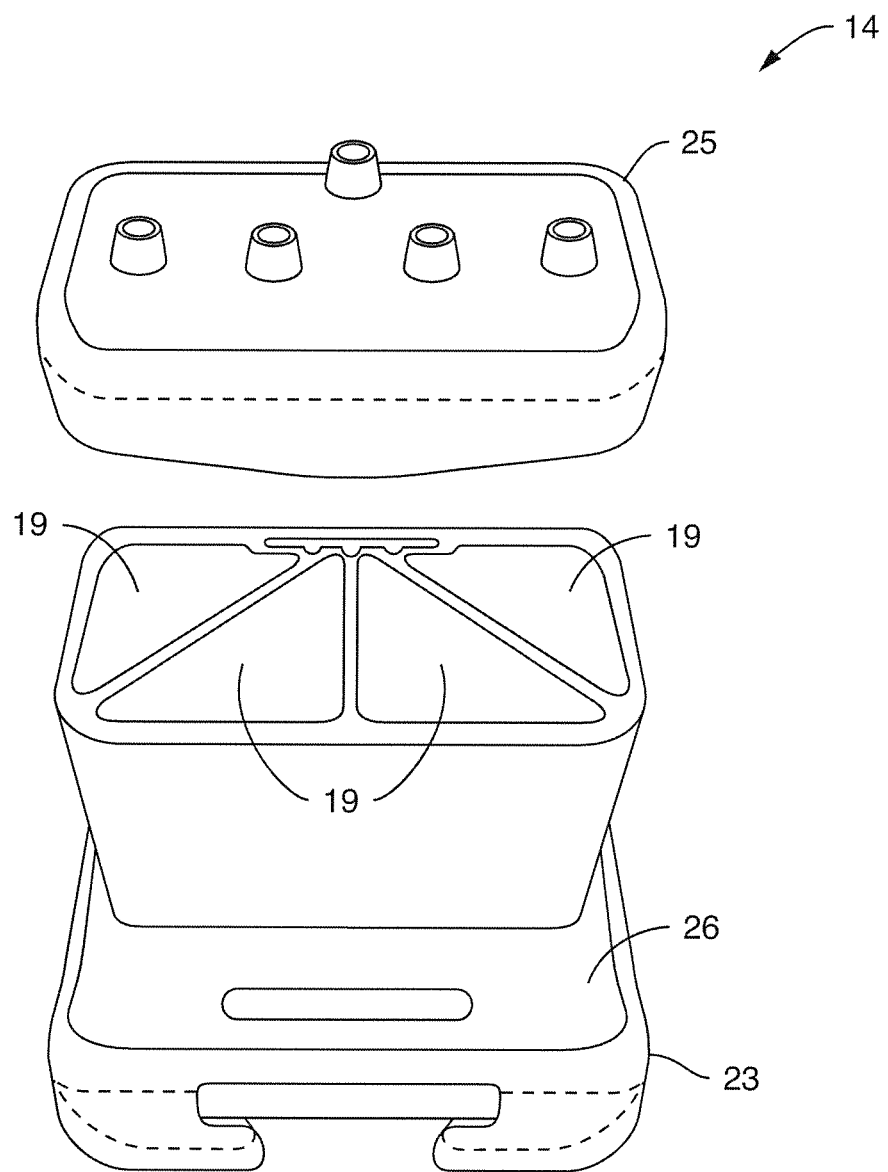
FIG. 74 shows an exemplary embodiment of a perfusion manifold assembly.
Figure 75:
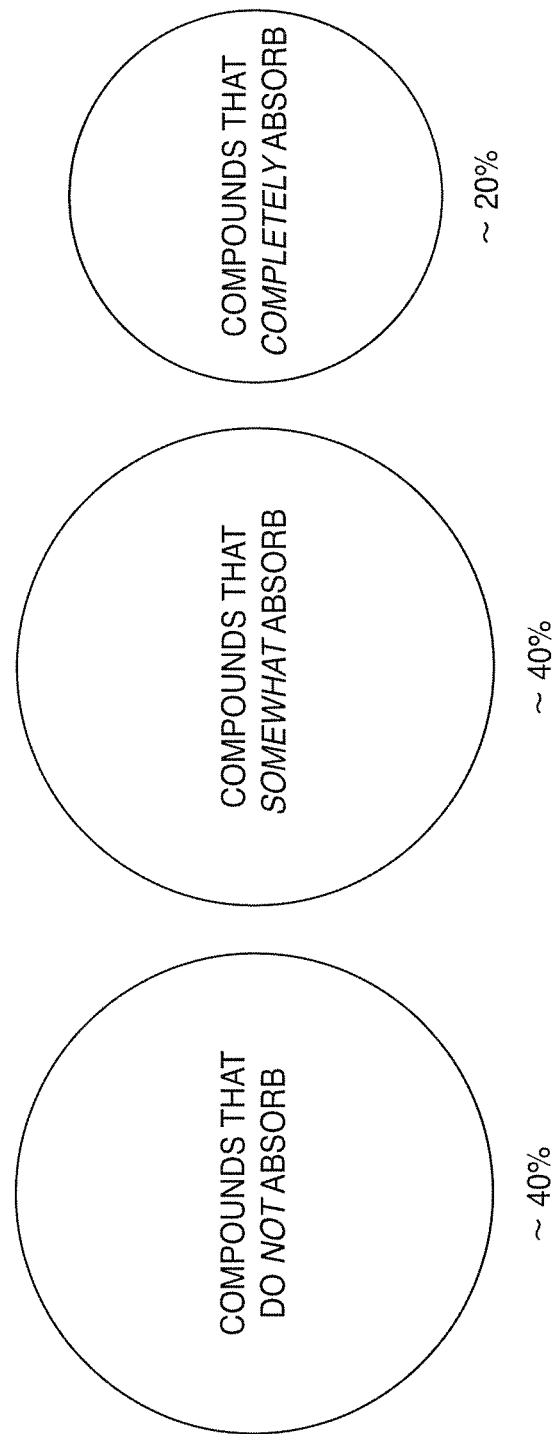
FIG. 75 shows the distribution of small-molecules and how likely they are to absorb into surrounding materials. Approximately ~40% of small-molecules previously tested do not absorb. Approximately ~40% of small-molecules somewhat absorb. Approximately ~20% of small-molecules effectively absorb completely on the time and length scales of an Organ-Chip.
Figure 77A:
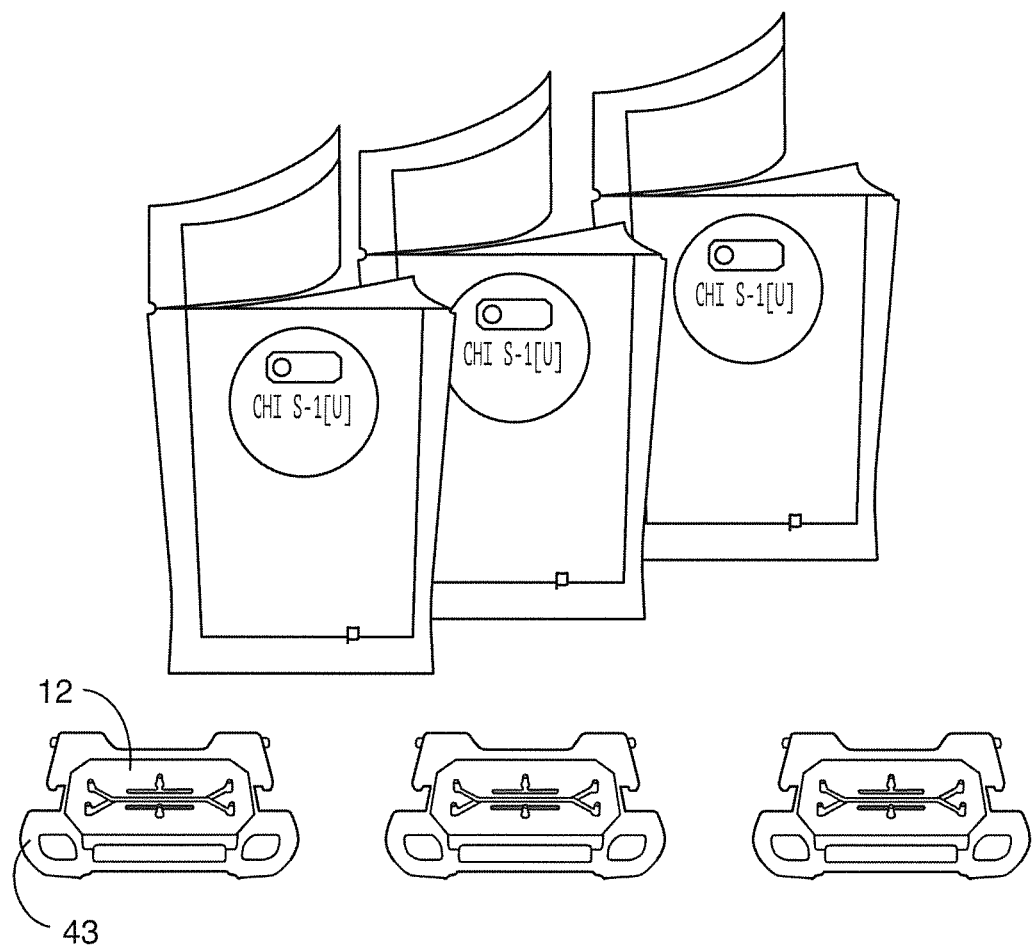
FIGS. 77A, 77B, and 77C show a selection of the physical components of the compound distribution kit. In one embodiment, the physical component of the compound distribution kit includes a plurality of microfluidic devices comprising a poreless membrane, a plurality of perfusion manifold assemblies, a plurality of filters, and a quick start guide.
Figure 77B:
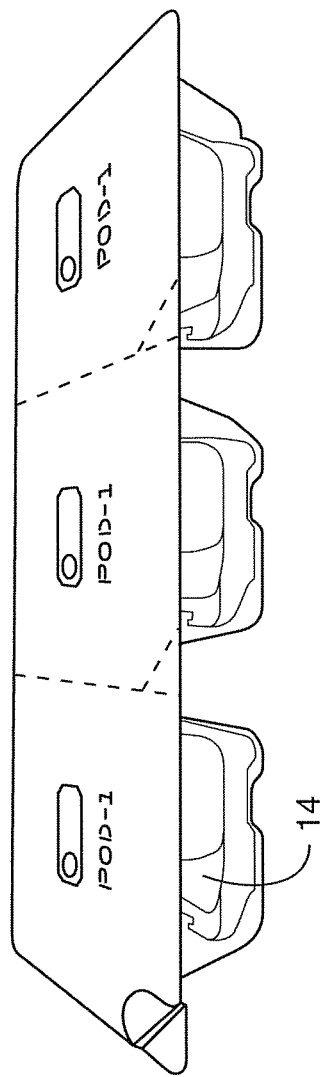
Figure 77C:
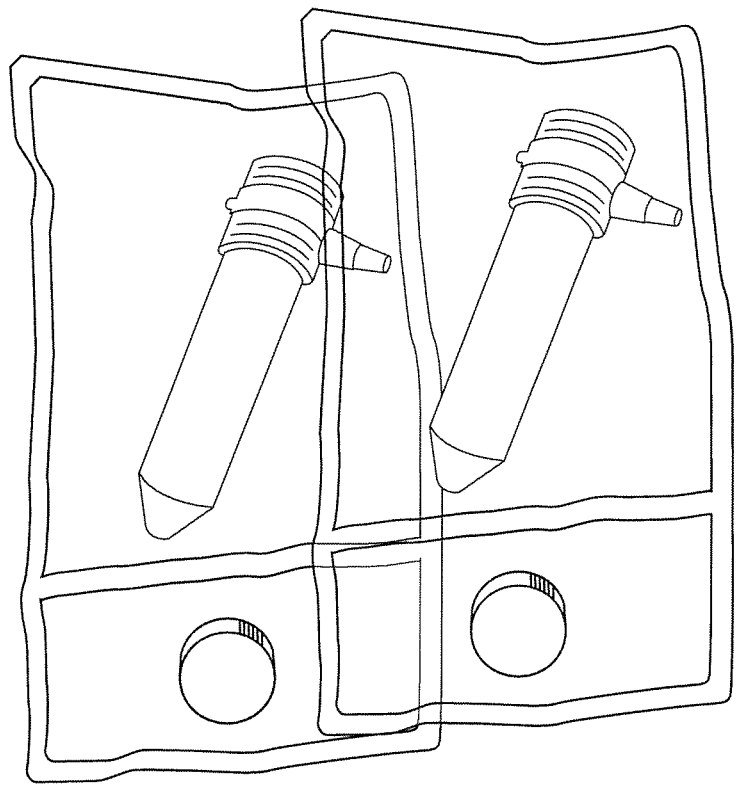
Figure 79:
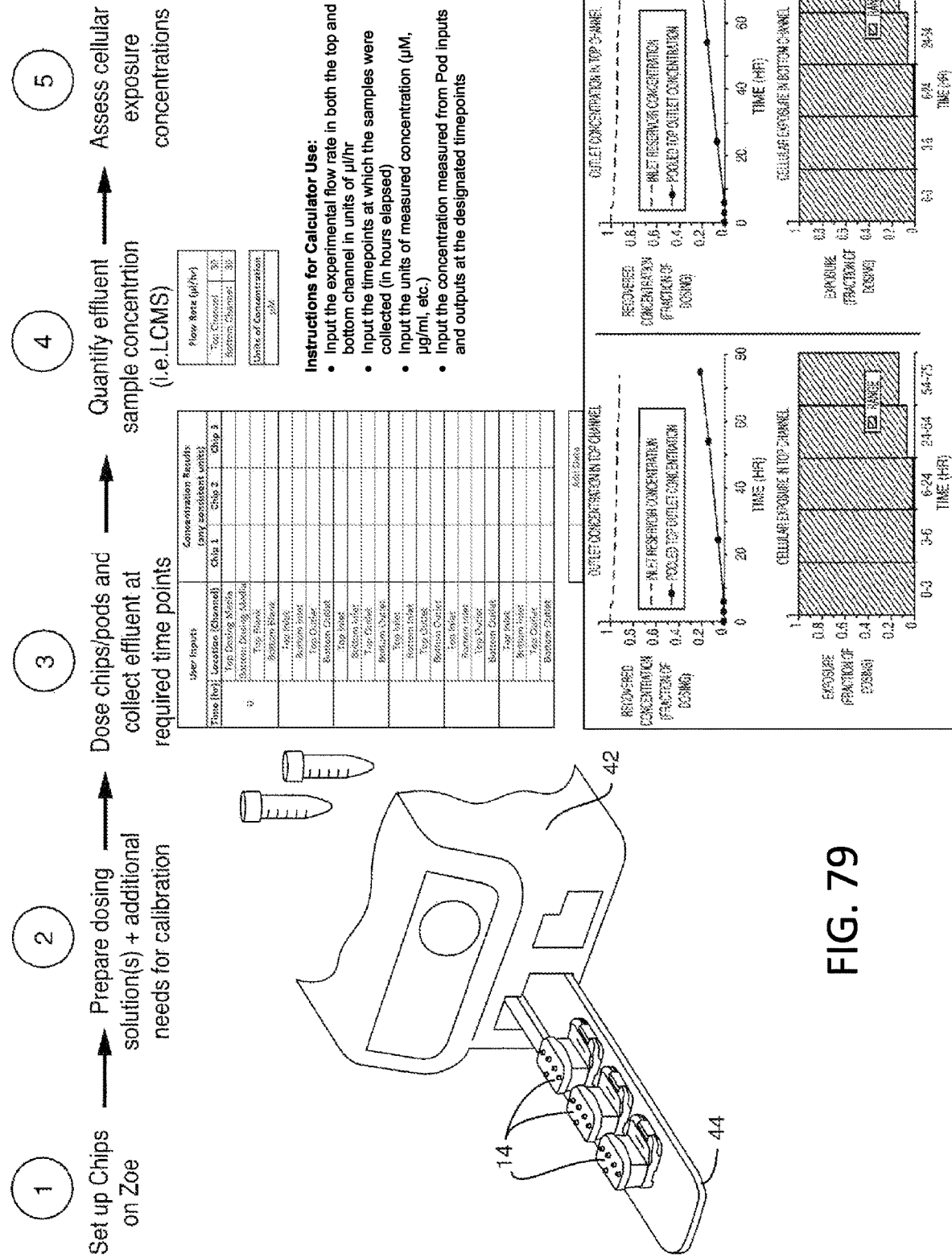
FIG. 79 shows one embodiment of a timeline for the compound distribution kit. The first step is to set up the culture module, which in one embodiment is an Emulate Zoe™. Step two is to prepare dosing solution(s) and additional needs for calibration. Step three is to dose the microfluidic devices (chips) and perfusion manifold assemblies (pods) at desired time points. The fourth step is to quantify effluent sample (compound) concentration, for example with an LCMS. The fifth step is to assess cellular exposure compound concentrations.
Figure 80:
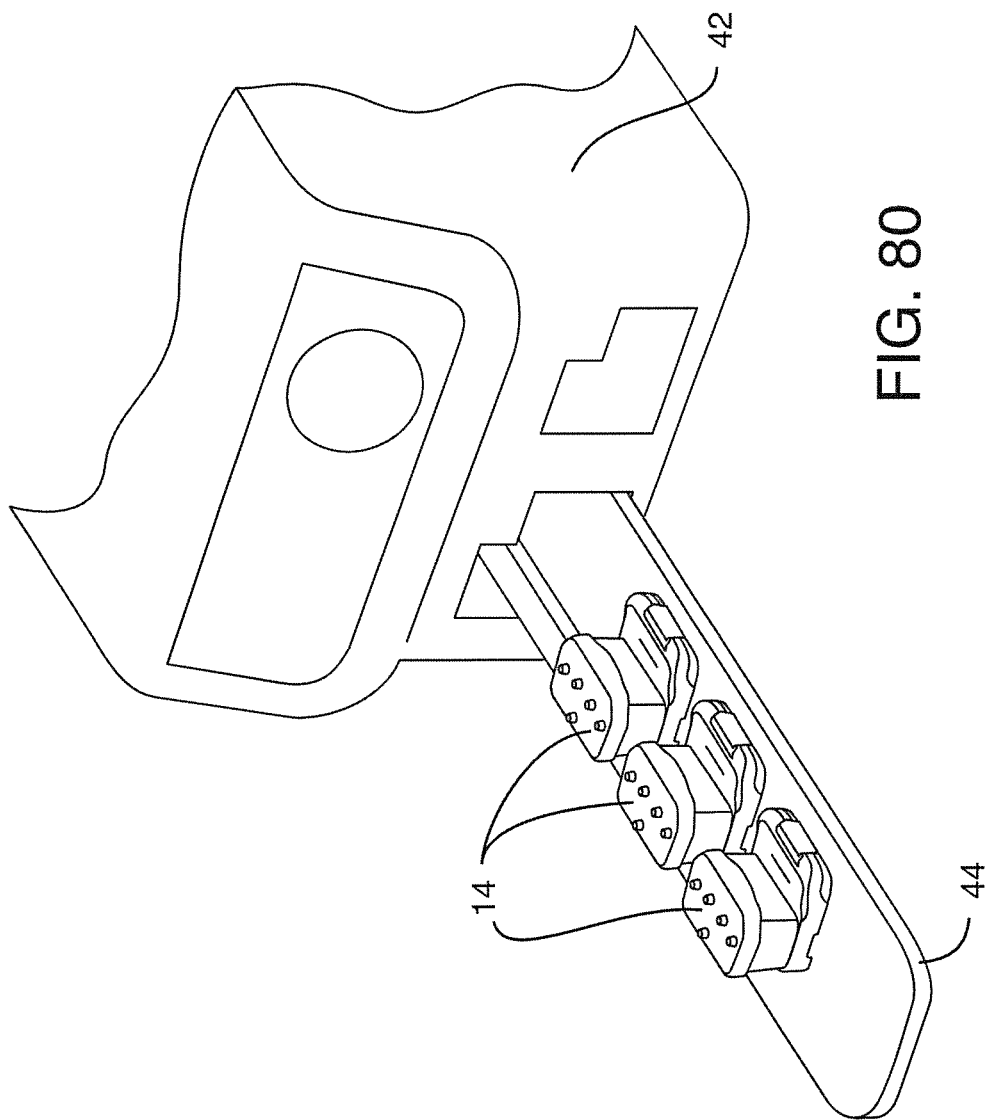
FIG. 80 shows one embodiment of three perfusion manifold assemblies preparing to be fluidically connected to a culture module.
Figure 81:
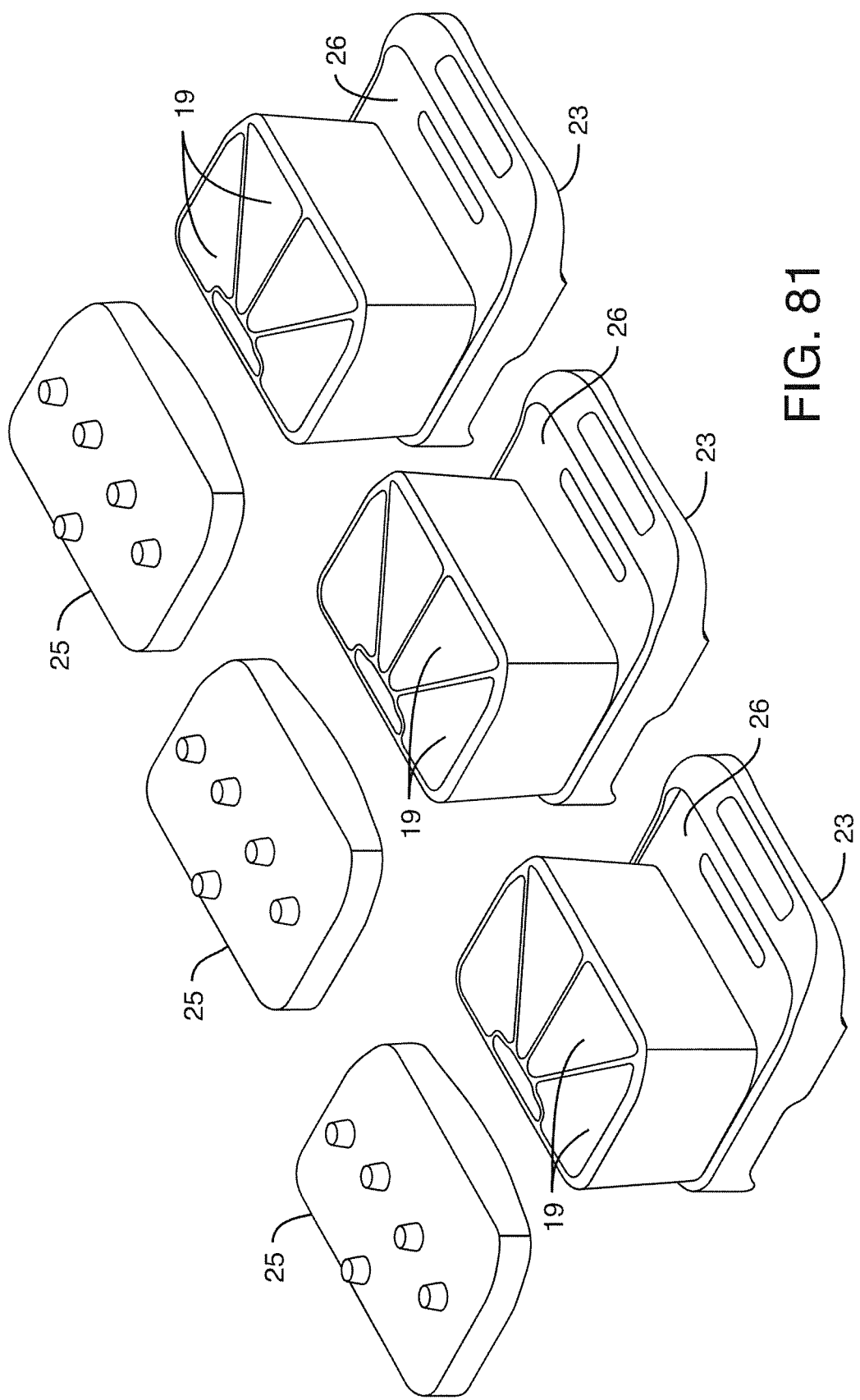
FIG. 81 shows three perfusion manifold assemblies with their lids removed.

Midazolam is a small-molecule medication used for anesthesia, sedation, as a treatment for epilepsy, and as a sleep aid. Midazolam has a log P value of 3.89, a PDMS partition value (K) of 201 and a SEBS partition value (K) of 4.05. FIG. 70 shows the recovered concentration of Midazolam from a solution that had been in contact with various materials, including glass, polypropylene, polystyrene, PDMS, SEBS and COP. The recovered concentrations were compared to the default dosing concentration. Midazolam did not absorb significantly into glass, polypropylene, polystyrene or COP. Midazolam absorbed somewhat into SEBS. Midazolam absorbed significantly into PDMS. FIG. 72 shows a computational model of Midazolam absorbing into a high-absorbing, gas-permeable microfluidic device fabricated from PDMS. FIG. 72 shows that only the cells at the beginning of the cell culture channel are contacted by the drug before it is absorbed into the PDMS as the media is perfused through the microfluidic device channel from left to right in the image.

Figure 71:
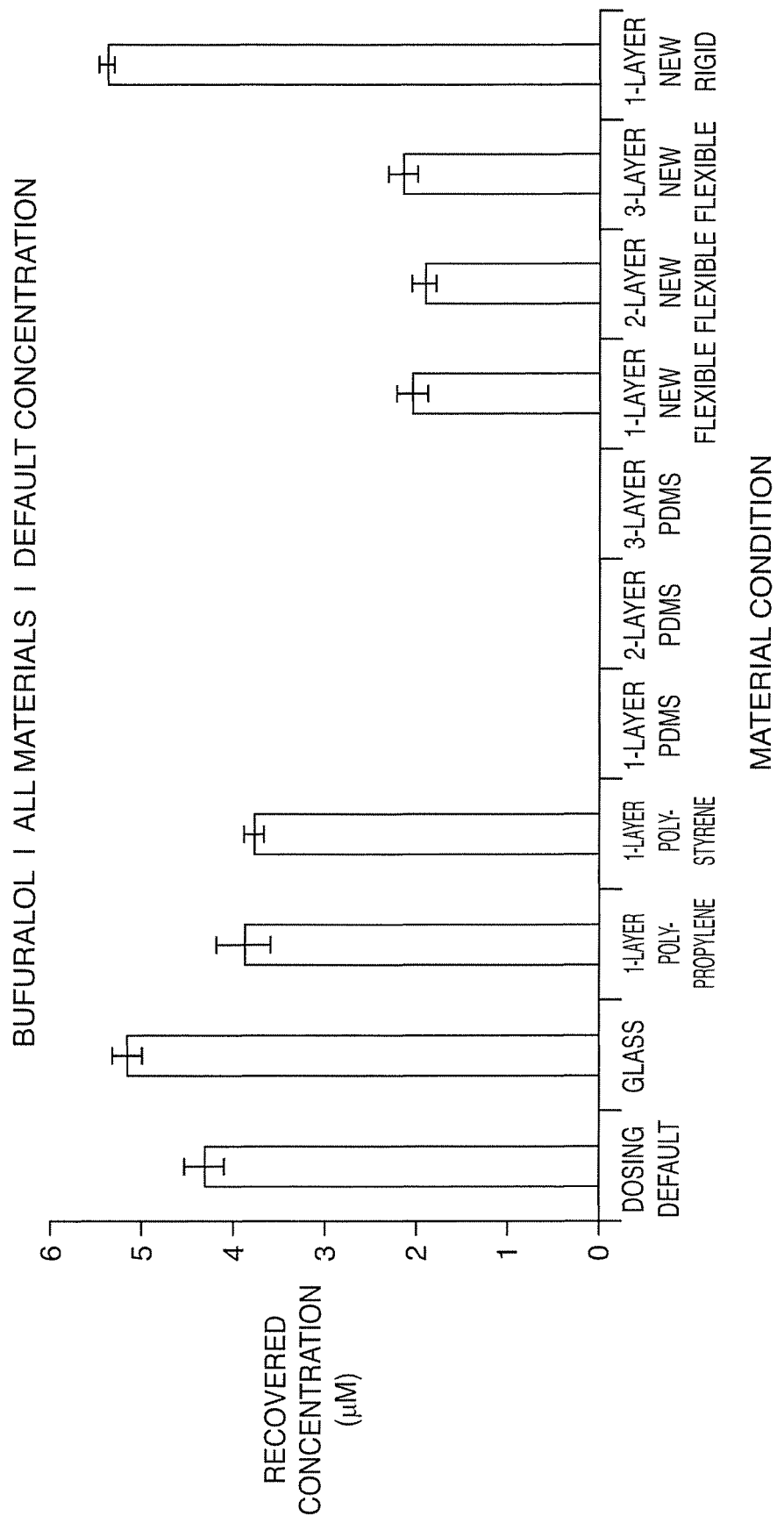
FIG. 71 shows the recovered concentration of Bufuralol, a compound known to absorb, from a solution that had been in contact with various materials, including glass, polypropylene, polystyrene, PDMS, SEBS and COP. Note that data is plotted for PDMS, but that the recovered concentrations were below the lower limit of detection (that is to say the compound effectively completely absorbed into the material and was removed from the dosing solution).

Bufuralol is a small-molecule beta blocker. Bufuralol has a log P value of 3.5, a PDMS partition value (K) greater than 216, and a SEBS partition value (K) of 4.77. FIG. 71 shows the recovered concentration of Bufuralol from a solution that had been in contact with various materials, including glass, polypropylene, polystyrene, PDMS, SEBS and COP. The recovered concentrations were compared to the default dosing concentration. Bufuralol did not absorb significantly into glass, polypropylene, polystyrene or COP as indicated by nearly 100% recovery of the dosed compound. Bufuralol absorbed somewhat into SEBS. Bufuralol absorbed almost entirely into PDMS—so much so that the recovered concentration from the PDMS experiments was below the lower limit of detection of LCMS. The inability to detect the compound on the LCMS highlights the severity of the challenge of working with small molecules in devices comprised of PDMS.

Material experiments were carried out with the drug Diazepam on both PDMS and COP. FIGS. 15A and 15B depicts the absorption of the drug Diazepam into both materials PDMS and COP over time, based on the recovered concentration of Diazepam remaining in the fluid contained in the glass vials where the material is contained. This depicts compound "loss" to the material over time. FIG. 15A depicts the difference between dosing concentration and compound recovery from the solution containing Diazepam when in contact with PDMS for up to 72 hours. By hour 12 almost two thirds of the Diazepam had been absorbed by the PDMS. Computational modeling is also shown in FIG. 15A to match samples taken at seven time points. FIG. 15B depicts the difference between dosing concentration and compound recovery from the solution containing Diazepam when in contact with COP for up to 72 hours. Over the course of 72 hours there was minimal, if not no, absorption into COP. The experiments emphasize the large absorbance difference between PDMS and COP.

Material coatings were also tested to gauge their effectiveness in protecting commonly used microfluidic device construction materials from absorption. Parylene is a trade name for a variety of poly(p-xylylene) polymers that may be used to coat materials via chemical vapor deposition. Parylene is of interest, as Parylene coated materials, such as PDMS or SEBS, may be effectively used to construct low-absorbing, yet flexible microfluidic devices since while the layer of deposited Parylene is rigid, it is thin enough to allow the flexibility of the material underneath to remain flexible.

Figure 31:
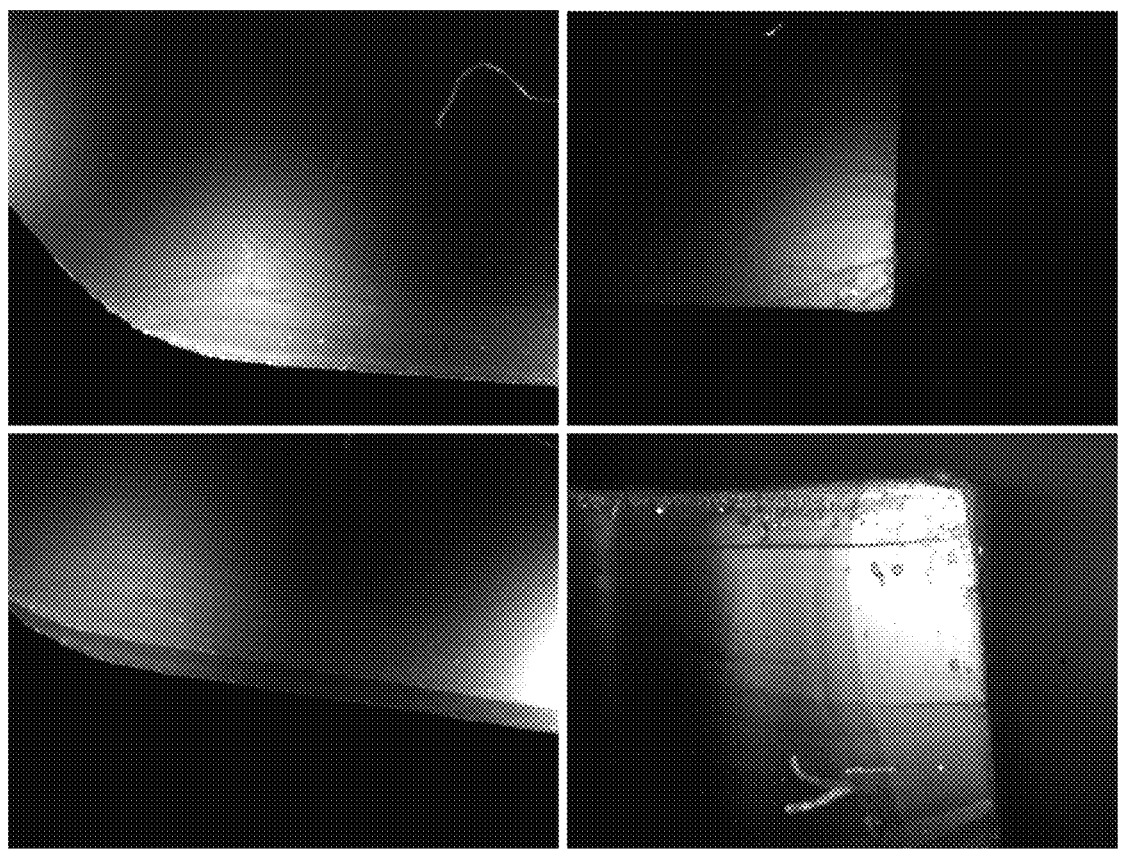
FIG. 31 depicts microscopy images of the Parylene-coated PDMS gaskets after having been exposed to Rhodamine B. A slight pinkish hue is visible, indicating some absorption is present on the corners of the gaskets, perhaps due to a poor coating on the edges.

Parylene-coated PDMS gaskets were exposed to the fluorescent molecule Rhodamine B and fluorescently imaged. FIG. 31 depicts microscopy images of the Parylene-coated PDMS gaskets after having been exposed to Rhodamine B. Only a slight pinkish hue is visible and only on some of the corners, indicating some absorption is present but localized to areas that might not have been fully coated. However, the absorption is primarily localized to areas with sharp corners. No absorption was seen within the microfluidic device ports leading into the channels, the actual region that is required be low-absorbing. Initial qualitative analysis of Parylene coating was found to be promising.

Figure 32:
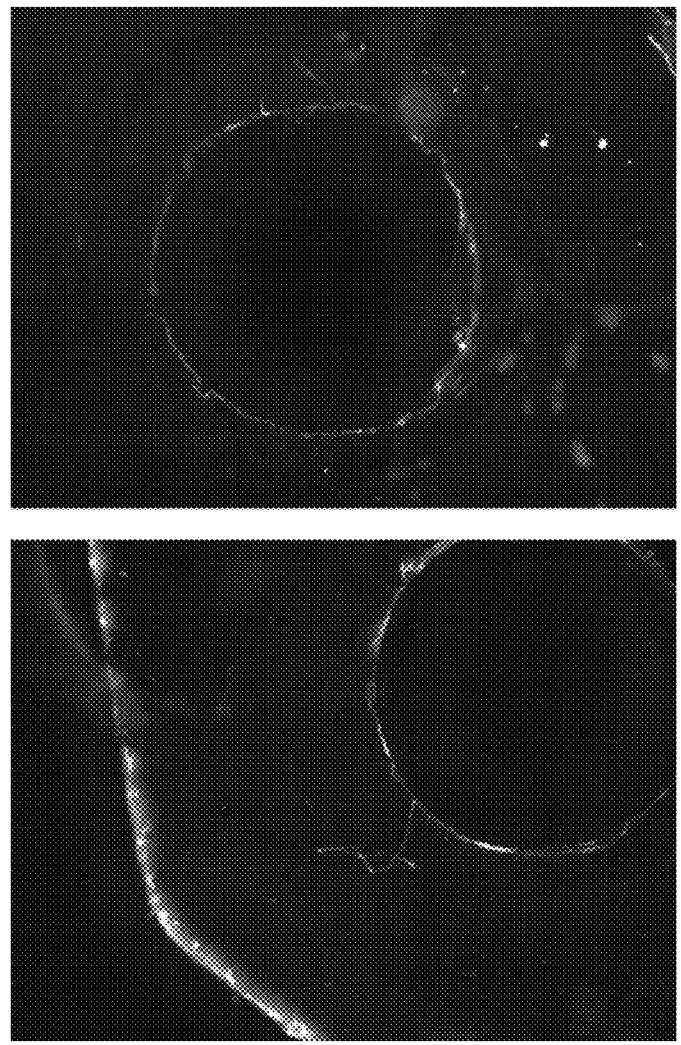
FIG. 32 depicts microscopy images of the Parylene-coated PDMS gaskets after having been exposed to Rhodamine B. A slight pinkish hue is visible, indicating some minimal absorption is present. However, the absorption is primarily localized to areas with sharp corners. Some absorption can be seen inside of the via, but it was minimal and difficult to visualize, and quite possibly an optical artifact unrelated to absorption.

Parylene-coated SEBS gaskets were exposed to the fluorescent molecule Rhodamine B and fluorescently imaged as well. FIG. 32 depicts microscopy images of the Parylene-coated PDMS gaskets after having been exposed to Rhodamine B. A slight pinkish hue is visible, indicating some minimal absorption is present. However, the absorption is primarily localized to areas with sharp corners. Some absorption can be seen inside of the via, but it was minimal, difficult to visualize, and quite possibly an optical artifact unrelated to absorption.

Two quantitative studies were run on Parylene coated materials in order to assess its effectiveness in minimizing small molecule absorbency. In the first study Parylene coated SEBS and Parylene coated PDMS were both exposed to Rhodamine B and Coumarin. In the second study the absorption of Parylene coated SEBS and Parylene coated E140 were compared to the absorption of known low-absorbing materials, such as glass and COP.

Figure 33A:
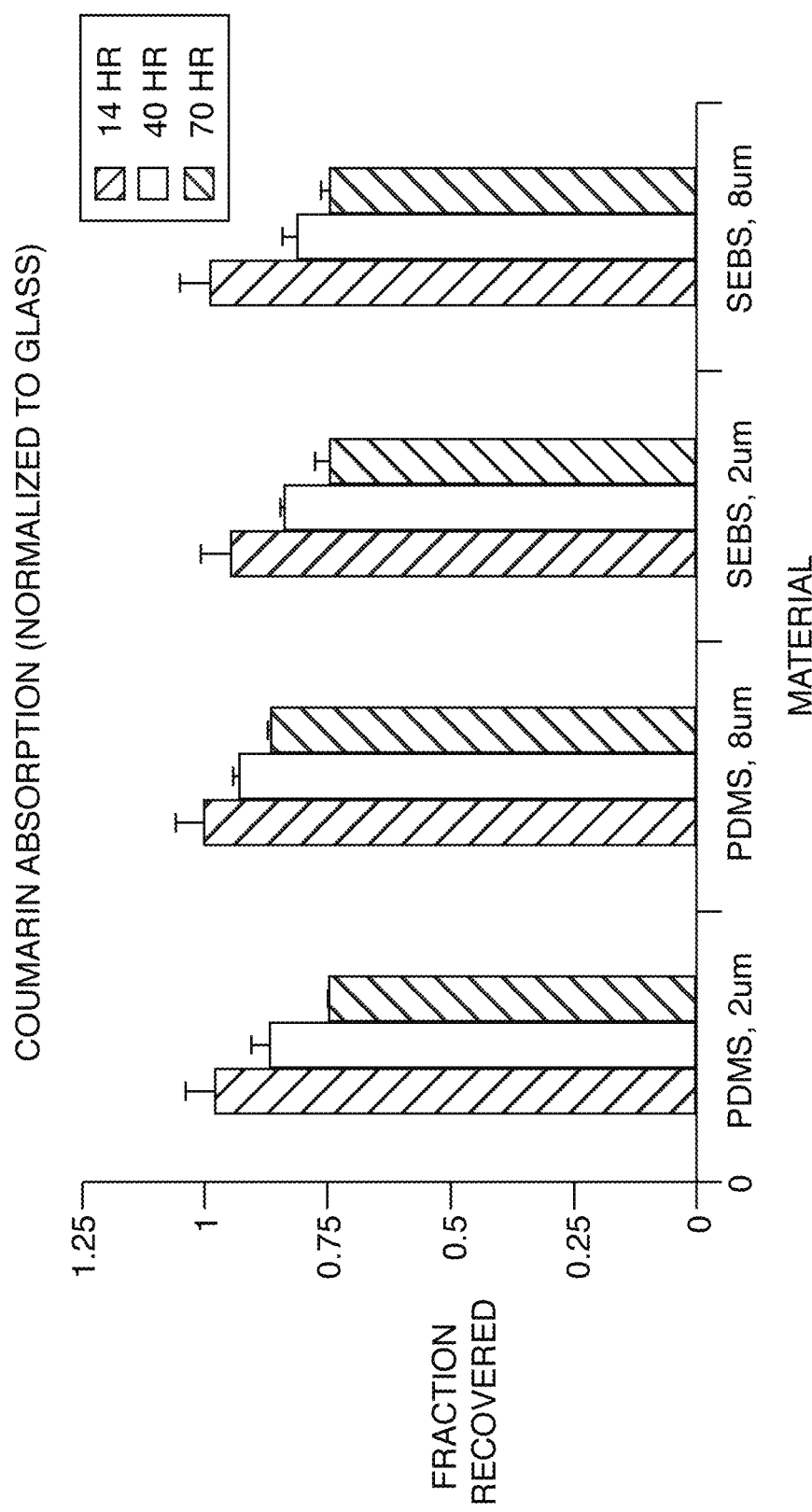
FIG. 33A-B shows the results of studies on absorption into Parylene coated materials.
Figure 33B:
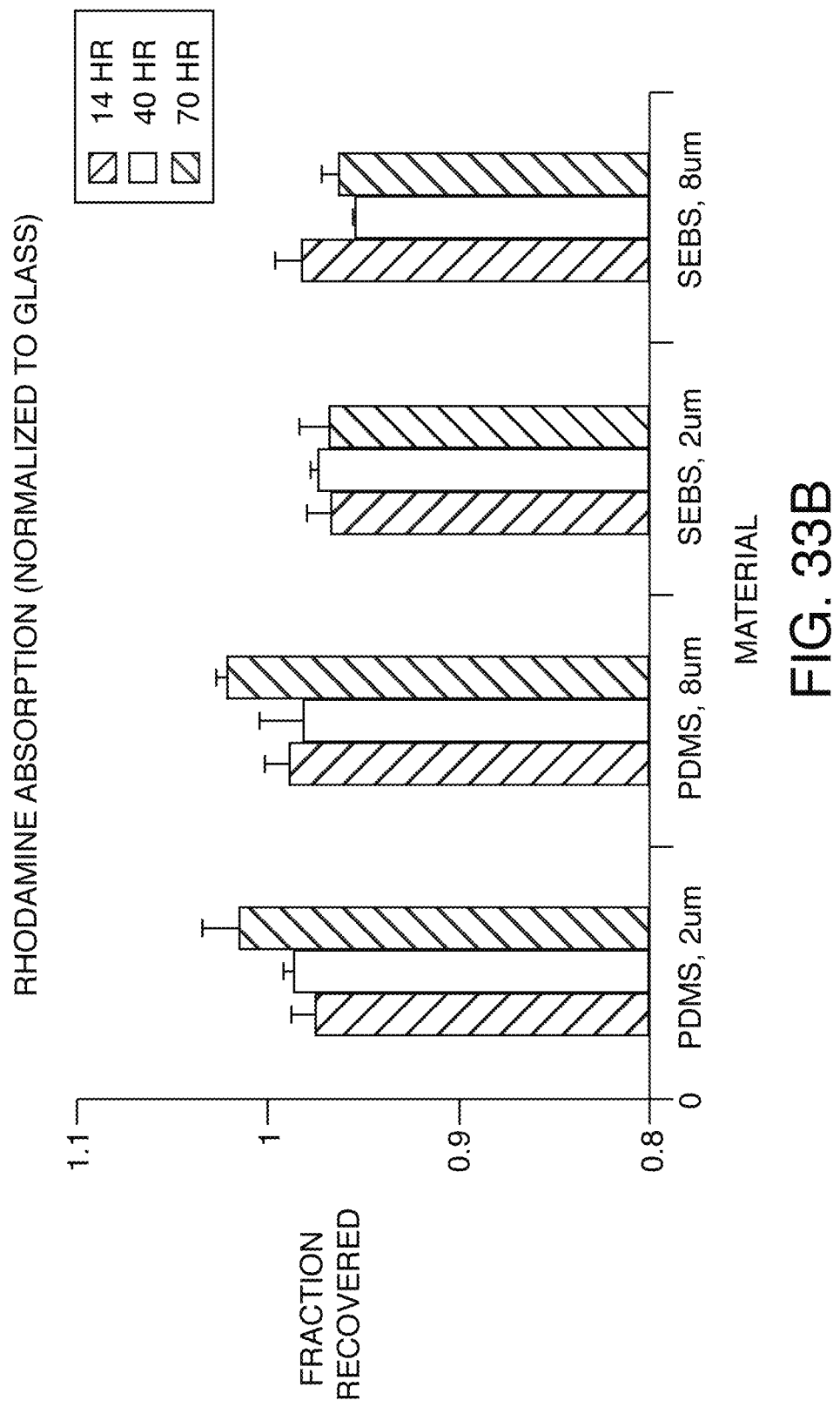

In the first round of absorption studies, SEBS and PDMS gaskets were coated with Parylene at two thicknesses: 2 μm and 8 μm. Parylene-coated gaskets were exposed to Rhodamine B and Coumarin for 0, 14, 40 and 72 hours. The remaining concentration of Rhodamine B and Coumarin in the exposure solution were measured on a plate reader. Each condition was tested on two gaskets. Limited replicates were available due to the number of conditions run. This "shotgun approach" was used in order to try many coating conditions and quickly determine the best options. FIG. 33A shows the results of studies on absorption into Parylene coated materials and depicts the fraction of Coumarin recovered from the solutions. FIG. 33B depicts the fraction of Rhodamine B recovered from the solutions for coatings of varying thickness on two materials known to absorb. FIG. 33A shows that some Coumarin was absorbed by both the coated PDMS and SEBS with different coating thicknesses. FIG. 33B shows that minimal Rhodamine B was absorbed by the PDMS and SEBS at the different coating thicknesses. One observation from the experiment was that the Parylene may crack, leading to gasket absorption. Another observation from the experiment was that Parylene adhesion to the PDMS and SEBS was poor, resulting in easy removal of Parylene. Finally, parts were difficult to handle, as the Parlene coating was extremely hydrophobic, and thus "slippery." These coating issues may be absolved by optimizing the masking strategy to prevent cracking or tearing prior to mask removal, optimizing the geometry of the gaskets to remove sharp edges and reducing the bulk gasket volume so that just the functional components of the microfluidic device interfaces with the perfusion manifold assembly instead of the gasket. Regardless, Parylene was shown to improve the absorbency issues of both PDMS and SEBS.

Figure 68:
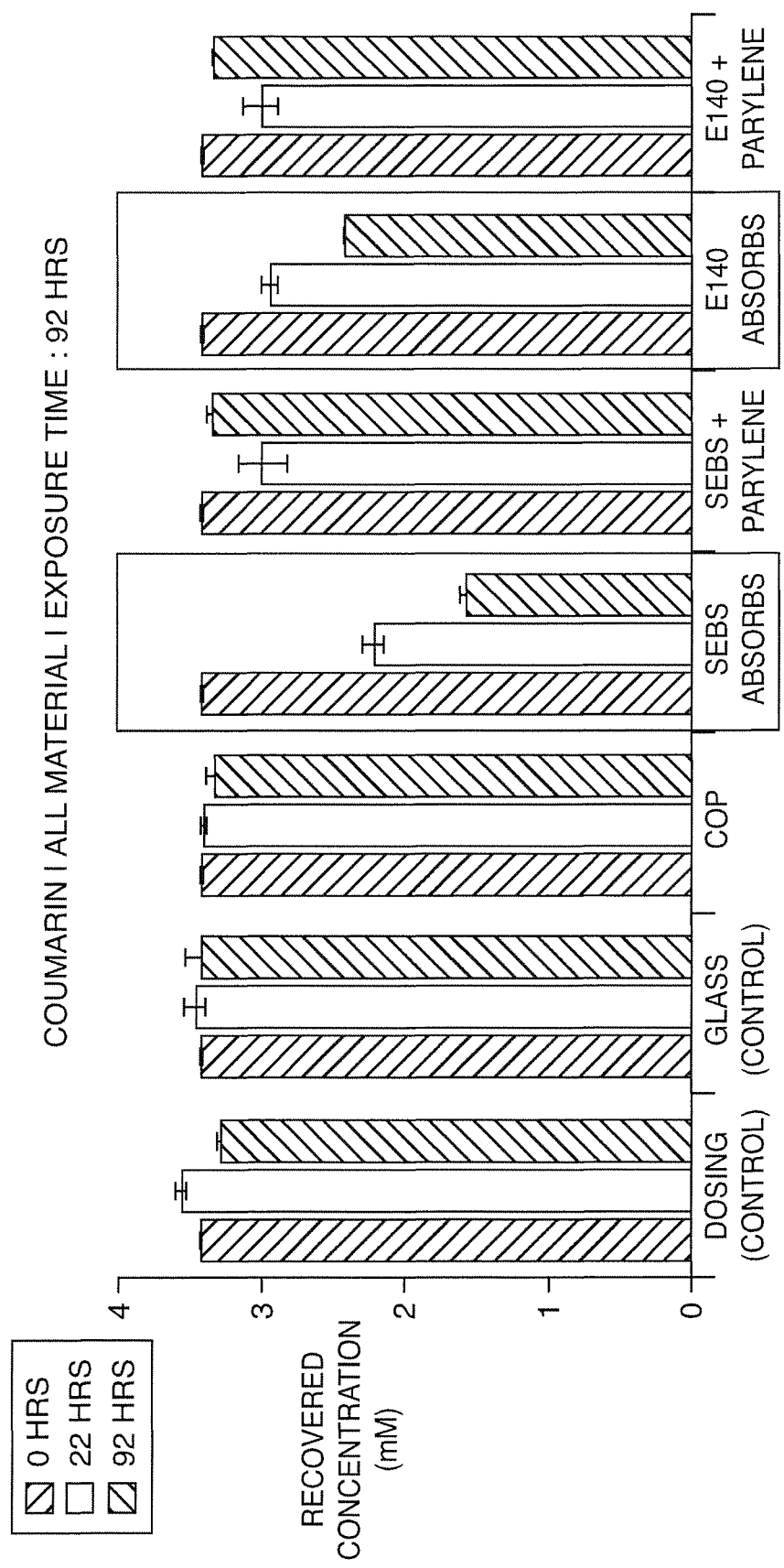
FIG. 68 shows the results of an experiment assessing the absorption of Parylene coated SEBS and Parylene coated E140 compared to the absorption of known low-absorbing materials, such as glass and COP, and a control solution of the drug (Coumarin, which is known to absorb highly) not in contact with a material. Only non-coated materials were seen to absorb.

In the second round of absorption studies, after parylene-coating process optimization, the absorption of Parylene coated SEBS and Parylene coated E140 were compared to both the absorption of known low-absorbing materials, such as glass and COP, and a control solution of the drug not in contact with a material. The coated materials were exposed to a solution carrying a known concentration of the drug, Coumarin. The solution was tested three times to quantify the remaining concentration of the Coumarin, before exposure to the material, at 22 hours and at 92 hours. The results of the experiment showed that the glass and COP did not absorb, when compared to the control solution. The results of the experiment showed that uncoated SEBS and E140 both absorb small molecules. SEBS absorbed more of the compound than E140. The results of the experiments show that materials coated with Parylene do not absorb significant amounts of small molecules. FIG. 68 shows the results of the experiment and only non-coated materials were seen to absorb in this experiment.

2. Absorbency Experiments on High-Absorbing, Gas-Permeable Microfluidic Devices

Figure 17:
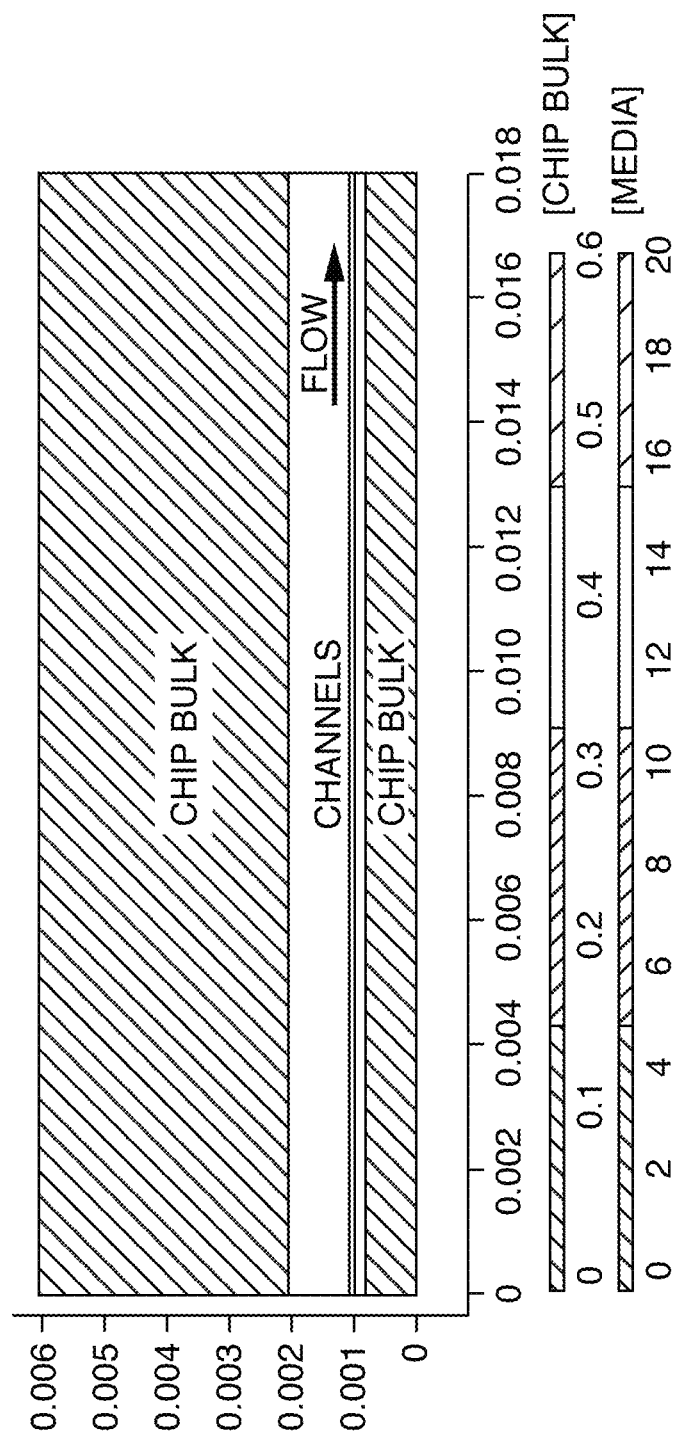
FIG. 17 shows a computational absorption model of a microfluidic device comprising a top channel, a bottom channel, and a membrane separating at least a portion of said top channel (3) and bottom channel was built. The model allows different variables to be changed, including permeability of the material, absorbance of the material, flow rate of the fluid in the top and bottom channels, diffusivity of the compound in the fluid, etc.

A computational absorption model of a microfluidic device comprising a top channel (3), a bottom channel (4), and a membrane (7) separating at least a portion of said top channel (3) and bottom channel (4) was built. The model allows different variables to be changed, including permeability of the material (D) and absorbance of the material or partition coefficient (K) (which are both deduced from the material testing experiments), flow rate of the fluid, diffusivity of the compound in the fluid, geometry of the microfluidic device channels and material, cellular phenomena like active and passive transport as well as metabolism, etc. A depiction of the computational model of a microfluidic device comprising a top channel, a bottom channel, and a membrane separating at least a portion of said top channel (3) and bottom channel may be seen in FIG. 17. The absorption models may be validated with commonly used or tool compounds. Stand-alone absorption experiments proved predictive of drug absorption. The ability to mathematically model drug absorption is useful in designing experiments, including permeability of the material, absorbance of the material, flow rate of the fluid in the top and bottom channels, diffusivity of the compound in the fluid, etc. Understanding an experiment, and the likely results, before the experiment is carried out enables scientists to better economize funds and time.

Figure 18A:
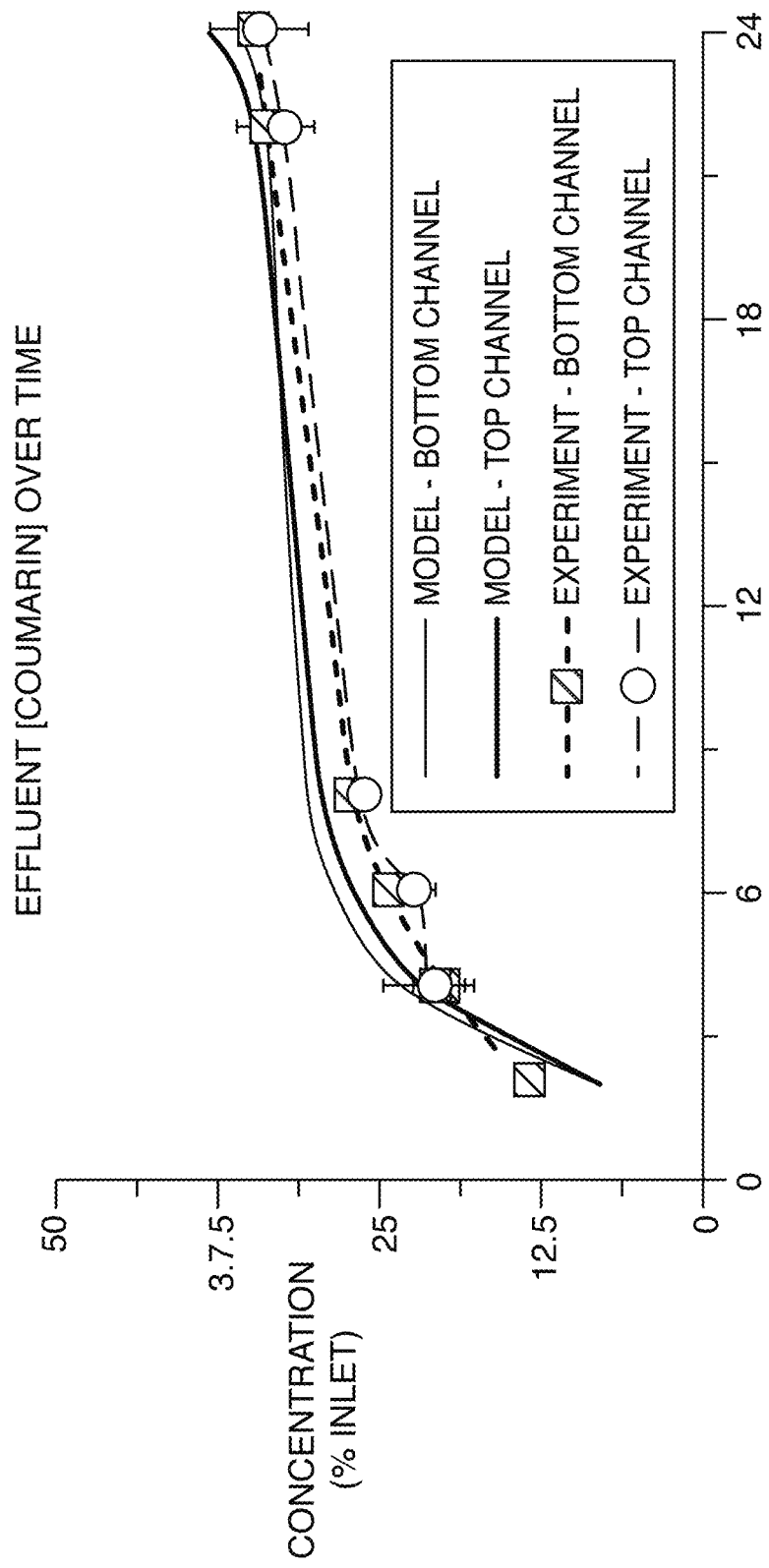
FIGS. 18A and 18B depict a comparison between computational model prediction of microfluidic device absorption and the results of experiments for the test compound Coumarin. Coumarin was flowed through a high-absorbing, gas-permeable microfluidic device fabricated out of PDMS and the recovered concentration in the bottom and top channels were sampled. The experiment was run at two different flow rates, 60 µL/hr as seen in FIG. 18A and 150 µL/hr as seen in FIG. 18B. These results were plotted vs the output of COMSOL models of the microfluidic device, as described above, with the measured material absorption parameters for Coumarin and the two flowrates flowrate as model inputs. The data and models are in good agreement.
Figure 18B:
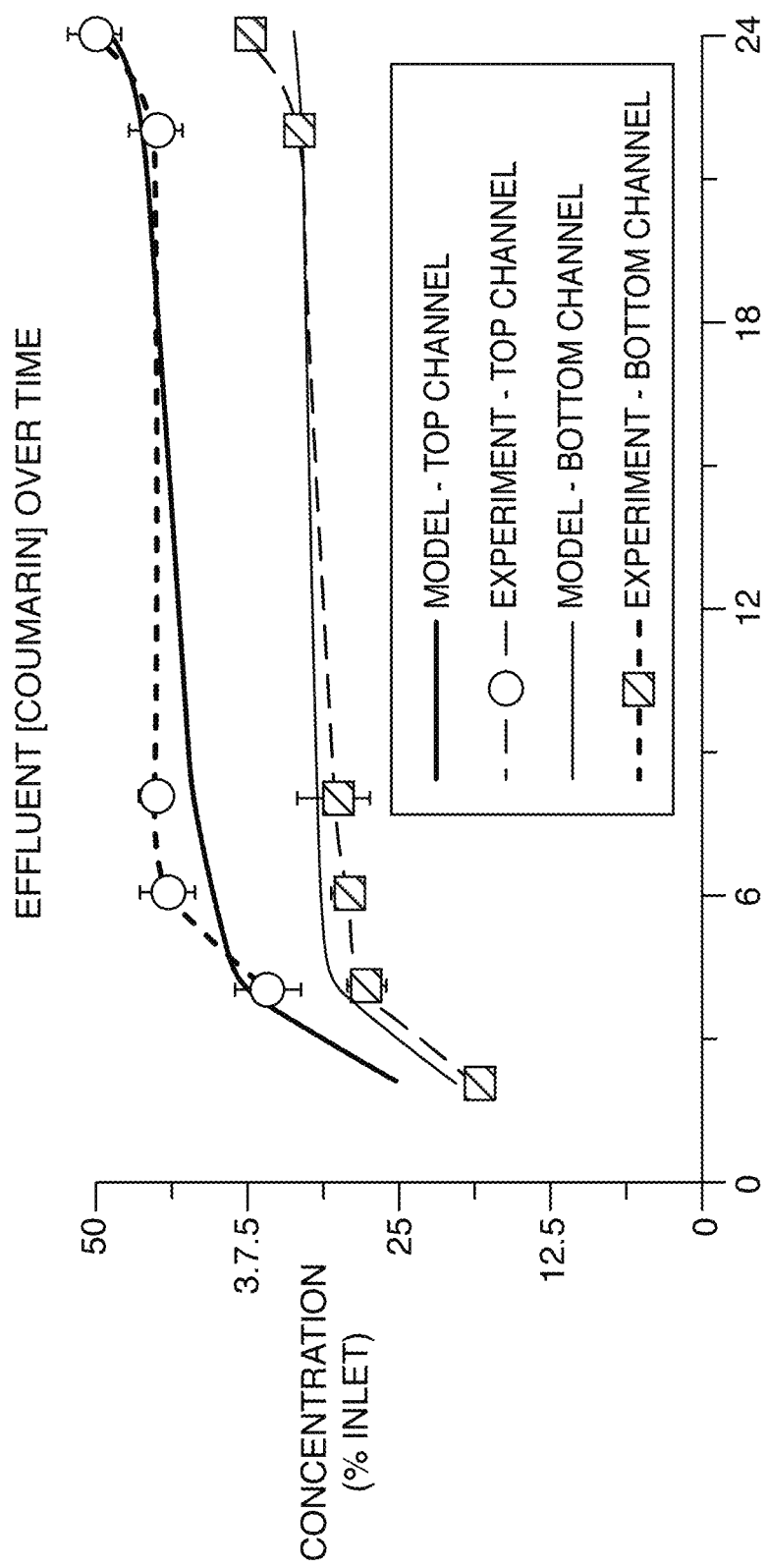

Absorption modeling to inform experimental design was tested using the compound Coumarin. Coumarin was flowed through an absorbing microfluidic device (13) and the recovered concentration in the bottom channel was sampled. The experiment was run at two different flow rates, 60 µL/hr as seen in FIG. 18A and 150 µL/hr as seen in FIG. 18B. The results of the experiment not only showed that less compound is absorbed into PDMS at faster flow rates, but also that the absorption modeling correctly hypothesized the results within a reasonable degree of error, validating the approach.

However, computational models are oftentimes not always enough. Computational models may not work at all, as some compounds absorb completely. Indeed, if models are used to correct data from an absorbing microfluidic device experiments (with cells), the models will not be able to account for total absorption. That is to say, if cells are exposed to a very low concentration of compound, even if we can predict this exposure level, it may be too low to be a useful correction. Regardless of the ability to correct data in only some situations, computational models also may require a complicated workflow. In order for computational modeling to work, absorption of every compound introduced into the system should be quantified first in material characterization studies. As well, running multiple computational models before every experiment to design the experiment to minimize absorption and then running an additional set of models to correct or account for absorption that did occur is not sustainable, especially for large scale experiments with many conditions. As well, computational models may not be able to accurately deconvolute data in cell-based experiments due to high numbers of variables, including those introduced by the cells. For example, concentration gradients due to absorption along the length of the absorbing microfluidic device and the fact that the concentration will also be changing with time makes concentration a "moving target." Even with the aid of computational models to account for many of these variables, in the presence of absorption there is still a decreased overall confidence in results in in vitro to in vivo extrapolation (IVIVE).

Figure 19:
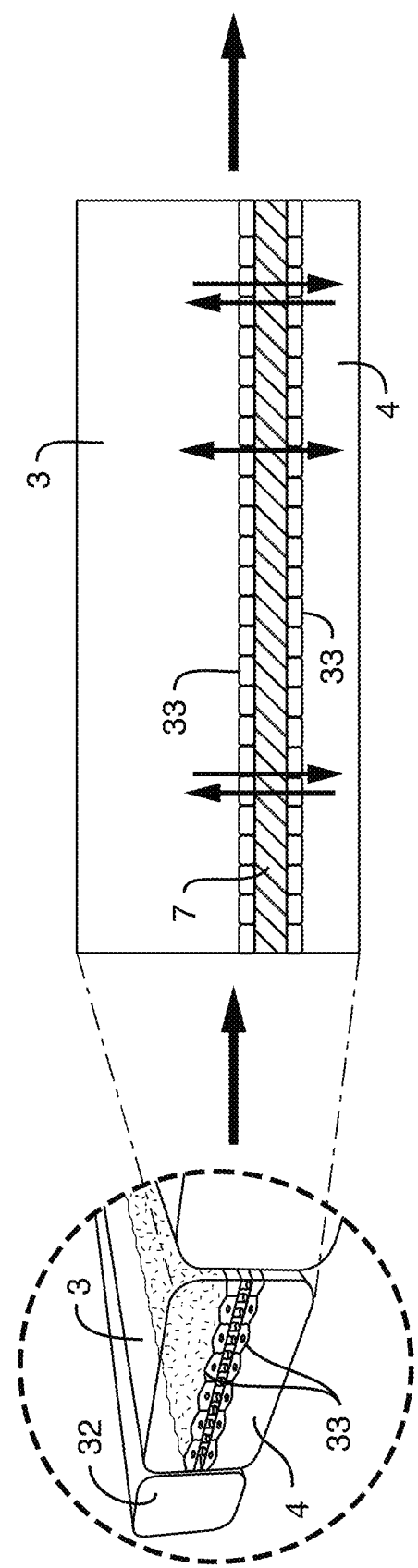
FIG. 19 depicts the complexity of modeling and understanding the dynamics of compound disposition in the interior of an absorbing microfluidic device, even in the absence of absorption. This includes biological/physiological factors such as passive cellular permeability, metabolism and transport across the membrane.

FIG. 19 depicts the complexity of modeling and understanding the dynamics of compound deposition in the interior of an absorbing microfluidic device (13) related just to cellular functions that change the concentration of a compound within the device. Indeed, even without the added complexity of absorption, the dynamics of such a microfluidic device are challenging to model because this may include biological/physiological factors such as passive cellular permeability, metabolism, and transport across the membrane.

FIG. 29A depicts an expected depletion model of the drug Diazepam in a plate culture calculated from in vivo drug clearance data versus actual data collected from a plate culture. FIG. 29B depicts an expected depletion model of the drug Diazepam in a microfluidic device when no absorption is present (theoretical) (12) compared to the results from a microfluidic device fabricated from an absorbing material—PDMS, and a low-absorbing microfluidic device (13) fabricated from COP. Both the COP microfluidic device (13) and the plate culture have depletion kinetics that are log-linear as would be expected, but only in the non-absorbing microfluidic device are the values close to those predicted by literature in vivo values. The results from the absorbing microfluidic device, fabricated out of PDMS, are not only off from those predicted from literature values, but the shape of the graph is not log-linear, as would be expected if metabolism was the only driver for compound loss. Indeed, the non-log-linear depletion of diazepam is a clear indication of another dynamic for compound loss, namely the material absorption that is known to occur. FIG. 30 shows the predicated clearance of Diazepam in vivo, on a plate, in an absorbing microfluidic device (12) fabricated from PDMS, and a low-absorbing, gas-impermeable microfluidic device (13) fabricated from COP. In summary, the plate culture underpredicts clearance, the absorbing microfluidic device overpredicts clearance, and the non-absorbing microfluidic device, here termed the "New Liver-Chip" accurately predicts intrinsic clearance.

Experimental outputs included concentration, C (µM) and time, t (minutes). Rate of reaction, $k_e$, was then calculated using the equation:

$$k_e = \frac{\ln\left(\frac{C_1}{C_2}\right)}{(t_2 - t_1)}$$

Chip clearance (CL), a measure of the ability of the microfluidic device to remove compound from the media passing through, was then calculated using the equation:

$$CL_{Media}$$

Intrinsic clearance ($CL_{int}$), the ability of an organ to remove compound from the blood passing through it, was then calculated using the equation:

$$CL_{int} = \frac{CL}{f_{u_{media}}} * \frac{\#Cells_{organ}}{\#Cells_{chip}} c$$

The governing equation for intrinsic clearance, which is consistent with methods previously published in literature for determination of clearance in an in vitro system, is then:

$$CL_{int} = \frac{\ln\left(\frac{C_1}{C_2}\right)}{(t_2 - t_1)} * V_{Media} * \frac{1}{fu_{media}} * \frac{\#Cells_{organ}}{\#Cells_{chip}}$$

Microfluidic device clearance was quantified as a function of the parent compound depletion. In vivo values were used for comparison to Diazepam hepatic intrinsic clearance or $CL_{int}$ values obtained from the two microfluidic device types. PDMS microfluidic device values were found to be artificially high due to absorption, which causes compound loss that is erroneously attributed to metabolism. As such, there was an overestimation of clearance in PDMS microfluidic devices. Plate culture values were significantly lower than in vivo values due to an underprediction of clearance.

FIG. 72 depicts a computational experiment wherein a solution containing the drug Midazolam was flowed through a high-absorbing, gas-permeable microfluidic device (12) fabricated from PDMS at 150 μL/hr for the short duration of a few hours. It may be seen in FIG. 72 that only the cells at the beginning of the channel see the Midazolam, as the PDMS rapidly absorbs the drug such that cells later in the channel are unable to interact with the drug. Further, it is more biologically relevant, and more cost effective to use lower media flow rates, such as 30 μL/hr. At these lower flow rates, even fewer cells would come into contact with the small molecule drug, as the media would be in contact with absorbing material at the beginning of the channel for longer periods of time, when compared to media at higher flow rates. Using microfluidic devices fabricated from absorbing materials, such as PDMS, could lead to an overestimation or underestimation of in vivo metabolism by as much as 100-fold depending on what is quantified to determine metabolism. If depletion of a compound is used to estimate metabolism, then metabolism would be overestimated. If quantification of a metabolite is used as a readout of metabolism, then metabolism would be underestimated. Further, it is difficult to know how much metabolism is being over or under estimated, as compound-material interactions and flow rates also play a part in the understanding of the metabolizing system. For midazolam specifically, for high flow rates, where metabolite quantification was used as a readout, there has been a consistent under-estimation of metabolism by anywhere between 10-fold and 100-fold, with greater under-estimation for lower flow rates. It is suggested that low-absorbing microfluidic devices would accurately estimate in vivo drug metabolism, assuming a rate of metabolism in the microfluidic device is similar to that seen at in vivo.

Figure 22:
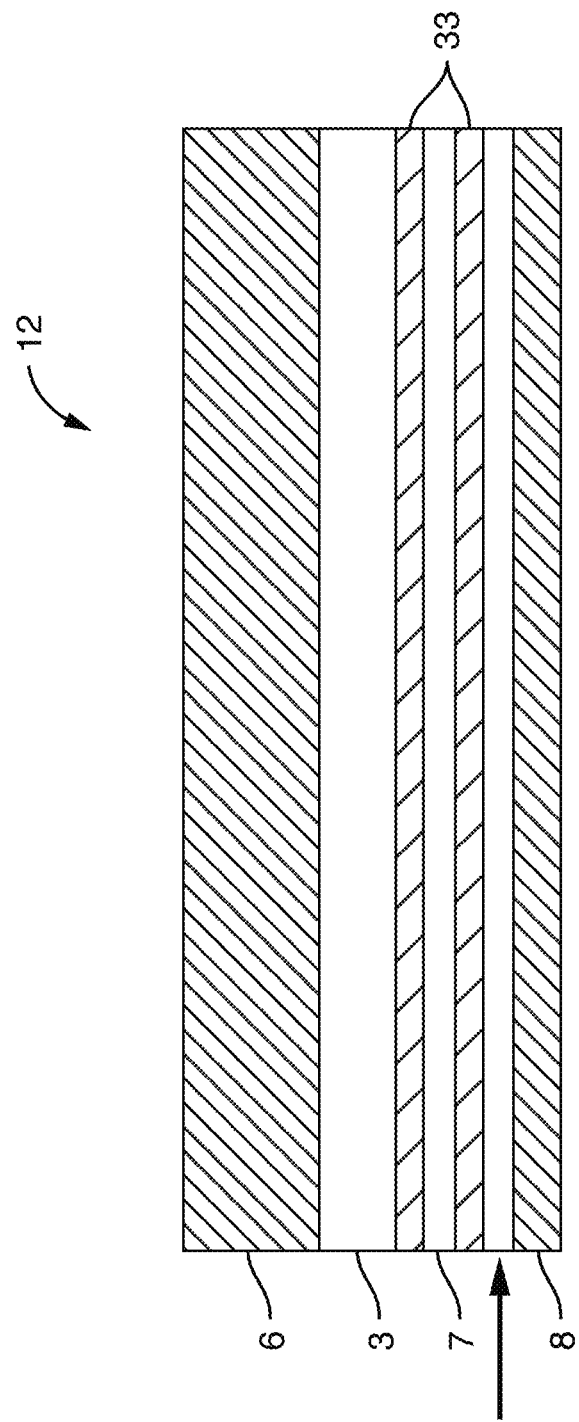
FIG. 22 shows a depiction of a 2D microfluidic device computational model for the use of running microfluidic device studies in silico, complete with the barrier created by the cell layer and cellular processes, like metabolism, included. These models can be used to design cell-based microfluidic device experiments based on material properties and expected rates of the cellular processes, including to design experiments to minimize the effects of absorption. When run in this manner, the models output the expected experimental result (e.g. microfluidic device effluent concentrations of a dosed compound). Conversely, the models can be run in some cases after experimental data is generated to "correct" for the contribution of compound loss due to absorption. For example, liver cell metabolism results in compound loss much like PDMS absorption causes compound loss. Given the intrinsic material properties, the amount of compound expected to be lost to PDMS absorption can be "subtracted out" from the total compound lost to both absorption and cellular metabolism in order to deduce the rate of cellular metabolism.
Figure 24:
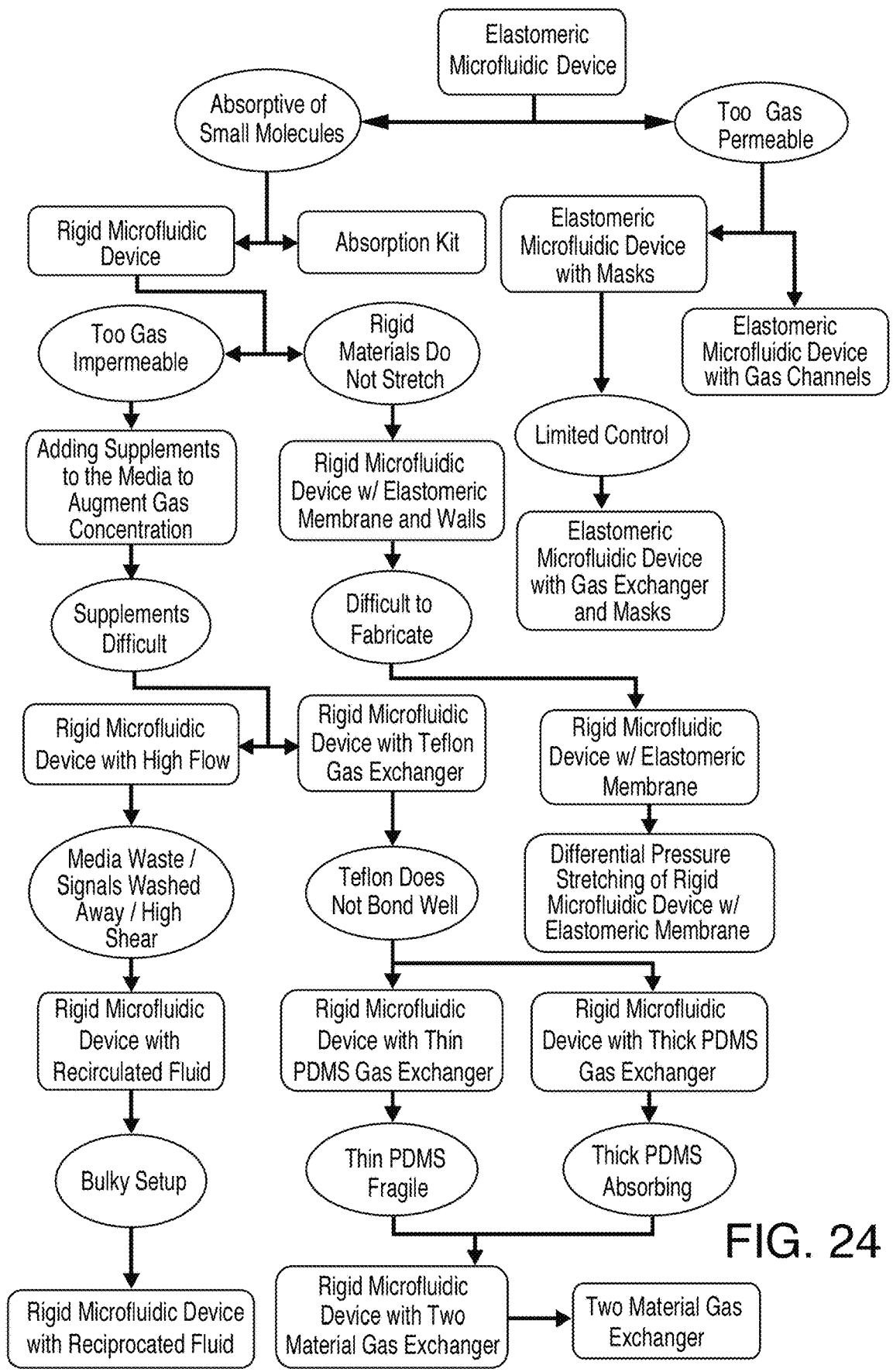
FIG. 24 shows a chart of different embodiments of the present invention and the problems that lead to their invention. The elastomeric microfluidic device, which is high-absorbing and gas-permeable, has been described in U.S. Pat. No. 8,647,861. It was noted that this microfluidic device fabricated from an elastomeric polymer (PDMS) was both highly gas-permeable and prone to absorption of small molecules or xenobiotics. In some instances, the microfluidic device was too gas-permeable. In other words, the body and channels of the microfluidic device were too susceptible to the gas concentration of the ambient environment due to the permeability of the elastomer. Resulting from that discovery two different embodiments were invented. The first was an elastomeric microfluidic device with gas channels running around working channels as shown in FIGS. 93 and 94. A gas, such as nitrogen, could be flowed through the gas channels in order to transport that gas into the working channels. Because the walls separating the gas channels from the working channels are highly gas-permeable, the gas channels act to set the oxygen concentration of both the bulk of the microfluidic device; the channels could be depleted of oxygen, by flowing nitrogen through the gas channels, for example, or any other gas for that matter. Alternatively, the gas channels may also, in one embodiment, work towards introducing more oxygen into the microfluidic device, such that the concentration of oxygen in the microfluidic device is higher than the ambient environment. The second embodiment resulting from the high permeability of the elastomeric, high-absorbing, gas-permeable microfluidic device was to contact the outside surfaces of the microfluidic device with a thin film or mask of rigid or gas-impermeable polymer in order to limit gas transport through the bulk of the microfluidic device. Resulting from the discovery that the microfluidic device of U.S. Pat. No. 8,647,861 was highly prone to absorption of small molecules an embodiment of a low-absorbing, gas-impermeable microfluidic device was fabricated from rigid materials. It was then discovered that the low-absorbing, gas-impermeable microfluidic device was too gas-impermeable for some experiments. One embodiment to overcome the gas-impermeability was to add supplements to the media or fluid, such as to augment (e.g. increase) the gas carrying capacity of the media or fluid. It was found, however, that these supplements are sometimes difficult to work with. Another embodiment to overcome the gas-impermeability was to flow fluids or media at high flow rates in order to introduce a higher concentration of dissolved oxygen into the channels of the microfluidic device. Unfortunately, there are some disadvantages to high flow rates including fluid or media waste. In the cases that cells are cultured in the microfluidic device, important cellular signals can be washed away. Further, higher flow rates result in higher levels of shear which may not always be favorable. In order to overcome these disadvantages, fluid or media may be recirculated. Sometimes, though, recirculation setups can be bulky and require equipment that is difficult to use. In those cases, fluid may be reciprocated, or flowed back and forth through the device. Reciprocation is non-obvious in the case of studying cells in vitro as fluid in vivo does not flow two ways. A surprising discovery was that cells in vitro displayed high levels of viability and organ-specific function with reciprocated media. Finally, another solution to the gas-impermeability of rigid microfluidic devices was to introduce a gas exchanger to the microfluidic device. In one embodiment, the gas exchanger could be built from a material such as Teflon (PTFE). However, materials such as Teflon are oftentimes difficult to bond or are not transparent. In one embodiment, the gas exchanger comprises a thin piece of polydimethylsiloxane (PDMS). However, thin pieces of PDMS are oftentimes fragile. In one embodiment, the gas exchanger comprises a thick piece of PDMS. However, thick pieces of PDMS are oftentimes absorbing. In one embodiment, a gas exchanger can comprise a gas-impermeable substrate with gas-permeable regions, or pores. The gas-impermeable material may be a rigid polymer. The gas-permeable material may be an elastomeric polymer. It is believed that gas-impermeable substrate with gas-permeable regions is itself a novel embodiment for use with any fluidic device. Finally, another embodiment to solve the problem the elastomeric, high-absorbing, gas-permeable microfluidic device of U.S. Pat. No. 8,647,861 is to both encapsulate one or more channels of said microfluidic device with said gas exchanger, and also put thin films or masks of rigid polymer in contact with said outside portions of said microfluidic device that are not the gas exchanger in order to limit gas transport from the ambient environment into the microfluidic device.

FIG. 22 depicts the COMSOL computational model of the absorbing microfluidic device (12).

A two-dimensional computational model was created that represented an absorbing microfluidic device (13), fabricated from PDMS and containing two cell layers (33). The microfluidic device comprised a top channel (3), a bottom channel (4), and a membrane (7) separating at least a portion of said top channel (3) and bottom channel (4). A representative small molecule compound was dosed only in the bottom channel (4). Absorption is minimized when the bottom channel (4) is dosed instead of the top channel (3), as the PDMS bulk on the bottom channel layer (8) is thinner than the PDMS bulk on the top channel layer (6). As there is less PDMS on the bottom channel layer (8), there is less volume for small molecule compounds to absorb into.

After computational models of the microfluidic devices discussed herein were created and analyzed, physical laboratory experiments were conducted in order to assess absorption in to microfluidic devices comprising cell layers.

Figure 28A:
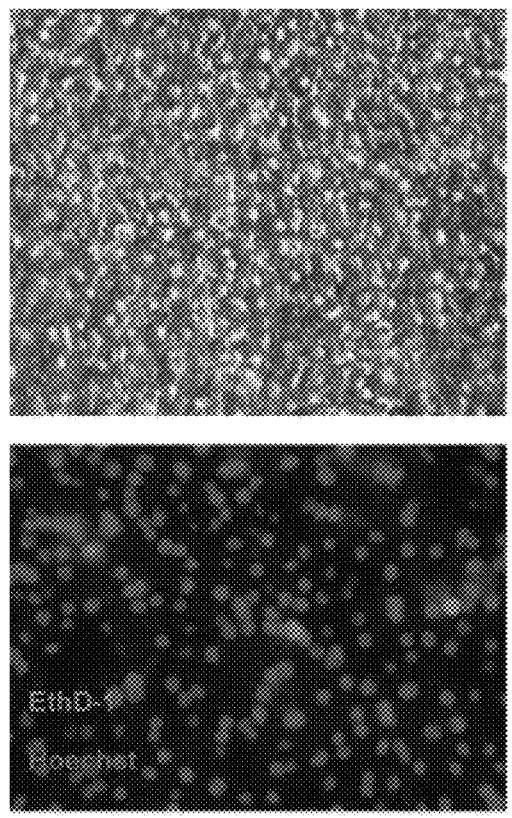
FIGS. 28A and 28B show results from an experiment wherein liver cells were seeded in a low-absorbing, gas-impermeable microfluidic device fabricated from COP.
Figure 28B:
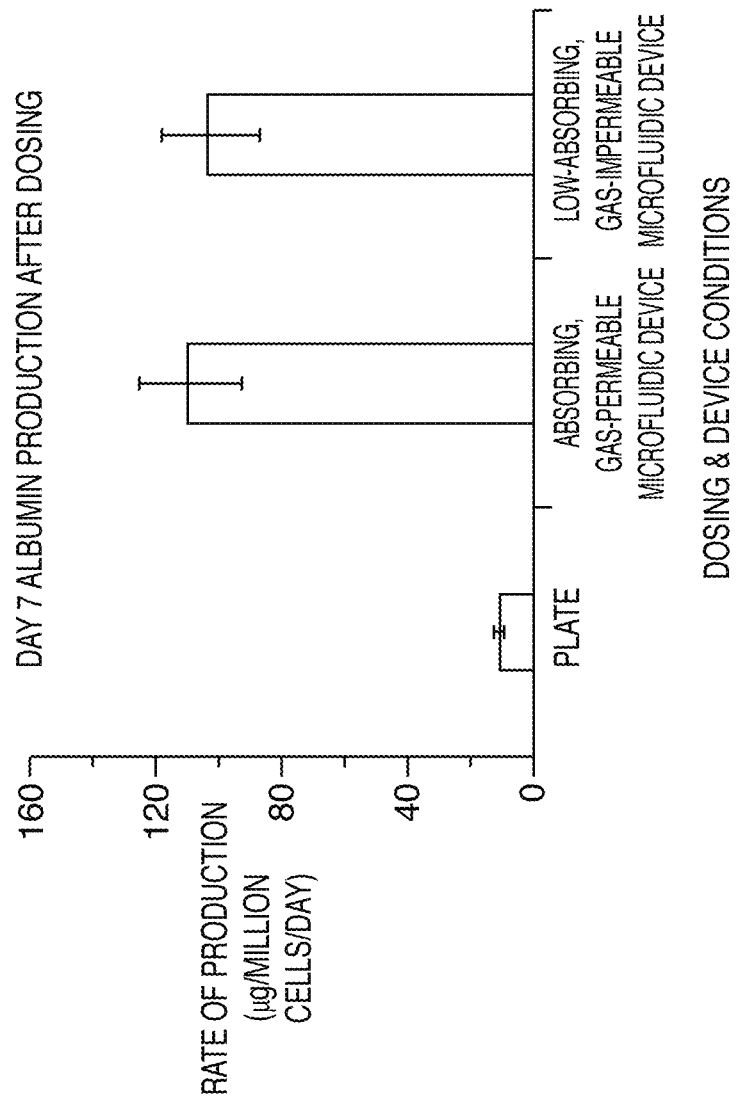

A low-absorbing, gas-impermeable microfluidic device (13) fabricated from COP, an absorbing microfluidic device (12) fabricated from PDMS and a cell culture plate were seeded with various liver cells, including hepatocytes, in order to assess liver cell viability and function. FIG. 28A depicts liver cells in a low-absorbing, gas-impermeable microfluidic device (13) fabricated from COP on day 7 of culture. FIG. 28B shows comparable albumin production in the liver cells in both the low-absorbing, gas-impermeable microfluidic device (13) fabricated from COP and the high-absorbing, gas-permeable microfluidic device (12) fabricated from PDMS. Albumin production in the plate culture was significantly lower than in both of the microfluidic devices. Protocols to increase oxygen delivery to hepatocytes were used in order to create the data shown in FIG. 28B. One such protocol includes increasing the flowrate entering the microfluidic devices.

Experiments were also run to assess whether high flow rates in the top and/or bottom channels of the microfluidic device impact absorption into the bulk material of the microfluidic device. Four conditions of microfluidic devices were seeded with two types of human liver cells, Hepatocytes and LSEC, and delivered oxygen through higher flow rates in the bottom or basal channel. Oxygen delivery to cells layers (33) in microfluidic devices is of great importance, as the cell layers (33) oftentimes demand a particular oxygen concentration or rate of delivery in order to survive and/or function. In some embodiments, cell layers (33) may need high levels of oxygen. In other embodiments, cell layers (33) may need very low levels of oxygen. The microfluidic devices tested include: five low-absorbing, gas-impermeable microfluidic devices (13) fabricated from COP with top channel flow rates of 0 μL/hr and bottom channel (4) flow rates of 300 μL/hr; five low-absorbing, gas-impermeable microfluidic devices (13) fabricated from COP with top channel (3) flow rates of 10 μL/hr and bottom channel (4) flow rates of 300 μL/hr; five absorbing, gas-permeable microfluidic devices (12) fabricated from PDMS with top channel (3) flow rates of 10 μL/hr and bottom channel (4) flow rates of 30 μL/hr; and five high-absorbing, gas-permeable microfluidic devices (12) fabricated from PDMS with top channel (3) flow rates of 10 μL/hr and bottom channel (4) flow rates of 300 μL/hr. All microfluidic devices had human hepatocytes seeded in the top channel (3) and human LSECs seeded in the bottom channel (4). All microfluidic devices were run on syringe pumps as opposed to culture modules. One question to be answered by the experiments was whether the microfluidic devices supported liver cell viability and function. Experiment readouts included phase imaging, albumin production, CYP540 production and RNA endpoint analysis.

FIGS. 55A, 55B and 55C show hepatocyte attachment and morphology in both a low-absorbing, gas-impermeable microfluidic device (13) fabricated from COP and a high-absorbing, gas-permeable microfluidic device (12) fabricated from PDMS on day 1, day 2 and day 3 of cell layer (33) growth. FIG. 55A shows hepatocyte attachment and morphology in a low-absorbing, gas-impermeable microfluidic device (13) fabricated from COP on day 1. FIG. 55B shows hepatocyte attachment and morphology in a low-absorbing, gas-impermeable microfluidic device (13) fabricated from COP on day 2. FIG. 55C shows hepatocyte attachment and morphology in a low-absorbing, gas-impermeable microfluidic device (13) fabricated from COP on day 3. FIG. 56A shows hepatocyte attachment and morphology in a high-absorbing, gas-permeable microfluidic device (12) fabricated from PDMS on day 1. FIG. 56B shows hepatocyte attachment and morphology in a high-absorbing, gas-permeable microfluidic device (12) fabricated from PDMS on day 2. FIG. 56C shows hepatocyte attachment and morphology in a high-absorbing, gas-permeable microfluidic device (12) fabricated from PDMS on day 3. On days 1, 2, and 3 hepatocyte attachment and morphology were similar in both microfluidic device designs.

FIGS. 57A and 57B show hepatocyte and LSEC morphologies on day 9 in a high-absorbing, gas-permeable microfluidic device (12) fabricated from PDMS. FIG. 57A shows hepatocyte morphology on day 9 in a high-absorbing microfluidic device (12) fabricated from PDMS. FIG. 57B shows LSEC morphology on day 9 in a high-absorbing microfluidic device (12) fabricated from PDMS. FIGS. 58A and 58B show hepatocyte and LSEC morphologies on day 9 in a low-absorbing, gas-impermeable microfluidic device (13) fabricated from COP. FIG. 58A shows hepatocyte morphology on day 9 in a low-absorbing, gas-impermeable microfluidic device (13) fabricated from COP. FIG. 58B shows LSEC morphology on day 9 in a low-absorbing, gas-impermeable microfluidic device (13) fabricated from COP. Both hepatocytes and LSECs showed comparable morphologies and maintained monolayers in both the low-absorbing, gas-impermeable microfluidic device (13) and the high-absorbing, gas-permeable microfluidic device (12) on day 9.

The portion of the experiment demonstrates a low-absorbing, gas-impermeable microfluidic device (13) can maintain the human liver cell morphology, while still offering low-absorbency. Low-absorbency is advantageous as it does not negatively impact small molecule studies as do high-absorbency microfluidic devices (12).

FIGS. 59A and 59B show bile canaliculi fluorescence staining via MRP2 at day 9 of cell layer (33) culture on two different microfluidic devices. FIG. 59A shows bile canaliculi fluorescence staining via MRP2 on a high-absorbing, gas-permeable microfluidic device (12) fabricated from PDMS using a 20× microscope objective on day 9 of cell layer (33) culture. FIG. 59B shows bile canaliculi fluorescence staining via MRP2 on a high-absorbing, gas-permeable microfluidic device (13) fabricated from COP using a 20× microscope objective on day 9 of cell layer (33) culture. There was similar development of bile canaliculi in both the microfluidic devices fabricated from PDMS and COP, although neither was ideal. Ideal cell layers (33) would show interconnected networks.

Figure 60:
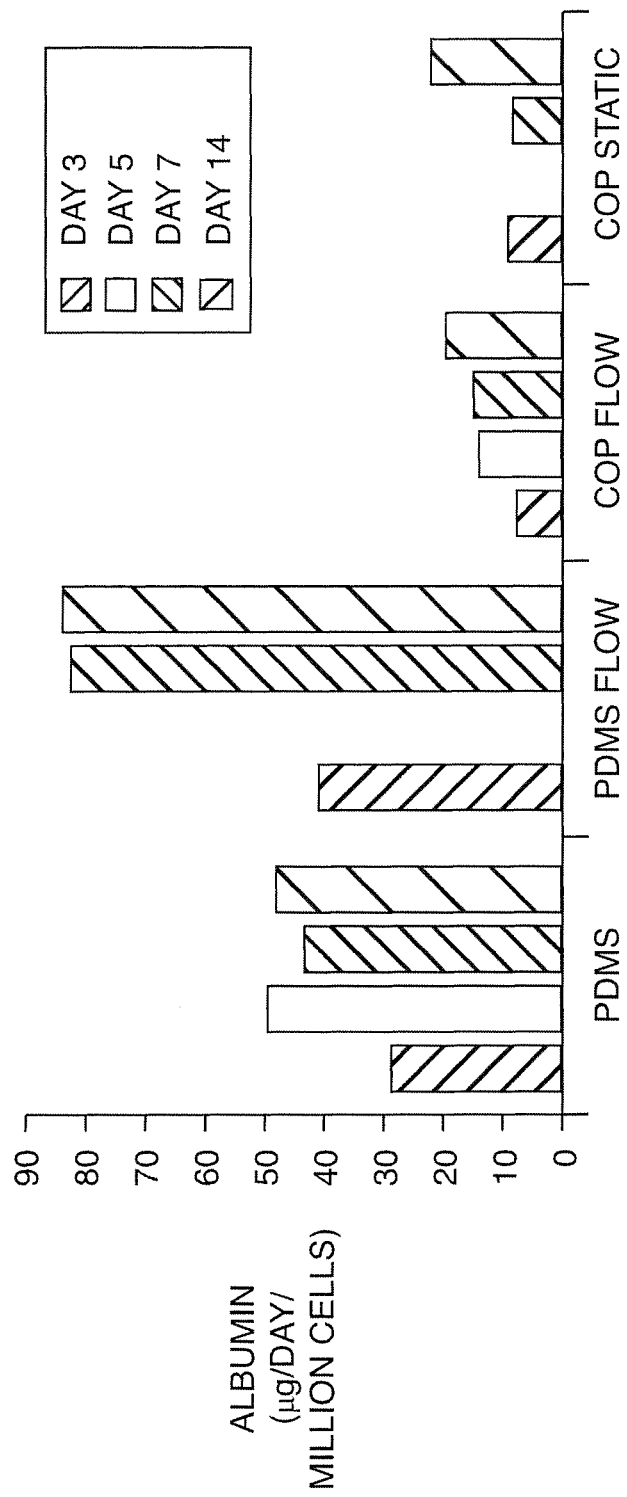
FIG. 60 depicts an overview of albumin production across four conditions. The microfluidic devices tested include: five low-absorbing, gas-impermeable microfluidic devices fabricated from COP with top channel flow rates of 0 µL/hr and bottom channel flow rates of 300 µL/hr; five low-absorbing, gas-impermeable microfluidic devices fabricated from COP with top channel flow rates of 10 µL/hr and bottom channel flow rates of 300 µL/hr; five absorbing, gas-permeable microfluidic devices fabricated from PDMS with top channel flow rates of 10 µL/hr and bottom channel flow rates of 30 µL/hr; and five high-absorbing, gas-permeable microfluidic devices fabricated from PDMS with top channel flow rates of 10 µL/hr and bottom channel flow rates of 300 µL/hr.

FIG. 60 depicts an overview of albumin production across the four conditions. The microfluidic devices tested include: five low-absorbing, gas-impermeable microfluidic devices (13) fabricated from COP with top channel flow rates of 0 µL/hr and bottom channel (4) flow rates of 300 µL/hr; five low-absorbing, gas-impermeable microfluidic devices (13) fabricated from COP with top channel (3) flow rates of 10 µL/hr and bottom channel (4) flow rates of 300 µL/hr; five absorbing, gas-permeable microfluidic devices (12) fabricated from PDMS with top channel (3) flow rates of 10 µL/hr and bottom channel (4) flow rates of 30 µL/hr; and five high-absorbing, gas-permeable microfluidic devices (12) fabricated from PDMS with top channel (3) flow rates of 10 µL/hr and bottom channel (4) flow rates of 300 Albumin levels significantly decreased in low-absorbing, gas-impermeable microfluidic devices (13) fabricated from COP. The microfluidic devices without flow suffered from lack of oxygen and non-physiologically relevant pHs due to failure to properly buffer media by exposing the media with sodium bicarbonate with the gas $CO_2$.

Figure 61:
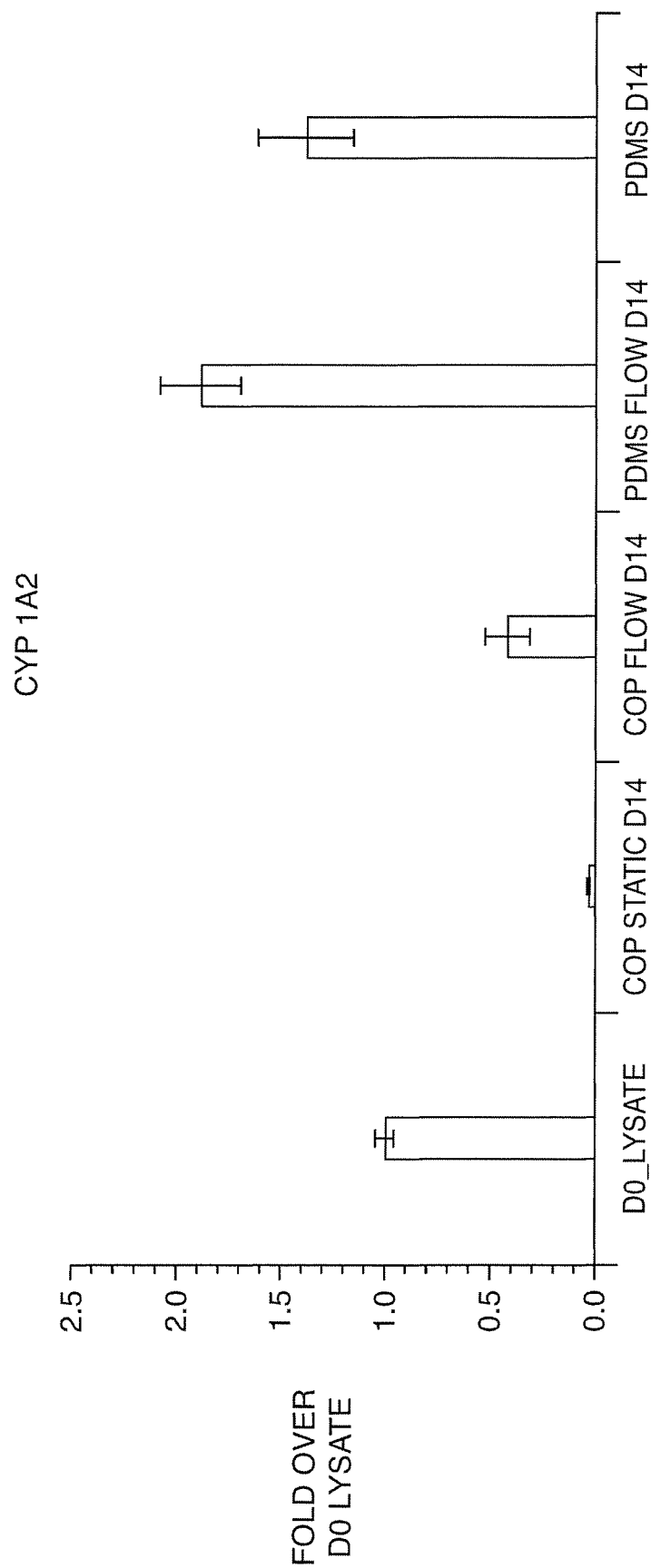
FIG. 61 shows CYP1A2 levels at day 14 following lysing of the microfluidic devices shown in FIG. 60.

FIG. 61 shows CYP1A2 enzyme levels on day 14 following lysing of the microfluidic devices. The high-absorbing, gas-permeable microfluidic devices (12) fabricated from PDMS showed higher levels of CYP1A2 than the low-absorbing, gas-impermeable microfluidic devices (13) fabricated from COP. The low-absorbing, gas-impermeable microfluidic devices (13) fabricated from COP lack much of the metabolic function seen in the high-absorbing, gas-permeable microfluidic devices (12) fabricated from PDMS.

Figure 62:
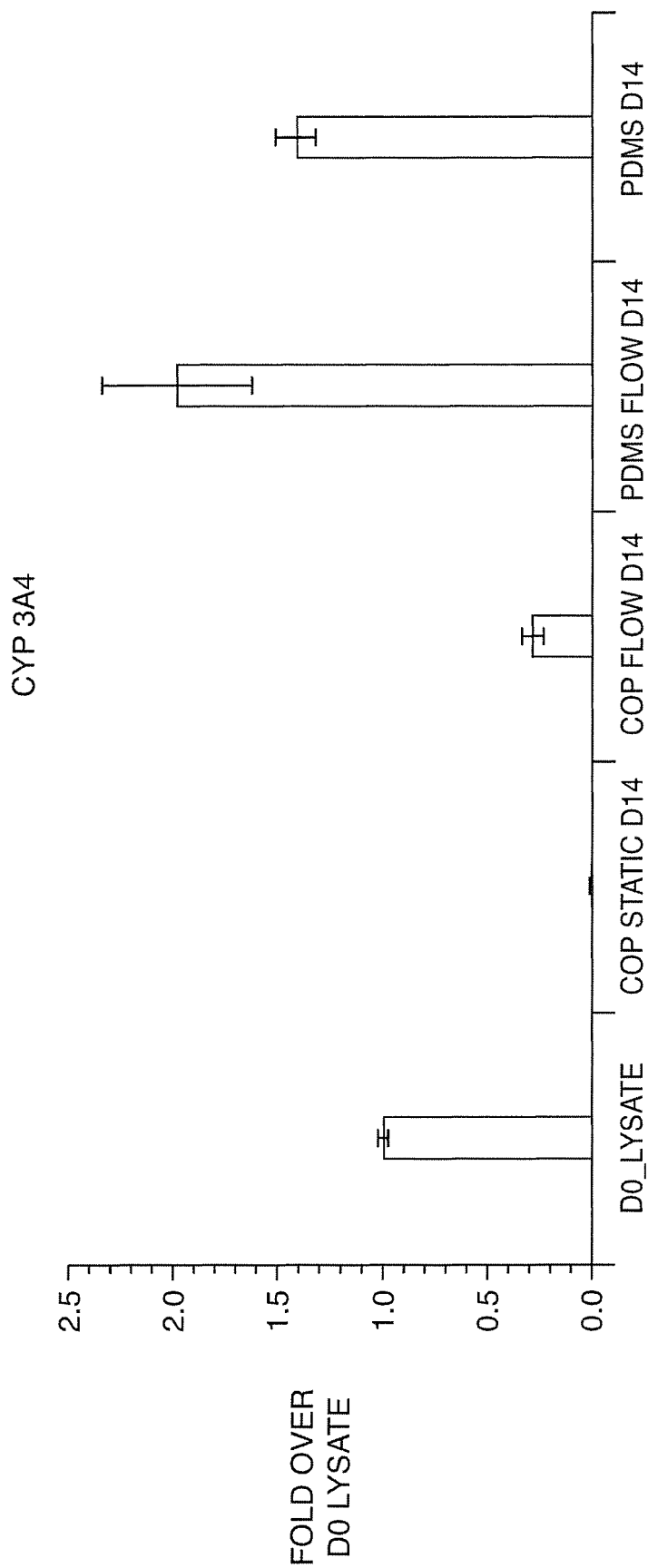
FIG. 62 shows CYP3A4 levels at day 14 following lysing of the microfluidic devices shown in FIG. 60.

FIG. 62 shows CYP3A4 levels at day 14 following lysing of the microfluidic devices. The high-absorbing, gas-permeable microfluidic devices (12) fabricated from PDMS showed higher levels of CYP3A4 than the low-absorbing, gas-impermeable microfluidic devices (13) fabricated from COP. The low-absorbing, gas-impermeable microfluidic devices (13) fabricated from COP lack much of the metabolic function seen in the high-absorbing, gas-permeable microfluidic devices (12) fabricated from PDMS.

Figure 63:
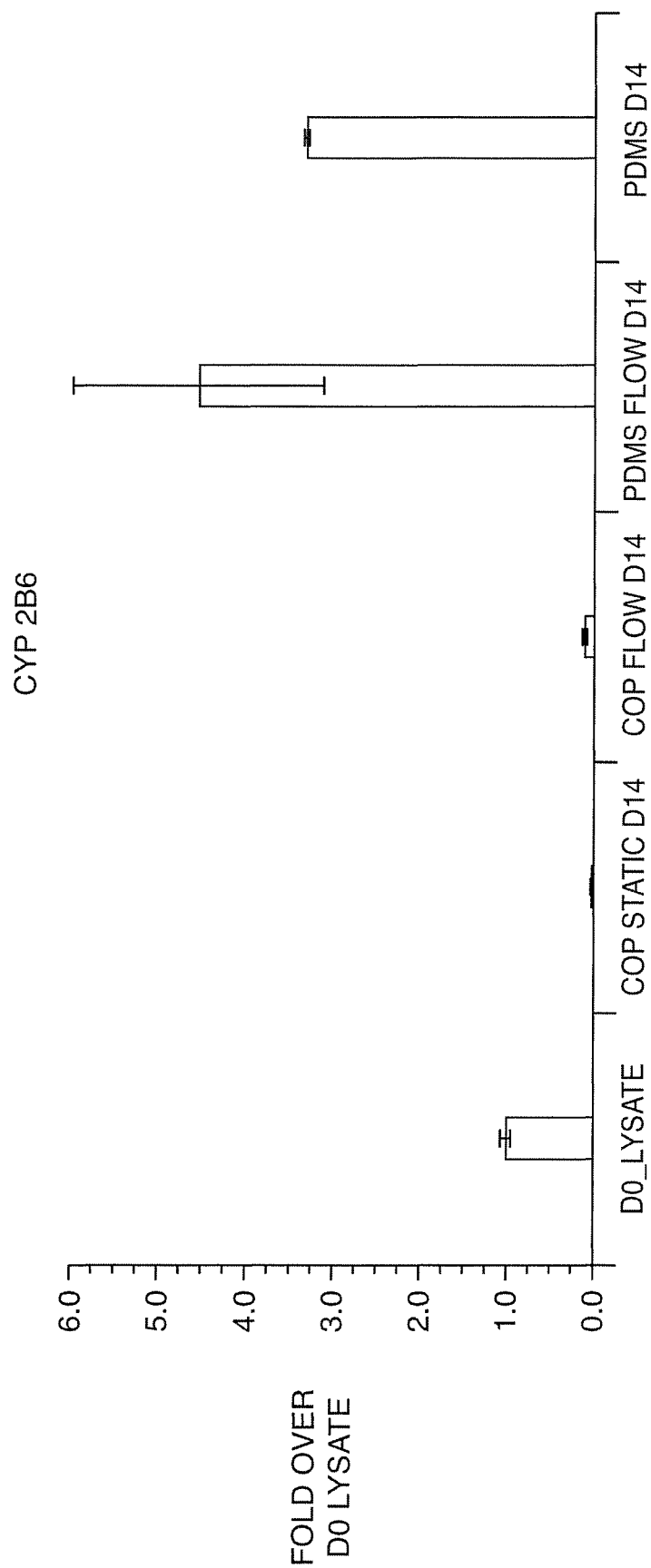
FIG. 63 shows CYP2A6 levels at day 14 following lysing of the microfluidic devices shown in FIG. 60.

FIG. 63 shows CYP2A6 levels at day 14 following lysing of the microfluidic devices. The high-absorbing, gas-permeable microfluidic devices (12) fabricated from PDMS showed higher levels of CYP2A6 than the low-absorbing, gas-impermeable microfluidic devices (13) fabricated from COP. The low-absorbing, gas-impermeable microfluidic devices (13) fabricated from COP lack much of the metabolic function seen in the high-absorbing, gas-permeable microfluidic devices (12) fabricated from PDMS.

Seventeen microfluidic devices of various conditions where seeded with human liver cells in order to assess the effect of higher flowrates in the apical or top channel (3). The microfluidic devices comprised: three low-absorbing, gas-impermeable microfluidic devices fabricated from COP with media equilibrated with 100% oxygen (i.e. 100 kPa, no $CO_2$ equilibration, with a 150 µL/hr flow rate in the top channel and a 150 µL/hr flow rate in the bottom channel being run on a culture module; three low-absorbing, gas-impermeable microfluidic devices fabricated from COP, with 21% oxygen media equilibration and 5% carbon dioxide, a 150 µL/hr flow rate in the top channel and a 150 µL/hr flow rate in the bottom channel being run on a culture module; three low-absorbing, gas-impermeable microfluidic devices fabricated from COP, with media equilibrated to 21% oxygen and 5% carbon dioxide, a 150 µL/hr flow rate in the top channel and a 150 µL/hr flow rate in the bottom channel, and additionally having 15 mM HEPES in the media to pH buffer the media, being run on a culture module; low-absorbing, gas-impermeable microfluidic devices fabricated from COP, with media equilibrated to 21% oxygen and 5% carbon dioxide, at a 300 µL/hr flow rate in the top channel and a 300 µL/hr flow rate in the bottom channel being run on a syringe pump; two high-absorbing, gas-permeable microfluidic devices fabricated from COP, with media equilibrated to 21% oxygen and 5% carbon dioxide, with a 300 µL/hr flow rate in the top channel and a 300 µL/hr flow rate in the bottom channel being run on a syringe pump; and two high-absorbing, gas-permeable microfluidic devices, fabricated from COP, with media equilibrated with 21% oxygen and 5% carbon dioxide, with a 30 µL/hr flow rate in the top channel and a 30 µL/hr flow rate in the bottom channel being run on a culture module. FIG. 64 shows an experimental matrix in which all the experimental conditions for an optimization study aimed at sustaining viability and function of liver cells in microfluidic devices may be seen.

Figure 65:
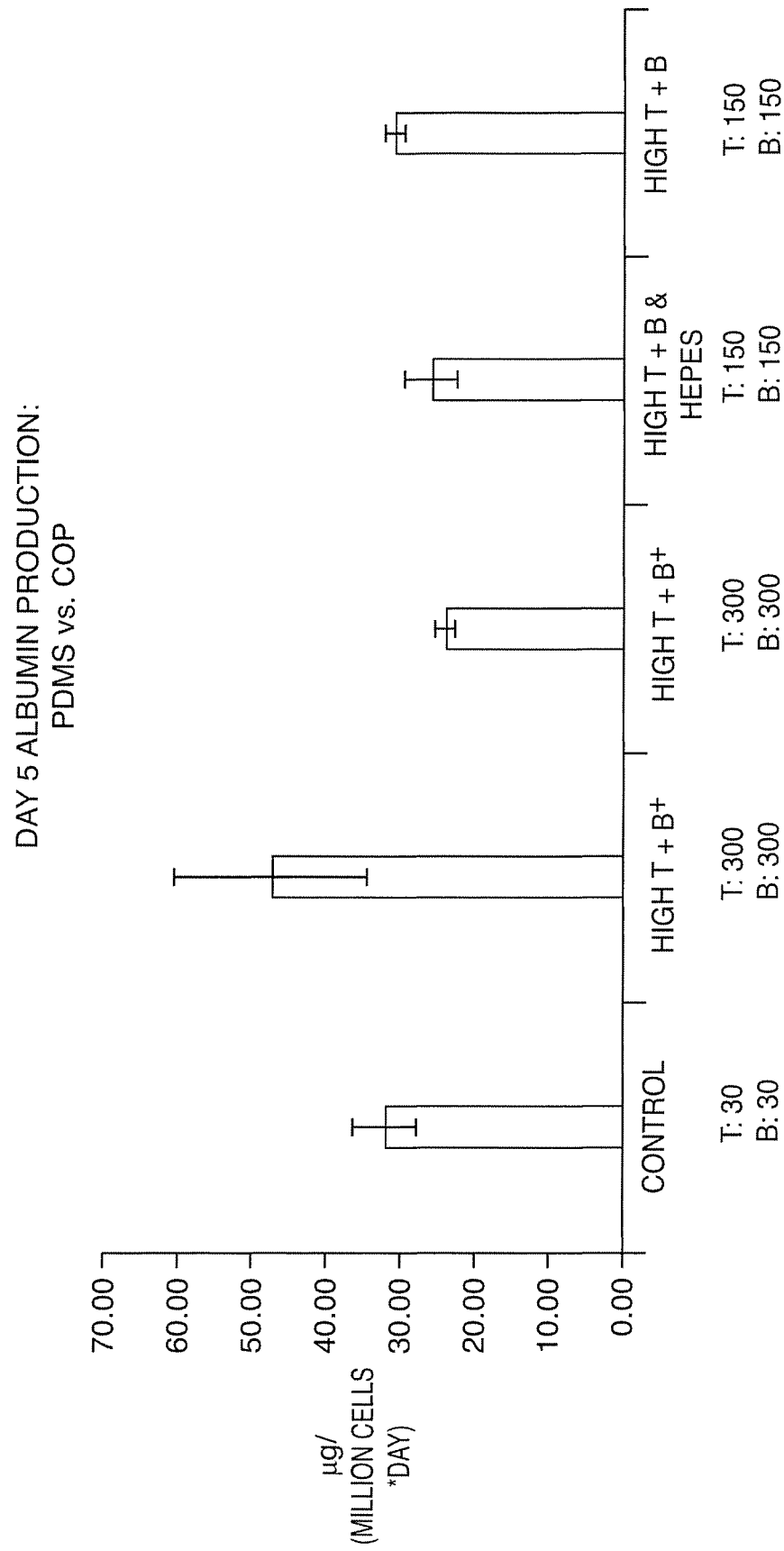
FIG. 65 depicts albumin production at each condition shown in FIG. 64.

In total seventeen microfluidic devices, three culture modules and one syringe pump were used. Three medias were used: WEM(-) 2% FBS; WEM(-) 2% FBS with 15 mM HEPES; and CSC 2% FBS. HEPES was tested in order to evaluate its cytotoxicity. The goal of the experiment was to test cell functionality as a reflection of oxygen perfusion within the microfluidic devices. Timepoint analysis included bright field imaging, albumin secretion analysis, LDH secretion analysis, and CYP450 analysis. FIG. 65 shows albumin production at each condition shown in FIG. 64. The graph shows that there was an improvement in the albumin production in the low-absorbing, gas-impermeable microfluidic device (13) fabricated from COP when there was a higher flow rate in both the top channel (3) and bottom channel (4) as compared to when the higher flow rate was solely in the bottom channel (4). Albumin production was about the same in the low-absorbing, gas-impermeable microfluidic device (13) fabricated from COP with top channel (3) and bottom channel (4) flow rates of 150 µL/hr as in the high-absorbing, gas-permeable microfluidic device (12) fabricated from PDMS with top channel (3) and bottom channel (4) flow rates of 30 µL/hr.

Figure 16:
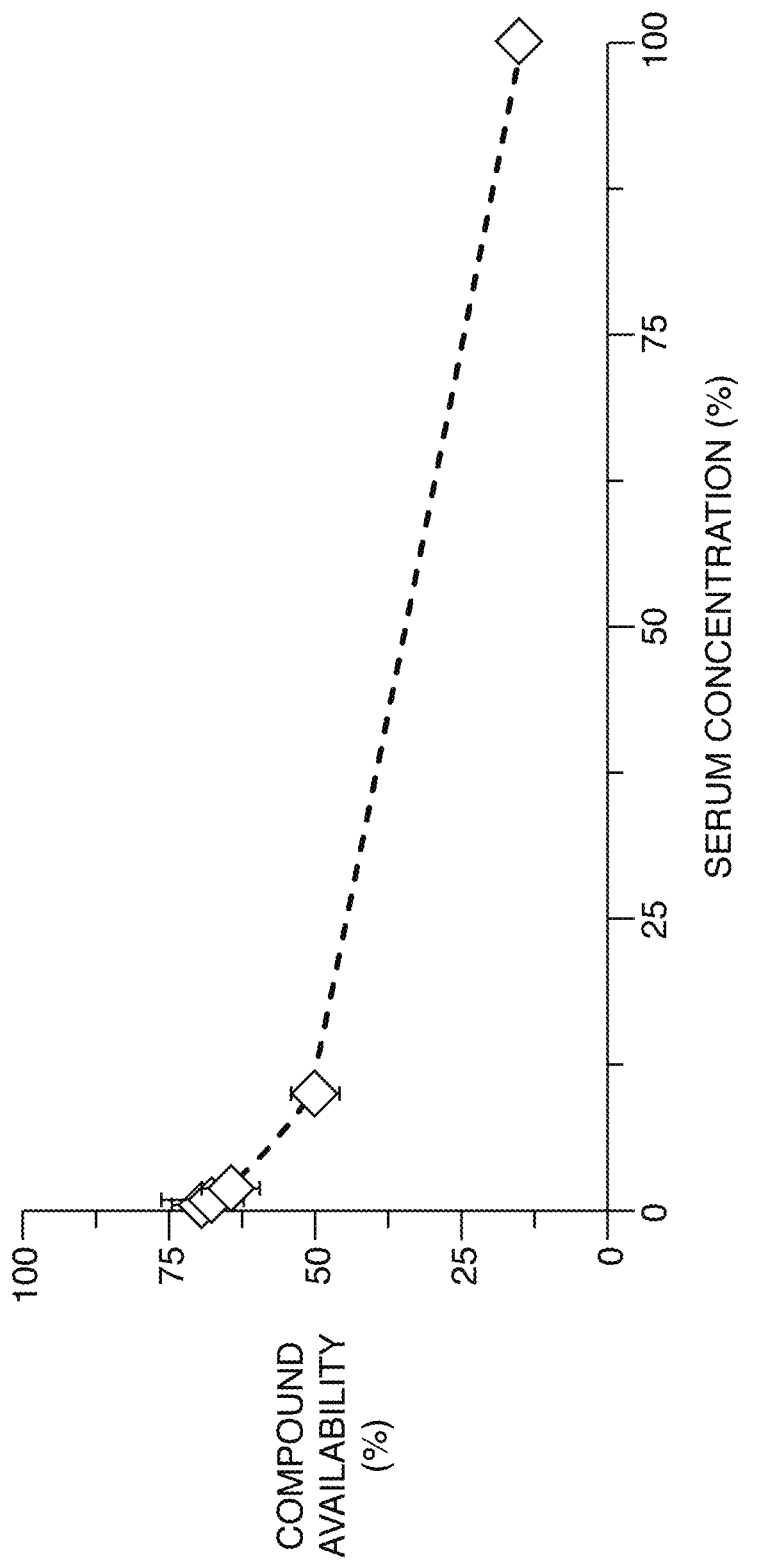
FIG. 16 depicts protein binding or "loss" of compound to proteins suspended in the cell culture media. As more protein is added to the media, in this case in the form of increasing concentrations of fetal bovine serum (FBS), there is additional loss of compound.

Protein binding in an absorbent microfluidic device (12) fabricated from PDMS seeded with liver cells was also quantified for different concentrations of fetal bovine serum (FBS). Not only do compounds absorb into materials, but proteins within the media may also bind to the compound causing effective compound loss, since the compound is carried past the cells and they are not exposed to the compound. Diazepam was used as the small molecule compound in these experiments. FIG. 16 depicts the results of the experiment. The higher the concentration of the FBS, the lower the compound availability to the cells due to protein binding. The experiment is important for establishing available fraction of compound concentration for absorption in absorption experiments, but also the fraction of compound available to cells, even without absorption causing additional "loss". Rapid Equilibrium Dialysis (RED) Devices were used to characterize binding. For media with 1% FBS, the compound availability of Diazepam was 67%. Protein binding data was used to convert the rate of metabolism to intrinsic clearance as seen in the equations above.

Figure 66A:
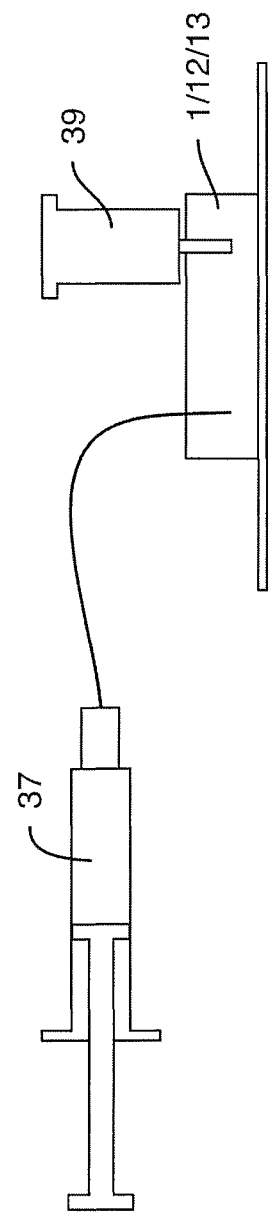
FIGS. 66A, 66B and 66C show an experimental setup for reciprocation of media. The setup involves pumping media through a low-absorbing, gas-impermeable microfluidic device fabricated from COP or a high-absorbing, gas-permeable microfluidic device using a syringe pump. The media collects in an external reservoir that is connected to the outlet port. Because this reservoir is "open" to the external environment, the media is able to equilibrate to the ambient oxygen concentration in the air. If the cells in the device have depleted the oxygen in the media, oxygen will quickly diffuse into the media to re-saturate with dissolved oxygen. Once most of the media has been pumped out of the syringe, the syringe pump reverses direction and begins to pump media from the external reservoir back into the syringe.
Figure 66B:
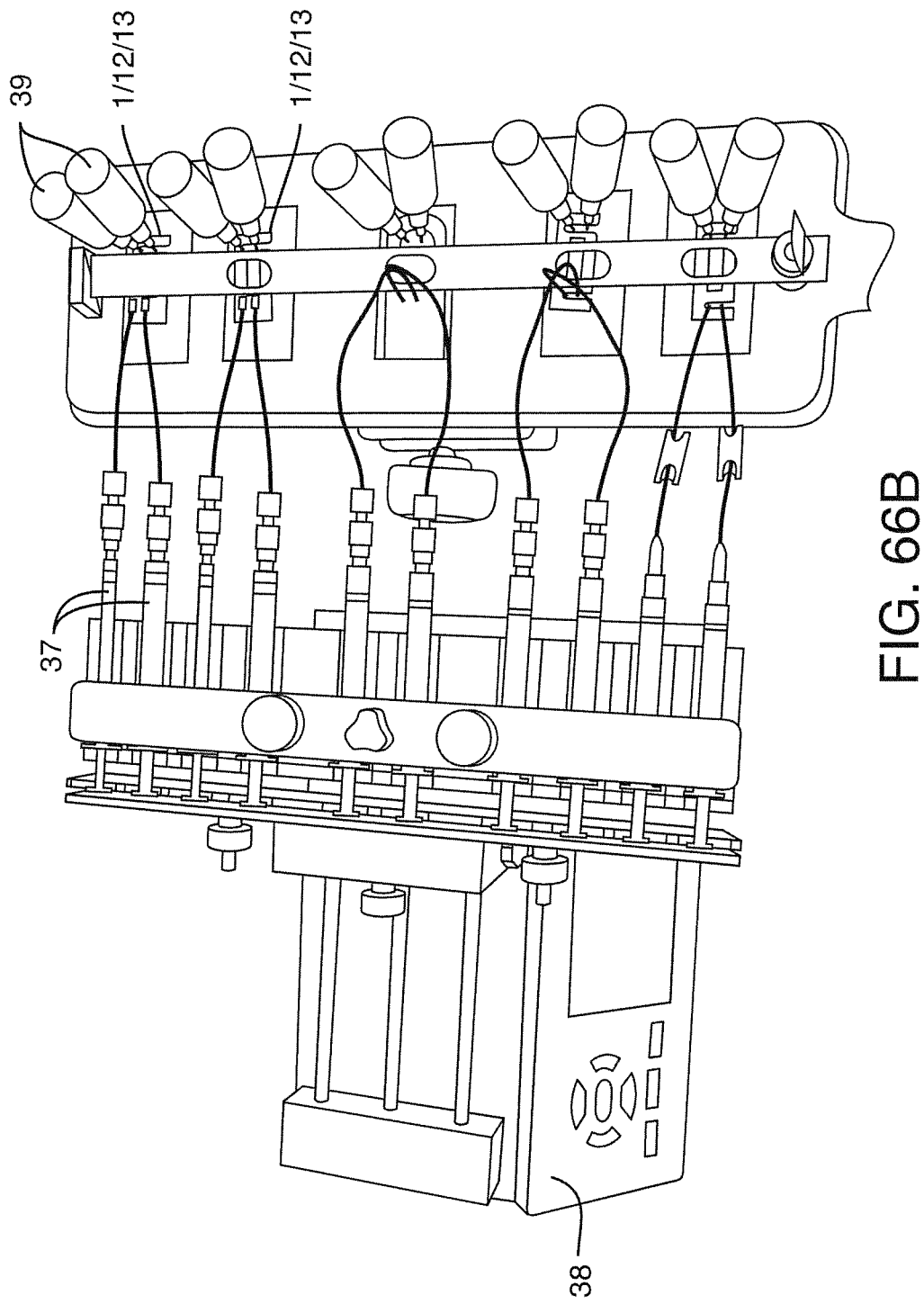
Figure 66C:
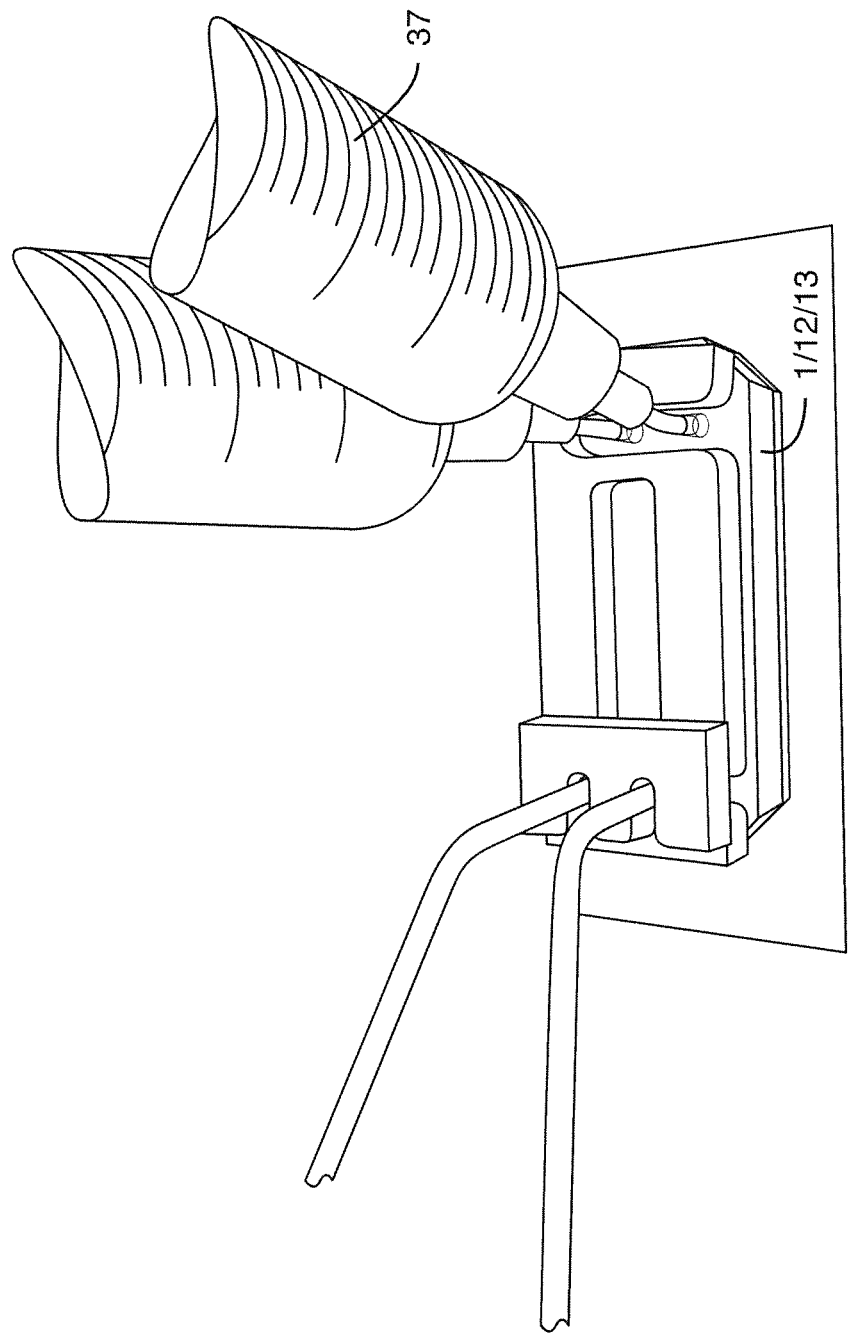
Figure 67:
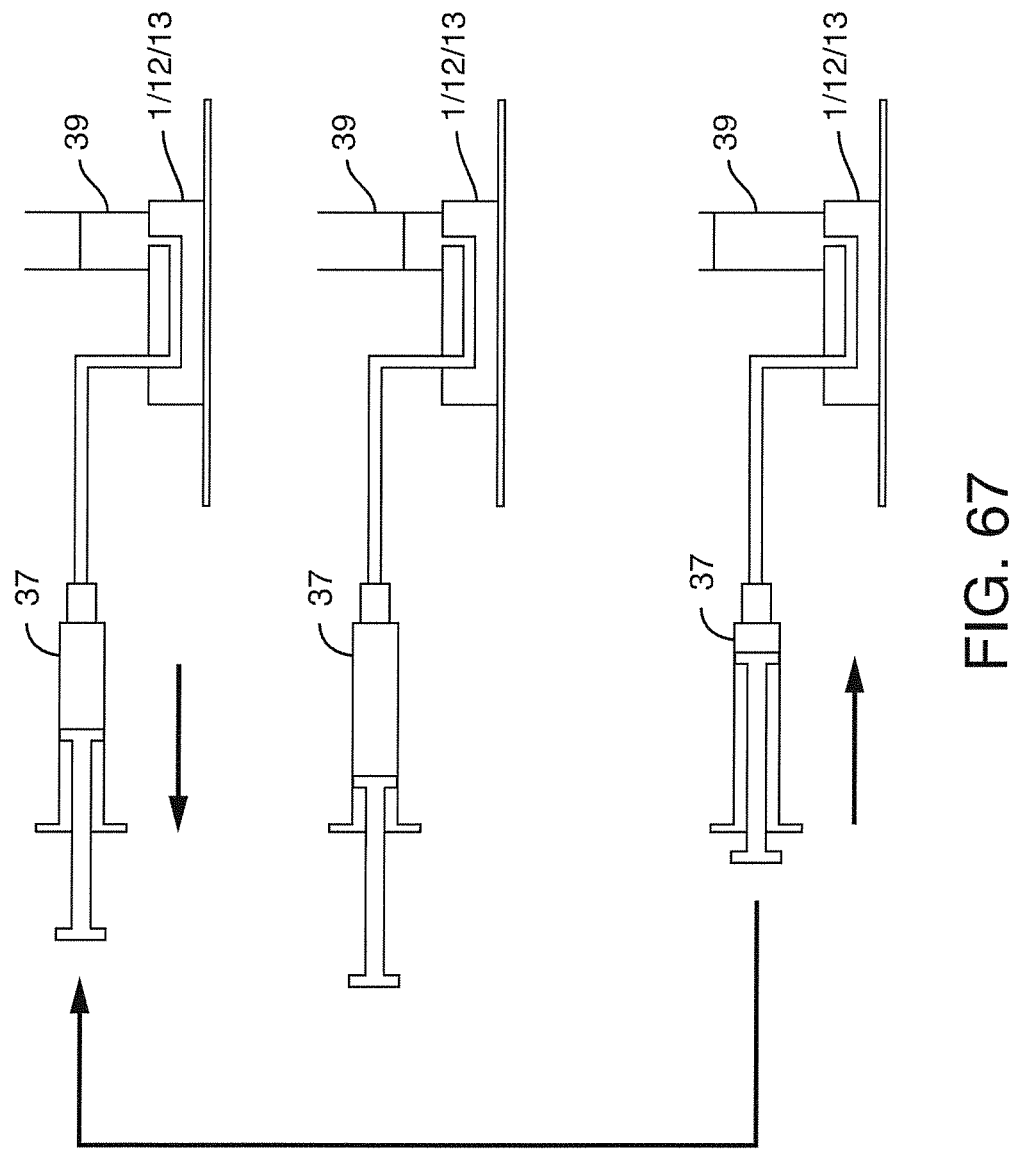
FIG. 67 depicts the flow process of the experimental setup shown in FIGS. 66A, 66B and 66C, where the media is pushed back and forth through the microfluidic device from the syringe and external reservoir.

Reciprocation of cell culture media was tested in order to assess the potential benefits, including oxygenation of media and ensuring that cells see the full dosing concentration of a drug in a small volume of media. FIGS. 66A, 66B and 66C show an experimental setup for reciprocation of media. The setup involves pumping media through a low-absorbing, gas-impermeable microfluidic device (12) fabricated from COP using a syringe pump (38). The media collects in an external reservoir that is connected to the outlet port (2). Once most of the media has been pumped out of the syringe (37), the syringe pump (38) reverses direction and begins to pump media from the external reservoir (39) back into the syringe (37). In the process of pumping the media back and forth, in one embodiment the media flows through gas-permeable tubing, which allows ambient gases to access the media. In another embodiment, the media that has collected in the outlet reservoir is exposed to the ambient atmospheric environment allowing it to rapidly equilibrate to the gas concentrations in the air, in this case supplying the needed oxygen levels for the cells to function properly. Because this reservoir is "open" to the external environment, the media is able to equilibrate to the ambient oxygen concentration in the air. If the cells in the device have depleted the oxygen in the media, oxygen will quickly diffuse into the media to re-saturate with dissolved oxygen. The experimental setup is not only low-absorbing, but also importantly decreases system volume. FIG. 67 depicts the flow process of the experimental setup shown in FIGS. 66A, 66B and 66C, where the media is pushed back and forth through the microfluidic device (13) from the syringe (37) and external reservoir (39), which exposes the media to the required gas concentrations. In FIG. 67, the media is first drawn from the external reservoir, through the microfluidic device, into the syringe. The media is then optionally held static in the syringe in the middle panel of the figure. The media is then pushed out of the syringe, back through the microfluidic device, into the external reservoir. The external reservoir may alternatively be known as a reservoir or fluid reservoir.

3. Absorbency Experiments on Low-Absorbing, Gas-Permeable Microfluidic Devices

Three of each of four different types of microfluidic devices were seeded with different varieties of liver cells to form a "Liver-On-Chip" or "Liver Chip" in order to assess viability in different microfluidic environments. The top channel (3) was seeded with human hepatocyte cells and the bottom channel (4) was seeded with human sinusoidal endothelial cells. The first condition was an absorbing microfluidic device (12) described in U.S. Pat. No. 8,647,861 fabricated from PDMS. The absorbing, PDMS microfluidic device (12) represented a negative control. The second condition was a low-absorbing, gas-impermeable microfluidic device (13) fabricated from COP. The gas-impermeable, low-absorbing microfluidic device (13) represented a positive control. The third condition was a low-absorbing, gas-permeable microfluidic device (1) comprising an 11% porous PET scaffold and PDMS thin film gas exchanger (9). The fourth condition was a low-absorbing, gas-permeable microfluidic device (1) comprising a PDMS thick film gas exchanger (9) but no porous PET scaffold. Media was flowed through the microfluidic devices at 30 µL/hr. Functional readouts of the experiment included morphology, albumin production, and bile canaliculi structure. Morphology was determined with brightfield imaging.

Figure 45A:
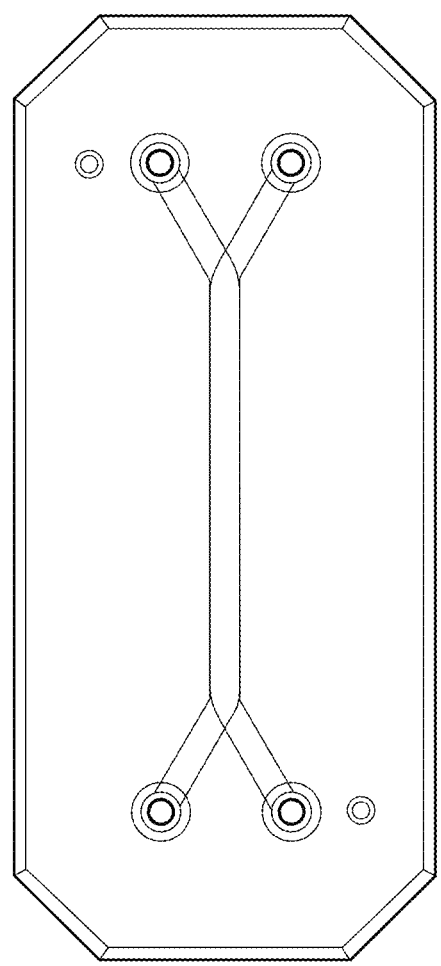
FIGS. 45A and 45B depict microfluidic devices for use in liver validation experiments.
Figure 45B:
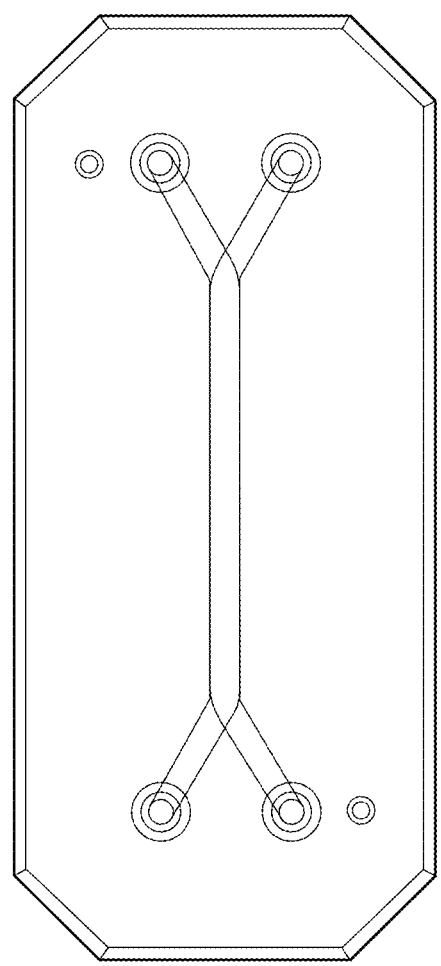

Albumin production was quantified with effluent collection and ELISA tests. The presence of a proper bile canaliculi structure was evaluated with immunofluorescence to visualize MRP2 expression. Slits were cut in the tray of the culture module used in order to achieve better oxygen transport through the gas exchanger (9). FIG. 45A depicts a gas-permeable, low-absorbing microfluidic device (1) comprising an 11% porous PET and PDMS thin-film gas exchanger (9). FIG. 45B depicts a low-absorbing, gas-permeable microfluidic device (1) comprising a PDMS thick film gas exchanger (9).

FIGS. 46A, 46B, 46C and 46D depict the morphology of the cell monolayer (33) in an absorbing microfluidic device (12). FIG. 46A shows the monolayer (33) on Day 1. FIG. 46B shows the monolayer (33) on Day 3. FIG. 46C shows the monolayer (33) on Day 6. FIG. 46D shows the monolayer (33) on Day 10. The monolayer (33) appeared to be maintained through Day 10, with slight morphological decline.

FIGS. 47A, 47B, 47C, and 47D depict the morphology of the cell monolayer (33) in a low-absorbing, gas-impermeable microfluidic device (13) constructed from COP. FIG. 47A shows the monolayer (33) on Day 1. FIG. 47B shows the monolayer (33) on Day 3. FIG. 47C shows the monolayer (33) on Day 6. FIG. 47D shows the monolayer (33) on Day 10. The monolayer (33) appeared to be declining rapidly over the course of the 10 days, with most cells completely dead or dying by Day 10.

FIGS. 48A, 48B, 48C and 48D depict the morphology of the cell monolayer (33) in a low-absorbing, gas-permeable microfluidic device (1) with a porous PET and thin film PDMS gas exchanger (9). FIG. 48A shows the monolayer (33) on Day 1. FIG. 48B shows the monolayer (33) on Day 3. FIG. 48C shows the monolayer (33) on Day 6. FIG. 48D shows the monolayer (33) on Day 10. The monolayer (33) appeared to be maintained through Day 10, with slight morphological decline (similar to the gas-permeable, but absorbing device in FIG. 46A-D).

FIGS. 49A, 49B, 49C and 49D depict the morphology of the cell monolayer (33) in a low-absorbing, gas-permeable microfluidic device (1) with a thin film PDMS gas exchanger (9). FIG. 49A shows the monolayer (33) on Day 1. FIG. 49B shows the monolayer (33) on Day 3. FIG. 49C shows the monolayer (33) on Day 6. FIG. 49D shows the monolayer (33) on Day 10. The monolayer (33) appeared to be maintained through Day 10, with slight morphological decline (similar to the gas-permeable, but absorbing device in FIG. 46A-D).

Figure 50A:
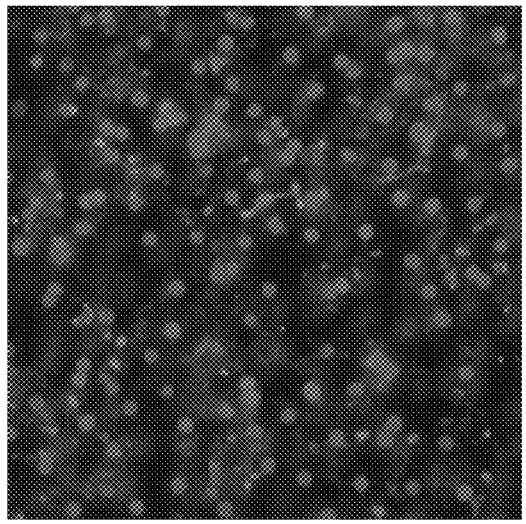
FIGS. 50A, 50B, 50C, and 50D depict the MRP2 signal of the Bile Canaliculi of all the conditions at Day 14.
Figure 50B:
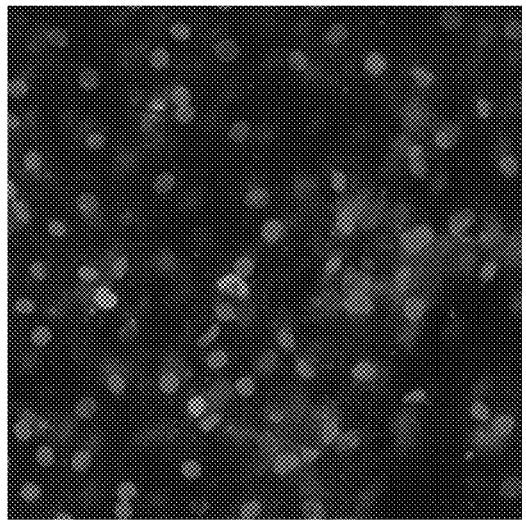
Figure 50C:
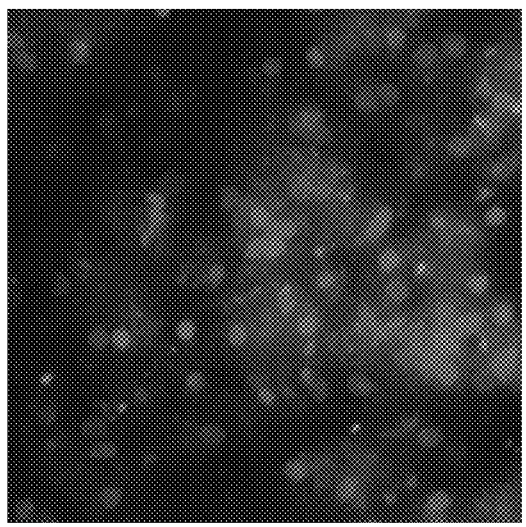
Figure 50D:
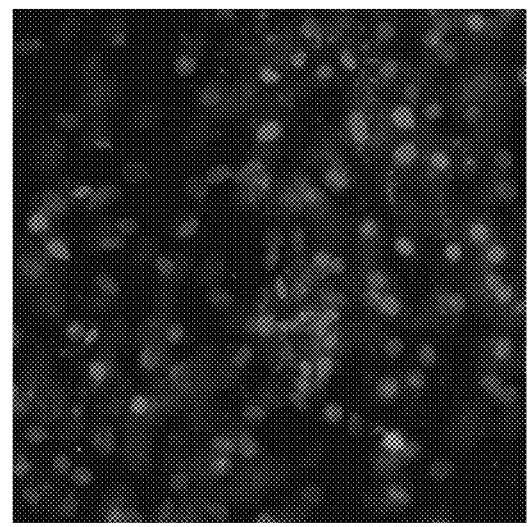

FIGS. 50A, 50B, 50C and 50D depict the MRP2 signal of the Bile Canaliculi of all the conditions at Day 14. FIG. 50A shows the Bile Canaliculi MRP2 signal on an absorbing microfluidic device (12) constructed from PDMS on Day 14. FIG. 50B shows the Bile Canaliculi MRP2 signal on a low-absorbing, gas-impermeable microfluidic device (13) constructed from COP on Day 14. FIG. 50C shows the Bile Canaliculi MRP2 signal on a low-absorbing, gas-permeable microfluidic device (1) with a porous PET and thin film PDMS gas exchanger (9) on Day 14. FIG. 50D shows the Bile Canaliculi MRP2 signal on a low-absorbing, gas-permeable microfluidic device (1) with a thin film PDMS gas exchanger (9) on Day 14. There was no MRP2 signal for any of the conditions on Day 14.

Figure 51A:
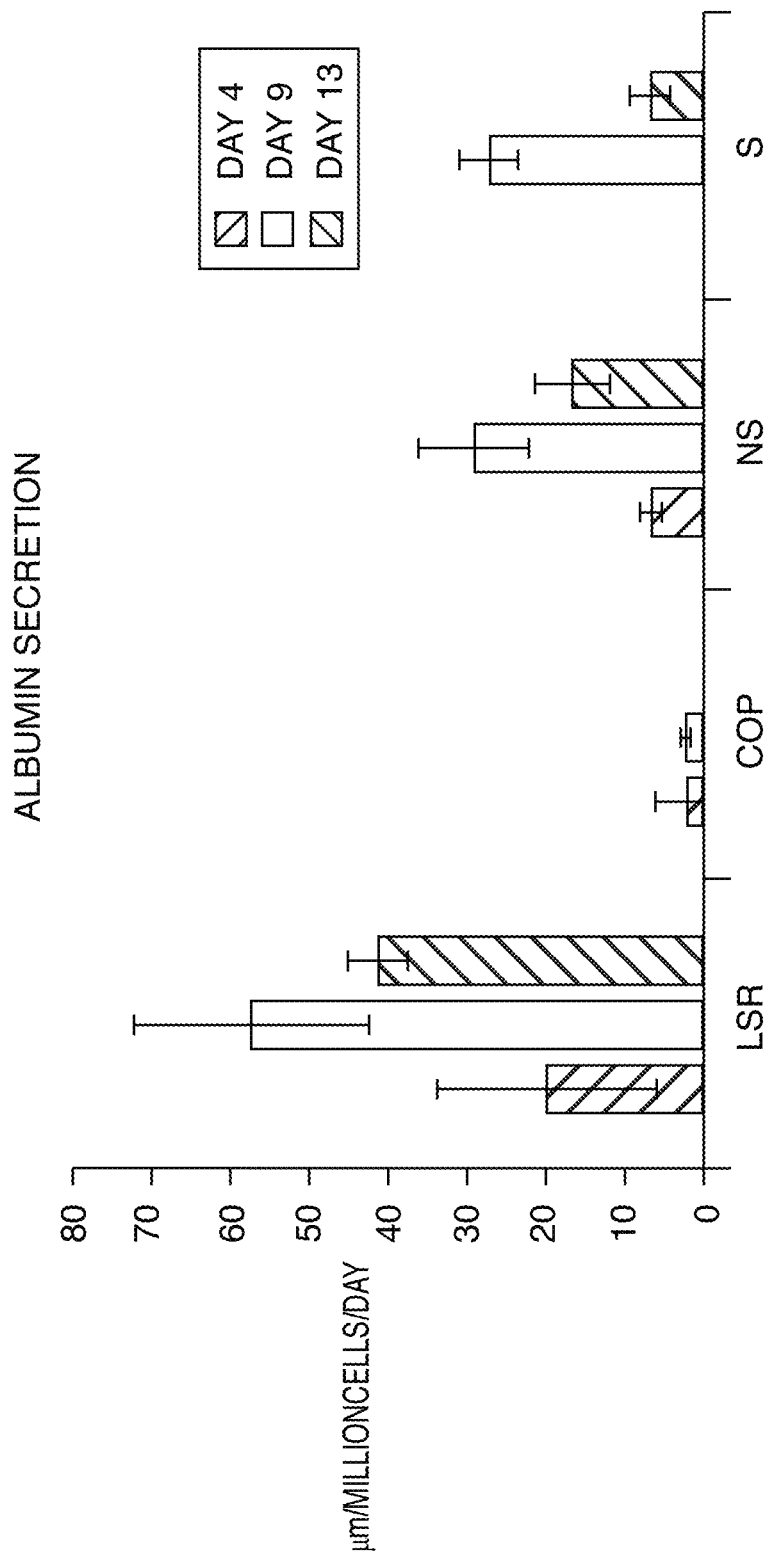
FIGS. 51A and 51B depict average Albumin secretion in four different microfluidic device conditions on Day 4, Day 9 and Day 13. Albumin secretion is lower in both the low-absorbing, gas-permeable microfluidic device with a porous PET and thin film PDMS gas exchanger and the low-absorbing, gas-permeable microfluidic device with a thin film PDMS gas exchanger than the absorbing microfluidic device constructed from PDMS. However, there is a significant improvement from the low-absorbing, gas-impermeable microfluidic device constructed from COP, which is gas-impermeable and non-absorbing.
Figure 51B:
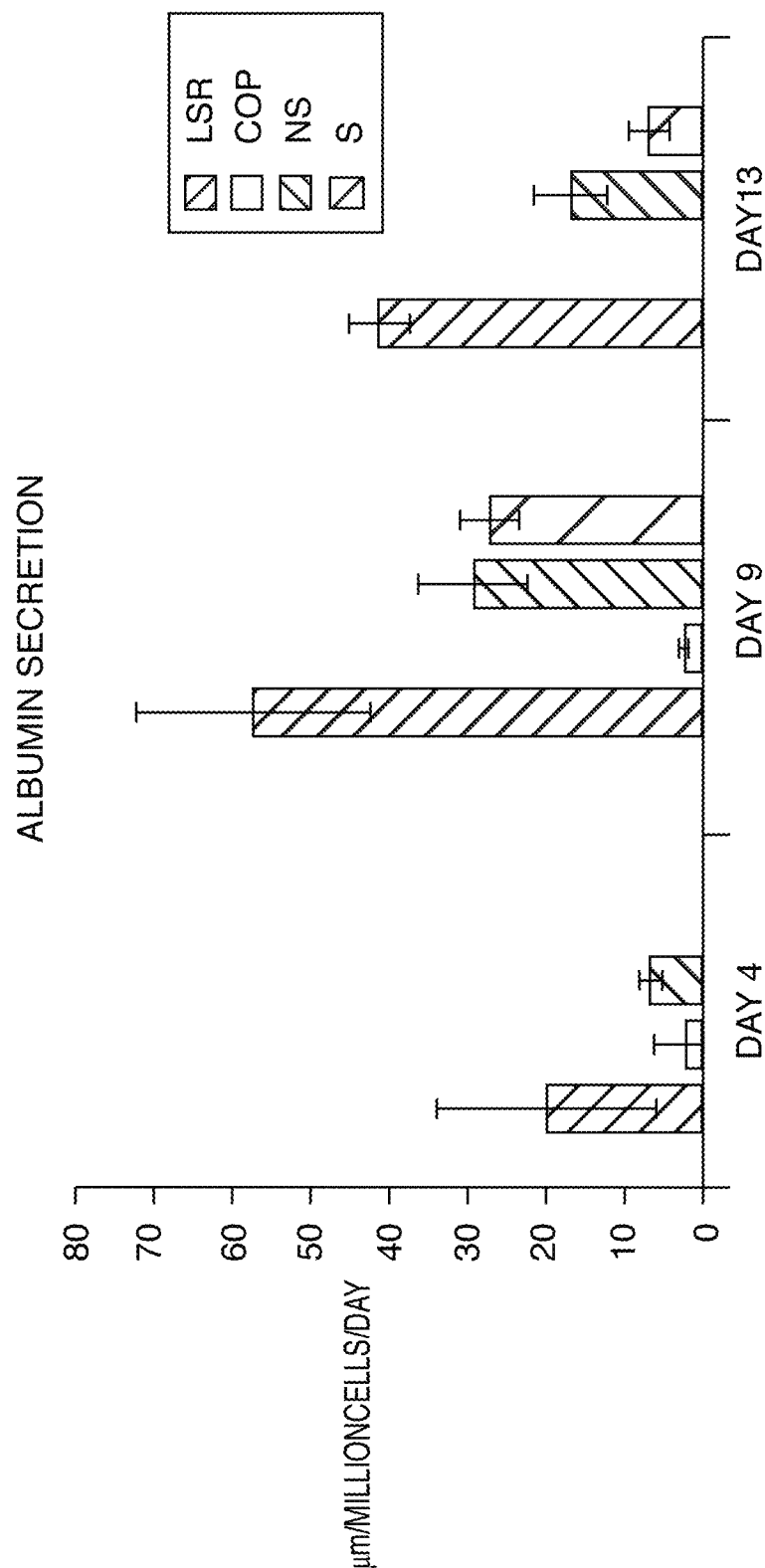

FIGS. 51A and 51B depict average Albumin secretion in each of the four conditions on Day 4, Day 9 and Day 13. Albumin secretion is lower in both the low-absorbing, gas-permeable microfluidic device (1) with a porous PET and thin film PDMS gas exchanger (9) and the low-absorbing, gas-permeable microfluidic device (1) with a thin film PDMS gas exchanger (9) than the absorbing microfluidic device (12) constructed from PDMS. However, there is a significant improvement from the low-absorbing, gas-impermeable microfluidic device (13) constructed from COP.

The absorbing microfluidic device (12) constructed from PDMS did not perform astonishingly well, however the cell layer (33) was alive at Day 14. The low-absorbing, gas-impermeable microfluidic device (13) constructed from COP was surprisingly still alive at Day 1, however it unsurprisingly was dead at Day 14. Both the low-absorbing, gas-permeable microfluidic device (1) with a porous PET and thin film PDMS gas exchanger (9) and the low-absorbing, gas-permeable microfluidic device (1) with a thin film PDMS gas exchanger (9) showed improvement compared to the low-absorbing, gas-impermeable microfluidic device (13) constructed from COP.

Experiments were also run to see if a low-absorbing, gas-permeable microfluidic device comprising a gas exchanger could be used to create oxygen gradients in the cell culture channels, also known as the top and bottom channels. A low-absorbing, gas-permeable microfluidic device (1) with a gas exchanger (9) was seeded with Caco-2 cells. The microfluidic device (1) was not seeded with endothelial cells. All media was equilibrated in a 5% oxygen environment for 24 hours. A hypoxic incubator was set to maintain a 5% oxygen environment or 5 kPa partial pressure.

Figure 53:
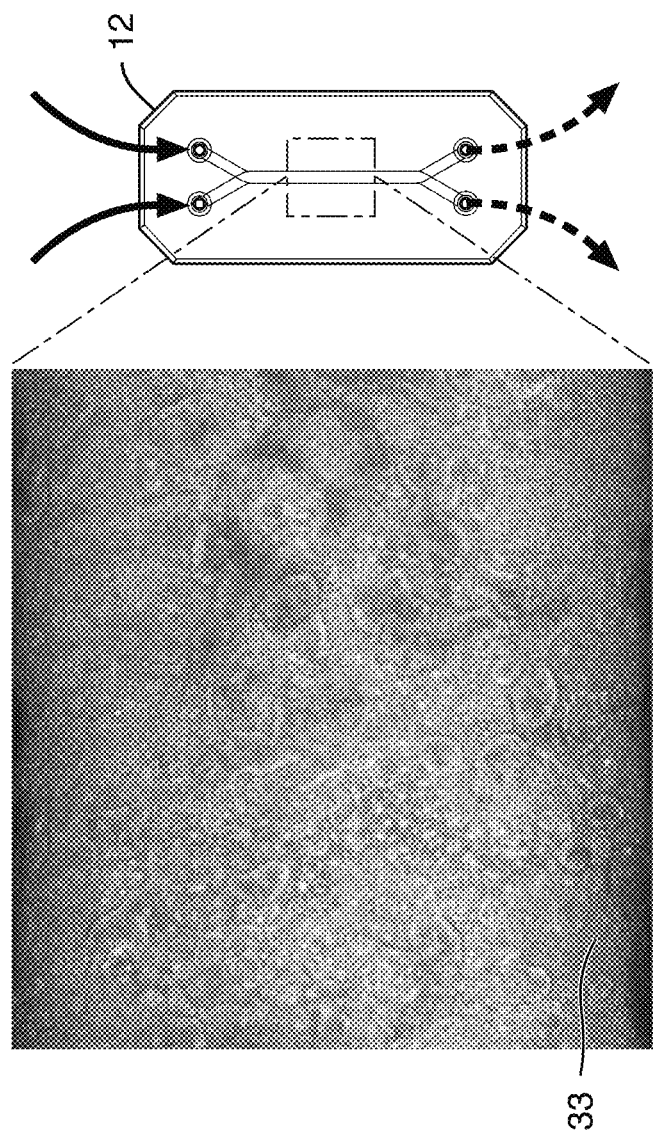
FIG. 53 depicts the morphology of the cell type Caco-2 in a low-absorbing, gas-permeable microfluidic device. This is an intestine cell line that could benefit from the creation of oxygen gradients from the vasculature channel into the apical channel, which represents the intestinal lumen.
Figure 54:
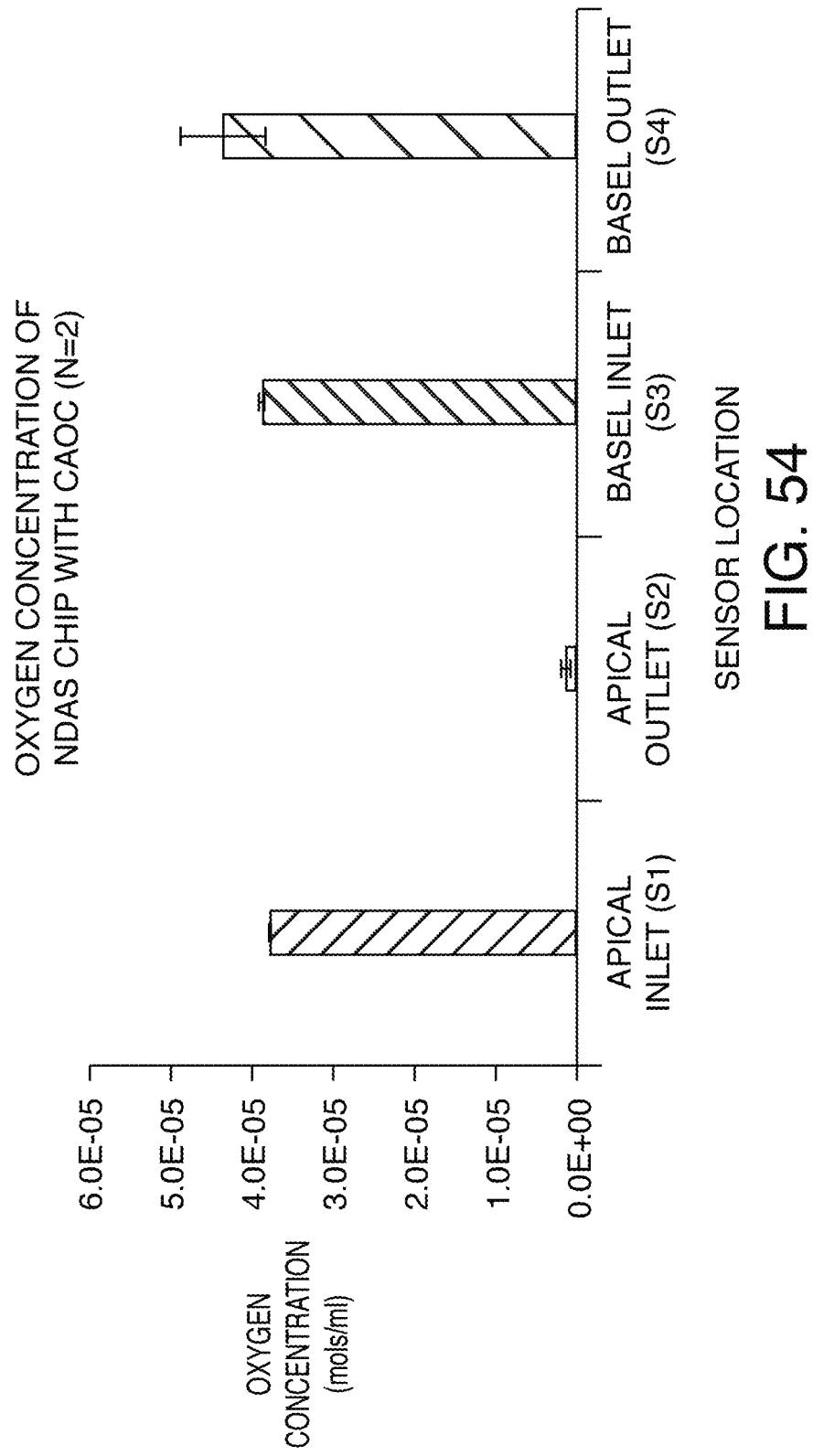
FIG. 54 depicts the oxygen concentration profile of the low-absorbing, gas-permeable microfluidic device sampled at the four different ports: top channel inlet port, top channel outlet port, bottom channel inlet port and bottom channel outlet port. In this experiment, oxygen-rich media was perfused into both the apical and basal inlets. Because of the gas exchanger, the basal channel remained oxygenated, while the apical channel became nearly depleted of oxygen. This is a highly desirable and sought-after result, as this recapitulates the oxygen gradients seen in the colon, which are necessary to imitate the in vivo condition. Specifically, this is important for maintaining adequate oxygen levels to supply intestinal cells with needed levels to maintain homeostasis, while creating a low-oxygen environment in the channel representing the lumen, where anaerobic bacteria, such as *clostridium symbiosum*, thrive.

The proof-of-concept study demonstrates that the low-absorbing, gas-permeable microfluidic device (1) establishes oxygen micro-gradients along the height of the microfluidic device that support Caco-2 epithelial grown and differentiation and a hypoxic environment in the apical chamber. FIG. 53 depicts Caco-2 morphology in the low-absorbing, gas-permeable microfluidic device, benefitting from the creation of oxygen gradients from the vascular channel into the apical channel, which represents the intestinal lumen (1). FIG. 54 depicts the oxygen concentration profile of the low-absorbing, gas-permeable microfluidic device (1) sampled at the four different ports (2): top channel (3) inlet port (2), top channel (3) outlet port (2), bottom channel (4) inlet port (2) and bottom channel (4) outlet port (2). Recreating the micro-anaerobic environments characteristic of the intestinal lumen enables first-in-kind co-cultures of mucosal host tissues with the predominant fastidious commensal microbial species of the human gut. An example of fastidious commensal microbial species of the human gut is firmicutes.

4. Absorbency Experiments on Perfusion Manifold Assemblies

Fluorescent molecule Rhodamine B (a fluorescent molecule that is also moderately absorbing into PDMS and SEBS) was dissolved in a buffer, flowed through a perfusion manifold assembly (14) and absorbing microfluidic device (12) fabricated out of PDMS at 30 µL/hr for 38 hours on a culture module. The perfusion manifold assemblies (14) were rinsed with buffer not containing the fluorescent molecule at 200 µL/hr for an hour before the start of the experiment.

Figure 25A:
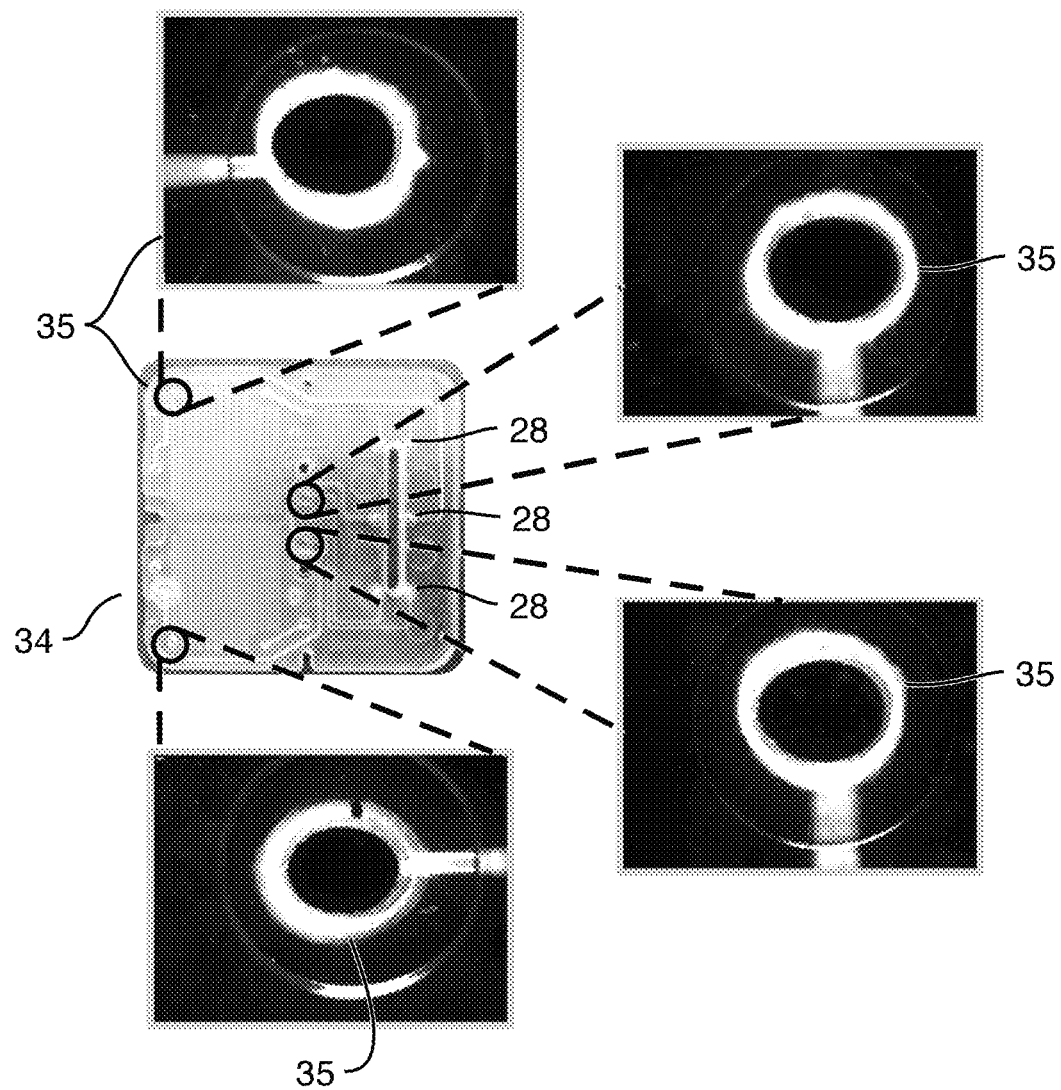
FIGS. 25A and 25B depict fluorescent images of fluidic layer assemblies of perfusion manifold assemblies, either comprising a combined gasketing and capping layer or separate, yet bonded low-absorbing capping and low-absorbing gasketing layers. The fluorescent signal is given off by the compound rhodamine, which was exposed to the system components. Bright white in the images indicate areas where compound has absorbed.
Figure 25B:
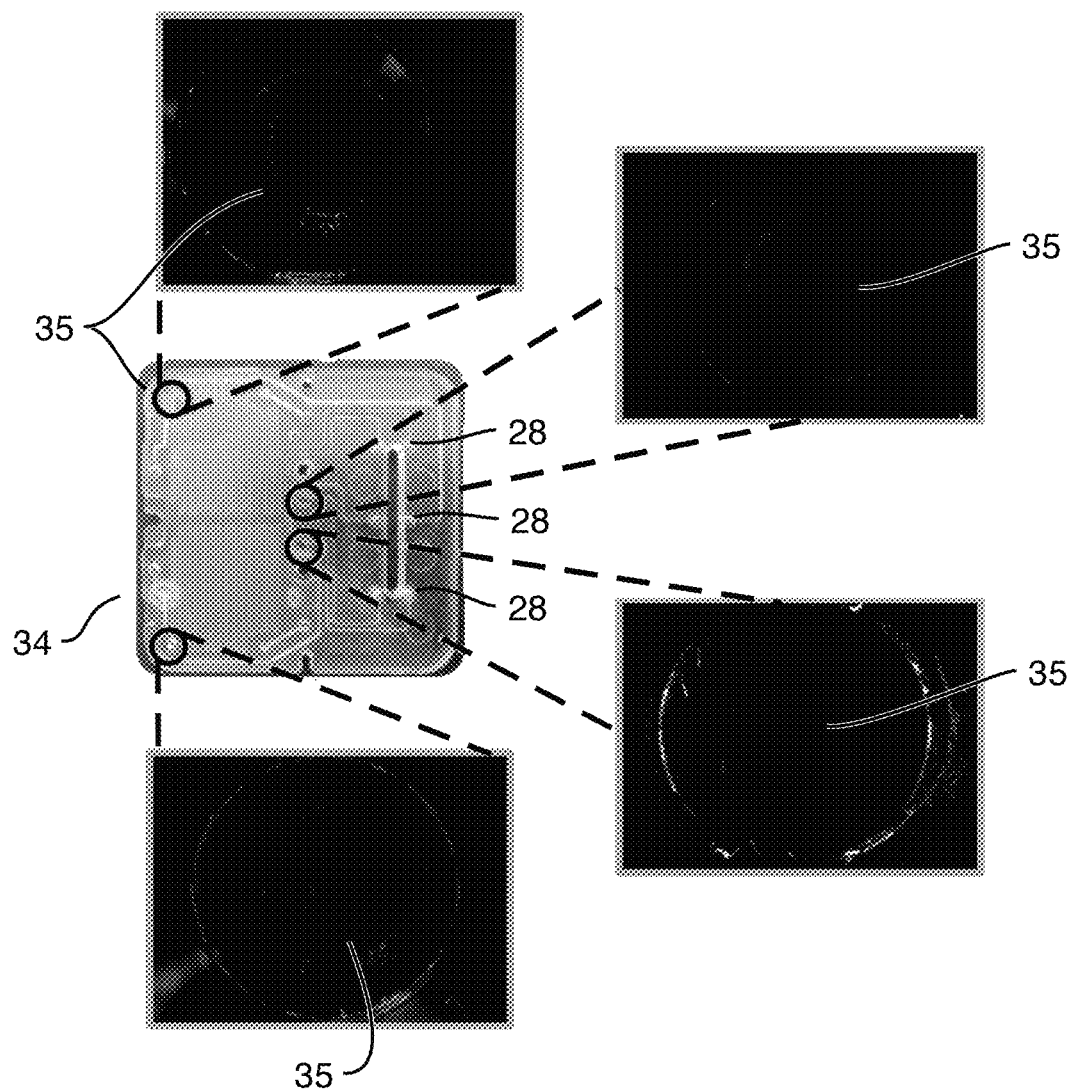

Following the experiment, the perfusion manifold assemblies (14) were disassembled and the vias (35) of the capping, gasketing and backplane assembly or fluidic layer assembly (34), as well as the perfusion manifold assembly (14) resistors (27), were imaged with fluorescent microscopy. FIG. 25A depicts the resulting fluorescence in the fluidic layer assembly (34) of an absorbing perfusion manifold assembly (14) comprising a combined gasketing and capping layer (26). FIG. 25B depicts the resulting fluorescence on one aspect the invention described herein, a low-absorbing perfusion manifold assembly comprising both a low-absorbing capping and low-absorbing gasketing layer. In the embodiment of the perfusion manifold assembly (14) used in the experiment, the capping layer was fabricated from COP and the gasketing layer was fabricated out of SEBS coated with Parylene. Bright white colors in FIGS. 25A and 25B correlate to greater degree of absorption of the fluorescent molecule Rhodamine B.

FIG. 25A shows sample images of absorption of fluorescent molecule around each of the four vias (35) in the fluidic layer assembly (34). FIG. 25B shows sample images of the little to no absorption of the fluorescent molecule around each of the four vias (35) in the fluidic layer assembly (34).

Figure 26:
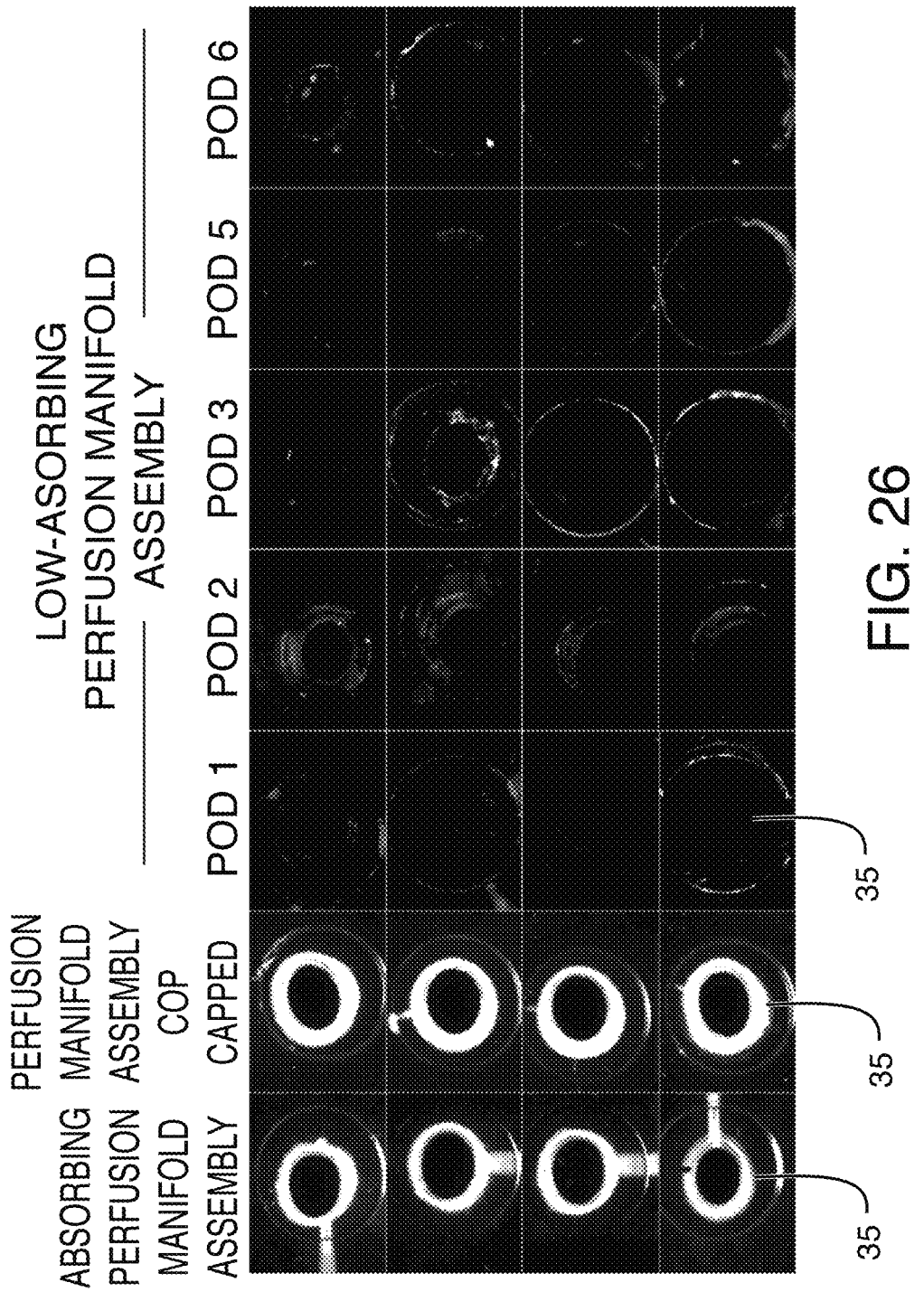
FIG. 26 shows comprehensive images of all the results of fluidic layer assembly small molecule absorption for multiple embodiments. An absorbing perfusion manifold assembly was tested. A supposedly low-absorbing perfusion manifold assembly was tested, comprising a COP capping layer and a non-coated SEBS gasketing layer was tested. Five low-absorbing perfusion manifold assemblies, comprising a COP capping layer and a Parylene coated SEBS gasketing layer were also tested. Bright white in the images indicate areas where the fluorescent molecule has absorbed.

FIG. 26 shows more comprehensive images of all of the experiment conditions. An absorbing perfusion manifold assembly (14) was tested. A supposedly low-absorbing perfusion manifold assembly (14) was tested, comprising a COP capping layer (21) and a non-coated SEBS gasketing layer (20) was tested. Five low-absorbing perfusion manifold assemblies (14), comprising a COP capping layer (21) and a Parylene coated SEBS gasketing layer (20) were also tested. FIG. 26 shows that the perfusion manifold assembly (14) comprising a combined gasketing and capping layer (26) absorbed the fluorescent molecule. Bright white in the images indicate areas where the fluorescent molecule Rhodamine has been absorbed. FIG. 26 shows that the perfusion manifold assembly (14) comprising a COP capping layer and non-coated SEBS gasketing layer absorbed the fluorescent molecule. The result is surprising, as it was not previously known that SEBS absorbed small molecules. FIG. 26 shows that the perfusion manifold assemblies (14) comprising a COP capping layer and Parylene coated SEBS gasketing layer did not absorb a significant amount of the fluorescent molecule.

Figure 27A:
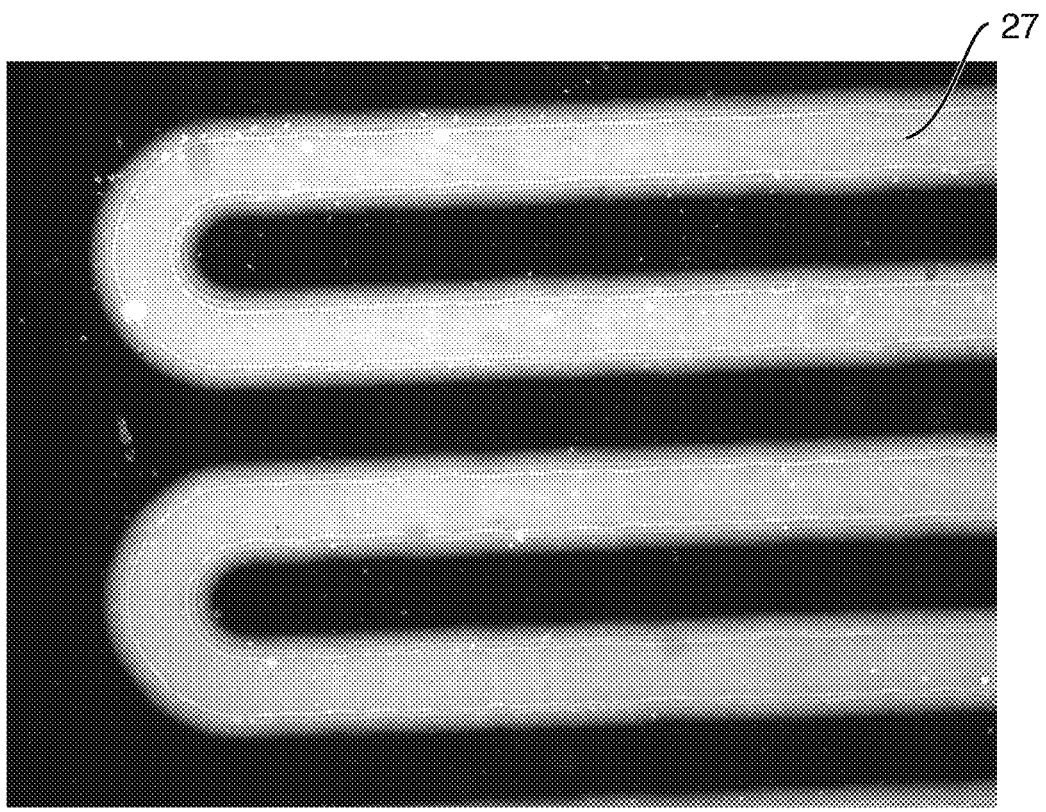
FIGS. 27A and 27B show fluorescent molecule absorption in the resistors (27), having been capped with SEBS and COP respectively. Note that in FIG. 27B the bright white lines represent an optical artifact (reflection of light by the walls of the channel) as opposed to emission of fluorescence.
Figure 27B:
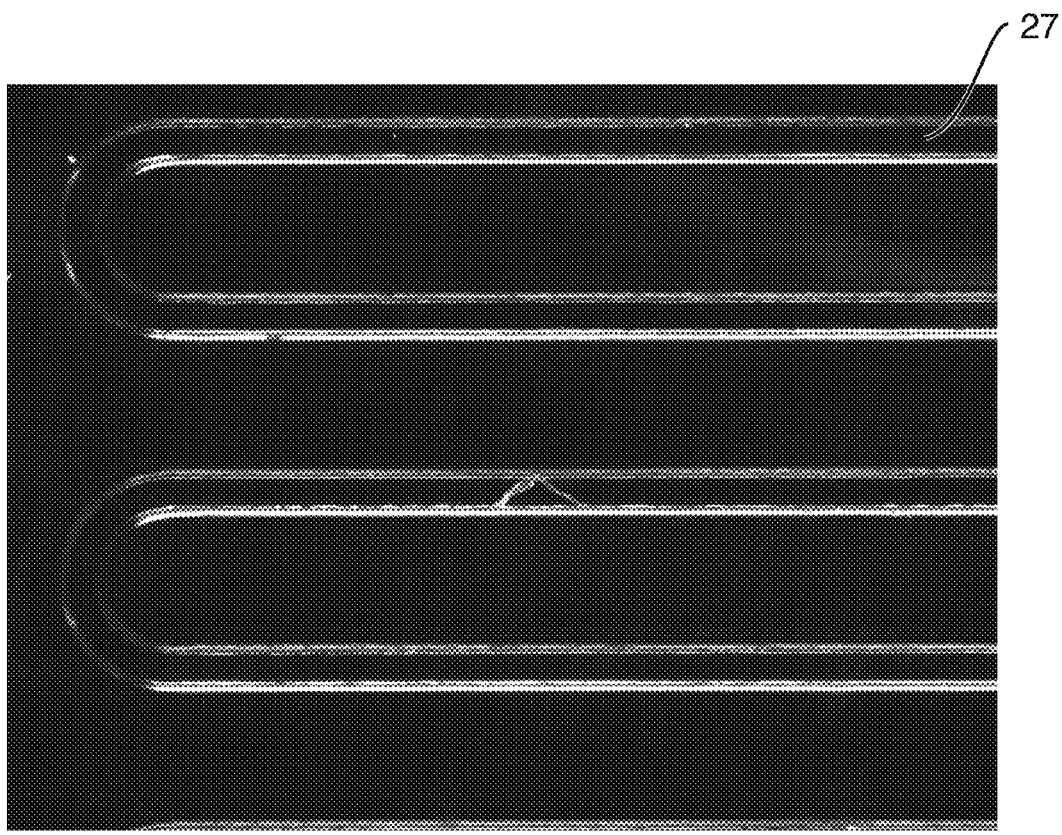

FIGS. 27A and 27B show fluorescent molecule absorption in the resistors (27), having capped with SEBS and COP respectively. FIG. 27A shows that the resistors capped with SEBS surprisingly absorb fluorescent small-molecules to a relatively high extent. FIG. 27B shows that the resistors capped with COP absorb very little of the fluorescent small-molecule rhodamine. Note that in FIG. 27B the bright white lines represent an optical artifact (reflection of light by the walls of the channel) as opposed to emission of Rhodamine fluorescence.

Perfusion manifold assemblies (14) comprising a low-absorbing capping layer (21) and low-absorbing gasketing layer (20) absorb significantly less small-molecule than perfusion manifold assemblies (14) comprising a single, absorbing capping and gasketing layer (26). This absorption study demonstrates visually the importance of having perfusion manifold assemblies fabricated from low-absorbing materials, such as COP, or treated with low-absorbing coatings, such as Parylene.

Experiments were also run using the perfusion manifold assembly in its entirety with microfluidic devices seeded with cell layers.

Figure 10A:
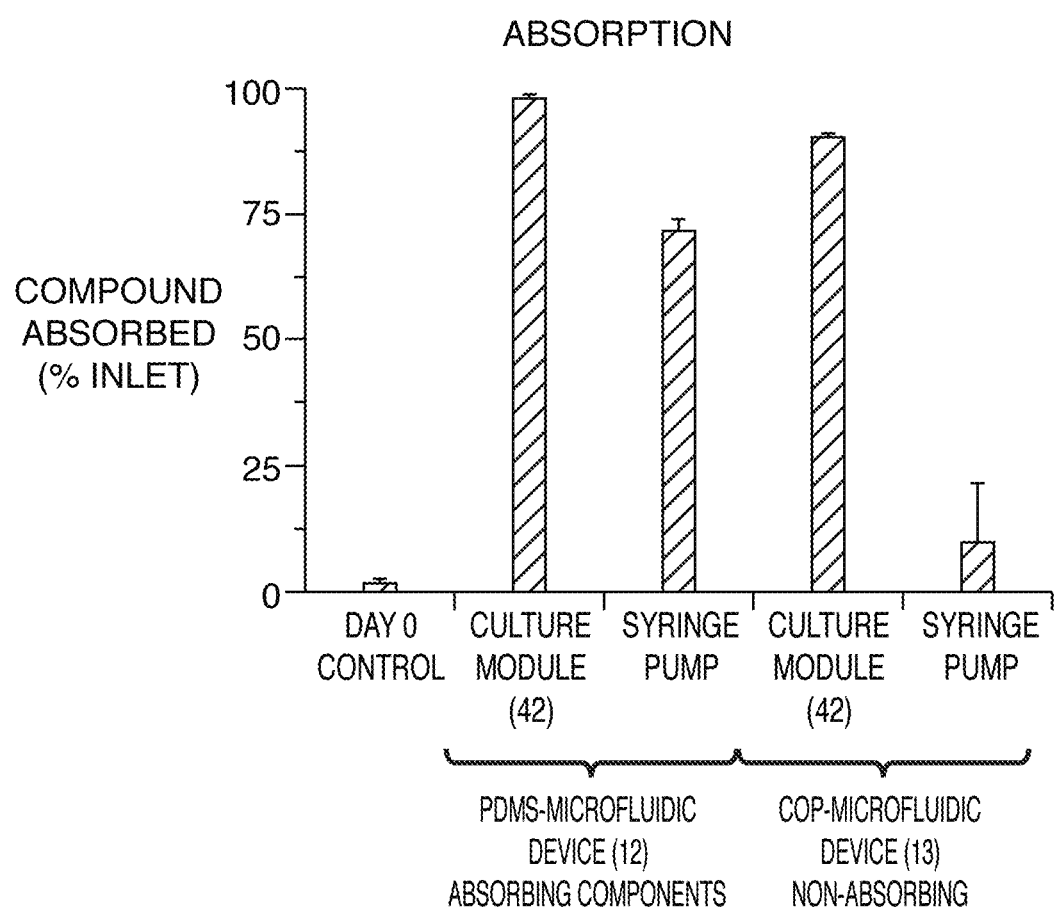
FIG. 10A depicts the absorption of a small molecule (Bupropion) in various embodiments of the microfluidic system comprising of a microfluidic device and perfusion manifold assembly, while 10B depicts the results of a test of that same compound in the same setup for liver metabolism by the metabolizing enzyme CYP2B6. The apparent metabolism of drug by liver cells in both an absorbent microfluidic device fabricated from PDMS and a gas-impermeable, low-absorbing microfluidic device fabricated from COP are depicted, demonstrating the effects of absorption on the apparent rate of metabolism, when quantified by production of a metabolite. It can be seen that the highly absorbing systems results in greater under-prediction of metabolism than the non-absorbing and lower-absorbing systems.
Figure 10B:
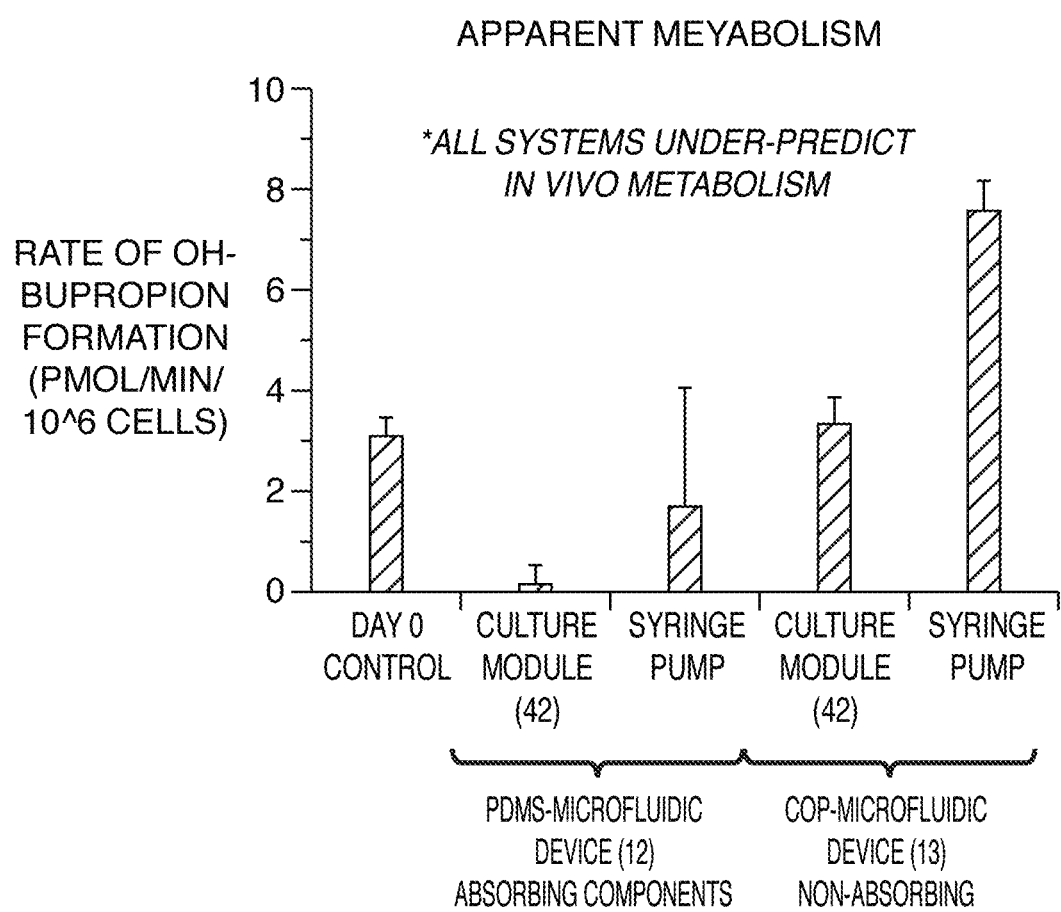

FIG. 10A depicts the absorption of a small molecule (Bupropion) in various embodiments of the microfluidic system comprising of a microfluidic device and perfusion manifold assembly, while FIG. 10B depicts the results of a test of that same compound in the same setup for liver metabolism by the metabolizing enzyme CYP2B6. The apparent metabolism of drug by liver cells in both an absorbent microfluidic device fabricated from PDMS and a gas-impermeable, low-absorbing microfluidic device fabricated from COP are depicted, demonstrating the effects of absorption on the apparent rate of metabolism, when quantified by production of a metabolite. It can be seen that the highly absorbing systems results in greater under-prediction of metabolism than the non-absorbing and lower-absorbing systems.

Oftentimes when cells come into contact with enzymes, they product a secondary compound which may then be used in the production of a biopharmaceutical. When the liver cells are able to access and metabolize the enzyme CYP2B6 they produce the compound OH-Bupropion. Both the absorption of the enzyme into the microfluidic device and connected infrastructure, as well as the formation of OH-Bupropion were measured. If the absorbency of microfluidic devices is ignored during experiments, then one would assume that cells were in contact with the concentration of enzyme that was dosed into the microfluidic device. However, if the bulk material of the microfluidic device is absorbing the enzyme, then it would appear as though the cells are under-producing expected compounds when in contact with the enzyme.

The results speak to a significant under-prediction of OH-Bupropion metabolism in the test-setup comprising an absorbent microfluidic device (12), the perfusion manifold assembly (14) comprising the combined gasketing and capping layer (26), and the culture module. When the variability of enzyme absorption into the bulk of the microfluidic device is eliminated from the experiment, such as using a low-absorbing, gas-impermeable microfluidic device (13) made from COP, then OH-Bupropion metabolism may more accurately be predicted.

5. Compound Distribution Kit Validation Experiments

Figure 92:
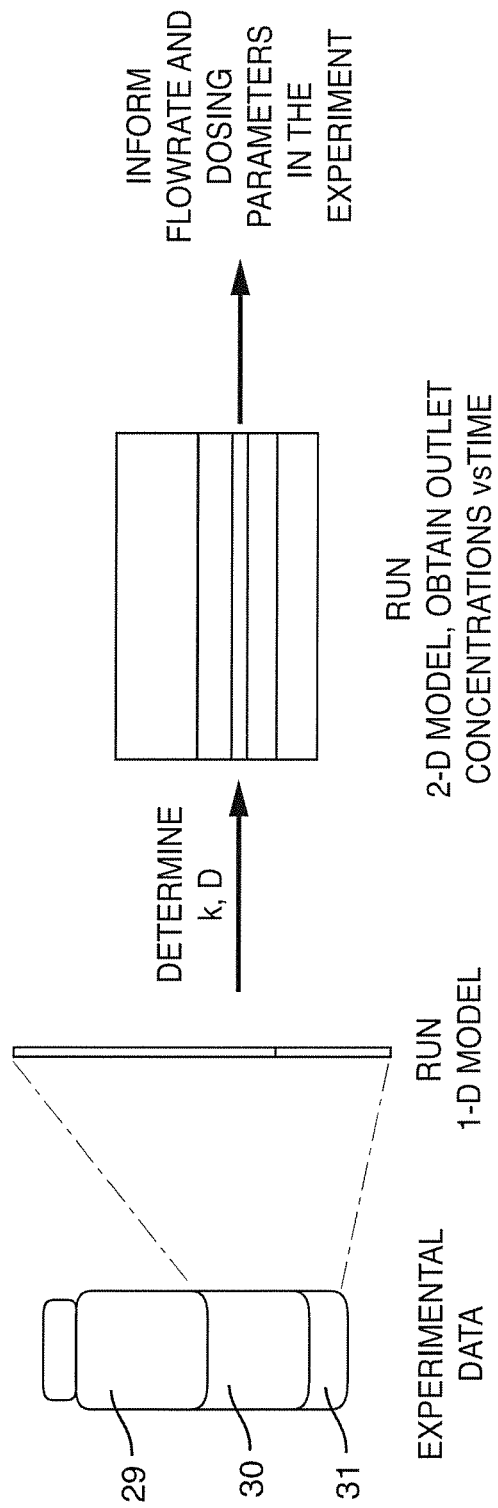
FIG. 92 shows a COMSOL model that can predict the outlet concentrations of compounds based on parameters obtained from static vial studies. COMSOL models can help inform flowrates and other experimental parameters.

Results from computational models, such as COMSOL Multiphysics (COMSOL), may be compared to results from the compound distribution kit presented herein in order to validate the effectiveness of the compound distribution kit. FIG. 92 that shows a COMSOL model can predict the outlet concentrations of compounds based on parameters obtained from static vial studies. COMSOL models can help inform flow rates and other experimental perimeters. Absorption studies may be performed on materials, such as polydimethylsiloxane (PDMS), in vials in order to characterize those materials. The results from these absorption studies on materials may be input into a computational model of a microfluidic device. Computational models can help inform flowrates and other experimental parameters.

Figure 95:
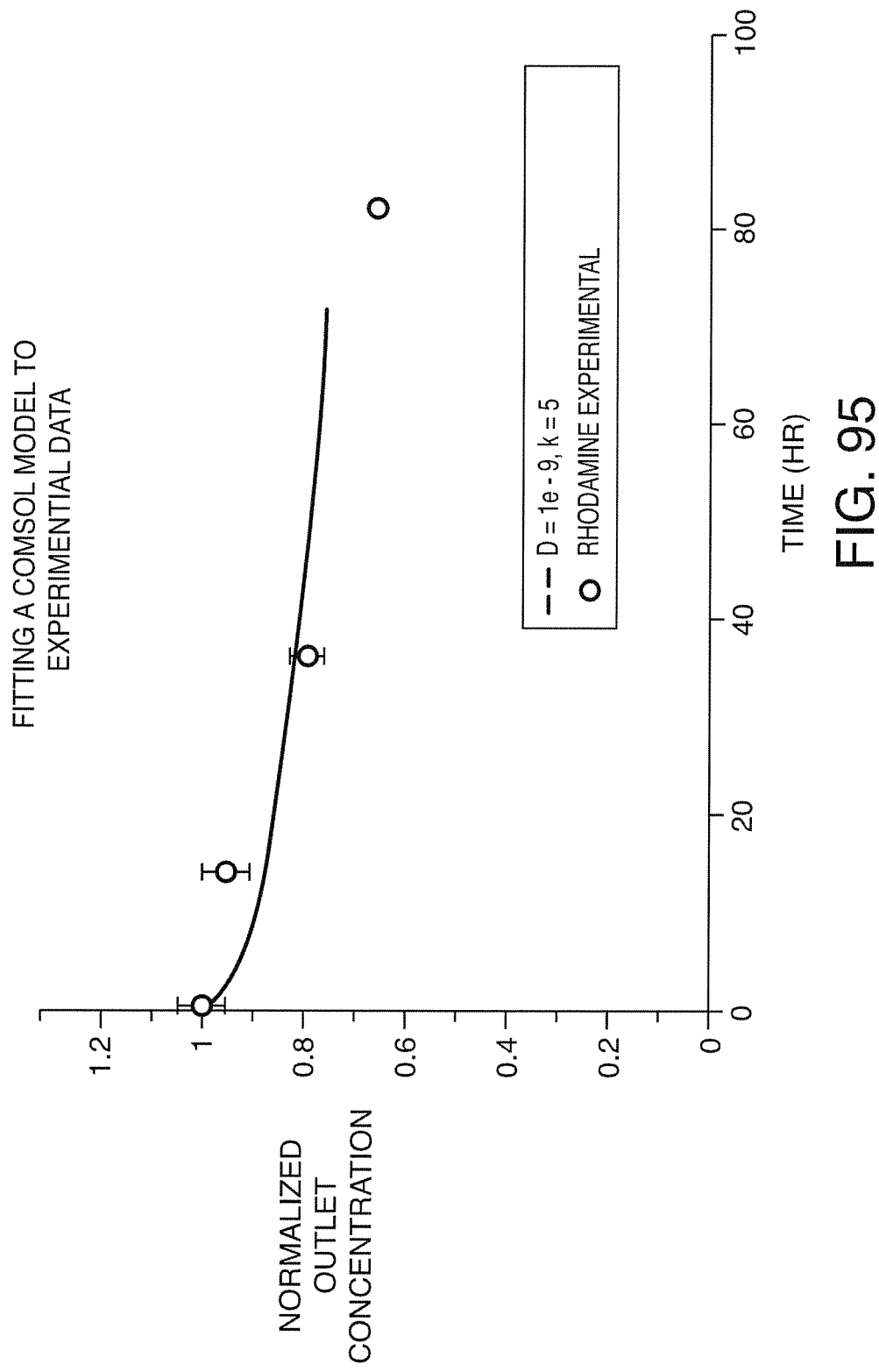
FIG. 95 shows a comparison of computational (COMSOL) model flow study results and actual flow study results for the small-molecule compound Rhodamine.

Once absorption studies are done on particular materials, they may be compared to computation models. FIG. 95 shows a comparison of computational (COMSOL) model flow study results and actual flow study results for the small-molecule compound Rhodamine. FIG. 95 shows that the flow results fit the COMSOL model for the outlet concentrations of the compound. Rhodamine tends to have a lower rate of absorption, but higher extent of absorption, which can saturate its surroundings over time. The importance of this is that despite initially seeing huge losses of Rhodamine, after a period of time, the rate of Rhodamine loss diminishes significantly.

Figure 96A:
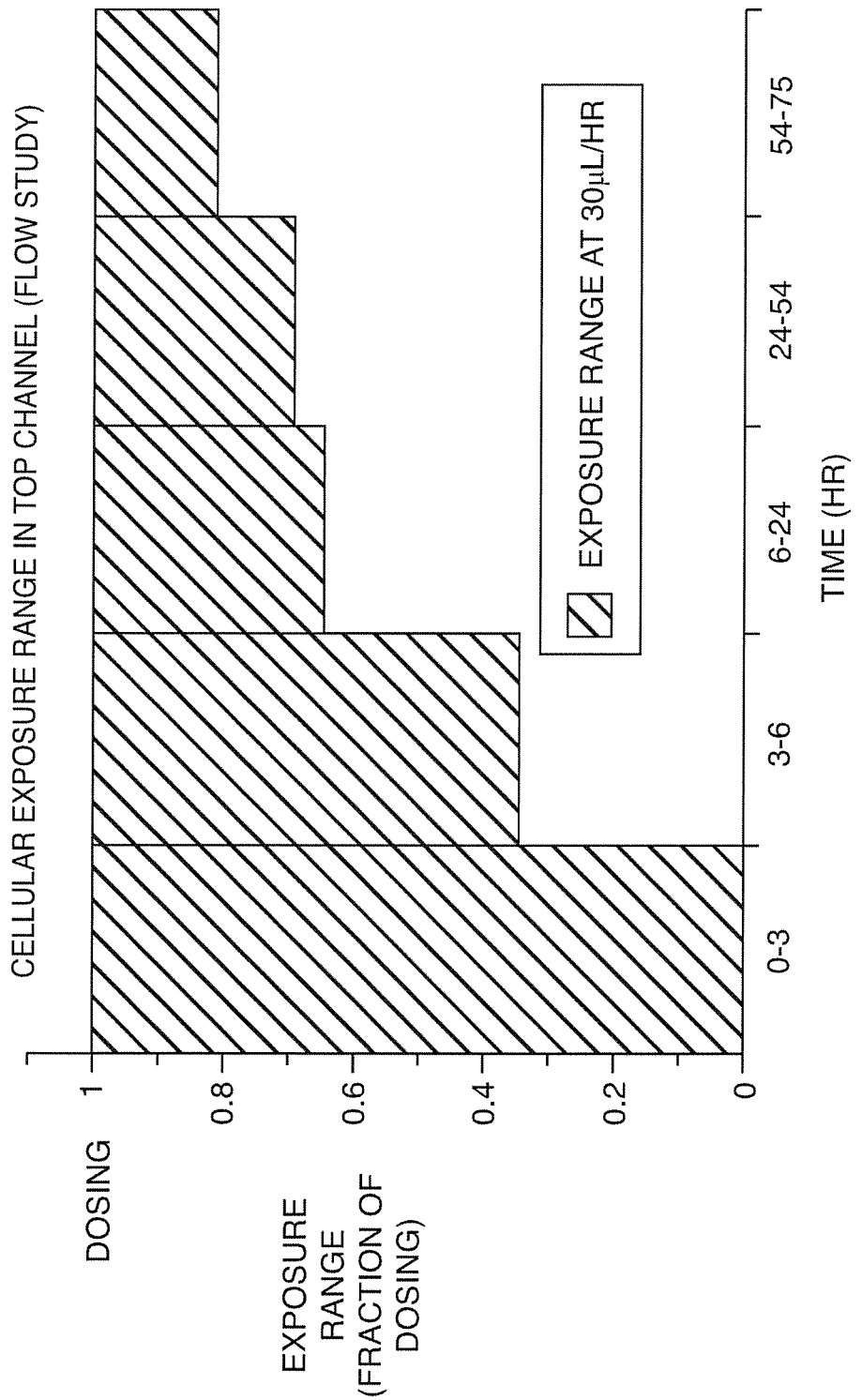
FIGS. 96A and 96B show a comparison between computational (COMSOL) model results and actual experimental results for cellular exposure ranges of the small-molecule compound Rhodamine.
Figure 96B:
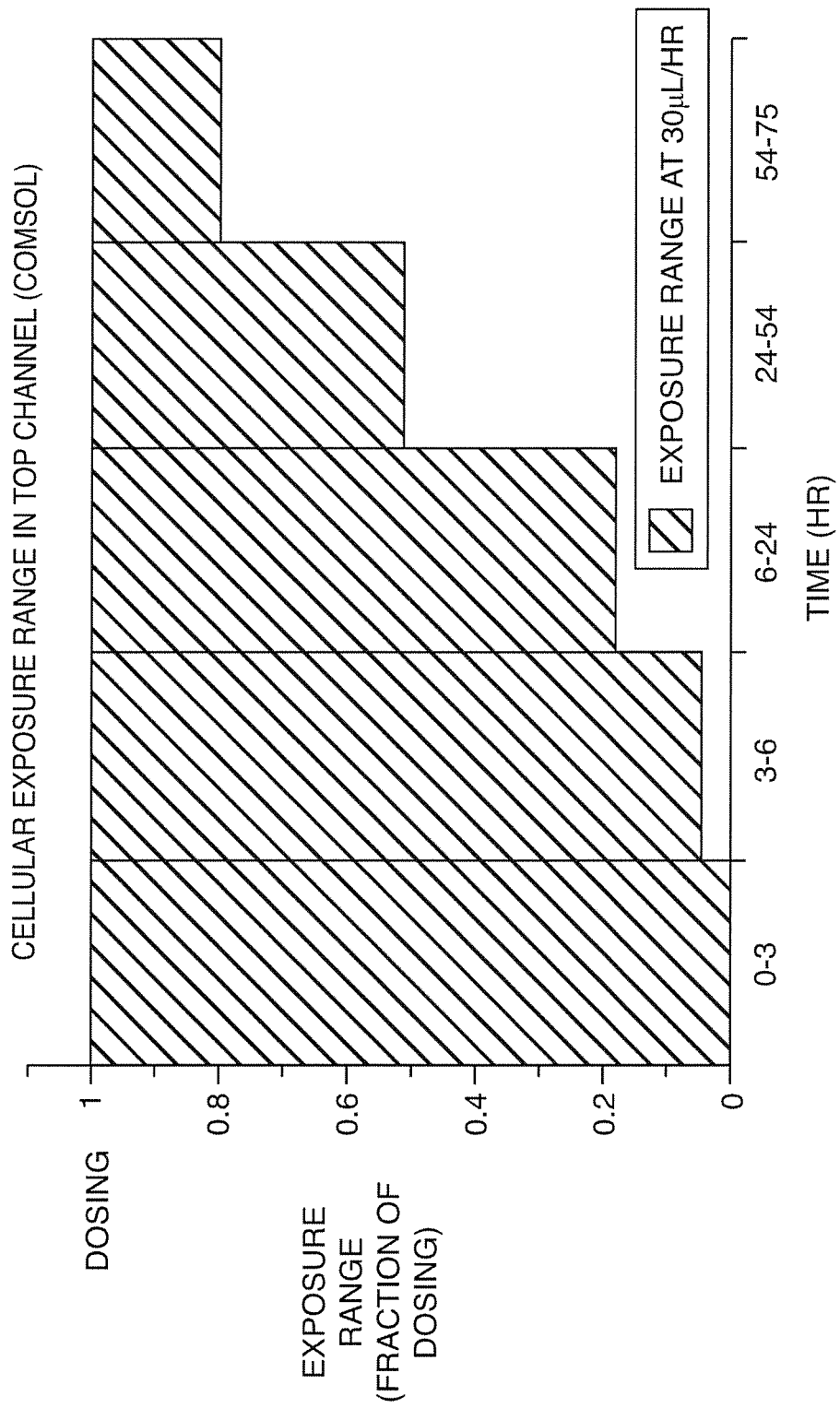

FIGS. 96A and 96B show a comparison between computational (COMSOL) model results and actual experimental results for cellular exposure ranges of the small-molecule compound Rhodamine. FIG. 96A shows experimental results of the cellular exposure range of the small-molecule compound Rhodamine for a first channel of a microfluidic device. FIG. 96B shows computational (COMSOL) model results of the cellular exposure range of the small-molecule compound Rhodamine for a single channel of a microfluidic device. The charts in FIGS. 96A and 96B show that the computational (COMSOL) model accurately predicted Rhodamine absorption into the materials making up microfluidic devices, particularly PDMS.

Figure 97B:
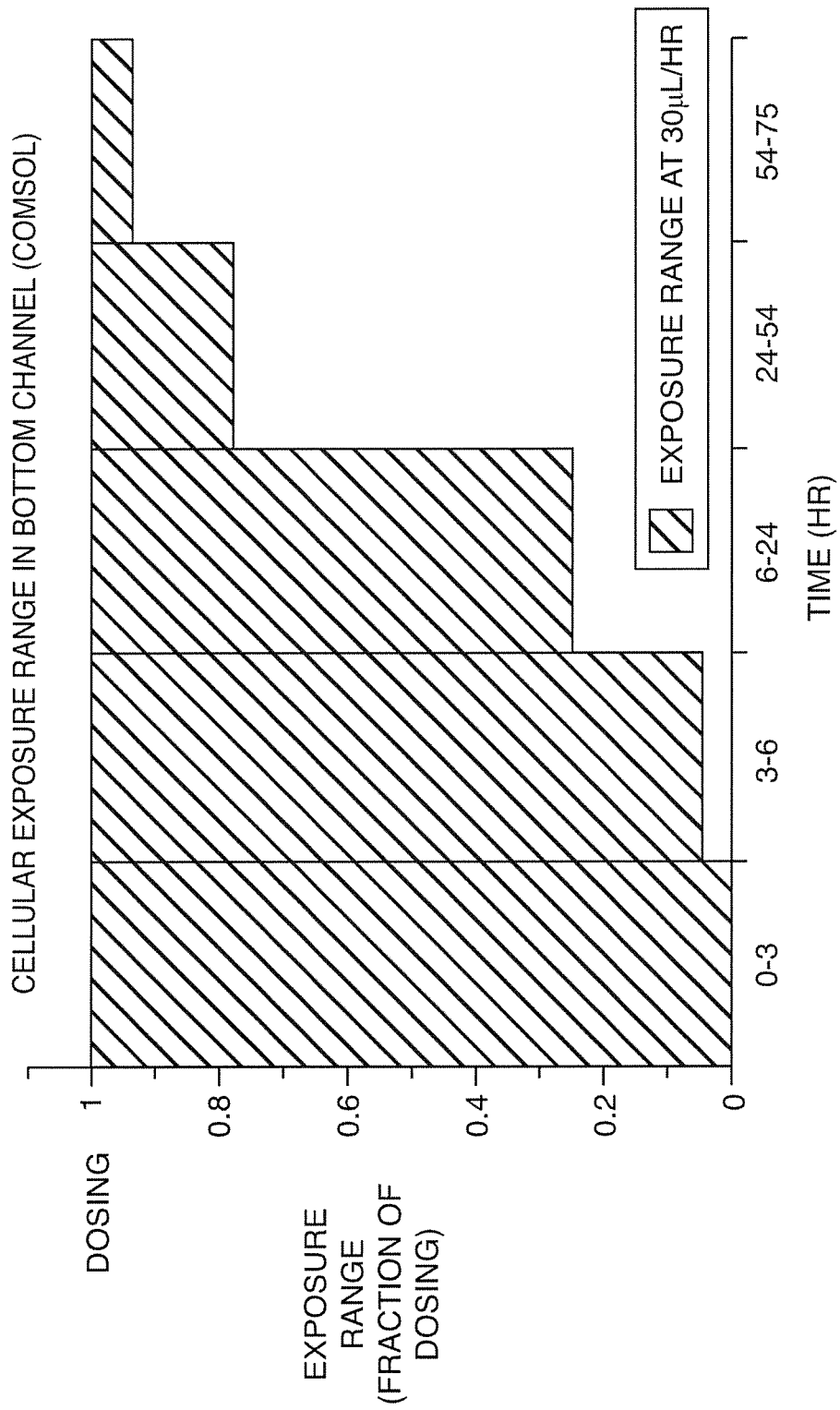

FIGS. 97A and 97B show a comparison between a computational (COMSOL) model results and actual experimental results for cellular exposure ranges of the small-molecule compound Rhodamine. FIG. 96A shows experimental results of the cellular exposure range of the small-molecule compound Rhodamine for a second channel of a microfluidic device. FIG. 96B shows computational (COMSOL) model results of the cellular exposure range of the small-molecule compound Rhodamine for a second channel of a microfluidic device. The charts in FIGS. 97A and 97B show that the computational (COMSOL) model accurately predicts small-molecule absorption into the materials making up microfluidic devices, particularly PDMS.

Figure 98A:
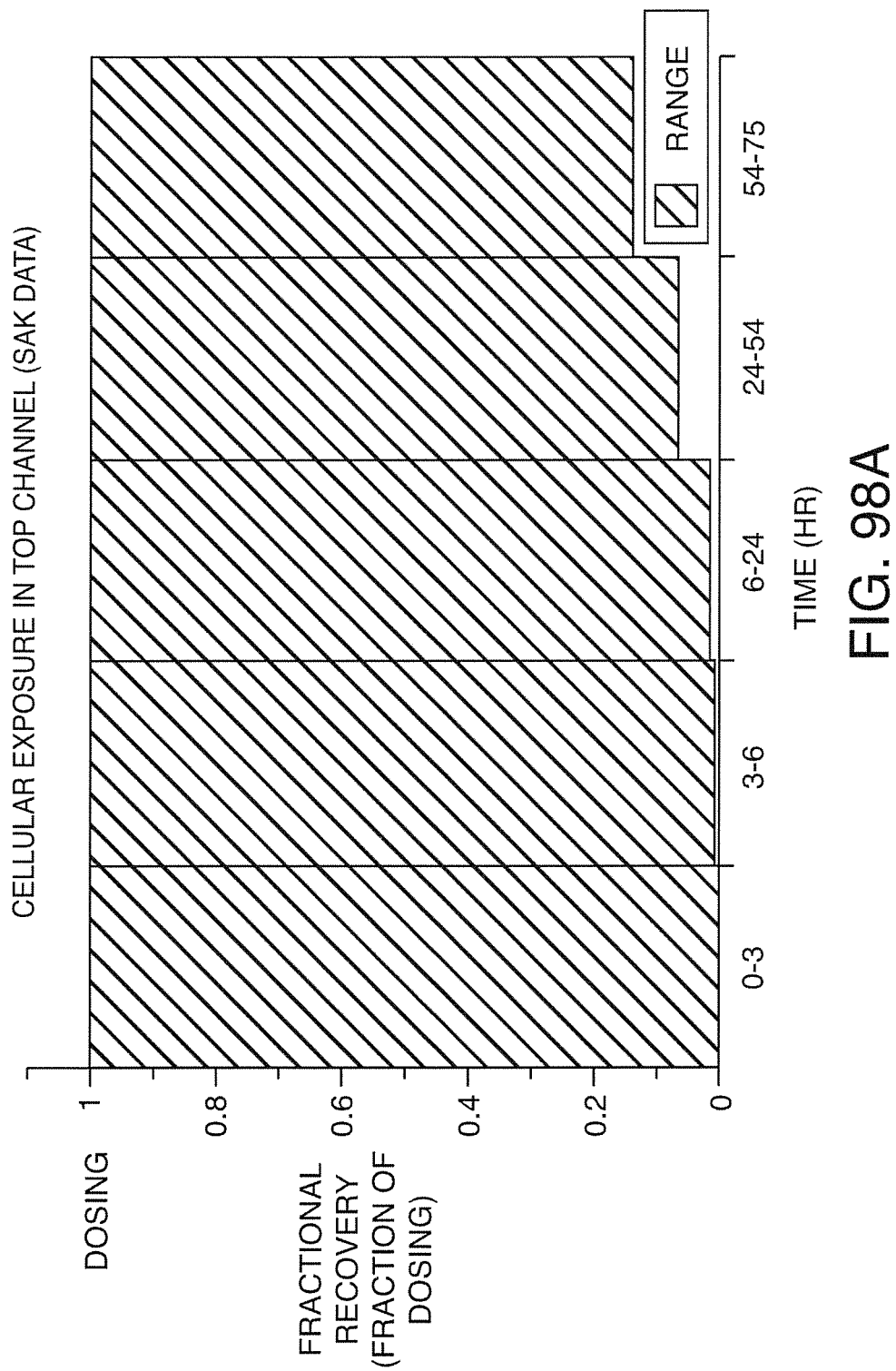

FIGS. 98A and 98B show a comparison between a computational (COMSOL) model results and actual experimental results for cellular exposure ranges of the small-molecule compound Coumarin. FIG. 98A shows experimental results of the cellular exposure range of the small-molecule compound Coumarin for a first channel of a microfluidic device. FIG. 98B shows computational (COMSOL) model results of the cellular exposure range of the small-molecule compound Coumarin for a first channel of a microfluidic device. It was found that the computational (COMSOL) model did not accurately predict the absorption, because the model did not take into account the rest of the flow system outside the microfluidic device. For this experiment the microfluidic device was in fluidic communication with a perfusion manifold assembly. The compound Coumarin was especially susceptible to absorption into one of the materials making up the perfusion manifold assembly, SEBS. As such, the computational (COMSOL) model did not accurately predict the absorption into the entire flow system.

Figure 99A:
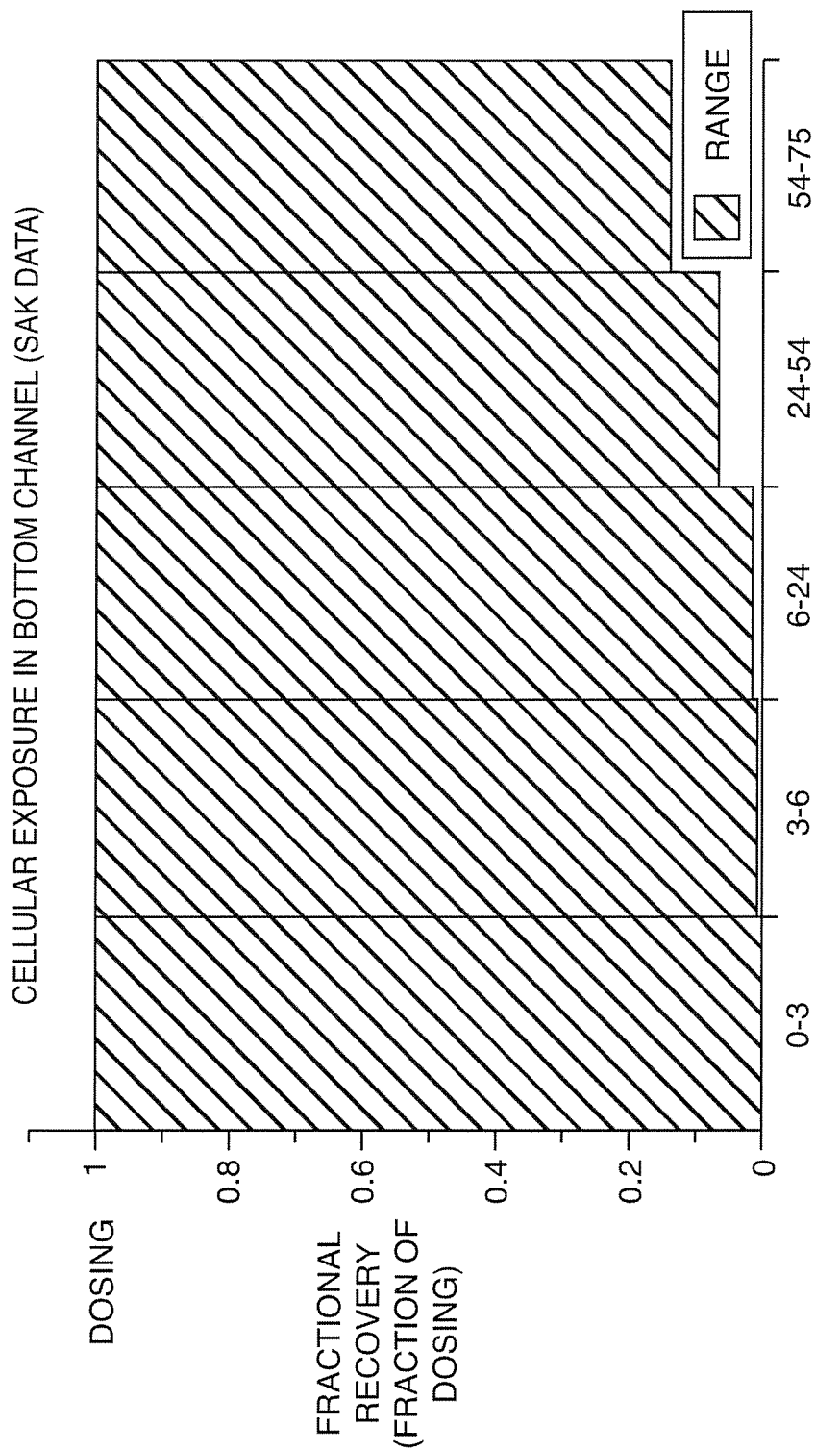
FIGS. 99A and 99B show a comparison between a computational (COMSOL) model results and actual experimental results for cellular exposure ranges of the small-molecule compound Coumarin.
Figure 99B:
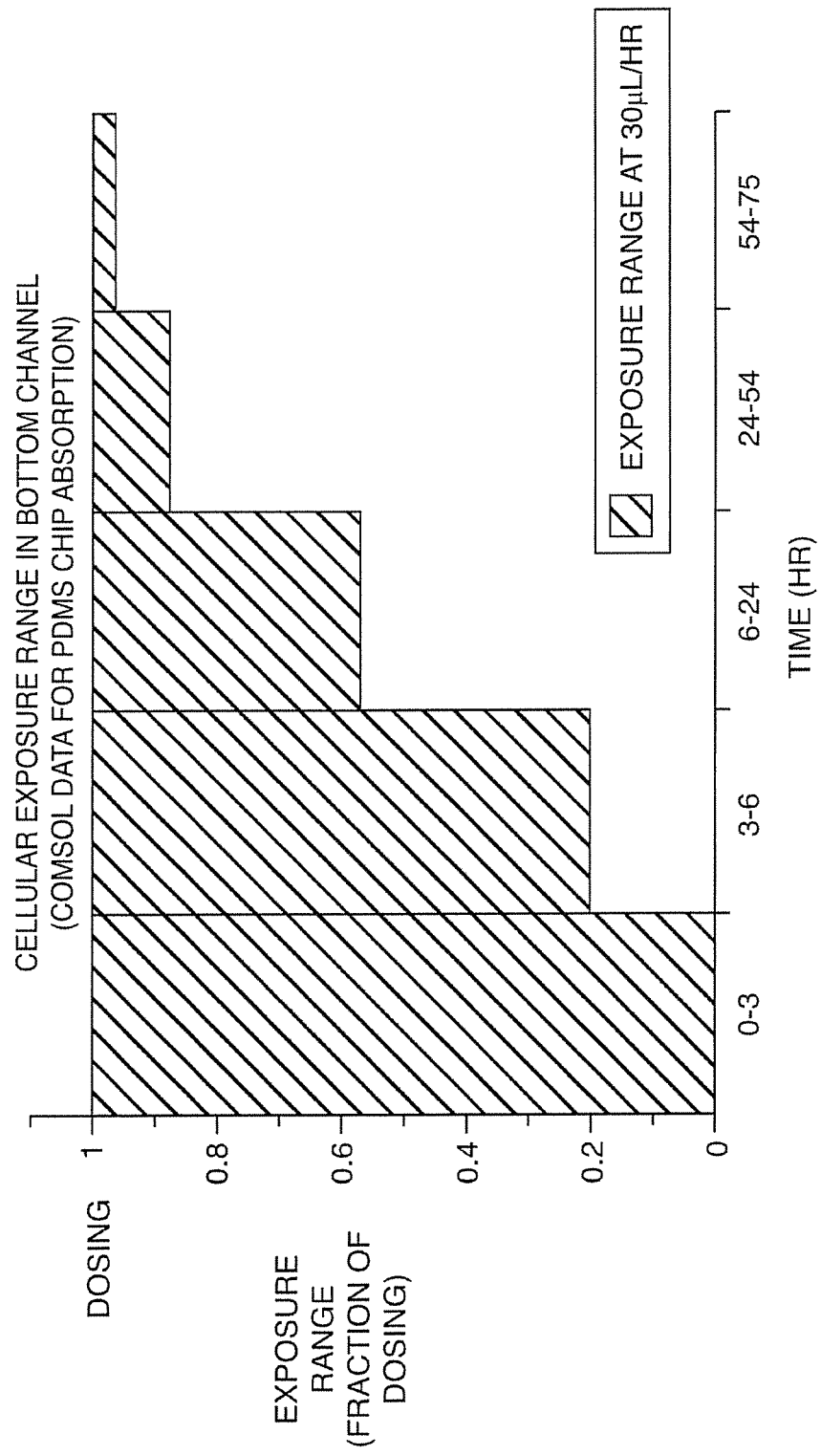

FIGS. 99A and 99B show a comparison between a computational (COMSOL) model results and actual experimental results for cellular exposure ranges of the small-molecule compound Coumarin. FIG. 99A shows experimental results of the cellular exposure range of the small-molecule compound Coumarin for a second channel of a microfluidic device. FIG. 99B shows computational (COMSOL) model results of the cellular exposure range of the small-molecule compound Coumarin for a second channel of a microfluidic device. It was found that the computational (COMSOL) model did not accurately predict the absorption, because the model did not take into account the rest of the flow system outside the microfluidic device. For this experiment the microfluidic device was in fluidic communication with a perfusion manifold assembly. The compound Coumarin was especially susceptible to absorption into one of the materials making up the perfusion manifold assembly, SEBS. As such, the computational (COMSOL) model did not accurately predict the absorption into the entire flow system.

Figure 100:
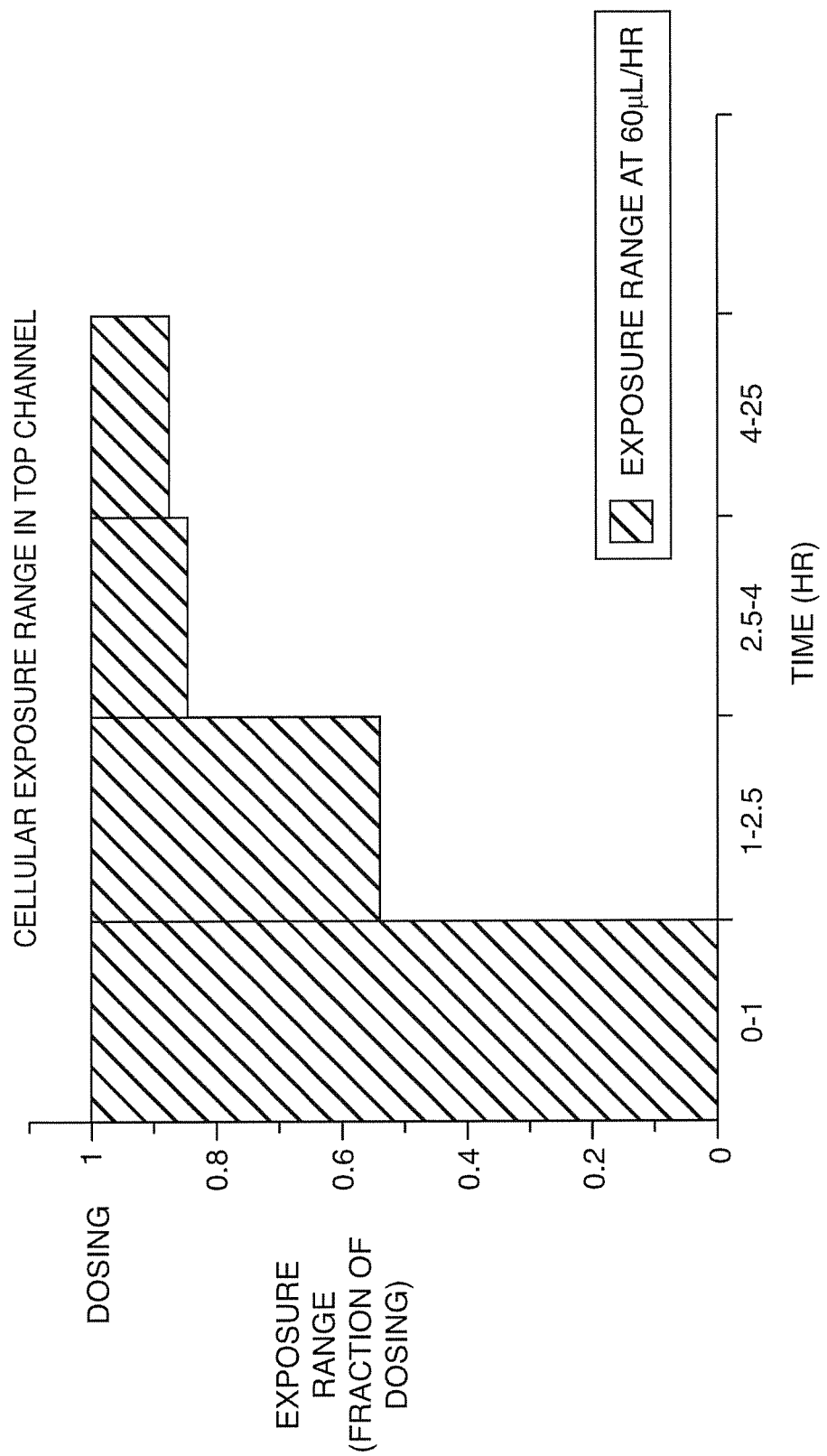
FIG. 100 shows experimental results for cellular exposure of the small-molecule compound Rhodamine in a two-channel microfluidic device comprising a PDMS membrane at a flow rate of 60 uL/hr.

FIG. 100 shows experimental results for cellular exposure of the small-molecule compound Rhodamine in a two-channel microfluidic device comprising a PDMS membrane at a flow rate of 60 uL/hr.

Figure 101:
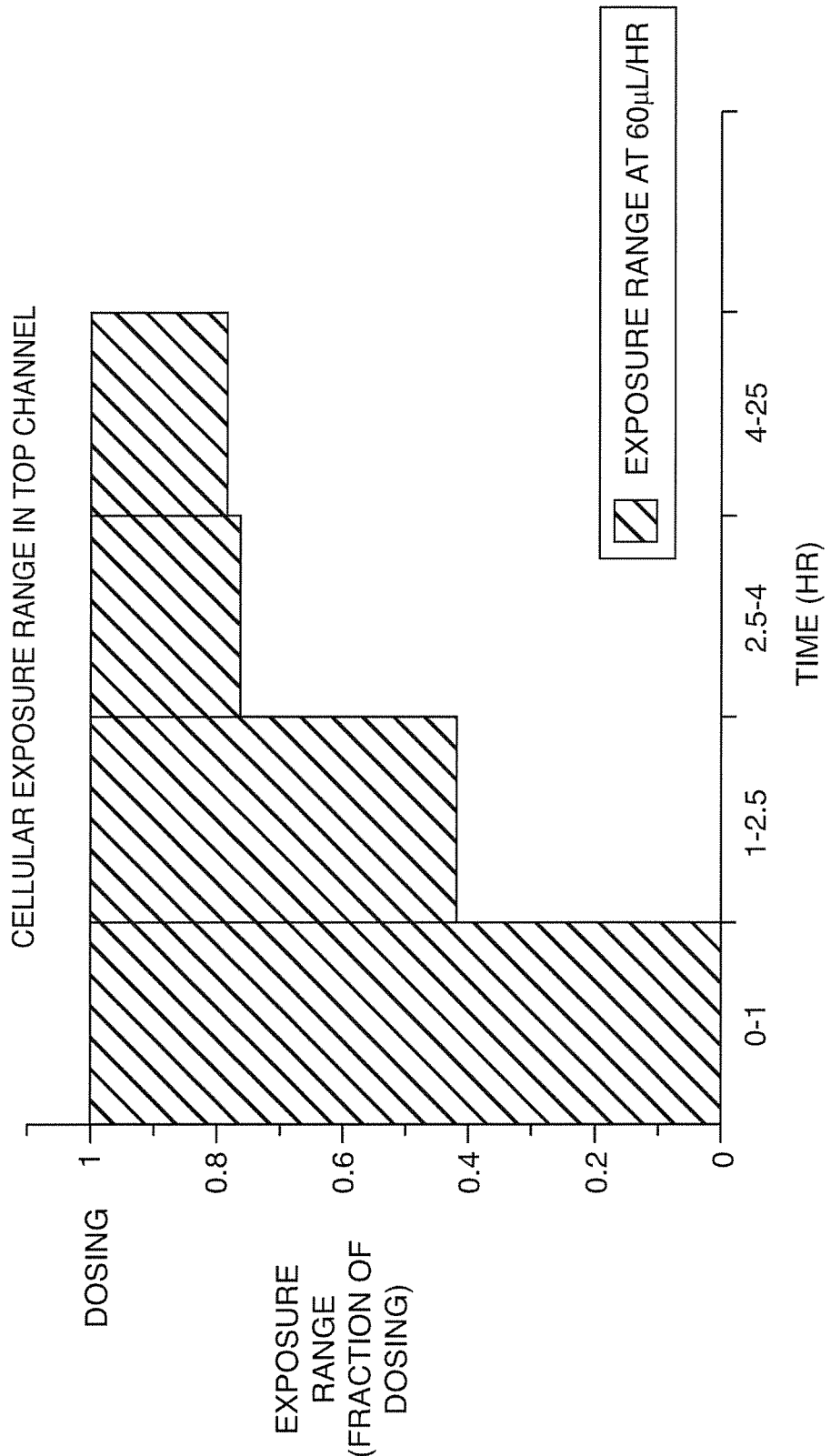
FIG. 101 shows experimental results for cellular exposure of the small-molecule compound Rhodamine in a two-channel microfluidic device comprising a PDMS membrane without pores at a flow rate of 60 uL/hr.

FIG. 101 shows experimental results for cellular exposure of the small-molecule compound Rhodamine in a two-channel microfluidic device comprising a PDMS membrane without pores at a flow rate of 60 uL/hr.

Figure 102:
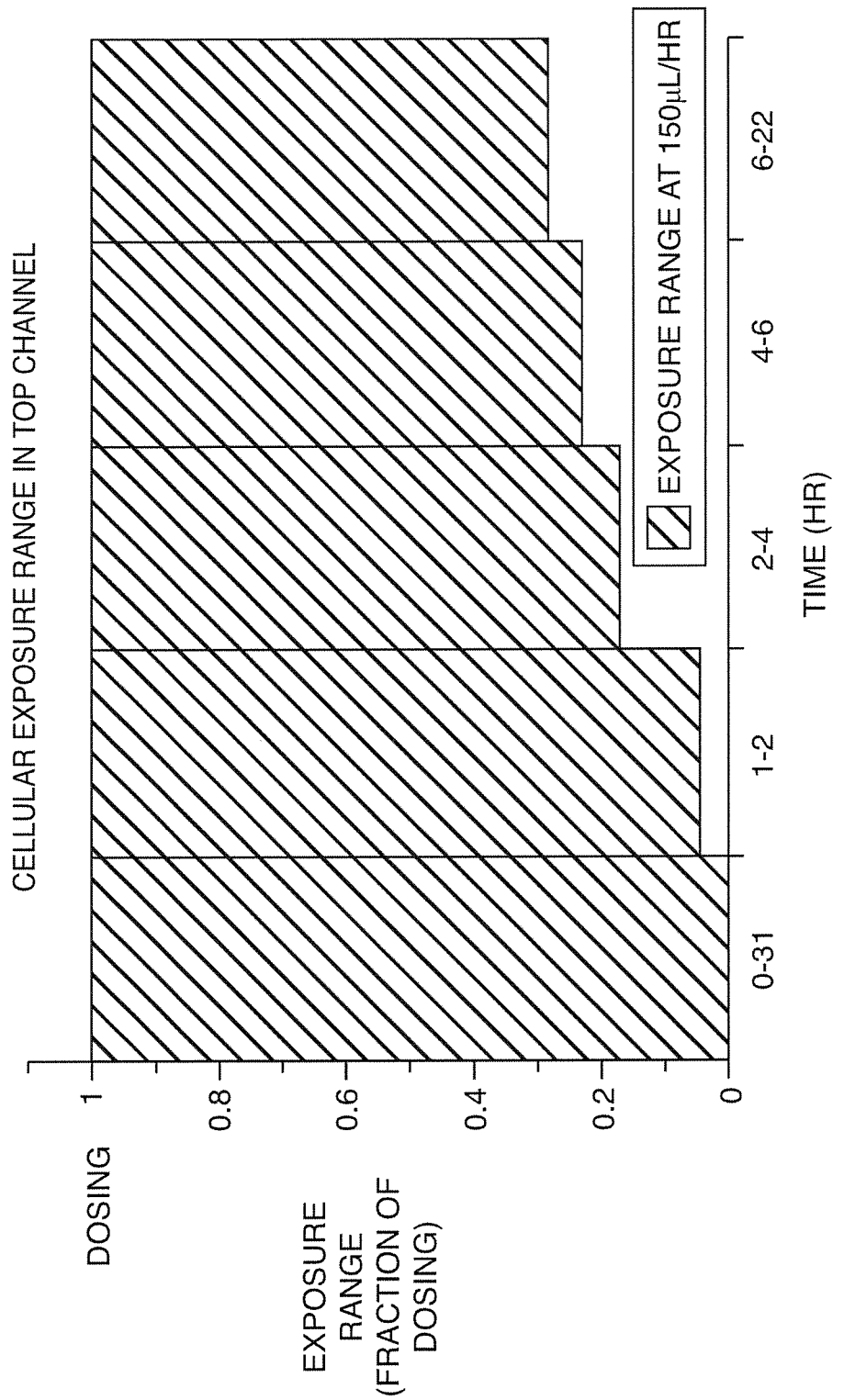
FIG. 102 shows experimental results for cellular exposure of the small-molecule compound Coumarin in a two-channel microfluidic device comprising a PDMS membrane at a flow rate of 150 uL/hr.

FIG. 102 shows experimental results for cellular exposure of the small-molecule compound Coumarin in a two-channel microfluidic device comprising a PDMS membrane at a flow rate of 150 uL/hr.

Figure 103:
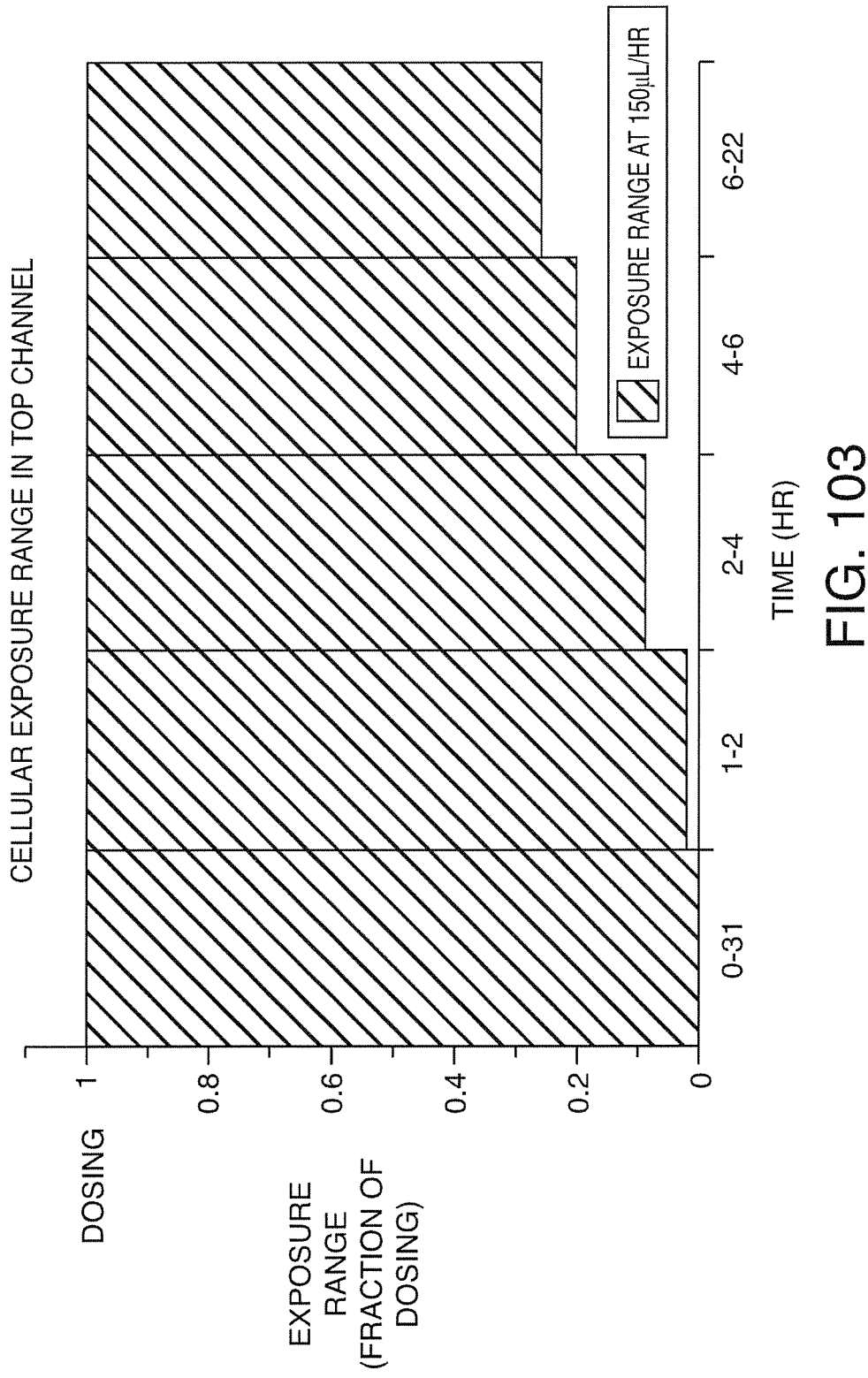
FIG. 103 shows experimental results for cellular exposure of the small-molecule compound Coumarin in a two-channel microfluidic device comprising a PDMS membrane without pores.
Figure 104:
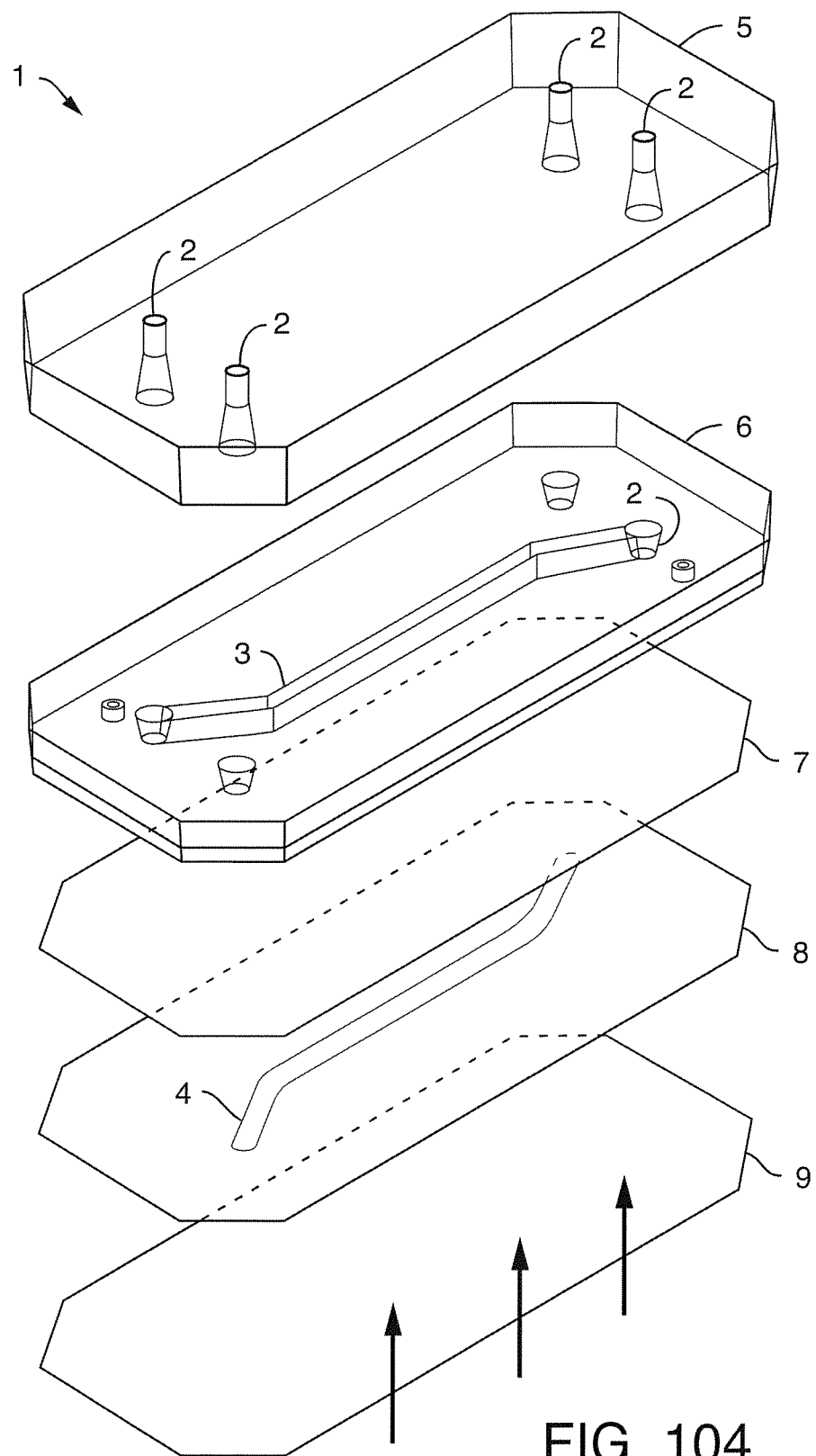
FIG. 104 shows the unilateral or unidirectional flow of gas, in this case oxygen, through the gas exchanger into the body of the low-absorbing, gas-permeable microfluidic device at a flow rate of 60 uL/hr.

FIG. 103 shows experimental results for cellular exposure of the small-molecule compound Coumarin in a two-channel microfluidic device comprising a PDMS membrane without pores.

Figure 105:
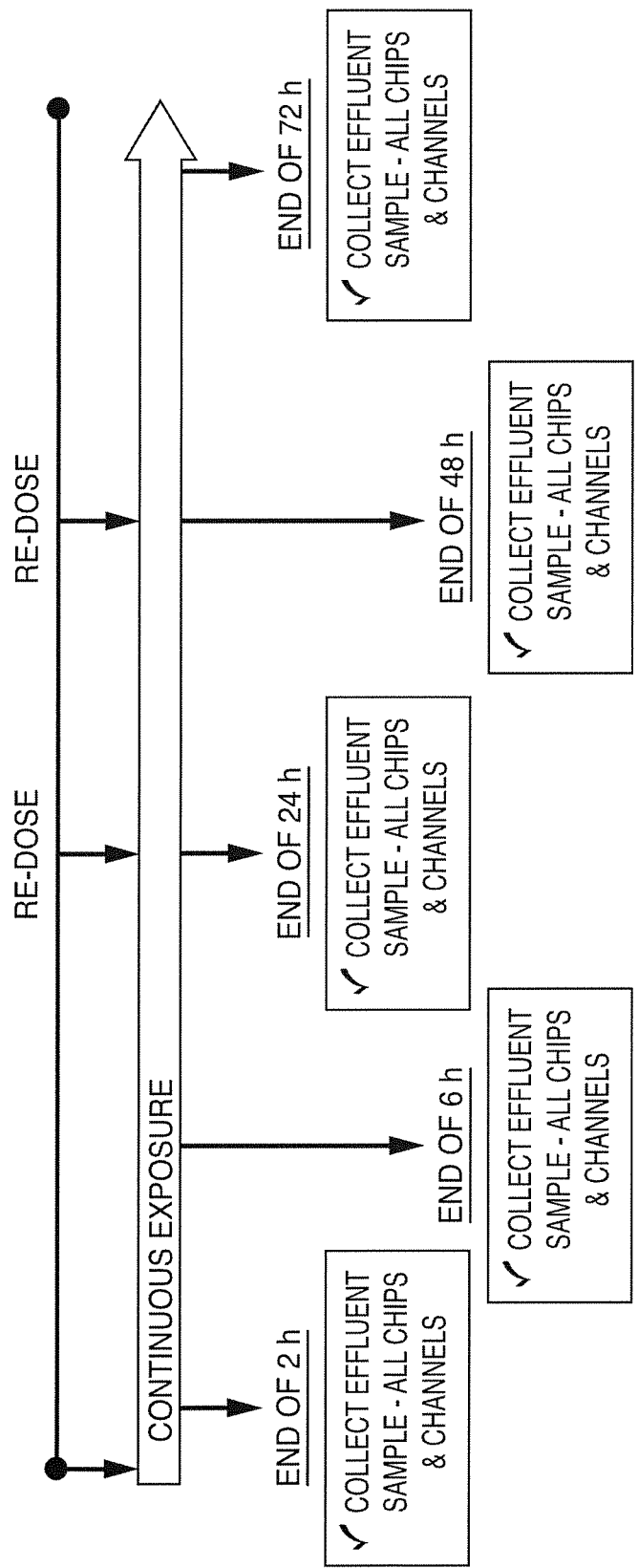
FIG. 105 shows a timeline for a flow test of two small-molecule compounds, Drug X and Drug Y. The dose concentration of Drug X was 10 μM and the dose concentration of Drug Y was 1 μM. For the experiment shown in FIG. 105 the end point analysis was liquid chromatography-mass spectrometry.

FIG. 105 shows a timeline for a flow test of two small-molecule compounds, Drug X and Drug Y. The dose concentration of Drug X was 10 µM and the dose concentration of Drug Y was 1 µM. For the experiment shown in FIG. 106 the end point analysis was liquid chromatography-mass spectrometry.

Figure 106A:
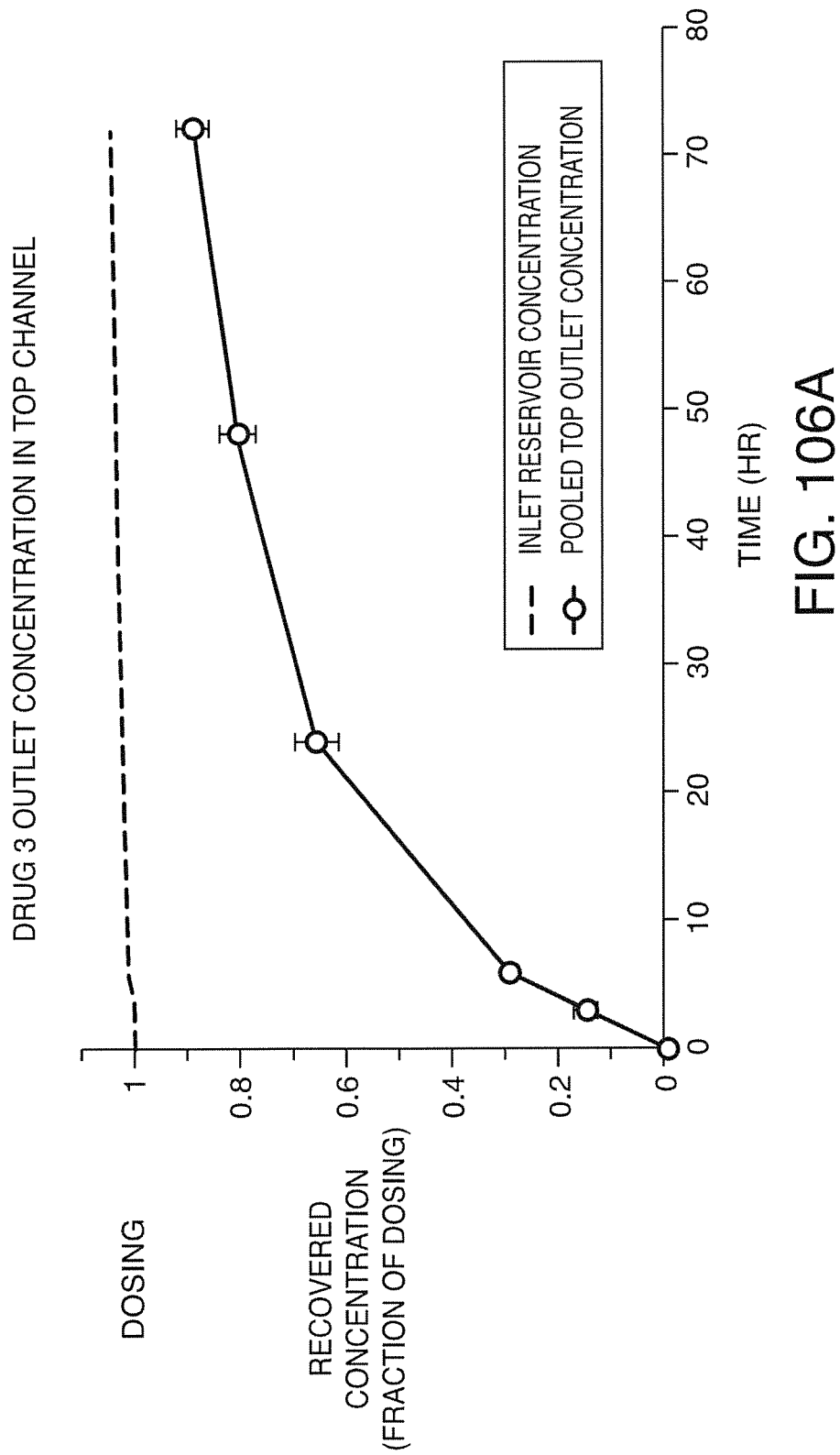
FIGS. 106A and 106B show a summary of flow studies of Drug X in a first channel of a two-channel microfluidic device.
Figure 106B:
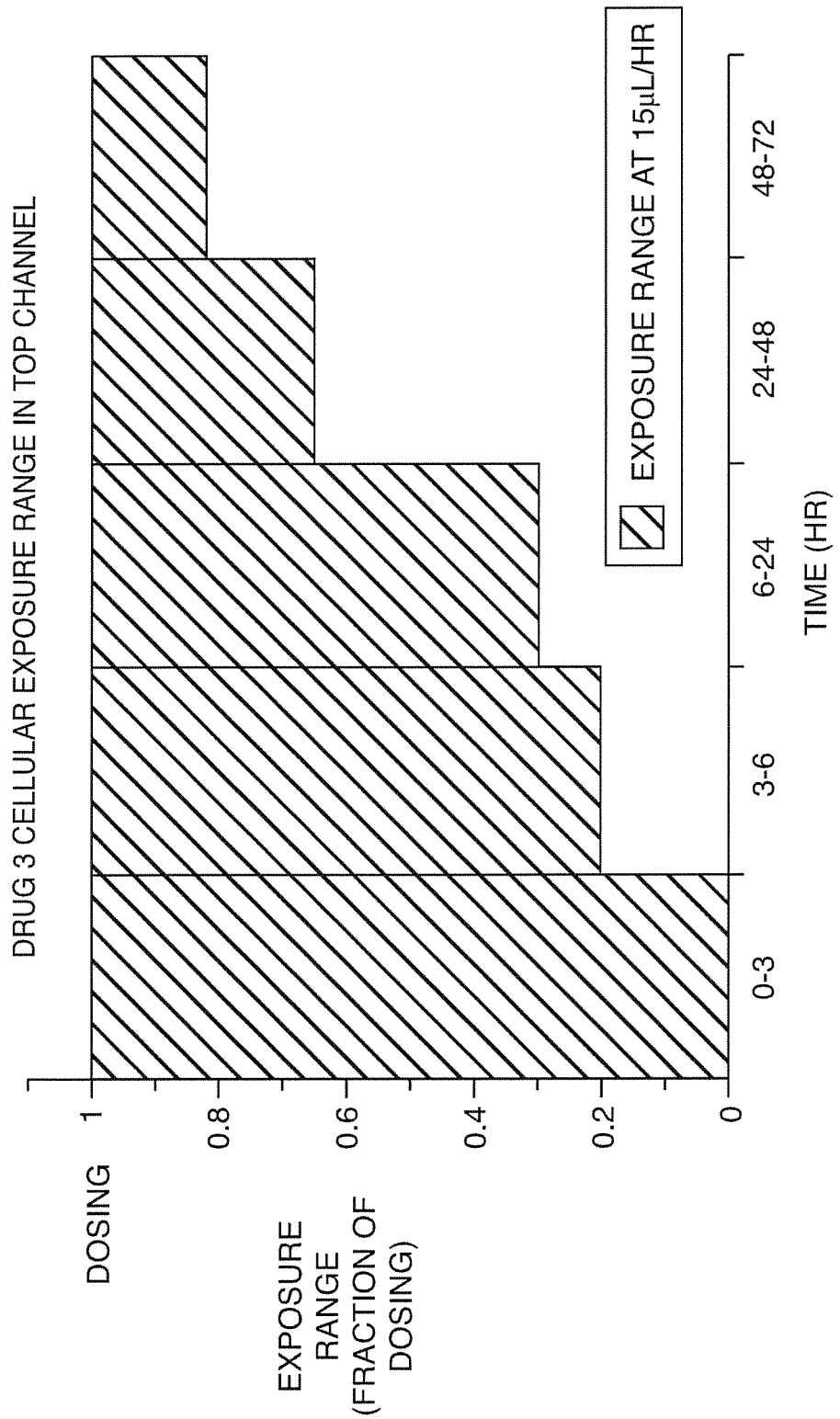

FIGS. 106A and 106B show a summary of flow studies of Drug X in a first channel of a two-channel microfluidic device. FIG. 106A shows the outlet concentration of Drug X over time. FIG. 106B shows cellular exposure ranges in the first channel. FIGS. 106A and 106B show that Drug X was absorbed into the system. The loss of Drug X is consistent with a highly absorbing molecule as nearly all the compound is recoverable at 72 hours, showing that the microfluidic device material became saturated. FIGS. 106A and 106B show that over time cell exposure to Drug X would be between 80-100%. The media carrying Drug X in FIGS. 106A and 106B also contained 2% fetal bovine serum (FBS).

Figure 107B:
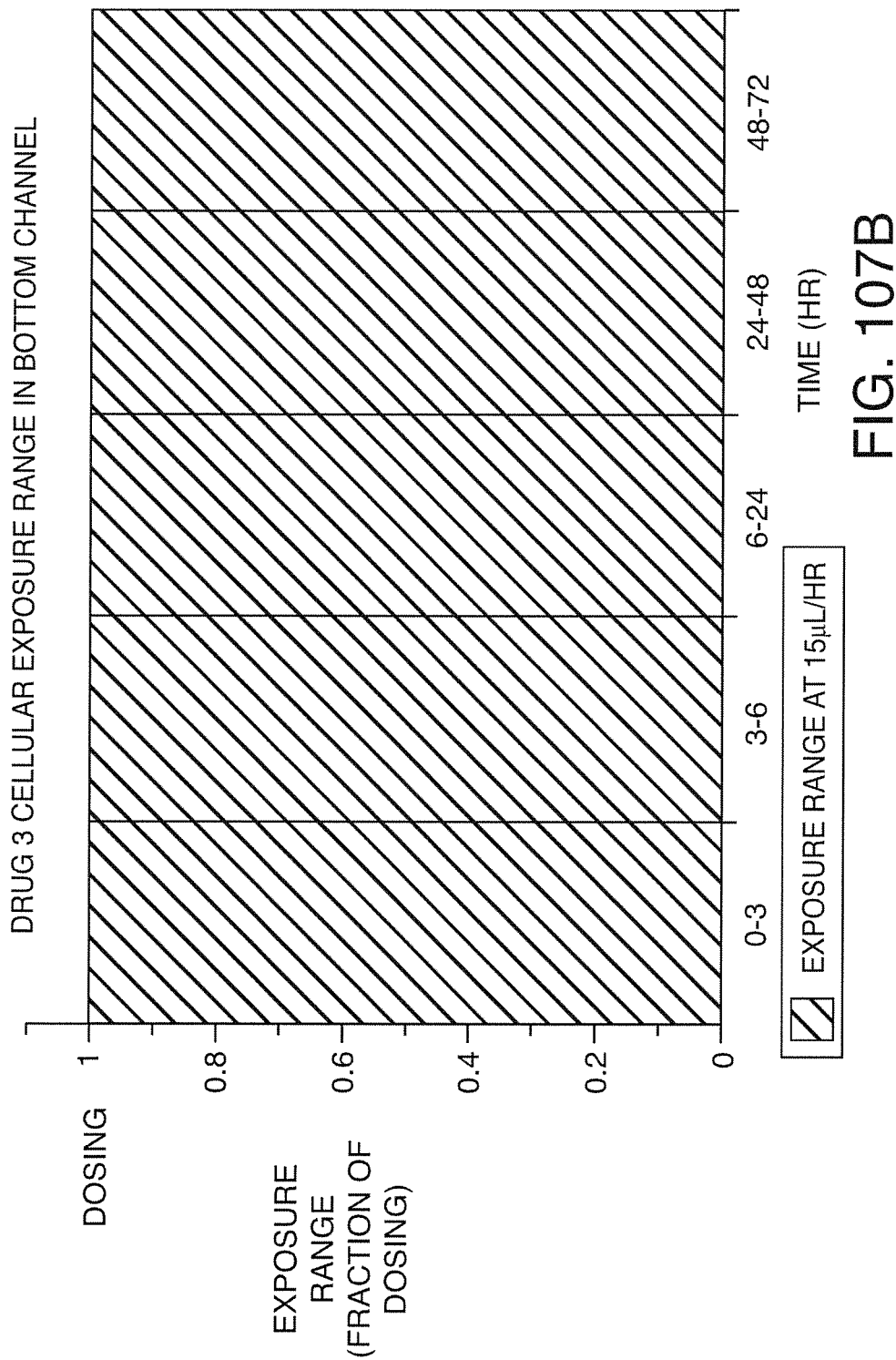

FIGS. 107A and 107B show a summary of flow studies of Drug X in a second channel of a two-channel microfluidic device. FIG. 107A shows the outlet concentration of Drug X over time. FIG. 107B shows cellular exposure ranges in the first channel. FIGS. 107A and 107B show that Drug X was absorbed into the system. The second channel flow rate may possibly be increased in order to lessen compound absorption.

Figure 108A:
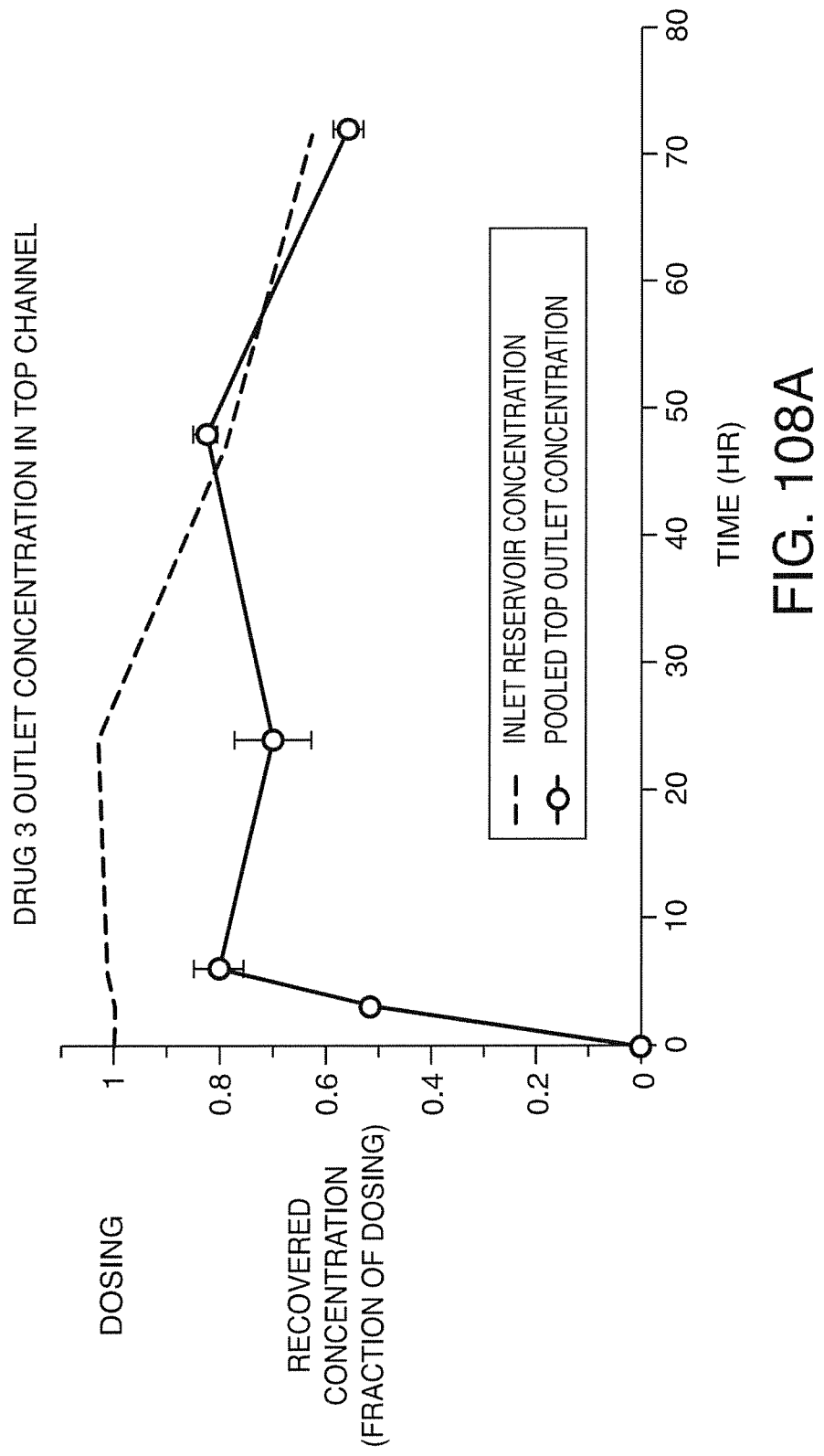
FIGS. 108A and 108B summarize flow studies of Drug Y in the first channel of a microfluidic device.
Figure 108B:
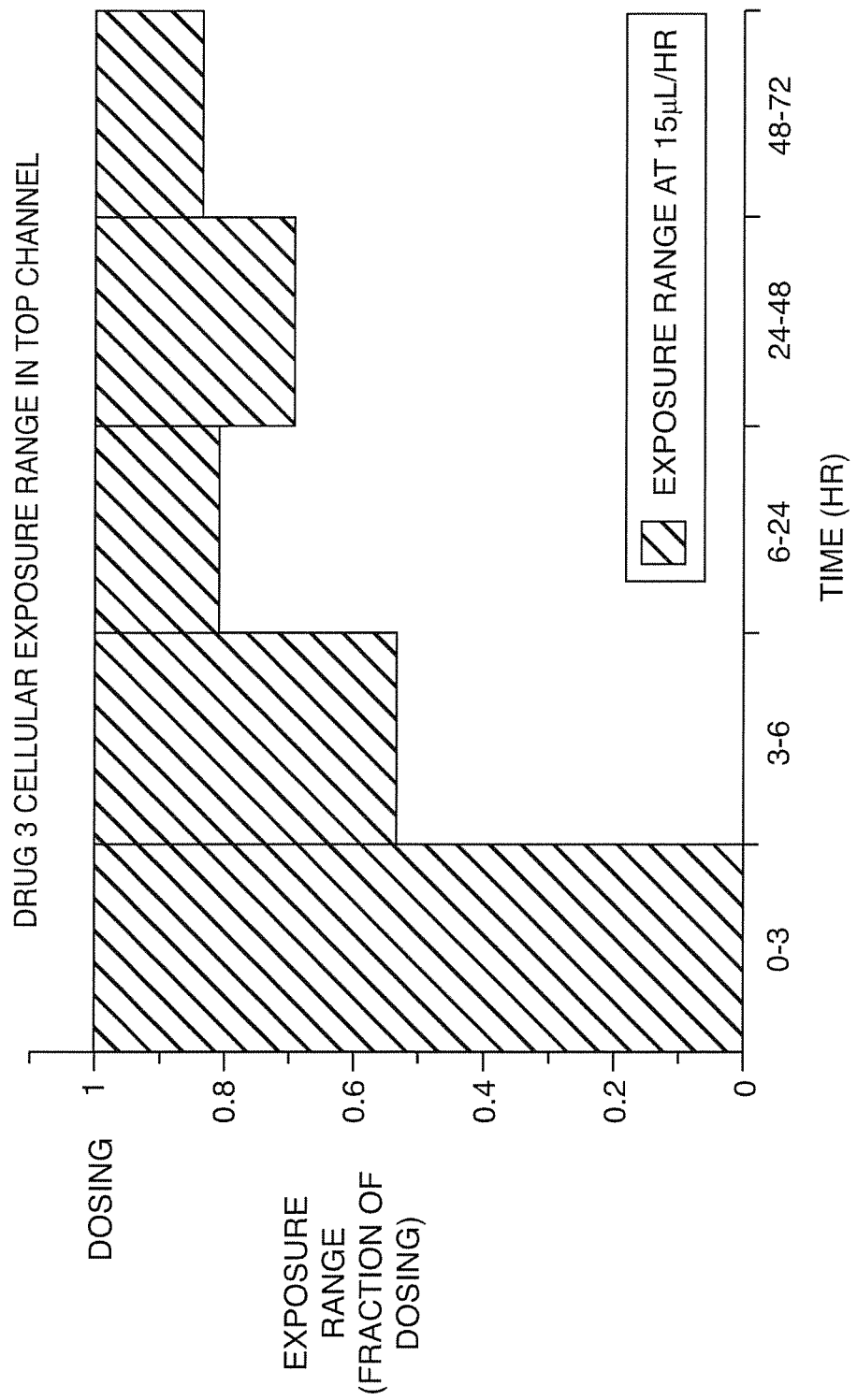

FIGS. 108A and 108B summarize flow studies of Drug Y in the first channel of a microfluidic device. FIG. 108A shows the outlet concentration of Drug Y over time. FIG. 108B shows the range of cellular exposure in the first channel of the microfluidic device over time. The compound loss is consistent with a highly absorbing molecule as nearly all the compound is recovered over 72 hours in the effluent, as the material making up the microfluidic device becomes saturated. Over time cellular exposure of Drug Y would be between 80-100%. The media carrying Drug Y in FIGS. 108A and 108B also contained 2% fetal bovine serum (FBS).

Figure 109A:
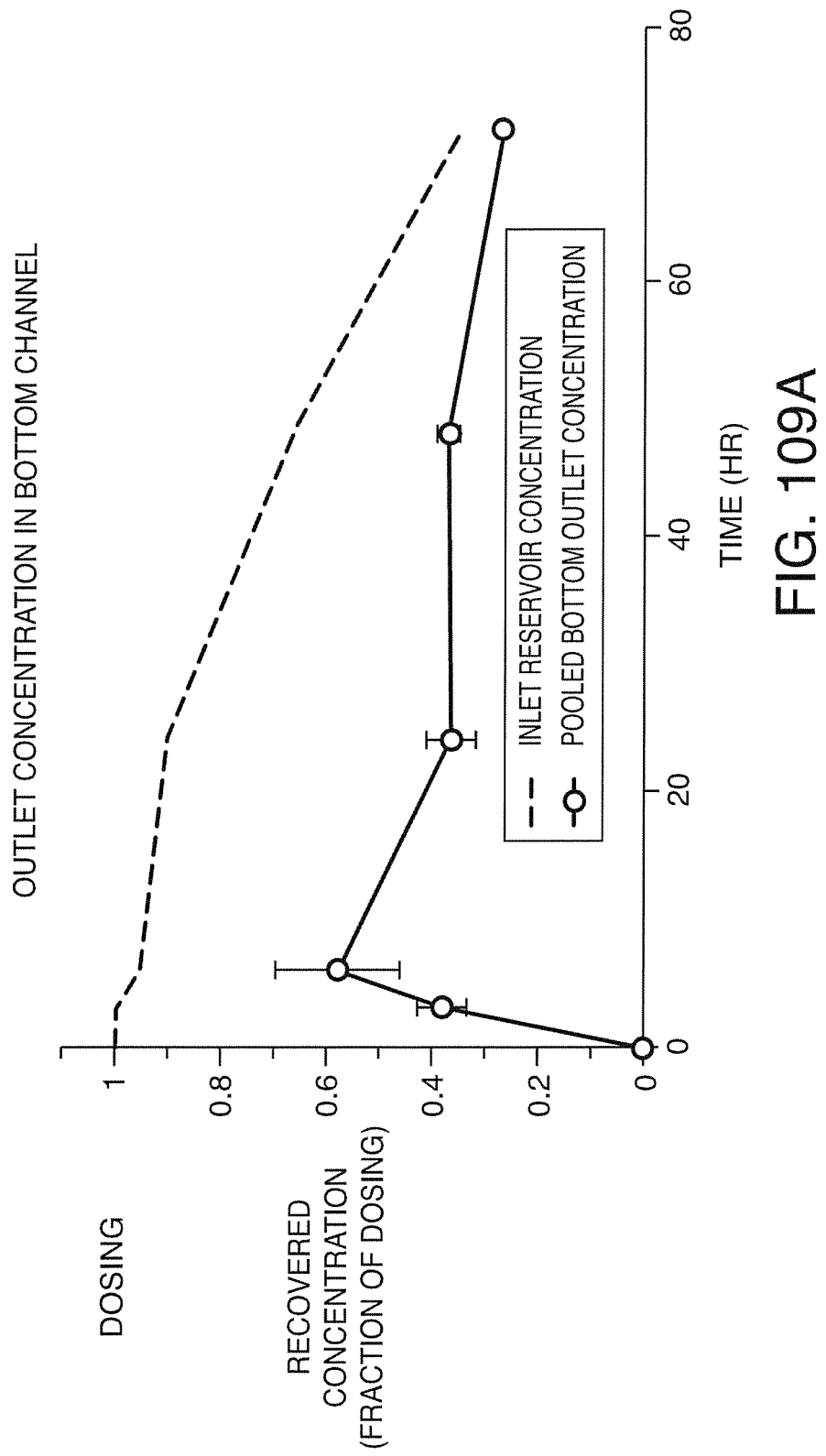
FIGS. 109A and 109B summarize flow studies of Drug Y in the second channel of a microfluidic device.
Figure 109B:
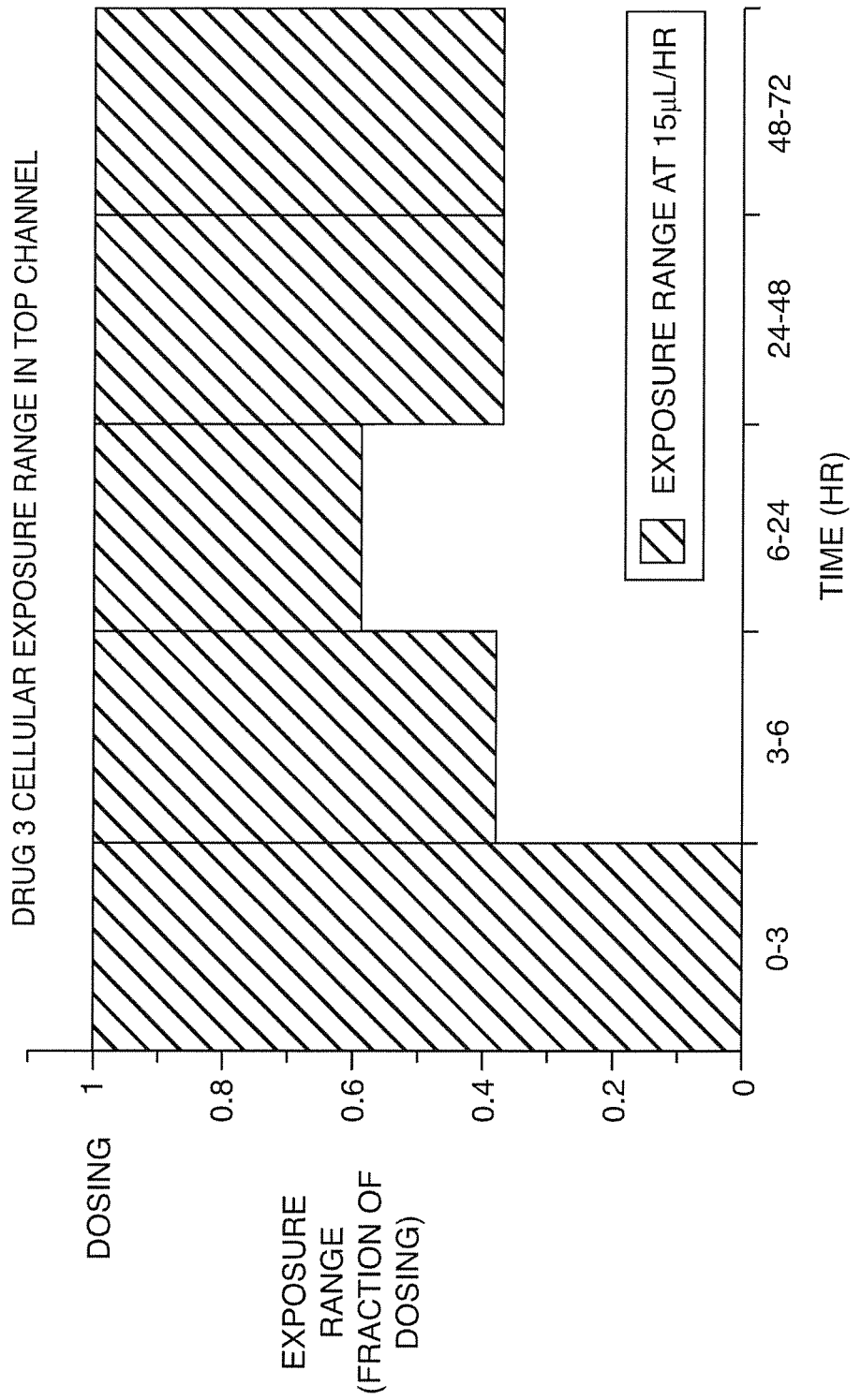

FIGS. 109A and 109B summarize flow studies of Drug Y in the second channel of a microfluidic device. FIG. 109A shows the outlet concentration of Drug Y over time. FIG. 109B shows the range of cellular exposure in the second channel of the microfluidic device over time. The compound loss in the second channel of the microfluidic device points towards absorption. The flow rate may be increased to perhaps decrease compound absorption.

The compound distribution kit was used successfully to decide whether or not to commence a drug-study in an Organ-Chip with cells. It was contemplated to test cannabidiol (CBD oil) in microfluidic devices seeded with cells (for liver, skin, lung, kidney, etc.) for toxicity, efficacy, and/or ADME. The compound distribution kit was run to assess the ability at several flow rates. The Compound Distribution Kit found complete/total absorption or loss of compound in the microfluidic device fabricated from entirely PDMS, which indicated that testing CBD on cells in PDMS microfluidic devices could most likely not be supported (compound loss was too significant) even at the highest flow rate. Measured outlet concentrations of the compound (CBD) were "0" and nothing could be detected. Decision was made not to pursue testing CBD on a microfluidic device fabricated entirely from PDMS. However, other, low-absorbing embodiments discussed herein would be excellent platforms to test the effects of CBD oil on cells.

Figure 115A:
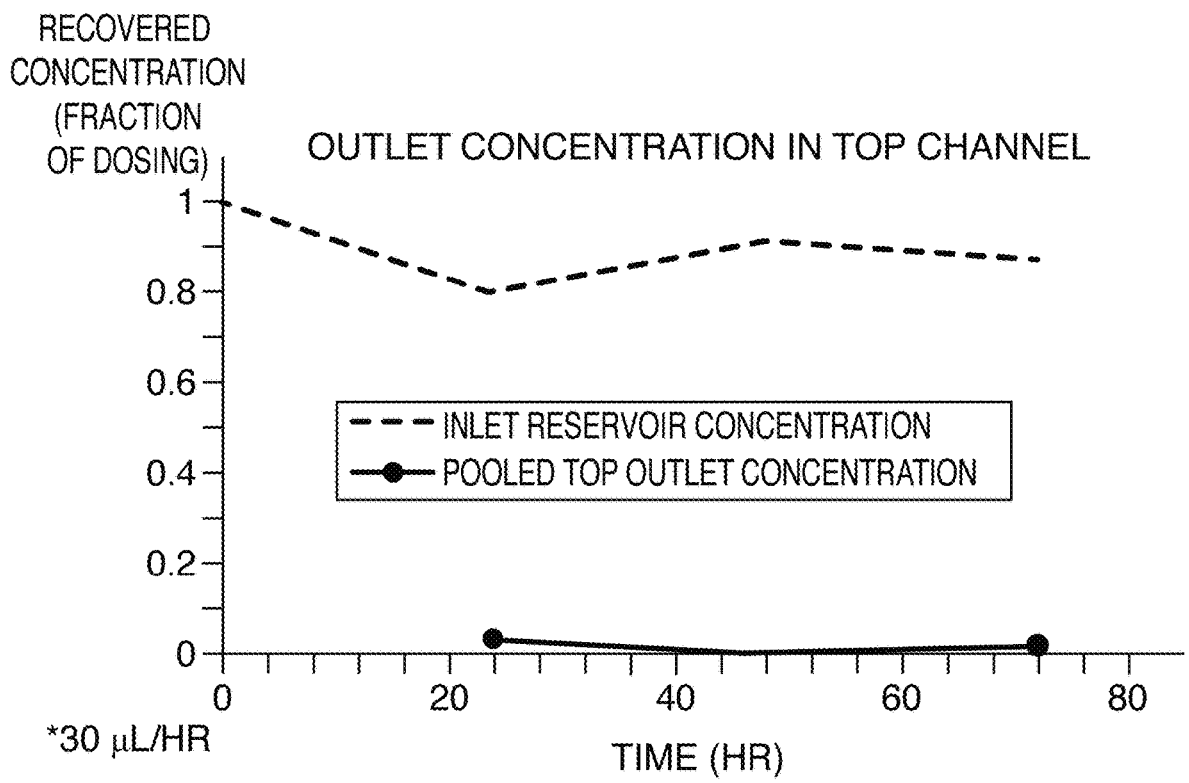
FIGS. 115A-D show the results of an experiment testing the absorption of a compound, herein called Compound Z, in a PDMS microfluidic device comprising liver cells using the Compound Distribution Kit.
Figure 115B:
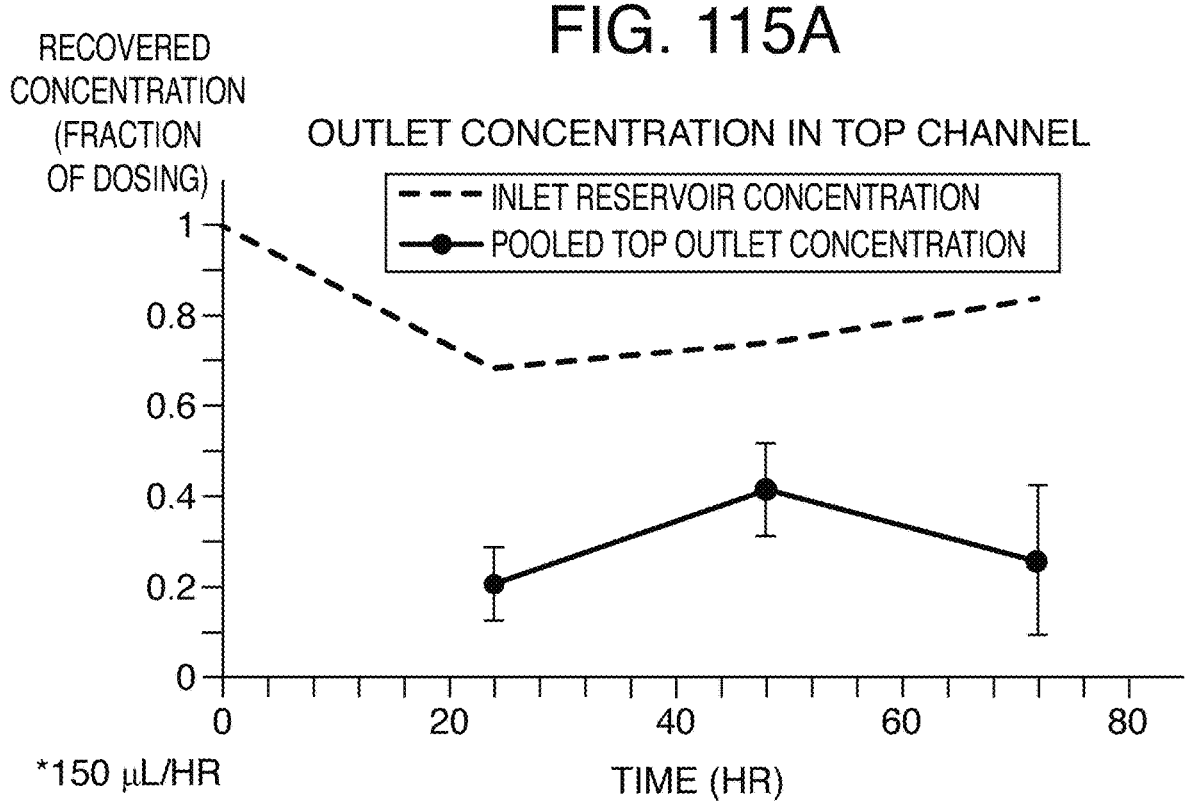
Figure 115C:
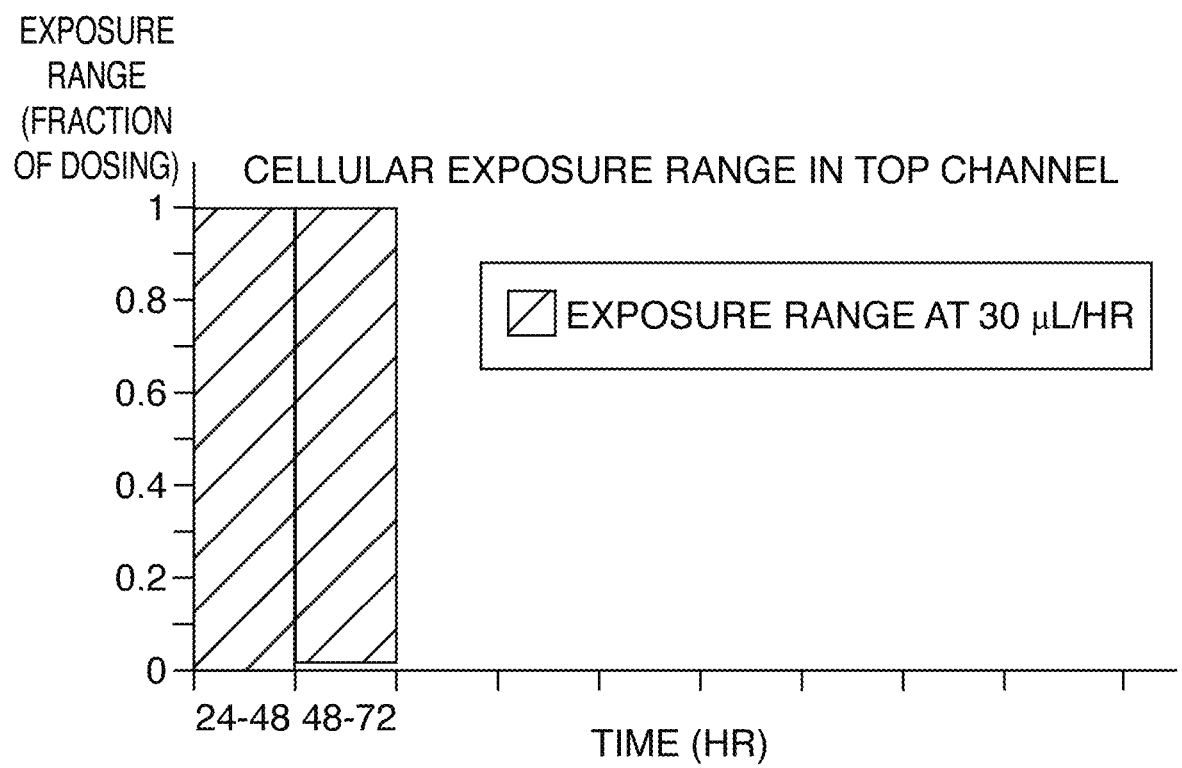
Figure 115D:
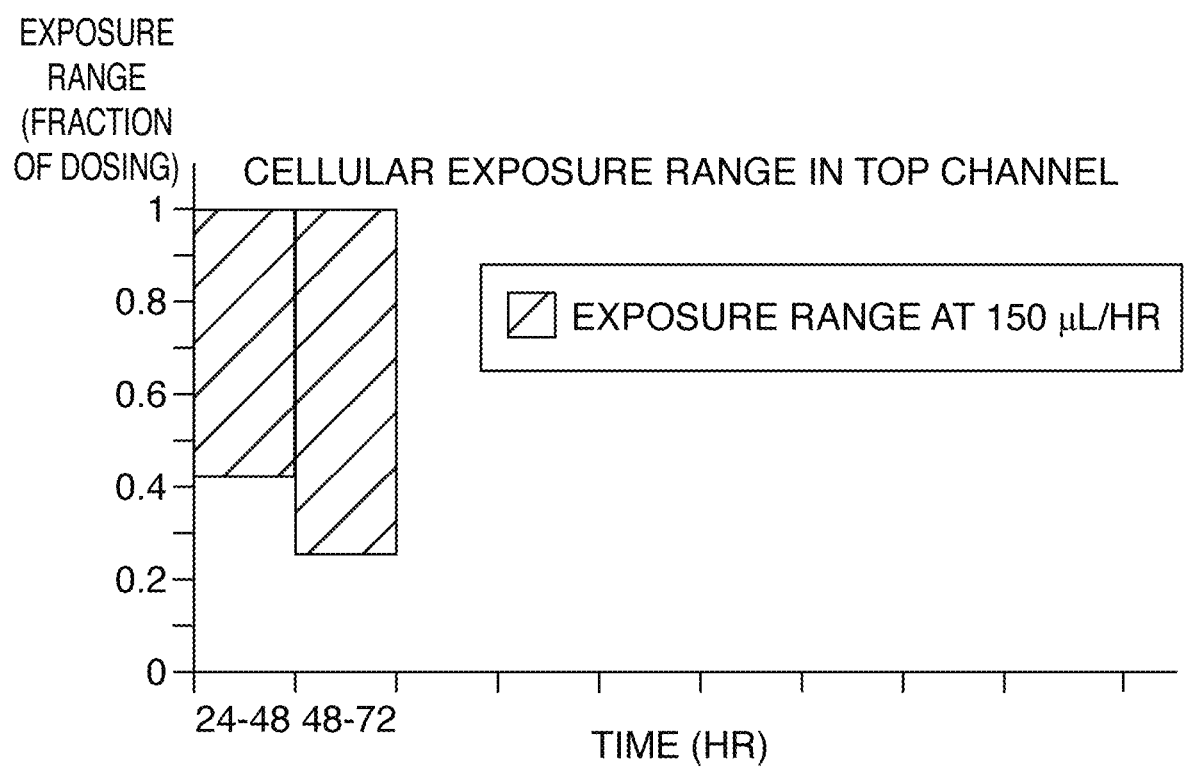

FIGS. 115A-D show the results of an experiment testing the absorption of a compound, herein called Compound Z, in a PDMS microfluidic device comprising liver cells using the compound distribution kit. FIG. 115A shows nearly complete absorption of Compound Z at low flow rates, such as 30 uL/hr. FIG. 115B shows that significant absorption (nearly 80% loss) of Compound Z at high flow rates, such as 150 uL/hr. FIG. 115C shows cellular exposure of Compound Z in said first channel of the compound at 30 uL/hr. FIG. 115D shows cellular exposure of Compound Z in said first channel of the compound at 150 uL/hr. Experiments were also run at a higher concentration to compensate for compound loss. Increased dosing concentration of Compound Z was conducted and the recovered outlet concentration was used as the effective "cellular exposure concentration." Increasing the dosing concentration increases the likelihood of a false positive (compound is not toxic, but a toxic effect is seen in the microfluidic device), but eliminates the possibility of a false negative (compound is actually toxic, but the microfluidic device does not show any toxic response). It is to be noted that liver cells were used in these experiments, however any cell type and related readout is contemplated.

Throughout the validation experiments several sources of variability were identified. These sources of variability may be targeted in order to decrease the total variability in the compound distribution kit. Variability may arise from differences between culture modules over time, including but not limited to the formation of bubbles. Variability may also arise from user inconsistencies, such as dosing concentration issues (precipitation, weighing error, dilution error, etc.), not aspirating perfusion manifold assembly outlet reservoirs between time points resulting in sample pooling, not aspirating perfusion manifold assembly reservoirs at the start of the experiment after the ignition flush resulting in sample dilution, pipetting errors, protocol deviation, etc. Variability may also arise from material equivalency, such as microfluidic devices fabricated from PDMS versus microfluidic devices fabricated from other polymers, or microfluidic devices that have or have not been treated. Variability may also arise from the exclusion of certain components in order to ease use of the compound distribution kit. For example, when using the compound distribution kit on microfluidic devices for use with testing cells, the cells may be excluded. However, the exclusion of cells may give rise to a slight variability.

6. Reciprocation Experiments

Experiments were run to see if reciprocating media through a perfusion manifold assembly to both COP and PDMS microfluidic devices comprising liver cells would improve liver recapitulation. Hepatocyte albumin production was measured as a readout of liver cell health. Any cell type is contemplated, however liver cells were chosen to be used.

Figure 112:
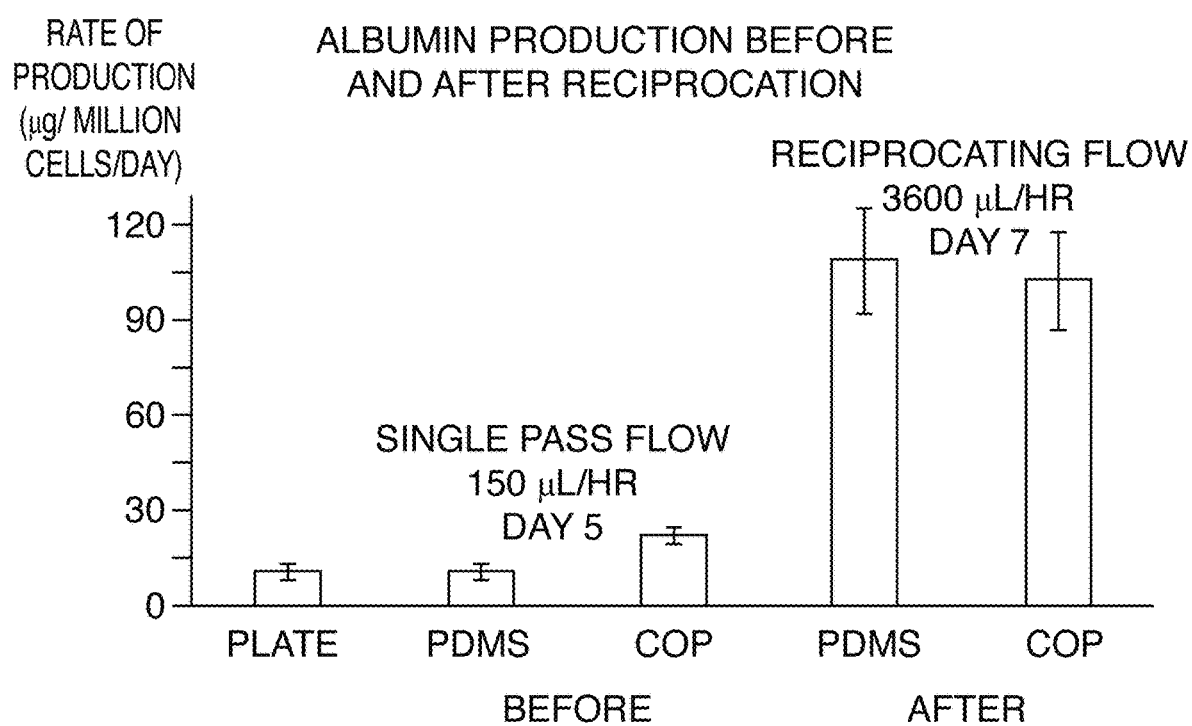
FIG. 112 shows a graph of albumin production in a PDMS and COP microfluidic devices comprising liver cells before and after reciprocating fluid. It may be seen in FIG. 112 that reciprocating fluid leads to an increase in albumin production as compared to single pass flow.

FIG. 112 shows a graph of albumin production in a PDMS and COP microfluidic devices comprising liver cells before and after reciprocating fluid. It may be seen in FIG. 112 that reciprocating fluid leads to an increase in albumin production as compared to single pass flow.

The results shown in FIG. 112 were surprising and completely unexpected. The expectation was that the rates of albumin production would be conserved, and would not decline as this would indicate decline of hepatocyte function. Increased albumin production rate indicates an increase in metabolic function. It was desired to confirm the understanding that rapid reciprocation leads to an increase in albumin production. To do this, the scientists: repeated the experimental plan of used to achieve the data shown in FIG. 112, hoping to replicate the results/albumin trend, took additional albumin samples after returning the microfluidic devices to single-pass/uni-directional flow (after reciprocating for 24 hrs). If the results shown in FIG. 112 were valid, the results of the following experiment would predict a similar increase in albumin production after reciprocating microfluidic devices for 24 hrs as was done in the prior experiment, and possibly see a return to lower albumin production levels after returning microfluidic devices to single-pass flow.

Figure 113:
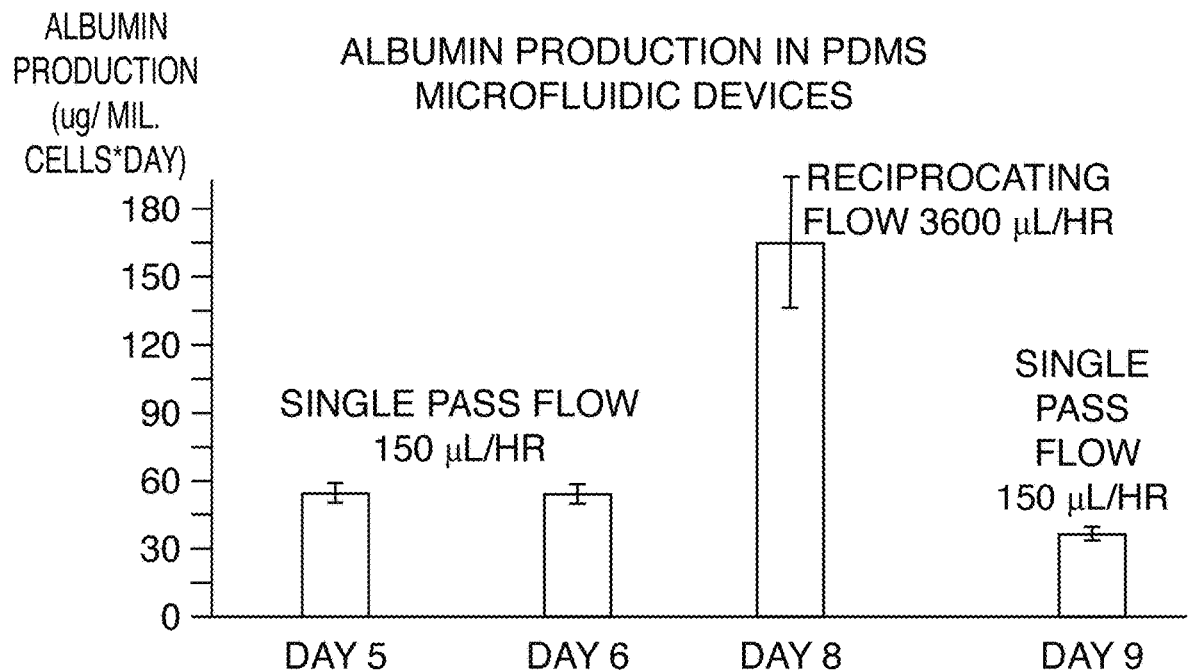
FIG. 113 shows albumin production in PDMS microfluidic devices comprising liver cells before and after reciprocating fluid. It may be seen that reciprocating fluid leads to an increase in albumin production.

FIG. 113 shows albumin production in PDMS microfluidic devices comprising liver cells before and after reciprocating fluid. The results of FIG. 113 confirm linkage between reciprocation protocol and increased albumin production and indicate reversibility of the phenomenon.

Based on the data shown in FIGS. 112 and 113, reciprocation was seen to improve albumin production in both COP and PDMS microfluidic devices. Furthermore, albumin production was at physiologically relevant levels in both the COP and PDMS microfluidic devices following the use of reciprocation.

7. Gas-Permeable Microfluidic Device Gas-Control Using Incubator Experiments

As was previously described, gas concentrations within microfluidic devices may be controlled using gas-control incubators. It is of note, that the experiments described below are related to entirely gas-permeable microfluidic devices (12) fabricated from gas-permeable materials, such as the microfluidic device of U.S. Pat. No. 8,647,861.

Figure 116:
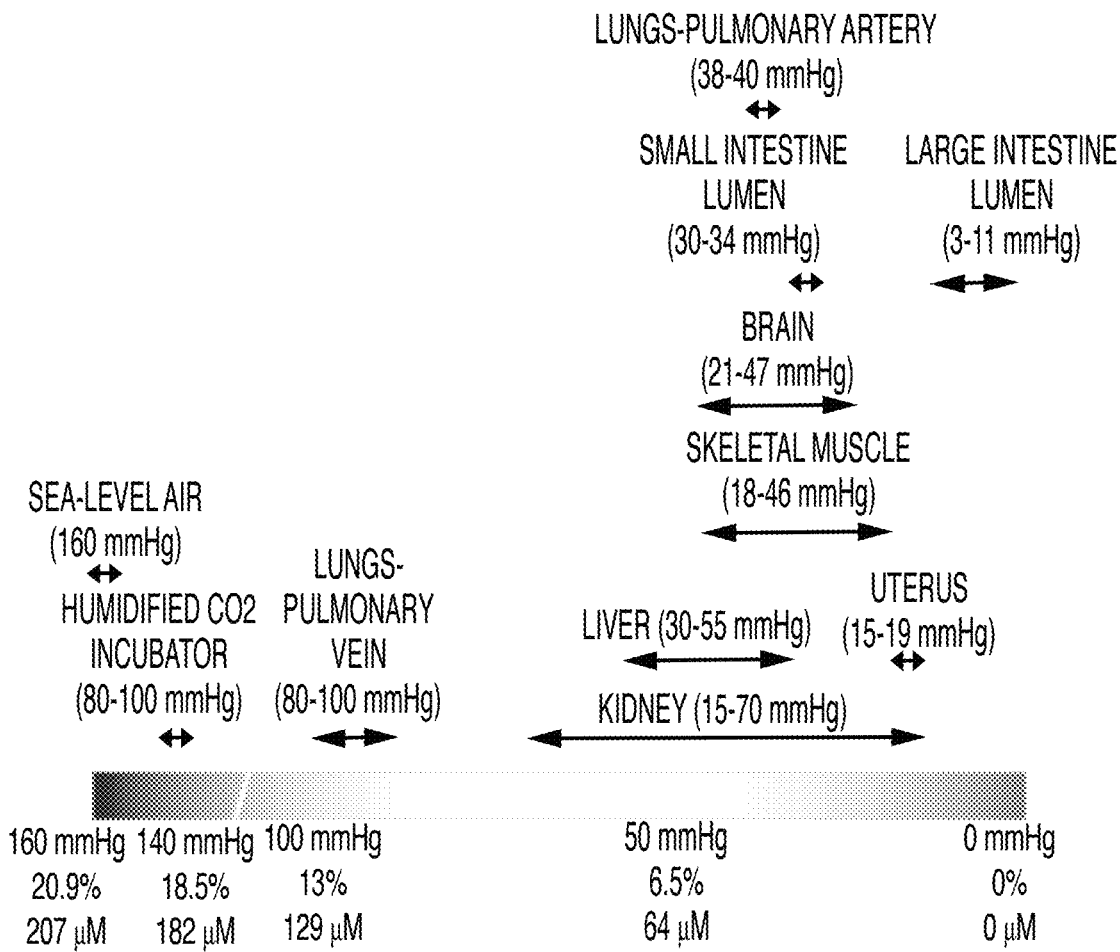
FIG. 116 shows a diagram of oxygen tensions in various human organs. Oxygen, carbon dioxide, and various gases are known to influence the biological function of cells and can have a profound effect in tissues and various disease states. For example, oxygen tension differs dramatically in the human body across organs, yet traditional cell culture techniques do not take this into account.

Of the various gases that cells are exposed to, oxygen, or lack thereof, is responsible for many fundamental cellular properties and processes. FIG. 116 shows a diagram of oxygen tensions in various human organs. Oxygen, carbon dioxide, and various gases are known to influence the biological function of cells and can have a profound effect in tissues and various disease states. For example, oxygen tension differs dramatically in the human body across organs, yet traditional cell culture techniques do not take this into account.

Figure 117:
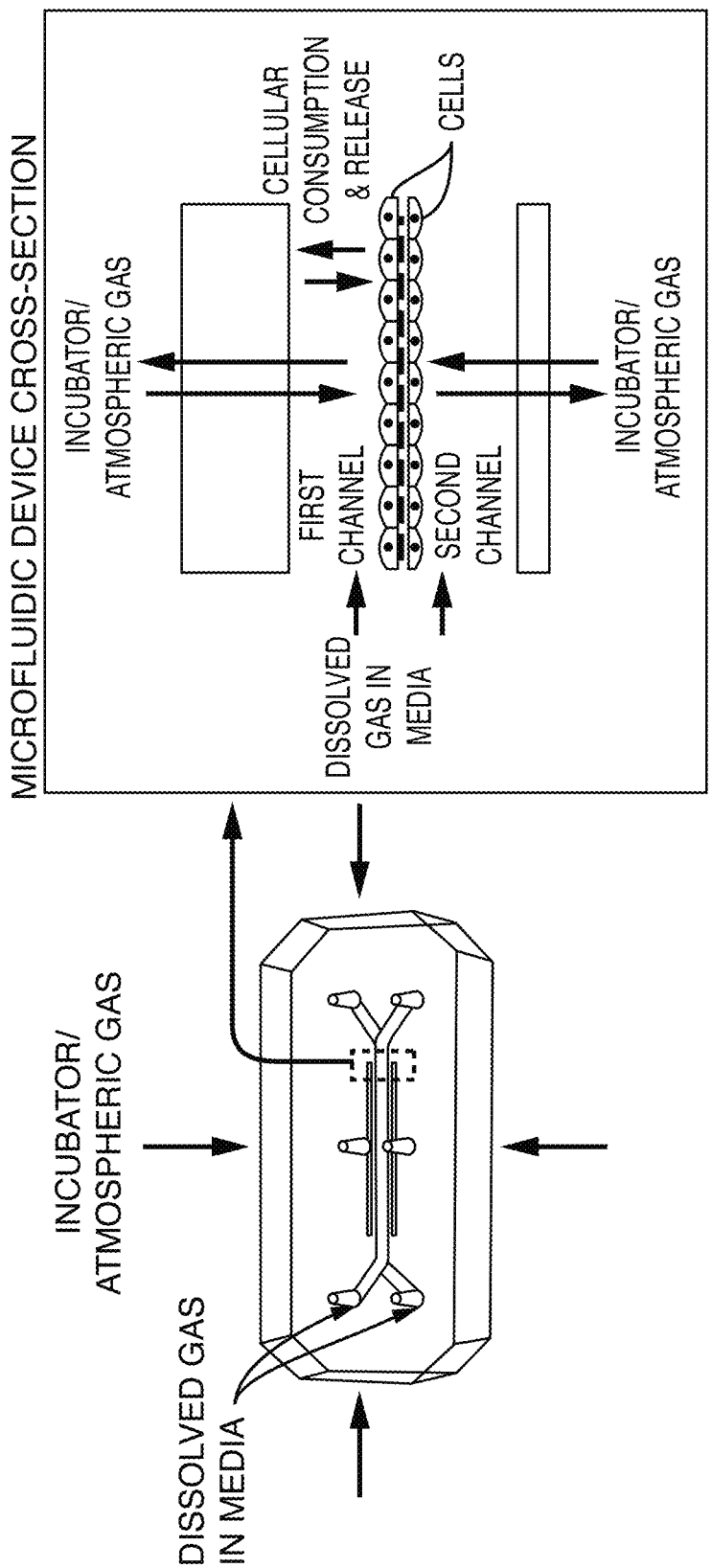
FIG. 117 shows a diagram of gas exchange in a PDMS microfluidic device. Per FIG. 117, the method of gas transport in the microfluidic device includes gas exchange between an incubator and the microfluidic device material, the microfluidic device material and the cell culture media, and the cell culture media and the cells.

To modify the oxygen microenvironment in gas-permeable microfluidic devices (12), a gas-controlled incubator may be set to the desired oxygen setpoint and a desired cell culture protocol may be followed. FIG. 117 shows a diagram of gas exchange in a gas-permeable microfluidic device (12). Per FIG. 117, the method of gas transport in the gas-permeable microfluidic device (12) includes gas exchange between an incubator and the microfluidic device material, the microfluidic device material and the cell culture media, and the cell culture media and the cells (33). When a gas-permeable microfluidic device (12) is equilibrated to the incubator oxygen, a first (3) and a second (4) channel may be considered experience equivalent oxygen concentrations. Additionally, when using highly permeable microfluidic devices (12), such as ones fabricated from silicone, inlet media oxygen concentrations in perfusion manifold assembly reservoirs and flow rate will not significantly influence the oxygen microenvironment in the gas-permeable microfluidic device (12). Note that the addition of cells (33) and microbes (36) will change the channel oxygen concentrations independently based on cellular oxygen consumption.

With regards to instrumentation, several exemplary pieces of equipment were found through experimentation. The Thermo Scientific™ Heracell™ 240i was found to be the best gas-control incubator for reliability and efficiency. It was found in general that any standard cell culture incubator may be used with a separate gas controller. The BioSphereix ProOx 360 was found to be the best gas controller, which injects nitrogen to displace oxygen within the incubator, being regulated by an oxygen sensor placed inside the incubator.

Figure 118:
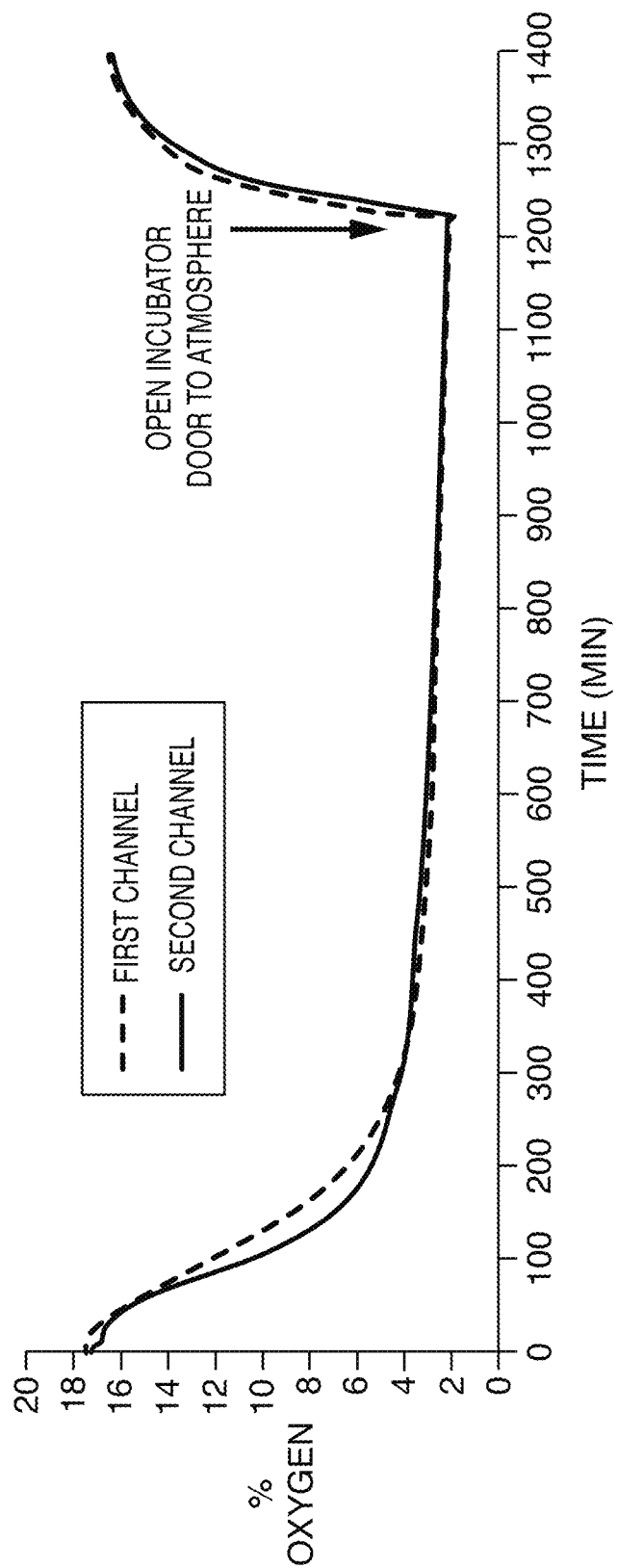
FIG. 118 shows a diagram of the results of microfluidic device response to various oxygen phases while in a cell culture incubator. Oxygen measurements were taken of a microfluidic device outlet under flow at 30 µL/hr flow in a culture module, wherein the flow is with 18.5% oxygen into the inlet.

To begin experiments the incubators are at atmospheric conditions. Inducing hypoxia in the incubator, and thus the gas-permeable microfluidic devices (12), perfusion manifold assemblies (14), and culture modules (42) may take a significant amount of time as may be seen in FIG. 118. FIG. 118 shows a diagram of the results of gas-permeable microfluidic device (12) response to various oxygen phases while in a cell culture incubator. Oxygen measurements were taken of a gas-permeable microfluidic device (12) outlet under flow at 30 µL/hr flow in a culture module, wherein the flow is with 18.5% oxygen into the inlet. As seen in FIG. 118 the incubator starts at atmospheric oxygen levels (18.5% in a humidified incubator), reaches 1% oxygen setpoint (seen with a long tail-end), and returns to atmospheric oxygen upon the incubator being opened to the atmosphere.

Figure 119:
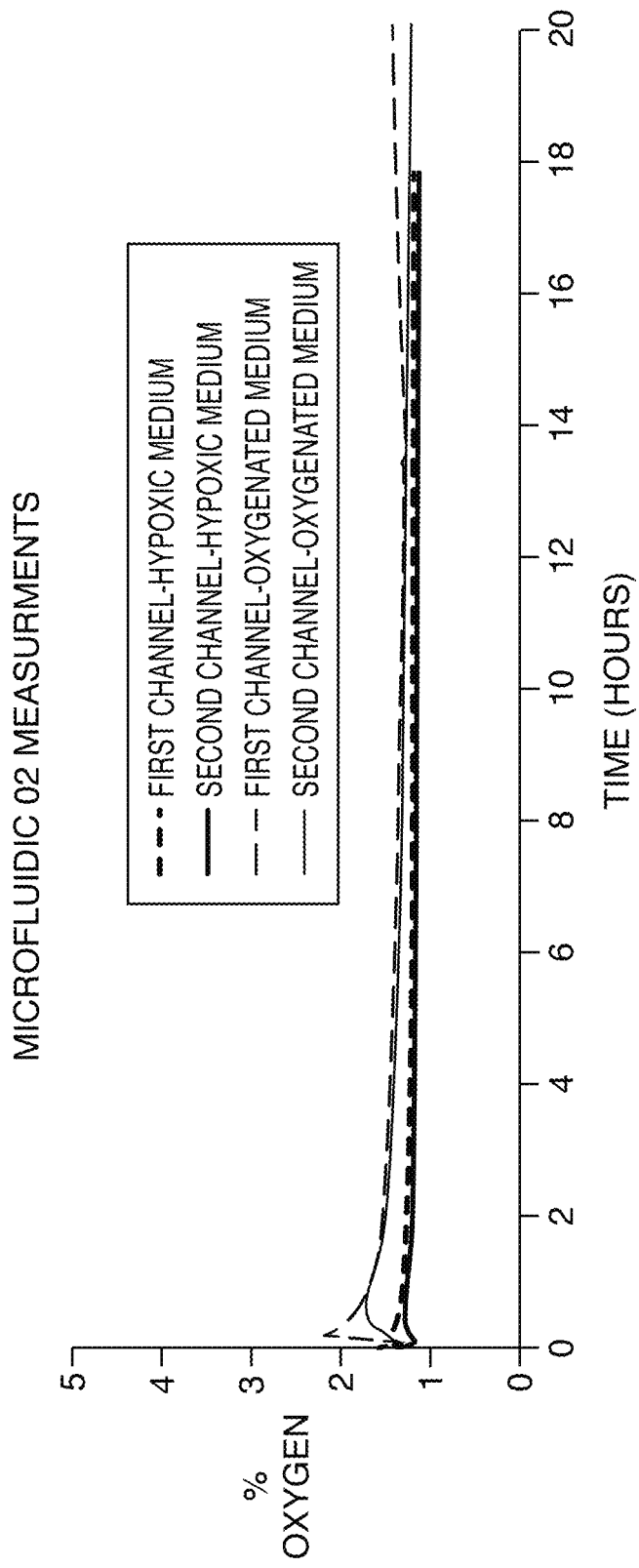
FIG. 119 shows a diagram of the results experimental oxygen measurements of microfluidic device outlets under water flow at 100 µL/hr in a culture module with either 18.5% oxygen (oxygenated), or 1-5% oxygen (hypoxic) concentrations, in a 1% oxygen incubator. The microfluidic device and system were equilibrated to the incubator environment for 12 hours prior.
Figure 120:
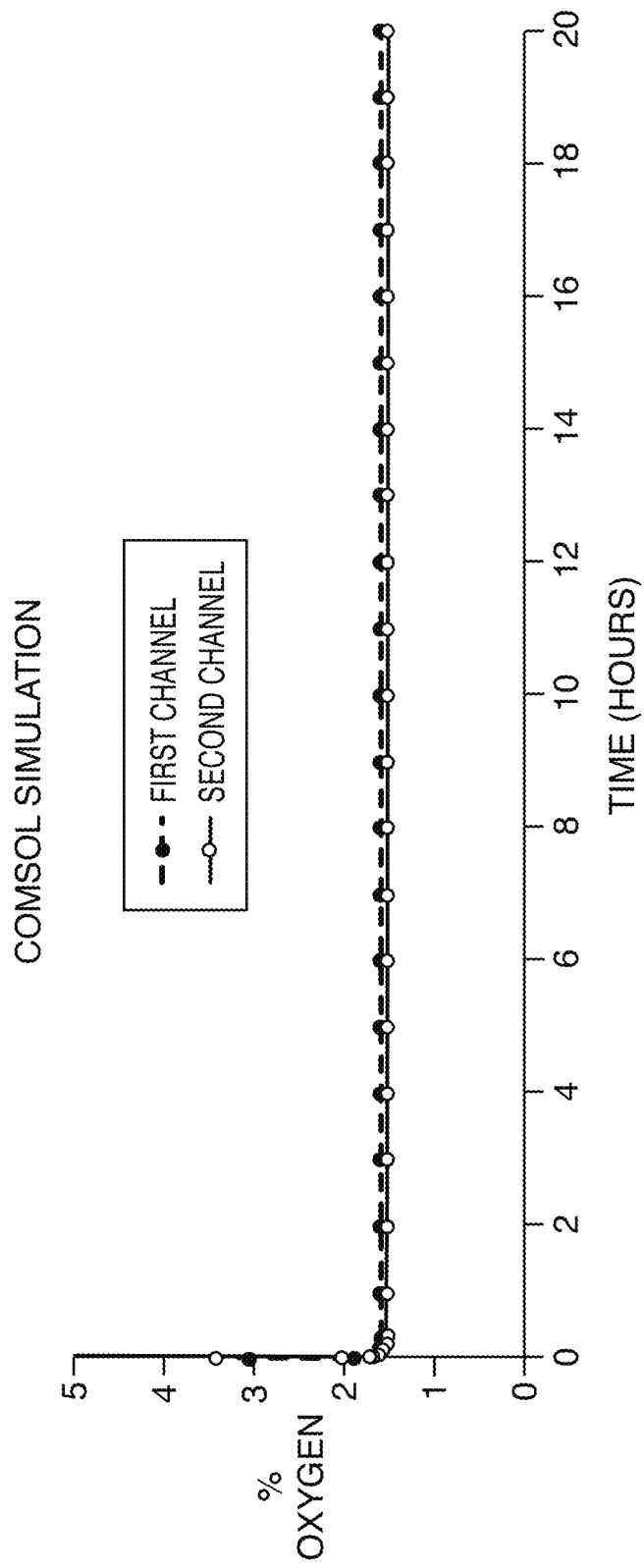
FIG. 120 shows a diagram of the results of a COMSOL Multiphysics simulation plot of a PDMS microfluidic device first channel and second channel volume averages of the same conditions with oxygenated media.

Once equilibrium is achieved in a gas-permeable microfluidic device (12), first (3) and second (4) channel gas concentrations will maintain the incubator oxygen setpoint when flowing fluid or media if the microfluidic device (12) is fabricated out of a high permeability microfluidic device material. Thus, the inlet fluid or media concentrations are largely inconsequential if the microfluidic device is highly permeable. This point was proven during experimentation, as seen in FIG. 119. FIG. 119 shows a diagram of the results experimental oxygen measurements of microfluidic device outlets under water flow at 100 µL/hr in a culture module with either 18.5% oxygen (oxygenated), or 1-5% oxygen (hypoxic) concentrations, in a 1% oxygen incubator. The gas-permeable microfluidic device (12) and system were equilibrated to the incubator environment for 12 hours prior. When flowing fully oxygenated water or hypoxic (1-5% oxygen) water at 100 uL/hr, first (3) and second (4) channel oxygen outputs reach below 1.5-2% oxygen within minutes. The experiment was also simulated and confirmed in a three-dimensional gas-permeable microfluidic device model using the finite element analysis software COMSOL Multiphysics as seen in FIG. 120. FIG. 120 shows a diagram of the results of a COMSOL Multiphysics simulation plot of a PDMS microfluidic device first channel and second channel volume averages of the same conditions with oxygenated media. Therefore, it may be seen that controlling the gas-concentration inside an entirely gas-permeable microfluidic device (12) using a gas-control incubator is highly effective.

Figure 121:
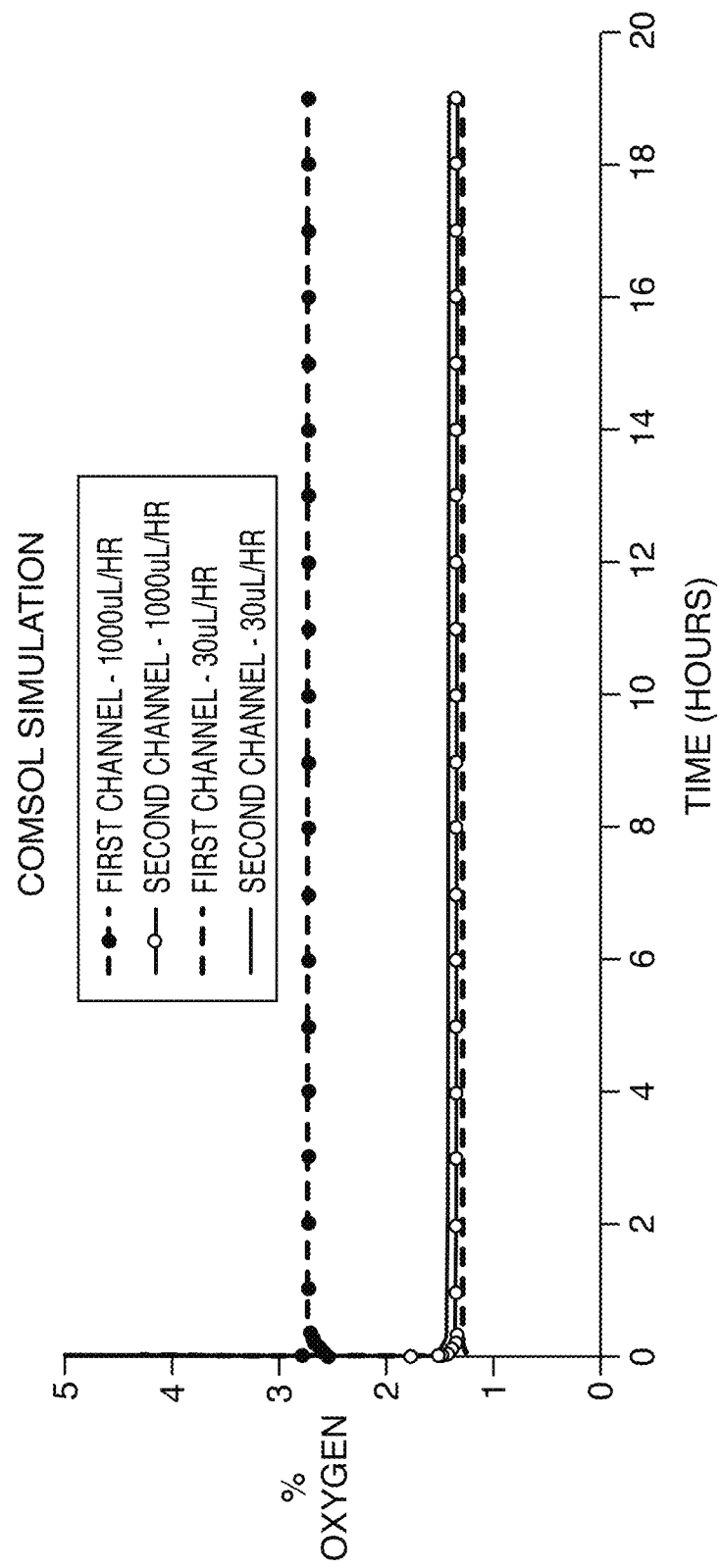
FIG. 121 shows a diagram of results of a COMSOL Multiphysics simulation plot of PDMS microfluidic device first and second channel volume averages for 30 µL/hr and 1000 µL/hr flow rates with oxygenated inlet water in a 1% oxygen incubator.

Furthermore, flow rates below 10004/hr minorly contribute to channel oxygen concentration because of the high diffusion rate of highly permeable materials making up these microfluidic devices (12) and the incubator itself. Oxygen diffuses out of the fluid or medium much faster than the oxygen being replaced in the flowing medium. FIG. 121 shows a diagram of results of a COMSOL Multiphysics simulation plot of PDMS microfluidic device first and second channel volume averages for 30 µL/hr and 1000 µL/hr flow rates with oxygenated inlet water in a 1% oxygen incubator. It may be seen in FIG. 121 that flow rate is not a substantial variable in controlling the gas environment of a gas-permeable microfluidic device (12) within a culture module (42).

Figure 7:
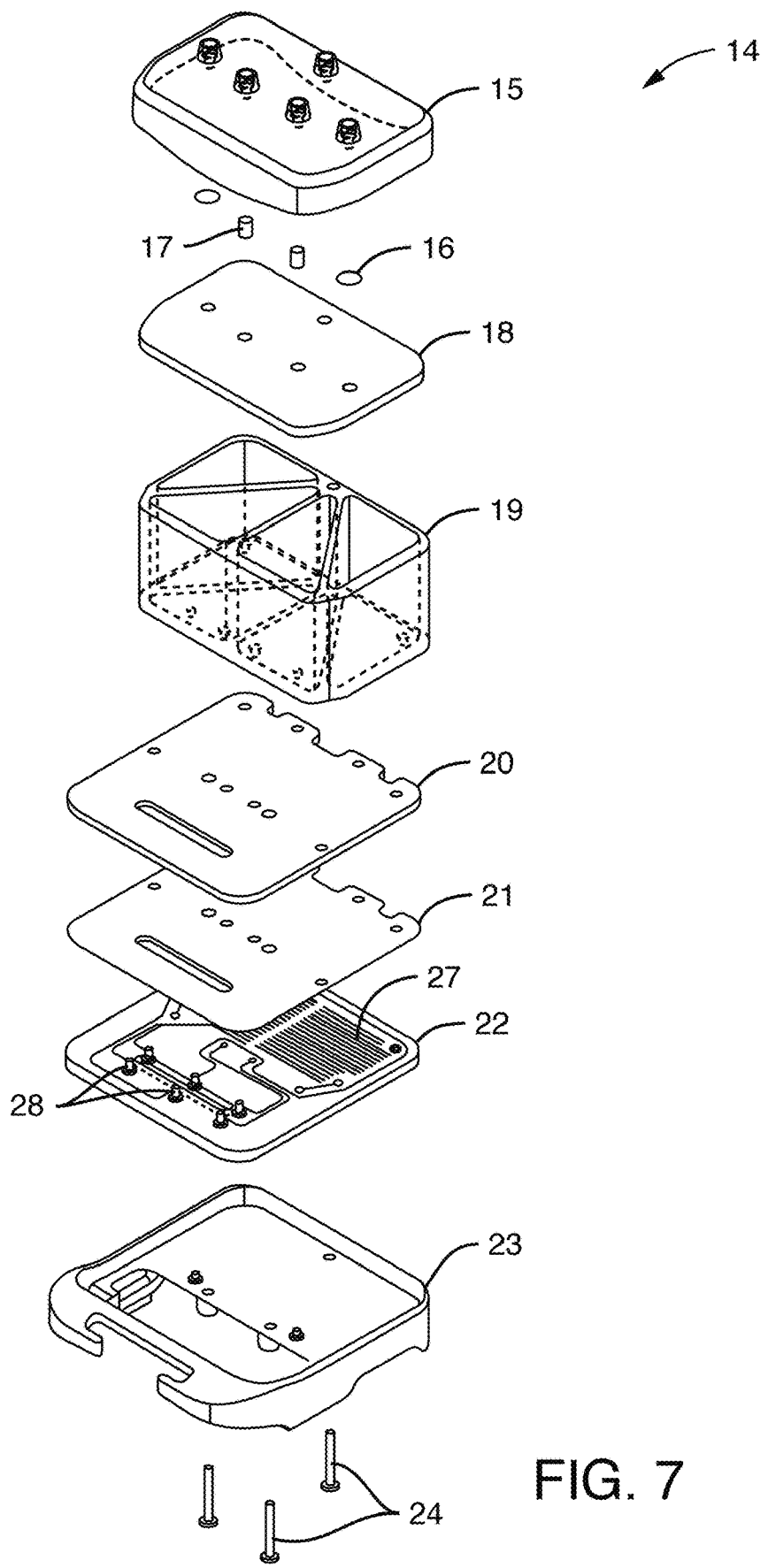
FIG. 7 shows one embodiment a perfusion manifold assembly comprising separate gasketing and capping layers. The embodiment of the perfusion manifold assembly also comprises a lid, different varieties of filters, a lid gasket, reservoirs, a fluidic backplane, a skirt and screws.

Additionally, high flow rates are less practical since it will require replenishing fluid reservoirs, such as fluid reservoirs (19) in FIG. 7, which involves opening the incubator door and resetting oxygen levels within the incubator. FIG. 118 shows the affect of opening the incubator door on the oxygen levels within the gas-permeable microfluidic device (12). When the incubator environment is disturbed, such as opening the door to change flow rate, access the microfluidic devices, access another experiment, etc., microfluidic device equilibration will be in flux. Since the diffusion of oxygen in the gas-permeable microfluidic devices (12) occurs in minutes, channels (3, 4) will re-equilibrate while the incubator oxygen concentration rises and reduces back to the setpoint. Quick door openings may only cause small oxygen rises in anaerobic incubators and a relatively short microfluidic device recovery time (in the range of a few hours): a five second door opening will result in an additional 1.5 hours to reach gas-permeable microfluidic device (12) oxygen concentrations below 2%, as seen in FIG. 122. FIG. 122 shows a diagram of results of recovery time when opening an incubator door. Oxygen measurements were taken at the outlet of a microfluidic device under 100 µL/hr water flow in a culture module inside an incubator set to 1% oxygen. The microfluidic device, culture module, and remainder of system were equilibrated to the incubator environment for 12 hours prior. The incubator door was opened for five seconds before starting measurements. The oxygen recovery time largely depends on the incubator and gas control system, as large single-doored incubators will be less efficient than multi-doored or high nitrogen pressure input systems.

Handling gas-permeable microfluidic devices outside a hypoxic incubator and perfusion manifold assembly (14) should be performed as quickly as possible during low-oxygen experiments on gas-permeable microfluidic devices. Only being able to access gas-permeable microfluidic devices (12) during low-oxygen experiments for very short periods of time may impact protocol steps that require direct access to a microfluidic device, such as inoculating microfluidic devices with bacteria. COMSOL simulations indicate oxygen concentrations will continuously double within minutes and reach atmospheric oxygen within 30 minutes as seen in FIG. 123. FIG. 123 shows a diagram of results of a COMSOL Multiphysics simulation plot of PDMS microfluidic device (12) first (3) and second (4) channel volume averages of a static PDMS microfluidic device (12) equilibrated to 1% oxygen and exposed to atmospheric oxygen. Experimental results concluded an oxygen half-life of around 6 minutes for the gas-permeable microfluidic device (12) outside the culture module (42) and perfusion manifold assembly (14). After five half-lives, steady-state is considered reached (97% of steady-state) which equates to around 30 minutes, confirming the COMSOL simulation.

Experimental timing was found for the present system, including gas-permeable microfluidic devices (12), perfusion manifold assemblies (14), and culture modules (42). Cell culture incubators were found to take 2-5 hours to reach low or anaerobic oxygen levels. Gas-permeable microfluidic devices (12) were found to reach low or anaerobic oxygen equilibration in 3 hours when in the incubator with connection to perfusion manifold assemblies (14) and culture modules (42), wherein the half-life of oxygen was found to be 35 minutes for the gas-permeable microfluidic devices (12) in that experimental setup. Gas-permeable microfluidic devices (12) were found to reach low or anaerobic oxygen equilibration in 30 minutes when in the incubator without contact to perfusion manifold assemblies (14) and culture modules (42), wherein the half-life of oxygen was found to be 6 minutes for the gas-permeable microfluidic devices (12) alone in the incubator.

Cellular oxygen consumption can be a significant contributor to the depletion of total oxygen within the gas-permeable microfluidic device (12). When considering highly metabolic cells such as colonic epithelial cells characterized by an oxygen uptake rate of 2020 nmol/hr, channel oxygen levels differ under standard oxygenated cell culturing conditions. Using COMSOL, the average top and bottom channel oxygen concentrations reach 14% and 12% respectively, as seen in FIG. 124. FIG. 124 shows a diagram of results of a COMSOL Multiphysics simulation plot of PDMS microfluidic device first and second channel volume averages of a microfluidic device with seeded Caco-2 cells in culture conditions or 18.5% oxygen incubator and 18.5% oxygen inlet water at 100 µL/hr water flow rate. However, a local microgradient is also formed where oxygen concentrations decrease close to the cell layer, reaching as low as 2% oxygen right at the center of the cell layer as seen in FIG. 125. FIG. 125 shows a diagram of a PDMS microfluidic device oxygen microenvironment with the addition of Caco-2 cells. FIG. 125 shows a cross-sectional surface pot of water oxygen concentrations in the center of the microfluidic device. The simulation which produced the results shown in FIGS. 124 and 125 highlights the importance of considering cellular oxygen uptake and release when designing experiments.

The above study demonstrates the gas-permeable microfluidic device gas environment can be easily modified with a culture module placed inside a gas-controlled incubator.

Other applications include high oxygen environments (hyperoxia) or introducing various gasotransmitters. Note, first and second channels are difficult to be controlled independently, the whole microfluidic devices experience the same gas composition if cell metabolism is not considered. Cell metabolism will significantly contribute to the gas microenvironment and even introduce local gas gradients. Additional endpoints and controls should be considered when performing gas-controlled experiments, such as incorporating hypoxia stains for low oxygen conditions.

The invention claimed is:

1. A method of determining compound distribution in a system, comprising:
   a) providing a system and an experimental protocol for said system comprising one or more biological elements; wherein said one or more biological elements are contacted by a compound;
   b) modifying said experimental protocol by excluding at least one of said one or more biological elements;
   c) performing said modified experimental protocol; and
   d) determining the distribution of said compound in said system using by measuring the concentration of said compound in said system.

2. The method of claim 1, wherein said experimental protocol comprises introducing fluid flow into said system.

3. The method of claim 2, wherein said experimental protocol comprises collecting effluent.

4. The method of claim 2, wherein said experimental protocol comprises assaying said effluent.

5. The method of claim 1, wherein said biological elements comprise cells.

6. The method of claim 1, wherein said biological elements comprise biological coatings.

7. The method of claim 1, wherein said system comprises one or more microfluidic devices.

8. The method of claim 1, wherein said distribution of said compound is used to calculate error bars for results from said experimental protocol.

9. The method of claim 1, wherein said distribution of said compound is used to calculate half maximal inhibitory concentration (IC50) for said experimental protocol.

* * * * *